United States Patent
Blum et al.

(10) Patent No.: US 9,765,075 B2
(45) Date of Patent: Sep. 19, 2017

(54) SUBSTITUTED BRIDGED UREA ANALOGS AS SIRTUIN MODULATORS

(71) Applicant: GLAXOSMITHKLINE LLC, Wilmington, DE (US)

(72) Inventors: Charles A. Blum, Waltham, MA (US); Richard Dana Caldwell, Brookline, MA (US); Rebecca Casaubon, Cambridge, MA (US); Jeremy S. Disch, Natick, MA (US); Ryan Michael Fox, Collegeville, PA (US); Karsten Koppetsch, Woburn, MA (US); Pui Yee Ng, Waltham, MA (US); Christopher Oalmann, Watertown, MA (US); Robert B. Perni, Marlborough, MA (US); Bruce G. Szczepankiewicz, Hopkinton, MA (US); Brian H. White, Malden, MA (US)

(73) Assignee: GLAXOSMITHKLINE LLC, Wilmington, DE (US)

(*) Notice: Subject to any disclaimer, the term of this patent is extended or adjusted under 35 U.S.C. 154(b) by 0 days.

(21) Appl. No.: 14/891,158

(22) PCT Filed: May 13, 2014

(86) PCT No.: PCT/US2014/037767
§ 371 (c)(1),
(2) Date: Nov. 13, 2015

(87) PCT Pub. No.: WO2014/186313
PCT Pub. Date: Nov. 20, 2014

(65) Prior Publication Data
US 2016/0083386 A1    Mar. 24, 2016

Related U.S. Application Data

(60) Provisional application No. 61/822,758, filed on May 13, 2013.

(51) Int. Cl.

| | |
|---|---|
| *A61K 31/439* | (2006.01) |
| *C07D 487/18* | (2006.01) |
| *C07D 471/18* | (2006.01) |
| *A61K 31/4995* | (2006.01) |
| *A61K 31/506* | (2006.01) |
| *A61K 31/551* | (2006.01) |
| *C07D 487/04* | (2006.01) |
| *C07D 513/18* | (2006.01) |
| *C07D 519/00* | (2006.01) |
| *A61K 45/06* | (2006.01) |

(52) U.S. Cl.
CPC ........ *C07D 471/18* (2013.01); *A61K 31/4995* (2013.01); *A61K 31/506* (2013.01); *A61K 31/551* (2013.01); *A61K 45/06* (2013.01); *C07D 487/04* (2013.01); *C07D 513/18* (2013.01); *C07D 519/00* (2013.01)

(58) Field of Classification Search
CPC .................................................. C07D 487/18
See application file for complete search history.

(56) References Cited

U.S. PATENT DOCUMENTS

| | | |
|---|---|---|
| 5,637,679 A | 6/1997 | Hassenruck et al. |
| 2010/0016279 A1 | 1/2010 | Bradbury et al. |
| 2011/0046110 A1 | 2/2011 | Vu et al. |
| 2011/0306609 A1 | 12/2011 | Oalmann et al. |
| 2012/0252780 A1 | 10/2012 | Ng et al. |
| 2014/0288052 A1 | 9/2014 | Blum et al. |
| 2015/0152108 A1 | 6/2015 | Blum et al. |

FOREIGN PATENT DOCUMENTS

| | | |
|---|---|---|
| WO | WO 2006/094248 A1 | 9/2006 |
| WO | PCT/US2014/037767 | 5/2014 |
| WO | WO2016/081692 A2 | 5/2016 |

OTHER PUBLICATIONS

Extended EP Search Report dated Apr. 24, 2017, Application No. 14798509.7, 5 pages.
International Search Report dated May 16, 2016, Application No. PCT/US15/61501, 3 pages.
Szczepankiewicz et al., "Sirtuin Modulators: Targets for Metabolic Diseases and Beyond", *Current Topics in Medicinal Chemistry*, vol. 8, No. 17, pp. 1533-1544 (2008).

*Primary Examiner* — Brian McDowell
(74) *Attorney, Agent, or Firm* — Nicole Ho; Kathryn A. Lutomski; Edward R. Gimmi

(57) ABSTRACT

Provided herein are novel substituted bridged urea and related analogs and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity. Also provided are compositions comprising a sirtuin-modulating compound in combination with another therapeutic agent.

(I)

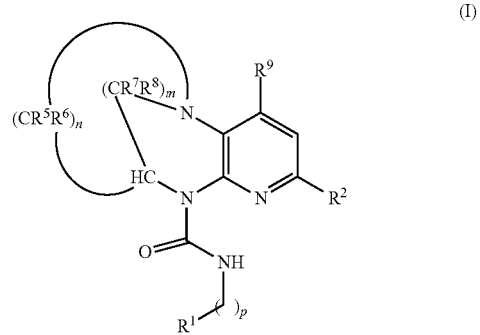

4 Claims, 17 Drawing Sheets

Figure 1. $^1$H-NMR Spectrum of Compound 1
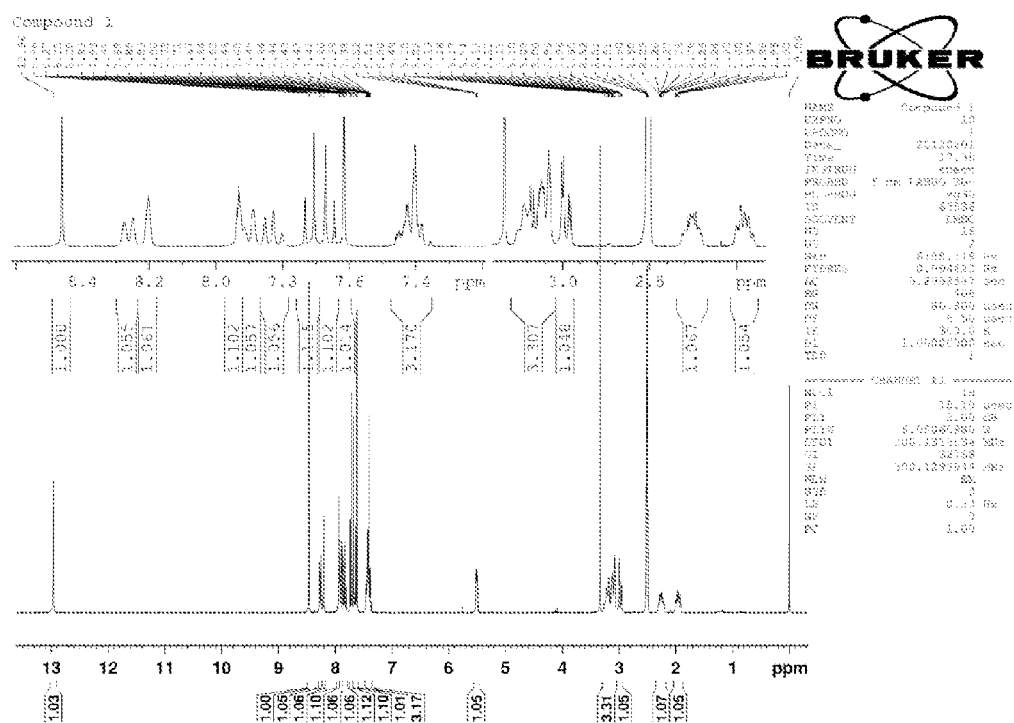

Figure 2. $^{13}$C-NMR and APT NMR Spectrum of Compound 1
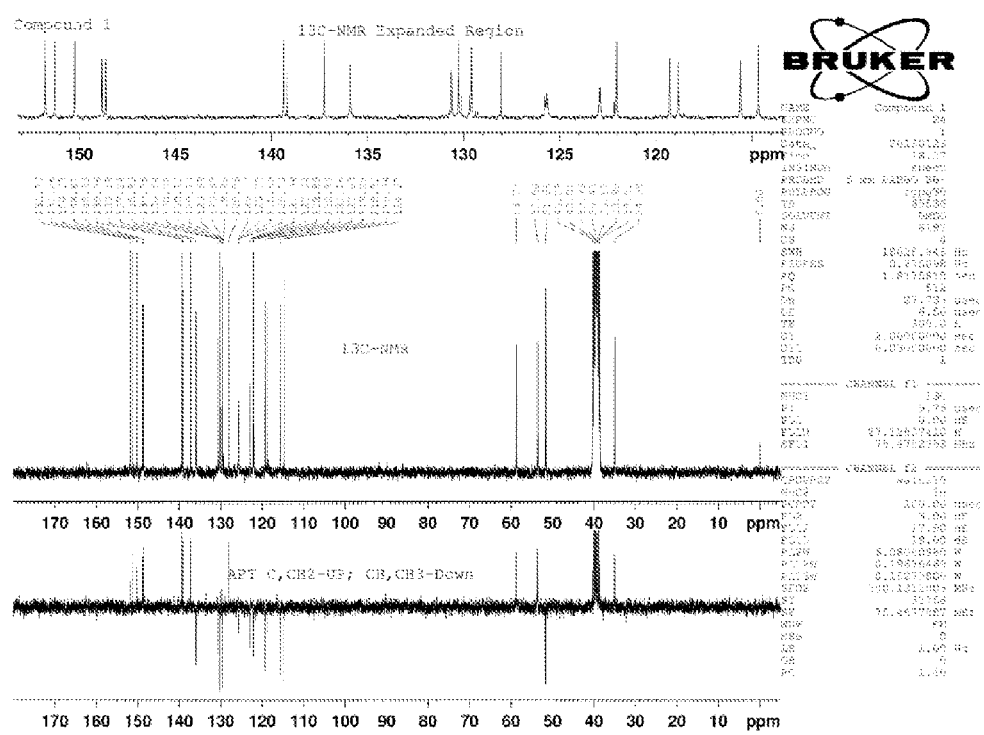

Figure 3. (A) HDX-MS of full length SIRT1, (B) Enzymatic characterization of effect of CBS on SIRT1cc activity, (C) Pivot plot the STAC activation of mini-hSIRT1(ΔN) vs. mini-hSIRT1, (D) Pivot plot the STAC activation of mini-hSIRT1(ΔCBS) vs. mini-hSIRT1 and (E) Pivot plot the STAC activation of mini-hSIRT1(E230K) vs. mini-hSIRT1

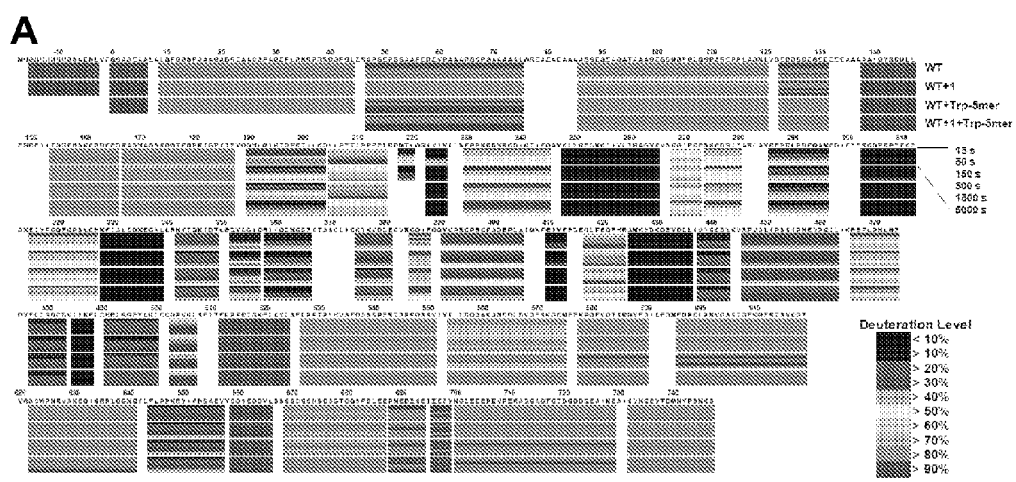

(A) HDX-MS of full length SIRT1. The warm colored regions represent high deuteron incorporation, reflecting the highly dynamic properties and the intrinsic flexibility of these regions. Conversely, the cold colored regions represent low deuteron incorporation, reflecting the rigidity of these regions.

Figure 3 (continued). (A) HDX-MS of full length SIRT1, (B) Enzymatic characterization of effect of CBS on SIRT1cc activity, (C) Pivot plot the STAC activation of mini-hSIRT1(ΔN) vs. mini-hSIRT1, (D) Pivot plot the STAC activation of mini-hSIRT1(ΔCBS) vs. mini-hSIRT1 and (E) Pivot plot the STAC activation of mini-hSIRT1(E230K) vs. mini-hSIRT1
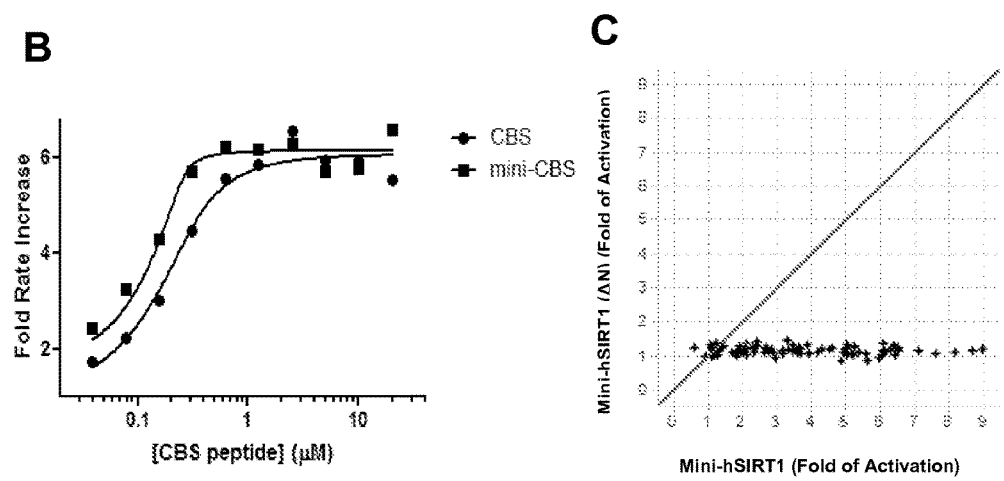

Figure 3 (continued). (A) HDX-MS of full length SIRT1, (B) Enzymatic characterization of effect of CBS on SIRT1cc activity, (C) Pivot plot the STAC activation of mini-hSIRT1(ΔN) vs. mini-hSIRT1, (D) Pivot plot the STAC activation of mini-hSIRT1(ΔCBS) vs. mini-hSIRT1 and (E) Pivot plot the STAC activation of mini-hSIRT1(E230K) vs. mini-hSIRT1
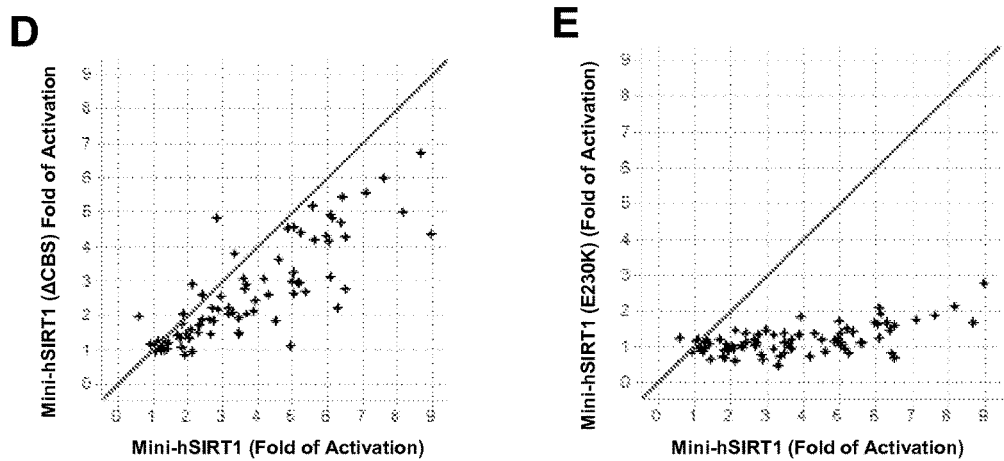

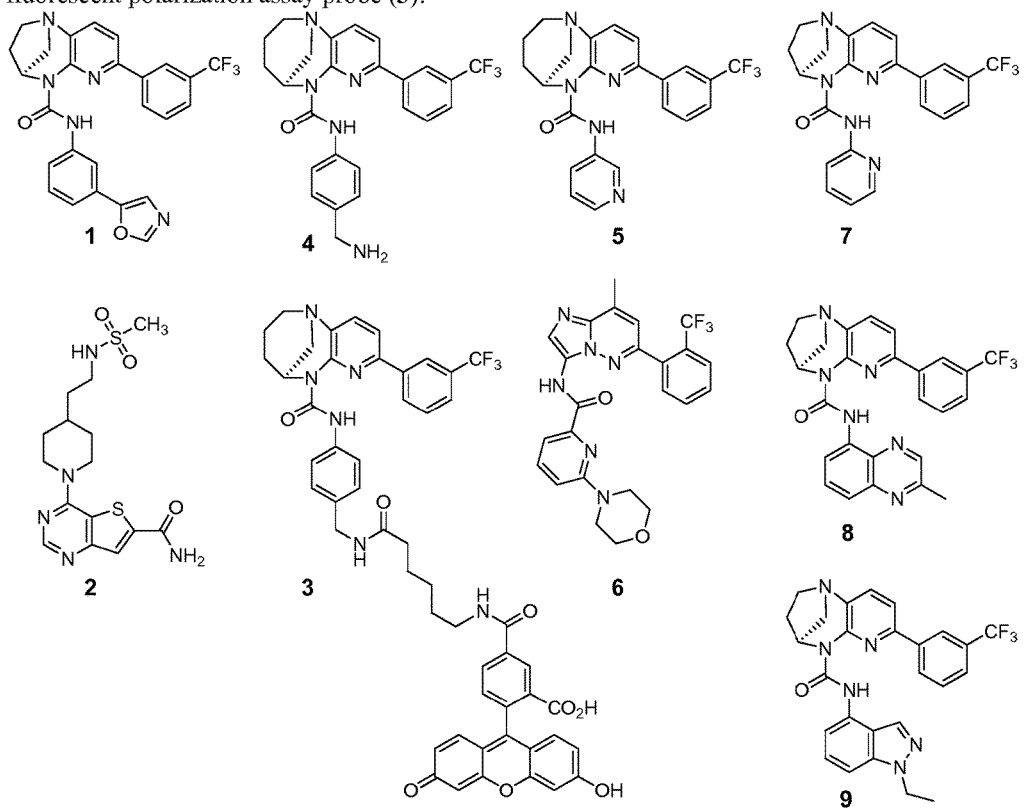
Figure 4. Chemical structures of synthetic SIRT1 activators (1, 4-9), inhibitor (2), and fluorescent polarization assay probe (3).

Figure 5. Size exclusion chromatography (SEC) of mini-hSIRT1 in the absence or presence of STACs.
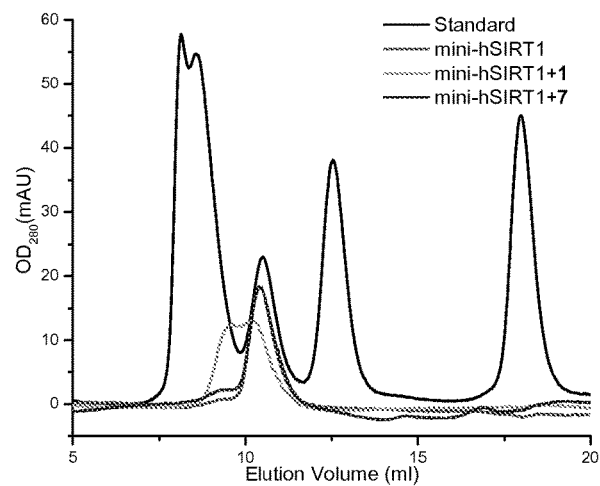

Figure 6. (A) Differential perturbation of the HDX-MS profile of SIRT1cc upon binding to CBS peptide (B) Structural comparison of Mini-hSIRT1/1 complex and ySIR2 (C) Structural comparison of the N-terminal SBD of Mini-hSIRT1/1 complex, Mini-hSIRT1/1/2 complex and Mini-hSIRT1/1/Ac-p53-7mer/CarbaNAD quaternary complex
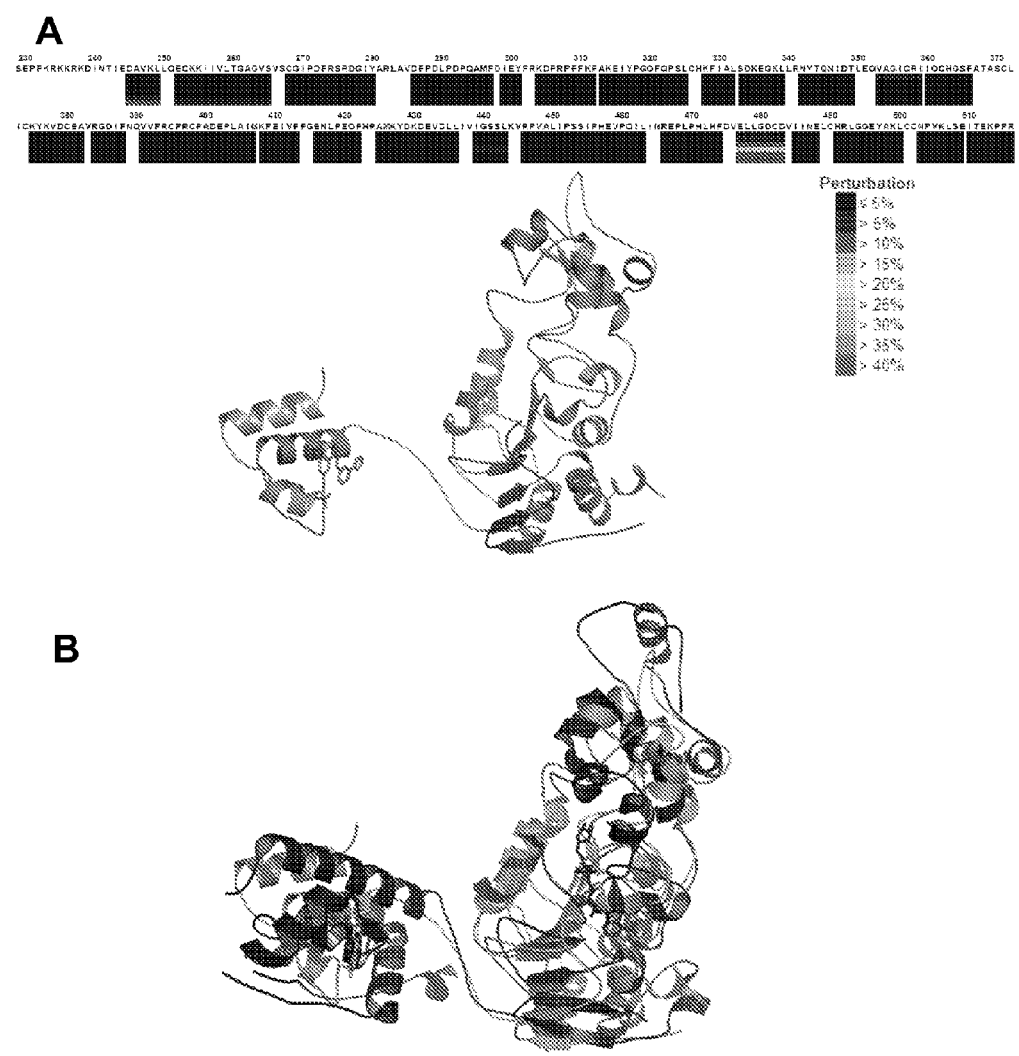

Figure 6 (continued). (A) Differential perturbation of the HDX-MS profile of SIRT1cc upon binding to CBS peptide (B) Structural comparison of Mini-hSIRT1/1 complex and ySIR2 (C) Structural comparison of the N-terminal SBD of Mini-hSIRT1/1 complex, Mini-hSIRT1/1/2 complex and Mini-hSIRT1/1/Ac-p53-7mer/CarbaNAD quaternary complex

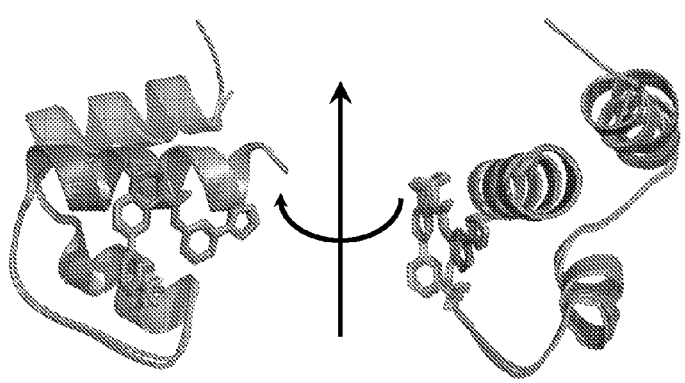

C (A) Differential perturbation of the HDX-MS profile of SIRT1cc upon binding to CBS peptide. The perturbed sequence is mapped on the Mini-hSIRT1/1 complex structure (gray) as green and the CBS peptide is shown in red. (B) Structural comparison of Mini-hSIRT1/1 complex (Green) and ySIR2 structure in the ySIR2/ySIR4 complex (Blue). (C) Structural comparison of the N-terminal SBD of Mini-hSIRT1/1 complex (Green), Mini-hSIRT1/1/2 complex (Magenta), and Mini-hSIRT1/1/Ac-p53-7mer/CarbaNAD quaternary complex (Orange).

Figure 7. Activation dose-response curves comparing wild-type and (A) I223A or (B) E230K SIRT1 using the OAcADPr assay with the Ac-p53(W5) substrate

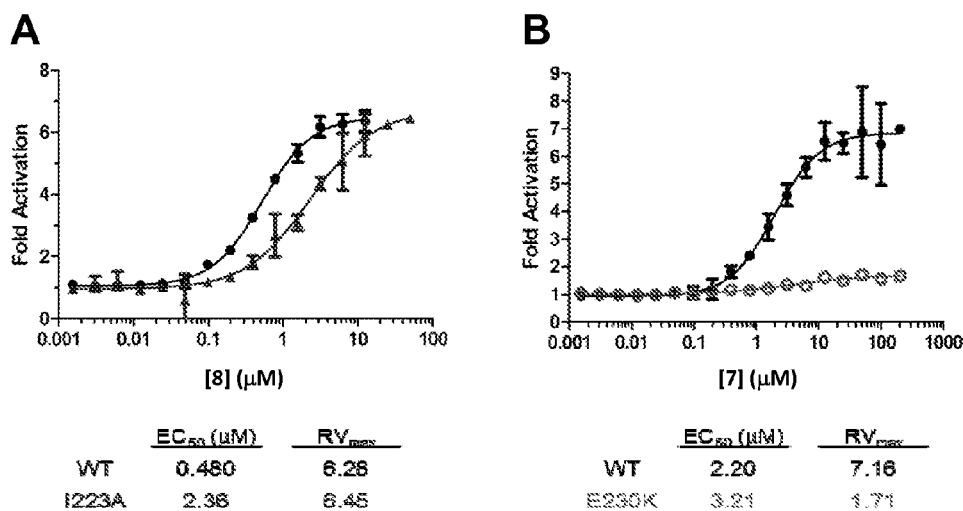

Activation dose-response curves comparing wild-type (black) and (A) I223A (blue) or (B) E230K (red) SIRT1 using the OAcADPr assay with the Ac-p53(W5) substrate. I223A causes a shift in the $EC_{50}$ value of 8 without changing the maximum activation. In contrast, E230K reduces the maximum activation without altering the $EC_{50}$ value of 7.

Figure 8. activation comparison of wild-type versus mutant full-length hSIRT1.
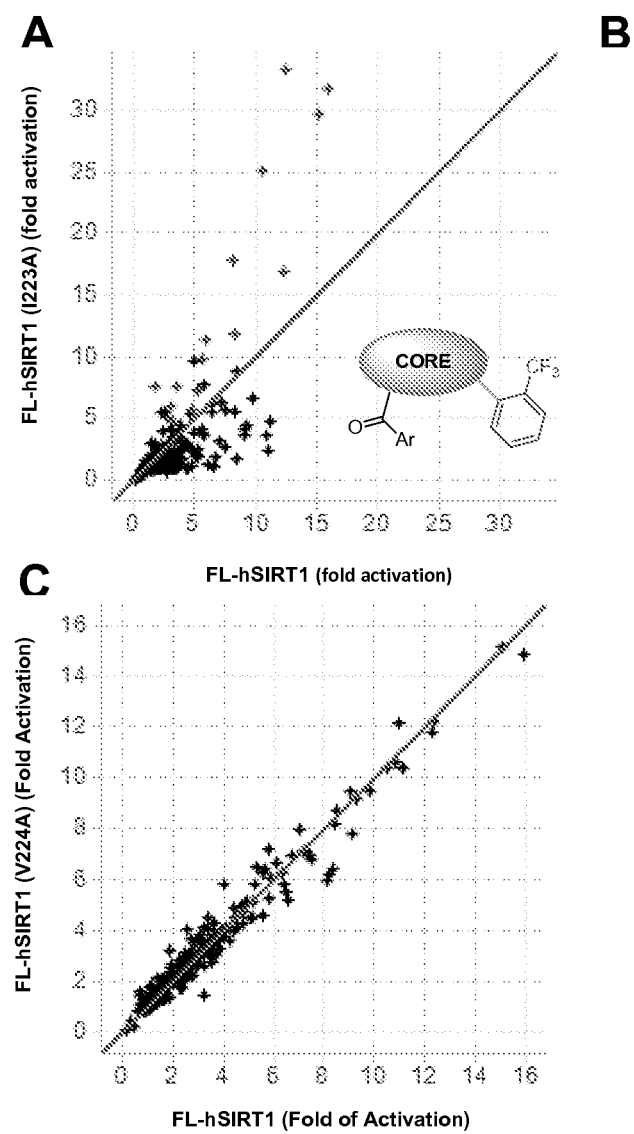

Figure 8 (continued). activation comparison of wild-type versus mutant full-length hSIRT1.

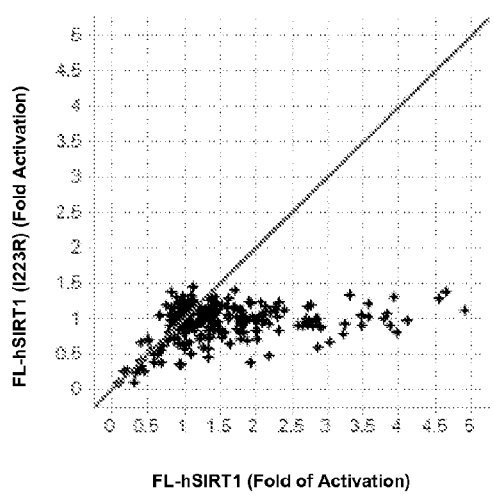

FL-hSIRT1 (Fold of Activation)

a) Fold-activation of I223A vs wild-type (WT) hSIRT1 using the Ac-p53(W5) peptide. Red colored markers denote I223A-selective activators with the ortho-CF$_3$ benzyl substituent pictured. b) Fold-activation of V224A vs wild-type (WT) SIRT1 using the Ac-p53(W5) peptide. c) Fold-activation of I223R vs wild-type (WT) SIRT1 using the FOXO-3a 21-mer substrate. All were tested against a 246-compound set (25 µM final) using the OAcADPr assay. A y=x reference line is shown in red.

Figure 9. (A) Interface of Mini-hSIRT1/Ac-p53 interaction. (B) Interface of Mini-hSIRT1/carbaNAD interaction. (C) Interface of Mini-hSIRT1/2 interaction.
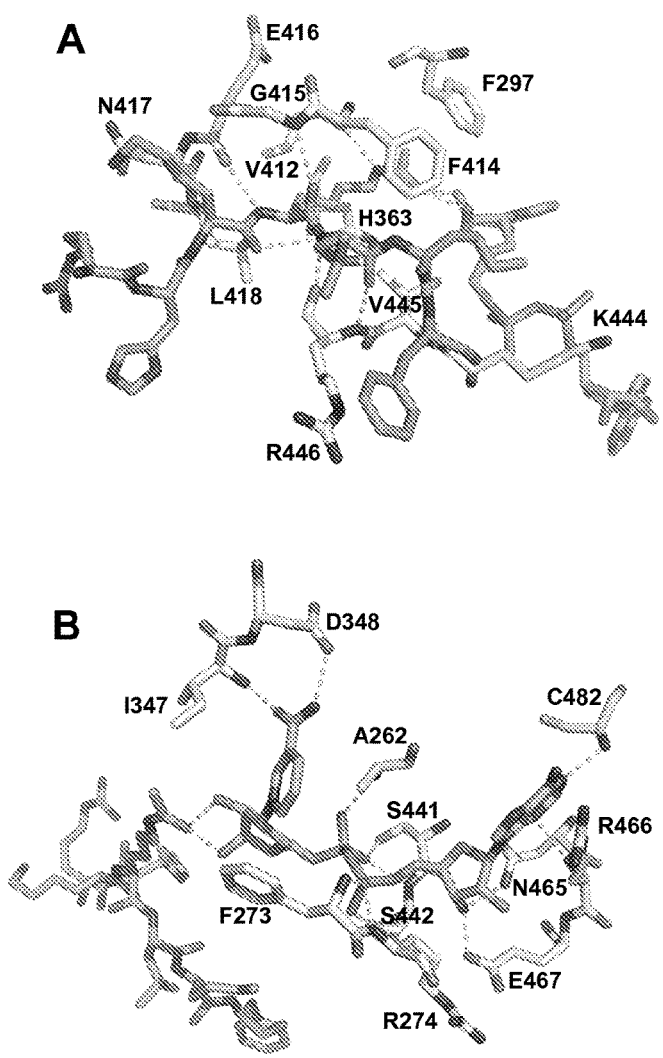

Figure 9 (continued). (A) Interface of Mini-hSIRT1/Ac-p53 interaction. (B) Interface of Mini-hSIRT1/carbaNAD interaction. (C) Interface of Mini-hSIRT1/2 interaction.
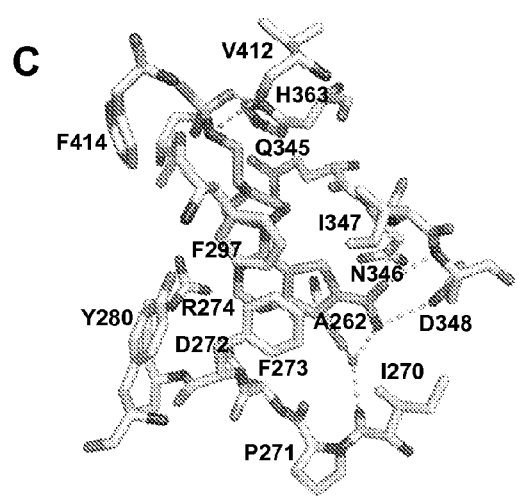

Figure 10. (A) Binding of FP probe 3 to SIRT1. (B) Competition of 4 against SIRT1/3 complex
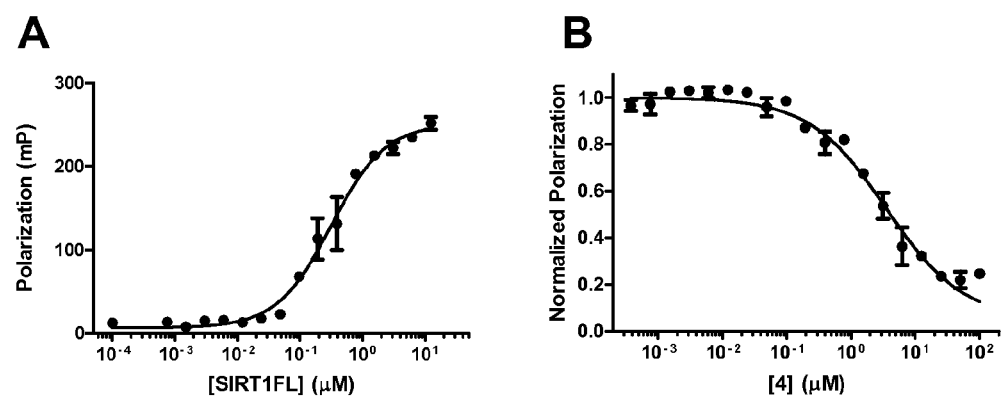

Figure 11. Impaired STAC binding by full-length I223R hSIRT1
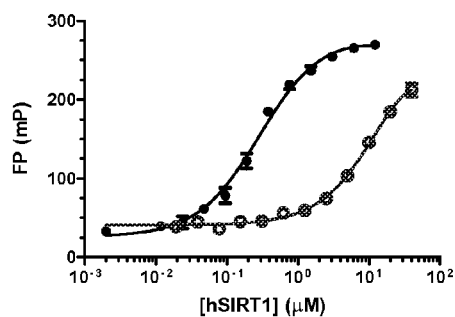
Binding of 3 to either wild-type (black) or I223R (blue) hSIRT1 using the fluorescence polarization binding assay. Using Eq. 2, $K_d$ values of $0.290 \pm 0.035$ μM and $19 \pm 5.2$ μM were determined for wild-type and I223R hSIRT1 respectively.

Figure 12. Pivot plot the STAC activation of mini-hSIRT1(R446A) vs. mini-hSIRT1
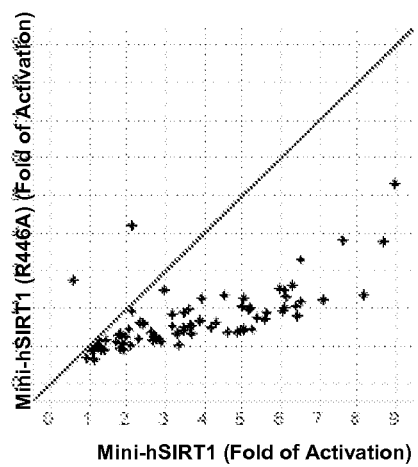

SUBSTITUTED BRIDGED UREA ANALOGS AS SIRTUIN MODULATORS

BACKGROUND

The Silent Information Regulator (SIR) family of genes represents a highly conserved group of genes present in the genomes of organisms ranging from archaeabacteria to eukaryotes. The encoded SIR proteins are involved in diverse processes from regulation of gene silencing to DNA repair. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The proteins encoded by members of the SIR gene family show high sequence conservation in a 250 amino acid core domain. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions, which can connect its biological role with cellular metabolism in yeast. Mammalian Sir2 homologs have NAD-dependent histone deacetylase activity.

Biochemical studies have shown that Sir2 can readily deacetylate the amino-terminal tails of histones H3 and H4, resulting in the formation of 2'/3'-O-acetyl-ADP-ribose (OAADPR) and nicotinamide. Strains with additional copies of SIR2 display increased rDNA silencing and a 30% longer life span. It has also been shown that additional copies of the *C. elegans* SIR2 homolog, sir-2.1, and the *D. melanogaster* dSir2 gene extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has $NAD^+$-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

In addition to therapeutic potential, structural and biophysical studies of SIRT1 activity and activation by small molecule sirtuin modulators would be useful to advance understanding of the biological function of sirtuins, to further the understanding of the mechanism of action of sirtuin activation and to aid in the development of assays that identify novel sirtuin modulators.

SUMMARY

Provided herein are novel sirtuin-modulating compounds and methods of use thereof.

In one aspect, the invention provides sirtuin-modulating compounds of Structural Formulas (I), (IIa), (IIb), (IIIa), (IIIb) and (IV) as are described in detail below.

In another aspect, the invention provides methods for using sirtuin-modulating compounds, or compositions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic-induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

BRIEF DESCRIPTION OF THE FIGURES

FIG. 1 shows $^1$H-NMR spectrum of Compound 1.

FIG. 2 shows $^{13}$C-NMR and APT NMR spectrum of Compound 1.

FIG. 3 depicts (A) HDX-MS of full length SIRT1, (B) Enzymatic characterization of effect of CBS on SIRT1cc activity, (C) Pivot plot the STAC activation of mini-hSIRT1 (ΔN) vs. mini-hSIRT1, (D) Pivot plot the STAC activation of mini-hSIRT1(ΔCBS) vs. mini-hSIRT1 and (E) Pivot plot the STAC activation of mini-hSIRT1(E230K) vs. mini-hSIRT1.

FIG. 4 shows chemical structures of synthetic SIRT1 activators (1, 4-9), inhibitor (2), and fluorescent polarization assay probe (3).

FIG. 5 depicts size exclusion chromatography (SEC) of mini-hSIRT1 in the absence or presence of STACs.

FIG. 6 depicts (A) Differential perturbation of the HDX-MS profile of SIRT1cc upon binding to CBS peptide (B) Structural comparison of Mini-hSIRT1/1 complex and ySIR2 (C) Structural comparison of the N-terminal SBD of Mini-hSIRT1/1 complex, Mini-hSIRT1/1/2 complex and Mini-hSIRT1/1/Ac-p53-7mer/CarbaNAD quaternary complex.

FIG. 7 depicts the activation dose-response curves comparing wild-type and (A) I223A or (B) E230K SIRT1 using the OAcADPr assay with the Ac-p53(W5) substrate.

FIG. 8 depicts activation comparison of wild-type versus mutant full-length hSIRT1.

FIG. 9 depicts (A) Interface of Mini-hSIRT1/Ac-p53 interaction. (B) Interface of Mini-hSIRT1/carbaNAD interaction. (C) Interface of Mini-hSIRT1/2 interaction.

FIG. 10 depicts (A) Binding of FP probe 3 to SIRT1. (B) Competition of 4 against SIRT1/3 complex.

FIG. 11 depicts impaired STAC binding by full-length I223R hSIRT1.

FIG. 12 depicts pivot plot the STAC activation of mini-hSIRT1(R446A) vs. mini-hSIRT1.

DETAILED DESCRIPTION

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues.

The term "bioavailable", when referring to a compound, is art-recognized and refers to a form of a compound that allows for all or a portion of the amount of compound administered to be absorbed by, incorporated into, or otherwise physiologically available to a subject or patient to whom it is administered.

"Biologically active portion of a sirtuin" refers to a portion of a sirtuin protein having a biological activity, such as the ability to deacetylate ("catalytically active"). Catalytically active portions of a sirtuin may comprise the core domain of sirtuins. Catalytically active portions of SIRT1 having GenBank Accession No. NP_036370 that encompass the NAD$^+$ binding domain and the substrate binding domain, for example, may include without limitation, amino acids 240-664 or 240-505 of GenBank Accession No. NP_036370, which are encoded by the polynucleotide of GenBank Accession No. NM_012238. Therefore, this region is sometimes referred to as the core domain. Other catalytically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238. Another "biologically active" portion of SIRT1 is amino acids 62-293 or 183-225 of GenBank Accession No. NP_036370, which comprise a domain N-terminal to the core domain that is important to the compound binding site.

The term "companion animals" refers to cats and dogs. As used herein, the term "dog(s)" denotes any member of the species Canis familiaris, of which there are a large number of different breeds. The term "cat(s)" refers to a feline animal including domestic cats and other members of the family Felidae, genus Felis.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "ED$_{50}$" refers to the art-recognized measure of effective dose. In certain embodiments, ED$_{50}$ means the dose of a drug which produces 50% of its maximum response or effect, or alternatively, the dose which produces a predetermined response in 50% of test subjects or preparations, such as isolated tissue or cells. The term "LD$_{50}$" refers to the art-recognized measure of lethal dose. In certain embodiments, LD$_{50}$ means the dose of a drug which is lethal in 50% of test subjects. The term "therapeutic index" is an art-recognized term which refers to the therapeutic index of a drug, defined as LD$_{50}$/ED$_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol-related disorders, such as gallstones, cholecystitis and cholelithiasis, gout, obstructive sleep apnea and respiratory problems, osteoarthritis, and bone loss, e.g., osteoporosis in particular.

The term "livestock animals" refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-modulating compound" refers to a compound that increases the level of a sirtuin protein and/or increases at least one activity of a sirtuin protein. In an exemplary embodiment, a sirtuin-modulating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

proteins include deacetylation, e.g., of an acetylated peptide substrate.

"Sirtuin protein" refers to a member of the sirtuin deacetylase protein family, or preferably to the sir2 family, which include yeast Sir2 (GenBank Accession No. P53685), *C. elegans* Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273).

"SIRT1 protein" refers to a member of the sir2 family of sirtuin deacetylases. In certain embodiments, a SIRT1 protein includes yeast Sir2 (GenBank Accession No. P53685), C. elegans Sir-2.1 (GenBank Accession No. NP_501912), human SIRT1 (GenBank Accession No. NM_012238 or NP_036370 (or AF083106)), mouse SIRT1 (GenBank Accession No. NM_019812 or NP_062786), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In certain embodiments, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In certain embodiments, a SIRT4 protein includes human SIRT4 (GenBank Accession No. NM_012240 or NP_036372). In certain embodiments, a SIRT5 protein includes human SIRT5 (GenBank Accession No. NM_012241 or NP_036373). In certain embodiments, a SIRT6 protein includes human SIRT6 (GenBank Accession No. NM_016539 or NP_057623). In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In certain embodiments, a SIRT3 protein includes a fragment of SIRT3 protein that is produced by cleavage with a mitochondrial matrix processing peptidase (MPP) and/or a mitochondrial intermediate peptidase (MIP).

The term "stereoisomer" as used herein is art-recognized and refers to any of two or more isomers that have the same molecular constitution and differ only in the three-dimensional arrangement of their atomic groupings in space. When used herein to describe a compounds or genus of compounds, stereoisomer includes any portion of the compound or the compound in its entirety. For example, diastereomers and enantiomers are stereoisomers.

The terms "systemic administration" and "administered systemically," are art-recognized and refer to the administration of a subject composition, therapeutic or other material enterally or parenterally.

The term "tautomer" as used herein is art-recognized and refers to any one of the possible alternative structures that may exist as a result of tautomerism, which refers to a form of constitutional isomerism in which a structure may exist in two or more constitutional arrangements, particularly with respect to the position of hydrogens bonded to oxygen. When used herein to describe a compound or genus of compounds, it is further understood that a "tautomer" is readily interconvertible and exists in equilibrium. For example, keto and enol tautomers exist in proportions determined by the equilibrium position for any given condition, or set of conditions:

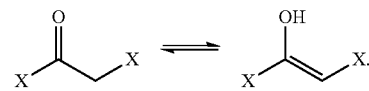

The term "therapeutic agent" is art-recognized and refers to any biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a beneficial local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Compounds

In one aspect, the invention provides novel compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Subject compounds, such as sirtuin-modulating compounds that increase the level and/or activity of a sirtuin protein, may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Compounds disclosed herein may be suitable for use in pharmaceutical compositions and/or one or more methods disclosed herein.

In certain embodiments, compounds of the invention are represented by Structural Formula (I):

The invention includes pharmaceutical compositions of any of the compounds of Structural Formulas (I), (IIa), (IIb), (IIIa), (IIIb), and (IV) or as otherwise set forth above. The pharmaceutical composition of the compound of Structural Formulas I), (IIa), (IIb), (IIIa), (IIIb), and (IV) may comprise one or more pharmaceutically acceptable carriers or diluents.

In one embodiment, sirtuin-modulating compounds of the invention are represented by Structural Formula (I):

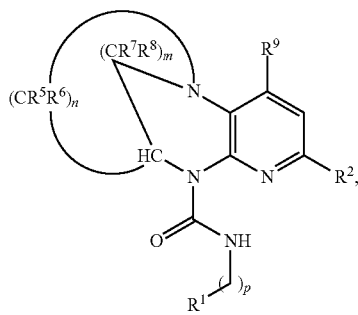

(I)

or a salt thereof wherein:
m is 1 or 2;
n is 2 or 3;
p is 0 to 4;
$R^1$ is selected from a carbocycle and heterocycle, wherein $R^1$ is optionally substituted with one or more substituents independently selected from halo, $C_1$-$C_4$ alkyl, fluoro-substituted $C_1$-$C_4$ alkyl, —C≡N, —Y, —X—C(=O)—Y, —X—O—Y, —X—OR$^4$, —X—C(=O)—NR$^3$R$^3$, —X—NH—C(=O)—Y—NR$^3$R$^3$, —X—NH—C(=O)—O—Y, —X—NR$^3$R$^3$, =O, —NH—S(=O)$_2$—R$_3$, —S(=O)$_2$—R$^3$, —S—R$^3$, —(C$_3$-C$_7$) cycloalkyl, —C(=N)—NR$^3$R$^3$, —C(=N)—NH—X—NR$^3$R$^3$, —X—NH—C(=O)—Y, —C(=O)—NH—X, —NH—X, phenyl, —O-phenyl, 3- to 6-membered saturated or unsaturated heterocycle and —O-(5- to 6-membered saturated heterocycle), wherein any phenyl, 3- to 6-membered saturated or unsaturated heterocycle or —O-5- to 6-membered saturated heterocycle substituent of $R^1$ is optionally substituted at any substitutable carbon atom with one or more substituents selected from halo, —OR$^4$, —X—O—Y, —CF$_3$, —Y, —X—R$^3$R$^3$, —X—NH—C(=O)—Y—NR$^3$R$^3$, —X—NH—C(=O)—O—Y-(5- to 6-membered saturated heterocycle or carbocycle), —X—C(=N)—NR$^3$R$^3$ and —S—Y and optionally substituted at any substitutable nitrogen atom with —Y, —C(=O)—Y, —C(=O)—O—Y, —C(=O)—OR$^4$, —Y—C(=O)—Y—NR$^3$R$^3$, —Y—NH—C(=O)—O—Y, —Y—NH—C(=O)—OR$^4$, —Y—NH$_2$, —C(=O)—NH—Y or —C(=O)-3- to 5-membered saturated carbocycle;

$R^2$ is selected from a carbocycle and a heterocycle, wherein $R^2$ is optionally substituted with one or more substituents independently selected from halo, $C_1$-$C_4$ alkyl, fluoro-substituted $C_1$-$C_4$ alkyl, —C≡N, —Y, —X—OR$^4$, —X—O—Y, —SO$_2$—R$^3$, —X—NR$^3$R$^3$, —NH—S(=O)$_2$R$^3$, —C(=O)—NR$^3$R$^3$, —C(=O)—Y, —C(=O)—O—Y, —SO$_2$—R$_y$, —SO$_2$—NH—R$_y$, —SO$_2$—NR$^3$R$^3$, 3- to 6-membered saturated carbocycle or heterocycle and phenyl, wherein any 3- to 6-membered saturated heterocycle substituent of $R^2$ is optionally substituted at any carbon atom with one or more substituents selected from halo, —CF$_3$, —Y, —X—O—Y, —NH—Y and —N(Y)$_2$, and is optionally substituted at any nitrogen atom with one or more substituents selected from —C(=O)—O—Y, —Y and —C(=O)—Y, and when $R^2$ is an N-linked 5- to 7-membered saturated or unsaturated heterocycle it is further substituted at any nitrogen atom with one or more substituents selected from —C(=O)—O—Y, —Y and —C(=O)—Y;

each $R^3$ is independently selected from hydrogen, —C(=N)—NH$_2$, —C(=O)—Y, —Y, —Y—NH—C(=O)—O—Y, —Y—NH—C(=O)—OH, —Y—NH—C(=O)—CF$_3$, —C(=O)—Y-3- to 5-membered saturated heterocycle, —C(=O)—O—Y-(3- to 5-membered saturated heterocycle), —C(=O)—CF$_3$, —C(=O)—O—Y, —C(=O)—OH, —C(=O)—O—CF$_3$, —S(=O)$_2$—Y, —S(=O)$_2$—OH;

two $R^3$ are taken together with the nitrogen or carbon atom to which they are bound to form a 4- to 8-membered saturated heterocycle optionally comprising one additional heteroatom selected independently from N, S, S(=O), S(=O)$_2$, and O, wherein the heterocycle formed by two $R^3$ is optionally substituted at any carbon atom with one or more of OH, halo, Y, NH$_2$, NH—Y, N(Y)$_2$, O—Y, and optionally substituted at any substitutable nitrogen atom with C(=O)—O—Y, Y or C(=O)—Y;

each $R^4$ is independently selected from hydrogen, Y, —CF$_3$, —C(=O)—Y, —C(=O)—O—Y, —Y—C(=O)—Y or —Y—C(=O)—O—Y;

$R^5$ and $R^6$ are independently selected from hydrogen, —OH, —OCF$_3$, —O—Y, —O—C(=O)—Y, —O—C(=O)—O—Y, —O—C(=O)—NH—Y, —O—C(=O)—N(Y)$_2$, —O—C(=O)-5- to 6-membered saturated or unsaturated heterocycle or carbocycle, wherein only one of $R^5$ and $R^6$ is O—C(=O)-5- to 6-membered saturated or unsaturated heterocycle or carbocycle, and when $R^5$ or $R^6$ is O—C(=O)-5- to 6-membered saturated or unsaturated heterocycle or carbocycle it is further substituted with halo, —OH, Y, —O—Y, —OCF$_3$ or —O—C(=O)—Y; or R$^5$ and R$^6$ can be taken together to the carbon atom to which they are bound to form =O;

R$^7$ and R$^8$ are independently selected from hydrogen, halo, —OH, —O—Y and Y;

R$^9$ is selected from hydrogen, halo, —OH, —OCF$_3$, —O—Y, Y, —O—C(=O)—Y, —NH—Y and —N(Y)$_2$;

each X is C$_0$-C$_5$ straight chain or branched alkyl, alkenyl or alkynyl; and each Y is C$_1$-C$_5$ straight chain or branched alkyl, alkenyl or alkynyl;

wherein any Y or X is optionally substituted with one or more of —OH, —C$_1$-C$_4$ straight chain or branched alkyl, —C$_1$-C$_4$ alkene, —C$_1$-C$_4$ alkynyl, —O—(C$_1$-C$_4$ alkyl), —O—(C$_1$-C$_4$ alkene), —O—(C$_1$-C$_4$ alkynyl), —C(=O)—C$_1$-C$_4$ straight chain or branched alkyl, —C(=O)—C$_1$-C$_4$ alkene, —C(=O)—C$_1$-C$_4$ alkynyl, —C(=O)—O—C$_1$-C$_4$ straight chain or branched alkyl, —C(=O)—O—C$_1$-C$_4$ alkene, —C(=O)—O—C$_1$-C$_4$ alkynyl, halo, —NH$_2$, —NH(C$_1$-C$_4$ alkyl), —N(C$_1$-C$_4$ alkyl)$_2$, —(C$_1$-C$_3$ straight chain or branched alkyl)-NH—(=NH)—NH$_2$, —NH(alkoxy-substituted C$_1$-C$_4$ alkyl), —NH(hydroxy-substituted C$_1$-C$_4$ alkyl), —N(alkoxy-substituted C$_1$-C$_4$ alkyl)(hydroxy-substituted C$_1$-C$_4$ alkyl), —N(hydroxy-substituted C$_1$-C$_4$ alkyl)$_2$ or —N(alkoxy-substituted C$_1$-C$_4$ alkyl)$_2$.

In certain embodiments, compounds or salts of Structural Formula (I) are characterized by the structure represented by Structural Formula (IIa):

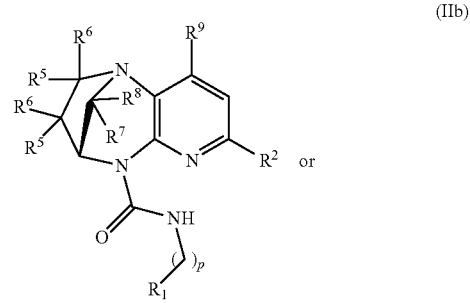

(IIa)

In certain embodiments, compounds or salts of Structural Formula (I) are characterized by the structure represented by Structural Formula (IIIa):

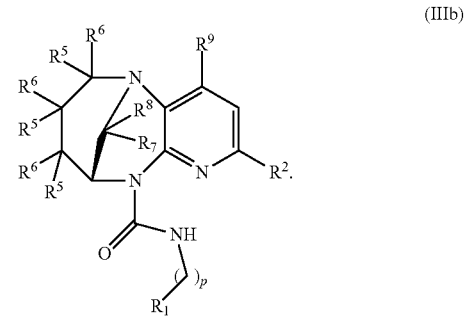

(IIIa)

In certain embodiments, compounds or salts of Structural Formula (I) are characterized by the structure represented by Structural Formulas (IIb) or (IIIb):

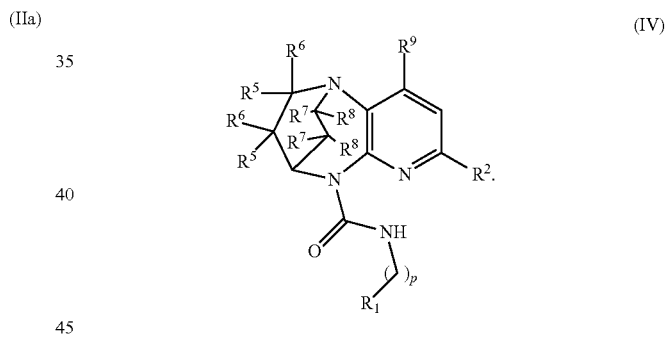

(IIb)

(IIIb)

In certain embodiments, compounds or salts of Structural Formula (I) are characterized by the structure represented by Structural Formula (IV):

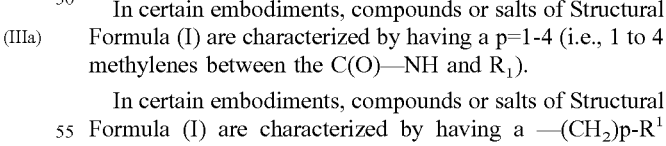

(IV)

In certain embodiments, compounds or salts of Structural Formula (I) are characterized by having a p=0 (i.e., no methylene between the C(O)—NH and R$_1$).

In certain embodiments, compounds or salts of Structural Formula (I) are characterized by having a p=1-4 (i.e., 1 to 4 methylenes between the C(O)—NH and R$_1$).

In certain embodiments, compounds or salts of Structural Formula (I) are characterized by having a —(CH$_2$)p-R$^1$ group selected from:

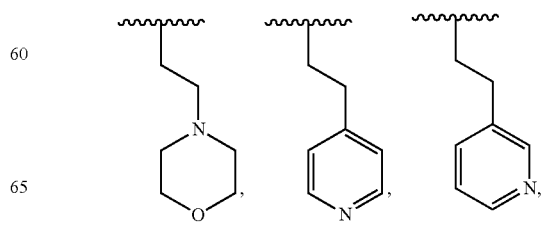

-continued

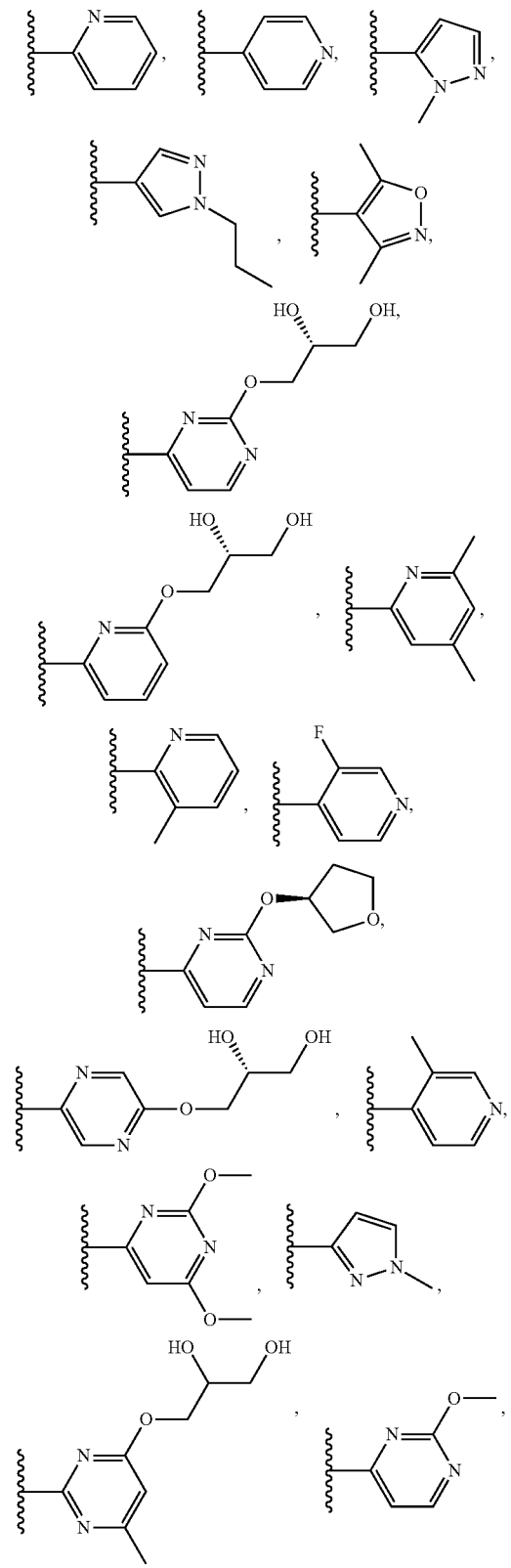

In certain embodiments, compounds or salts of Structural Formula (I) are characterized by an $R^1$ group that is phenyl, a saturated or unsaturated 5- to 6-membered heterocycle, or a fused bicyclic 8- to 11-membered saturated or unsaturated carbocycle or heterocycle.

In particular embodiments, compounds or salts of Structural Formula (I) are characterized by an $R^1$ that is a fused bicyclic 8- to 11-membered saturated or unsaturated heterocycle.

In certain embodiments, compounds or salts of Structural Formula (I) are characterized by an $R^1$ group that is selected from any one of:

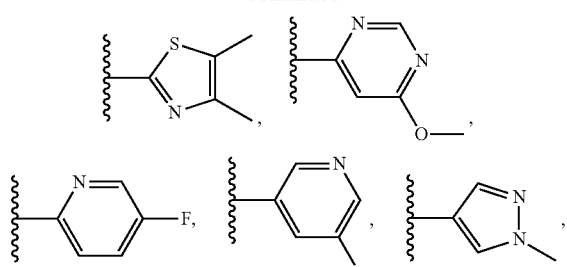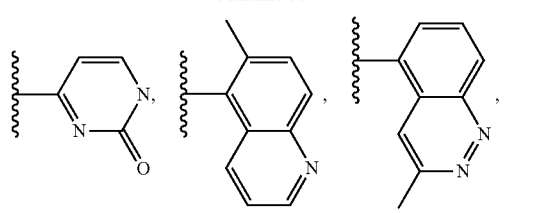

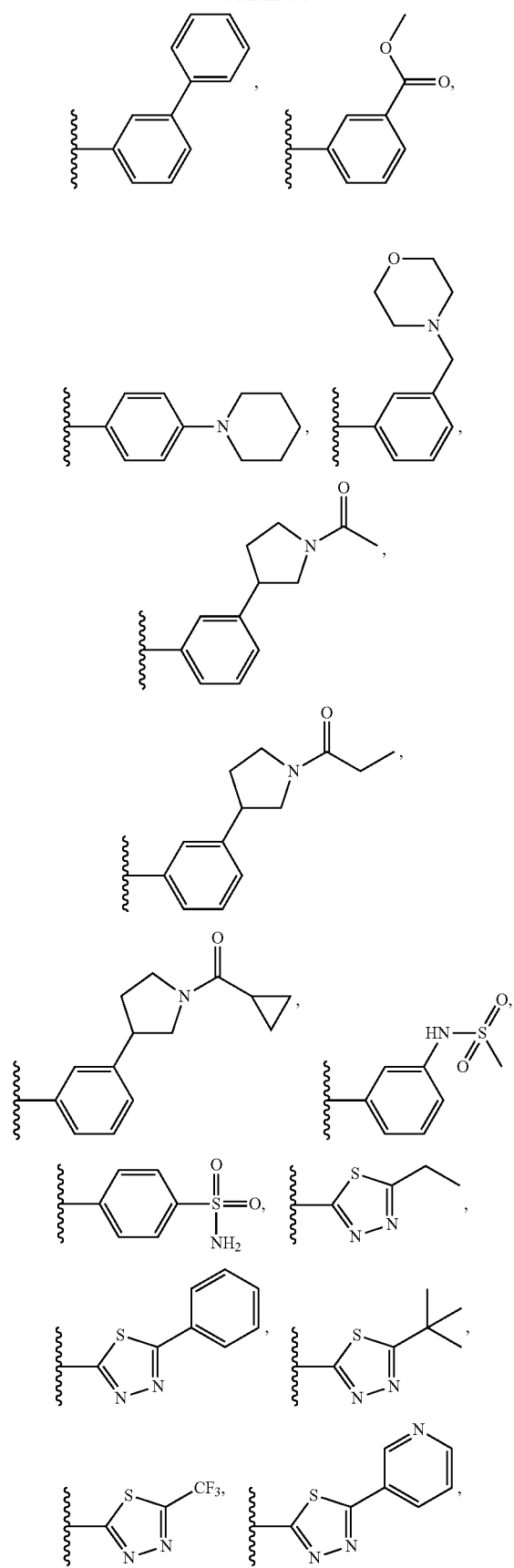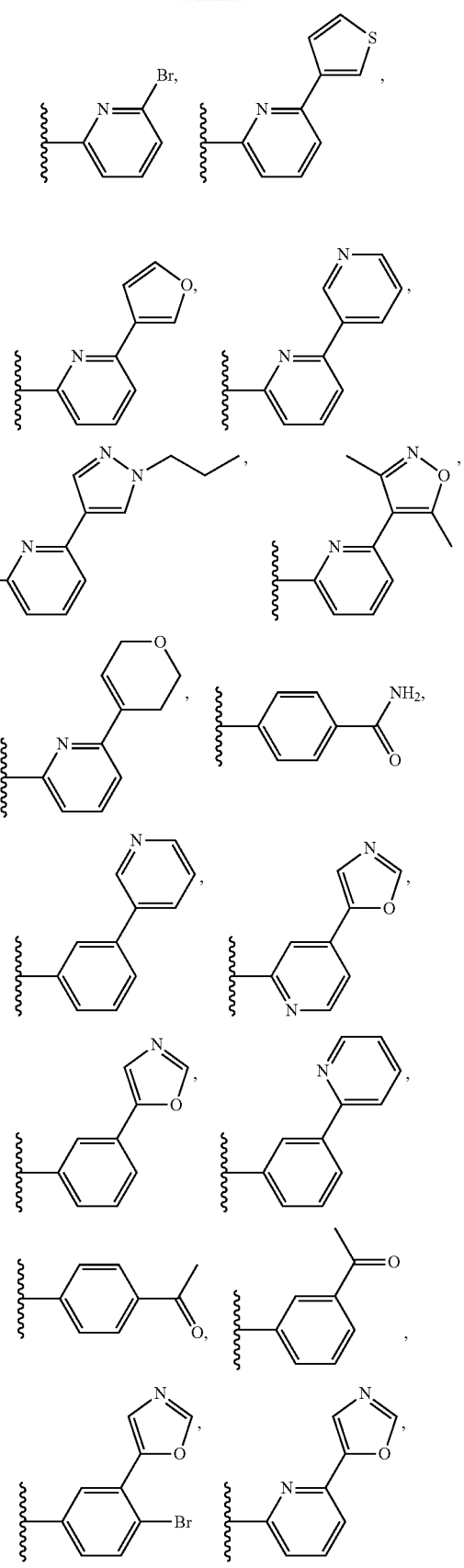

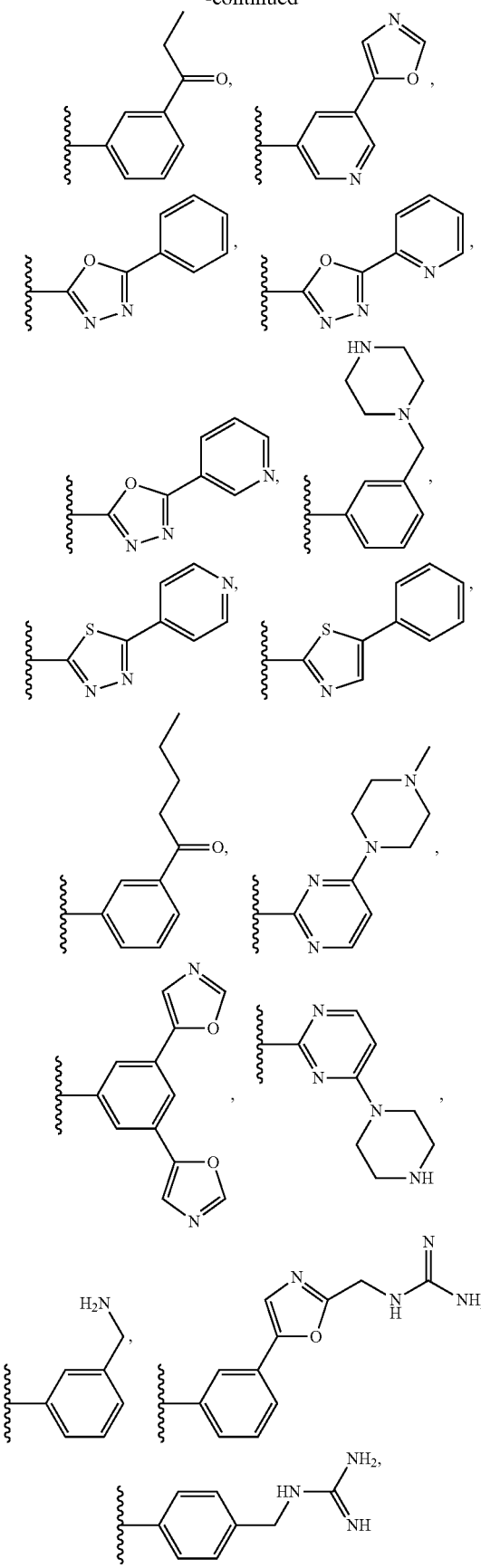
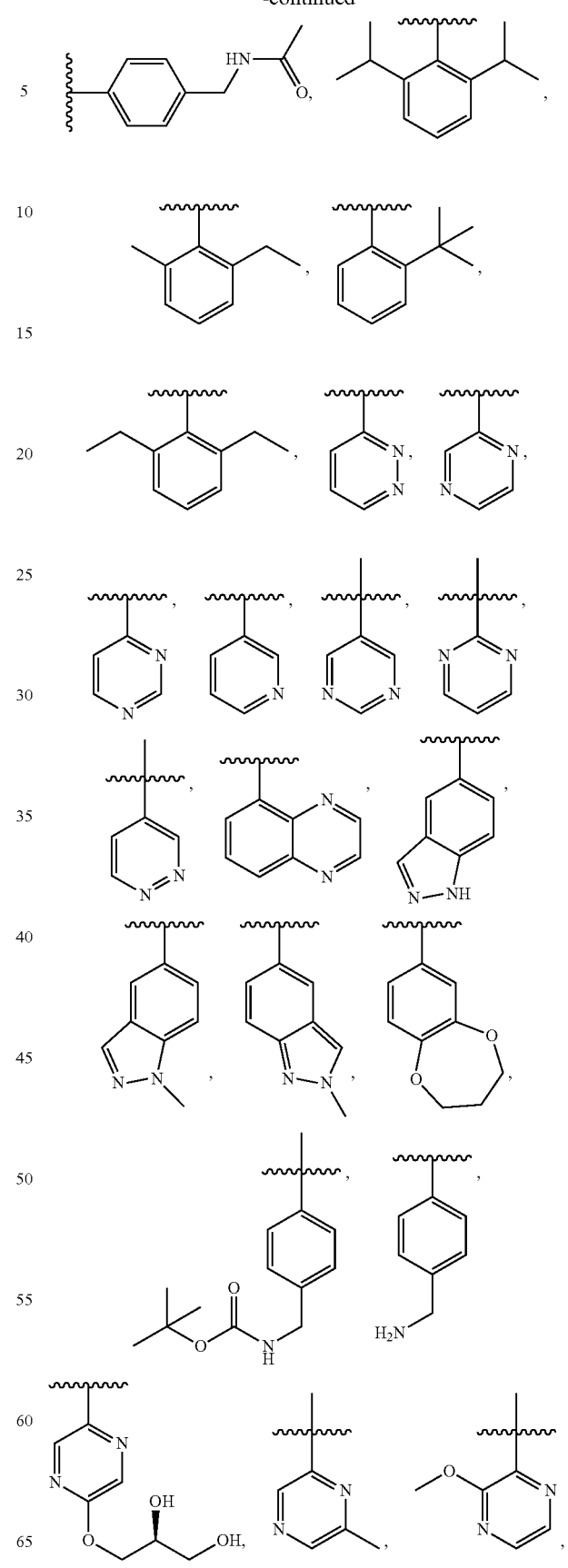

21
-continued
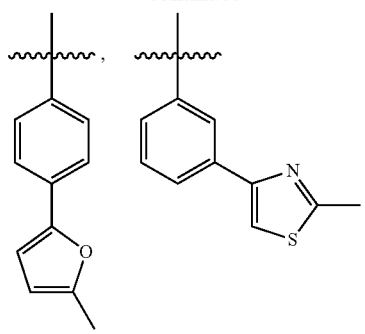
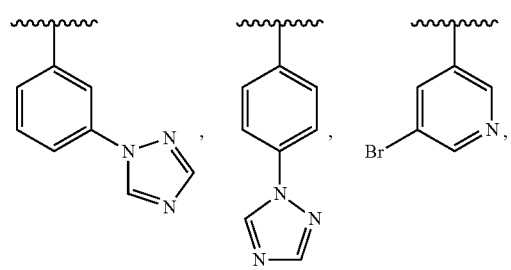
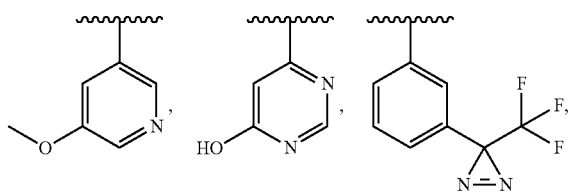
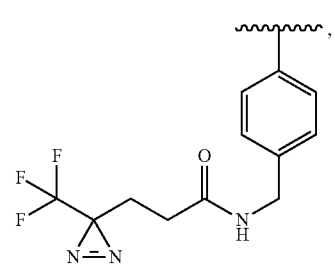
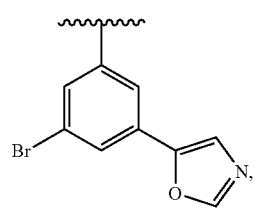
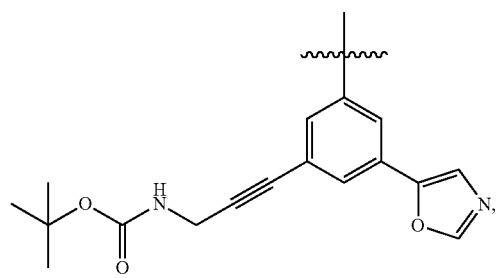
22
-continued
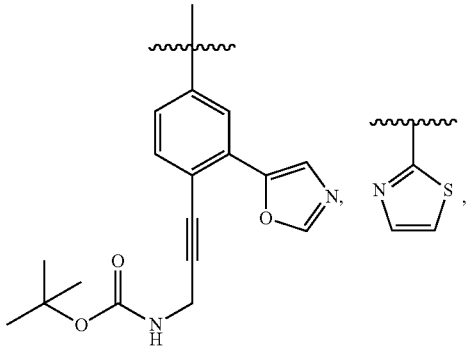
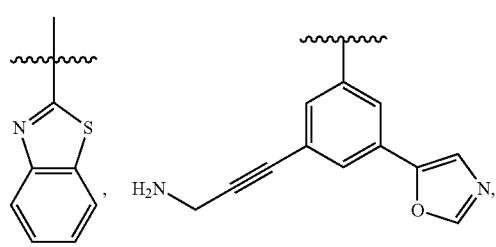
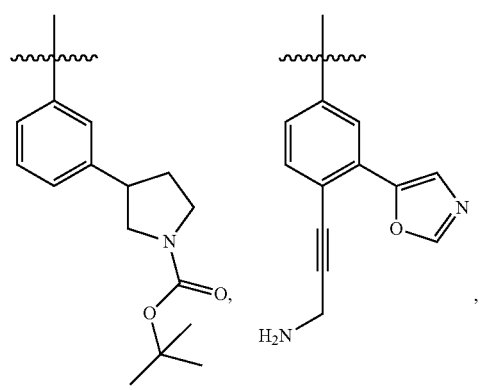
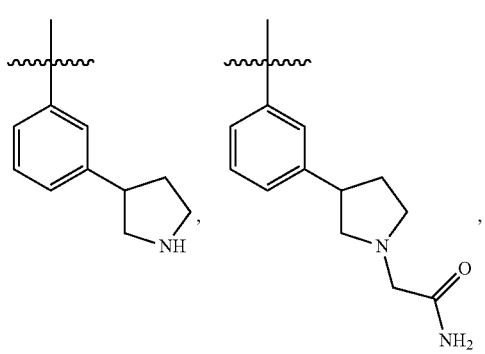
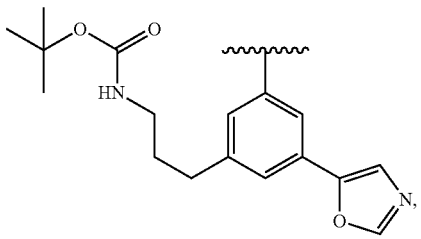

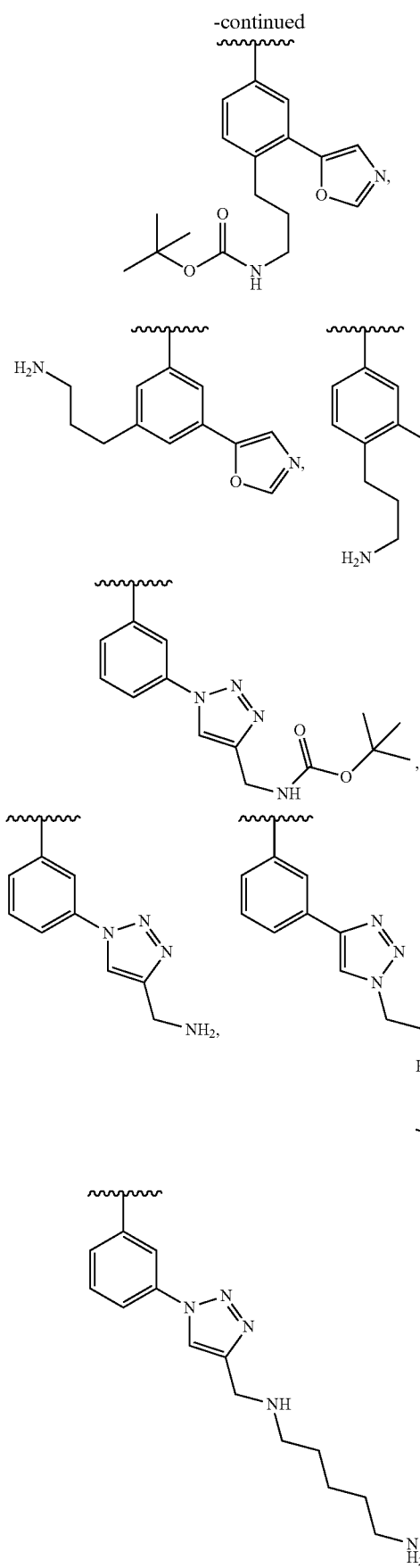
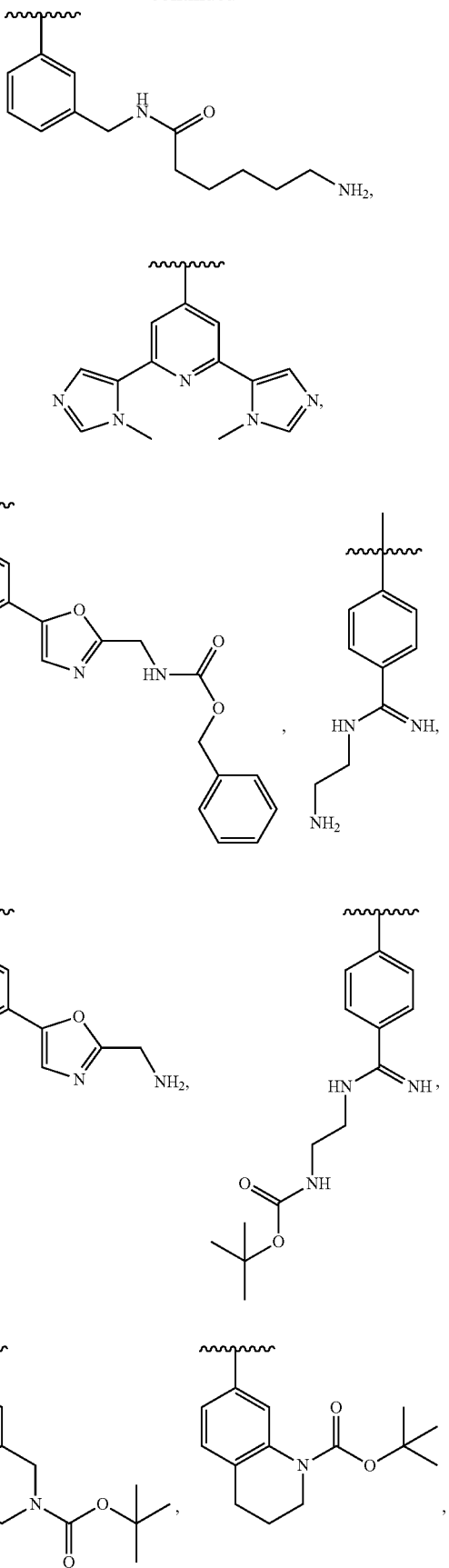

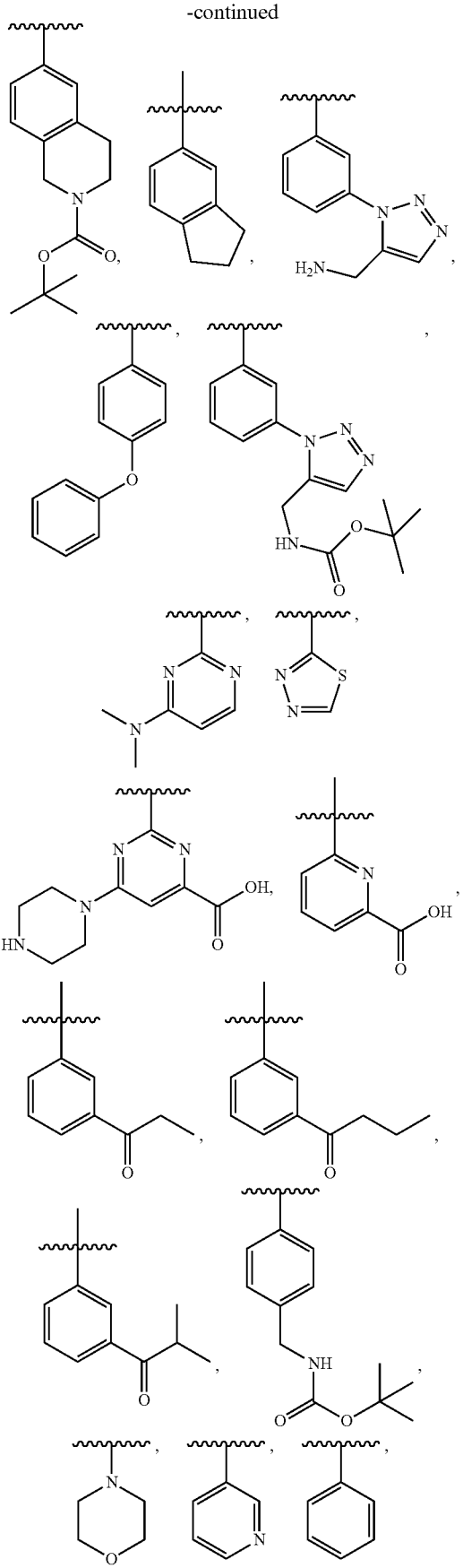

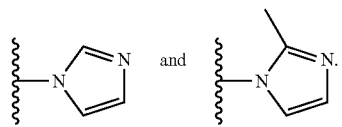

In particular embodiments, compounds or salts of Structural Formula (I) are characterized by an R¹ group that is selected from any one of:

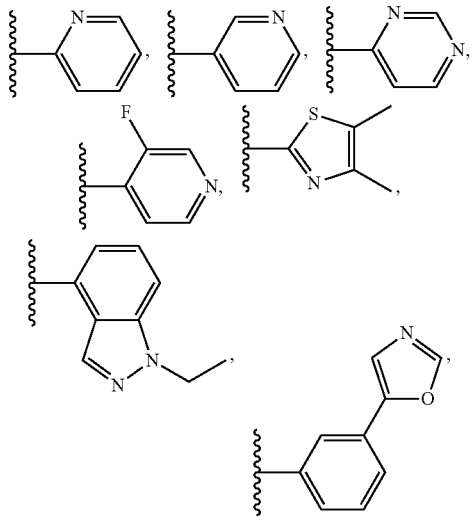

In certain embodiments, compounds or salts of Structural Formula (I) are characterized by an R² group that is selected from a 5- to 7-membered saturated carbocycle or heterocycle, an N-linked heterocycle, and an 8- to 11-membered saturated or unsaturated heterocycle.

In particular embodiments, compounds or salts of Structural Formula (I) are characterized by an R² group that is an N-linked 5- to 7-membered saturated or unsaturated heterocycle.

In certain embodiments of the above, the compound is selected from any one of:

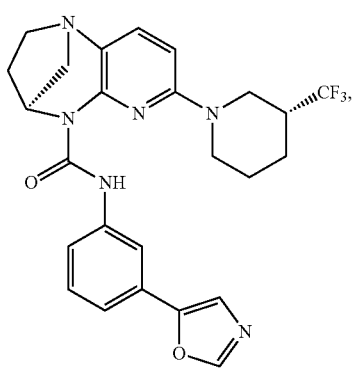

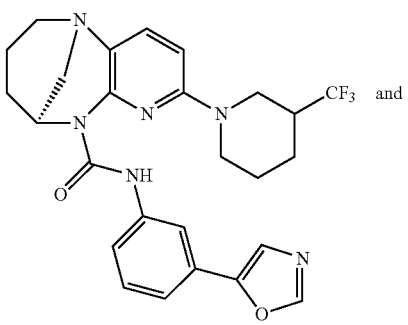

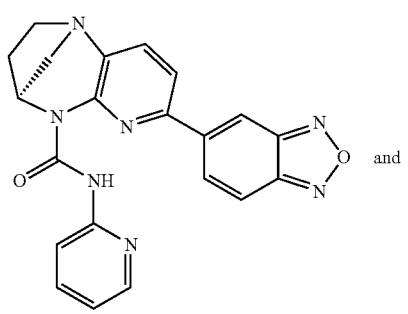

In certain embodiments, compounds or salts of Structural Formula (I) are characterized by an $R^2$ group that is a fused bicyclic 8- to 11-membered saturated or unsaturated heterocycle.

In certain embodiments of the above, the compound is selected from any one of:

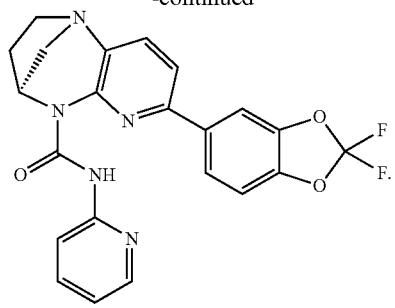

In certain embodiments, compounds or salts of Structural Formula (I) are characterized by an $R^2$ group that is selected from any one of:

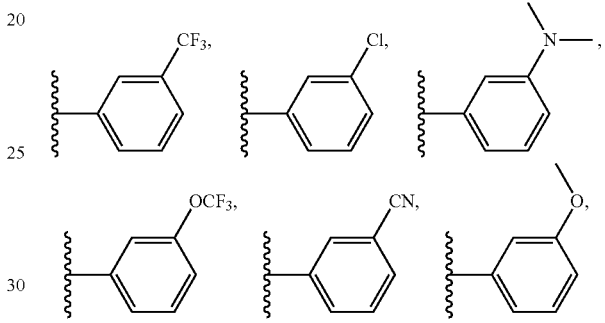

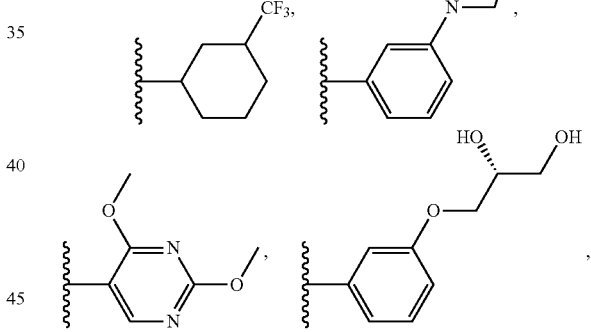

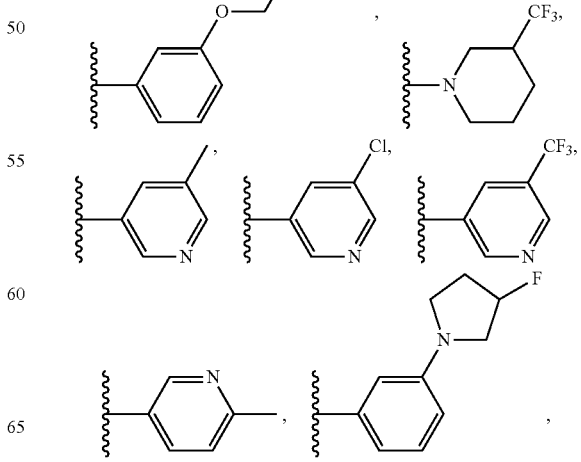

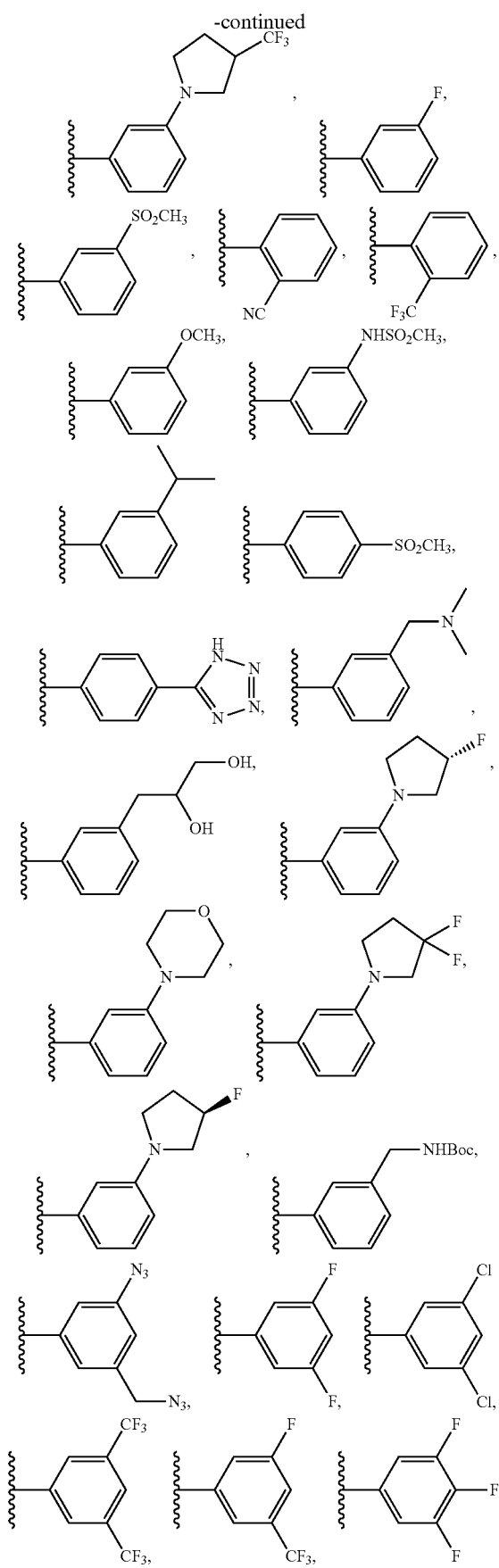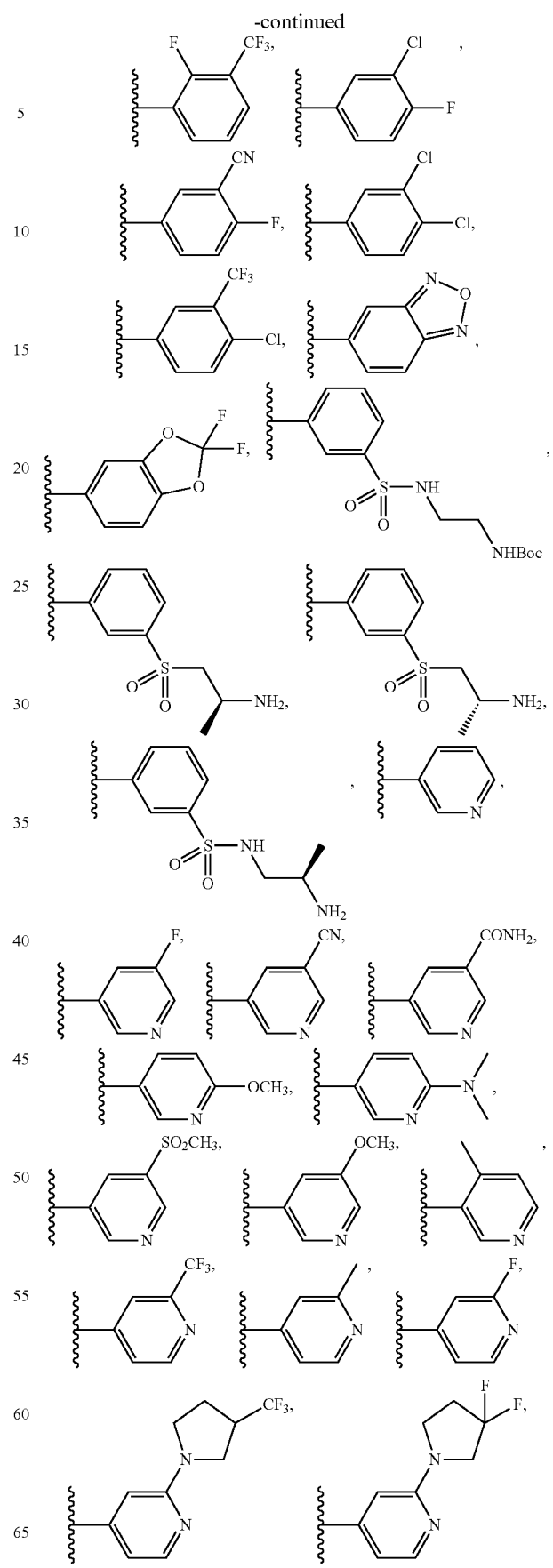

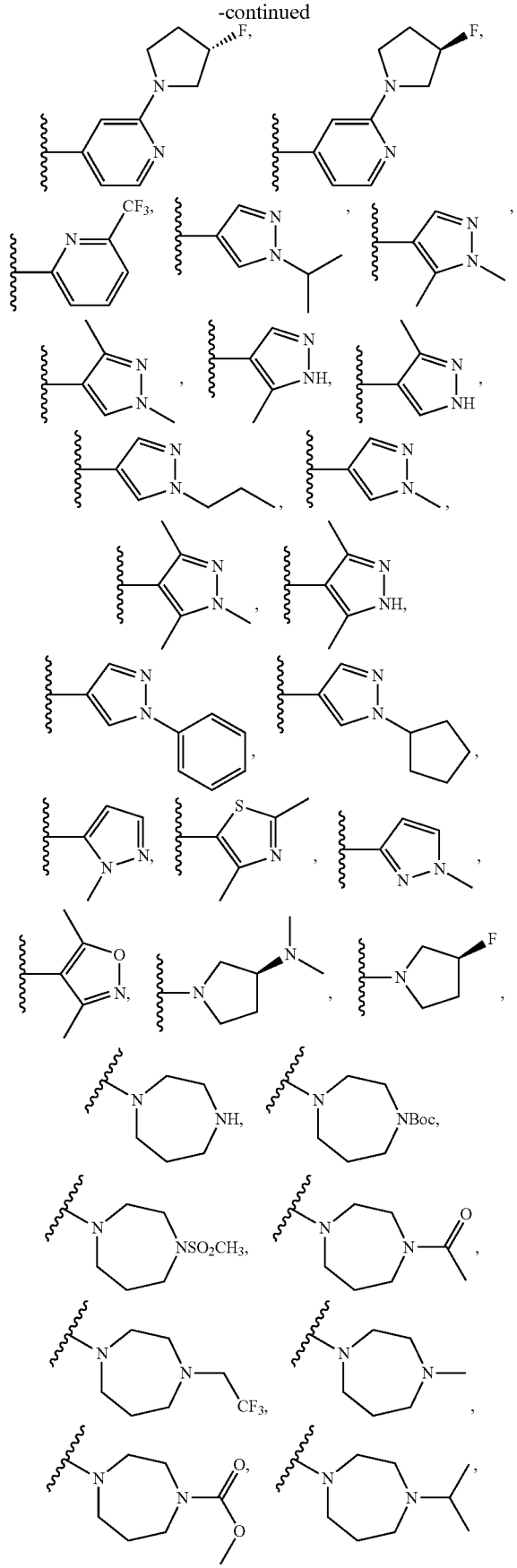
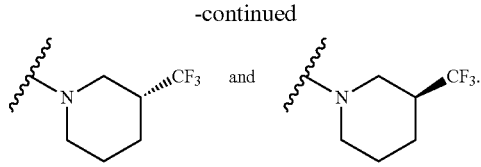
In particular embodiments, compounds or salts of Structural Formula (I) are characterized by an $R^2$ group that is selected from any one of:
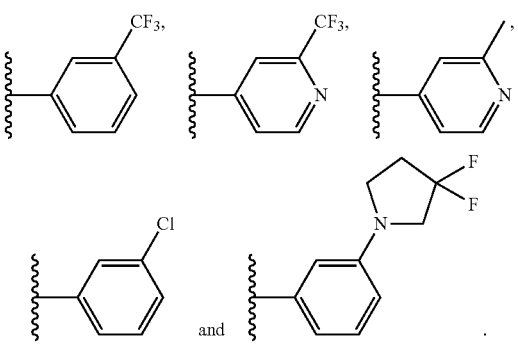
In certain embodiments, compounds or salts of Structural Formula (I) are selected from any one of:
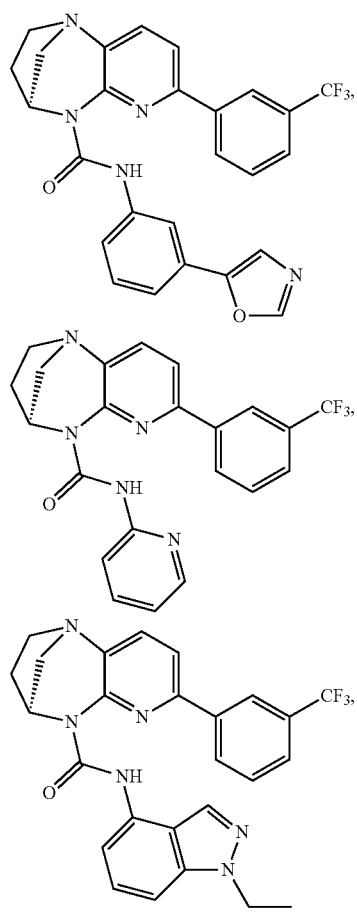

-continued
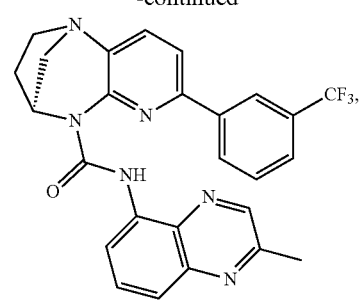
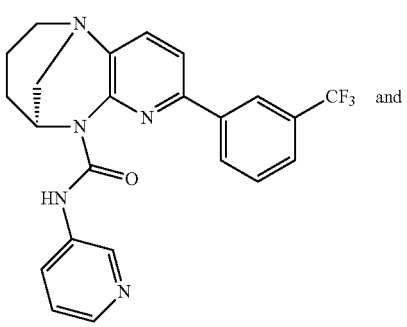
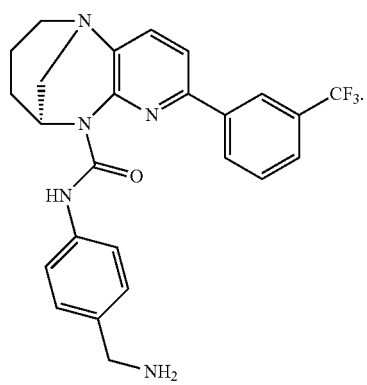 [SMILES: NCc1ccc(NC(=O)N2c3nc(-c4cccc(C(F)(F)F)c4)ccc3N3CCC[C@H]2C3)cc1]
In certain embodiments, compounds or salts of Structural Formula (IIa) are selected from any one of:
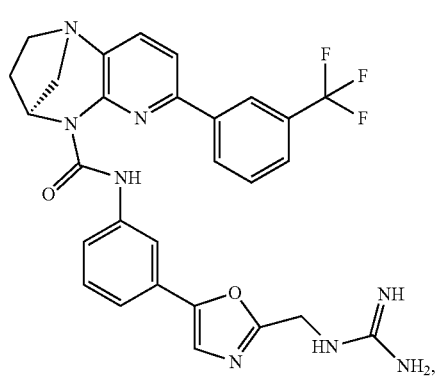
-continued
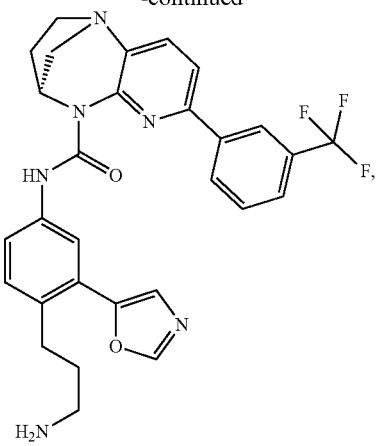
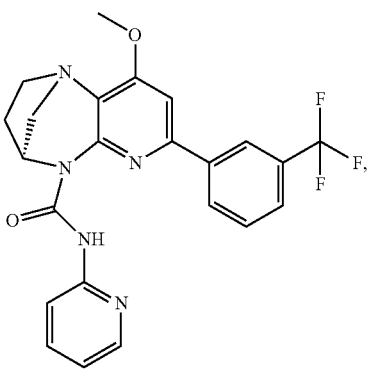
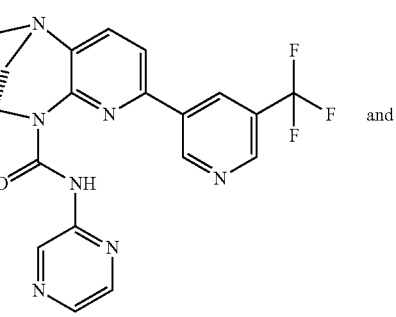 and
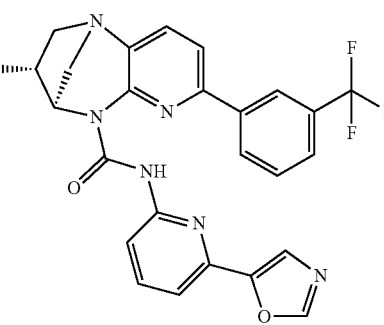
In certain embodiments, compounds or salts of Structural Formula (Ma) are selected from any one of:

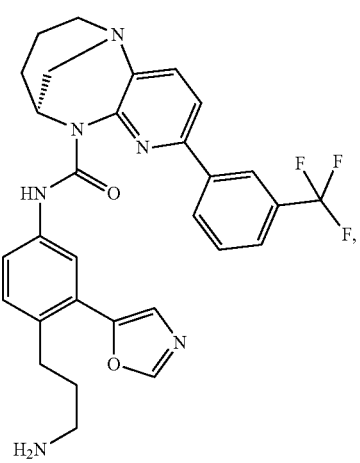
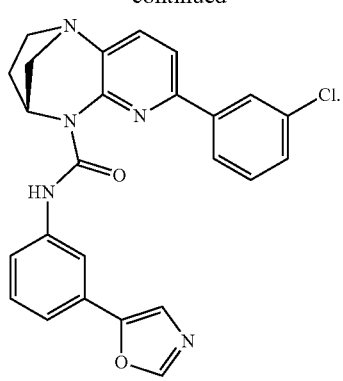
-continued
In certain embodiments, compounds or salts of Structural Formula (IIIb) are selected from:
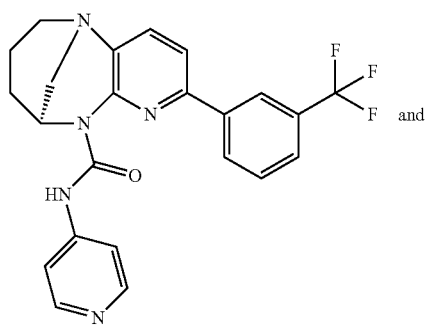
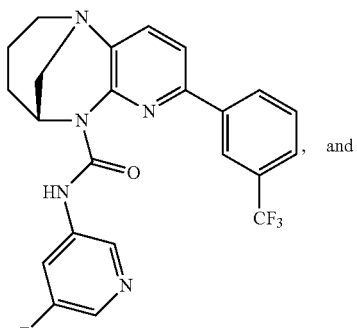
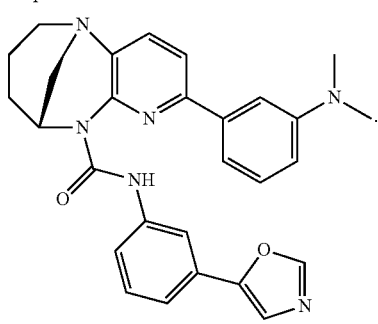
In certain embodiments, compounds or salts of Structural Formula (IV) are selected from any one of:
In certain embodiments, compounds or salts of Structural Formula (IIb) are selected from:
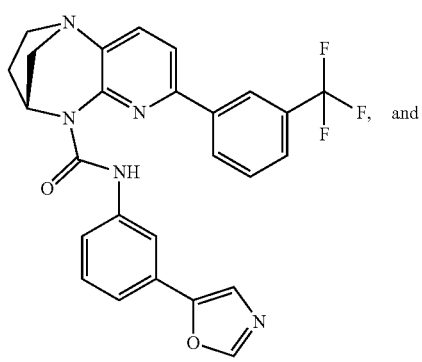
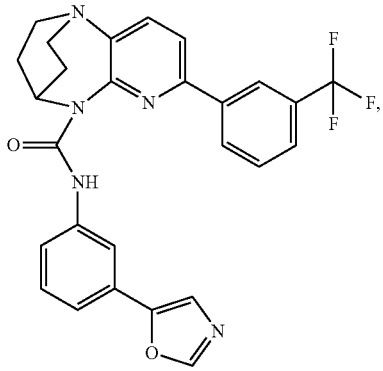

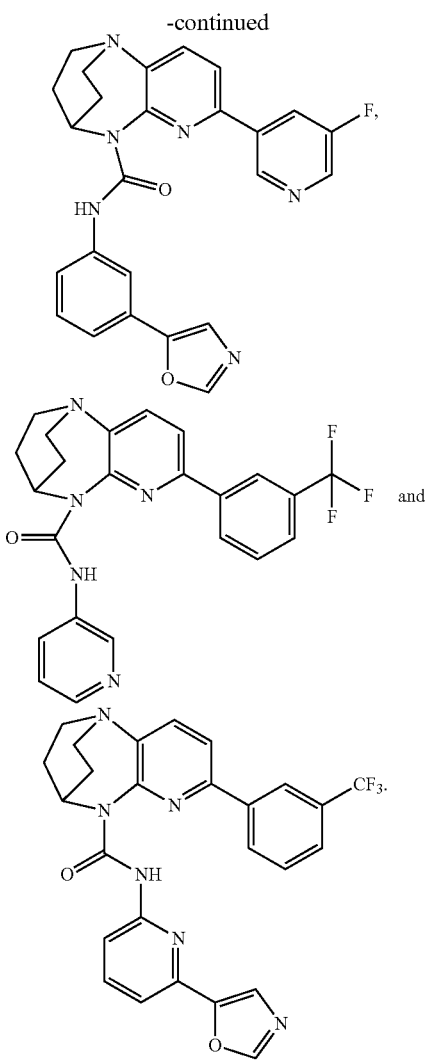

Compounds of the invention, including novel compounds of the invention, can also be used in the pharmaceutical compositions and the methods described herein.

In any of the preceding embodiments, a $C_1$-$C_4$ alkoxy-substituted group may include one or more alkoxy substituents such as one, two or three methoxy groups or a methoxy group and an ethoxy group, for example. Exemplary $C_1$-$C_4$ alkoxy substituents include methoxy, ethoxy, isopropoxy, and tert-butoxy.

In any of the preceding embodiments, a hydroxy-substituted group may include one or more hydroxy substituents, such as two or three hydroxy groups.

In any of the preceding embodiments, a "halo-substituted" group includes from one halo substituent up to perhalo substitution. Exemplary halo-substituted $C_1$-$C_4$ alkyl includes $CFH_2$, $CClH_2$, $CBrH_2$, $CF_2H$, $CCl_2H$, $CBr_2H$, $CF_3$, $CCl_3$, $CBr_3$, $CH_2CH_2F$, $CH_2CH_2Cl$, $CH_2CH_2Br$, $CH_2CHF_2$, $CHFCH_3$, $CHClCH_3$, $CHBrCH_3$, $CF_2CHF_2$, $CF_2CHCl_2$, $CF_2CHBr_2$, $CH(CF_3)_2$, and $C(CF_3)_3$. Perhalo-substituted $C_1$-$C_4$ alkyl, for example, includes $CF_3$, $CCl_3$, $CBr_3$, $CF_2CF_3$, $CCl_2CF_3$ and $CBr_2CF_3$.

In any of the preceding embodiments, a "carbocycle" group may refer to a monocyclic carbocycle embodiment and/or a polycyclic carbocycle embodiment, such as a fused, bridged or bicyclic carbocycle embodiment. "Carbocycle" groups of the invention may further refer to an aromatic carbocycle embodiment and/or a non-aromatic carbocycle embodiment, or, in the case of polycyclic embodiments, a carbocycle having both one or more aromatic rings and/or one or more non-aromatic rings. Polycyclic carbocycle embodiments may be a bicyclic ring, a fused ring or a bridged bicycle. Non-limiting exemplary carbocycles include phenyl, cyclohexane, cyclopentane, or cyclohexene, amantadine, cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, adamantane, decalin, naphthalene, 1,2,3,4-tetrahydronaphthalene, norbornane, decalin, spiropentane, memantine, biperiden, rimantadine, camphor, cholesterol, 4-phenylcycicohexanol, bicyclo[4.2.0]octane, memantine and 4,5,6,7-tetrahydro-1H-indene and bicyclo[4.1.0]hept-3-ene.

In any of the preceding embodiments, a "heterocycle" group may refer to a monocyclic heterocycle embodiment and/or a polycyclic heterocycle embodiment, such as a fused, bridged or bicyclic heterocycle embodiment. "Heterocycle" groups of the invention may further refer to an aromatic heterocycle embodiment and/or a non-aromatic heterocycle embodiment, or, in the case of polycyclic embodiments, a heterocycle having both one or more aromatic rings and/or one or more non-aromatic rings. Polycyclic heterocycle embodiments may be a bicyclic ring, a fused ring or a bridged bicycle. Non-limiting exemplary heterocycles include pyridyl, pyrrolidine, piperidine, piperazine, pyrrolidine, morpholine, pyrimidine, benzofuran, indole, quinoline, lactones, lactams, benzodiazepine, indole, quinoline, purine, adenine, guanine, 4,5,6,7-tetrahydrobenzo[d]thiazole, hexamine and methenamine.

Certain compounds of the present invention may exist in particular geometric or stereoisomeric forms. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The compounds and salts thereof described herein can also be present as the corresponding hydrates (e.g., hemihydrate, monohydrate, dihydrate, trihydrate, tetrahydrate) or solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_4$ straight chained or branched alkyl group is also referred to as a "lower alkyl" group.

The terms "alkenyl" ("alkene") and "alkynyl" ("alkyne") refer to unsaturated aliphatic groups analogous in length and possible substitution to the alkyl groups described above, but that contain at least one double or triple bond respectively.

The term "aromatic carbocycle" refers to an aromatic hydrocarbon ring system containing at least one aromatic ring. The ring may be fused or otherwise attached to other aromatic carbocyclic rings or non-aromatic carbocyclic rings. Examples of aromatic carbocycle groups include carbocyclic aromatic groups such as phenyl, naphthyl, and anthracyl.

"Azabicyclo" refers to a bicyclic molecule that contains a nitrogen atom in the ring skeleton. The two rings of the bicycle may be fused at two mutually bonded atoms, e.g., indole, across a sequence of atoms, e.g., azabicyclo[2.2.1] heptane, or joined at a single atom, e.g., spirocycle.

"Bicycle" or "bicyclic" refers to a two-ring system in which one, two or three or more atoms are shared between the two rings. Bicycle includes fused bicycles in which two adjacent atoms are shared by each of the two rings, e.g., decalin, indole. Bicycle also includes spiro bicycles in which two rings share a single atom, e.g., spiro[2.2]pentane, 1-oxa-6-azaspiro[3.4]octane. Bicycle further includes bridged bicycles in which at least three atoms are shared between two rings, e.g., norbornane.

"Bridged bicycle" compounds are bicyclic ring systems in which at least three atoms are shared by both rings of the system, i.e., they include at least one bridge of one or more atoms connecting two bridgehead atoms. Bridged azabicyclo refers to a bridged bicyclic molecule that contains a nitrogen atom in at least one of the rings.

The term "Boc" refers to a tert-butyloxycarbonyl group (a common amine protecting group).

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from non-aromatic and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from non-aromaticaromatic rings. In an exemplary embodiment, an aromatic ring, e.g., phenyl, may be fused to a non-aromatic or aromatic ring, e.g., cyclohexane, cyclopentane, or cyclohexene. Any combination of non-aromatic and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0] oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated (non-aromatic). Typically, a cycloalkyl group has from 3 to about 10 carbon atoms, more typically 3 to 8 carbon atoms unless otherwise defined. A "cycloalkenyl" group is a cyclic hydrocarbon containing one or more double bonds.

A "halogen" designates F, Cl, Br or I.

A "halogen-substitution" or "halo" substitution designates replacement of one or more hydrogens with F, Cl, Br or I.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocyclyl. Heteroaryl groups include, for example, pyrrole, furan, thiophene, imidazole, oxazole, thiazole, pyrazole, pyridine, pyrazine, pyridazine, and pyrimidine.

The terms "heterocycle", and "heterocyclic", as used herein, refers to a non-aromatic or aromatic ring comprising one or more heteroatoms selected from, for example, N, O, B and S atoms, preferably N, O, or S. The term "heterocycle" includes both "aromatic heterocycles" and "non-aromatic heterocycles." Heterocycles include 4-7 membered monocyclic and 8-U membered bicyclic rings. Heterocycle includes bicyclic molecules in which one, two or three or more atoms are shared between the two rings. Each ring of a bicyclic heterocycle may be selected from non-aromatic and aromatic rings. The term "fused heterocycle" refers to a bicyclic heterocycle in which each of the rings shares two adjacent atoms with the other ring. Each ring of a fused heterocycle may be selected from non-aromatic and aromatic rings. In an exemplary embodiment, an aromatic ring, e.g., pyridyl, may be fused to a non-aromatic or aromatic ring, e.g., cyclohexane, cyclopentane, pyrrolidine, 2,3-dihydrofuran or cyclohexene. "Heterocycle" groups include, for example, piperidine, piperazine, pyrrolidine, morpholine, pyrimidine, benzofuran, indole, quinoline, lactones, and lactams. Exemplary "fused heterocycles" include benzodiazepine, indole, quinoline, purine, and 4,5,6,7-tetrahydrobenzo[d]thiazole. "Heterocycles" may be substituted at any one or more positions capable of bearing a hydrogen atom.

"Monocyclic rings" include 5-7 membered aromatic carbocycle or heteroaryl, 3-7 membered cycloalkyl or cycloalkenyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

As used herein, "substituted" means substituting a hydrogen atom in a structure with an atom or molecule other than hydrogen. A substitutable atom such as a "substitutable nitrogen" is an atom that bears a hydrogen atom in at least one resonance form. The hydrogen atom may be substituted for another atom or group such as a $CH_3$ or an OH group. For example, the nitrogen in a piperidine molecule is substitutable if the nitrogen is bound to a hydrogen atom. If, for example, the nitrogen of a piperidine is bound to an atom other than hydrogen, the nitrogen is not substitutable. An atom that is not capable of bearing a hydrogen atom in any resonance form is not substitutable.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. In certain embodiments, deuterated variants may be used for kinetic studies. One of skill in the art can select the sites at which such deuterium atoms are present.

Also included in the present invention are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In an exemplary embodiment, a therapeutic compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

In certain embodiments, a sirtuin-modulating compound does not have any substantial ability to inhibit a histone deacetylase (HDAC) class I, and/or an HDAC class II at concentrations (e.g., in vivo) effective for modulating the deacetylase activity of the sirtuin. For instance, in preferred embodiments, the sirtuin-modulating compound is a sirtuin-modulating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In certain embodiments, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-modulating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida, S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In some embodiments, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In some embodiments, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In some embodiments, a SIRT3 modulator does not have any substantial ability to modulate a SIRT1 protein.

In certain embodiments, a sirtuin-modulating compound may have a binding affinity for a sirtuin protein of about $10^{-9}$M, $10^{-10}$M, $10^{-11}$M, $10^{-12}$M or less. A sirtuin-modulating compound may reduce (activator) or increase (inhibitor) the apparent Km of a sirtuin protein for its substrate or $NAD^+$ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an $ED_{50}$ for modulating the deacetylase activity of a SIRT1 and/or SIRT3 protein of less than about 1 nM, less than about 10 nM, less than about 100 nM, less than about 1 μM, less than about 10 μM, less than about 100 μM, or from about 1-10 nM, from about 10-100 nM, from about 0.1-1 μM, from about 1-10 μM or from about 10-100 μM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-modulating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an $ED_{50}$ for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-modulating compound.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In certain embodiments, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid or nicotinamide riboside. In another embodiment, a sirtuin-modulating compound that decreases the level and/or activity of a sirtuin protein may be administered with one or more of the following compounds: nicotinamide (NAM), suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4', 5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8, 3',4'-hexahydroxyflavone), sirtinol; and splitomicin. In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the compound(s) and other therapeutic agent(s) are in separate vessels). When using separate formulations, the sirtuin-modulating compound may be administered simultaneous with, intermittent with, staggered with, prior to, subsequent to, or combinations thereof, the administration of another therapeutic agent.

In certain embodiments, methods for reducing, preventing or treating diseases or disorders using a compound described herein may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one aspect, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-modulating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one aspect, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another aspect, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In certain embodiments, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In certain embodiments, a sirtuin-modulating compound that increases the level and/or activity of a sirtuin protein may be administered as part of a combination therapy with another cardiovascular agent. In certain embodiments, a sirtuin-modulating compound that increases the level and/or activity of a sirtuin protein may be administered as part of a combination therapy with an anti-arrhythmia agent. In another embodiment, a sirtuin-modulating compound that increases the level and/or activity of a sirtuin protein may be administered as part of a combination therapy with another cardiovascular agent.

Cell Death/Cancer

Sirtuin-modulating compounds that increase the level and/or activity of a sirtuin protein may be administered to subjects who have recently received or are likely to receive a dose of radiation or toxin. In certain embodiments, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine.

ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin-modulating compound may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In certain embodiments, apoptotic or necrotic cell death may be prevented. In still a further embodiment, ischemic-mediated damage, such as cytotoxic edema or central nervous system tissue anoxemia, may be prevented. In each embodiment, the central nervous system cell may be a spinal cell or a brain cell.

Another aspect encompasses administrating a sirtuin-modulating compound to a subject to treat a central nervous system ischemic condition. A number of central nervous system ischemic conditions may be treated by the sirtuin-modulating compounds described herein. In certain embodiments, the ischemic condition is a stroke that results in any type of ischemic central nervous system damage, such as apoptotic or necrotic cell death, cytotoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin-modulating compound may be administered to reduce infarct size of the ischemic core following a central nervous system ischemic condition. Moreover, a sirtuin-modulating compound may also be beneficially administered to reduce the size of the ischemic penumbra or transitional zone following a central nervous system ischemic condition.

In certain embodiments, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compound that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In certain embodiments, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g., Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g., *Candida* choroiditis, histoplasmosis), protozoal infections (e.g., toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, or a drug that raises intraocular pressure, such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In certain embodiments, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In certain embodiments, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In certain embodiments, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin-modulating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetics, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more sirtuin-modulating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of a sirtuin-modulating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin-modulating compounds may be used for reducing the rate of decline in muscular functional capacities and for improving muscular functional status in patients with muscular dystrophy.

In certain embodiments, sirtuin-modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin-modulating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin-modulating compounds may be useful for treating diseases or disorders associated with mitochondrial deregulation.

Muscle Performance

In other embodiments, the invention provides methods for enhancing muscle performance by administering a therapeutically effective amount of a sirtuin-modulating compound. For example, sirtuin-modulating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin-modulating compound that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In certain embodiments, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In certain embodiments, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

In another embodiment, the screening assay may detect the formation of a 2'/3'-O-acetyl-ADP-ribose product of sirtuin-mediated NAD-dependent deacetylation. This 0-acetyl-ADP-ribose product is formed in equimolar quantities with the deacetylated peptide product of the sirtuin deacetylation reaction. Accordingly, the screening assay may include (i) contacting a sirtuin with a test agent and an acetylated substrate under conditions appropriate for the sirtuin to deacetylate the substrate in the absence of the test agent; and (ii) determining the amount of O-acetyl-ADP-ribose formation, wherein an increase in O-acetyl-ADP-ribose formation in the presence of the test agent relative to the absence of the test agent indicates that the test agent stimulates deacetylation by the sirtuin, while a decrease in O-acetyl-ADP-ribose formation in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 μM to about 10 mM, preferably from about 10 μM to 1 mM, even more preferably from about 100 μM to 1 mM, such as about 200 μM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 μM, preferably from about 0.1 to 10 μM, such as 1 μM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The compounds described herein may be formulated in a conventional manner using one or more physiologically or pharmaceutically acceptable carriers or excipients. For example, compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, a compound may be administered locally, at the site where the target cells are present, i.e., in a specific tissue, organ, or fluid (e.g., blood, cerebrospinal fluid, etc.).

The compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection. Thus, for example, compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well known by those skilled in the art. Liposomes can be formed from a variety of phospholipids, such as cholesterol, stearylamine of phosphatidylcholines. Liposomes usable for the method of invention encompass all types of liposomes including, but not limited to, small unilamellar vesicles, large unilamellar vesicles and multilamellar vesicles.

Another way to produce a formulation, particularly a solution, of a compound described herein, is through the use of cyclodextrin. By cyclodextrin is meant α-, β-, or γ-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In some embodiments, a compound described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

The compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

The compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

The compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

The compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

The compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a compound, or by insertion of a sustained release device that releases a compound. A compound may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

The compounds described herein may be stored in oxygen free environment. For example, a composition can be prepared in an airtight capsule for oral administration, such as Capsugel from Pfizer, Inc.

Cells, e.g., treated ex vivo with a compound as described herein, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more compounds as described herein, e.g., in premeasured doses. A kit may optionally comprise devices for contacting cells with the compounds and instructions for use. Devices include syringes, stents and other devices for introducing a compound into a subject (e.g., the blood vessel of a subject) or applying it to the skin of a subject.

In yet another embodiment, the invention provides a composition of matter comprising a compound of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The compound and the other agent are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a compound of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2$^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

Example 1. Preparation of (4S)—N-(pyridin-2-yl)-7-(3-(trifluoromethyl)phenyl)-3,4-dihydro-1,4-methanopyrido[2,3-b][1,4]diazepine-5-(2H)-carboxamide Step 1. Synthesis of (S)-dimethyl 2-((6-chloro-3-nitropyridin-2-yl)amino)succinate

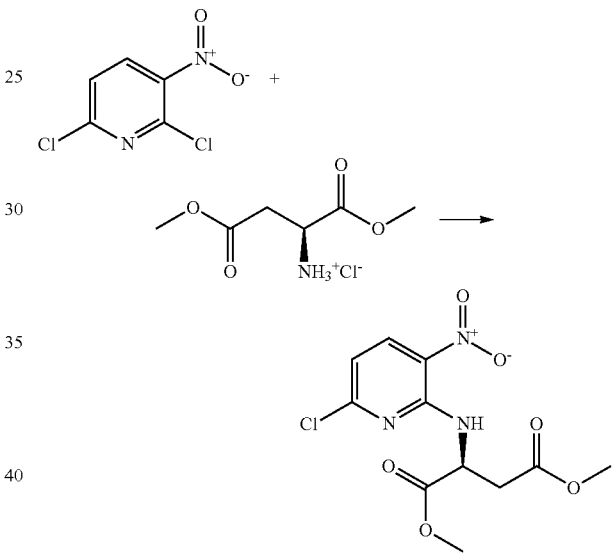

To a 2 L flask equipped with a thermometer, a reflux condenser, and a mechanical stirrer was added (100 g, 0.52 mol) of 2,6-dichloro-3-nitropyridine (205 g, 1.04 mol) of (S)-aspartic acid dimethyl ester hydrochloride (174 g, 2.07 mol) of NaHCO$_3$ and 1 L of tetrahydrofuran. The reaction was stirred at 40° C. for 16 h, and was monitored for the disappearance of 2,6-dichloropyridine by HPLC. After the reaction was complete, the solids were filtered away and washed with ethyl acetate (3×300 mL). The combined filtrate and washings were concentrated to dryness, and the residue was taken up in 1 L of ethyl acetate. The solution was stirred with 200 g of charcoal at ambient temperature for 2 h, and the charcoal was filtered away and washed with additional ethyl acetate (3×200 mL). The combined filtrate and washings were concentrated in vacuo to give the crude product (S)-dimethyl 2-((6-chloro-3-nitropyridin-2-yl)amino)succinate (180 g) as a yellow oil. This was used in the next step without further purification. MS (ESI) calcd for $C_{11}H_{12}ClN_3O_6$: 317.0. found: 318.0 (M+H)$^+$.

An analogous procedure could be used to prepare (R)-dimethyl 2-((6-chloro-3-nitropyridin-2-yl)amino)succinate by starting with (R)-aspartic acid dimethyl ester hydrochloride.

Step 2. Synthesis of (S)-methyl 2-(6-chloro-2-oxo-1,2,3,4-tetrahydropyrido[2,3-b]pyrazin-3-yl)acetate

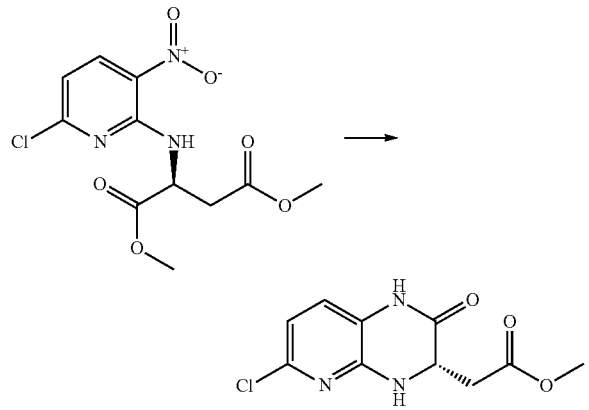

A 5 L three necked flask equipped with a thermometer, a reflux condenser, and a mechanical stirrer was charged with crude (S)-dimethyl 2-((6-chloro-3-nitropyridin-2-yl)amino) succinate (180 g, 0.52 mol) of iron powder (146 g, 2.59 mol), 2 L of 2-propanol, and 700 mL of water. The mixture was stirred at 40° C., acetic acid (15.5 g, 0.259 mmol) was added at a rate sufficient to keep the inner temperature below 70° C. The reaction was stirred at 70° C. for 30 min, HPLC indicated that the reaction was complete. The mixture was cooled to 40° C., then $Na_2CO_3$ (165 g, 1.55 mol) was added, and the mixture was stirred for 1 h. The solids were filtered away, then the solids were washed with tetrahydrofuran (3×500 mL). The combined filtrate and washings were concentrated in vacuo, then the residue was stirred in 1 L of ethanol for 12 hrs. The solid was filtered and washed with cold ethanol. This was dried in vacuo to give (S)-methyl 2-(6-chloro-2-oxo-1,2,3,4-tetrahydropyrido[2,3-b]pyrazin-3-yl)acetate (91 g, 68%) as an off-white solid. MS (ESI) calcd for $C_{10}H_{10}ClN_3O_3$: 255.0. found: 256.0 $(M+H)^+$.

An analogous procedure could be used to prepare (R)-methyl 2-(6-chloro-2-oxo-1,2,3,4-tetrahydropyrido[2,3-b]pyrazin-3-yl)acetate by starting with (R)-dimethyl 2-((6-chloro-3-nitropyridin-2-yl)amino)succinate.

Step 3. Synthesis of (S)-2-(6-chloro-1,2,3,4-tetrahydropyrido[2,3-b]pyrazin-3-yl)ethanol

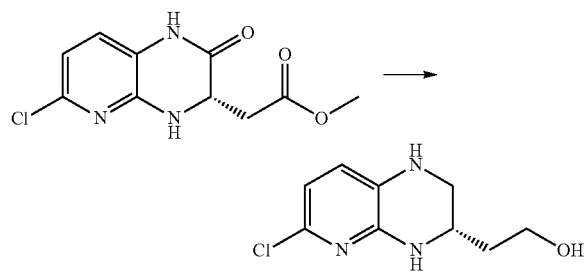

A 5 L 3-necked flask equipped with a mechanical stirrer, a reflux condenser, and a nitrogen inlet was charged with of $LiAlH_4$ (60 g, 1.58 mol). The flask was cooled with an ice bath, then 500 mL of tetrahydrofuran was added. The stirred mixture was cooled to 0° C., a solution of (S)-methyl 2-(6-chloro-2-oxo-1,2,3,4-tetrahydropyrido[2,3-b]pyrazin-3-yl)acetate (81 g, 0.32 mol) in 2 L of tetrahydrofuran was added, while keeping the internal temperature below 5° C. After the addition was complete, the reaction was heated at reflux for 16 h, monitoring by HPLC for the appearance of product. The ester reduction occurred rapidly, while the lactam reduction required longer for complete reduction. The reaction was cooled to 5° C., then 60 mL of water was added, keeping the internal temperature below 10° C. After addition was complete, the reaction was stirred for 15 min. Next, 60 mL of 15% (w/w) $NaOH_{(aq)}$ was added, keeping the internal temperature below 5° C. After addition was complete, the reaction was stirred for 15 min. To complete the workup, 180 mL of water was added, then the mixture was stirred at ambient temperature for 1 h. The solids were filtered and washed with tetrahydrofuran (3×150 mL). The filtrate and washings were concentrated in vacuo, then the solid residue was dried in vacuo to give (S)-2-(6-chloro-1,2,3,4-tetrahydropyrido[2,3-b]pyrazin-3-yl)ethanol (55 g, 81%) as a brown solid. MS (ESI) calcd for $C_9H_{12}ClN_3O$: 213.1. found: 214.1 $(M+H)^+$.

An analogous procedure could be used to prepare (R)-2-(6-chloro-1,2,3,4-tetrahydropyrido[2,3-b]pyrazin-3-yl)ethanol by starting with (R)-methyl 2-(6-chloro-2-oxo-1,2,3,4-tetrahydropyrido[2,3-b]pyrazin-3-yl)acetate.

Step 4. Synthesis of (4S)-7-chloro-2,3,4,5-tetrahydro-1,4-methanopyrido[2,3-b][1,4]diazepine

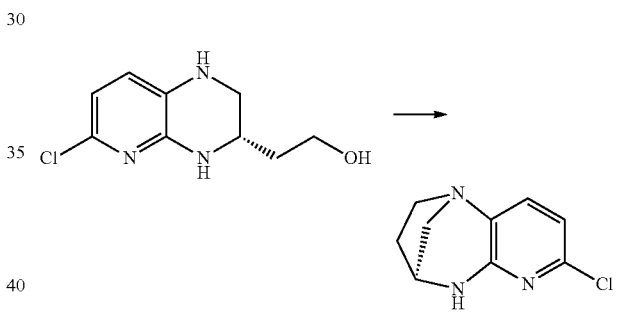

To a solution of (S)-2-(6-chloro-1,2,3,4-tetrahydropyrido[2,3-b]pyrazin-3-yl)ethanol (50 g, 0.234 mol) in 500 mL of $CH_2Cl_2$ was added triethylamine (95 g, 0.936 mol). The mixture was stirred at ambient temperature until it was homogeneous, then it was cooled to 0° C. Next, $POCl_3$ (54 g, 0.351 mol) was added, dropwise, maintaining the temperature at 0° C. 5. Cooling was removed, and the reaction was stirred at ambient temperature for 2 h and monitored by HPLC for the disappearance of the starting alcohol. After the reaction was complete, 200 mL of 1.2M $NaNCO_{3(aq)}$ was added. The layers were separated, and the aqueous layer was extracted with $CH_2Cl_2$. The combined $CH_2Cl_2$ layers were extracted with 1M $HCl_{(aq)}$ (4×300 mL), and the combined HCl layers were adjusted to pH=8 with $NaHCO_{3(sat.)}$. The resulting mixture was extracted with $CH_2Cl_2$ (4×300 mL), and the combined $CH_2Cl_2$ layers were dried over $Na_2SO_4$, filtered, and treated with 50 g of charcoal. The mixture was stirred at ambient temperature for 3 h, filtered through charcoal, and the charcoal washed with an additional 200 mL of $CH_2Cl_2$. The combined filtrate and wash solution was concentrated to dryness. The solid residue was dried in vacuo to give (4S)-7-chloro-2,3,4,5-tetrahydro-1,4-methanopyrido[2,3-b][1,4]diazepine (30 g, 66%) as an off-white crystalline solid. MS (ESI) calcd for $C_9H_{10}ClN_3$: 195.1. found: 196.1 $(M+H)^+$.

An analogous procedure could be used to prepare (4R)-7-chloro-2,3,4,5-tetrahydro-1,4-methanopyrido[2,3-b][1,4]diazepine by starting with (R)-2-(6-chloro-1,2,3,4-tetrahydropyrido[2,3-b]pyrazin-3-yl)ethanol.

Step 5. Synthesis of (4S)-7-(3-(trifluoromethyl)phenyl)-2,3,4,5-tetrahydro-1,4-methanopyrido[2,3-b][1,4]diazepine

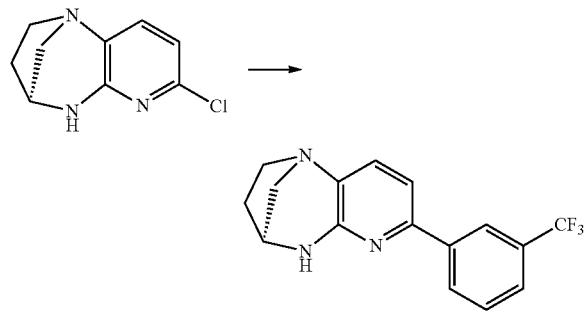 [SMILES: Clc1ccc2c(n1)N[C@H]1CCN2C1 ; FC(F)(F)c1cccc(-c2ccc3c(n2)N[C@H]2CCN3C2)c1]

A mixture of (4S)-7-chloro-2,3,4,5-tetrahydro-1,4-methanopyrido[2,3-b][1,4]diazepine (1.88 g, 9.6 mmol), (3-trifluoromethylphenyl)boronic acid (2.4 g, 12.6 mmol), Pd(OAc)$_2$ (0.228 g, 1.02 mmol), 2-dicyclohexylphosphino-2',4',6'-triisopropylbiphenyl (0.972 g, 2.04 mmol), and Cs$_2$CO$_3$ (6.6 g, 20.4 mmol) was dissolved in dioxane/H$_2$O (50 mL, v/v=9:1). The reaction mixture was heated to 90° C. overnight. After cooling to room temp., it was diluted with EtOAc (120 mL) and washed with water. The aqueous layer was extracted with EtOAc, and the combined organic layers were washed with brine, dried over MgSO$_4$, filtered, and concentrated. Purification by silica gel chromatography (0 to 100% EtOAc in pentane gradient) afforded (4S)-7-(3-(trifluoromethyl)phenyl)-2,3,4,5-tetrahydro-1,4-methanopyrido[2,3-b][1,4]diazepine as a light yellow solid (2.26 g, 77%). MS (ESI) calcd for C$_{16}$H$_{14}$F$_3$N$_3$: 305.1. found: 306 [M+H].

An analogous coupling procedure using Pd(OAc)$_2$ could be used to prepare (4S)-7-(3-substituted phenyl)-2,3,4,5-tetrahydro-1,4-methanopyrido[2,3-b][1,4]diazepines by using the appropriate 3-substituted phenylboronic acids or esters. The analogous enantiomers could be made starting with (4R)-7-chloro-2,3,4,5-tetrahydro-1,4-methanopyrido[2,3-b][1,4]diazepine.

Step 6. Synthesis of (4S)—N-(pyridin-2-yl)-7-(3-(trifluoromethyl)phenyl)-3,4-dihydro-1,4-methanopyrido[2,3-b][1,4]diazepine-5(2H)-carboxamide

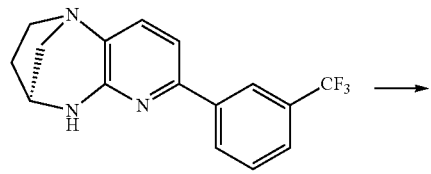

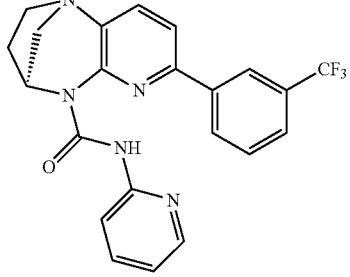

To a solution of (4S)-7-(3-(trifluoromethyl)phenyl)-2,3,4,5-tetrahydro-1,4-methanopyrido[2,3-b][1,4]diazepine (0.100 g, 0.328 mmol) and Et$_3$N (160 μL, 1.15 mmol) in THF (4 mL) was added triphosgene (0.050 g, 0.164 mmol). After stirring for 30 min. at room temp., 2-pyridylamine (0.092 g, 0.983 mmol) was added. The reaction mixture was heated to 60° C. overnight, and the reaction mixture was concentrated and the residue taken up in CH$_2$Cl$_2$ (30 mL). The solution was washed with water and brine, dried over MgSO$_4$, filtered, and concentrated. Purification by silica gel chromatography (0 to 100% EtOAc in pentane gradient) afforded (4S)—N-(pyridin-2-yl)-7-(3-(trifluoromethyl)phenyl)-3,4-dihydro-1,4-methanopyrido[2,3-b][1,4]diazepine-5(2H)-carboxamide (0.086 g, 62%). MS (ESI) calcd for C$_{22}$H$_{18}$F$_3$N$_5$O: 425.2. found: 426.2 [M+H].

An analogous procedure could be used to prepare a variety of (4S)-7-(3-trifluoromethylphenyl)-N-(aryl)-3,4-dihydro-1,4-methanopyrido[2,3-b][1,4]diazepine-5(2H)-carboxamides by substituting the appropriate amine moiety for 2-pyridylamine. The analogous enantiomers could be made by starting with (4R)-7-(3-trifluoromethylphenyl)-N-(aryl)-3,4-dihydro-1,4-methanopyrido[2,3-b][1,4]diazepine-5(2H)-carboxamide.

Analogously, (9S)-2-(3-(trifluoromethyl)phenyl)-N-(aryl)-8,9-dihydro-6H-5,9-methanopyrido[2,3-b][1,4]diazocine-10(7H)-carboxamides could be prepared by this general procedure from (9S)-2-(3-(trifluoromethyl)phenyl)-7,8,9,10-tetrahydro-6H-5,9-methanopyrido[2,3-b][1,4]diazocine and the appropriate amine moiety.

Example 2. Preparation of (4S)—N-phenethyl-7-(3-(trifluoromethyl)phenyl)-3,4-dihydro-1,4-methanopyrido[2,3-b][1,4]diazepine-5(2H)-carboxamide

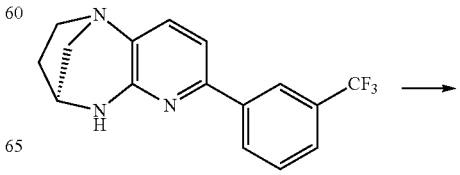

-continued

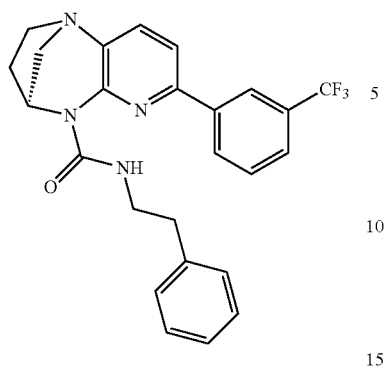

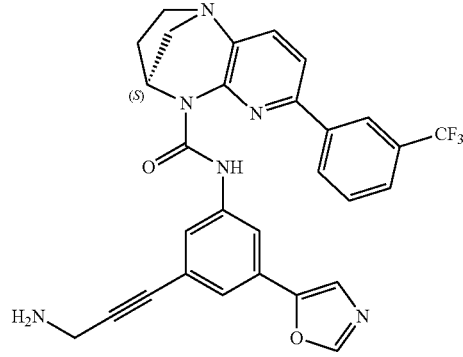

To a solution of (4S)-7-(3-(trifluoromethyl)phenyl)-2,3,4,5-tetrahydro-1,4-methanopyrido[2,3-b][1,4]diazepine (0.100 g, 0.326 mmol) in CH$_2$Cl$_2$ (10 mL) was added pyridine (0.0775 g, 0.980 mmol) and phenyl chloroformate (0.06117 g, 0.392 mmol) at 0° C. After 2 h, the mixture was quenched with sat. aqueous Na$_2$CO$_3$, extracted with CH$_2$Cl$_2$ (3×75 mL), washed with brine, dried with Na$_2$SO$_3$, and concentrated. The residue was purified by flash silica gel chromatography to give (4S)-phenyl 7-(3-(trifluoromethyl)phenyl)-3,4-dihydro-1,4-methanopyrido[2,3-b][1,4]diazepine-5(2H)-carboxylate (0.120 g, yield 84%).

(4S)-phenyl 7-(3-(trifluoromethyl)phenyl)-3,4-dihydro-1,4-methanopyrido[2,3-b][1,4]diazepine-5(2H)-carboxylate, 2-phenylethanamine (0.057 g, 0.470 mmol), and DMAP (0.035 g, 0.282 mmol) in MeCN (3 mL) were stirred at 80° C. overnight. After cooling to room temperature, the mixture was concentrated and the residue purified by Prep-TLC eluting with CH$_2$Cl$_2$:MeOH (10:1) to give (4S)—N-phenethyl-7-(3-(trifluoromethyl)phenyl)-3,4-dihydro-1,4-methanopyrido[2,3-b][1,4]diazepine-5(2H)-carboxamide (0.020 g, yield 18%). MS (ESI) calcd for C$_{25}$H$_{23}$F$_3$N$_4$O: 452.18. found: 453 [M+H].

Example 3. Preparation of (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5(2H)-carboxamide

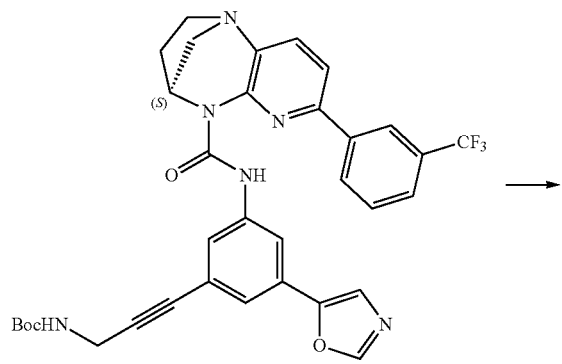

A suspension of (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5(2H)-carboxamide (A, 0.050 g, 0.08 mmol) in 4N HCl indioxane (10 mL) was stirred for 16 h at room temp. The mixture was concentrated under reduced pressure and triturated with CH$_3$CN. The residue was dissolved in CH$_3$CN:H$_2$O and lyophilized to give (4S)—N-(3-(3-aminoprop-1-yn-1-yl)-5-(oxazol-5-yl)phenyl)-7-(3-(trifluoromethyl)phenyl)-3,4-dihydro-1,4-methanopyrido[2,3-b][1,4]diazepine-5(2H)-carboxamide (0.030 g, yield 70%). MS (ESI) calcd for C$_{29}$H$_{23}$F$_3$N$_6$O$_2$: 544.18. found: 545 [M+H].

Example 4. Preparation of (4S)—N-methyl-N-(pyridin-2-yl)-7-(3-(trifluoromethyl)phenyl)-3,4-dihydro-1,4-methanopyrido[2,3-b][1,4]diazepine-5(2H)-carboxamide

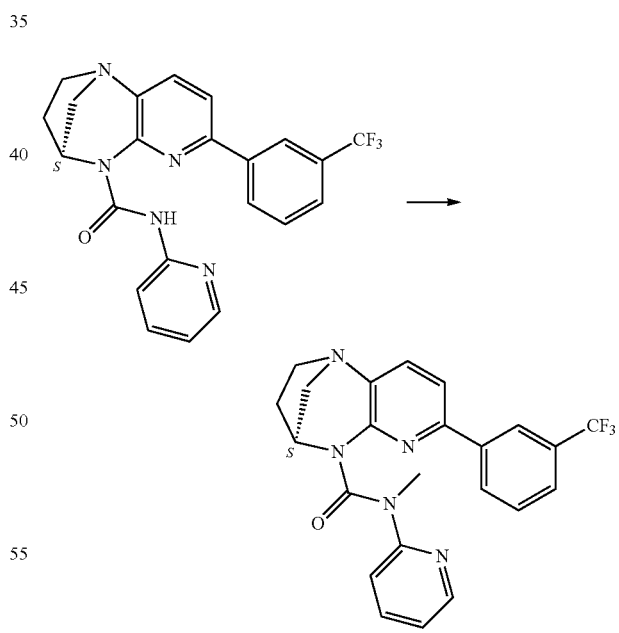

(4S)—N-(pyridin-2-yl)-7-(3-(trifluoromethyl)phenyl)-3,4-dihydro-1,4-methanopyrido[2,3-b][1,4]diazepine-5(2H)-carboxamide (0.267 g, 0.63 mmol) was dissolved in dimethylacetamide and one equivalent of NaH (0.025 g, 60% in oil) was added. The solution was stirred for 5 minutes before the addition of MeI (39 µL). The mixture was stirred overnight at room temperature then diluted with ethyl acetate and washed sequentially with brine (2×), water (2×), and brine. The solution was dried (Na₂SO₄) and concentrated under reduced pressure and loaded onto a silica gel cartridge (ethyl acetate: pentane eluent). Concentration of the pure fractions afforded pure (4S)—N-methyl-N-(pyridin-2-yl)-7-(3-(trifluoromethyl)phenyl)-3,4-dihydro-1,4-methanopyrido[2,3-b][1,4]diazepine-5(2H)-carboxamide. MS (ESI) calcd for C₂₃H₂₀F₃N₅O: 439.16. found: 440.1 [M+H].

Example 5. Preparation of (4S)—N-(3-fluoropyridin-4-yl)-7-(3-(trifluoromethyl)phenyl)-3,4-dihydro-1,4-methanopyrido[2,3-b][1,4]diazepine-5(2H)-carboxamide

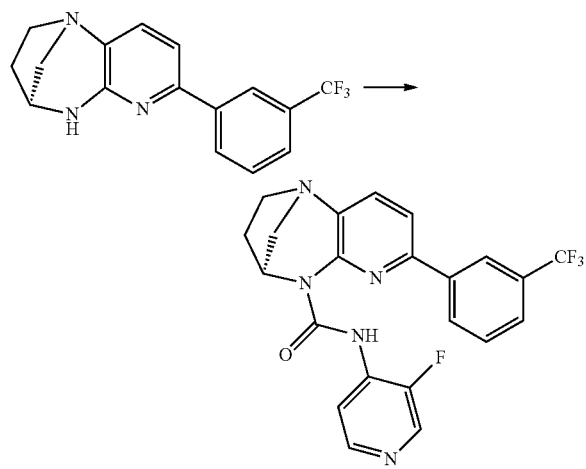

Phenyl chloroformate (1.46 g, 9.37 mmol) was added dropwise to a cooled solution of 3-fluoropyridin-4-amine (1 g, 8.92 mmol) and pyridine (0.95 mL, 11.16 mmol) in THF (10 mL). The reaction was stirred at room temp. overnight. Purification by prep-TLC afforded phenyl (3-fluoropyridin-4-yl)carbamate as a yellow solid.

A mixture of phenyl (3-fluoropyridin-4-yl)carbamate (72 mg, 0.31 mmol), (4S)-7-(3-(trifluoromethyl)phenyl)-2,3,4,5-tetrahydro-1,4-methanopyrido[2,3-b][1,4]diazepine (50 mg, 0.16 mmol) and DMAP (24 mg, 0.20 mmol) in 3 mL of acetonitrile was stirred at 60° C. overnight. The mixture was directly loaded onto prep-TLC and purified using ethyl acetate/pet.ether=1:3~1:8 as eluent to afford (4S)—N-(3-fluoropyridin-4-yl)-7-(3-(trifluoromethyl)phenyl)-3,4-dihydro-1,4-methanopyrido[2,3-b][1,4]diazepine-5(2H)-carboxamide (18 mg, 25%) as a white solid. MS (ESI) calcd for C₂₂H₁₇F₄N₅O: 443.1. found: 444.1 [M+H].

This general urea formation procedure using phenyl carbamates could be used to prepare a variety of (4S)-7-(aryl)-N-(aryl)-3,4-dihydro-1,4-methanopyrido[2,3-b][1,4]diazepine-5(2H)-carboxamides by substituting the appropriate (4S)-7-(aryl)-2,3,4,5-tetrahydro-1,4-methanopyrido[2,3-b][1,4]diazepine for (4S)-7-(3-(trifluoromethyl)phenyl)-2,3,4,5-tetrahydro-1,4-methanopyrido[2,3-b][1,4]diazepine and by substituting the appropriate amine moiety for 3-fluoropyridin-4-amine. The enantiomer series could be made by starting with (4R)-7-(aryl)-2,3,4,5-tetrahydro-1,4-methanopyrido[2,3-b][1,4]diazepines.

Example 6. Preparation of (4S)-7-(3-chlorophenyl)-N-(pyridin-2-yl)-3,4-dihydro-1,4-methanopyrido[2,3-b][1,4]diazepine-5(2H)-carboxamide Step 1. Synthesis of (4S)-7-(3-chlorophenyl)-2,3,4,5-tetrahydro-1,4-methanopyrido[2,3-b][1,4]diazepine

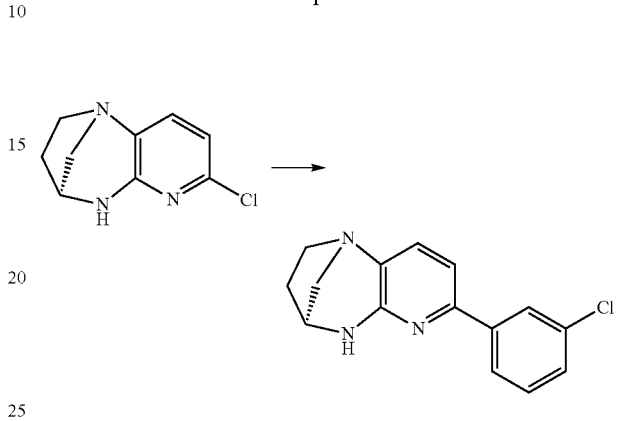

To dioxane/H₂O (10 mL/1 mL) was added (4S)-7-chloro-2,3,4,5-tetrahydro-1,4-methanopyrido[2,3-b][1,4]diazepine (500 mg, 2.56 mmol), (3-chlorophenyl)boronic acid (807 mg, 5.11 mmol), Pd(dppf)Cl₂ (212 mg, 0.26 mmol), and Cs₂CO₃ (2.08 g, 6.4 mmol). The mixture was stirred at 90° C. overnight. The mixture was concentrated and purified by column chromatography (ethyl acetate/pet. ether=1/4) to afford (4S)-7-(3-chlorophenyl)-2,3,4,5-tetrahydro-1,4-methanopyrido[2,3-b][1,4]diazepine (506 mg, 81%). MS (ESI) calcd for C₁₅H₁₄ClN₃: 271.1. found: 272.1 [M+H].

An analogous procedure could be used to prepare (4S)-7-(3-fluorophenyl)-2,3,4,5-tetrahydro-1,4-methanopyrido[2,3-b][1,4]diazepine or (4S)-7-(3-methoxyphenyl)-2,3,4,5-tetrahydro-1,4-methanopyrido[2,3-b][1,4]diazepine by using the appropriate boronic acid or ester. The enantiomer series could be made by starting with the appropriate (4R)-7-(3-substituted phenyl)-2,3,4,5-tetrahydro-1,4-methanopyrido[2,3-b][1,4]diazepine. Also made via this method using the appropriate starting chloride were: (9S)-2-(3-(trifluoromethyl)phenyl)-7,8,9,10-tetrahydro-6H-5,9-methanopyrido[2,3-b][1,4]diazocine, (9R)-2-(3-(trifluoromethyl)phenyl)-7,8,9,10-tetrahydro-6H-5,9-methanopyrido[2,3-b][1,4]diazocine, 3-((9R)-7,8,9,10-tetrahydro-6H-5,9-methanopyrido[2,3-b][1,4]diazocin-2-yl)benzonitrile, 3-((9S)-7,8,9,10-tetrahydro-6H-5,9-methanopyrido[2,3-b][1,4]diazocin-2-yl)benzonitrile, (9S)-2-(5-(methylsulfonyl)pyridin-3-yl)-7,8,9,10-tetrahydro-6H-5,9-methanopyrido[2,3-b][1,4]diazocine, (9S)-2-(5-(trifluoromethyl)pyridin-3-yl)-7,8,9,10-tetrahydro-6H-5,9-methanopyrido[2,3-b][1,4]diazocine, N,N-dimethyl-3-((9R)-7,8,9,10-tetrahydro-6H-5,9-methanopyrido[2,3-b][1,4]diazocin-2-yl)aniline, N,N-dimethyl-3-((9S)-7,8,9,10-tetrahydro-6H-5,9-methanopyrido[2,3-b][1,4]diazocin-2-yl)aniline, (9S)-2-(6-methylpyridin-3-yl)-7,8,9,10-tetrahydro-6H-5,9-methanopyrido[2,3-b][1,4]diazocine, (9S)-2-(pyridin-3-yl)-7,8,9,10-tetrahydro-6H-5,9-methanopyrido[2,3-b][1,4]diazocine, (9S)-2-(3-chlorophenyl)-7,8,9,10-tetrahydro-6H-5,9-methanopyrido[2,3-b][1,4]diazocine.

Step 2. Synthesis of (4S)-7-(3-chlorophenyl)-N-(pyridin-2-yl)-3,4-dihydro-1,4-methanopyrido[2,3-b][1,4]diazepine-5(2H)-carboxamide

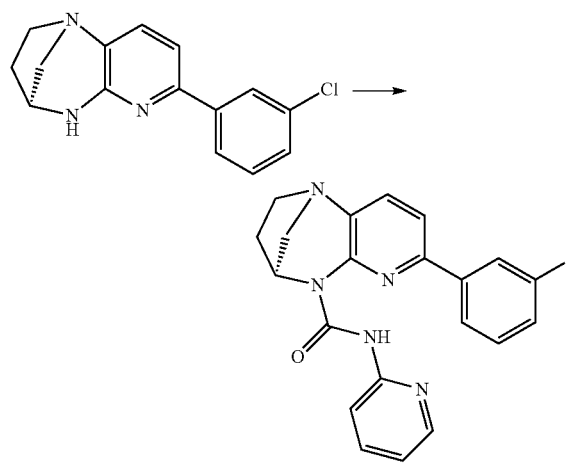

Phenyl chloroformate (6.99 mL, 55.79 mmol) was added dropwise to a cooled solution of 2-pyridylamine (5 g, 53.10 mmol) and pyridine (5.65 mL, 66.41 mmol) in THF (50 mL). The reaction was stirred at room temp. overnight. Brine was added slowly and the mixture was extracted with ethyl acetate. The layers were separated and organic layer was washed with sat. sodium bicarbonate and brine. The organic layer was then dried over anhydrous sodium sulfate and concentrated under reduced pressure. The residue was washed with pet. ether to afford phenyl pyridin-2-ylcarbamate (2.1 g, 18%).

A mixture of phenyl pyridin-2-ylcarbamate (66 mg, 0.30 mmol), (4S)-7-(3-chlorophenyl)-2,3,4,5-tetrahydro-1,4-methanopyrido[2,3-b][1,4]diazepine (40 mg, 0.15 mmol) and DMAP (23 mg, 0.18 mmol) in 3 mL of acetonitrile was stirred at 65° C. overnight. Reaction progress was monitored by TLC and LC-MS. The mixture was directly loaded on prep-TLC using ethyl acetate/petroleum ether=1:3~1:8 as eluent to give (4S)-7-(3-chlorophenyl)-N-(pyridin-2-yl)-3,4-dihydro-1,4-methanopyrido[2,3-b][1,4]diazepine-5(2H)-carboxamide (28 mg, 48%) as a white solid. MS (ESI) calcd for $C_{21}H_{18}ClN_5O$: 391.1. found: 392.1 [M+H].

This general urea formation procedure using phenyl carbamates could be used to prepare a variety of (4S)-7-(3-chloro, -fluoro, or -methoxyphenyl)-N-(aryl)-3,4-dihydro-1,4-methanopyrido[2,3-b][1,4]diazepine-5(2H)-carboxamides by using (4S)-7-(3-chloro, -fluoro or -methoxyphenyl)-2,3,4,5-tetrahydro-1,4-methanopyrido[2,3-b][1,4]diazepine and the appropriate amine moiety. The enantiomer series could be made by starting with the appropriate (4R)-7-(3-substituted phenyl)-2,3,4,5-tetrahydro-1,4-methanopyrido[2,3-b][1,4]diazepine. Analogously, (9S)-2-(5-fluoro- or chloropyridin-3-yl)-N-(aryl)-8,9-dihydro-6H-5,9-methanopyrido[2,3-b][1,4]diazocine-10(7H)-carboxamides could be prepared via this urea formation procedure; see the following example for preparation of the starting (9S)-2-(5-fluoro- or chloropyridin-3-yl)-7,8,9,10-tetrahydro-6H-5,9-methanopyrido[2,3-b][1,4]diazocines.

The analogous procedure used to prepare (4S)-7-(3-chlorophenyl)-N-(pyridin-2-yl)-3,4-dihydro-1,4-methanopyrido[2,3-b][1,4]diazepine-5(2H)-carboxamide (steps 1 and 2 above) can be used to make the following compounds starting with commercially available boronic esters:

Example 7. Preparation of (9S)-2-(5-chloropyridin-3-yl)-7,8,9,10-tetrahydro-6H-5,9-methanopyrido[2,3-b][1,4]diazocine

Step 1. Synthesis of (S)-dimethyl 2-((6-chloro-3-nitropyridin-2-yl)amino)glutarate

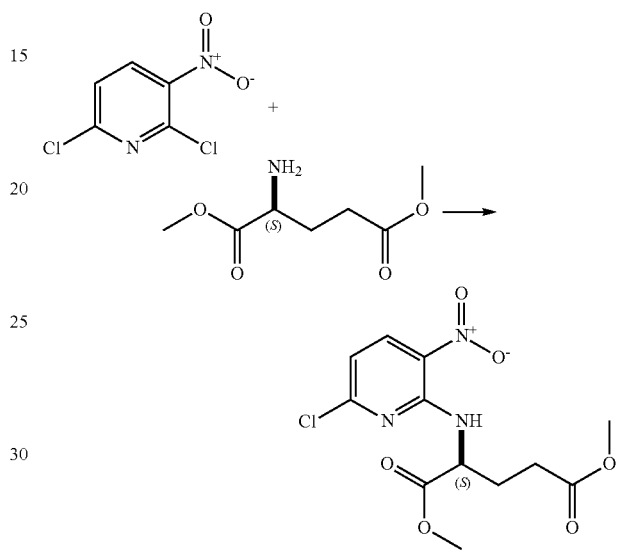

This moiety was made using the following protocol. To a mixture of 40.0 g (207 mmol) of 2,6-dichloro-3-nitropyridine, 87.7 g (414 mmol) of L-glutamic acid dimethyl ester hydrochloride, and 69.6 g (829 mmol) of NaHCO$_3$ was added 600 mL of tetrahydrofuran. The mixture was stirred at 40° C. for 24 h, monitoring for the disappearance of 2,6-dichloro-3-nitropyridine by HPLC. After the reaction was complete, the solids were filtered away and washed with ethyl acetate (3×100 mL). The combined filtrate and washings were concentrated in vacuo, then the residue was purified via silica gel chromatography, eluting with 10/1 (v/v) hexanes/ethyl acetate to give 60 g (87%) of the product as a yellow solid. MS (ESI) calcd for $C_{12}H_{14}ClN_3O_6$: 331.0. found: 332.1 (M+H)$^+$.

Step 2. Synthesis of (S)-methyl 3-(6-chloro-2-oxo-1,2,3,4-tetrahydropyrido[2,3-b]pyrazin-3-yl)propanoate

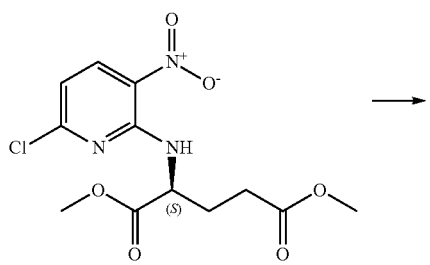

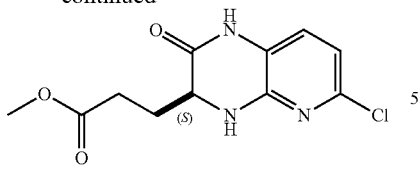

This moiety was made using the following protocol. To a mixture of 20 g (60.2 mmol) of (S)-dimethyl 2-((6-chloro-3-nitropyridin-2-yl)amino)pentanedioate, and 16.8 g (301 mmol) of iron powder was added 375 mL of 2-propanol, then 125 mL of water. To the stirred mixture was added 5.5 g (90.3 mmol) of acetic acid, then the reaction was stirred at reflux for 1 h. The reaction was monitored for the disappearance of starting material by HPLC. After the reaction was complete, the solids were filtered off and washed with 2-propanol (3×50 mL). The combined filtrate and washings were concentrated to dryness, then the residue was dried in vacuo to give 15 g (81%) of the product as a dark yellow solid. This was used without further purification in the next step. MS (ESI) calcd for $C_{11}H_{12}ClN_3O_3$: 269.0. found: 270.1.

Step 3. Synthesis of (S)-3-(6-chloro-1,2,3,4-tetrahydropyrido[2,3-b]pyrazin-3-yl)propan-1-ol

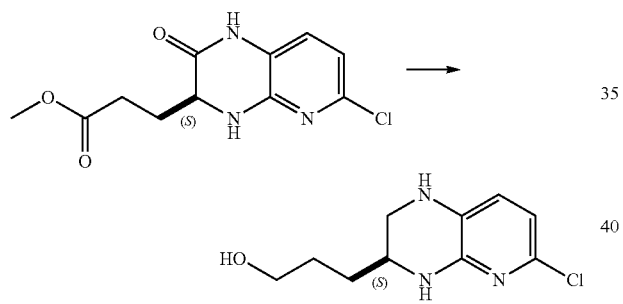

This moiety was made using the following protocol. To a solution of 17.78 g (133.3 mmol) of $AlCl_3$ in 260 mL of tetrahydrofuran (THF) under $N_2$ was added 200 mL of 2M $LiAlH_4$ in THF, dropwise, at a rate to control gas evolution. This gave a solution of alane ($AlH_3$) in THF. In a separate flask, a solution of 26.0 g (96.4 mmol) of (S)-methyl 3-(6-chloro-2-oxo-1,2,3,4-tetrahydropyrido[2,3-b]pyrazin-3-yl)propanoate in 460 mL of THF was prepared under $N_2$, then cooled with a dry ice/acetone bath. To this was added the alane solution, dropwise with stirring, over 2 h. When the addition was complete, the cooling bath was removed, and the reaction was allowed to warm to ambient temperature. After 1.5 h, LCMS analysis showed that the reaction was complete. Next, a solution of 17.6 g NaOH in 65 mL of water was added slowly to control the evolution of $H_2$. The suspension was allowed to stir for 18 h, then the solids were filtered away. The precipitate was washed with ethyl acetate, then the filtrate and washings were concentrated in vacuo. The product was purified via silica gel chromatography, (330 g prepacked column) eluting with $CH_2Cl_2$, followed by a gradient of 0 to 10% methanol in $CH_2Cl_2$ to give 15.21 g (69%) of a yellow-orange solid. MS (ESI) calcd for $C_{10}H_{14}ClN_3O$: 227.1. found: 228.1.

Step 4. Synthesis of (5R,9S)-2-chloro-7,8,9,10-tetrahydro-6H-5,9-methanopyrido[2,3-b][1,4]diazocine

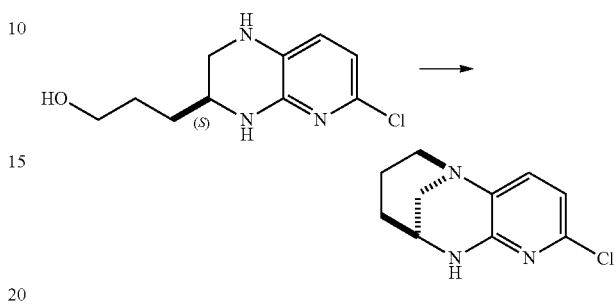

To 12 g (52.7 mmol) of (S)-3-(6-chloro-1,2,3,4-tetrahydropyrido[2,3-b]pyrazin-3-yl)propan-1-ol was added 160 mL of 48% (w/w) $HBr_{(aq)}$, then the reaction was stirred at 90° C. for 18 h. The reaction was monitored by HPLC for the disappearance of the starting alcohol. After the reaction was complete, it was cooled to ambient temperature, then 1.2 M $NaHCO_{3(aq)}$ was added until pH=8. The mixture was extracted with ethyl acetate (3×100 mL), then the organic phase was back extracted with brine (1×100 mL), dried over $Na_2SO_4$, filtered, and concentrated to dryness. The residue was purified via silica gel chromatography, eluting with 2/1 (v/v) hexanes/ethyl acetate to give 6.0 g (55%) of the product as a light yellow solid. MS (ESI) calcd for $C_{10}H_{12}ClN_3$: 209.1. found: 210.1.

Step 5. Synthesis of (9S)-tert-butyl 2-chloro-8,9-dihydro-6H-5,9-methanopyrido[2,3-b][1,4]diazocine-10(7H)-carboxylate

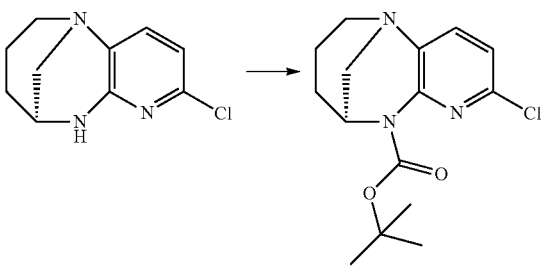 [SMILES: Clc1ccc2c(n1)N[C@H]1CCCN2C1 ; CC(C)(C)OC(=O)N1c2nc(Cl)ccc2N2CCC[C@H]1C2]

(9S)-2-chloro-7,8,9,10-tetrahydro-6H-5,9-methanopyrido[2,3-b][1,4]diazocine (1.3 g, 6.19 mmol, Note: the 5R stereochemistry is implied), $Boc_2O$ (2.02 g, 9.28 mmol, 1.5 equiv.) and DMAP (1.51 g, 12.38 mmol, 2.0 equiv.) in 5 mL THF were stirred at 60° C. for 2 h. Reaction progress was monitored by TLS and LC/MS. Water (30 mL) was added, and the mixture was extracted with DCM (3×15 mL). The organics were concentrated and the residue was purified via silica gel column chromatography to give (9S)-tert-butyl 2-chloro-8,9-dihydro-6H-5,9-methanopyrido[2,3-b][1,4]diazocine-10(7H)-carboxylate as a white solid (1.3 g, 92%). MS (ESI) calcd for $C_{15}H_{20}ClN_3O_2$: 309.1.

Step 6. Synthesis of (9S)-tert-butyl 2-(5-chloropyridin-3-yl)-8,9-dihydro-6H-5,9-methanopyrido[2,3-b][1,4]diazocine-10(7H)-carboxylate

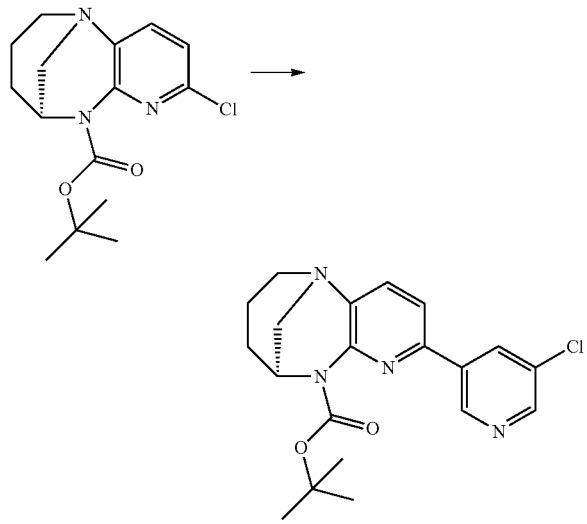

To a degassed mixture of dioxane/water (10 mL/1 mL) was added (9S)-tert-butyl 2-chloro-8,9-dihydro-6H-5,9-methanopyrido[2,3-b][1,4]diazocine-10(7H)-carboxylate (650 mg, 2.096 mmol), (5-chloropyridin-3-yl)boronic acid (658 mg, 4.19 mmol), Pd(dppf)Cl$_2$ (171 mg, 0.209 mmol), and Cs$_2$CO$_3$ (2.04 g, 6.29 mmol). The mixture was stirred at 110° C. for 12 h, then concentrated and purified via column chromatography (PE/EA=3/1) to give (9S)-tert-butyl 2-(5-chloropyridin-3-yl)-8,9-dihydro-6H-5,9-methanopyrido[2,3-b][1,4]diazocine-10(7H)-carboxylate (600 mg, 63%). MS (ESI) calcd for C$_{20}$H$_{23}$ClN$_4$O$_2$: 386.2.

(9S)-tert-butyl 2-(5-fluoropyridin-3-yl)-8,9-dihydro-6H-5,9-methanopyrido[2,3-b][1,4]diazocine-10(7H)-carboxylate was prepared via the same method, starting with (5-fluoropyridin-3-yl)boronic acid.

Step 7. Synthesis of (9S)-2-(5-chloropyridin-3-yl)-7,8,9,10-tetrahydro-6H-5,9-methanopyrido[2,3-b][1,4]diazocine

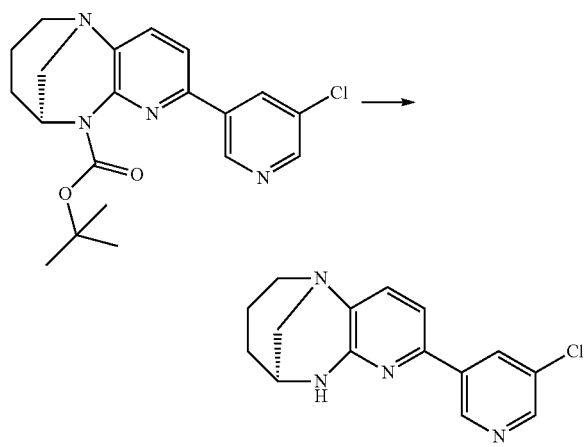

This moiety was made using the following protocol. (9S)-tert-butyl 2-(5-chloropyridin-3-yl)-8,9-dihydro-6H-5,9-methanopyrido[2,3-b][1,4]diazocine-10(7H)-carboxylate (600 mg, 1.55 mmol) was dissolved in HCl/MeOH (1M, 20 mL) and the reaction was stirred at room temp. for 1.5 h, then concentrated in vacuo. Water (20 mL) and K$_2$CO$_3$ (3 g) were added, and the mixture was stirred at room temp. for 2 h, then extracted with DCM (3×15 mL) to give (9S)-2-(5-chloropyridin-3-yl)-7,8,9,10-tetrahydro-6H-5,9-methanopyrido[2,3-b][1,4]diazocine (450 mg, quant.). MS (ESI) calcd for C$_{15}$H$_{15}$ClN$_4$: 286.1.

(9S)-2-(5-fluoropyridin-3-yl)-7,8,9,10-tetrahydro-6H-5,9-methanopyrido[2,3-b][1,4]diazocine was prepared via the same method.

These moieties were used to prepare urea compounds via the general urea coupling procedure described in the previous example.

Example 8. Preparation of (9S)-2-(5-methylpyridin-3-yl)-7,8,9,10-tetrahydro-6H-5,9-methanopyrido[2,3-b][1,4]diazocine

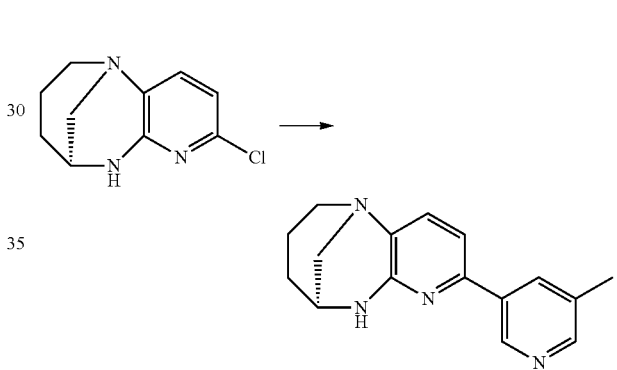

This moiety was made using the following protocol. To degassed 1,4-dioxane/H$_2$O (20 ml, v/v=10/1) were added (9S)-2-chloro-7,8,9,10-tetrahydro-6H-5,9-methanopyrido[2,3-b][1,4]diazocine (600 mg, 2.87 mmol), 5-methylpyridin-3-ylboronic acid (1.18 g, 3.0 equiv.), PCy$_3$ (644 mg, 0.8 equiv.) and Pd$_2$(dba)$_3$ (330 mg, 0.2 equiv.). The mixture was heated to 110° C. in a sealed tube. After stirring 12 hr at 110° C., the black suspension was cooled to room temp and concentrated under reduced pressure. The concentrate was suspended in EtOAc (300 ml), washed with water (4×80 ml), brine (80 ml), dried over Na$_2$SO$_4$ and concentrated under reduced pressure. The concentrate was purified by column (DCM/MeOH=10/1) to afford the product as a light brown solid (756 mg, 99%). MS (ESI) calcd for C$_{16}$H$_{18}$N$_4$: 266.1. found: 267.2 [M+H].

These conditions were also used to prepare (9S)-2-(4-methylpyridin-3-yl)-7,8,9,10-tetrahydro-6H-5,9-methanopyrido[2,3-b][1,4]diazocine and 4-(3-((9S)-7,8,9,10-tetrahydro-6H-5,9-methanopyrido[2,3-b][1,4]diazocin-2-yl)phenyl)morpholine by starting with the appropriate boronic acid.

The resulting moieties were used to prepare urea compounds via the general urea coupling procedure described above.

Example 9. Preparation of (9S)—N-(pyridazin-3-yl)-2-(pyridin-3-yl)-8,9-dihydro-6H-5,9-methanopyrido[2,3-b][1,4]diazocine-10(7H)-carboxamide

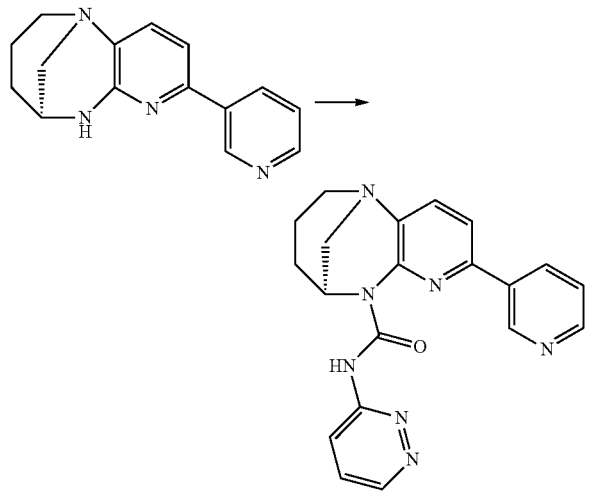

This moiety was prepared via the analogous carbamate protocol described for (4S)-7-(3-chlorophenyl)-N-(pyridin-2-yl)-3,4-dihydro-1,4-methanopyrido[2,3-b][1,4]diazepine-5(2H)-carboxamide, using the p-chlorophenyl carbamate instead of the phenyl carbamate. MS (ESI) calcd for $C_{20}H_{19}N_7O$: 373.2. found: 374.3 [M+H].

Example 10. Preparation of (4S)-7-(3-chlorophenyl)-N-(6-(2,3-dihydroxypropoxy)pyrazin-2-yl)-3,4-dihydro-1,4-methanopyrido[2,3-b][1,4]diazepine-5(2H)-carboxamide

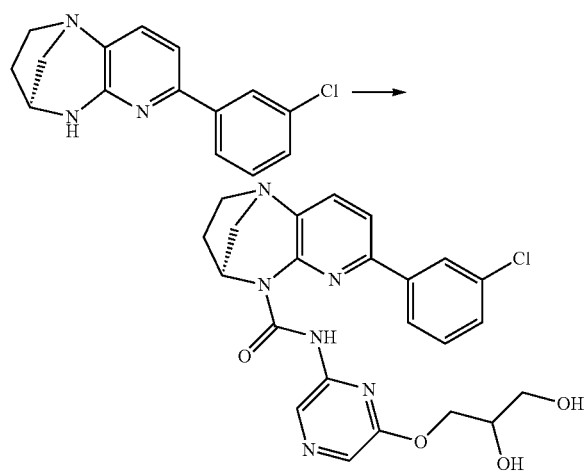

To the mixture of 6-((2,2-dimethyl-1,3-dioxolan-4-yl)methoxy)pyrazin-2-amine (83 mg, 0.37 mmol) and pyridine (29 mg, 1.37 mmol) in 3 mL of THF was added triphosgene (43 mg, 0.14 mmol). The above mixture was stirred at 60° C. for 2 hrs. Then (4S)-7-(3-chlorophenyl)-2,3,4,5-tetrahydro-1,4-methanopyrido[2,3-b][1,4]diazepine (50 mg, 0.18 mmol) was added to the reaction mixture and stirred overnight at 60° C. The crude product was purified by prep-TLC to afford the urea intermediate as a yellow solid. To a solution of this material in THF (3 mL) was added conc. HCl and the reaction was stirred at room temp. for 15 min. Sat. NaHCO$_3$ was added to adjust pH to 7-8. The reaction mixture was extracted with EtOAc and the organic layer washed with brine. Purification by prep-TLC afforded (4S)-7-(3-chlorophenyl)-N-(6-(2,3-dihydroxypropoxy)pyrazin-2-yl)-3,4-dihydro-1,4-methanopyrido[2,3-b][1,4]diazepine-5(2H)-carboxamide (8.9 mg, 40%) as a white solid. MS (ESI) calcd for $C_{23}H_{23}ClN_6O_4$: 482.2. found: 483.1 [M+H].

This general urea formation procedure using triphosgene could be used to prepare a variety of (4S)-7-(3-chloro or -fluorophenyl)-N-(aryl)-3,4-dihydro-1,4-methanopyrido[2,3-b][1,4]diazepine-5(2H)-carboxamides by also using (4S)-7-(3-fluorophenyl)-2,3,4,5-tetrahydro-1,4-methanopyrido[2,3-b][1,4]diazepine and the appropriate amine moiety.

Example 11. Preparation of (9S)-2-(3-cyanophenyl)-N-(pyridin-3-yl)-8,9-dihydro-6H-5,9-methanopyrido[2,3-b][1,4]diazocine-10(7H)-carboxamide

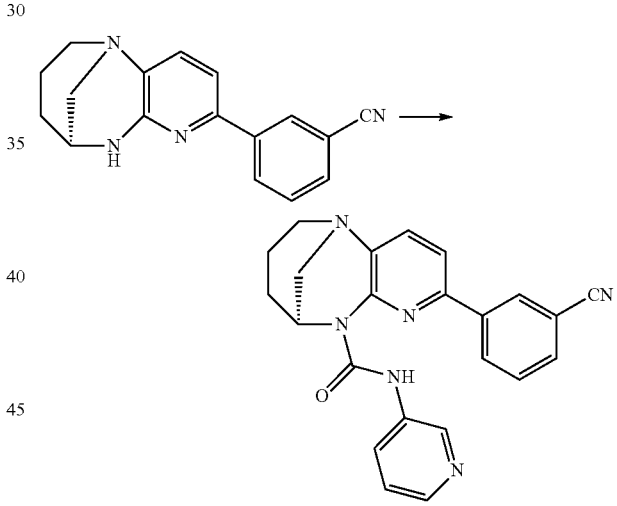

DIPEA (97 μL, 0.54 mmol) was added to a mixture of 3-((9S)-7,8,9,10-tetrahydro-6H-5,9-methanopyrido[2,3-b][1,4]diazocin-2-yl)benzonitrile (50 mg, 0.18 mmol) and triphosgene (27 mg, 0.10 mmol) in THF (12 mL) at room temperature. The mixture was heated at 60° C. for 30 minutes. 3-aminopyridine (102 mg, 1.09 mmol) was added and the reaction mixture was heated at reflux for 32 h. CH$_3$OH was added after cooling to room temperature. The mixture was concentrated and purified by prep HPLC. The TFA salt was suspended in CH$_3$CN, 1N HCl was added and the mixture lyophilized to give (9S)-2-(3-cyanophenyl)-N-(pyridin-3-yl)-8,9-dihydro-6H-5,9-methanopyrido[2,3-b][1,4]diazocine-10(7H)-carboxamide (48 mg, 61%) as the hydrochloride salt. MS (ESI) calcd for $C_{23}H_{20}N_6O$: 396.2. found: 397.1 [M+H].

85

Example 12. Preparation of (9S)—N-(pyridin-2-yl)-2-(5-(trifluoromethyl)pyridin-3-yl)-8,9-dihydro-6H-5,9-methanopyrido[2,3-b][1,4]diazocine-10(7H)-carboxamide

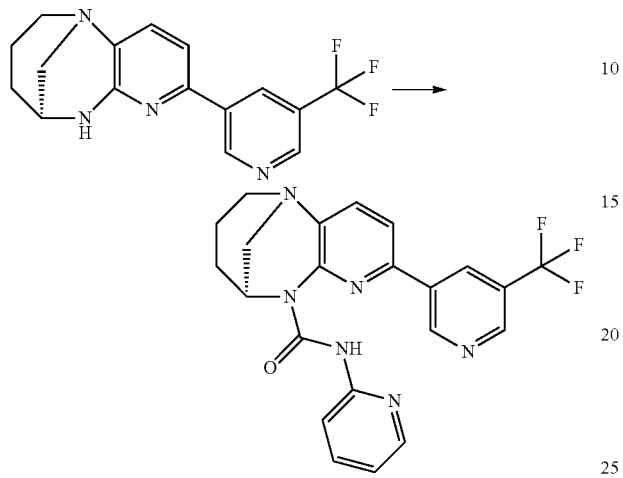

A mixture of 4-chlorophenyl pyridin-2-ylcarbamate (325 mg, 1.31 mmol), (9S)-2-(5-(trifluoromethyl)pyridin-3-yl)-7,8,9,10-tetrahydro-6H-5,9-methanopyrido[2,3-b][1,4]diazocine (70 mg, 0.22 mmol) and DMAP (160 mg, 1.31 mmol) in DMF (3 mL) was heated at 100° C. in a sealed tube for 24 h. The mixture was cooled to room temperature then portioned between EtOAc/H₂O (60 mL/30 mL). The organic layer was separated, washed with H₂O, brine, dried (Na₂SO₄) and concentrated. The crude product was purified by prep-TLC (eluting with CH₂Cl₂/EtOAc/CH₃OH, 120:40:2) to afford (9S)—N-(pyridin-2-yl)-2-(5-(trifluoromethyl)pyridin-3-yl)-8,9-dihydro-6H-5,9-methanopyrido[2,3-b][1,4]diazocine-10(7H)-carboxamide as a tan solid (80 mg, 83%). MS (ESI) calcd for $C_{22}H_{19}F_3N_6O$: 440.2. found: 441.2 [M+H].

Example 13. Preparation of (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide Step 1. Synthesis of (4S)-7-(2-methylpyridin-4-yl)-2,3,4,5-tetrahydro-1,4-methanopyrido[2,3-b][1,4]diazepine

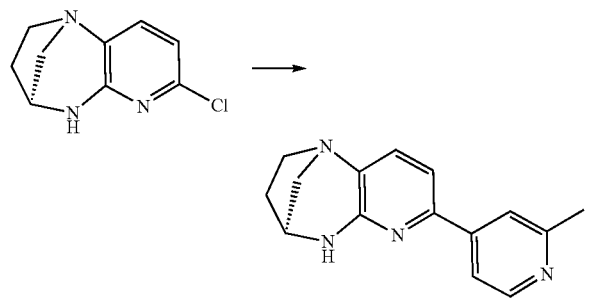

86

To a solution of (4S)-7-chloro-2,3,4,5-tetrahydro-1,4-methanopyrido[2,3-b][1,4]-diazepine (500 mg, 2.55 mmol) in degassed dioxane/H₂O (14 mL, v/v=10/1) was added 2-methylpyridin-4-boronic acid (1.048 g, 7.65 mmol), PCy₃ (286 mg, 1.02 mmol), K₃PO₄·3H₂O (1.698 g, 6.375 mmol) and Pd₂(dba)₃ (234 mg, 0.255 mmol). The resulting mixture was stirred at 110° C. overnight. The mixture was cooled to room temperature then concentrated. The residue was partitioned between EtOAc and water (50 mL each). The organic layer was washed with water and brine, dried over Na₂SO₄, and concentrated to dryness. The residue was purified by silica gel chromatography (CH₂Cl₂/THF=3/2) to give (4S)-7-(2-methylpyridin-4-yl)-2,3,4,5-tetrahydro-1,4-methanopyrido[2,3-b][1,4]diazepine (418 mg, 82%) as a light yellow solid. MS (ESI) calcd for $C_{15}H_{16}N_4$: 252.1. found: 253.2 [M+H].

The following intermediates were prepared using the above protocol substituting the appropriate boronic acid and 2-chloropyridine. 2-((9S)-7,8,9,10-tetrahydro-6H-5,9-methanopyrido[2,3-b][1,4]diazocin-2-yl)benzonitrile, 5-((9S)-7,8,9,10-tetrahydro-6H-5,9-methanopyrido[2,3-b][1,4]diazocin-2-yl)nicotinonitrile Step 2. Synthesis of (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide

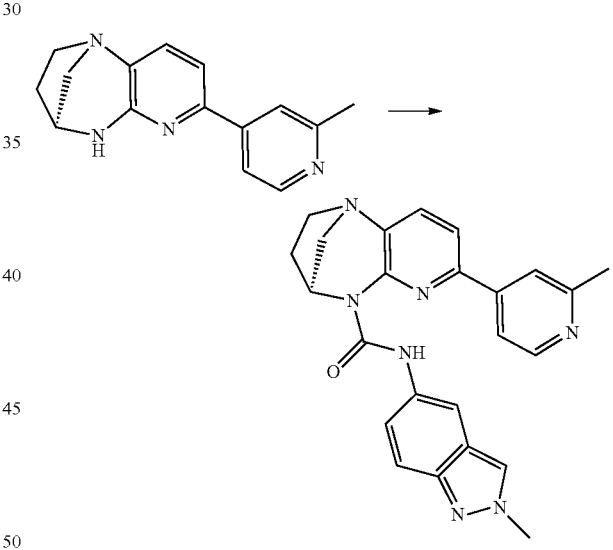

To a solution of phenyl chloroformate (0.2 mL, 1.6 mmol) and pyridine (0.16 mL, 1.95 mmol) in CH₂Cl₂ (18 mL) was added 2-methyl-2H-indazol-5-amine (180 mg, 1.22 mmol). The mixture was stirred at room temperature for 30 min., then quenched with sat. NaHCO₃ solution (10 mL). The aqueous phase was extracted with CH₂Cl₂ (10 mL). The combined organic phases were washed with brine (20 mL), dried over Na₂SO₄, and concentrated to dryness. The residue was washed with hexane (5 mL×3) to afford phenyl (2-methyl-2H-indazol-5-yl)carbamate (304 mg, 93%).

A mixture of (4S)-7-(2-methylpyridin-4-yl)-2,3,4,5-tetrahydro-1,4-methanopyrido[2,3-b][1,4]diazepine (90 mg, 0.36 mmol), phenyl (2-methyl-2H-indazol-5-yl)carbamate (285 mg, 1.07 mmol) and DMAP (130 mg, 1.07 mmol) in THF (3 mL) was heated to 80° C. in a sealed tube. After heating for 36 hrs at 80° C., the mixture was then cooled to room tem. and concentrated. The residue was suspended in EtOAc (60 mL) and filtered. The filtrate was washed with water (20 mL×3), then brine (20 mL), and dried over $Na_2SO_4$ and concentrated under reduced pressure. The concentrate was purified by prep-TLC ($CH_2Cl_2$/EtOAc/MeOH=23/1/drops) to afford (4S)—N-(2-methyl-2H-indazol-5-yl)-7-(2-methylpyridin-4-yl)-3,4-dihydro-1,4-methanopyrido[2,3-b][1,4]diazepine-5(2H)-carboxamide (60 mg, 40%) as a brown solid. MS (ESI) calcd for $C_{24}H_{23}N_7O$: 425.2. found: 426.3 [M+H].

This general urea formation procedure using phenyl carbamates could be used to prepare a variety of (4S)—N-(aryl)-7-(2-methylpyridin-4-yl)-3,4-dihydro-1,4-methanopyrido[2,3-b][1,4]diazepine-5(2H)-carboxamides by using the appropriate amine moiety.

Example 14: Preparation of (4S)—N-(2,6-diethylphenyl)-7-(3-(trifluoromethyl)phenyl)-3,4-dihydro-1,4-methanopyrido[2,3-b][1,4]diazepine-5(2H)-carboxamide

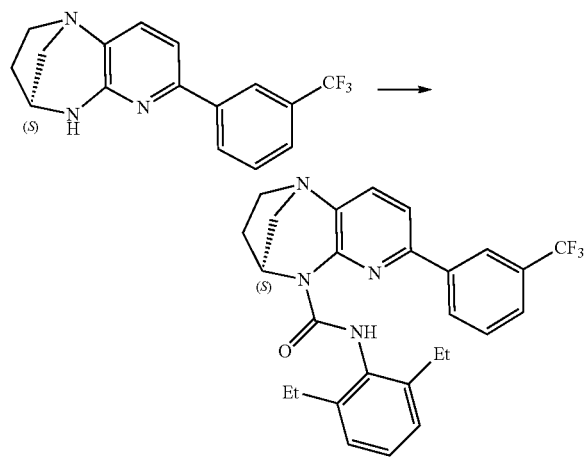

Under nitrogen atmosphere, to a mixture of 2,6-diethylaniline (39.1 mg, 0.262 mmol, 2.0 eq) and pyridine (0.5 ml, excessive) in dry THF (3 mL) was added triphosgene (54.4 mg, 0.183 mmol). The mixture was stirred at 60° C. for 2 hours and (4S)-7-(3-(trifluoromethyl)phenyl)-2,3,4,5-tetrahydro-1,4-methanopyrido[2,3-b][1,4]diazepine (40 mg, 0.131 mmol, 1.0 eq) was added to the reaction mixture and stirred for an additional 18 hours. Saturated sodium bicarbonate solution (5 ml) and dichloromethane (10 ml) were added to the reaction mixture; the organic layer was successively washed with water (10 mL) and brine, dried ($Na_2SO_4$) and concentrated in vacuuo. The crude product was purified by prep-TLC using 15:1 Ethyl Acetate in $CH_2Cl_2$ as eluent to afford (4S)—N-(2,6-diethylphenyl)-7-(3-(trifluoromethyl)phenyl)-3,4-dihydro-1,4-methanopyrido[2,3-b][1,4]diazepine-5(2H)-carboxamide a white solid. (5.1 mg, 8% Yield). MS (ESI) calcd for $C_{27}H_{27}F_3N_4O$: 480.21. found: 481 [M+H].

This general urea formation procedure using triphosgene could be used to prepare a variety of (4S)-7-(3-trifluoromethylphenyl)-N-(aryl)-3,4-dihydro-1,4-methanopyrido[2,3-b][1,4]diazepine-5(2H)-carboxamides by substituting the appropriate amine moiety for 2,6-diethylaniline.

Example 15. Preparation of (4S)-7-(2-methylpyridin-4-yl)-N-(pyrazin-2-yl)-3,4-dihydro-1,4-methanopyrido[2,3-b][1,4]diazepine-5(2H)-carboxamide Step 1. Synthesis of (4S)-7-chloro-N-(pyrazin-2-yl)-3,4-dihydro-1,4-methanopyrido[2,3-b][1,4]diazepine-5(2H)-carboxamide

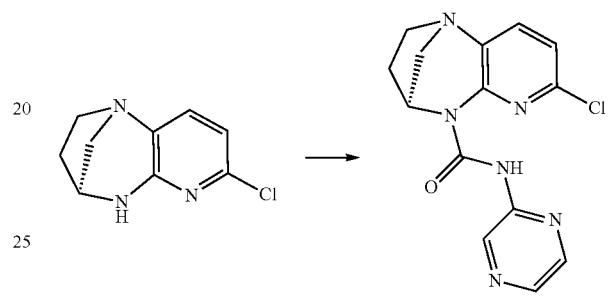

A mixture of (4S)-7-chloro-2,3,4,5-tetrahydro-1,4-methanopyrido[2,3-b][1,4]diazepine (400 mg, 2.04 mmol), phenyl pyrazin-2-ylcarbamate (1.32 g, 6.13 mmol) and DMAP (249 mg, 2.04 mmol) in DMF (8 mL) was heated to 82° C. in a sealed flask. After heating for 22 hrs, the mixture was then cooled to room temp. and diluted with EtOAc (100 mL). The mixture was washed with water (8 mL×9), then with brine, and dried over $Na_2SO_4$ and concentrated. The residue was purified by column chromatography ($CH_2Cl_2$/MeOH=50/1) to afford (4S)-7-chloro-N-(pyrazin-2-yl)-3,4-dihydro-1,4-methanopyrido[2,3-b][1,4]diazepine-5(2H)-carboxamide (600 mg, 93%) as a white solid. MS (ESI) calcd for $C_{14}H_{13}ClN_6O$: 316.1.

This general procedure could be used to prepare a variety of (4S)-7-chloro-N-(aryl)-3,4-dihydro-1,4-methanopyrido[2,3-b][1,4]diazepine-5(2H)-carboxamides by substituting the appropriate carbamate moiety for phenyl pyrazin-2-ylcarbamate.

Step 2. Synthesis of (4S)-7-(2-methylpyridin-4-yl)-N-(pyrazin-2-yl)-3,4-dihydro-1,4-methanopyrido[2,3-b][1,4]diazepine-5(2H)-carboxamide

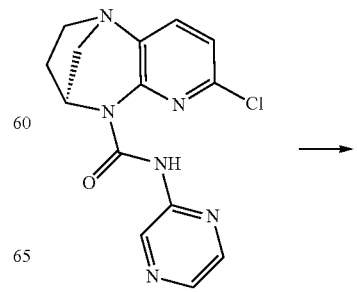

-continued

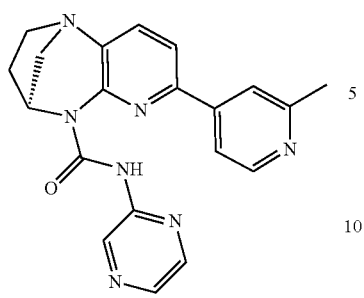

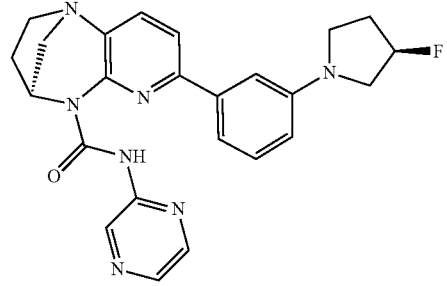

To a mixture of (4S)-7-chloro-N-(pyrazin-2-yl)-3,4-dihydro-1,4-methanopyrido[2,3-b][1,4]diazepine-5(2H)-carboxamide (40 mg, 0.126 mmol), 2-methylpyridin-4-boronic acid (44 mg), and NaHCO$_3$ (32 mg) in toluene/EtOH/H$_2$O (1.9 mL, v/v/v=10/6/3) was added PdCl$_2$(PPh$_3$)$_2$ (9 mg) under a nitrogen atmosphere. The reaction mixture was heated at reflux for 6 hrs. Another portion of 2-methylpyridin-4-boronic acid (44 mg), NaHCO$_3$ (32 mg), and PdCl$_2$(PPh$_3$)$_2$ (8 mg) was added and the mixture was degassed. After stirring at reflux overnight, the reaction mixture was cooled to room temp. and concentrated. The concentrate was suspended in EtOAc (30 mL) and water (5 mL). The aqueous suspension was extracted with EtOAc (8 mL). The combined EtOAc phases were washed with brine (10 mL), dried over MgSO$_4$, and concentrated. Purification by prep-TLC (CH$_2$Cl$_2$/MeOH=50/1) afforded (4S)-7-(2-methylpyridin-4-yl)-N-(pyrazin-2-yl)-3,4-dihydro-1,4-methanopyrido[2,3-b][1,4]diazepine-5(2H)-carboxamide (18 mg, 38%) as an off-white solid. MS (ESI) calcd for C$_{20}$H$_{19}$N$_7$O: 373.2. found: 374.3 [M+H].

This general procedure using PdCl$_2$(PPh$_3$)$_2$ could be used to prepare a variety of (4S)-7-(2-methylpyridin-4-yl)-N-(aryl)-3,4-dihydro-1,4-methanopyrido[2,3-b][1,4]diazepine-5(2H)-carboxamides and (4S)-7-(6-methylpyridin-3-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 16. Preparation of (4S)-7-(3-((R)-3-fluoropyrrolidin-1-yl)phenyl)-N-(pyrazin-2-yl)-3,4-dihydro-1,4-methanopyrido[2,3-b][1,4]diazepine-5(2H)-carboxamide A mixture of (4S)-7-chloro-N-(pyrazin-2-yl)-3,4-dihydro-1,4-methanopyrido[2,3-b][1,4]diazepine-5(2H)-carboxamide (40 mg, 0.126 mmol), (R)-3-fluoro-1-(3-(4,4,5,5-tetramethyl-1,3,2-dioxaborolan-2-yl)phenyl)pyrrolidine (74 mg, 0.252 mmol), Pd(OAc)$_2$ (2 mg, 0.0126 mmol), 2-dicyclohexylphosphino-2',4',6'-triisopropylbiphenyl (12 mg, 0.0252 mmol), and Cs$_2$CO$_3$ (82 mg, 0.252 mmol) in dioxane/H$_2$O (1.5 mL, v/v=9/1) was heated at 110° C. in a sealed flask. After heating overnight, the mixture was cooled and filtered to remove insoluble materials. The filtrate was diluted with EtOAc (30 mL), washed with H$_2$O (5 mL×2), washed with brine (5 mL), dried over Na$_2$SO$_4$, and concentrated. Purification by prep-TLC (CH$_2$Cl$_2$/EtOAc=3/1) afforded (4S)-7-(3-((R)-3-fluoropyrrolidin-1-yl)phenyl)-N-(pyrazin-2-yl)-3,4-dihydro-1,4-methanopyrido[2,3-b][1,4]diazepine-5(2H)-carboxamide (18 mg, 32%) as a pale yellow solid. MS (ESI) calcd for C$_{24}$H$_{24}$FN$_7$O: 445.2. found: 446.3 [M+H].

This general procedure using Pd(OAc)$_2$ could be used to prepare a variety of (4S)-7-(3- and 2-substituted phenyl)-N-(aryl)-3,4-dihydro-1,4-methanopyrido[2,3-b][1,4]diazepine-5(2H)-carboxamides and (4S)-7-(2-(trifluoromethyl)pyridin-4-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 17. Preparation of (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide Step 1. Synthesis of (4S)-7-chloro-N-(pyridin-2-yl)-3,4-dihydro-1,4-methanopyrido[2,3-b][1,4]diazepine-5(2H)-carboxamide

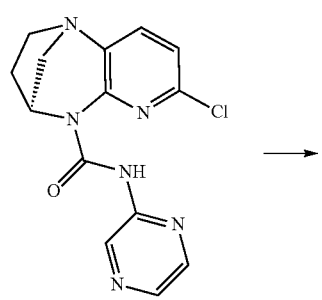

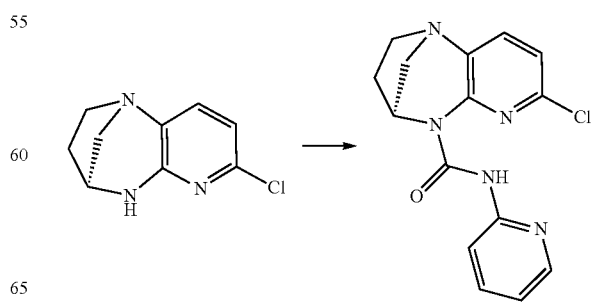

The mixture of (4S)-7-chloro-2,3,4,5-tetrahydro-1,4-methanopyrido[2,3-b][1,4]diazepine (300 mg, 1.53 mmol), phenyl pyridin-2-ylcarbamate (986 mg, 4.59 mmol) and DMAP (188 mg, 1.53 mmol) in DMF (6 mL) was degassed and heated to 80° C. in the sealed flask. After stirring overnight at 80° C., the reaction mixture was cooled to room temp. and partitioned into EtOAc/H$_2$O (150 mL/50 mL). The organic phase was washed with water (20 mL×6), brine (20 mL), dried over Na$_2$SO$_4$ and concentrated under reduced pressure. The concentrate was then purified by column (CH$_2$Cl$_2$/EtOAc=1/1) to afford (4S)-7-chloro-N-(pyridin-2-yl)-3,4-dihydro-1,4-methanopyrido[2,3-b][1,4]diazepine-5(2H)-carboxamide (409 mg, 84%) as an off-white solid. MS (ESI) calcd for C$_{15}$H$_{14}$ClN$_5$O: 315.1. found: 316.1 [M+H].

Step 2. (4S)-7-(3-hydroxyphenyl)-N-(pyridin-2-yl)-3,4-dihydro-1,4-methanopyrido[2,3-b][1,4]diazepine-5(2H)-carboxamide

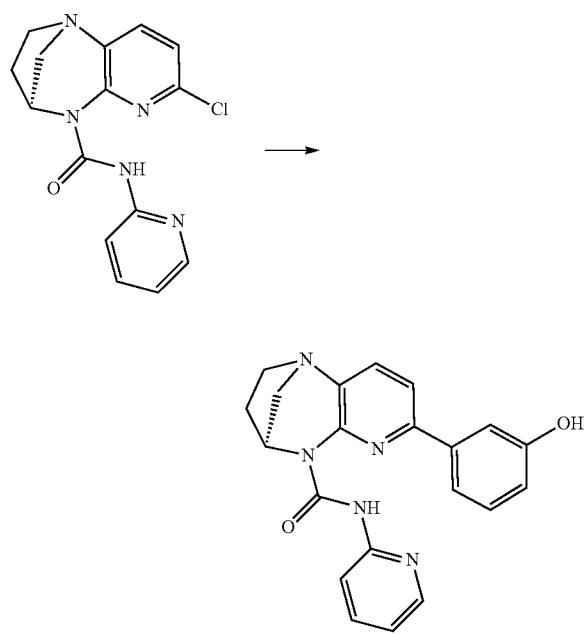

A mixture of (4S)-7-chloro-N-(pyridin-2-yl)-3,4-dihydro-1,4-methanopyrido[2,3-b][1,4]diazepine-5(2H)-carboxamide (80 mg, 0.284 mmol), (3-hydroxyphenyl)boronic acid (78 mg, 0.568 mmol), Pd(OAc)$_2$ (6 mg, 0.0384 mmol), 2-dicyclohexylphosphino-2',4',6'-triisopropylbiphenyl (27 mg, 0.0568 mmol) and Cs$_2$CO$_3$ (185 mg, 0.568 mmol) in dioxane/H$_2$O (3 mL, v/v=9/1) was degassed and heated at 110° C. overnight in sealed tube, then cooled to room temp. and concentrated under reduced pressure. The concentrate was suspended in EtOAc (20 mL), washed with water (5 mL×2), brine (5 mL), dried over Na$_2$SO$_4$, and concentrated. The residue was purified by column (CH$_2$Cl$_2$/EtOAc=1/1) to afford (4S)-7-(3-hydroxyphenyl)-N-(pyridin-2-yl)-3,4-dihydro-1,4-methanopyrido[2,3-b][1,4]diazepine-5(2H)-carboxamide (65 mg, 61%) as an off-white solid. MS (ESI) calcd for C$_{21}$H$_{19}$N$_5$O$_2$: 373.2. found: 374.2 [M+H].

Step 3. Synthesis of (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide

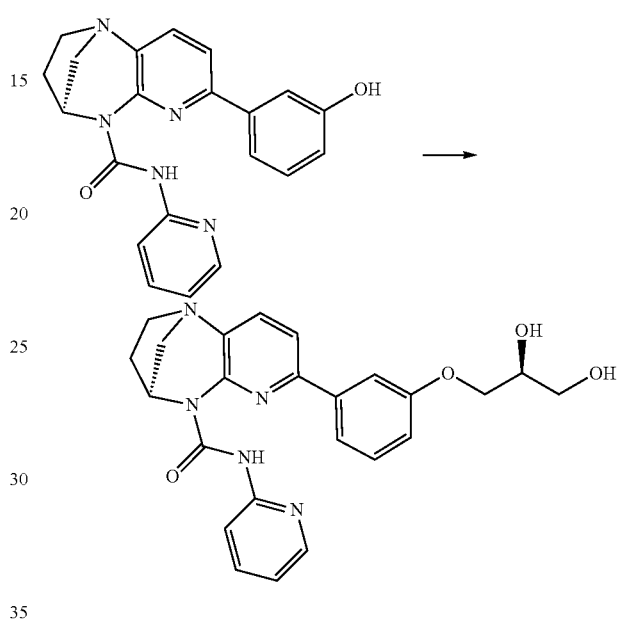

To a solution of (4S)-7-(3-hydroxyphenyl)-N-(pyridin-2-yl)-3,4-dihydro-1,4-methanopyrido[2,3-b][1,4]diazepine-5(2H)-carboxamide (90 mg, 0.241 mmol) in DMF (3 mL) was added NaH (24 mg, 0.603 mmol). After stirring for 30 min at room temp., (S)-4-(chloromethyl)-2,2-dimethyl-1,3-dioxolane (217 mg, 1.45 mmol) was added and the mixture was heated to 85° C. for 32 hrs in a sealed flask. The mixture was cooled to room temp. and diluted with EtOAc and washed with water and brine. The organic phase was dried over Na$_2$SO$_4$ and concentrated. The concentrate was dissolved in CH$_2$Cl$_2$ (3 mL) and HCl solution in dioxane (6 mL) was added. The mixture thus obtained was stirred at room temp. for 4 hrs. The solvent was removed under reduced pressure and the concentrated was suspended in sat. NaHCO$_3$ (5 mL). The mixture was extracted with CH$_2$Cl$_2$ (5 mL×3) and the combined organic phases were dried over Na$_2$SO$_4$ and concentrated. Purification by prep-TLC afforded (4S)-7-(3-((S)-2,3-dihydroxypropoxy)phenyl)-N-(pyridin-2-yl)-3,4-dihydro-1,4-methanopyrido[2,3-b][1,4]diazepine-5(2H)-carboxamide (24 mg, 33%) as an off-white powder. MS (ESI) calcd for C$_{24}$H$_{25}$N$_5$O$_4$: 447.2. found: 448.3 [M+H].

This general procedure could be used to prepare a variety of (4S)-7-(3-((S)-2,3-dihydroxypropoxy)phenyl)-N-(aryl)-3,4-dihydro-1,4-methanopyrido[2,3-b][1,4]diazepine-5(2H)-carboxamides by using the appropriate (4S)-7-(3-hydroxyphenyl)-N-(aryl)-3,4-dihydro-1,4-methanopyrido[2,3-b][1,4]diazepine-5(2H)-carboxamide.

Example 18. Preparation of (4S)-7-(1-propyl-1H-pyrazol-4-yl)-N-(pyridin-3-yl)-3,4-dihydro-1,4-methanopyrido[2,3-b][1,4]diazepine-5(2H)-carboxamide

Step 1. Synthesis of (4S)-7-chloro-N-(pyradyl-3-yl)-3,4-dihydro-1,4-methanopyrido[2,3-b][1,4]diazepine-5(2H)-carboxamide

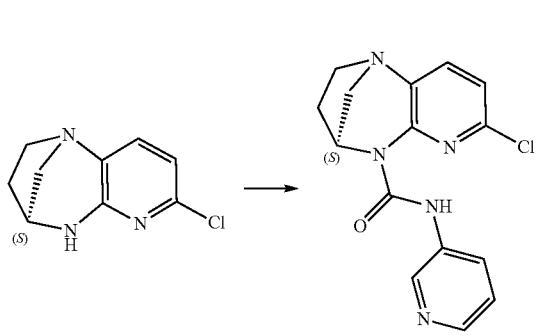

(4S)-7-chloro-2,3,4,5-tetrahydro-1,4-methanopyrido[2,3-b][1,4]diazepine (999 mg, 3.26 mmol, 1.0 eq) as combined with DIEA (1.7 mL, 9.78 mmol, 3.0 eq) into methylene chloride (30 mL) and cooled to 0° C. on an icebath. Triphosgene (482 mg, 1.63 mmol, 0.5 eq) was then added in several small portions to the stirring solution. The icebath was the removed and the reaction was allowed to warm to room temperature. The reaction was then left stirring overnight. Pyridine-3-amine (800 mg, 3.60 mmol, 1.1 eq) was then added slowly in small portions over several minutes. The mixture was then stirred at room temperature for 2 hours. The mixture was then treated with water (100 mL) diluted with EtOAc (100 mL). Phases were separated and the organic phase was dried over Na$_2$SO$_4$ and concentrated. The residue was purified by column chromatography using a gradient of 15-100% (EtOAc/Pentane) to afford (4S)-7-chloro-N-(pyradyl-3-yl)-3,4-dihydro-1,4-methanopyrido[2,3-b][1,4]diazepine-5(2H)-carboxamide (761 mg, yield 47%). MS (ESI) calcd for C$_{15}$H$_{14}$ClN$_5$O 315.1. found: 315.7 [M+H].

Step 2. (4S)-7-(1-propyl-1H-pyrazol-4-yl)-N-(pyridin-3-yl)-3,4-dihydro-1,4-methanopyrido[2,3-b][1,4]diazepine-5(2H)-carboxamide

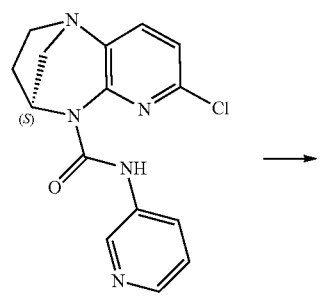

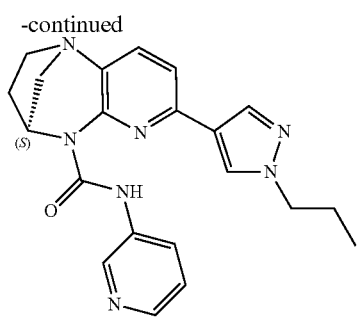

The title compound was prepared using the following protocol: A mixture of (4S)-7-chloro-N-(pyradyl-3-yl)-3,4-dihydro-1,4-methanopyrido[2,3-b][1,4]diazepine-5(2H)-carboxamide (100 mg, 0.32 mmol, 1.0 eq), 1-ethyl-1H-pyrazole-4-boronic acid (151 mg, 0.64 mmol, 2.0 eq), Pd(dppf)Cl$_2$ (26.7 mg, 0.06 mmol, 0.2 eq) and Cs$_2$CO$_3$ (208 mg, 0.64 mmol, 2.0 eq) in dioxane/H$_2$O (5 mL) was stirred at 100° C. for 6 h. Water was added and the mixture was extracted with EtOAc. The organics were dried over anhydrous Na$_2$SO$_4$, concentrated and purified by pre-TLC to give (4S)-7-(1-propyl-1H-pyrazol-4-yl)-N-(pyridin-3-yl)-3,4-dihydro-1,4-methanopyrido[2,3-b][1,4]diazepine-5(2H)-carboxamide. (37.1 mg, yield 30%) MS (ESI) calcd for C$_{21}$H$_{23}$N$_7$O 389.2. found: 390.3 [M+H].

This general procedure using Pd(dppf)Cl$_2$ could be used to prepare a variety of (4S)-7-(pyridin-3-yl)-N-(aryl)-3,4-dihydro-1,4-methanopyrido[2,3-b][1,4]diazepine-5(2H)-carboxamides by substituting the appropriate boronic acid or ester moiety for 2,2-difluorobenzo[d][1,3]dioxole-5-boronic acid.

Example 19: Preparation of (4S)-7-(2,2-difluorobenzo[d][1,3]dioxol-5-yl)-N-(pyridin-3-yl)-3,4-dihydro-1,4-methanopyrido[2,3-b][1,4]diazepine-5(2H)-carboxamide

Step 1. Synthesis of 3-(Pyridin-2-yl)-2H-pyrido[1,2-a][1,3,5]triazine-2,4(3H)-dione

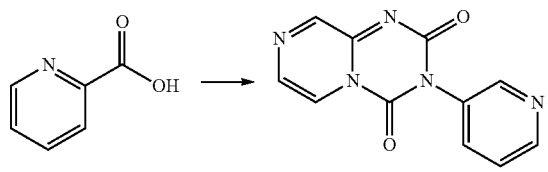 [SMILES: O=C(O)c1ccccn1 ; O=c1nc2cnccn2c(=O)n1-c1cccnc1]

The title compound was prepared using the following protocol: 10.0 g of picolinic acid (81.2 mmol, 1 eq) was suspended in 250 mL of Toluene. 20.0 mL of diphenyl phosphoryl azide (92.6 mmol, 1.14 eq) was added. 13.4 mL of triethylamine (95.8 mmol, 1.18 eq) was added dropwise. The reaction mixture was stirred at room temperature for 30 minutes, then for 2 hrs at 80° C. The reaction mixture was allowed to cool to room temperature. Solids were filtered and washed with ethyl acetate and pentane. The solid was dried under high vacuum. Obtained 6.46 g (66% yield) of a brown solid. MS (ESI) calcd for C$_{15}$H$_{14}$ClN$_5$O: 240.06. found: 241.31 [M+H].

This general procedure could be used to prepare 3-(Pyridin-2-yl)-2H-pyrido[1,2-a][1,3,5]triazine-2,4(3H)-dione and 3-(pyrazin-2-yl)-2H-pyrazino[1,2-a][1,3,5]triazine-2,4(3H)-dione by substituting the appropriate heteroaryl carboxylic acid bearing nitrogen heteroatom in the 2 position on the six membered aromatic ring.

Step 2. Synthesis of (4S)-7-chloro-N-(pyridin-2-yl)-3,4-dihydro-1,4-methanopyrido[2,3-b][1,4]diazepine-5(2H)-carboxamide (4S)-7-chloro-N-(pyridin-2-yl)-3,4-dihydro-1,4-methanopyrido[2,3-b][1,4]diazepine-5(2H)-carboxamide

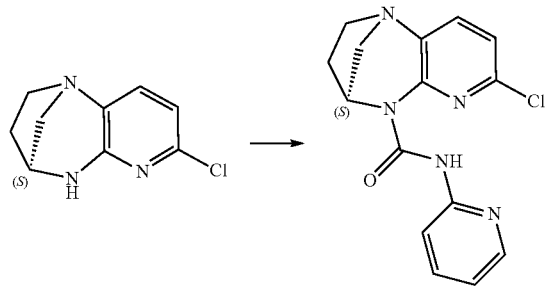

The title compound was prepared using the following protocol: (4S)-7-chloro-2,3,4,5-tetrahydro-1,4-methanopyrido[2,3-b][1,4]diazepine (2.0 g, 10.2 mmol, 1.0 eq) was dissolved in 2-methyl-tetrahydrofuran (40 mL) and treated with NaH (1.7 g, 30.6 mmol, 3.0 eq) at room temperature. The resulting mixture was then stirred at RT for 30 minutes. 3-(pyridin-2-yl)-2H-pyrido[1,2-a][1,3,5]triazine-2,4(3H)-dione (2.4 g, 10.2 mmol, 1.0 eq) was then added and the reaction was then fitted with a reflux condenser and heated to 80° C. overnight. The reaction was then cooled RT, placed on an icebath, and quenched with slow addition of NaHCO$_3$ (65 mL). Crude reaction was then extracted 3×'s EtOAc (75 mL each) and organics were dried over anhydrous MgSO$_4$ and concentrated. Reaction was purified via column chromatography using a gradient of 10-100% EtOAc/Pentane to give (4S)-7-chloro-N-(pyridin-2-yl)-3,4-dihydro-1,4-methanopyrido[2,3-b][1,4]diazepine-5(2H)-carboxamide (4S)-7-chloro-N-(pyridin-2-yl)-3,4-dihydro-1,4-methanopyrido[2,3-b][1,4]diazepine-5(2H)-carboxamide (2.5 g, 78%). MS (ESI) calcd for C$_{15}$H$_{14}$ClN$_5$O: 315.09. found: 316.10 [M+H].

Step 3. Synthesis of (4S)-7-(2,2-difluorobenzo[d][1,3]dioxol-5-yl)-N-(pyridin-2-yl)-3,4-dihydro-1,4-methanopyrido[2,3-b][1,4]diazepine-5(2H)-carboxamide

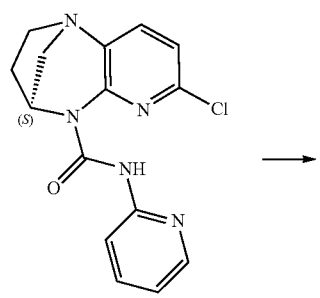

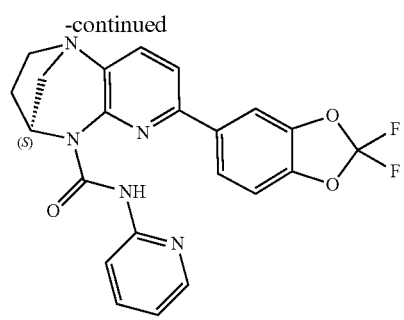

(4S)-7-chloro-N-(pyridin-2-yl)-3,4-dihydro-1,4-methanopyrido[2,3-b][1,4]diazepine-5(2H)-carboxamide (79 mg, 0.250 mmols, 1.0 eq) was combined with Pd$_2$(dba)$_3$ (2.3 mg, 0.006 mmols, 0.02 eq), K$_3$PO$_4$ (80 mg, 0.380 mmols, 2 eq), S-Phos (4.8 mg, 0.012 mmol, 0.05 eq) and the flask was purged with N$_2$ and sealed. N-butanol (1 mL) was then added via syringe and the reaction was heated to 100° C. for 3 hrs. Reaction was then cooled to room temperature filtered then purified directly via reverse phase chromatography using a gradient of 5-95% CH$_3$CN/H$_2$O (0.1% TFA) to give (4S)-7-(2,2-difluorobenzo[d][1,3]dioxol-5-yl)-N-(pyridin-3-yl)-3,4-dihydro-1,4-methanopyrido[2,3-b][1,4]diazepine-5(2H)-carboxamide (11 mg, 10%). C$_{15}$H$_{14}$ClN$_5$O: 437.13. found: 438.17 [M+H].

This general procedure using Pd(dppf)Cl$_2$ could be used to prepare a variety of (4S)-7-(pyridin-2-yl)-N-(aryl)-3,4-dihydro-1,4-methanopyrido[2,3-b][1,4]diazepine-5(2H)-carboxamides and (4S)—N-(pyrazin-2-yl)-3,4-dihydro-1,4-methanopyrido[2,3-b][1,4]diazepine-5(2H)-carboxamide by substituting the appropriate boronic acid or ester moiety for 2,2-difluorobenzo[d][1,3]dioxole-5-boronic acid.

Example 20. Preparation of (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide Step 1. Synthesis of (4S)-7-chloro-N-(5-fluoropyridin-2-yl)-3,4-dihydro-1,4-methanopyrido[2,3-b][1,4]diazepine-5(2H)-carboxamide

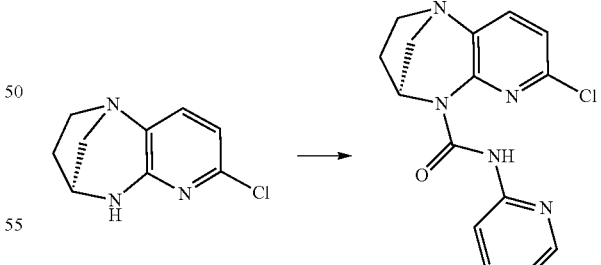

A mixture of (4S)-7-chloro-2,3,4,5-tetrahydro-1,4-methanopyrido[2,3-b][1,4]diazepine (280 mg, 1.43 mmol), 4-chlorophenyl (5-fluoropyridin-2-yl)carbamate (1.14 g, 4.29 mmol) and DMAP (174 mg, 1.43 mmol) in DMF (7 mL) was heated to 80° C. in a sealed flask. After stirring overnight at 80° C., the reaction mixture was cooled to room temp. and diluted with EtOAc (100 mL). The organic phase was washed with water (50 mL×1, 10 mL×6), then brine (50 mL), and dried over Na₂SO₄ and concentrated. The concentrate was then purified by column (CH₂Cl₂/EtOAc=1/1) to afford (4S)-7-chloro-N-(5-fluoropyridin-2-yl)-3,4-dihydro-1,4-methanopyrido[2,3-b][1,4]diazepine-5(2H)-carboxamide (360 mg, 75%) as an off-white solid. MS (ESI) calcd for C₁₅H₁₃ClFN₅O: 333.1.

Step 2. Synthesis of (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide

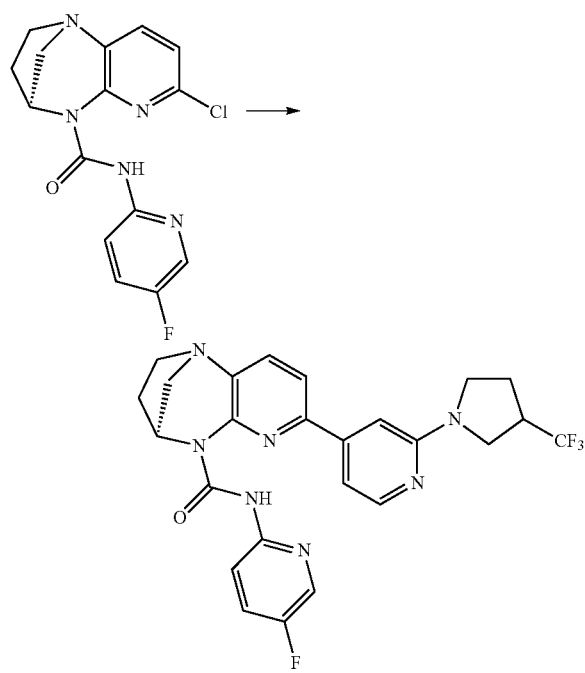

A mixture of (4S)-7-chloro-N-(5-fluoropyridin-2-yl)-3,4-dihydro-1,4-methanopyrido[2,3-b][1,4]diazepine-5(2H)-carboxamide (50 mg, 0.149 mmol), 4-(4,4,5,5-tetramethyl-1,3,2-dioxaborolan-2-yl)-2-(3-(trifluoromethyl)pyrrolidin-1-yl)pyridine (102 mg, 0.298 mmol), PCy₃ (8 mg, 0.0298 mmol), Pd₂(dba)₃ (14 mg, 0.0149 mmol), and K₃PO₄·3H₂O (79 mg, 0.373 mmol) in degassed dioxane/H₂O (2 mL, v/v=9/1) was heated to 120° C. in a sealed flask. After stirring overnight, the mixture was cooled to room temperature and diluted with EtOAc (60 mL). The diluted solution was washed with H₂O (20 mL×1, 10 mL×5) and brine (20 mL), dried over Na₂SO₄ and concentrated. Purification by prep-TLC (CH₂Cl₂/EtOAc/MeOH=3/1/2 drops) afforded (4S)—N-(5-fluoropyridin-2-yl)-7-(2-(3-(trifluoromethyl)pyrrolidin-1-yl)pyridin-4-yl)-3,4-dihydro-1,4-methanopyrido[2,3-b][1,4]diazepine-5(2H)-carboxamide (54 mg, 71%) as an off-white solid. MS (ESI) calcd for C₂₅H₂₃F₄N₇O: 513.2. found: 514.3 [M+H].

This general procedure using Pd₂(dba)₃ could be used to prepare a variety of (4S)-7-(2-(3-substituted-pyrrolidin-1-yl) pyridin-4-yl)-N-(aryl)-3,4-dihydro-1,4-methanopyrido[2,3-b][1,4]diazepine-5(2H)-carboxamides by using the appropriate (4S)-7-chloro-N-(aryl)-3,4-dihydro-1,4-methanopyrido[2,3-b][1,4]diazepine-5(2H)-carboxamide and the appropriate boronic acid or ester.

Example 21. Preparation of (4S)-7-(3-chlorophenyl)-9-methoxy-N-(pyrazin-2-yl)-3,4-dihydro-1,4-methanopyrido[2,3-b][1,4]diazepine-5(2H)-carboxamide Step 1. Synthesis of 2,6-dichloro-4-methoxypyridine

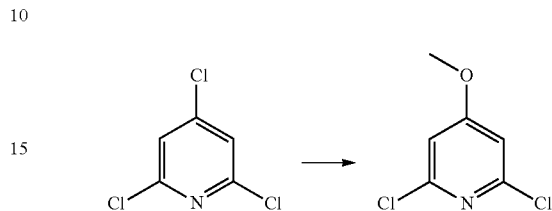

To a solution of 2,4,6-trichloropyridine (30 g, 165 mmol) in MeOH was slowly added sodium methoxide (10.7 g, 197 mmol). The mixture was stirred overnight and quenched with 300 ml of water. The suspension was filtered, washed with water and petroleum ether to obtain 2,6-dichloro-4-methoxypyridine as a white solid (18.0 g, 61% yield). MS (ESI) calcd for C₆H₅Cl₂NO: 176.97.

Step 2. Synthesis of 2,6-dichloro-4-methoxy-3-nitropyridine

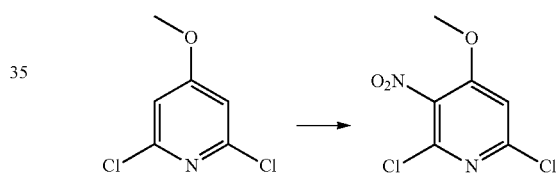

To a solution of 2,6-dichloro-4-methoxypyridine (18.1 g, 102 mmol) in sulfuric acid (110 mL) was added nitric acid (15.6 mL) dropwise at 0° C., and then the mixture was heated to 100° C. for 2 hours. The reaction mixture was poured into ice-water, the suspension was filtered and washed with water to obtain 2,6-dichloro-4-methoxy-3-nitropyridine as a white solid (19.9 g, 88% yield). MS (ESI) calcd for C₆H₄Cl₂N₂O₃: 221.96.

Step 3. Synthesis of (S)-di-tert-butyl 2-((6-chloro-4-methoxy-3-nitropyridin-2-yl)amino)succinate

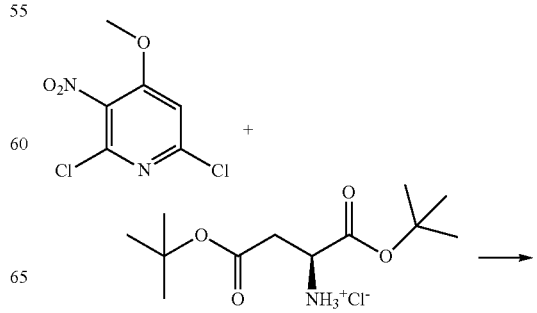

-continued

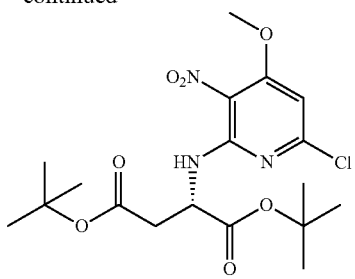

To a solution of 2,6-dichloro-4-methoxy-3-nitropyridine (14.5 g, 65 mmol) and (S)-1,4-di-tert-butoxy-1,4-dioxobutan-2-aminium chloride (22 g, 78 mmol) in DMF (150 mL) was added DIEA (32.3 mL), and the mixture was heated to 80° C. for 3 hours. DMF was removed under vacuum and the residue was dissolved in ethyl acetate, washed with brine, dried over anhydrous $Na_2SO_4$ and purified by flash chromatography (10% Ethyl Acetate in Petroleum Ether) to obtain (S)-di-tert-butyl 2-((6-chloro-4-methoxy-3-nitropyridin-2-yl)amino)succinate as a yellow oil (4.8 g, 16% yield). MS (ESI) calcd for $C_{18}H_{26}ClN_3O_7$: 431.15.

Step 4. Synthesis of (S)-tert-butyl 2-(6-chloro-8-methoxy-2-oxo-1,2,3,4-tetrahydropyrido[2,3-b]pyrazin-3-yl)acetate

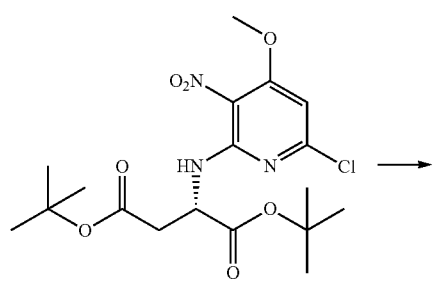

To a mixture of (S)-di-tert-butyl 2-((6-chloro-4-methoxy-3-nitropyridin-2-yl)amino)succinate (4.7 g, 10.9 mmol) in AcOH (60 ml) was added iron powder (6.107 g, 109 mmol) and the reaction mixture was stirred at 100° C. for 2 hours. The reaction was quenched with 1 N NaOH, and extracted with ethyl acetate. The organics were washed with brine and purified by flash chromatography (40% ethyl acetate in petroleum ether) to obtain (S)-tert-butyl 2-(6-chloro-8-methoxy-2-oxo-1,2,3,4-tetrahydropyrido[2,3-b]pyrazin-3-yl)acetate as a yellow oil (1.87 g, 52% yield). MS (ESI) calcd for $C_{14}H_{18}ClN_3O_4$: 327.10.

Step 5. Synthesis of (S)-2-(6-chloro-8-methoxy-1,2,3,4-tetrahydropyrido[2,3-b]pyrazin-3-yl)ethanol

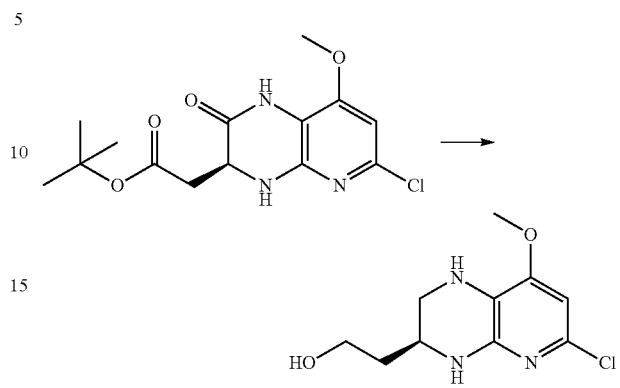

To a solution of (S)-tert-butyl 2-(6-chloro-8-methoxy-2-oxo-1,2,3,4-tetrahydropyrido[2,3-b]pyrazin-3-yl)acetate (1.7 g, 5.2 mmol) in THF (20 mL) was added $BH_3$-$Me_2S$ (5.2 mL, 10 M in $Me_2S$, 52 mL), and the reaction mixture was then heated at 50° C. overnight. Upon cooling to room temperature, the reaction was quenched with dropwise addition of water, then 1N aqueous HCl (10 mL) was added and the mixture was stirred at 50° C. for 2 hours. Saturated $NaHCO_3$ was added and the mixture was extracted with $CH_2Cl_2$, and concentrated to an oil. The oil was treated with TFA (15 mL) in $CH_2Cl_2$ (15 mL) for 2 hours and the DCM and TFA were removed under vacuum. The residue was dissolved in MeOH (20 mL) and $Cs_2CO_3$ (2 g) was added. The mixture was stirred for 1 hour, concentrated and purified by flash chromatography (30:1 $CH_2Cl_2$/MeOH) to obtain (S)-2-(6-chloro-8-methoxy-1,2,3,4-tetrahydropyrido[2,3-b]pyrazin-3-yl)ethanol as a yellow oil (997 mg, 79% yield). MS (ESI) calcd for $C_{10}H_{14}ClN_3O_2$: 243.08.

Step 6. Synthesis of (4S)-7-chloro-9-methoxy-2,3,4,5-tetrahydro-1,4-methanopyrido[2,3-b][1,4]diazepine

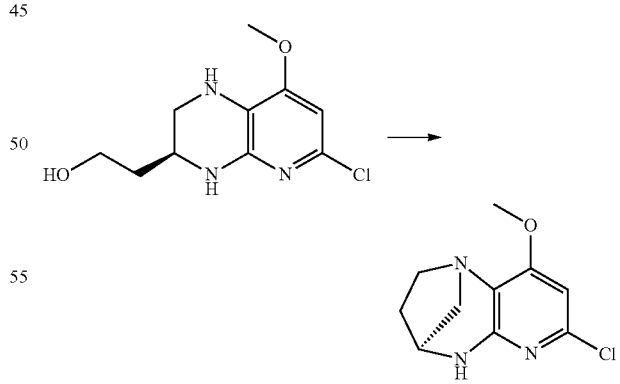

To a solution of $PPh_3$ (1.003 g, 3.83 mmol) in $CH_2Cl_2$ (50 mL) was added DDQ (869 mg, 3.83 mmol), then (S)-2-(6-chloro-8-methoxy-1,2,3,4-tetrahydropyrido[2,3-b]pyrazin-3-yl)ethanol (620 mg, 2.55 mmol) was added. The mixture was stirred for 30 min, concentrated and purified by flash chromatography (33 to 100% Ethyl acetate in Petroleum Ether) to obtain (4S)-7-chloro-9-methoxy-2,3,4,5-tetrahydro-1,4-methanopyrido[2,3-b][1,4]diazepine as a yellow solid (413 mg, 72% yield). MS (ESI) calcd for $C_{10}H_{12}ClN_3O$: 225.07.

Step 7. Synthesis of (4S)-7-(3-chlorophenyl)-9-methoxy-2,3,4,5-tetrahydro-1,4-methanopyrido[2,3-b][1,4]diazepine

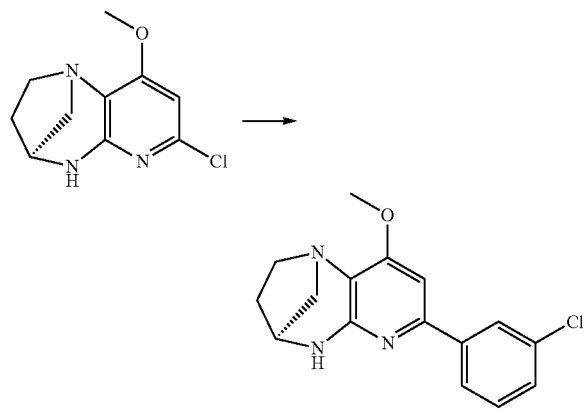

A mixture of (4S)-7-chloro-9-methoxy-2,3,4,5-tetrahydro-1,4-methanopyrido[2,3-b][1,4]diazepine (226 mg, 1.0 mmol), (3-chlorophenyl)boronic acid (187 mg, 1.2 mmol), $Cs_2CO_3$ (654 mg, 2.0 mmol) and Pd(dppf)Cl$_2$.DCM (40 mg, 0.05 mmol) in 10:1 Dioxane/Water (6 mL) solution was microwave heated (130° C.×1 h). The reaction mixture was concentrated to dryness, suspended in $CH_2Cl_2$, washed with sat. NaHCO$_3$, water, brine, dried over MgSO$_4$ and concentrated. The reaction mixture was initially purified by silica gel chromatography (0 to 10% MeOH in $CH_2Cl_2$ gradient) and subsequently purified by Prep HPLC. The reaction was repeated a 2$^{nd}$ time at the same scale, and the combined HPLC fractions were lyophilized to obtain (4S)-9-methoxy-7-(3-chlorophenyl)-2,3,4,5-tetrahydro-1,4-methanopyrido[2,3-b][1,4]diazepine (199 mg, 33% yield). MS (ESI) calcd for $C_{16}H_{16}ClN_3O$: 301.10. found: 302 [M+H].

This general procedure could be used to prepare (4S)-9-methoxy-7-(3-(trifluoromethyl)phenyl)-2,3,4,5-tetrahydro-1,4-methanopyrido[2,3-b][1,4]diazepine by substituting (3-(trifluoromethyl)phenyl)boronic acid for (3-chlorophenyl)boronic acid.

Step 8. Synthesis of (4S)-7-(3-chlorophenyl)-9-methoxy-N-(pyrazin-2-yl)-3,4-dihydro-1,4-methanopyrido[2,3-b][1,4]diazepine-5(2H)-carboxamide

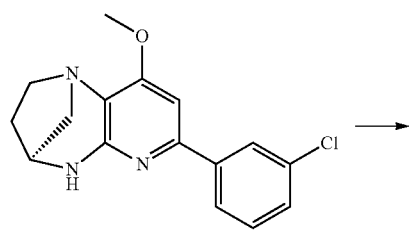

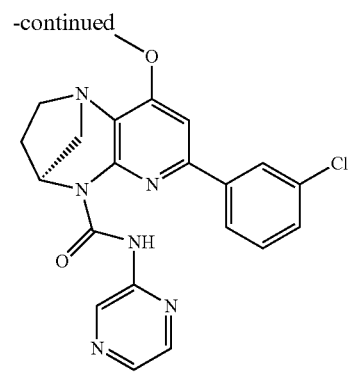

To a solution of (4S)-7-(3-chlorophenyl)-9-methoxy-2,3,4,5-tetrahydro-1,4-methanopyrido[2,3-b][1,4]diazepine (60 mg, 0.2 mmol) in THF (10 mL) was added 60% NaH suspension in mineral oil (24 mg, 1 mmol). The mixture was heated to reflux for 1 hour, 3-(pyrazin-2-yl)-2H-pyrazino[1,2-a][1,3,5]triazine-2,4(3H)-dione (73 mg, 0.3 mmol) was added and the mixture was heated at reflux for an additional 2 hours. The reaction mixture was cooled to room temperature, concentrated to dryness, diluted with sat. NaHCO$_3$, and extracted with $CH_2Cl_2$ (3×). The organics were washed with Brine, dried (Na$_2$SO$_4$), concentrated and purified by prep-HPLC and lyophilized to afford (4S)-7-(3-chlorophenyl)-9-methoxy-N-(pyrazin-2-yl)-3,4-dihydro-1,4-methanopyrido[2,3-b][1,4]diazepine-5(2H)-carboxamide (54 mg, 64% yield). MS (ESI) calcd for $C_{21}H_{19}ClN_6O_2$: 422.13. found: 423 [M+H].

Example 22. Preparation of (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide

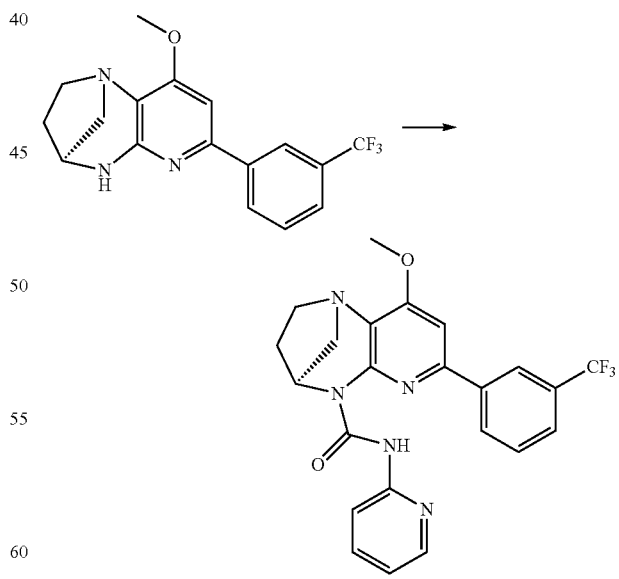

A mixture of the phenyl pyridin-2-ylcarbamate (191.6 mg, 0.8995 mmol), (4S)-9-methoxy-7-(3-(trifluoromethyl)phenyl)-2,3,4,5-tetrahydro-1,4-methanopyrido[2,3-b][1,4]diazepine (150 mg, 0.4477 mmol) and DMAP (65.55 mg, 0.5373 mmol) in 15 ml of acetonitrile were stirred at 60° C.

overnight. The mixture was directly loaded on prep-TLC and purified (using ethyl acetate as eluent) to afford (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide as a white solid (150 mg, Yield: 74%). MS (ESI) calcd for $C_{23}H_{20}F_3N_5O_2$: 455.2. found: 456 [M+H].

This general procedure could be used to prepare (4S)-9-methoxy-N-(Aryl)-7-(3-(trifluoromethyl)phenyl)-3,4-dihydro-1,4-methanopyrido[2,3-b][1,4]diazepine-5(2H)-carboxamides by substituting the appropriate carbamate moiety for phenyl pyridin-2-ylcarbamate.

Example 23. Preparation of (4S)-9-hydroxy-N-(pyridin-2-yl)-7-(3-(trifluoromethyl)phenyl)-3,4-dihydro-1,4-methanopyrido[2,3-b][1,4]diazepine-5(2H)-carboxamide

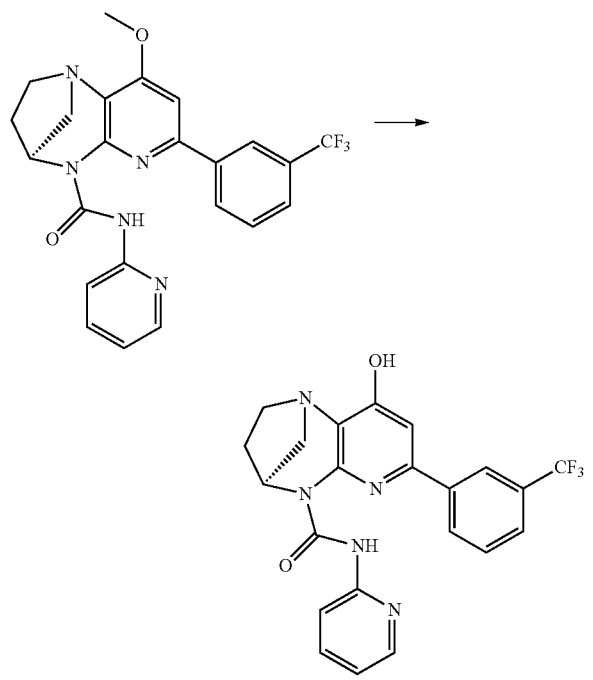

Under nitrogen atmosphere, to the mixture of (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide (50 mg, 0.1098 mmol) in 3 ml of dry $CH_2Cl_2$ was added $BBr_3$ (0.5 mL, 0.5494 mmol) dropwise at 0° C. Then reaction mixture was stirred at 50° C. overnight. Sodium bicarbonate solution (5 mL) and dichloromethane (10 mL) were added to the reaction mixture and the organic layer was washed with water, brine, dried with anhydrous sodium sulfate and concentrated in vacuuo. The crude product was purified by prep-TLC using (1:20 MeOH in $CH_2Cl_2$) as eluent to afford (4S)-9-hydroxy-N-(pyridin-2-yl)-7-(3-(trifluoromethyl)phenyl)-3,4-dihydro-1,4-methanopyrido[2,3-b][1,4]diazepine-5(2H)-carboxamide as a white solid (18 mg, 35% yield). MS (ESI) calcd for $C_{22}H_{18}F_3N_5O_2$: 441.1. found: 442 [M+H].

This general procedure could be used to prepare ((4S)-9-hydroxy-N-(Aryl)-7-(3 (trifluoromethyl)phenyl)-3,4-dihydro-1,4-methanopyrido[2,3-b][1,4]diazepine-5(2H)-carboxamides by substituting the appropriate (4S)-9-methoxy-N-(Aryl)-7-(3-(trifluoromethyl)phenyl)-3,4-dihydro-1,4-methanopyrido[2,3-b][1,4]diazepine-5(2H)-carboxamide for (4S)-9-methoxy-N-(pyridin-2-yl)-7-(3-(trifluoromethyl)phenyl)-3,4-dihydro-1,4-methanopyrido[2,3-b][1,4]diazepine-5(2H)-carboxamide.

Example 24. Preparation of (4S)—N-(4-((3-(3-methyl-3H-diazirin-3-yl)propanamido)methyl)phenyl)-7-(3-(trifluoromethyl)phenyl)-3,4-dihydro-1,4-methanopyrido[2,3-b][1,4]diazepine-5(2H)-carboxamide

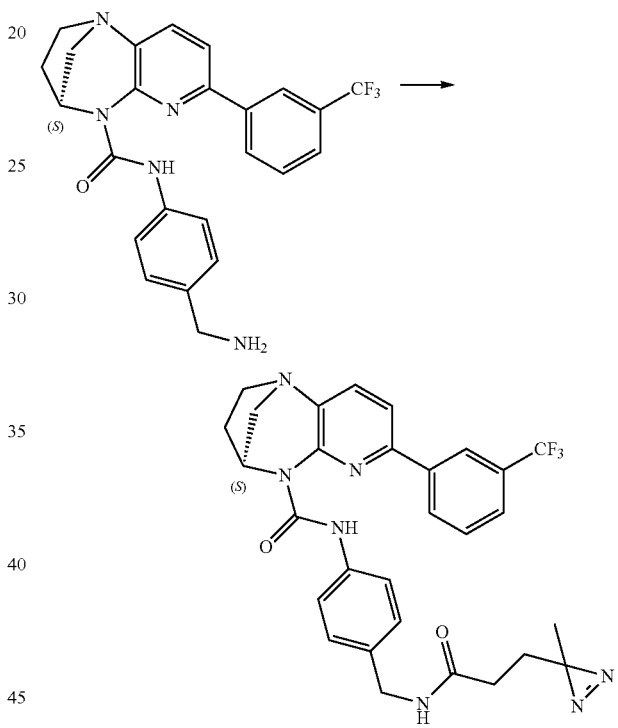

A solution of (4S)—N-(4-(aminomethyl)phenyl)-7-(3-(trifluoromethyl)phenyl)-3,4-dihydro-1,4-methanopyrido[2,3-b][1,4]diazepine-5(2H)-carboxamide hydrochloride (49 mg, 0.1 mmol), 2,5-dioxopyrrolidin-1-yl 3-(3-methyl-3H-diazirin-3-yl)propanoate (23 mg, 0.1 mmol), and triethylamine (70 μL, 0.5 mmol) in DMF (2 mL) was stirred at room temperature for 1 hour. Water (10 mL) and sat. $NaHCO_3$ (5 mL) was added, and the reaction mixture was extracted with $CH_2Cl_2$ (3×) and concentrated to dryness. The crude product was purified on silica gel chromatography (0 to 10% MeOH gradient in $CH_2Cl_2$), concentrated, chased with diethylether and pentane, and dried under vacuum to afford (4S)—N-(4-((3-(3-methyl-3H-diazirin-3-yl)propanamido)methyl)phenyl)-7-(3-(trifluoromethyl)phenyl)-3,4-dihydro-1,4-methanopyrido[2,3-b][1,4]diazepine-5(2H)-carboxamide as a white foam (39 mg, 68% yield). MS (ESI) calcd for $C_{29}H_{28}F_3N_7O_2$: 563.23. found: 564 [M+H].

Example 25: Preparation of (4S)—N-(3-(3-(trifluoromethyl)-3H-diazirin-3-yl)phenyl)-7-(3-(trifluoromethyl)phenyl)-3,4-dihydro-1,4-methanopyrido[2,3-b][1,4]diazepine-5(2H)-carboxamide

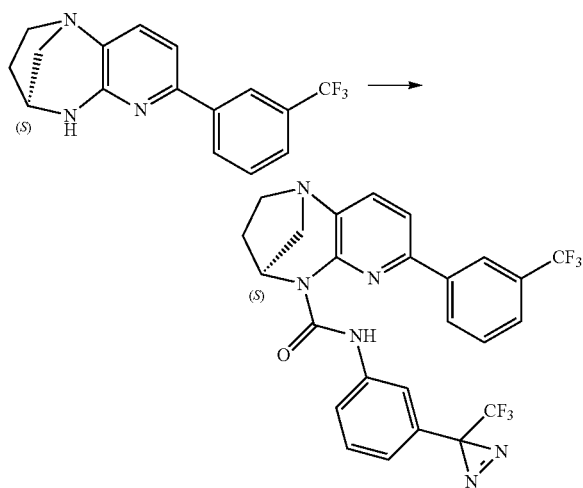

To a solution of (4S)-7-(3-(trifluoromethyl)phenyl)-2,3,4,5-tetrahydro-1,4-methanopyrido[2,3-b][1,4]diazepine (46 mg, 0.15 mmol) and triphosgene (36 mg, 120 mmol) in CH$_2$Cl$_2$ (2 mL) was added triethylamine (56 μL, 0.45 mmol). The reaction mixture was stirred at 40° C. for 2.5 hours and 3-(3-(trifluoromethyl)-3H-diazirin-3-yl)aniline (40 mg, 0.2 mmol) dissolved in CH$_2$Cl$_2$ (1 mL) was added. The reaction mixture was stirred at room temperature for 2 hours. The organic layer was washed with Sat. NaHCO$_3$, water, brine dried over Na$_2$SO$_4$ and conc. The residue was purified by flash chromatography (eluting first with a 0 to 100% CH$_2$Cl$_2$ gradient in pentane, then 0 to 10% MeOH in CH$_2$Cl$_2$) to afford (4S)—N-(3-(3-(trifluoromethyl)-3H-diazirin-3-yl)phenyl)-7-(3-(trifluoromethyl)phenyl)-3,4-dihydro-1,4-methanopyrido[2,3-b][1,4]diazepine-5(2H)-carboxamide (40 mg, 50% yield). MS (ESI) calcd for C$_{25}$H$_{18}$F$_6$N$_6$O: 532.14. found: 533 [M+H].

The above 3-(3-(Trifluoromethyl)-3H-diazirin-3-yl)aniline was prepared according to Biasotti B. et. al., Bioorganic and Medicinal Chemistry, 2003, 11, 2247-2254.

This general procedure was used to prepare a variety of (3-(3-(trifluoromethyl)-3H-diazirin-3-yl)phenyl)ureas by substituting (4S)-7-(3-(trifluoromethyl)phenyl)-2,3,4,5-tetrahydro-1,4-methanopyrido[2,3-b][1,4]diazepine with the appropriate amine.

Example 26. Preparation of (3R,4R)-7-chloro-3-((trimethylsilyl)oxy)-2,3,4,5-tetrahydro-1,4-methanopyrido[2,3-b][1,4]diazepine Step 1. Synthesis of (S)-dimethyl 2-benzamidosuccinate

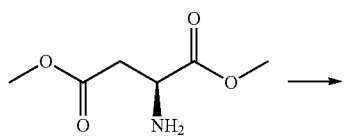

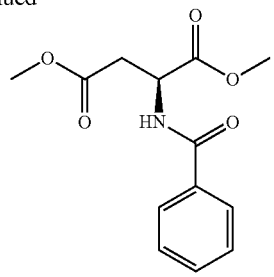

To a 5 L three-necked flask, equipped with a thermometer, a condenser, and a mechanical stirrer was added 161 g (1.00 mol) of L-aspartic acid dimethyl ester, 2500 mL of dichloromethane, and 198 g (1.96 mol) of triethylamine. The solution was cooled to −5° C., then 156 g (1.11 mol) of benzoyl chloride was added, dropwise, keeping the internal temperature at −5° C. The mixture was stirred at −5° C. for 1 h, then it was filtered. The precipitate was washed three times with additional dichloromethane, then the combined filtrate and washings were extracted with saturated aqueous K$_2$CO$_3$ solution. The dichloromethane layer was dried over Na$_2$SO$_4$ and then concentrated in vacuo to give 200 g (75%) of the product as a white solid. MS (ESI) calcd for C$_{13}$H$_{15}$NO$_5$: 265.1.

Step 2. Synthesis of (4S,5S)-dimethyl 2-phenyl-4,5-dihydrooxazole-4,5-dicarboxylate

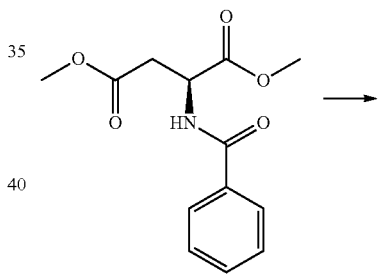

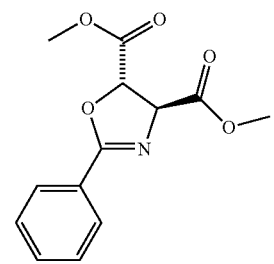

To a 10 L four necked flask, equipped with a thermometer, a mechanical stirrer, and a N$_2$ inlet was added 100 g (0.377 mol) of (S)-dimethyl 2-benzamidosuccinate, then 4 L of dry tetrahydrofuran. The mixture was stirred and cooled to 0° C. To the solution was added 770 mL (0.77 mol) of a 1.0 M solution of lithium bis(trimethylsilyl)amide in tetrahydrofuran, keeping the internal temperature at 0° C. during the addition. The reaction was stirred at 0° C. for 30 min, then it was cooled to −78° C. To this was added a solution of 195 g (0.77 mol) of iodine in 2 L of tetrahydrofuran, dropwise, at −78° C. The reaction was stirred at −78° C. for 1 h, then it was quenched by the addition of 2 L of saturated NH$_4$Cl$_{(aq)}$, and 400 g (2.53 mol) of Na$_2$S$_2$O$_3$. The mixture was stirred at ambient temperature for 30 min, then 2 L of ethyl acetate was added, and the layers were separated. The aqueous phase was extracted with additional ethyl acetate (3×2 L). The combined ethyl acetate layers were dried over Na$_2$SO$_4$ and then concentrated in vacuo. The residue was purified via silica gel chromatography, eluting with 20:1 (v/v) heptanes: ethyl acetate to give 30 g (30%) of the product as a white solid. MS (ESI) calcd for C$_{13}$H$_{13}$NO$_5$: 263.1.

Step 3. Synthesis of (2S,3S)-2-amino-3-hydroxysuccinic acid

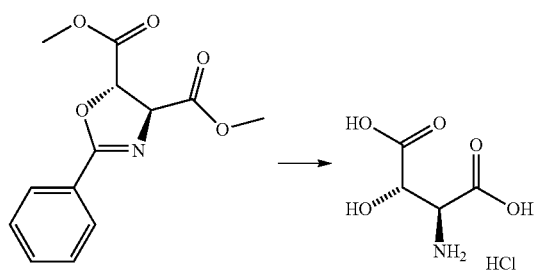 [SMILES: COC(=O)[C@H]1N=C(c2ccccc2)O[C@@H]1C(=O)OC ; N[C@H](C(=O)O)[C@H](O)C(=O)O ; Cl]

To a 500 mL flask equipped with a reflux condenser was added 13 g (50 mmol) of (4S,5S)-dimethyl 2-phenyl-4,5-dihydrooxazole-4,5-dicarboxylate, and 200 mL (2.4 mol) of 12M HCl$_{(aq)}$. The reaction was stirred at 50° C. for 16 h, then the solvent was removed in vacuo. The residue was taken up in 1000 mL of water, and extracted with ethyl acetate until no benzoic acid was present in the aqueous layer by HPLC. The organic layers were discarded, and the aqueous layer was concentrated in vacuo to give 8.6 g (94%) of (2S,3S)-2-amino-3-hydroxysuccinic acid hydrochloride as a white crystalline solid. MS (ESI) calcd for C$_4$H$_7$NO$_5$: 149.0.

Step 4. Synthesis of (2S,3S)-dimethyl 2-amino-3-hydroxysuccinate.0

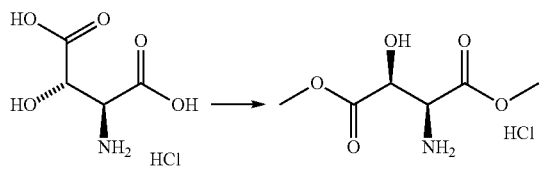

To a 500 mL three-necked flask equipped with a reflux condenser was added 170 mL of methanol. The methanol was cooled to −5° C., then 23.6 g (198 mmol) of SOCl$_2$, was added dropwise. After the addition was complete, 8.6 g (46 mmol) of (2S,3S)-2-amino-3-hydroxysuccinic acid HCl salt was added, and the solution was stirred at ambient temperature for 16 h. The solvent was removed in vacuo, to give crude (2S,3S)-dimethyl 2-amino-3-hydroxysuccinate HCl salt as a yellow oil, which was used without further purification in the next step. MS (ESI) calcd for C$_6$H$_{11}$NO$_5$: 177.1.

Step 5. Synthesis of (2S,3S)-dimethyl 2-((6-chloro-3-nitropyridin-2-yl)amino)-3-hydroxysuccinate

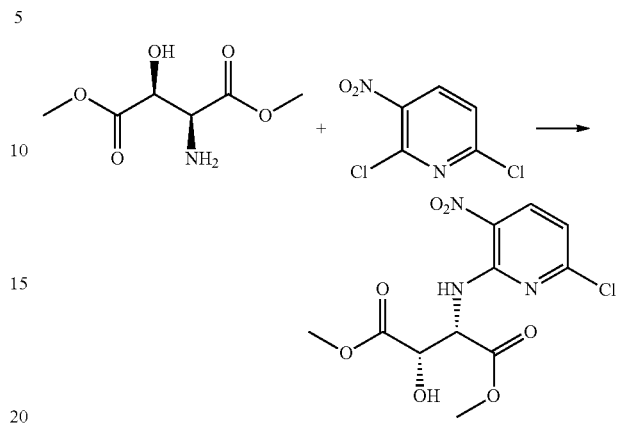

To a 500 mL round-bottomed flask equipped with a reflux condenser was added 18 g (84.3 mmol) of (2S,3S)-dimethyl 2-amino-3-hydroxysuccinate HCl, 29 g (150 mmol) of 2,6-dichloro-3-nitropyridine, 42.5 g NaHCO$_3$ (506 mmol), and 350 mL of THF. The reaction was stirred at 40° C. for 36 h. The solids were filtered away and washed with additional THF (30 mL×3). The filtrate and washings were combined and concentrated in vacuo. The residue was purified via silica gel chromatography, eluting with a gradient of 5:1 (v/v) to 1:1 (v/v) heptanes: ethyl acetate to give 22 g (63%) of (2S,3S)-dimethyl 2-((6-chloro-3-nitropyridin-2-yl) amino)-3-hydroxysuccinate as a yellow crystalline solid. MS (ESI) calcd for C$_{11}$H$_{12}$ClN$_3$O$_7$: 333.0.

This procedure could be used to prepare dimethyl 2-((6-chloro-3-nitropyridin-2-yl)amino)-3-hydroxysuccinate by substituting dimethyl 2-amino-3-hydroxysuccinate hydrochloride for (2S,3S)-dimethyl 2-amino-3-hydroxysuccinate hydrochloride.

Step 6. Synthesis of (S)-methyl 2-((S)-6-chloro-2-oxo-1,2,3,4-tetrahydropyrido[2,3-b]pyrazin-3-yl)-2-hydroxyacetate

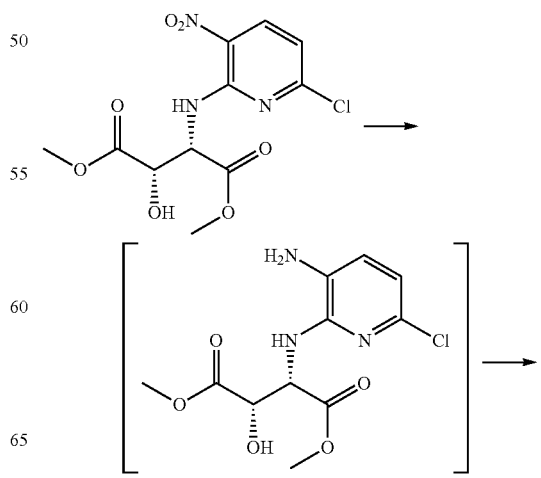

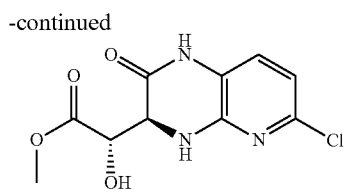

A slurry of 10 g Raney Ni in H₂O was decanted to remove the water, diluted with 2-propanol and decanted again to give a wet mixture weighing 10 g. To a 500 mL flask was added 10 g (30 mmol) of (2S,3S)-dimethyl 2-((6-chloro-3-nitropyridin-2-yl)amino)-3-hydroxysuccinate, 200 mL of 2-propanol, then 10 g of Raney Ni. The reaction was put under vacuum and back filled with hydrogen 3 times, then it was stirred under 1 atm. of H₂ for 3 h, or until no starting nitro compound remained by HPLC. The Raney Ni was filtered away, then the filtrate was put into a 500 mL round bottomed flask, and 5 mL (87 mmol) of glacial acetic acid was added. The flask was fitted with a reflux condenser, then the reaction was stirred at 80° C. for 16 h, until no intermediate diaminopyridine was present by HPLC. The solvents were removed in vacuo. The residue was purified via silica gel chromatography, eluting with 5/1 (v/v) heptanes/ethyl acetate to give 6 g (72%) of the product as a light yellow solid. MS (ESI) calcd for $C_{10}H_{10}ClN_3O_4$: 271.0.

This procedure could be used to prepare methyl 2-(6-chloro-2-oxo-1,2,3,4-tetrahydropyrido[2,3-b]pyrazin-3-yl)-2-hydroxyacetate by substituting dimethyl 2-((6-chloro-3-nitropyridin-2-yl)amino)-3-hydroxysuccinate for (2S,3S)-dimethyl 2-((6-chloro-3-nitropyridin-2-yl)amino)-3-hydroxysuccinate.

Step 7. Synthesis of (S)-1-((R)-6-chloro-1,2,3,4-tetrahydropyrido[2,3-b]pyrazin-3-yl)ethane-1,2-diol

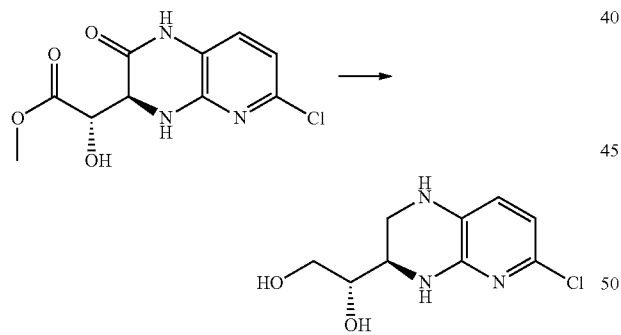

To a 100 mL 3-necked round bottomed flask equipped with a reflux condenser and a thermometer was added 20 mL of tetrahydrofuran, then 1.19 g (30 mmol) of LiAlH₄. The stirred mixture was cooled to −5° C., then a solution of 0.5 g (2 mmol) of (S)-methyl 2-((S)-6-chloro-2-oxo-1,2,3,4-tetrahydropyrido[2,3-b]pyrazin-3-yl)-2-hydroxyacetate in 20 mL of tetrahydrofuran was added dropwise. The reaction was stirred at 70° C. for 16 h, or until the reaction was complete by HPLC. (Lactam reduction was slower than ester reduction.) The reaction was cooled to −10° C., then 1.2 mL of water was added, dropwise, and the reaction was stirred for 10 min. Next, 1.2 mL of 15% (w/v) NaOH(aq.) was added dropwise, and the reaction was stirred for 20 min. To complete the quench of the excess LiAlH₄, another 3.6 mL of water was added dropwise, then the reaction was stirred for 20 min. The reaction was filtered, and the precipitate was washed with tetrahydrofuran (3×20 mL). The combined filtrate and washings were concentrated in vacuo to give about 1.5 g of a solid. This was diluted with 16 mL of ethyl acetate and filtered. The filtrate was concentrated in vacuo to give 310 mg (80%) of the product as a brown solid. MS (ESI) calcd for $C_9H_{12}ClN_3O_2$: 229.1.

This procedure could be used to prepare 1-(6-chloro-1,2,3,4-tetrahydropyrido[2,3-b]pyrazin-3-yl)ethane-1,2-diol by substituting methyl 2-((S)-6-chloro-2-oxo-1,2,3,4-tetrahydropyrido[2,3-b]pyrazin-3-yl)-2-hydroxyacetate for (S)-methyl 2-(6-chloro-2-oxo-1,2,3,4-tetrahydropyrido[2,3-b]pyrazin-3-yl)-2-hydroxyacetate.

Step 8. Synthesis of (1S,4R)-7-chloro-2,3,4,5-tetrahydro-1,4-methanopyrido[2,3-b][1,4]diazepin-3-ol

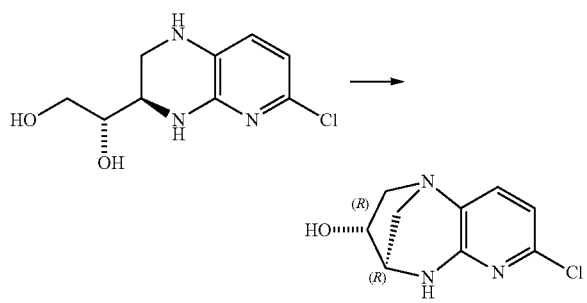

To a 10 mL round bottomed flask equipped with a reflux condenser was added 250 mg (1.1 mmol) of (S)-1-((R)-6-chloro-1,2,3,4-tetrahydropyrido[2,3-b]pyrazin-3-yl)ethane-1,2-diol, then 5 mL of 48% HBr$_{(aq)}$. The reaction was heated at 105° C. for 16 h, or until HPLC showed that all of the starting material had been consumed. The reaction was cooled, then $K_2CO_{3(S)}$ was slowly added until pH=8. The solvent was removed in vacuo, then the residue was purified via silica gel chromatography, eluting with 20/1 (v/v) dichloromethane/methanol to give 110 mg (47%) of the product as a white crystalline solid. MS (ESI) calcd for $C_9H_{10}ClN_3O$: 211.1.

This procedure could be used to prepare 7-chloro-2,3,4,5-tetrahydro-1,4-methanopyrido[2,3-b][1,4]diazepin-3-ol by substituting 6-chloro-1,2,3,4-tetrahydropyrido[2,3-b]pyrazin-3-yl)ethane-1,2-diol for (S)-1-((R)-1-(6-chloro-1,2,3,4-tetrahydropyrido[2,3-b]pyrazin-3-yl)ethane-1,2-diol.

Step 9. Synthesis of (1S,4R)-7-chloro-3-((trimethylsilyl)oxy)-2,3,4,5-tetrahydro-1,4-methanopyrido[2,3-b][1,4]diazepine

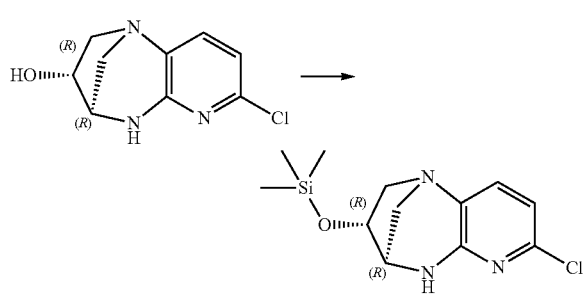

To a 10 mL round bottomed flask was added 1.68 g (7.9 mmol) of (1S,4R)-7-chloro-2,3,4,5-tetrahydro-1,4-methanopyrido[2,3-b][1,4]diazepin-3-ol, 5 mL of N,N-dimethylformamide, and 2.8 mL (24 mmol) of 2,6-dimethylpyridine. The mixture was stirred until it was homogeneous, then 1.5 mL (12 mmol) of chlorotrimethylsilane was added, dropwise, at ambient temperature. The reaction was stirred at ambient temperature for 3 h, then it was diluted with 100 mL of dichloromethane, and extracted with saturated NaHCO$_{3(aq)}$ (1×50 mL), then brine (3×50 mL), and concentrated in vacuo to give 2.04 g (91%) of the product as a white crystalline solid. MS (ESI) calcd for C$_{12}$H$_{18}$ClN$_3$OSi: 283.1.

This procedure could be used to prepare 7-chloro-3-((trimethylsilyl)oxy)-2,3,4,5-tetrahydro-1,4-methanopyrido[2,3-b][1,4]diazepine by substituting 7-chloro-2,3,4,5-tetrahydro-1,4-methanopyrido[2,3-b][1,4]diazepin-3-ol for (1S,4R)-7-chloro-2,3,4,5-tetrahydro-1,4-methanopyrido[2,3-b][1,4]diazepin-3-ol.

Example 27. Preparation of (3R,4R)-7-(3-(trifluoromethyl)phenyl)-3-((trimethylsilyl)oxy)-2,3,4,5-tetrahydro-1,4-methanopyrido[2,3-b][1,4]diazepine

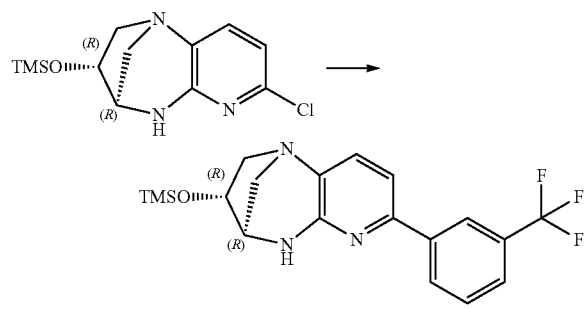

A mixture of (3R,4R)-7-chloro-3-((trimethylsilyl)oxy)-2,3,4,5-tetrahydro-1,4-methanopyrido[2,3-b][1,4]diazepine (283 mg, 1.0 mmol), (3-(trifluoromethyl)phenyl)boronic acid (285 mg, 1.5 mmol), XPhos (24 mg, 0.05 mmol), Pd(OAc)$_2$ (5.6 mg, 0.025 mmol), Cs$_2$CO$_3$ (977 mg, 3.0 mmol) in 10:1 dioxane:water (8.8 mL) was degassed and microwave heated at 100° C. for 25 min. The dioxane layer was concentrated and purified by flash chromatography (0 to 7% MeOH gradient in CH$_2$Cl$_2$) to obtain (3R,4R)-7-(3-(trifluoromethyl)phenyl)-3-((trimethylsilyl)oxy)-2,3,4,5-tetrahydro-1,4-methanopyrido[2,3-b][1,4]diazepine. The fractions were concentrated, dissolved in EtOAc, washed with sat. NaHCO$_3$, water, brine, dried (Na$_2$SO$_4$) and concentrated to obtain (3R,4R)-7-(3-(trifluoromethyl)phenyl)-3-((trimethylsilyl)oxy)-2,3,4,5-tetrahydro-1,4-methanopyrido[2,3-b][1,4]diazepine (338 mg, 85% yield). MS (ESI) calcd for C$_{19}$H$_{22}$F$_3$N$_3$OSi: 393.15. found: 394 [M+H].

This general coupling procedure using Sodium hydride could be used to prepare (3R,4R)-3-hydroxy-N-aryl-7-(3-(trifluoromethyl)phenyl)-3,4-dihydro-1,4-methanopyrido[2,3-b][1,4]diazepine-5(2H)-carboxamide by substituting the appropriate aryl isocyanate or aryl isocyante dimer for 3-(pyridin-2-yl)-2H-pyrido[1,2-a][1,3,5]triazine-2,4(3H)-dione. The non-stereospecific series could be made starting with the 7-(3-(trifluoromethyl)phenyl)-3-((trimethylsilyl)oxy)-2,3,4,5-tetrahydro-1,4-methanopyrido[2,3-b][1,4]diazepine.

Example 28. Preparation of (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide

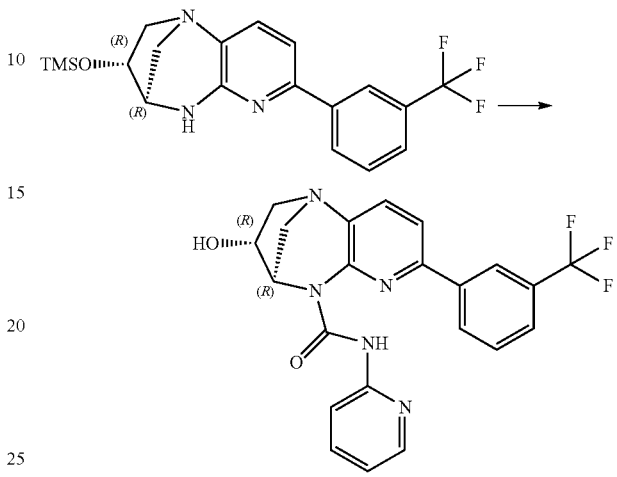

A solution of (3R,4R)-7-(3-(trifluoromethyl)phenyl)-3-((trimethylsilyl)oxy)-2,3,4,5-tetrahydro-1,4-methanopyrido[2,3-b][1,4]diazepine (215 mg, 0.55 mmol) and 60% NaH in mineral oil (66 mg, 1.65 mmol) in THF (30 mL) was heated to reflux for 20 min. 3-(pyridin-2-yl)-2H-pyrido[1,2-a][1,3,5]triazine-2,4(3H)-dione (197 mg, 0.82 mmol) was added and the reaction mixture was heated at reflux for 2 hours. The reaction mixture was cooled, concentrated to dryness, diluted with CH$_2$Cl$_2$. The organic layer was washed with sat. NaHCO$_3$, water, brine dried (Na$_2$SO$_4$) and concentrated to dryness. The residue was purified by Prep-HPLC, and the fractions were concentrated to dryness and triturated with a mixture of diethyl ether and pentane to obtain (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate as a white solid (132 mg, 44% yield). MS (ESI) calcd for C$_{22}$H$_{18}$F$_3$N$_5$O$_2$: 441.14. found: 442 [M+H].

Example 29. Preparation of (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide

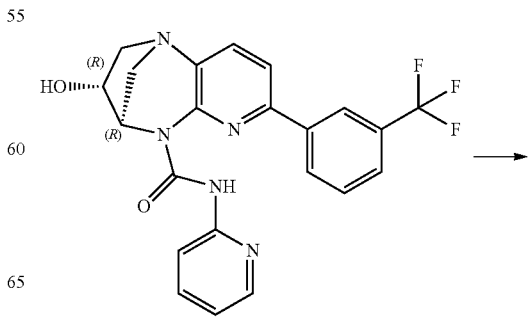

113

-continued

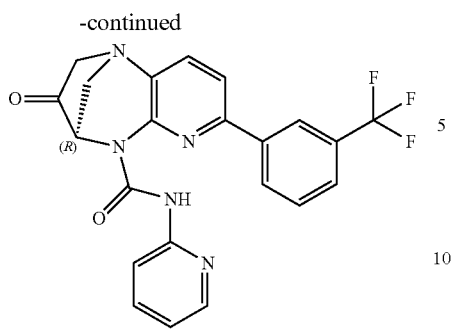

To a solution of (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (92 mg, 0.166 mmol) in CH₂Cl₂ (20 mL) was added Dess-Martin Periodane (105 mg, 0.25 mmol). The reaction mixture was stirred at room temperature for 1.5 hours. A second aliquot of Dess-Martin-Periodane (105 mg, 0.25 mmol) was charged and the reaction mixture was stirred at room temperature for 0.5 hours. A solution of Sat. NaHCO₃ (aq) was added and the reaction mixture was extracted with CH₂Cl₂. The organic layer was washed with brine, dried (Na₂SO₄), and concentrated to a white foam. The residue was purified by flash chromatography (0 to 100% Ethyl Acetate in Penate), and then purified by Prep-HPLC and lyophilized to obtain (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (62 mg, 67% yield). MS (ESI) calcd for C₂₂H₁₆F₃N₅O₂: 439.13. found: 440 [M+H].

This general procedure was used to prepare (4R)—N-(3-(oxazol-5-yl)phenyl)-3-oxo-7-(3-(trifluoromethyl)phenyl)-3,4-dihydro-1,4-methanopyrido[2,3-b][1,4]diazepine-5(2H)-carboxamide by substituting (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide with (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5(2H)-carboxamide Example 30. Preparation of (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide

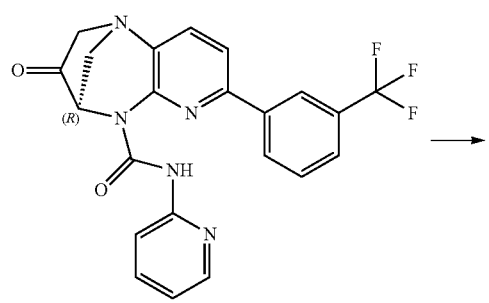

114

-continued

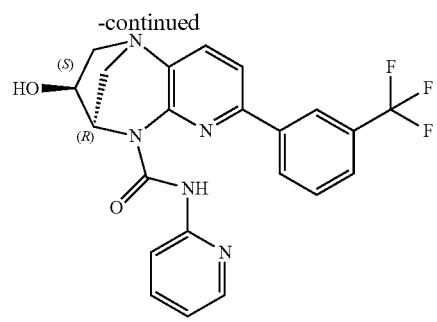

To a solution of (4R)-3-oxo-N-(pyridin-2-yl)-7-(3-(trifluoromethyl)phenyl)-3,4-dihydro-1,4-methanopyrido[2,3-b][1,4]diazepine-5(2H)-carboxamide 2,2,2-trifluoroacetate (50 mg, 0.09 mmol) in THF (10 mL) at −78° C., under nitrogen atmosphere, was dropwise added a solution of 1 M SuperHydride in THF (0.45 mL, 0.45 mmol). The reaction mixture was stirred at −78° C. for 30 min, quenched with the addition of EtOAc (5 mL), warmed to room temperature and concentrated. The residue was purified by flash chromatography (0 to 10% MeOH gradient in CH₂Cl₂) to afford (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide (22 mg, 55% yield). MS (ESI) calcd for C₂₂H₁₈F₃N₅O₂: 441.14. found: 442 [M+H].

Example 31. Preparation of (3S,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl acetate

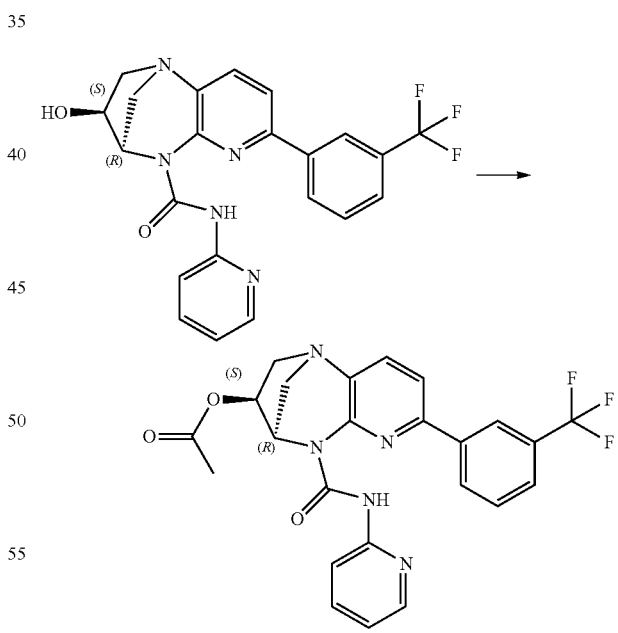

To a solution of (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide (15 mg, 0.034 mmol) in CH₂Cl₂ was added triethylamine (10 μL, 0.07 mmol) followed by DMAP (1 mg) and acetic anhydride (10 μL, 0.011 mmol). The reaction mixture was stirred at room temperature for 2 hours, concentrated to dryness and purified by Prep-HPLC. The fractions were lyophilized to obtain (3S,4R)-5-(pyridin-2-ylcarbamoyl)-7-(3-(trifluoromethyl) phenyl)-2,3,4,5-tetrahydro-1,4-methanopyrido[2,3-b][1,4] diazepin-3-yl acetate 2,2,2-trifluoroacetate (5.9 mg, 29% yield). MS (ESI) calcd for $C_{24}H_{20}F_3N_5O_3$: 483.15. found: 484 [M+H].

This general procedure was used to prepare (3R,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl acetate by substituting (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide with (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide.

This general procedure was used to prepare (3R,4R)-5-(pyridin-2-ylcarbamoyl)-7-(3-(trifluoromethyl)phenyl)-2,3,4,5-tetrahydro-1,4-methanopyrido[2,3-b][1,4]diazepin-3-yl benzoate substituting (3S,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide with (3R,4R)-3-hydroxy-N-(pyridin-2-yl)-7-(3-(trifluoromethyl)phenyl)-3,4-dihydro-1,4-methanopyrido[2,3-b][1,4]diazepine-5(2H)-carboxamide, and substituting acetic anhydride and benzoic anhydride.

Example 32. Preparation of (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5(2H)-carboxamide

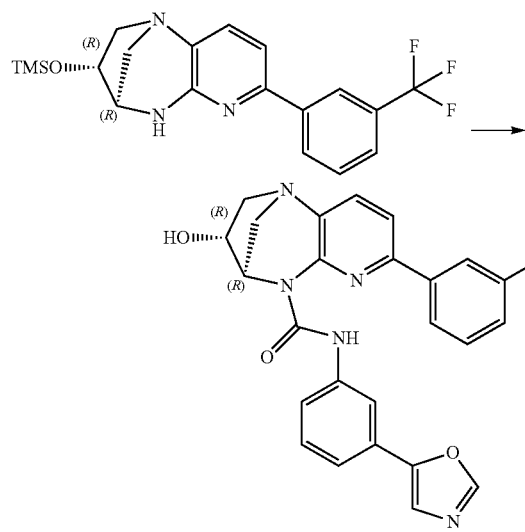

A solution of (3R,4R)-7-(3-(trifluoromethyl)phenyl)-3-((trimethylsilyl)oxy)-2,3,4,5-tetrahydro-1,4-methanopyrido[2,3-b][1,4]diazepine (284 mg, 0.722 mmol), phenyl (3-(oxazol-5-yl)phenyl)carbamate (404 mg, 1.44 mmol) and DMAP (44 mg, 0.36 mmol) in $CH_3CN$ (20 mL) was heated at 60° C. (overnight) and then 80° C. (2 h). Then to the reaction mixture was added an additional quantity of phenyl (3-(oxazol-5-yl)phenyl)carbamate (202 mg, 0.72 mmol) and DMAP (88 mg, 0.72 mmol). The reaction mixture was heated at 80° C. overnight and concentrated to dryness. The reaction mixture was initially purified by column chromatography (0 to 100% ethyl acetate in pentane gradient) and then purified by prep-HPLC and lyophilized to obtain (3R,4R)-3-hydroxy-N-(3-(oxazol-5-yl)phenyl)-7-(3-(trifluoromethyl)phenyl)-3,4-dihydro-1,4-methanopyrido[2,3-b][1,4]diazepine-5(2H)-carboxamide as the trifluoroacetic acid salt (161 mg, 36%). MS (ESI) calcd for $C_{26}H_{20}F_3N_5O_3$: 507.15. found: 508 [M+H].

Example 33. Preparation of (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide Step 1. Synthesis of (3R,4R)-3-((tert-butyldimethylsilyl)oxy)-7-chloro-2,3,4,5-tetrahydro-1,4-methanopyrido[2,3-b][1,4]diazepine

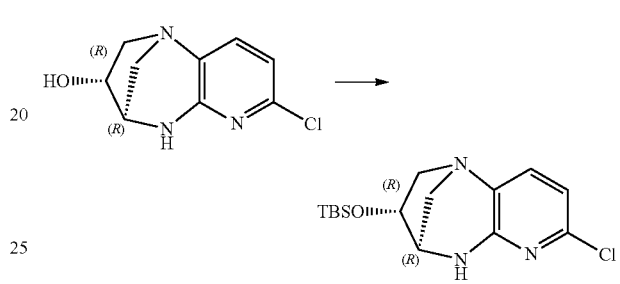

TBSOTf (111 mg, 0.42 mmol) was added slowly to a solution of (3R,4R)-7-chloro-2,3,4,5-tetrahydro-1,4-methanopyrido[2,3-b][1,4]diazepin-3-ol (90 mg, 0.28 mmol) in 2 mL of $CH_2Cl_2$ under $N_2$ at −20° C. The mixture was stirred for 1 h then washed with 1N HCl and water, dried over anhydrous $Na_2SO_4$ and evaporated to dryness. The residue was purified by Prep.TLC (DCM/EA=20:1) to give (3R,4R)-3-((tert-butyldimethylsilyl)oxy)-7-chloro-2,3,4,5-tetrahydro-1,4-methanopyrido[2,3-b][1,4]diazepine as a yellow solid (90 mg, 73% yield), MS (ESI) calcd for $C_{15}H_{24}ClN_3OSi$: 325.14;

Step 2. Synthesis of (3R,4R)-3-((tert-butyldimethylsilyl)oxy)-7-(3-chlorophenyl)-2,3,4,5-tetrahydro-1,4-methanopyrido[2,3-b][1,4]diazepine

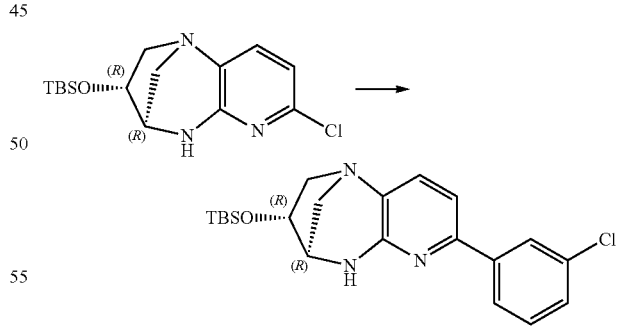

A mixture of (3R,4R)-3-((tert-butyldimethylsilyl)oxy)-7-chloro-2,3,4,5-tetrahydro-1,4-methanopyrido[2,3-b][1,4]diazepine (1.08 g, 3.32 mmol), (3-chlorophenyl)boronic acid (570 mg, 3.65 mmol), $CS_2CO_3$ (2.48 g, 7.63 mmol), Pd(dppf)$Cl_2$ (300 mg, 0.33 mmol) in dioxane/$H_2O$ (11 mL, 10:1) was heated at 130° C. for 2.5 h in a microwave reactor. The mixture was poured into water, and diluted with EtOAc. The organic phase washed with water and brine, dried over anhydrous $Na_2SO_4$, and evaporated to dryness. The residue was purified by prep. HPLC to give (3R,4R)-3-((tert-butyldimethylsilyl)oxy)-7-(3-chlorophenyl)-2,3,4,5-tetrahydro-1,4-methanopyrido[2,3-b][1,4]diazepine as a light yellow solid (850 mg, 63% yield), MS (ESI) calcd for $C_{21}H_{28}ClN_3OSi$: 401.17;

This general procedure was used to prepare (3R,4R)-3-((tert-butyldimethylsilyl)oxy)-7-(5-(trifluoromethyl)pyridin-3-yl)-2,3,4,5-tetrahydro-1,4-methanopyrido[2,3-b][1,4]diazepine.

Step 3. Synthesis of (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide

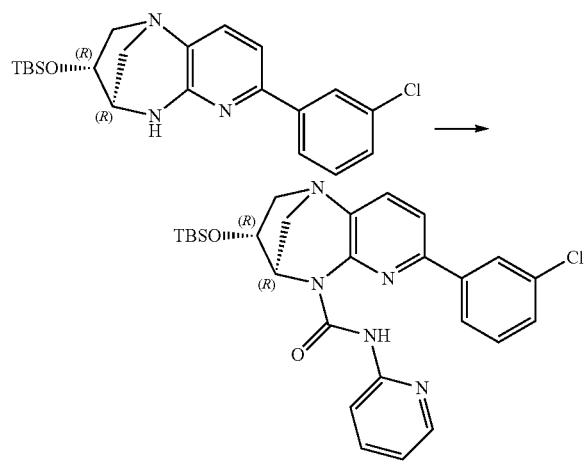

A mixture of phenyl pyridine-2-ylcarbamate (86 mg, 0.20 mmol), (3R,4R)-3-((tert-butyldimethylsilyl)oxy)-7-(3-chlorophenyl)-2,3,4,5-tetrahydro-1,4-methanopyrido[2,3-b][1,4]diazepine (80 mg, 0.20 mmol) and DMAP (24 mg, 0.20 mmol) in 5 ml of MeCN was stirred at 65° C. overnight. The crude reaction mixture was purified by prep. TLC eluting with DCM:EA=20:1 to give (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide (110 mg). MS (ESI) calcd for $C_{27}H_{32}ClN_5O_2Si$: 521.2;

Step 4. Synthesis of (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide

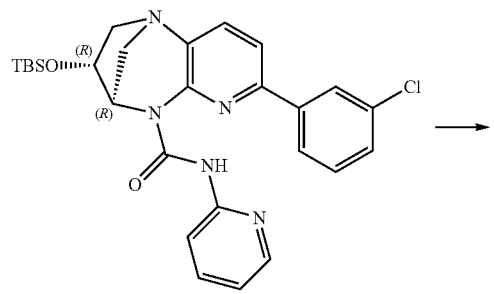

A solution of (3R,4R)-3-((tert-butyldimethylsilyl)oxy)-7-(3-chlorophenyl)-N-(pyridin-2-yl)-3,4-dihydro-1,4-methanopyrido[2,3-b][1,4]diazepine-5(2H)-carboxamide (110 mg, 0.21 mmol) in 10 mL of THF and conc. HCl (1 mL) was stirred at room temperature for 48 h. The mixture was concentrated under reduced pressure. The pH was adjusted to 8 using sat. aq NaHCO$_3$. The mixture was extracted with EtOAc, washed with brine, dried (Na$_2$SO$_4$) and concentrated. The residue was triturated in EtOAc to give (3R,4R)-7-(3-chlorophenyl)-3-hydroxy-N-(pyridin-2-yl)-3,4-dihydro-1,4-methanopyrido[2,3-b][1,4]diazepine-5(2H)-carboxamide (34 mg, 39% yield) as a white solid MS (ESI) calcd for $C_{21}H_{18}ClN_5O_2$: 407.1. found: 408 [M+H].

Example 34. Preparation of (3R,4R)—N-(4,5-dimethylthiazol-2-yl)-3-hydroxy-7-(3-(trifluoromethyl)phenyl)-3,4-dihydro-1,4-methanopyrido[2,3-b][1,4]diazepine-5(2H)-carboxamide

Step 1. Synthesis of (3R,4R)-7-(3-(trifluoromethyl)phenyl)-2,3,4,5-tetrahydro-1,4-methanopyrido[2,3-b][1,4]diazepin-3-ol

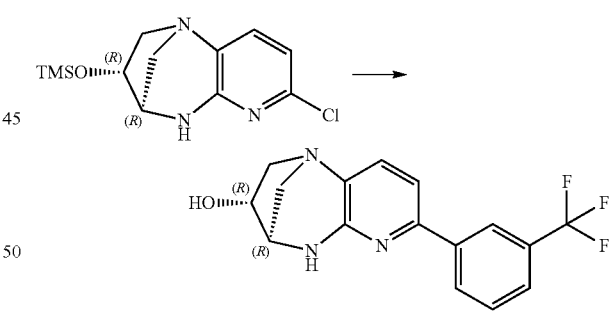

A mixture of (3R,4R)-7-chloro-3-((trimethylsilyl)oxy)-2,3,4,5-tetrahydro-1,4-methanopyrido[2,3-b][1,4]diazepine (1 g, 3.53 mmol), ((3-trifluoromethyl)phenyl)boronic acid (1.34 g, 7.06 mmol), Cs$_2$CO$_3$ (3.44 g, 10.6 mmol), Pd(dppf)Cl$_2$ (300 mg, 0.35 mmol) in dioxane/H$_2$O (30 mL, 10:1) was reacted under microwave at 130° C. for 2.5 h. Then reaction mixture was poured into water, extracted with EtOAc, washed with water then brine, dried (Na$_2$SO$_4$), concentrated. The residue was purified through silica gel chromatography (PE/EA=4:1) to give (3R,4R)-7-(3-(trifluoromethyl)phenyl)-2,3,4,5-tetrahydro-1,4-methanopyrido[2,3-b][1,4]diazepin-3-ol (600 mg, 39% yield). MS (ESI) calcd for $C_{16}H_{14}F_3N_3O$: 321.1;

Step 2. Synthesis of (3R,4R)-3-((tert-butyldimethyl-silyl)oxy)-7-(3-(trifluoromethyl)phenyl)-2,3,4,5-tetrahydro-1,4-methanopyrido[2,3-b][1,4]diazepine

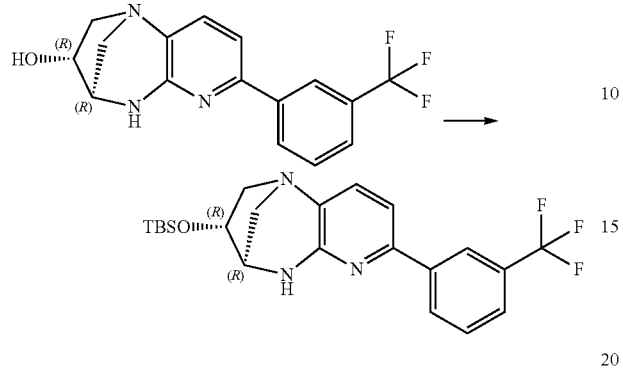

A mixture of TBSCl (338 mg, 2.24 mmol), (3R,4R)-7-chloro-2,3,4,5-tetrahydro-1,4-methanopyrido[2,3-b][1,4]diazepin-3-ol (600 mg, 1.87 mmol), triethyl amine (415 mg, 4.11 mmol) and DMAP (22 mg, 0.20 mmol) was stirred for 48 h. Additional TBSCl and TEA were required to consume the starting material. The crude residue was purified by column chromatography to give (3R,4R)-3-((tert-butyldimethylsilyl)oxy)-7-chloro-2,3,4,5-tetrahydro-1,4-methanopyrido[2,3-b][1,4]diazepine (90 mg, 73% yield). MS (ESI) calcd for $C_{22}H_{28}F_3N_3OSi$: 435.20;

Step 3. Synthesis of (3R,4R)-3-((tert-butyldimethyl-silyl)oxy)-N-(4,5-dimethylthiazol-2-yl)-7-(3-(trifluoromethyl)phenyl)-3,4-dihydro-1,4-methanopyrido[2,3-b][1,4]diazepine-5(2H)-carboxamide

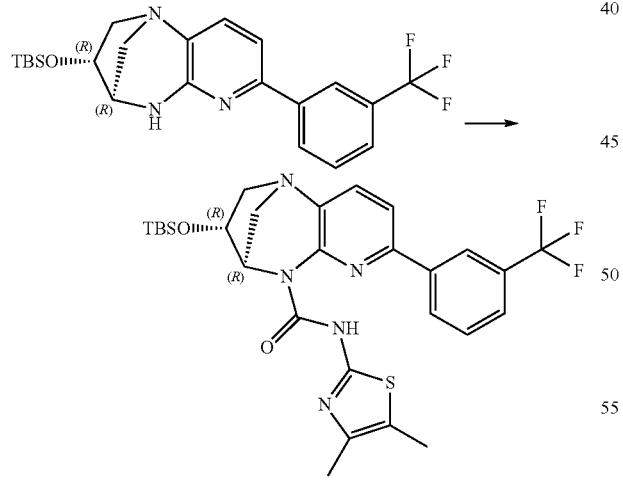

A mixture of phenyl (4,5-dimethylthiazol-2-yl)carbamate (25 mg, 0.10 mmol), (3R,4R)-3-((tert-butyldimethylsilyl)oxy)-7-(3-chlorophenyl)-2,3,4,5-tetrahydro-1,4-methanopyrido[2,3-b][1,4]diazepine (30 mg, 0.05 mmol) and DMAP (6 mg, 0.05 mmol) in 5 ml of MeCN was stirred at 65° C. overnight. The crude reaction mixture was purified by prep. TLC to give (3R,4R)-3-((tert-butyldimethylsilyl)oxy)-N-(4,5-dimethylthiazol-2-yl)-7-(3-(trifluoromethyl)phenyl)-3,4-dihydro-1,4-methanopyrido[2,3-b][1,4]diazepine-5(2H)-carboxamide (30 mg, quant.). MS (ESI) calcd for $C_{28}H_{34}F_3N_5O_2SSi$: 589.22;

Step 4. Synthesis of (3R,4R)—N-(4,5-dimethylthi-azol-2-yl)-3-hydroxy-7-(3-(trifluoromethyl)phenyl)-3,4-dihydro-1,4-methanopyrido[2,3-b][1,4]diazepine-5(2H)-carboxamide

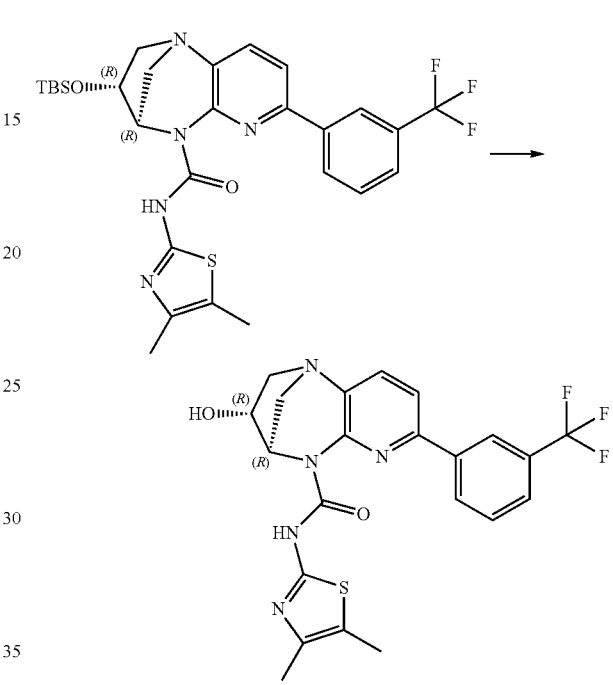

To a solution of (3R,4R)-3-((tert-butyldimethylsilyl)oxy)-N-(4,5-dimethylthiazol-2-yl)-7-(3-(trifluoromethyl)phenyl)-3,4-dihydro-1,4-methanopyrido[2,3-b][1,4]diazepine-5(2H)-carboxamide (30 mg, 0.051 mmol) in THF (2 mL) was added TBAF/THF (0.1 mL, 0.1 mmol). The mixture was stirred at room temperature overnight, poured into water and extracted with EtOAc. The organic layer was washed with water then brine, dried over anhydrous $Na_2SO_4$, filtered and evaporated to dryness. The residue was purified by prep. TLC (EtOAc) to give (3R,4R)—N-(4,5-dimethylthiazol-2-yl)-3-hydroxy-7-(3-(trifluoromethyl)phenyl)-3,4-dihydro-1,4-methanopyrido[2,3-b][1,4]diazepine-5(2H)-carboxamide as a white solid (12 mg, 50% yield). MS (ESI) calcd for $C_{22}H_{20}F_3N_5O_2S$: 475.13. found: 476 [M+H].

Example 35: Preparation of (4S)—N-(4-(oxazol-5-yl)pyridin-2-yl)-7-(3-(trifluoromethyl)phenyl)-3,4-dihydro-1,4-methanopyrido[2,3-b][1,4]diazepine-5(2H)-carboxamide

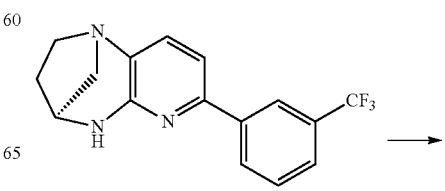

-continued

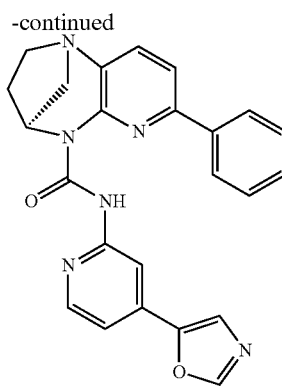

To a solution of 4-(oxazol-5-yl)pyridin-2-amine (500 mg, 3.10 mmol) in pyridine (7804, 9.65 mmol) and dichloromethane (10 mL), cooled to 0° C., was added phenyl chloroformate (466 µL, 3.72 mmol) over 1.5 h. The reaction was stirred at 0° C. for 2 h. Water (15 mL) was added slowly, and additional dichloromethane was added. The organic layer was separated, washed with saturated sodium carbonate (20 mL) and brine (20 mL), dried with sodium sulfate, and all solvent removed in vacuo. The residue was suspended in 5:1 petroleum ether:ethyl acetate for 30 min, then the suspension filtered to give phenyl (4-(oxazol-5-yl)pyridin-2-yl)carbamate (547 mg, 1.94 mmol, 63% yield).

A solution of (4S)-7-(3-(trifluoromethyl)phenyl)-2,3,4,5-tetrahydro-1,4-methanopyrido[2,3-b][1,4]diazepine (110 mg, 0.361 mmol), phenyl (4-(oxazol-5-yl)pyridin-2-yl)carbamate (203 mg, 0.722 mmol) and 4-(dimethylamino)pyridine (53.0 mg, 0.434 mmol) in acetonitrile (5 mL) was stirred at 60° C. overnight. The mixture was purified by preparative HPLC to give (4S)—N-(4-(oxazol-5-yl)pyridin-2-yl)-7-(3-(trifluoromethyl)phenyl)-3,4-dihydro-1,4-methanopyrido[2,3-b][1,4]diazepine-5(2H)-carboxamide (24.3 mg, 0.0493 mmol, 14% yield). MS (ESI) calcd for $C_{25}H_{19}F_3N_6O_2$: 492.2. found: 493.2 [M+H].

Example 36: Synthesis of (4S)—N-(3,5-bis(oxazol-5-yl)phenyl)-7-(3-(trifluoromethyl)phenyl)-3,4-dihydro-1,4-methanopyrido[2,3-b][1,4]diazepine-5(2H)-carboxamide Step 1. Synthesis of phenyl (3,5-bis(oxazol-5-yl)phenyl)carbamate

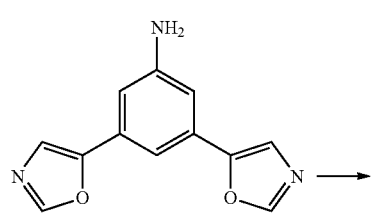

A mixture of 3,5-bis(oxazol-5-yl)aniline (100 mg, 0.44 mmol), phenyl chloroformate (76 mg, 0.48 mmol) and pyridine (0.20 mL) in dichloromethane (15 mL) was stirred at room temperature for 2 h. The solvent was removed in vacuo, and the remaining material purified by preparative TLC (1:1 petroleum ether:ethyl acetate) to give phenyl (3,5-bis(oxazol-5-yl)phenyl)carbamate (140 mg, 0.40 mmol, 92% yield). MS (ESI) calcd for $C_{19}H_{13}N_3O_4$: 347.1.

Step 2. Synthesis of (4S)—N-(3,5-bis(oxazol-5-yl)phenyl)-7-(3-(trifluoromethyl)phenyl)-3,4-dihydro-1,4-methanopyrido[2,3-b][1,4]diazepine-5(2H)-carboxamide

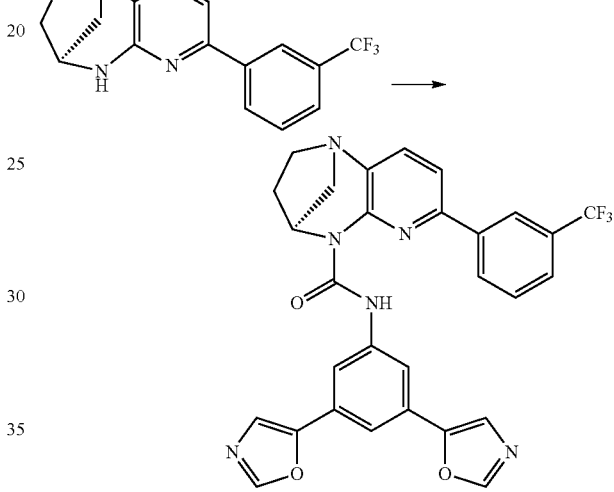

A mixture of (4S)-7-(3-(trifluoromethyl)phenyl)-2,3,4,5-tetrahydro-1,4-methanopyrido[2,3-b][1,4]diazepine (70 mg, 0.23 mmol), phenyl (3,5-bis(oxazol-5-yl)phenyl)carbamate (140 mg, 0.40 mmol) and DMAP (56 mg, 0.46 mmol) in acetonitrile (2 mL) was refluxed overnight. The solvent was removed in vacuo, and the remaining residue purified by preparative TLC (10:1 dichloromethane:methanol) to give (4S)—N-(3,5-bis(oxazol-5-yl)phenyl)-7-(3-(trifluoromethyl)phenyl)-3,4-dihydro-1,4-methanopyrido[2,3-b][1,4]diazepine-5(2H)-carboxamide (13.7 mg, 0.0245 mmol, 11% yield). MS (ESI) calcd for $C_{29}H_{21}F_3N_6O_3$: 558.2. found: 559.0.

Example 37. Preparation of tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate

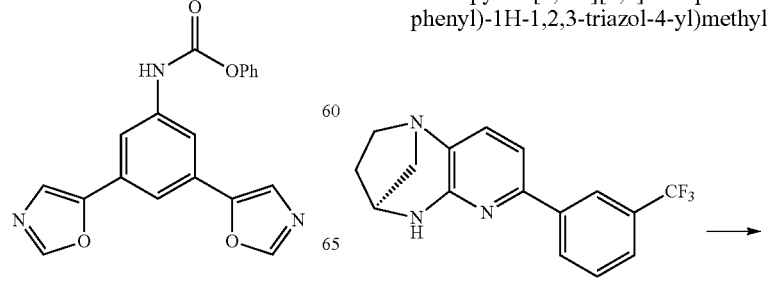

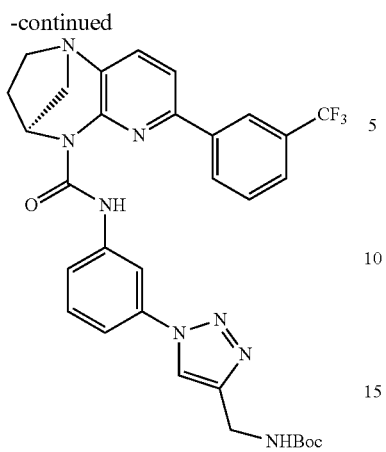

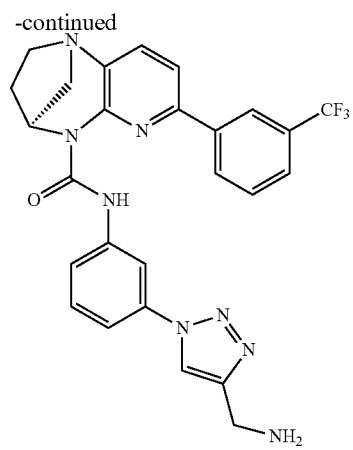

To a solution of triphosgene (214 mg, 0.721 mmol) in acetonitrile (5 mL) was added a solution of tert-butyl ((1-(3-aminophenyl)-1H-1,2,3-triazol-4-yl)methyl)carbamate (417 mg, 1.44 mmol) in acetonitrile (5 mL) and triethylamine (2 mL). The resulting suspension was stirred at room temperature for 10 min, then (4S)-7-(3-(trifluoromethyl)phenyl)-2,3,4,5-tetrahydro-1,4-methanopyrido[2,3-b][1,4]diazepine (Compound #; 302 mg, 0.989 mmol) and 4-(dimethylamino)pyridine (122 mg, 1.00 mmol) were added as solids. The reaction was stirred at 80° C. for 15 min. The reaction was cooled to room temperature, methanol (2 mL) was added, and the reaction was poured into saturated sodium bicarbonate (50 mL), and extracted with dichloromethane (3×50 mL). The combined organic layers were dried with magnesium sulfate, the solvent removed in vacuo, and the remaining material purified by flash chromatography (0% to 8% methanol in dichloromethane) to give tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (579 mg, 0.933 mmol, 94% yield). MS (ESI) calcd for $C_{31}H_{31}F_3N_8O_3$: 620.3. found: 621.0 [M+H].

Example 38. Preparation of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

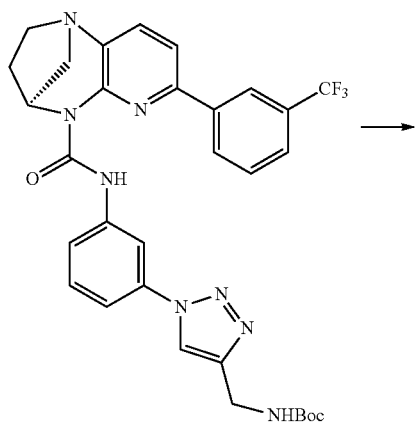

tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (160 mg, 0.258 mmol) was dissolved in trifluoroacetic acid (1.6 mL). The reaction was stirred at 50° C. for 10 min, then all solvent was removed in vacuo to give (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide trifluoroacetic acid salt (164 mg, 0.258 mmol, 100% yield). MS (ESI) calcd for $C_{26}H_{23}F_3N_8O$: 520.2. found: 521.0 [M+H].

Example 39: Synthesis of (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5(2H)-carboxamide Step 1: Preparation of (4S)—N-(6-bromopyridin-2-yl)-7-(3-(trifluoromethyl)phenyl)-3,4-dihydro-1,4-methanopyrido[2,3-b][1,4]diazepine-5(2H)-carboxamide

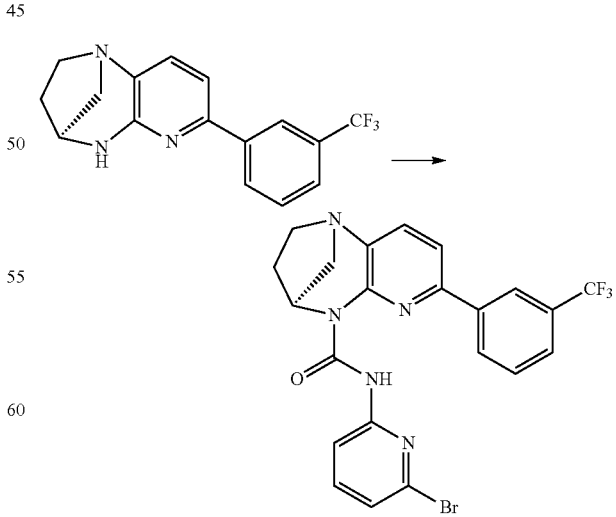

To a solution of triphosgene (1.81 g, 6.10 mmol) in acetonitrile (25 mL) was added a solution of 6-bromopyridin-2-amine (2.26 g, 13.1 mmol) in acetonitrile (25 mL). Triethylamine (8.00 mL, 57.4 mmol) was added, and the reaction stirred at 80° C. for 30 min. (4S)-7-(3-(trifluoromethyl)phenyl)-2,3,4,5-tetrahydro-1,4-methanopyrido[2,3-b][1,4]diazepine (1.04 g, 3.41 mmol) and 4-(dimethylamino)pyridine (410 mg, 3.36 mmol) were added as solids, and the reaction stirred at 80° C. for 1 h. The reaction was cooled to room temperature, poured into water (30 mL), and extracted with dichloromethane (2×50 mL). The combined organic layers were dried with magnesium sulfate, and all solvents removed in vacuo. The remaining residue was purified by flash chromatography (30% to 100% ethyl acetate in pentane) to give (4S)—N-(6-bromopyridin-2-yl)-7-(3-(trifluoromethyl)phenyl)-3,4-dihydro-1,4-methanopyrido[2,3-b][1,4]diazepine-5(2H)-carboxamide (1.12 g, 2.22 mmol, 65% yield). MS (ESI) calcd for $C_{22}H_{17}BrF_3N_5O$: 503.1. found: 503.8 [M+H].

Step 2: Preparation of (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5(2H)-carboxamide

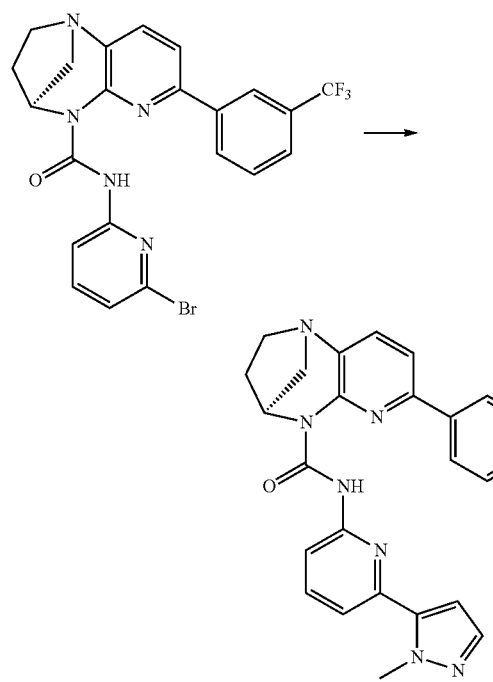

A microwave vial was charged with (4S)—N-(6-bromopyridin-2-yl)-7-(3-(trifluoromethyl)phenyl)-3,4-dihydro-1,4-methanopyrido[2,3-b][1,4]diazepine-5(2H)-carboxamide (46.0 mg, 0.0912 mmol), tetrakis(triphenylphosphine)palladium (4.8 mg, 0.0042 mmol), cesium fluoride (180 mg, 1.18 mmol), 1-methyl-5-(4,4,5,5-tetramethyl-1,3,2-dioxaborolan-2-yl)-1H-pyrazole (60.0 mg, 0.288 mmol), DME (1.5 mL), and water (150 μL). The microwave vial was sealed, and heated in the microwave at 100° C. for 3 h. The organic layer was separated, and the aqueous layer extracted with 10:1 ethyl acetate:methanol (2×2 mL). The combined organic layers were dried with magnesium sulfate, the solvent removed in vacuo, and the remaining residue dissolved in DMSO (4 mL), filtered, and the filtrate purified by preparative HPLC to give (4S)—N-(6-(1-methyl-1H-pyrazol-5-yl)pyridin-2-yl)-7-(3-(trifluoromethyl)phenyl)-3,4-dihydro-1,4-methanopyrido[2,3-b][1,4]diazepine-5(2H)-carboxamide trifluoroacetic acid salt (28.4 mg, 0.0460 mmol, 50% yield). MS (ESI) calcd for $C_{26}H_{22}F_3N_7O$: 505.2. found: 506.0 [M+H].

Example 40: Synthesis of (4S)—N-(3-(piperazin-1-ylmethyl)phenyl)-7-(3-(trifluoromethyl)phenyl)-3,4-dihydro-1,4-methanopyrido[2,3-b][1,4]diazepine-5(2H)-carboxamide

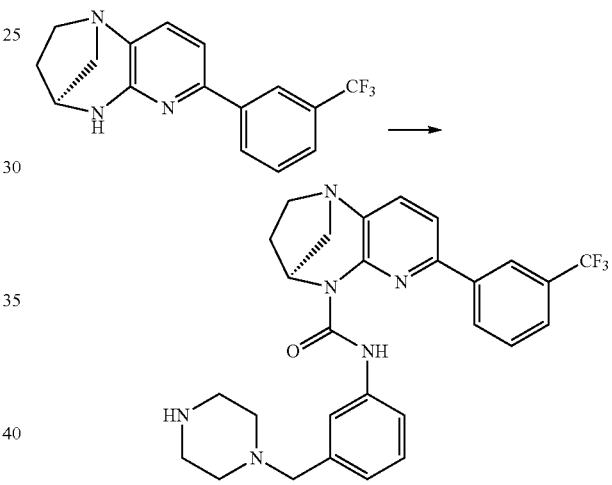

A vial was charged with triphosgene (75.0 mg, 0.253 mmol), and this was dissolved in acetonitrile (2.5 mL). A solution of (4S)-7-(3-(trifluoromethyl)phenyl)-2,3,4,5-tetrahydro-1,4-methanopyrido[2,3-b][1,4]diazepine (150 mg, 0.491 mmol) in acetonitrile (2.5 mL) was added, followed by triethylamine (0.50 mL, 3.59 mmol). The reaction was stirred at room temperature for 4 h, and tert-butyl 4-(3-aminobenzyl)piperazine-1-carboxylate (480 mg, 1.65 mmol) was added as a solid, followed by DMAP (360 mg, 2.95 mmol). The reaction was stirred at 80° C. for 16 h, and all solvents were removed in vacuo. The remaining material was dissolved in trifluoroacetic acid (5.0 mL), and the solution stirred at 50° C. for 20 min. Excess trifluoroacetic acid was removed in vacuo, the remaining material dissolved in DMSO, and the resulting solution purified by preparative HPLC to give (4S)—N-(3-(piperazin-1-ylmethyl)phenyl)-7-(3-(trifluoromethyl)phenyl)-3,4-dihydro-1,4-methanopyrido[2,3-b][1,4]diazepine-5(2H)-carboxamide trifluoroacetate (89.1 mg, 0.140 mmol, 29% yield). MS (ESI) calcd for $C_{28}H_{29}F_3N_6O$: 522.2.

Example 41: Synthesis of (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide Step 1. Synthesis of tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate

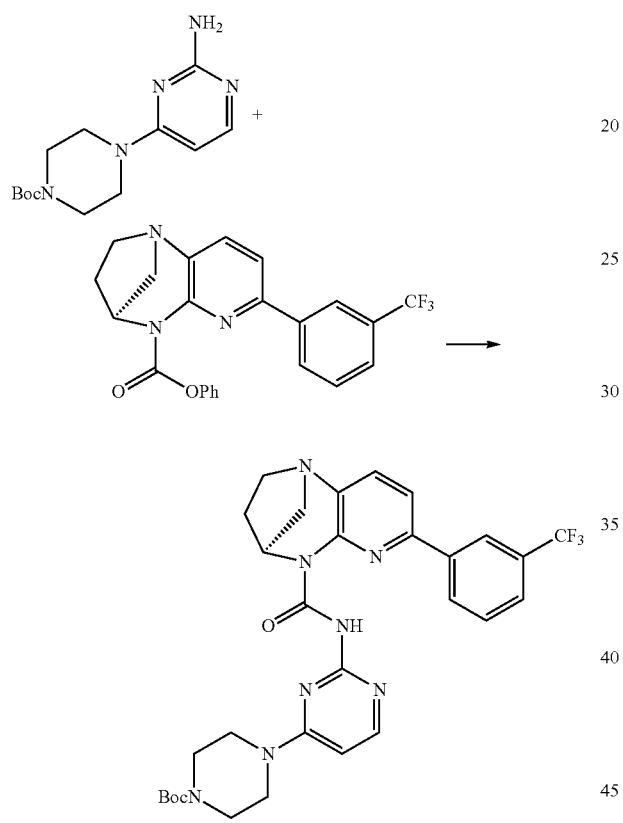

To a solution of tert-butyl 4-(2-aminopyrimidin-4-yl)piperazine-1-carboxylate (200 mg, 0.716 mmol) in THF (20 mL) at 0° C. was added sodium bis(trimethylsilyl)amide solution (1.0 M in THF, 1.50 mL, 1.50 mmol). The reaction was warmed to room temperature and stirred for 30 min, and a solution of (4S)-phenyl 7-(3-(trifluoromethyl)phenyl)-3,4-dihydro-1,4-methanopyrido[2,3-b][1,4]diazepine-5(2H)-carboxylate (327 mg, 1.07 mmol) in THF (5 mL) was added. The reaction was stirred at room temperature for 1.5 h, then the solvent removed in vacuo and the remaining residue purified by prep TLC (3:1 petroleum ether:ethyl acetate) to give tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate (160 mg, 0.262 mmol, 37% yield). MS (ESI) calcd for $C_{30}H_{33}F_3N_8O_3$: 610.3.

Step 2. Synthesis of (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide

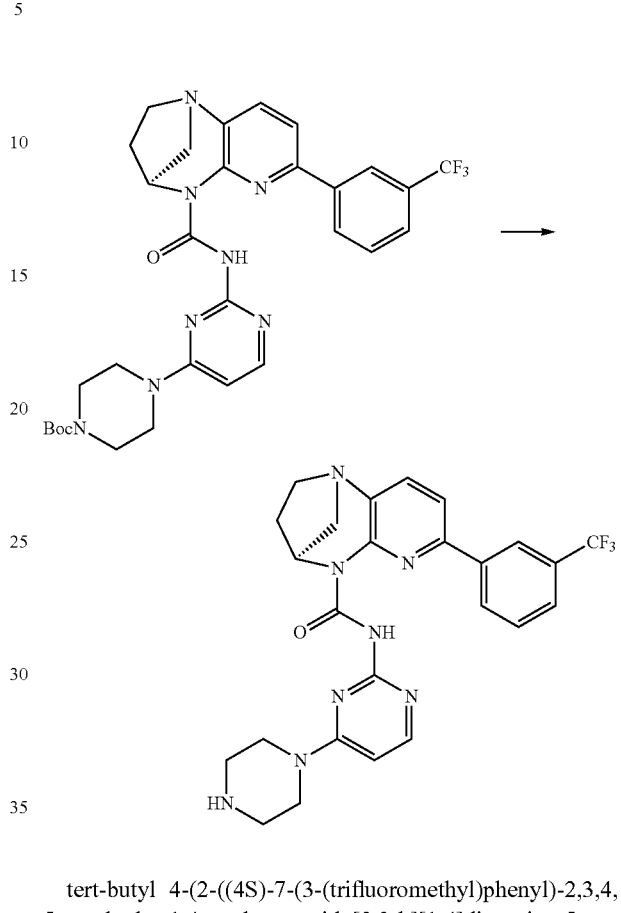

tert-butyl 4-(2-((4S)-7-(3-(trifluoromethyl)phenyl)-2,3,4,5-tetrahydro-1,4-methanopyrido[2,3-b][1,4]diazepine-5-carboxamido)pyrimidin-4-yl)piperazine-1-carboxylate (160 mg, 0.262 mmol) was dissolved in hydrochloric acid in ethyl acetate (2 M, 10 mL), and stirred for 30 min. All solvents were removed in vacuo to give (4S)—N-(4-(piperazin-1-yl)pyrimidin-2-yl)-7-(3-(trifluoromethyl)phenyl)-3,4-dihydro-1,4-methanopyrido[2,3-b][1,4]diazepine-5(2H)-carboxamide (47 mg, 0.092 mmol, 35% yield). MS (ESI) calcd for $C_{25}H_{25}F_3N_8O$: 510.2. found: 511.0 [M+H].

Example 42: Synthesis of tert-butyl (2-(4-(3-((9S)-2-(3-(trifluoromethyl)phenyl)-7,8,9,10-tetrahydro-6H-5,9-methanopyrido[2,3-b][1,4]diazocine-10-carboxamido)phenyl)-1H-1,2,3-triazol-1-yl)ethyl)carbamate

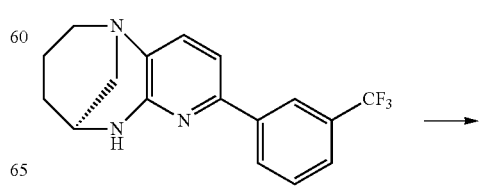

-continued

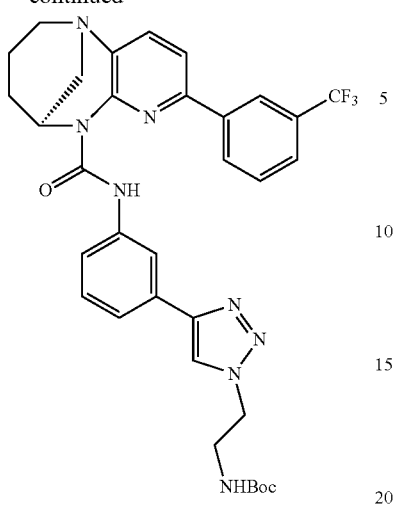

A vial was charged with triphosgene (180 mg, 0.607 mmol), and this was dissolved in dichloromethane (3 mL). A solution of (9S)-2-(3-(trifluoromethyl)phenyl)-7,8,9,10-tetrahydro-6H-5,9-methanopyrido[2,3-b][1,4]diazocine (320 mg, 1.00 mmol) was added, and N,N-diisopropylethylamine (1.00 mL, 5.74 mmol) was added. The reaction was stirred at room temperature for 25 min, and then a solution of tert-butyl (2-(4-(3-aminophenyl)-1H-1,2,3-triazol-1-yl)ethyl)carbamate (415 mg, 1.37 mmol) in dichloromethane (5 mL) was added. The reaction was stirred at 40° C. for 16 h, then heated in a microwave at 120° C. for 1 h. After cooling, the solvent was removed in vacuo, and the remaining residue purified by flash chromatography (0% to 8% methanol in dichloromethane) to give tert-butyl (2-(4-(3-((9S)-2-(3-(trifluoromethyl)phenyl)-7,8,9,10-tetrahydro-6H-5,9-methanopyrido[2,3-b][1,4]diazocine-10-carboxamido)phenyl)-1H-1,2,3-triazol-1-yl)ethyl)carbamate (99.0 mg, 0.153 mmol, 15% yield). MS (ESI) calcd for $C_{33}H_{35}F_3N_8O_3$: 648.3.

Example 43: Preparation of (4S)—N-(3-(2-(guanidinomethyl)oxazol-5-yl)phenyl)-7-(3-(trifluoromethyl)phenyl)-3,4-dihydro-1,4-methanopyrido[2,3-b][1,4]diazepine-5(2H)-carboxamide

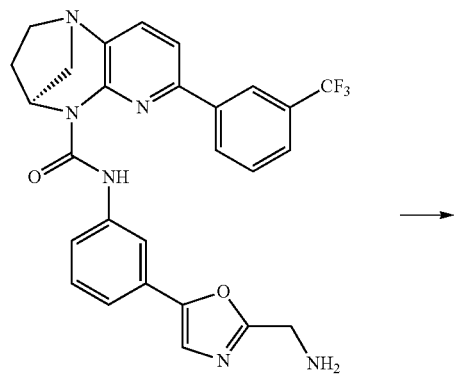

-continued

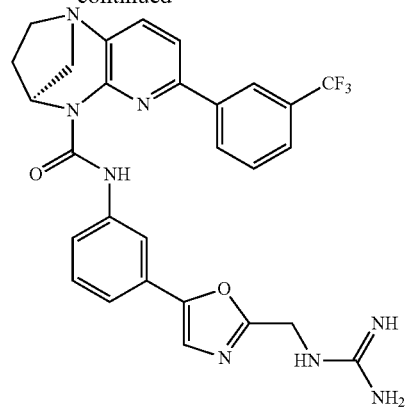

A solution of 1H-pyrazole-1-carboximidamide hydrochloride (15 mg, 0.10 mmol) and DIEA (17 μL, 0.10 mmol) in DMF (1 mL) was stirred at room temperature for 10 min, the (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide (52 mg, 0.10 mmol) was added. The reaction mixture was stirred at room temperature overnight and then purified by prep-HPLC and lyophilized to obtain (4S)—N-(3-(2-(guanidinomethyl)oxazol-5-yl)phenyl)-7-(3-(trifluoromethyl)phenyl)-3,4-dihydro-1,4-methanopyrido[2,3-b][1,4]diazepine-5(2H)-carboxamide trifluoroacetic acid salt (25.5 mg, 38% yield). MS (ESI) calcd for C28H25F3N8O2: 562.21. found: 563 [M+H].

This general procedure was used to prepare other guanidines by substituting (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide with the appropriate amine.

Example 44: Synthesis of (4S)—N-(pyrimidin-4-yl)-7-(3-(trifluoromethyl)piperidin-1-yl)-3,4-dihydro-1,4-methanopyrido[2,3-b][1,4]diazepine-5(2H)-carboxamide Step 1. Synthesis of (9S)-2-(3-(trifluoromethyl)piperidin-1-yl)-7,8,9,10-tetrahydro-6H-5,9-methanopyrido[2,3-b][1,4]diazocine

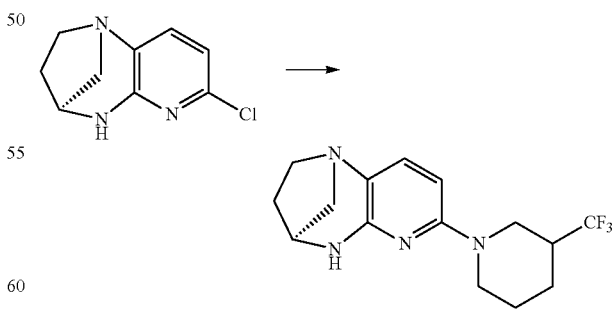

A 20 mL microwave vial was charged with a magnetic stir bar, (9S)-2-chloro-7,8,9,10-tetrahydro-6H-5,9-methanopyrido[2,3-b][1,4]diazocine (629 mg, 3.00 mmol), [1,3-Bis(2,6-di-isopropylphenyl)-4,5-dihydroimidazol-2-ylidene]chloro]allylpalladium(II) (62.1 mg, 0.120 mmol), 3-trifluoromethylpiperidine (919 mg, 6.00 mmol) and potassium tert-butoxide (673 mg, 6.00 mmol). DME (7.0 mL) was added, the microwave vial capped, and heated to 90° C. for 2 h. After cooling to room temperature, methanol (5 mL) and silica gel (5 g) were added, and all solvents were removed in vacuo. The remaining silica gel slurry was loaded atop a 40 g silica gel column, and flash chromatography (50% to 100% ethyl acetate in pentane) gave (9S)-2-(3-(trifluoromethyl)piperidin-1-yl)-7,8,9,10-tetrahydro-6H-5,9-methanopyrido[2,3-b][1,4]diazocine 2 as a 1:1 mixture of diastereomers (713 mg, 2.18 mmol, 73% yield). MS (ESI) calcd for $C_{16}H_{21}F_3N_4$: 326.2.

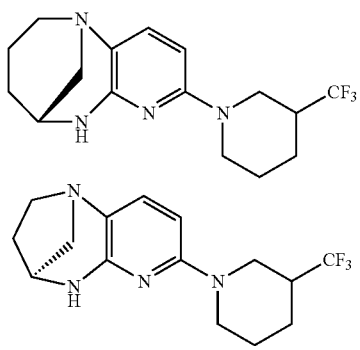

Step 2. Synthesis of (4S)—N-(pyrimidin-4-yl)-7-(3-(trifluoromethyl)piperidin-1-yl)-3,4-dihydro-1,4-methanopyrido[2,3-b][1,4]diazepine-5(2H)-carboxamide

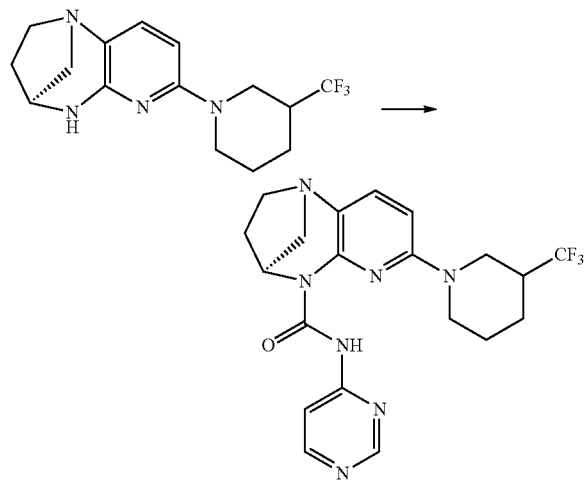

To a solution of (4S)-7-(3-(trifluoromethyl)piperidin-1-yl)-2,3,4,5-tetrahydro-1,4-methanopyrido[2,3-b][1,4]diazepine (40.0 mg, 0.128 mmol) in acetonitrile (2 mL) and pyridine (1 mL) was added triphosgene (26.0 mg, 0.0876 mmol) as a solid. The resulting red solution was stirred at 50° C. for 1 h. 4-aminopyrimidine (95.0 mg, 1.00 mmol) was then added as a solid, and the reaction stirred at 70° C. for 6 h. After 6 h, most of the acetonitrile was removed under a nitrogen stream, and methanol (1 mL) and DMSO (2 mL) was added to the reaction. The resulting solution was purified by prep HPLC, and the isolated material lyophilized from acetonitrile/aqueous 1N HCl to give (4S)—N-(pyrimidin-4-yl)-7-(3-(trifluoromethyl)piperidin-1-yl)-3,4-dihydro-1,4-methanopyrido[2,3-b][1,4]diazepine-5(2H)-carboxamide hydrochloride (34.9 mg, 0.0743 mmol, 58% yield). MS (ESI) calcd for $C_{20}H_{22}F_3N_7O$: 433.2.

Example 45: Synthesis of (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide Step 1. Synthesis of (3S)—N,N-dimethyl-1-((4S)-2,3,4,5-tetrahydro-1,4-methanopyrido[2,3-b][1,4]diazepin-7-yl)pyrrolidin-3-amine

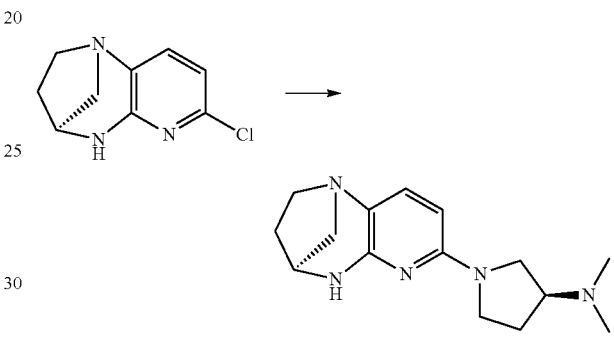

A 20 mL microwave vial was charged with a magnetic stir bar, (4S)-7-chloro-2,3,4,5-tetrahydro-1,4-methanopyrido[2,3-b][1,4]diazepine (978 mg, 5.00 mmol), [1,3-Bis(2,6-diisopropylphenyl)-4,5-dihydroimidazol-2-ylidene]chloro]allylpalladium(II) (51.7 mg, 0.100 mmol), (S)—N,N-dimethylpyrrolidin-3-amine (1.14 g, 10.00 mmol) and potassium tert-butoxide (1.12 mg, 10.00 mmol). DME (10.0 mL) was added, the microwave vial capped, and heated to 100° C. for 4 h. After cooling to room temperature, methanol (20 mL) and silica gel (5 g) were added, and all solvents were removed in vacuo. The remaining silica gel slurry was loaded atop a 40 g silica gel column, and flash chromatography (0% to 10% methanol in pentane) gave (3S)—N,N-dimethyl-1-((4S)-2,3,4,5-tetrahydro-1,4-methanopyrido[2,3-b][1,4]diazepin-7-yl)pyrrolidin-3-amine (524 mg, 1.92 mmol, 38% yield). MS (ESI) calcd for $C_{15}H_{23}N_5$: 273.2.

Step 2. Synthesis of (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide

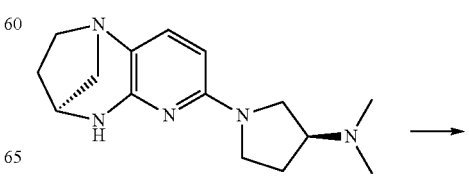

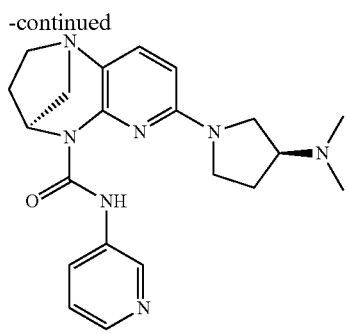

To a solution of (3S)—N,N-dimethyl-1-((4S)-2,3,4,5-tetrahydro-1,4-methanopyrido[2,3-b][1,4]diazepin-7-yl)pyrrolidin-3-amine (40.0 mg, 0.146 mmol) in acetonitrile (540 μL) and pyridine (150 μL) was added a solution of triphosgene (28.9 mg, 0.0975 mmol) in acetonitrile (310 μL). The reaction was stirred at 50° C. for 30 min, then triethylamine (40 μL) was added. 3-aminopyridine (94 mg, 1.00 mmol) was added as a solid, and the reaction stirred at 60° C. for 16 h. After 16 h, the reaction was cooled to room temperature, methanol (1 mL) was added, and the resulting solution purified by preparative HPLC. The isolated material was lyophilized from acetonitrile/aqueous 1N HCl to give (4S)-7-((S)-3-(dimethylamino)pyrrolidin-1-yl)-N-(pyridin-3-yl)-3,4-dihydro-1,4-methanopyrido[2,3-b][1,4]diazepine-5(2H)-carboxamide hydrochloride (30.6 mg, 0.0712 mmol, 49% yield). MS (ESI) calcd for $C_{21}H_{27}N_7O$: 393.2.

Example 46: Synthesis of tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate Step 1. Synthesis of tert-butyl 4-((9S)-7,8,9,10-tetrahydro-6H-5,9-methanopyrido[2,3-b][1,4]diazocin-2-yl)-1,4-diazepane-1-carboxylate

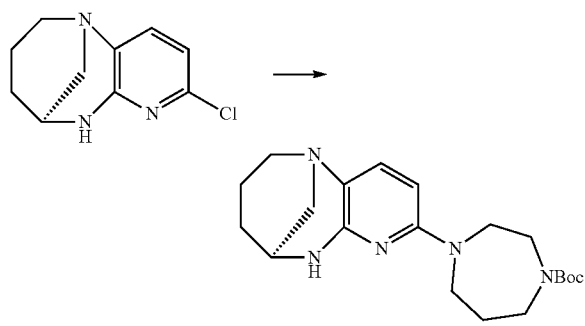

A 20 mL microwave vial was charged with a magnetic stir bar, (9S)-2-chloro-7,8,9,10-tetrahydro-6H-5,9-methanopyrido[2,3-b][1,4]diazocine (500 mg, 2.38 mmol), [1,3-Bis(2,6-di-isopropylphenyl)-4,5-dihydroimidazol-2-ylidene]chloro]allylpalladium(II) (12.4 mg, 0.0240 mmol), tert-butyl homopiperazine-1-carboxylate (953 mg, 4.76 mmol) and potassium tert-butoxide (534 mg, 4.76 mmol). DME (5.0 mL) was added, the vial was sealed, and heated in the microwave at 85° C. for 4 h. After cooling to room temperature, methanol (20 mL) and silica gel (5 g) were added, all solvents were removed in vacuo, and the remaining silica gel slurry was loaded atop a 40 g silica gel column. Flash chromatography (0% to 8% methanol in dichloromethane) gave tert-butyl 4-((9S)-7,8,9,10-tetrahydro-6H-5,9-methanopyrido[2,3-b][1,4]diazocin-2-yl)-1,4-diazepane-1-carboxylate (550 mg, 1.48 mmol, 62% yield). MS (ESI) calcd for $C_{20}H_{31}N_5O_2$: 373.2. found: 374.2 [M+H].

Step 2. Synthesis of tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate

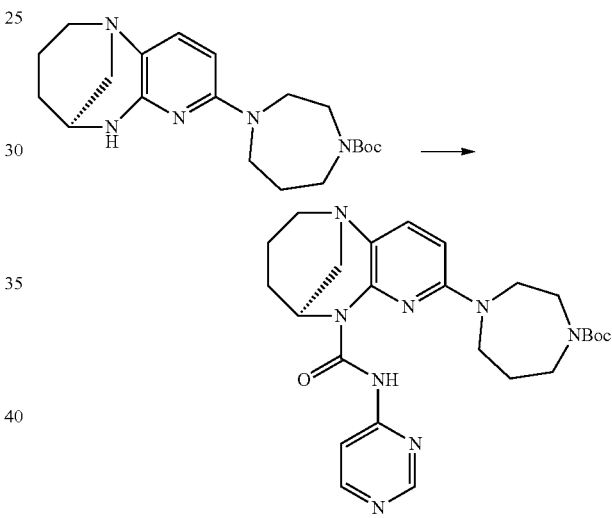

A mixture of tert-butyl 4-((9S)-7,8,9,10-tetrahydro-6H-5,9-methanopyrido[2,3-b][1,4]diazocin-2-yl)-1,4-diazepane-1-carboxylate (500 mg, 1.34 mmol), pyrimidin-4-yl-carbamic acid phenyl ester (570 mg, 2.65 mmol), 4-dimethylaminopyridine (190 mg, 1.56 mmol) in acetonitrile (30 mL) was stirred at 60° C. for 3.5 h. Solvent was removed under reduced pressure, the residue was dissolved in dichloromethane, washed with water, brine, and the organic layer dried over anhydrous $Na_2SO_4$. All solvent was removed in vacuo, and the remaining residue purified through silica gel chromatography with dichloromethane: ethyl acetate (2:1), then purified through preparative thin layer chromatography with 3% methanol in dichloromethane to give tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate (363 mg, 0.734 mmol, 55% yield). MS (ESI) calcd for $C_{25}H_{34}N_8O_3$: 494.3. found: 495.4 [M+H].

Example 47: Synthesis of (9S)-2-(1,4-diazepan-1-yl)-N-(pyrimidin-4-yl)-8,9-dihydro-6H-5,9-methanopyrido[2,3-b][1,4]diazocine-10(7H)-carboxamide

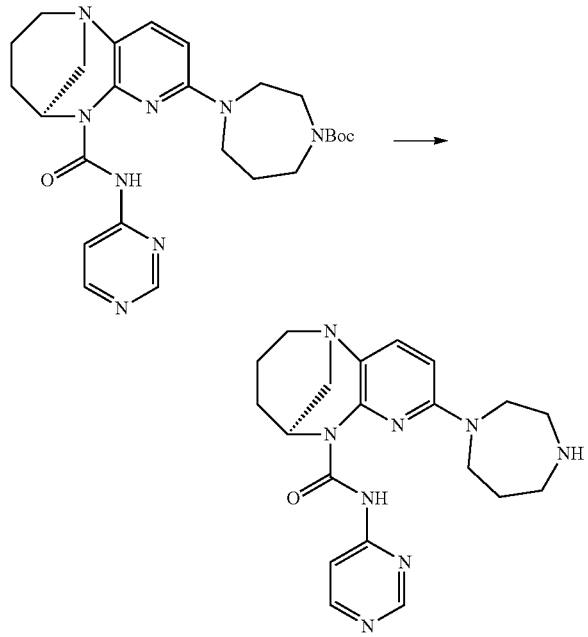

tert-butyl 4-((9S)-10-(pyrimidin-4-ylcarbamoyl)-7,8,9,10-tetrahydro-6H-5,9-methanopyrido[2,3-b][1,4]diazocin-2-yl)-1,4-diazepane-1-carboxylate (400 mg, 0.808 mmol) was dissolved in 1M HCl in MeOH (20 mL), and the reaction mixture was stirred at room temperature for 1.5 h. All solvent was removed in vacuo. Water (20 mL) and potassium carbonate (344 mg, 2.42 mmol) were added, and the mixture was stirred at room temperature for 1 h. Extraction with dichloromethane (3×5 mL) and drying the solvent in vacuo gave (9S)-2-(1,4-diazepan-1-yl)-N-(pyrimidin-4-yl)-8,9-dihydro-6H-5,9-methanopyrido[2,3-b][1,4]diazocine-10(7H)-carboxamide (300 mg, 0.761 mmol, 94% yield). MS (ESI) calcd for $C_{20}H_{26}N_8O$: 394.2.

Example 48: Synthesis of (9S)-2-(4-(methylsulfonyl)-1,4-diazepan-1-yl)-N-(pyrimidin-4-yl)-8,9-dihydro-6H-5,9-methanopyrido[2,3-b][1,4]diazocine-10(7H)-carboxamide

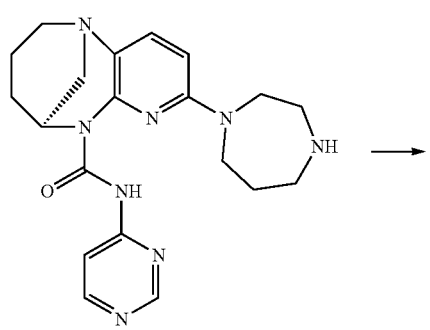

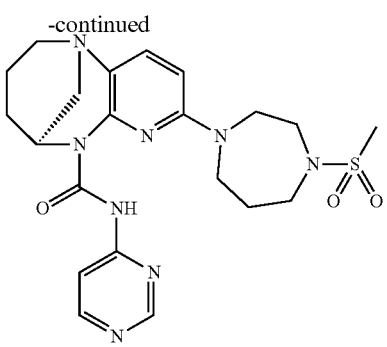

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (60.0 mg, 0.152 mmol) in dichloromethane (3 mL) was added triethylamine (46.1 mg, 0.457 mmol) and methanesulfonyl chloride (18.1 mg, 0.152 mmol). The mixture was stirred at 0° C. for 1 h. The solution was washed with water, brine, and the organic layer dried over anhydrous $Na_2SO_4$. The remaining solution was purified through preparative thin layer chromatography with 3% methanol in dichloromethane to give (9S)-2-(4-(methylsulfonyl)-1,4-diazepan-1-yl)-N-(pyrimidin-4-yl)-8,9-dihydro-6H-5,9-methanopyrido[2,3-b][1,4]diazocine-10(7H)-carboxamide (30.0 mg, 0.0635 mmol, 42% yield). MS (ESI) calcd for $C_{21}H_{28}N_8O_3S$: 472.2.

Example 49: Synthesis of (9S)-2-(4-methyl-1,4-diazepan-1-yl)-N-(pyrimidin-4-yl)-8,9-dihydro-6H-5,9-methanopyrido[2,3-b][1,4]diazocine-10(7H)-carboxamide

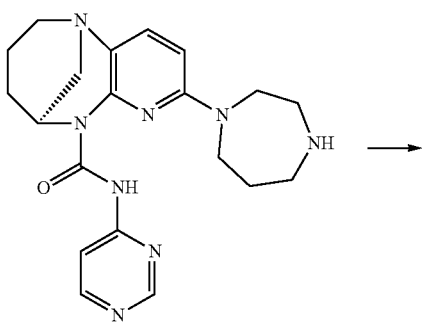

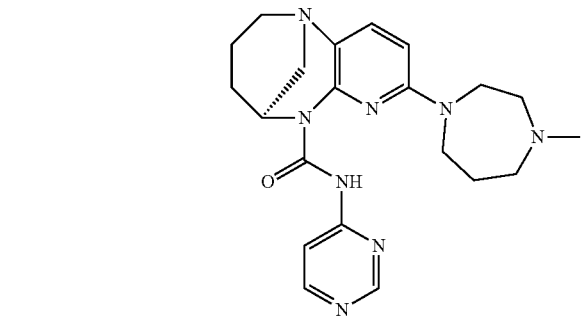

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (100 mg, 0.254 mmol) in methanol (3 mL) was added formaldehyde (37% in water, 20 μL) and 10% palladium on carbon (10 mg). The reaction was stirred under hydrogen atmosphere for 1 h. The solvent was removed in vacuo, and the remaining residue purified by preparative thin layer chromatography with 3% methanol in dichloromethane to give (9S)-2-(4-methyl-1,4-diazepan-1-yl)-N-(pyrimidin-4-yl)-8,9-dihydro-6H-5,9-methanopyrido[2,3-b][1,4]diazocine-10(7H)-carboxamide (22.2 mg, 0.0543 mmol, 21% yield). MS (ESI) calcd for $C_{21}H_{28}N_8O$: 408.2.

Example 50: Synthesis of (9S)-2-(4-isopropyl-1,4-diazepan-1-yl)-N-(pyrimidin-4-yl)-8,9-dihydro-6H-5,9-methanopyrido[2,3-b][1,4]diazocine-10(7H)-carboxamide

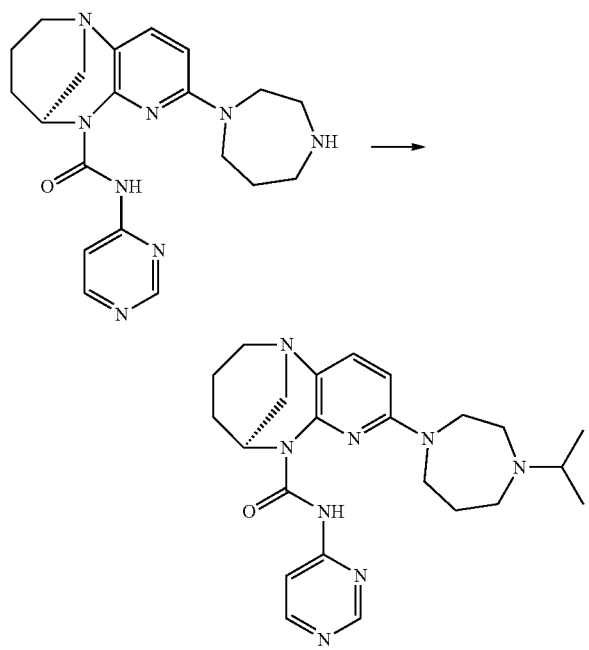

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (50.0 mg, 0.127 mmol) in dichloromethane (3 mL) was added acetone (12.9 mg, 0.254 mmol). The mixture was stirred for 30 min, and sodium cyanoborohydride (20.1 mg, 0.0759 mmol) was added as a solid, and the reaction stirred at room temperature overnight. All solvent was removed in vacuo, and the remaining residue purified by preparative thin layer chromatography (100% ethyl acetate) to give (9S)-2-(4-isopropyl-1,4-diazepan-1-yl)-N-(pyrimidin-4-yl)-8,9-dihydro-6H-5,9-methanopyrido[2,3-b][1,4]diazocine-10(7H)-carboxamide (16.8 mg, 0.0385 mmol, 30% yield). MS (ESI) calcd for $C_{23}H_{32}N_8O$: 436.3.

Example 51: Synthesis of (9S)—N-(pyrimidin-4-yl)-2-(4-(2,2,2-trifluoroethyl)-1,4-diazepan-1-yl)-8,9-dihydro-6H-5,9-methanopyrido[2,3-b][1,4]diazocine-10(7H)-carboxamide

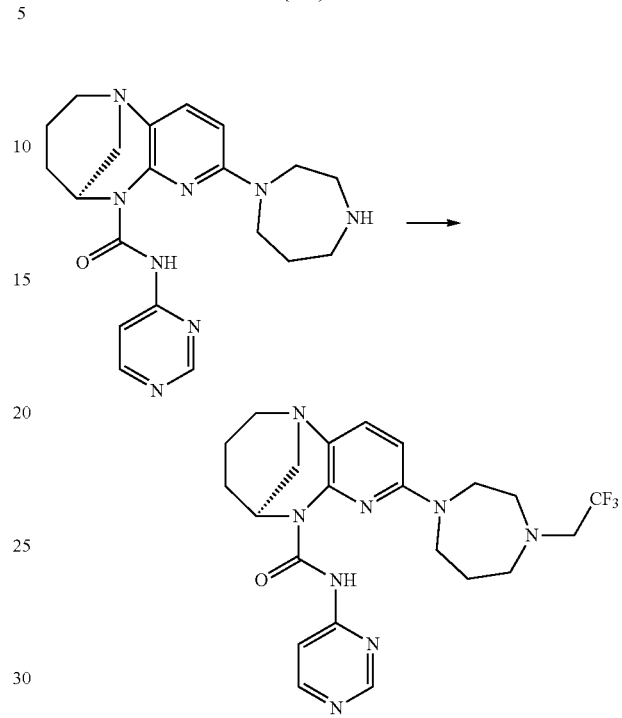

To a solution of (9S)-2-(1,4-diazepan-1-yl)-N-(pyrimidin-4-yl)-8,9-dihydro-6H-5,9-methanopyrido[2,3-b][1,4]diazocine-10(7H)-carboxamide (100 mg, 0.254 mmol) in DMF (3 mL) was added sodium carbonate (80.7 mg, 0.761 mmol) and 2,2,2-trifluoroethyl trifluoromethanesulfonate (163 mg, 0.508 mmol). The reaction was stirred at room temperature overnight, then diluted with dichloromethane (10 mL), and washed with water, brine, and dried with sodium sulfate. All solvent was removed in vacuo, and the remaining residue purified by preparative thin layer chromatography with 3% methanol in dichloromethane to give (9S)—N-(pyrimidin-4-yl)-2-(4-(2,2,2-trifluoroethyl)-1,4-diazepan-1-yl)-8,9-dihydro-6H-5,9-methanopyrido[2,3-b][1,4]diazocine-10(7H)-carboxamide (19.5 mg, 0.0409 mmol, 16% yield). MS (ESI) calcd for $C_{22}H_{27}F_3N_8O$: 476.2.

Example 52: Synthesis of (4S)-7-(4-(2,2,2-trifluoroethyl)-1,4-diazepan-1-yl)-2,3,4,5-tetrahydro-1,4-methanopyrido[2,3-b][1,4]diazepine Step 1. Synthesis of tert-butyl 4-((4S)-2,3,4,5-tetrahydro-1,4-methanopyrido[2,3-b][1,4]diazepin-7-yl)-1,4-diazepane-1-carboxylate

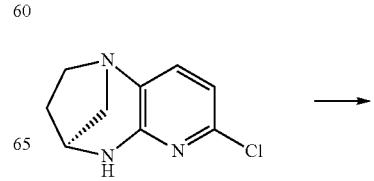

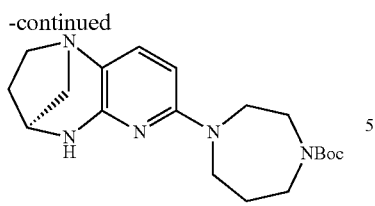

To a solution of (4S)-7-chloro-2,3,4,5-tetrahydro-1,4-methanopyrido[2,3-b][1,4]diazepine (500 mg, 2.56 mmol), N-Boc homopiperazine (953 mg, 4.76 mmol), potassium tert-butoxide (534 mg, 4.76 mmol) in DME (5 mL) was added [1,3-bis(2,6-di-isopropylphenyl)-4,5-dihydroimidazol-2-ylidene]chloro]allylpalladium(II) (12.4 mg, 0.0240 mmol). The mixture was heated to 90° C. for 3 h. After cooling, water was added, and the mixture extracted with ethyl acetate (3×15 mL). The combined organic layers were washed with brine, dried with sodium sulfate, filtered, and concentrated. The remaining residue was purified by silica gel chromatography (5:1 pentane:ethyl acetate) to give tert-butyl 4-((4S)-2,3,4,5-tetrahydro-1,4-methanopyrido[2,3-b][1,4]diazepin-7-yl)-1,4-diazepane-1-carboxylate (610 mg, 1.70 mmol, 66% yield). MS (ESI) calcd for $C_{19}H_{29}N_5O_2$: 359.2.

Step 2. Synthesis of (4S)-7-(1,4-diazepan-1-yl)-2,3,4,5-tetrahydro-1,4-methanopyrido[2,3-b][1,4]diazepine

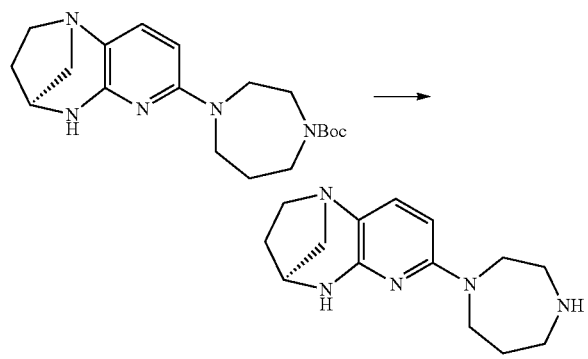

A mixture of tert-butyl 4-((4S)-2,3,4,5-tetrahydro-1,4-methanopyrido[2,3-b][1,4]diazepin-7-yl)-1,4-diazepane-1-carboxylate (610 mg, 1.70 mmol) and HCl in EtOAc (5M, 10 mL) was stirred at room temperature for 30 min. The solvent was removed to give (4S)-7-(1,4-diazepan-1-yl)-2,3,4,5-tetrahydro-1,4-methanopyrido[2,3-b][1,4]diazepine (418 mg, 1.61 mmol, 95% yield). MS (ESI) calcd for $C_{14}H_{21}N_5$: 259.2.

Step 3. Synthesis of (4S)-7-(4-(2,2,2-trifluoroethyl)-1,4-diazepan-1-yl)-2,3,4,5-tetrahydro-1,4-methanopyrido[2,3-b][1,4]diazepine

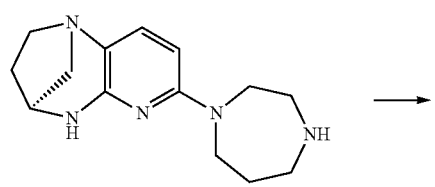

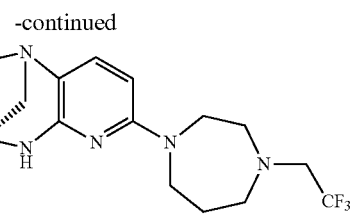

To a solution of (4S)-7-(1,4-diazepan-1-yl)-2,3,4,5-tetrahydro-1,4-methanopyrido[2,3-b][1,4]diazepine (418 mg, 1.61 mmol) in DMF (5 mL) was added 2,2,2-trifluoroethyltrifluoromethanesulfonate (748 mg, 3.23 mmol) and potassium carbonate (666 mg, 4.83 mmol). The reaction was stirred at room temperature overnight. The reaction was diluted with water, extracted with ethyl acetate (3×10 mL), and the combined organic layers washed with brine, dried with sodium sulfate, filtered, and concentrated. The remaining residue was purified by silica gel chromatography (6:1 pentane:ethyl acetate) to give (4S)-7-(4-(2,2,2-trifluoroethyl)-1,4-diazepan-1-yl)-2,3,4,5-tetrahydro-1,4-methanopyrido[2,3-b][1,4]diazepine (320 mg, 0.937 mmol, 58% yield). MS (ESI) calcd for $C_{16}H_{22}F_3N_5$: 341.2.

Example 53: Synthesis of (4S)—N-(3-(oxazol-5-yl)phenyl)-7-((R)-3-(trifluoromethyl)piperidin-1-yl)-3,4-dihydro-1,4-methanopyrido[2,3-b][1,4]diazepine-5(2H)-carboxamide and (4S)—N-(3-(oxazol-5-yl)phenyl)-7-((S)-3-(trifluoromethyl)piperidin-1-yl)-3,4-dihydro-1,4-methanopyrido[2,3-b][1,4]diazepine-5(2H)-carboxamide

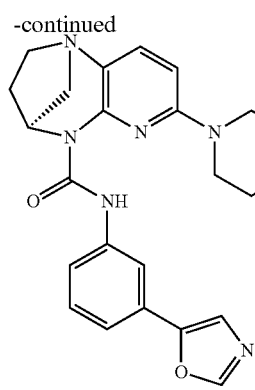

(4S)—N-(3-(oxazol-5-yl)phenyl)-7-(3-(trifluoromethyl) piperidin-1-yl)-3,4-dihydro-1,4-methanopyrido[2,3-b][1,4] diazepine-5(2H)-carboxamide (120 mg, 0.241 mmol) was loaded onto a 30×250 mm chiralcel OD-H column. Elution with 20:80 ethanol:heptanes first eluted (4S)—N-(3-(oxazol-5-yl)phenyl)-7-((R)-3-(trifluoromethyl)piperidin-1-yl)-3,4-dihydro-1,4-methanopyrido[2,3-b][1,4]diazepine-5 (2H)-carboxamide (41.3 mg, 0.0828 mmol, 34% yield), $[\alpha]_D^{25}$=+32 (c, 0.09, MeOH), followed by (4S)—N-(3-(oxazol-5-yl)phenyl)-7-((S)-3-(trifluoromethyl)piperidin-1-yl)-3,4-dihydro-1,4-methanopyrido[2,3-b][1,4]diazepine-5 (2H)-carboxamide (44.8 mg, 0.0899 mmol, 37% yield) $[\alpha]_D^{25}$=+18.5 (c, 0.11, MeOH). MS (ESI) calcd for $C_{25}H_{25}F_3N_6O_2$: 498.2. found: 499.3 [M+H].

Example 54. Preparation of (5S)—N-(5-fluoropyridin-3-yl)-8-(3-(trifluoromethyl)phenyl)-4,5-dihydro-2,5-methanopyrido[2,3-g][1,2,6]thiadiazocine-6 (3H)-carboxamide 1,1-dioxide Step 1. Synthesis of (S)-tert-butyl (1-((2,6-dichloropyridin-3-yl)sulfonyl)pyrrolidin-3-yl)carbamate

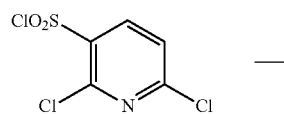

To a solution of 2,6-dichloropyridine-3-sulfonyl chloride (Org. Process Res. Dev. 2009, 13, 875-879) (3.40 g, 13.8 mmol) in dichloromethane (10 mL) was added (S)-tert-butyl pyrrolidin-3-ylcarbamate (2.82 g, 14.5 mmol), followed by triethylamine (3.00 mL, 21.5 mmol). The reaction was stirred at room temperature for 30 min, then poured into saturated sodium bicarbonate, and extracted with dichloromethane. The organic layer was washed with brine, dried with $Na_2SO_4$, and the solvent removed in vacuo, to give (S)-tert-butyl (1-((2,6-dichloropyridin-3-yl)sulfonyl)pyrrolidin-3-yl)carbamate (5.47 g, 13.8 mmol, 100% yield).

Step 2. Synthesis of (5S)-8-chloro-3,4,5,6-tetrahydro-2,5-methanopyrido[2,3-g][1,2,6]thiadiazocine 1,1-dioxide

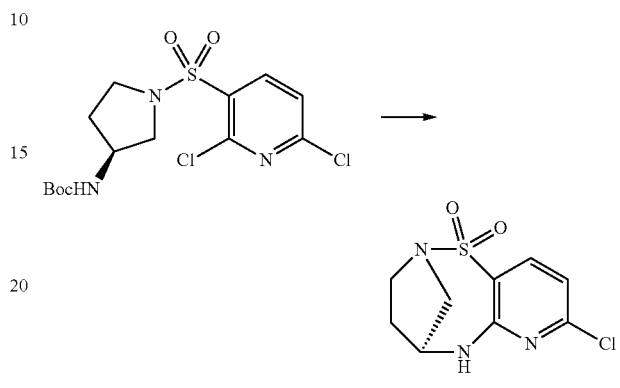

To a solution of (S)-tert-butyl (1-((2,6-dichloropyridin-3-yl)sulfonyl)pyrrolidin-3-yl)carbamate (5.47 g, 13.8 mmol) in dichloromethane (30 mL) was added trifluoroacetic acid (10 mL). The reaction was stirred at room temperature overnight, and all solvent removed in vacuo. The remaining residue was dissolved in DMF (30 mL), and sodium carbonate (10.0 g, 94.3 mmol) was added. The reaction was stirred at 90° C. for 2 h. The reaction was cooled to room temperature, poured into ice water, and the resulting solution was filtered, and the solids washed with water. The collected solid was dried, and purified by silica gel chromatography to give (5S)-8-chloro-3,4,5,6-tetrahydro-2,5-methanopyrido[2, 3-g][1,2,6]thiadiazocine 1,1-dioxide (1.80 g, 6.93 mmol, 50% yield).

Step 3. Synthesis of (5S)-8-(3-(trifluoromethyl) phenyl)-3,4,5,6-tetrahydro-2,5-methanopyrido[2,3-g] [1,2,6]thiadiazocine 1,1-dioxide

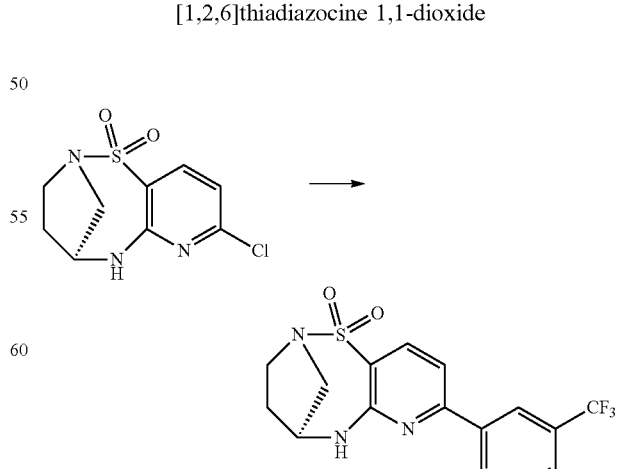

A mixture of (5S)-8-chloro-3,4,5,6-tetrahydro-2,5-methanopyrido[2,3-g][1,2,6]thiadiazocine 1,1-dioxide (800 mg, 3.08 mmol), 3-trifluoromethylbenzeneboronic acid (1.17 g, 6.16 mmol), cesium carbonate (3.00 g, 9.21 mmol) and [1,1'-bis(diphenylphosphino)ferrocene]dichloropalladium (II) (370 mg, 0.453 mmol) in 10:1 dioxane:water (45 mL) was stirred at 110° C. overnight. After cooling, the solvent was removed in vacuo, and the residue partitioned between dichloromethane and water. The organic layer was separated, washed with water, brine, dried with Na$_2$SO$_4$, and the solvent removed in vacuo. The remaining residue was purified by silica gel chromatography to give (5S)-8-(3-(trifluoromethyl)phenyl)-3,4,5,6-tetrahydro-2,5-methanopyrido[2,3-g][1,2,6]thiadiazocine 1,1-dioxide (1.00 g, 2.71 mmol, 88% yield).

Step 4. Synthesis of (5S)-8-((S)-3-fluoropyrrolidin-1-yl)-3,4,5,6-tetrahydro-2,5-methanopyrido[2,3-g][1,2,6]thiadiazocine 1,1-dioxide

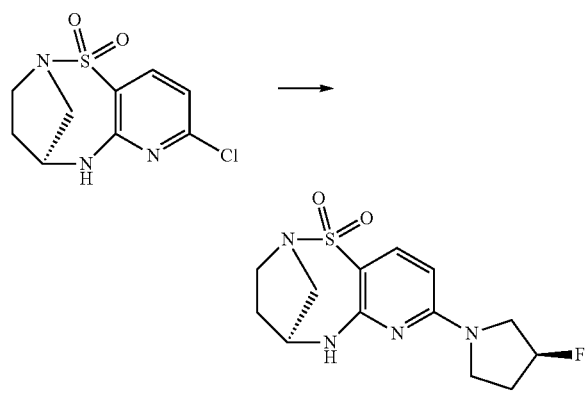

(S)-3-fluoropyrrolidine hydrochloride (1.10 g, 8.76 mmol) was added to a solution of (5S)-8-chloro-3,4,5,6-tetrahydro-2,5-methanopyrido[2,3-g][1,2,6]thiadiazocine 1,1-dioxide (800 mg, 3.08 mmol) and sodium carbonate (1.60 g, 15.1 mmol) in DMF (10 mL). The reaction was stirred at 90° C. for 6 h, then poured onto crushed ice, stirred, and filtered. The collected solid was washed with water, dried, and purified by silica gel chromatography to give (5S)-8-((S)-3-fluoropyrrolidin-1-yl)-3,4,5,6-tetrahydro-2,5-methanopyrido[2,3-g][1,2,6]thiadiazocine 1,1-dioxide (680 mg, 2.18 mmol, 71% yield).

Step 5. Synthesis of (5S)—N-(5-fluoropyridin-3-yl)-8-(3-(trifluoromethyl)phenyl)-4,5-dihydro-2,5-methanopyrido[2,3-g][1,2,6]thiadiazocine-6(3H)-carboxamide 1,1-dioxide

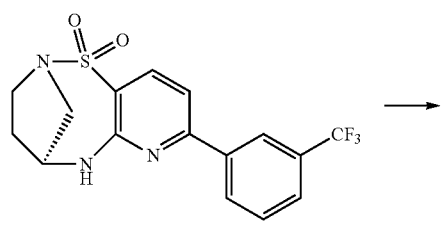

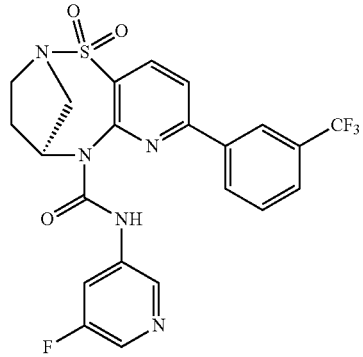

(5S)-8-(3-(trifluoromethyl)phenyl)-3,4,5,6-tetrahydro-2,5-methanopyrido[2,3-g][1,2,6]thiadiazocine 1,1-dioxide (70.0 mg, 0.190 mmol) was dissolved in DMF (3 mL), and sodium hydride (54 mg, 60% in oil, 1.35 mmol) was added. The reaction was stirred at room temperature for 2 h, and phenyl (5-fluoropyridin-3-yl)carbamate (176 mg, 0.768 mmol) was added. The reaction was stirred at room temperature for 1 h, poured into water, and extracted with dichloromethane. The organic layer was concentrated in vacuo, and the remaining residue purified by preparative thin-layer chromatography to give (5S)—N-(5-fluoropyridin-3-yl)-8-(3-(trifluoromethyl)phenyl)-4,5-dihydro-2,5-methanopyrido[2,3-g][1,2,6]thiadiazocine-6(3H)-carboxamide 1,1-dioxide (24.0 mg, 0.0473 mmol, 25% yield). MS (ESI) calcd for C$_{22}$H$_{17}$F$_4$N$_5$O$_3$S: 507.1. found: 508.1 (M+H)$^+$.

The following compound was made in an analogous manner: (5S)—N-(5-fluoropyridin-3-yl)-8-((S)-3-fluoropyrrolidin-1-yl)-4,5-dihydro-2,5-methanopyrido[2,3-g][1,2,6]thiadiazocine-6(3H)-carboxamide 1,1-dioxide.

Example 55. Synthesis of (4S)—N-(3-(4-((6-aminohexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

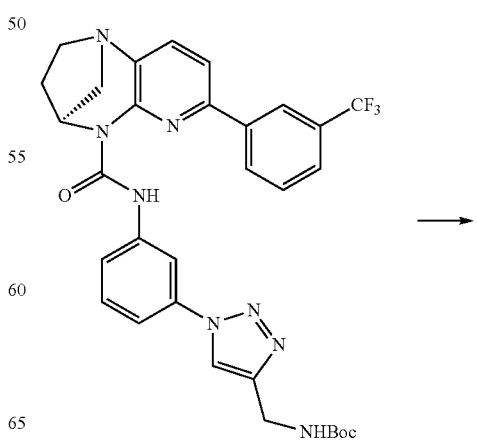

145

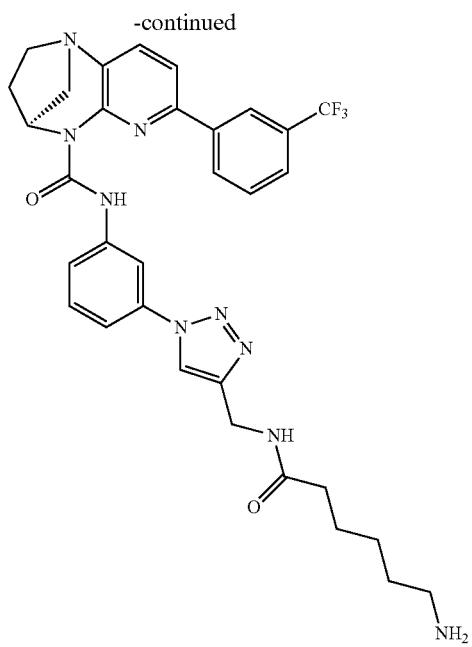

146

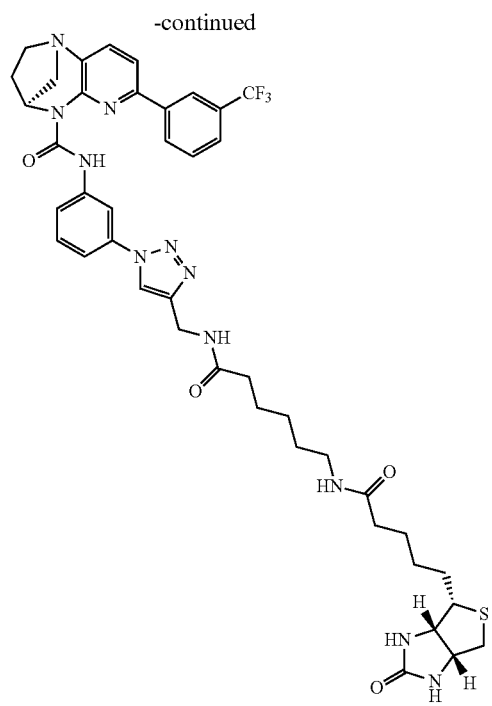

A solution of tert-butyl ((1-(3-((4S)-7-(3-(trifluoromethyl)phenyl)-2,3,4,5-tetrahydro-1,4-methanopyrido[2,3-b][1,4]diazepine-5-carboxamido)phenyl)-1H-1,2,3-triazol-4-yl)methyl)carbamate (190 mg, 0.306 mmol) in trifluoroacetic acid (3.0 mL) was stirred at room temperature for 1 h, then the excess trifluoroacetic acid removed in vacuo. The remaining residue was dissolved in DMF (5.0 mL) and triethylamine (1.0 mL), and 2,5-dioxopyrrolidin-1-yl 6-((tert-butoxycarbonyl)amino)hexanoate (250 mg, 0.761 mmol) was added. The reaction was stirred at 80° C. for 30 min, then cooled to 65° C. and 4N HCl (4 mL) was added. The reaction was stirred at 65° C. for 2 h, then filtered, and the filtrate purified by preparative HPLC. The isolated material was lyophilized from acetonitrile/1N HCl to give (4S)—N-(3-(4-((6-aminohexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide hydrochloride (208 mg, 0.310 mmol, 100% yield). MS (ESI) calcd for $C_{32}H_{34}F_3N_9O_2$: 633.3. found: 634.3 $(M+H)^+$.

Example 56. Synthesis of (4S)—N-(3-(4-((6-(5-((3aS,4S,6aR)-2-oxohexahydro-1H-thieno[3,4-d]imidazol-4-yl)pentanamido)hexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (44.2 mg, 0.0850 mmol) in acetonitrile (1.3 mL) and triethylamine (0.13 mL, 0.933 mmol) was added biotinamidohexanoic acid N-hydroxysuccinimide ester (40.9 mg, 0.090 mmol). The reaction was stirred at 65° C. for 2 h, then DMF (1 mL) was added, and the resulting reaction mixture filtered, and the filtrate purified by preparative HPLC to give (4S)—N-(3-(4-((6-(5-((3aS,4S,6aR)-2-oxohexahydro-1H-thieno[3,4-d]imidazol-4-yl)pentanamido)hexanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (43.6 mg, 0.0448 mmol, 53% yield).

Example 57. Synthesis of (4S)—N-(3-(4-((3-(3',6'-dihydroxy-3-oxo-3H-spiro[isobenzofuran-1,9'-xanthen]-5-yl)thioureido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

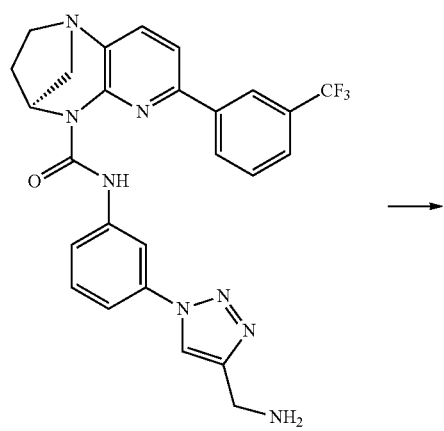

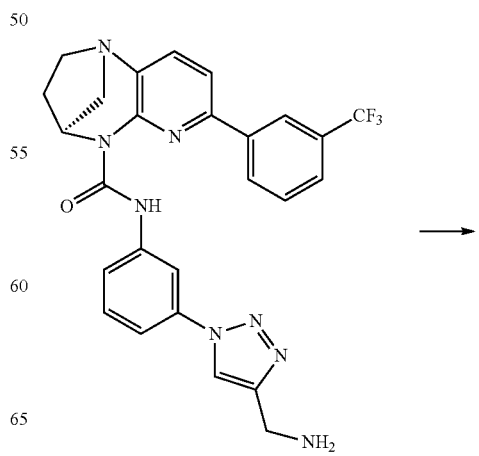

147

-continued

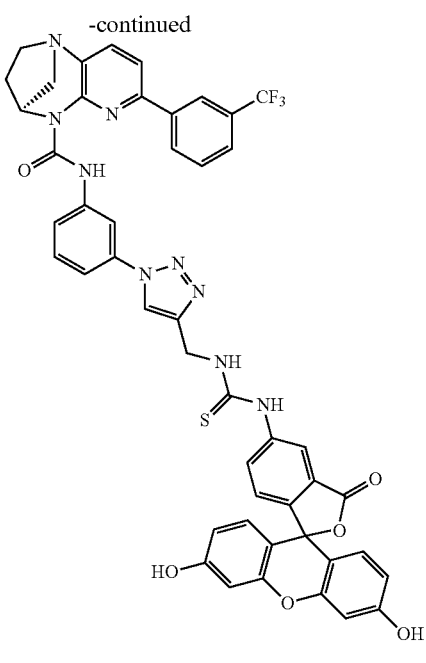

To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (44.2 mg, 0.0850 mmol) in acetonitrile (1.3 mL) and triethylamine (0.13 mL, 0.933 mmol) was added fluorescein isothiocyanate isomer I (35.0 mg, 0.090 mmol). The reaction was stirred at 65° C. for 2 h, then DMF (1 mL) was added, and the resulting reaction mixture filtered, and the filtrate purified by preparative HPLC to give (4S)—N-(3-(4-((3-(3',6'-dihydroxy-3-oxo-3H-spiro[isobenzofuran-1,9'-xanthen]-5-yl)thioureido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (51.0 mg, 0.0498 mmol, 58% yield).

Example 58. Synthesis of (4S)—N-(3-(4-((3-((Z)-2-((1-(difluoroboryl)-1H-pyrrol-2-yl)methylene)-2H-pyrrol-5-yl)propanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide

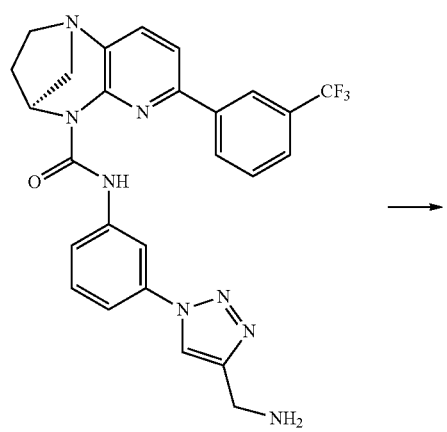

148

-continued

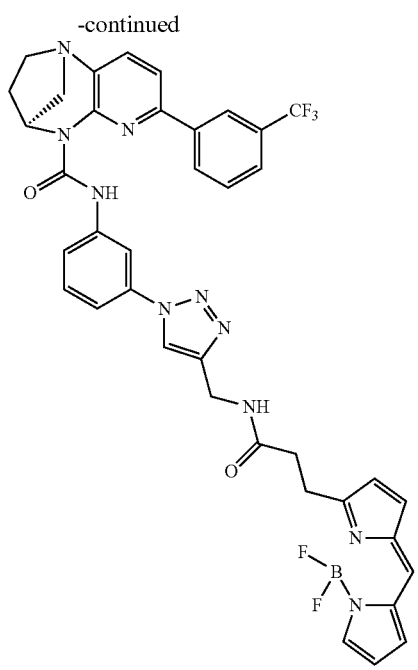

To a solution of (4S)—N-(3-(4-(aminomethyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (12.2 mg, 0.0234 mmol) in acetonitrile (0.35 mL) and triethylamine (0.035 mL, 0.251 mmol) was added 4,4-difluoro-5,7-dimethyl-4-bora-3a,4a-diaza-s-indacene-3-propionic acid, succinimidyl ester (10 mg, 0.0257 mmol). The reaction was stirred at 60° C. for 30 min, then the reaction mixture purified by preparative HPLC to give (4S)—N-(3-(4-((3-((Z)-2-((1-(difluoroboryl)-1H-pyrrol-2-yl)methylene)-2H-pyrrol-5-yl)propanamido)methyl)-1H-1,2,3-triazol-1-yl)phenyl)-7-(3-(trifluoromethyl)phenyl)-3,4-dihydro-1,4-methanopyrido[2,3-b][1,4]diazepine-5(2H)-carboxamide (5.8 mg, 0.0064 mmol, 27% yield).

Example 59. Synthesis of (9S)—N-(4-(acetamidomethyl)phenyl)-2-(3-(trifluoromethyl)phenyl)-8,9-dihydro-6H-5,9-methanopyrido[2,3-b][1,4]diazocine-10(7H)-carboxamide

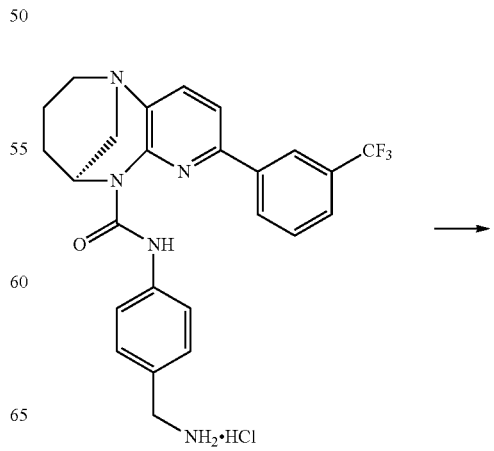

-continued

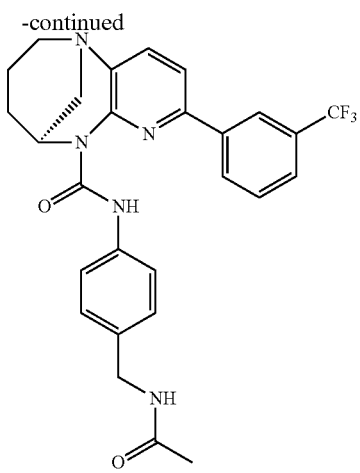

To a solution of (9S)—N-(4-(aminomethyl)phenyl)-2-(3-(trifluoromethyl)phenyl)-8,9-dihydro-6H-5,9-methanopyrido[2,3-b][1,4]diazocine-10(7H)-carboxamide hydrochloride (108 mg, 0.214 mmol) in pyridine (3.0 mL) was added acetic anhydride (28.0 μL, 0.300 mmol). The reaction was stirred at room temperature for 4 h, and the reaction mixture purified by preparative HPLC to give (9S)—N-(4-(acetamidomethyl)phenyl)-2-(3-(trifluoromethyl)phenyl)-8,9-dihydro-6H-5,9-methanopyrido[2,3-b][1,4]diazocine-10(7H)-carboxamide trifluoroacetate (111 mg, 0.178 mmol, 83% yield). MS (ESI) calcd for $C_{27}H_{26}F_3N_5O_2$: 509.2. found: 510.2 (M+H)$^+$.

Example 60. Preparation of (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide Step 1: Synthesis of tert-butyl 3-(3-((4S)-7-(3-(trifluoromethyl)phenyl)-2,3,4,5-tetrahydro-1,4-methanopyrido[2,3-b][1,4]thiazepine-5-carboxamido)phenyl)pyrrolidine-1-carboxylate

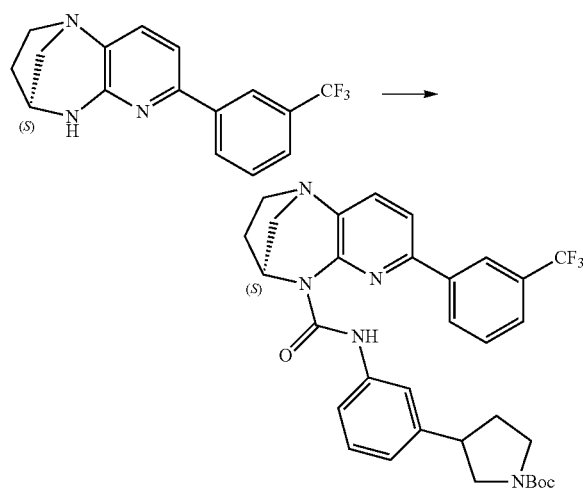

(4S)-7-(3-(trifluoromethyl)phenyl)-2,3,4,5-tetrahydro-1,4-methanopyrido[2,3-b][1,4]diazepine (A7, 0.150 g, 0.490 mmol) was dissolved in 5 ml methylene chloride and treated with DIEA (193 ul, 1.08 mmol). The mixture was stirred at room temperature for 30 minutes. Tert-butyl 3-(3-aminophenyl)pyrrolidine-1-carboxylate (0.141 g, 0.539 mmol) was then added and the solution was stirred over night at room temperature. The reaction was diluted with 5 ml methylene chloride and washed with 10 ml of a saturated solution of sodium hydrogen carbonate. Organics were collected and concentrated to dryness. Purification by silica column chromatography using 5-100% ethylacetate in pentane afforded tert-butyl 3-(3-((4S)-7-(3-(trifluoromethyl)phenyl)-2,3,4,5-tetrahydro-1,4-methanopyrido[2,3-b][1,4]diazepine-5-carboxamido)phenyl)pyrrolidine-1-carboxylate (0.077 g, 26%). MS (ESI) calcd for $C_{32}H_{34}F_3N_5O_3$: 593.3. found: 594 [M+H].

Step 2: Synthesis of (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide

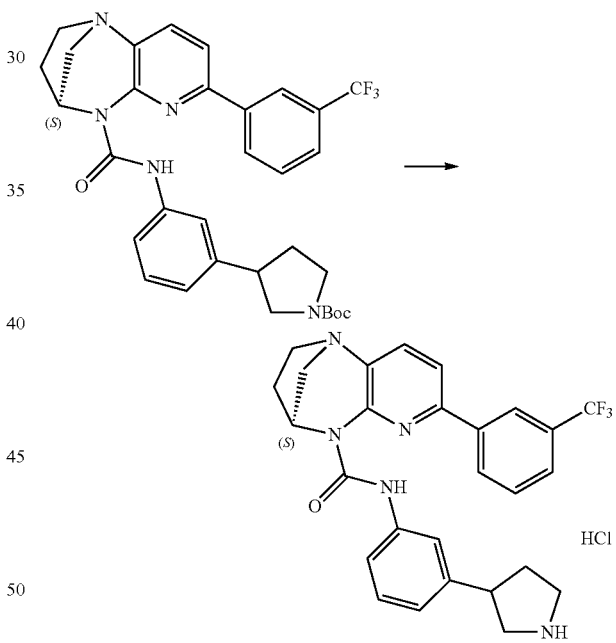

(S)Tert-butyl 3-(3-((4S)-7-(3-(trifluoromethyl)phenyl)-2,3,4,5-tetrahydro-1,4-methanopyrido[2,3-b][1,4]diazepine-5-carboxamido)phenyl)pyrrolidine-1-carboxylate: (0.077 g, 0.130 mmol) was dissolved in 5 mL of 4 N HCl in 1,4-dioxane and stirred under nitrogen for 3 hours at room temperature. All solvent was then removed under reduced pressure and the resulting solid was dried over night under vacuum to give (4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide (0.078 g, 100%). MS (ESI) calcd for $C_{27}H_{26}F_3N_5O$: 493.21. found: 494 [M+H].

Example 61. Preparation of (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide

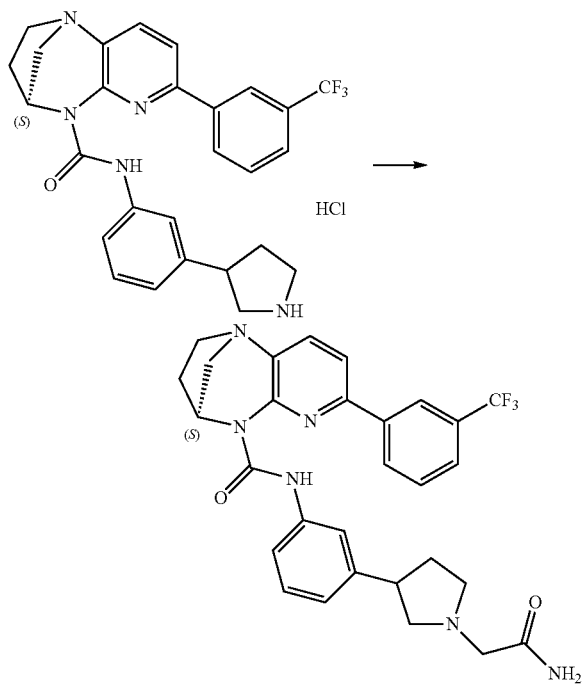

(4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide (B579, 0.029 g, 0.058 mmol) was dissolved in 2 ml methylene chloride and then treated with DIEA (31 ul, 0.174 mmol). Chloroacetamide (0.006 g, 0.064 mmol) was then added and the reaction was heated to 60° C. over night. The reaction was then cooled to room temperature and diluted with 5 ml methylene chloride and washed with 10 ml of a saturated solution of sodium hydrogen carbonate. Organics were concentrated to dryness and purified via reverse phase chromatography on C18 using a gradient of 5-95% acetonitrile in water with 0.1% trifluoroacetic acid as additive to give (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide (0.008 g, 23%). MS (ESI) calcd for $C_{29}H_{29}F_3N_6O_2$: 550.2. found: 551 [M+H].

Example 62: Preparation of (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide

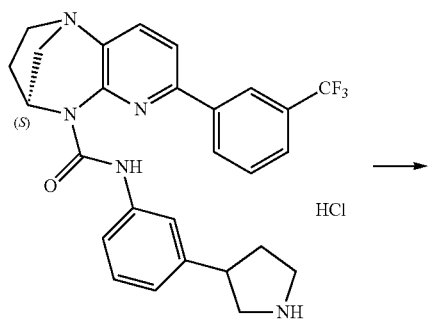

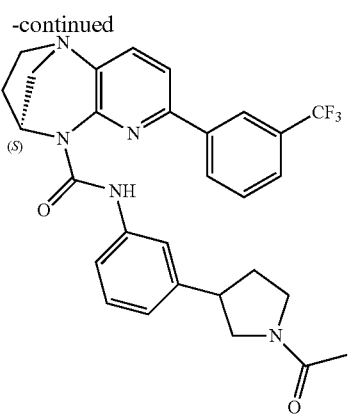

(4S)—N-(3-(pyrrolidin-3-yl)phenyl)-7-(3-(trifluoromethyl)phenyl)-3,4-dihydro-1,4-methanopyrido[2,3-b][1,4]diazepine-5(2H)-carboxamide (B579, 0.020 g, 0.038 mmol) was dissolved in 1.5 ml methylene chloride and then treated with DIEA (13 ul, 0.076 mmol). Acetylchloride (0.005 g, 0.042 mmol) was then added and the reaction was stirred at room temperature over night. The reaction was then diluted with 5 ml methylene chloride and washed with 10 ml of a saturated solution of sodium hydrogen carbonate. Organics were concentrated to dryness and purified via reverse phase chromatography on C18 to give (4S)—N-(3-(1-(2-amino-2-oxoethyl)pyrrolidin-3-yl)phenyl)-7-(3-(trifluoromethyl)phenyl)-3,4-dihydro-1,4-methanopyrido[2,3-b][1,4]diazepine-5(2H)-carboxamide (0.023 g, 88%). MS (ESI) calcd for $C_{29}H_{28}F_3N_5O_2$: 535.2. found: 536 [M+H].

This general acylation procedure was used to prepare (4S)—N-(3-(1-propionylpyrrolidin-3-yl)phenyl)-7-(3-(trifluoromethyl)phenyl)-3,4-dihydro-1,4-methanopyrido[2,3-b][1,4]diazepine-5(2H)-carboxamide and (4S)—N-(3-(1-(cyclopropanecarbonyl)pyrrolidin-3-yl)phenyl)-7-(3-(trifluoromethyl)phenyl)-3,4-dihydro-1,4-methanopyrido[2,3-b][1,4]diazepine-5(2H)-carboxamide.

Example 63. Preparation of benzyl ((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate

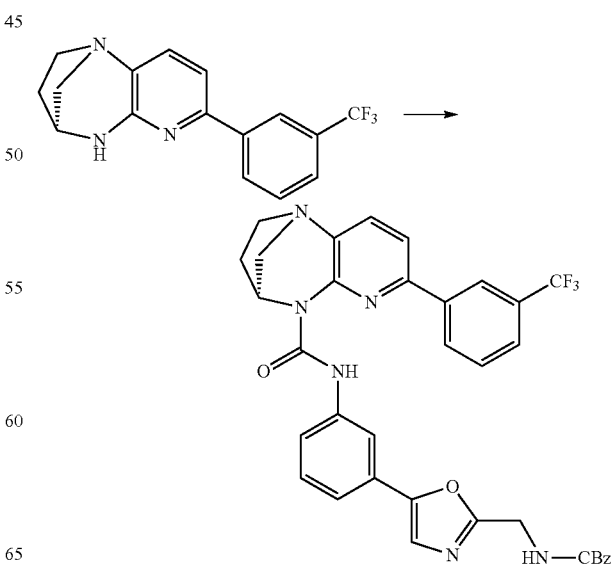

(4S)-7-(3-(trifluoromethyl)phenyl)-2,3,4,5-tetrahydro-1,4-methanopyrido[2,3-b][1,4]diazepine (0.276 g, 0.902 mmol) in 4 mL methylene chloride was combined with DIEA (400 uL, 2.261 mmol) and triphosgene (0.200 g, 0.676 mmol). The mixture was then heated to 65° C. at which point benzyl ((5-(3-aminophenyl)oxazol-2-yl)methyl)carbamate (0.321 g, 0.992 mmol) in 4 mL methylene chloride was added dropwise slowly. The mixture was then heated at 65° C. for 5 hours. The reaction was then cooled to RT and 10 mL methylene chloride was then added followed by wash with 50 mL of a saturated solution of sodium hydrogen carbonate. The organic layer was collected and concentrated to dryness under reduced pressure. Residue was then purified via silica gel chromatography to afford benzyl ((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate (0.082 g, 14%). MS (ESI) calcd for $C_{35}H_{29}F_3N_6O_4$: 654.22. found: 655 [M+H].

Example 64. Preparation of (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide

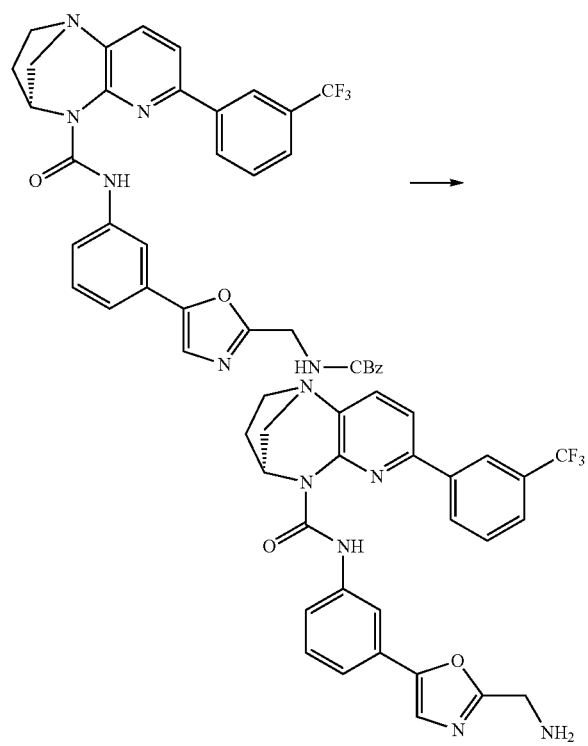

Benzyl((5-(3-((4S)-7-(3-(trifluoromethyl)phenyl)-2,3,4,5-tetrahydro-1,4-methanopyrido[2,3-b][1,4]diazepine-5-carboxamido)phenyl)oxazol-2-yl)methyl)carbamate (0.040 g, 0.06 mmol) was dissolved in 10 mL ethylacetate and degassed three times under vacuum. Approximately 5 mg of Palladium (10% on Carbon degaussa type) was then added and the reaction vessel was purged with nitrogen then fitted with a hydrogen balloon. Stirring was then initiated and the mixture was stirred under hydrogen for 2 hours. The reaction vessel was then evacuated and purged with nitrogen. The solids were removed via filtration and the solvent was removed under reduced pressure to give (4S)—N-(3-(2-(aminomethyl)oxazol-5-yl)phenyl)-7-(3-(trifluoromethyl)phenyl)-3,4-dihydro-1,4-methanopyrido[2,3-b][1,4]diazepine-5(2H)-carboxamide (0.032 g, 100%) that was used without purification. MS (ESI) calcd for $C_{27}H_{23}F_3N_6O_2$: 520.51. found: 521 [M+H].

Example 65. Preparation of (4S)—N-(5-phenyl-1,3,4-oxadiazol-2-yl)-7-(3-(trifluoromethyl)phenyl)-3,4-dihydro-1,4-methanopyrido[2,3-b][1,4]diazepine-5(2H)-carboxamide Step 1. Synthesis of (4S)-phenyl 7-(3-(trifluoromethyl)phenyl)-3,4-dihydro-1,4-methanopyrido[2,3-b][1,4]diazepine-5(2H)-carboxylate

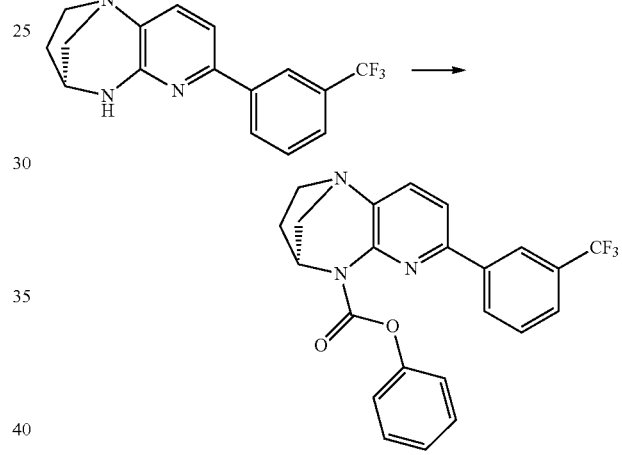

To a solution of (4S)-7-(3-(trifluoromethyl)phenyl)-2,3,4,5-tetrahydro-1,4-methanopyrido[2,3-b][1,4]diazepine (1.5 g, 4.92 mmol) and pyridine (0.74 mL, 9.84 mmol) in DCM (15 mL) was added phenyl chloroformate (1.1 mL, 8.85 mmol) at 0° C. dropwise. The resulting mixture was stirred at that temperature for 2 h, then washed with saturated aqueous $NaHCO_3$, dried over anhydrous $Na_2SO_4$, concentrated to afford the crude phenyl carbamate (1.8 g) as a brown oil, which was used in the next step without further purification.

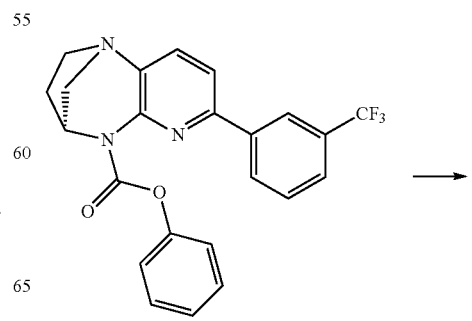

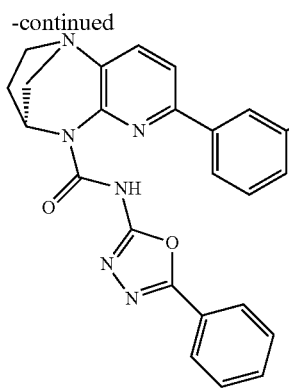

Step 2. Synthesis of (4S)—N-(5-phenyl-1,3,4-oxadiazol-2-yl)-7-(3-(trifluoromethyl)phenyl)-3,4-dihydro-1,4-methanopyrido[2,3-b][1,4]diazepine-5(2H)-carboxamide To a solution of amine 5-phenyl-1,3,4-oxadiazol-2-amine (30 mg, 0.18 mmol) in dry THF (5 mL) was added NaH (18 mg, 0.75 mmol) in portions at 0° C., the reaction mixture was stirred at room temperature for 30 min. (4S)-phenyl 7-(3-(trifluoromethyl)phenyl)-3,4-dihydro-1,4-methanopyrido[2,3-b][1,4]diazepine-5(2H)-carboxylate (157 mg, 0.37 mmol) was then added and the mixture was stirred overnight. The resulting mixture was quenched with MeOH (2 mL), concentrated in vacuo by evaporator. The residue was purified by prep-TLC to give 2-(3-((2,2-dimethyl-1,3-dioxolan-4-yl)methyl)phenyl)-4,4,5,5-tetramethyl-1,3,2-dioxaborolane (50 mg, yield 54.9%) as a white solid.

This general procedure using (4S)-phenyl 7-(3-(trifluoromethyl)phenyl)-3,4-dihydro-1,4-methanopyrido[2,3-b][1,4]diazepine-5(2H)-carboxylate could be used to prepare a variety of carboxamides by using the appropriate arylamines in place of 5-phenyl-1,3,4-oxadiazol-2-amine.

Example 66. Preparation of (4S)—N-(3-(oxazol-5-yl)phenyl)-7-(3-(trifluoromethyl)phenyl)-3,4-dihydro-1,4-methanopyrido[2,3-b][1,4]diazepine-5(2H)-carbothioamide Step 1. Synthesis of 5-(3-isothiocyanatophenyl)oxazole

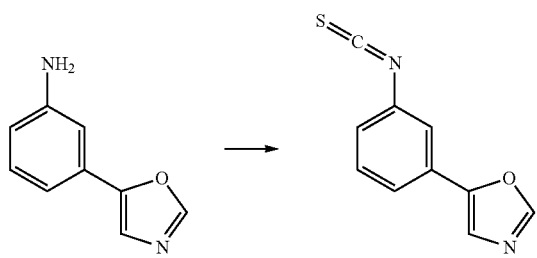 [SMILES: Nc1cccc(-c2cnco2)c1 ; S=C=Nc1cccc(-c2cnco2)c1]

To a solution of 3-(oxazol-5-yl)aniline (160 mg, 1.0 mmol) and TEA (0.4 mL, 3.0 mmol) in dry THF (6 mL) was added a solution of thiophosgene (0.152 mL, 2.0 mmol) in dry THF (1.5 mL) dropwise over 10 min at 0° C. under Argon atmosphere. The reaction mixture was stirred at ambient temperature for 30 min, TLC showed 3-(oxazol-5-yl)aniline was fully consumed. The solvent was removed by evaporator under reduced pressure, the residue was diluted with water (10 mL) and ethyl acetate (25 mL), the organic layer was separated. The aqueous phase was extracted with ethyl acetate (3×30 mL), the combined organic layers were washed with saturated aqueous NaHCO$_3$ followed by water and brine, dried over anhydrous sodium sulfate, filtered and concentrated to give 5-(3-isothiocyanatophenyl)oxazole which was used for the next reaction without any further purification.

Step 2. Synthesis of (4S)—N-(3-(oxazol-5-yl)phenyl)-7-(3-(trifluoromethyl)phenyl)-3,4-dihydro-1,4-methanopyrido[2,3-b][1,4]diazepine-5(2H)-carbothioamide

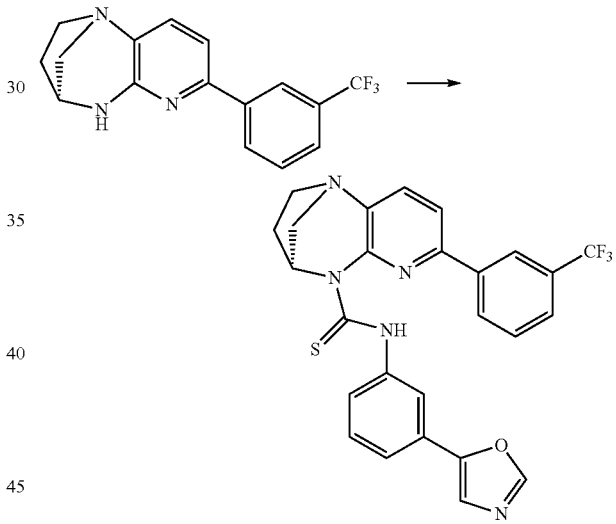

(4S)-7-(3-(trifluoromethyl)phenyl)-2,3,4,5-tetrahydro-1,4-methanopyrido[2,3-b][1,4]diazepine (244 mg, 0.8 mmol) was dissolved in dry DMF (5 mL) and NaH (128 mg, 60%, 3.2 mmol) was added in portions at 0° C. under Argon atmosphere. The mixture was warmed to room temperature and stirred for 1 h. A solution of 5-(3-isothiocyanatophenyl)oxazole prepared above in DMF (3 mL) was added dropwise and the reaction mixture was stirred at ambient temperature overnight. The resulting mixture was then quenched with saturated aqueous NH$_4$Cl, extracted with ethyl acetate (3×15 mL), washed with water and brine, dried over anhydrous Na$_2$SO$_4$, filtered and concentrated. The crude was purified through silica gel chromatography using DCM:MeOH=10:1 to give title compound (4S)—N-(3-(oxazol-5-yl)phenyl)-7-(3-(trifluoromethyl)phenyl)-3,4-dihydro-1,4-methanopyrido[2,3-b][1,4]diazepine-5(2H)-carbothioamide (186.1 mg, yield 46%).

Example 67. Preparation of (4S)—N-(3-(oxazol-5-yl)phenyl)-7-(3-(trifluoromethyl)phenyl)-3,4-dihydro-1,4-methanobenzo[b][1,4]diazepine-5(2H)-carboxamide Step 1. Synthesis of (S)-dimethyl 2-((5-bromo-2-nitrophenyl)amino)succinate

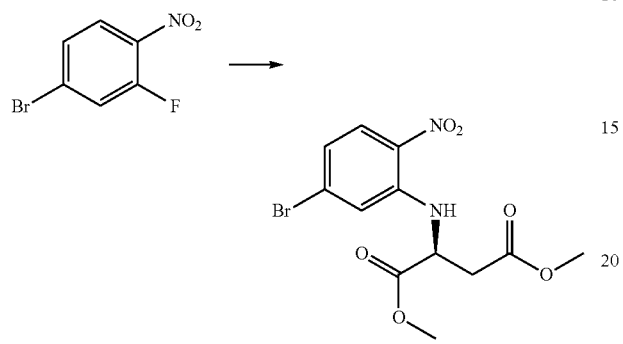

The mixture of 4-bromo-2-fluoro-1-nitrobenzene (15.0 g, 68 mmol), (S)-dimethyl 2-aminosuccinate hydrochloride (15 g, 75 mmol) and DIPEA (36 mL) in DMSO (127 mL) was stirred at 100° C. for 2 h. After cooling down, water (200 mL) was added and the mixture was extracted with ethyl acetate (3×300 mL). The combined organic layers were washed with water and brine, dried over anhydrous sodium sulfate, filtered and concentrated. The residue was purified by silica gel chromatography (petroleum ether/ethyl acetate=4/1) to give (S)-dimethyl 2-((5-bromo-2-nitrophenyl)amino)succinate (12.4 g, yield 51%)

Step 2. Synthesis of (S)-methyl 2-(7-bromo-3-oxo-1,2,3,4-tetrahydroquinoxalin-2-yl)acetate (Sundia E655-523-23)

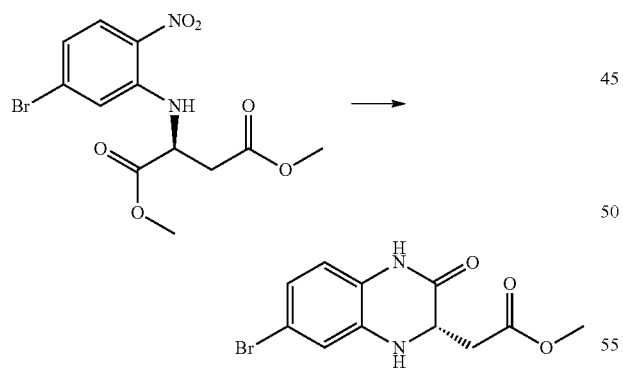

The mixture of (S)-dimethyl 2-((5-bromo-2-nitrophenyl)amino)succinate (12.4 g, 34.4 mmol), Fe (22 g, 392 mmol) and AcOH (1.2 mL) in i-PrOH (250 mL) and water (50 mL) was stirred at reflux for 2 h. After cooling, the solid was filtered and the filtrate was concentrated. The residue was diluted with DCM (300 mL) and water (300 mL), the organic layer was separated, and the aqueous phase was extracted with DCM (3×300 mL). The combined organic layers were washed with water and brine, dried over anhydrous sodium sulfate, filtered and concentrated. The residue was purified by silica gel chromatography (petroleum ether/ethyl acetate=4/1) to give (S)-methyl 2-(7-bromo-3-oxo-1,2,3,4-tetrahydroquinoxalin-2-yl)acetate (8.8 g, yield 86%) $^1$H NMR (DMSO-$d_6$, 400 MHz): δ 10.43 (s, 1H), 6.84 (s, 1H), 6.75-6.73 (m, 1H), 6.66-6.63 (m, 1H), 6.32 (s, 1H), 4.19-4.16 (m, 1H), 3.60 (s, 3H), 2.78-2.72 (m, 1H), 2.68-2.61 (m, 1H).

Step 3. Synthesis of (S)-2-(7-bromo-1,2,3,4-tetrahydroquinoxalin-2-yl)ethanol

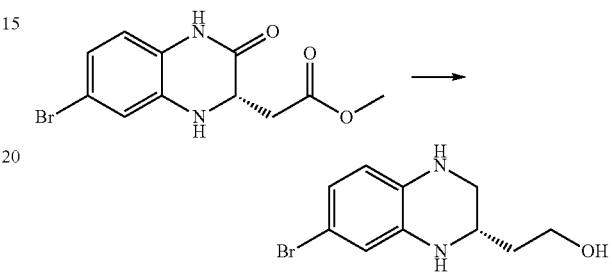

To the solution of (S)-methyl 2-(7-bromo-3-oxo-1,2,3,4-tetrahydroquinoxalin-2-yl)acetate (4.4 g, 14.7 mmol) in THF (30 mL) was added $BH_3Me_2S$ (10 M, 10 mL) at 0° C. over 15 min in a dropwise fashion. The reaction was heated to reflux overnight. After cooling down, the mixture was quenched with 6N HCl (10 mL) and the resulting mixture stirred at 50° C. for 2 h. The mixture was then basified using 2N NaOH and brought to pH-8. The mixture was extracted with DCM (3×50 mL) and the combined organic layers were washed with water and brine, dried over anhydrous sodium sulfate, filtered and concentrated. The residue was purified by silica gel chromatography (DCM/MeOH=20/1) to give (S)-2-(7-bromo-1,2,3,4-tetrahydroquinoxalin-2-yl)ethanol (2.4 g, yield 63%).

Step 4. Synthesis of (4S)-7-bromo-2,3,4,5-tetrahydro-1,4-methanobenzo[b][1,4]diazepine

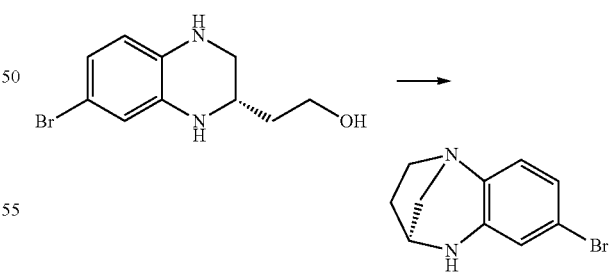

DDQ (2.7 g, 11.7 mmol) was added to a solution of $PPh_3$ (3.0 g, 11.7 mmol) in DCM (100 mL) at room temperature. (S)-2-(7-bromo-1,2,3,4-tetrahydroquinoxalin-2-yl)ethanol (2.0 g, 7.8 mmol) was added. The mixture was stirred at room temperature for 2 h. After removing the solvent, the residue was purified by silica gel chromatography (DCM/MeOH=40/1) to give (4S)-7-bromo-2,3,4,5-tetrahydro-1,4-methanobenzo[b][1,4]diazepine (1.5 g, yield 81%).

Step 5. Synthesis of (4S)-7-(3-(trifluoromethyl)phenyl)-2,3,4,5-tetrahydro-1,4-methanobenzo[b][1,4]diazepine

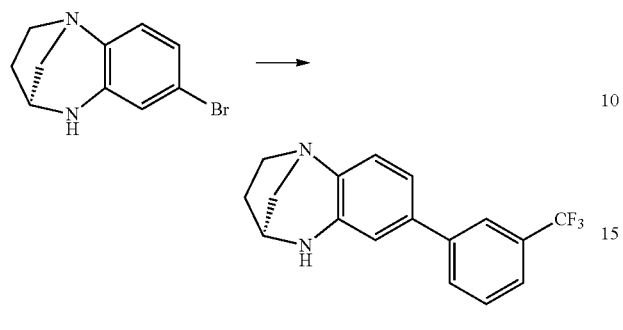

To the mixture of (4S)-7-bromo-2,3,4,5-tetrahydro-1,4-methanobenzo[b][1,4]diazepine (600 mg, 2.5 mmol), (3-(trifluoromethyl)phenyl)boronic acid (950 mg, 5.0 mmol), $Cs_2CO_3$ (2.4 g, 7.5 mmol) in dioxane (60 mL) and water (6 mL) was added $Pd(dppf)Cl_2$ (204 mg, 0.25 mmol) at room temperature under $N_2$ atmosphere. The mixture was stirred at 110° C. overnight. After cooling down, the solid was filtered and the filtrate was concentrated. The residue was diluted with DCM (30 mL) and water (30 mL), the organic layer was separated and the aqueous phase was extracted with DCM (3×30 mL). The combined organic layers were washed with water and brine, dried over anhydrous sodium sulfate, filtered and concentrated. The residue was purified by silica gel chromatography (DCM/MeOH=20/1) to give (4S)-7-(3-(trifluoromethyl)phenyl)-2,3,4,5-tetrahydro-1,4-methanobenzo[b][1,4]diazepine (700 mg, yield 95%).

Step 6. Synthesis of (4S)—N-(3-(oxazol-5-yl)phenyl)-7-(3-(trifluoromethyl)phenyl)-3,4-dihydro-1,4-methanobenzo[b][1,4]diazepine-5(2H)-carboxamide

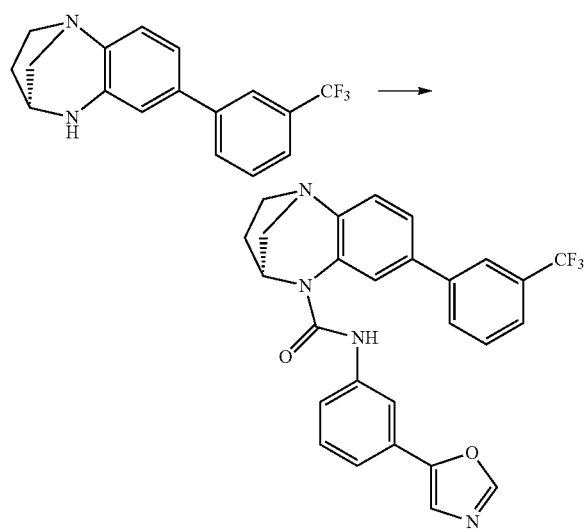

The mixture of (4S)-7-(3-(trifluoromethyl)phenyl)-2,3,4,5-tetrahydro-1,4-methanobenzo[b][1,4]diazepine (50 mg, 0.16 mmol), TEA (0.1 mL) and triphosgene (40 mg, 0.13 mmol) in THF (5 mL) was stirred at 60° C. for 2 h. 3-(oxazol-5-yl)aniline (38 mg, 0.24 mmol) was added. The mixture was stirred at 60° C. overnight. After cooling down, the resulting mixture was concentrated, the residue was purified by prep-TLC (DCM/MeOH=20/1) to give (4S)—N-(3-(oxazol-5-yl)phenyl)-7-(3-(trifluoromethyl)phenyl)-3,4-dihydro-1,4-methanobenzo[b][1,4]diazepine-5(2H)-carboxamide (26.1 mg, yield 33%).

Example 68. Preparation of (4S)—N-(pyridin-2-yl)-7-(3-(trifluoromethyl)phenyl)-3,4-dihydro-1,4-methanobenzo[b][1,4]diazepine-5(2H)-carboxamide

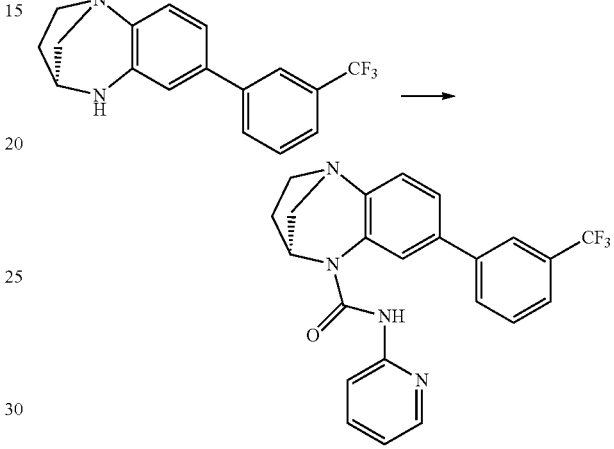

The mixture of (4S)-7-(3-(trifluoromethyl)phenyl)-2,3,4,5-tetrahydro-1,4-methanobenzo[b][1,4]diazepine (50 mg, 0.16 mmol), DMAP (52 mg, 0.42 mmol) and phenyl pyridin-2-ylcarbamate (89 mg, 0.42 mmol) in $CH_3CN$ (2.5 mL) was refluxed overnight. After cooling down, the solvent was removed. The residue was purified by prep-TLC (DCM/MeOH=20/1) to give (4S)—N-(pyridin-2-yl)-7-(3-(trifluoromethyl)phenyl)-3,4-dihydro-1,4-methanobenzo[b][1,4]diazepine-5(2H)-carboxamide (24.4 mg, yield 35%).

Example 69. Preparation of (4S)—N-(pyridin-3-yl)-7-(3-(trifluoromethyl)cyclohexyl)-3,4-dihydro-1,4-methanopyrido[2,3-b][1,4]diazepine-5(2H)-carboxamide Step 1. Synthesis of (4S)-7-(3-(trifluoromethyl)cyclohexyl)-2,3,4,5-tetrahydro-1,4-methanopyrido[2,3-b][1,4]diazepine

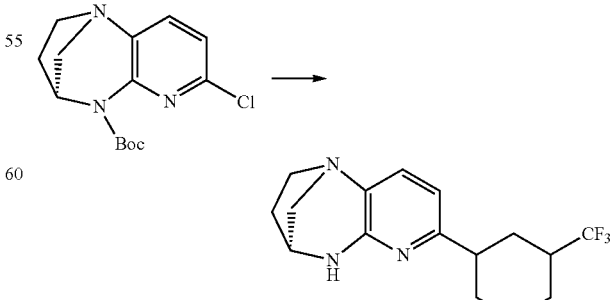

This moiety was made using the general Negishi coupling procedure above to give (4S)-7-(3-(trifluoromethyl)cyclohexyl)-2,3,4,5-tetrahydro-1,4-methanopyrido[2,3-b][1,4]diazepine as a 11:1 mixture of diastereomers (482 mg, 36%). MS (ESI) calcd for $C_{16}H_{20}F_3N_3$: 311.16. found: 312 [M+H].

Step 2. Synthesis of (4S)—N-(pyridin-3-yl)-7-(3-(trifluoromethyl)cyclohexyl)-3,4-dihydro-1,4-methanopyrido[2,3-b][1,4]diazepine-5(2H)-carboxamide

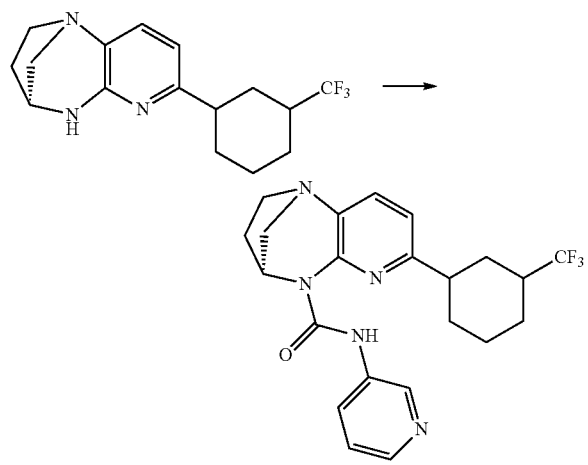

These compounds were made using the triphosgene urea coupling procedure above to give (4S)—N-(pyridin-3-yl)-7-(3-(trifluoromethyl)cyclohexyl)-3,4-dihydro-1,4-methanopyrido[2,3-b][1,4]diazepine-5(2H)-carboxamide as a 9:1 mixture of diastereomers (38 mg, 62%). MS (ESI) calcd for $C_{22}H_{24}F_3N_5O$: 431.19. found: 432 [M+H].

Example 70. Preparation of (4S)—N-(pyrimidin-4-yl)-7-(3-(trifluoromethyl)cyclohexyl)-3,4-dihydro-1,4-methanopyrido[2,3-b][1,4]diazepine-5(2H)-carboxamide

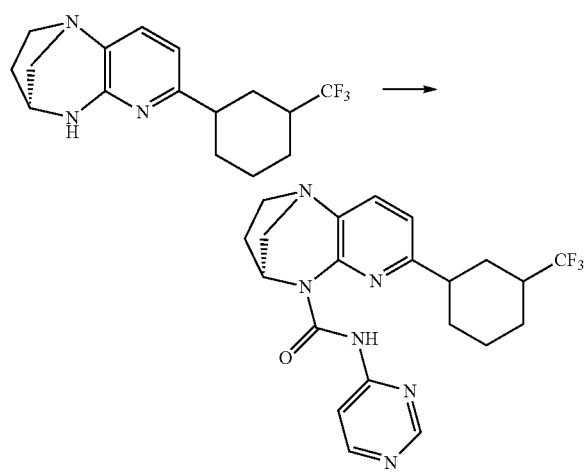

This mixture of diastereomers was made using the following protocol. Carbonyldiimidazole (CDI, 21 mg, 0.13 mmol) was slurried in DCM (1.5 mL), followed by addition of 4-aminopyrimidine (13 mg, 0.13 mmol). To get everything into solution, dioxane was added (0.5 mL). The mixture was allowed to stir at room temp for 1 h under nitrogen atmosphere. (4S)-7-(3-(trifluoromethyl)cyclohexyl)-2,3,4,5-tetrahydro-1,4-methanopyrido[2,3-b][1,4]diazepine (41 mg, 0.13 mmol) was added in DCM (1 mL), and the reaction was allowed to stir overnight, then more CDI was added (21 mg) and the reaction heated to reflux for 4 h. The reaction was monitored by LCMS and the intermediate (before addition of 4-aminopyrimidine) was the major reaction component. The reaction was cooled to room temp, concentrated, then more 4-aminopyrimidine (25 mg) was added in 1 mL DMSO (for better solubility). The reaction was warmed to 60° C. overnight, then 100° C. in a sealed tube for a second night. More 4-aminopyrimidine (25 mg) was added and the reaction sealed and heated to 120° C. in microwave for 1 h. DCM (10 mL) was added, then 1 N HCl (3 mL). This was extracted with DCM (3×15 mL). Combined organics were washed with brine, dried with $Na_2SO_4$, filtered and concentrated. The crude product was purified by silica gel column chromatography (0-10% MeOH/DCM), then again by prep HPLC to give (4S)—N-(pyrimidin-4-yl)-7-(3-(trifluoromethyl)cyclohexyl)-3,4-dihydro-1,4-methanopyrido[2,3-b][1,4]diazepine-5(2H)-carboxamide (4 mg, 7%). MS (ESI) calcd for $C_{21}H_{23}F_3N_6O$: 432.19. found: 433 [M+H].

Example 71. Preparation of (4S)—N-(4,5-dimethylthiazol-2-yl)-7-(3-(trifluoromethyl)cyclohexyl)-3,4-dihydro-1,4-methanopyrido[2,3-b][1,4]diazepine-5(2H)-carboxamide

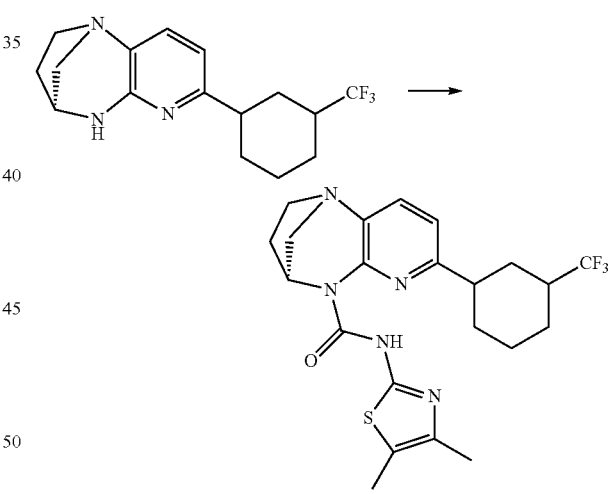

This mixture of diastereomers was made using the following protocol.
General Procedure for Carbamate Formation:
Phenyl chloroformate (2.09 g, 13.3 mmol, 1.05 equiv.) was added dropwise over 1.5 h to a cooled solution of 4,5-dimethylthiazol-2-amine (1.63 g, 12.7 mmol, 1.0 equiv.) and pyridine (3.01 g, 38.2 mmol, 3.0 equiv.) in DCM (16 mL). The reaction was stirred with continued cooling for 2 h. Water (15 mL) was added slowly over 30 min, and then the mixture was diluted with DCM. The layers were separated and the organic layer was washed with saturated aq. Sodium carbonate (20 mL), then brine (20 mL). The organic layer was then dried over $Na_2SO_4$, then concentrated under reduced pressure. The residue was suspended in EA/PE (1:5)

for 30 min, then filtered to afford the phenyl (4,5-dimethylthiazol-2-yl)carbamate (1.7 g, 54%).

General Procedure for Urea Coupling Via Carbamate:

A mixture of phenyl (4,5-dimethylthiazol-2-yl)carbamate (80 mg, 0.322 mmol, 2.0 equiv.), (4S)-7-(3-(trifluoromethyl)cyclohexyl)-2,3,4,5-tetrahydro-1,4-methanopyrido[2,3-b][1,4]diazepine (75 mg, 0.161 mmol, 1.0 equiv.) and DMAP (24 mg, 0.193 mmol, 1.2 equiv.) in acetonitrile (4 mL) were stirred at 60° C. overnight. TLC and LC/MS were used to monitor reaction progress. The mixture was purified by prep HPLC to give (4S)—N-(4,5-dimethylthiazol-2-yl)-7-(3-(trifluoromethyl)cyclohexyl)-3,4-dihydro-1,4-methanopyrido[2,3-b][1,4]diazepine-5(2H)-carboxamide (14.5 mg, 12%). MS (ESI) calcd for $C_{22}H_{26}F_3N_5OS$: 465.18. found: 466 [M+H].

Example 72. Preparation of N-(pyridazin-3-yl)-7-(3-(trifluoromethyl)phenyl)-3,4-dihydro-1,4-ethanopyrido[2,3-b][1,4]diazepine-5(2H)-carboxamide (Compound xx)

Step 1: Diethyl 3-aminopent-2-enedioate

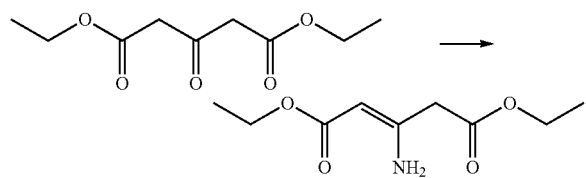

A 250 mL 3-necked flask was charged with 6.00 g (29.7 mmol) of 1,3-acetonedicarboxylate diethyl ester, 4.70 g (59.4 mmol) of ammonium bicarbonate, and 80 mL of ethanol. The reaction was stirred at ambient temperature for 24 h, then it was concentrated in vacuo. The residue was taken up in 100 mL of water and extracted with ethyl acetate (3×100 mL). The combined organic layers were back extracted with brine (1×200 mL), dried over $Na_2SO_4$, filtered, and concentrated to give 5 g (87%) of the product as a colorless oil. This was used in the next reaction without further purification.

Step 2: Diethyl 3-aminopentanedioate

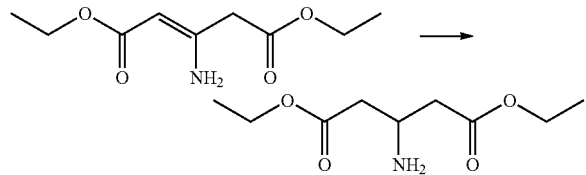

A 250 mL 3-necked flask was charged with 5.00 g (24.8 mmol) of diethyl 3-aminopent-2-enedioate, 40 mL of ethanol, 10 mL of glacial acetic acid, and 3.1 g (49.6 mmol) of $NaBH_3CN$. The reaction was stirred at ambient temperature for 2 h, then the solvents were removed in vacuo. The residue was taken up in water and extracted with ethyl acetate (3×100 mL). The combined ethyl acetate layers were back extracted with brine (1×200 mL), dried over $Na_2SO_4$, filtered, and concentrated in vacuo to give 4 g (80%) of the product as a colorless oil. This was used in the next reaction without further purification.

Step 3: Diethyl 3-((6-chloro-3-nitropyridin-2-yl)amino)pentanedioate

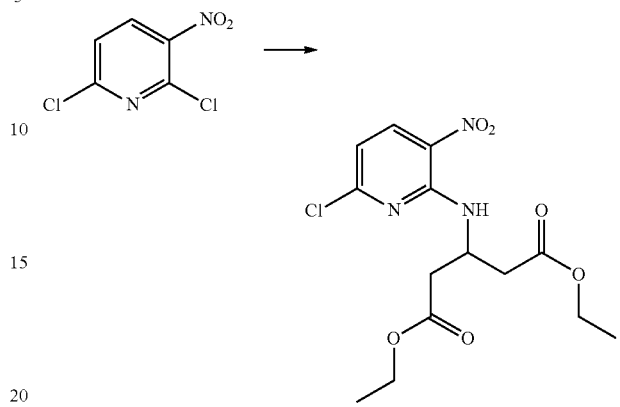

A 250 mL 3-necked flask was charged with 1.8 g (9.8 mmol) of 2,6-dichloro-3-nitropyridine, 4.0 g (19.7 mmol) of crude diethyl 3-aminopentanedioate, 3.2 g (39.0 mmol) of $NaHCO_3$, and 60 mL of tetrahydrofuran. The reaction was stirred at 40° C. for 24 h, then the solvent was removed in vacuo. The residue was dissolved in 100 mL of water, then extracted with ethyl acetate (3×100 mL). The combined organic phases were back extracted with brine (1×200 mL), dried over $Na_2SO_4$, filtered, and concentrated in vacuo. The residue was purified via silica gel chromatography, eluting with 20/1 (v/v) hexanes/ethyl acetate to give 2.7 g (80%) of the product as a light yellow solid.

Step 4: Diethyl 3-((3-amino-6-chloropyridin-2-yl)amino)pentanedioate

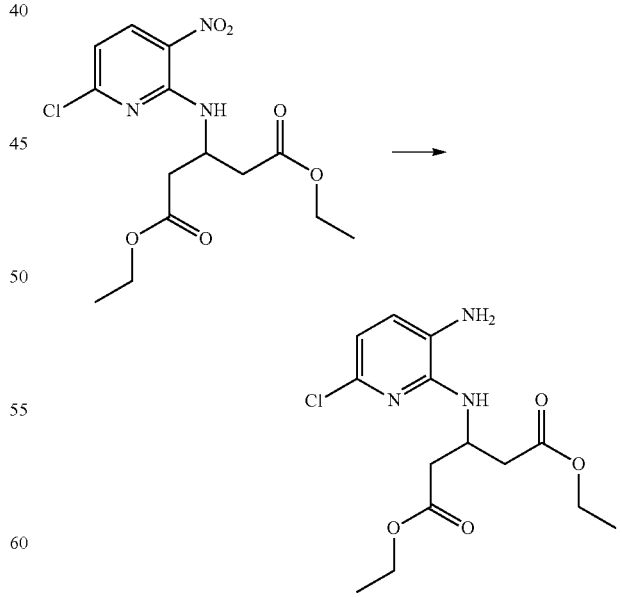

A 250 mL 3-necked flask equipped with a thermometer and a magnetic stir bar was charged with 2.7 g (7.5 mmol) of diethyl 3-((6-chloro-3-nitropyridin-2-yl)amino)pentanedioate, 2.1 g (37.5 mmol) of iron powder, 60 mL of 2-propanol, 20 mL of water, and 675 mg (11.0 mmol) of acetic acid. The mixture was stirred at 100 C for 1 h, monitoring by HPLC for the disappearance of the starting nitro compound. After the reaction was complete, the solids were filtered and washed with 2-propanol (3×50 mL), then the combined filtrate and washings was concentrated in vacuo. The residue was dissolved in 100 mL of water and extracted with dichloromethane (3×50 mL). The combined organic layers were back extracted with brine (1×50 mL), dried over $Na_2SO_4$, filtered, and concentrated to dryness. The crude product was purified via silica gel chromatography, eluting with 4/1 (v/v) hexanes/ethyl acetate to give 1.8 g (75%) of the product as a gray solid.

Step 5: Ethyl 2-(7-chloro-2-oxo-2,3,4,5-tetrahydro-1H-pyrido[2,3-b][1,4]diazepin-4-yl)acetate

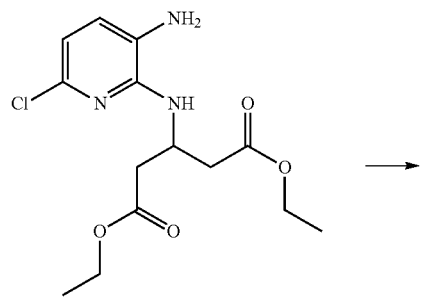

A 100 mL 3-necked flask equipped with a thermometer and a reflux condenser was charged with 1.8 g (5.4 mmol) of diethyl 3-((3-amino-6-chloropyridin-2-yl)amino)pentanedioate, 20 mL of toluene, and 1.0 mL (13.4 mmol) of trifluoroacetic acid. The mixture was stirred at reflux for 5 h, and the reaction was monitored by HPLC for the disappearance of starting material. After the reaction was complete, the solvents were removed in vacuo, then the residue was purified via silica gel chromatography, eluting with 3/1 (v/v) hexanes/ethyl acetate to give 1.1 g (70%) of the product as an off-white solid.

Step 6: 2-(7-chloro-2,3,4,5-tetrahydro-1H-pyrido[2,3-b][1,4]diazepin-4-yl)ethanol

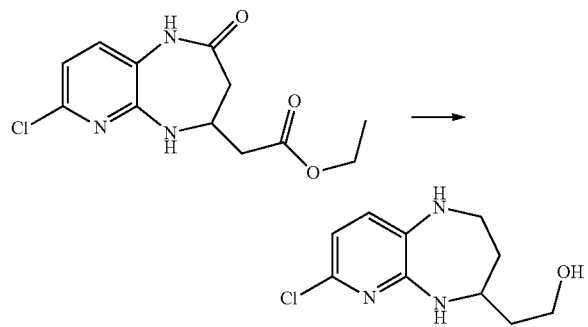

A 50 mL 3-necked flask equipped with a nitrogen inlet, a reflux condenser, and a thermometer was charged with 1.0 g (3.5 mmol) of ethyl 2-(7-chloro-2-oxo-2,3,4,5-tetrahydro-1H-pyrido[2,3-b][1,4]diazepin-4-yl)acetate, 530 mg (14.0 mmol) of $LiAlH_4$, and 10 mL of tetrahydrofuran. The reaction was stirred under $N_2$ at 60° C. for 6 h, monitoring for the appearance of product by HPLC. The ester was reduced rapidly, but the lactam required a longer time for complete reduction. When the reaction was complete, the mixture was cooled with an ice bath, 530 μL of water was added while keeping the internal temperature below 5° C., then the mixture was stirred for 15 min. Next, 530 μL of 15% (w/w) NaOH(aq.) was added while keeping the internal temperature below 5 C, then the mixture was stirred for 15 min. To complete the workup, 1590 μL water was added, then the mixture was stirred at ambient temperature for 30 min. The solids were filtered, then the precipitate was washed with tetrahydrofuran (3×50 mL). The filtrate was concentrated in vacuo, then the residue was purified via silica gel chromatography, eluting with 2/1 hexanes/ethyl acetate to give 520 mg (65%) of the product as a light yellow solid.

Step 7: 7-chloro-2,3,4,5-tetrahydro-1,4-ethanopyrido[2,3-b][1,4]diazepine

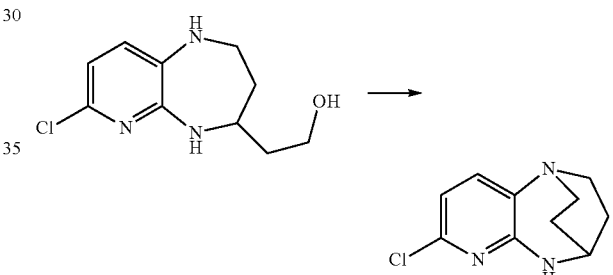

A 50 mL 3-necked flask was charged with 500 mg (2.2 mmol) of 2-(7-chloro-2,3,4,5-tetrahydro-1H-pyrido[2,3-b][1,4]diazepin-4-yl)ethanol, and 10 mL of 40% (w/w) HBr (aq.). The mixture was stirred at reflux for 18 h, then it was cooled to ambient temperature and neutralized with saturated $NaHCO_{3(aq.)}$. The aqueous mixture was extracted with ethyl acetate (3×50 mL), then the combined organic layers were back extracted with brine (1×50 mL), dried over $Na_2SO_4$, filtered, and concentrated in vacuo. The residue was purified via silica gel chromatography, eluting with 3/1 hexanes/ethyl acetate to give 320 mg (70%) of the product as an off-white solid.

Step 8. Synthesis of 7-(3-(trifluoromethyl)phenyl)-2,3,4,5-tetrahydro-1,4-ethanopyrido[2,3-b][1,4]diazepine

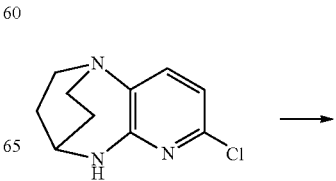

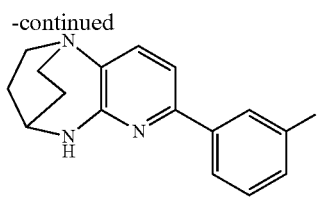

A dioxane/water mixture (10 mL/1 mL) was degassed and 7-chloro-2,3,4,5-tetrahydro-1,4-ethanopyrido[2,3-b][1,4]diazepine (250 mg, 1.196 mmol) was added, followed by 3-(trifluoromethyl)phenylboronic acid (454 mg, 2.392 mmol), Pd(dppf)Cl$_2$ (97 mg, 0.19 mmol), and Cs$_2$CO$_3$ (1.16 g, 3.588 mmol). The mixture was stirred at 110° C. for 12 hours, then concentrated and purified by column chromatography (PE/EtOAc=4/1) to give 7-(3-(trifluoromethyl)phenyl)-2,3,4,5-tetrahydro-1,4-ethanopyrido[2,3-b][1,4]diazepine (200 mg, 48%). MS (ESI) calcd for C$_{17}$H$_{16}$F$_3$N$_3$: 319.13.

Step 9. Synthesis of N-(pyridazin-3-yl)-7-(3-(trifluoromethyl)phenyl)-3,4-dihydro-1,4-ethanopyrido[2,3-b][1,4]diazepine-5(2H)-carboxamide

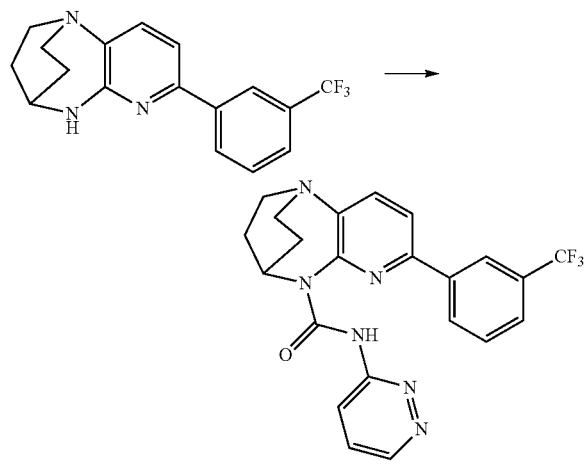

The following general urea coupling procedure was used:

The carbamate of pyridazin-3-amine (53.9 mg, 0.25 mmol, 2.0 equiv.), 7-(3-(trifluoromethyl)phenyl)-2,3,4,5-tetrahydro-1,4-ethanopyrido[2,3-b][1,4]diazepine (40 mg, 0.12 mmol, 1.0 equiv.), and DMAP (18.4 mg, 0.15 mmol, 1.2 equiv.) in acetonitrile (5 mL) were stirred at 60° C. overnight. Reaction progress was monitored by TLC and LC/MS. The reaction mixture was loaded directly onto prep. TLC using 100% EtOAc as eluent to give N-(pyridazin-3-yl)-7-(3-(trifluoromethyl)phenyl)-3,4-dihydro-1,4-ethanopyrido[2,3-b][1,4]diazepine-5(2H)-carboxamide as a white solid (16.9 mg, 30.6%). MS (ESI) calcd for C$_{22}$H$_{19}$F$_3$N$_6$O: 440.16. found: 440.9 [M+H].

This general urea coupling procedure could be used to prepare a variety of 7-(3-(trifluoromethyl)phenyl)-, 7-(3-chlorophenyl)-, 7-(5-chloropyridin-3-yl)-, and 7-(5-fluoropyridin-3-yl)-3,4-dihydro-1,4-ethanopyrido[2,3-b][1,4]diazepine-5(2H)-carboxamides by substituting the appropriate amine moiety for pyridazin-3-amine.

Example 73. Preparation of 7-(3-chlorophenyl)-N-(pyridin-3-yl)-3,4-dihydro-1,4-ethanopyrido[2,3-b][1,4]diazepine-5(2H)-carboxamide Step 1. Synthesis of tert-butyl 7-chloro-3,4-dihydro-1,4-ethanopyrido[2,3-b][1,4]diazepine-5(2H)-carboxylate

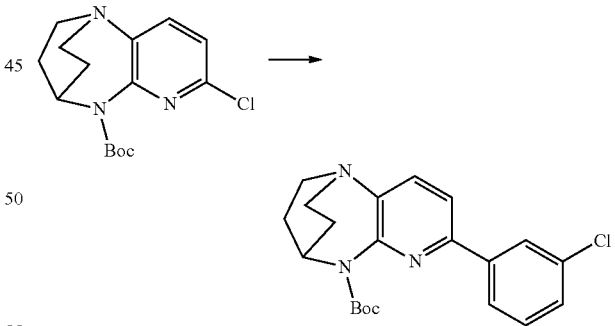

This moiety was made using the following protocol. A mixture of 7-chloro-2,3,4,5-tetrahydro-1,4-ethanopyrido[2,3-b][1,4]diazepine (3.0 g, 14.31 mmol), (Boc)$_2$O (4.6 g, 21.05 mmol, 1.5 equiv.), and DMAP (3.49 g, 28.62 mmol, 2.0 equiv.) in THF (5 mL) was stirred at 60° C. for 2 h. TLC and LC/MS were used to monitor reaction progress. Water (30 mL) was added and the mixture was extracted with DCM (3×15 mL). The organics were concentrated and the residue was purified by column chromatography to give tert-butyl 7-chloro-3,4-dihydro-1,4-ethanopyrido[2,3-b][1,4]diazepine-5(2H)-carboxylate as a white solid (4.5 g, 92%). MS (ESI) calcd for C$_{15}$H$_{20}$ClN$_3$O$_2$: 309.12.

Step 2. Synthesis of tert-butyl 7-(3-chlorophenyl)-3,4-dihydro-1,4-ethanopyrido[2,3-b][1,4]diazepine-5(2H)-carboxylate: (Sundia Prop. 455)

This moiety was made using the following protocol. To a degassed mixture of dioxane/water (20 mL/1 mL) was added tert-butyl 7-chloro-3,4-dihydro-1,4-ethanopyrido[2,3-b][1,4]diazepine-5(2H)-carboxylate (1.5 g, 4.85 mmol), (3-chlorophenyl)boronic acid (1.51 g, 9.70 mmol), Pd(dppf)Cl$_2$ (0.396 g, 0.485 mmol), and Cs$_2$CO$_3$ (4.74 g, 14.56 mmol). The mixture was stirred at 110° C. for 12 h, then concentrated and purified by column chromatography (PE/EA=2/1) to give tert-butyl 7-(3-chlorophenyl)-3,4-dihydro-1,4-ethanopyrido[2,3-b][1,4]diazepine-5(2H)-carboxylate (1.2 g, 89%). MS (ESI) calcd for C$_{21}$H$_{24}$ClN$_3$O$_2$: 385.16.

This general coupling procedure could be used to prepare a variety of 7-(3-substituted phenyl or pyridyl)-2,3,4,5-tetrahydro-1,4-ethanopyrido[2,3-b][1,4]diazepines by substituting the appropriate boronic acid or boronic ester moiety for (3-chlorophenyl)boronic acid.

Step 3. Synthesis of 7-(3-chlorophenyl)-2,3,4,5-tetrahydro-1,4-ethanopyrido[2,3-b][1,4]diazepine: (Sundia Prop. 455)

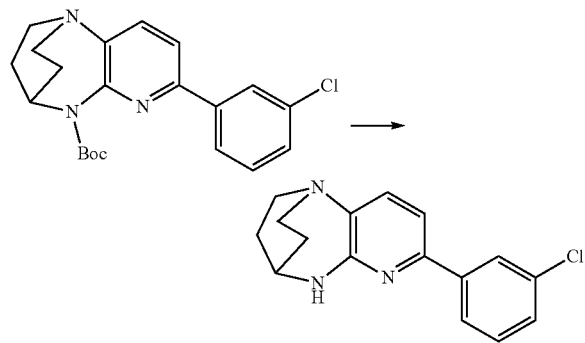

This moiety was made using the following protocol. Tert-butyl 7-(3-chlorophenyl)-3,4-dihydro-1,4-ethanopyrido[2,3-b][1,4]diazepine-5(2H)-carboxylate (1.2 g, 3.1 mmol) was dissolved in HCl/MeOH (1 M, 20 mL) and the reaction mixture was stirred at room temp for 1.5 h, then concentrated in vacuo. Water (20 mL) and $K_2CO_3$ (3 g) were added. The mixture was stirred at room temp for 2 h, then extracted with DCM (3×15 mL). The organics were concentrated to give 7-(3-chlorophenyl)-2,3,4,5-tetrahydro-1,4-ethanopyrido[2,3-b][1,4]diazepine (800 mg, 90%). MS (ESI) calcd for $C_{16}H_{16}ClN_3$: 285.10.

Step 4. Synthesis of 7-(3-chlorophenyl)-N-(pyridin-3-yl)-3,4-dihydro-1,4-ethanopyrido[2,3-b][1,4]diazepine-5(2H)-carboxamide

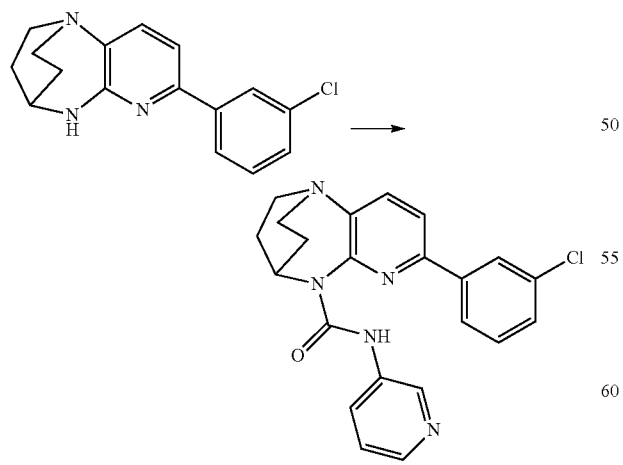

This compound was made using the general urea coupling procedure to give 7-(3-chlorophenyl)-N-(pyridin-3-yl)-3,4-dihydro-1,4-ethanopyrido[2,3-b][1,4]diazepine-5(2H)-carboxamide (20.4 mg, 24%). MS (ESI) calcd for $C_{22}H_{20}ClN_5O$: 405.14. found: 406 [M+H].

Example 74. Preparation of 7-(5-fluoropyridin-3-yl)-N-(pyridin-3-yl)-3,4-dihydro-1,4-ethanopyrido[2,3-b][1,4]diazepine-5(2H)-carboxamide

Step 1. Synthesis of tert-butyl 7-(5-fluoropyridin-3-yl)-3,4-dihydro-1,4-ethanopyrido[2,3-b][1,4]diazepine-5(2H)-carboxylate

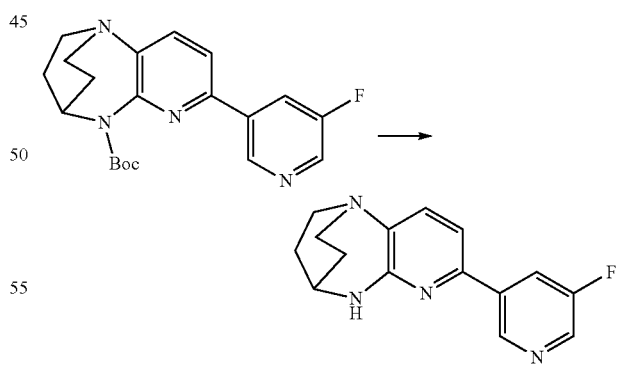

This moiety was made using the following protocol. To a degassed mixture of dioxane/water (30 mL/3 mL) was added tert-butyl 7-chloro-3,4-dihydro-1,4-ethanopyrido[2,3-b][1,4]diazepine-5(2H)-carboxylate (1.39 g, 4.5 mmol), (5-fluoropyridin-3-yl)boronic acid (1.27 g, 9.0 mmol), Pd(dppf)Cl$_2$ (0.37 g, 0.45 mmol), and Cs$_2$CO$_3$ (4.40 g, 13.5 mmol). The mixture was stirred at 110° C. for 12 h, then concentrated and purified by column chromatography (PE/EA=2/1) to give tert-butyl 7-(5-fluoropyridin-3-yl)-3,4-dihydro-1,4-ethanopyrido[2,3-b][1,4]diazepine-5(2H)-carboxylate (1.5 g, 89%). MS (ESI) calcd for $C_{20}H_{23}FN_4O_2$: 370.18.

Step 2. Synthesis of 7-(5-fluoropyridin-3-yl)-2,3,4,5-tetrahydro-1,4-ethanopyrido[2,3-b][1,4]diazepine This moiety was made using the following protocol. TFA (20 mL) was added to a solution of tert-butyl 7-(5-fluoropyridin-3-yl)-3,4-dihydro-1,4-ethanopyrido[2,3-b][1,4]diazepine-5(2H)-carboxylate (1.50 g) in DCM (20 mL), and the reaction mixture was stirred at room temp for 3 h, then concentrated in vacuo. The residue was basified with saturated NaHCO$_3$ solution and extracted with DCM (3×15 mL). The organics were concentrated to give 7-(5-fluoropyridin- 3-yl)-2,3,4,5-tetrahydro-1,4-ethanopyrido[2,3-b][1,4]diazepine (1.2 g, 100%). MS (ESI) calcd for $C_{15}H_{15}FN_4$: 270.13.

Step 3. Synthesis of 7-(5-fluoropyridin-3-yl)-N-(pyridin-3-yl)-3,4-dihydro-1,4-ethanopyrido[2,3-b][1,4]diazepine-5(2H)-carboxamide

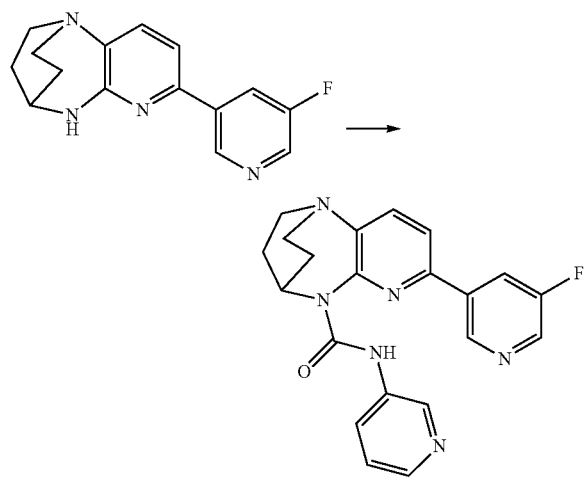

This compound was made using the general urea coupling procedure to give 7-(5-fluoropyridin-3-yl)-N-(pyridin-3-yl)-3,4-dihydro-1,4-ethanopyrido[2,3-b][1,4]diazepine-5(2H)-carboxamide (12.8 mg, 15%). MS (ESI) calcd for $C_{21}H_{19}FN_6O$: 390.16. found: 391 [M+H].

Example 75. Preparation of 3-bromo-5-(oxazol-5-yl)aniline

Step 1. Synthesis of 5-(3-bromo-5-nitrophenyl)oxazole

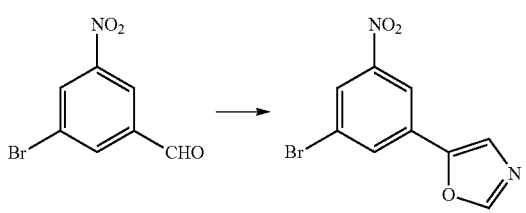 [SMILES: O=Cc1cc(Br)cc([N+](=O)[O-])c1 ; O=[N+]([O-])c1cc(Br)cc(-c2cnco2)c1]

To a solution of 3-bromo-5-nitrobenzaldehyde (1 g, 4.34 mmol) in DME (10 mL) was added $K_2CO_3$ (1.2 g, 8.68 mmol), followed by 1-((isocyanomethyl)sulfonyl)-4-methylbenzene (891 mg, 4.56 mmol). The reaction mixture was stirred at reflux overnight. After cooling to room temp., EtOAc was added and the mixture was washed with $H_2O$ twice then with brine. The organic layers were dried over $MgSO_4$, filtered, and concentrated. Purification by silica gel chromatography (0% to 100% EtOAc in pentane gradient) afforded 5-(3-bromo-5-nitrophenyl)oxazole (762 mg, 65%) as an orange solid. MS (ESI) calcd for $C_9H_5BrN_2O_3$: 268.0, 270.0.

Step 2. Synthesis of 3-bromo-5-(oxazol-5-yl)aniline

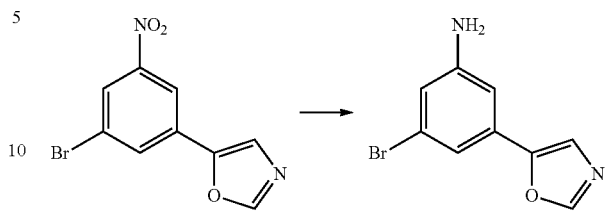

To a solution of 5-(3-bromo-5-nitrophenyl)oxazole (762 mg, 2.83 mmol) in THF (14 mL) was added acetic acid (13.6 mL), followed by iron powder (474 mg, 8.49 mmol). The reaction mixture was stirred at 60° C. overnight. After cooling to room temperature, the mixture was poured into a saturated $Na_2CO_3$ solution (175 mL) and extracted with EtOAc (50 mL×2). The combined organic layers were washed with brine, dried over $MgSO_4$, filtered, and concentrated to afford 3-bromo-5-(oxazol-5-yl)aniline (697 mg) as a brown oil. This material was used without further purification. MS (ESI) calcd for $C_9H_7BrN_2O$: 238.0, 240.0.

This general two-step procedure of oxazole formation followed by nitro reduction could be used to prepare 4-bromo-5-(oxazol-5-yl)aniline by using 4-bromo-5-nitrobenzaldehyde.

Example 76. Preparation of 6-(oxazol-5-yl)pyridin-2-amine

Step 1. Synthesis of 6-amino-N-methoxy-N-methylpicolinamide

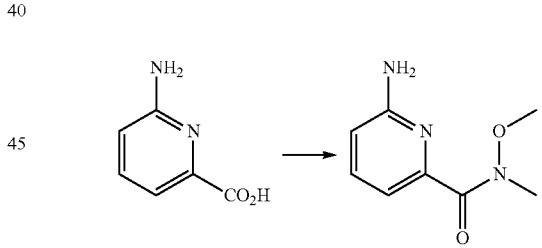

To a slurry of 6-aminopicolinic acid (10.0 g, 72.5 mmol) in acetonitrile (150 mL) was added N,O-dimethylhydroxylamine hydrochloride (8.52 g, 87.0 mmol), 1-hydroxybenzotriazole (11.8 g, 87.0 mmol), N-(3-dimethylamino)-N'-ethylcarbodiimide hydrochloride (16.7 g, 87.0 mmol), and N,N-diisopropylethylamine (37.7 mL, 217 mmol). The mixture was stirred at room temperature overnight, and the solvent removed in vacuo. The residue was partitioned between 1N NaOH and ethyl acetate, and the aqueous layer was extracted three times with ethyl acetate. The combined organic layers were washed with brine, dried with sodium sulfate, and the solvent removed in vacuo. The remaining residue was purified by flash chromatography (ethyl acetate with 0.1% triethylamine) to give 6-amino-N-methoxy-N-methylpicolinamide (4.30 g, 23.7 mmol, 33% yield). MS (ESI) calcd for $C_8H_{11}N_3O_2$: 181.1.

Step 2. Synthesis of 6-(oxazol-5-yl)pyridin-2-amine

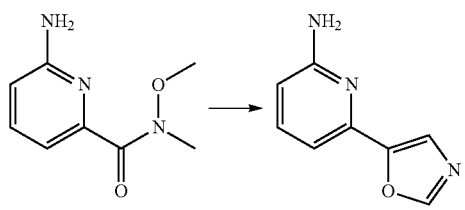

Lithium aluminum hydride (1.08 g, 28.5 mmol) was added to a solution of 6-amino-N-methoxy-N-methylpicolinamide (4.30 g, 23.7 mmol) in THF (30 mL). The reaction was stirred at room temperature for 90 min. Ethyl acetate (30 mL) was added slowly, the reaction was filtered, and the filtrate taken and all the solvent removed in vacuo to give 6-aminopicolinaldehyde, which was taken on crude to the next step.

To a solution of the above aldehyde in methanol (20 mL) was added p-toluenesulfonylmethyl isocyanide (13.9 g, 71.2 mmol) and potassium carbonate (19.4 g, 140 mmol). The reaction was stirred at reflux for 2 h, then all solvent removed in vacuo. The residue was partitioned between ethyl acetate (150 mL) and water (70 mL). The organic layer was washed with brine, dried with sodium sulfate, and the solvent removed in vacuo. The remaining residue was purified by flash chromatography (10% methanol in dichloromethane) to give 6-(oxazol-5-yl)pyridin-2-amine (2.00 g, 12.4 mmol, 52% yield over two steps). MS (ESI) calcd for $C_8H_7N_3O$: 161.1.

The following compounds were prepared in an analogous manner: 4-(oxazol-5-yl)pyridin-2-amine; 5-(oxazol-5-yl)pyridin-3-amine.

Example 77: Synthesis of 3,5-bis(oxazol-5-yl)aniline

Step 1. Synthesis of $N^1,N^3$-dimethoxy-$N^1,N^3$-dimethyl-5-nitroisophthalamide

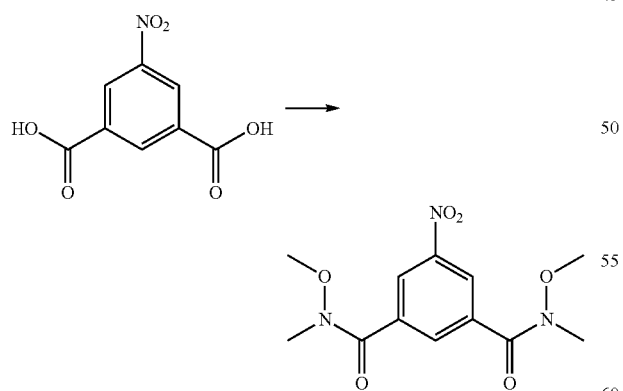

To a solution of 5-nitroisophthalic acid (5.00 g, 23.7 mmol) in dichloromethane (100 mL) was added oxalyl chloride (5.00 mL, 59.1 mmol), and the solution cooled to 0° C. DMF (1.0 mL) was added dropwise over 30 min. The mixture was warmed to room temperature and stirred for 4 h. All solvents were removed in vacuo.

To a mixture of N,O-dimethylhydroxylamine hydrochloride (4.6 g, 47.1 mmol) and triethylamine (6.60 mL, 47.4 mmol) in dichloromethane (80 mL) was added a solution of the above acid chloride in dichloromethane (20 mL) at 0° C. Once the reaction was complete, the reaction mixture was concentrated in vacuo. The residue was partitioned between 1N sodium hydroxide and ethyl acetate, the organic layer separated, and the aqueous layer extracted with ethyl acetate. The combined organic layers were dried with sodium sulfate, the solvents removed in vacuo, and the residue purified by silica gel chromatography (1:1 petroleum ether:ethyl acetate) to give $N^1,N^3$-dimethoxy-$N^1,N^3$-dimethyl-5-nitroisophthalamide (4.00 g, 13.5 mmol, 57% yield). MS (ESI) calcd for $C_{12}H_{15}N_3O_6$: 297.1.

Step 2. Synthesis of 5-nitroisophthalaldehyde

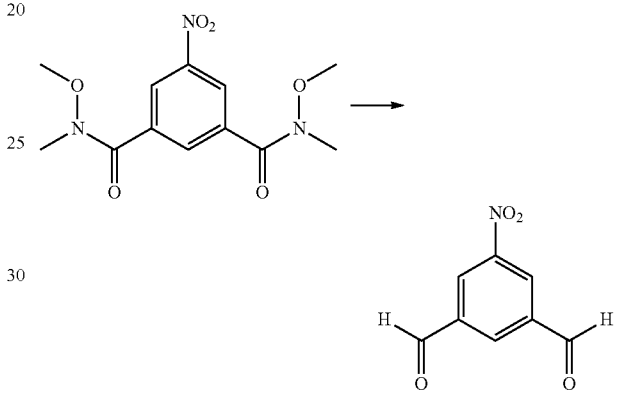

Lithium aluminum hydride (2.70 g, 71.1 mmol) was added to a stirred solution of $N^1,N^3$-dimethoxy-$N^1,N^3$-dimethyl-5-nitroisophthalamide (5.00 g, 16.9 mmol) in THF (150 mL) at −40° C. The reaction was stirred at −40° C. for 4 h. 10% sodium hydroxide solution (2.7 mL) was added slowly, followed by water (2.7 mL). The resulting solid was filtered, and the filtrate concentrated in vacuo to give 5-nitroisophthalaldehyde (1.37 g, 7.65 mmol, 45% yield). MS (ESI) calcd for $C_8H_5NO_4$: 179.0.

Step 3. Synthesis of 5,5'-(5-nitro-1,3-phenylene)bis(oxazole)

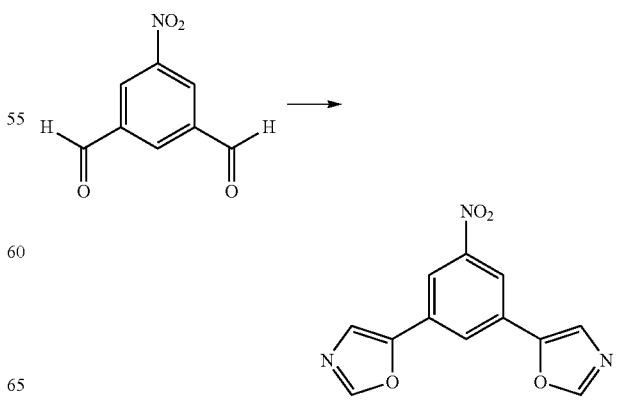

1-Isocyanomethanesulfonyl-4-methyl-benzene (7.40 g, 37.8 mmol) and anhydrous potassium carbonate (5.20 g, 37.8 mmol) were added to a solution of 5-nitroisophthalaldehyde (1.37 g, 7.65 mmol) in methanol (100 mL). The reaction was refluxed under nitrogen for 2 h. After cooling, the solvent was removed in vacuo. The residue was partitioned between ethyl acetate (150 mL) and water (70 mL). The organic layer was removed, and the aqueous layer extracted with ethyl acetate (3×150 mL). The combined organic layers were washed with brine, dried with sodium sulfate, and concentrated to give crude 5,5'-(5-nitro-1,3-phenylene)bis(oxazole) (1.70 g, 6.61 mmol, 86% yield). MS (ESI) calcd for $C_{12}H_7N_3O_4$: 257.0.

Step 4. Synthesis of 3,5-bis(oxazol-5-yl)aniline

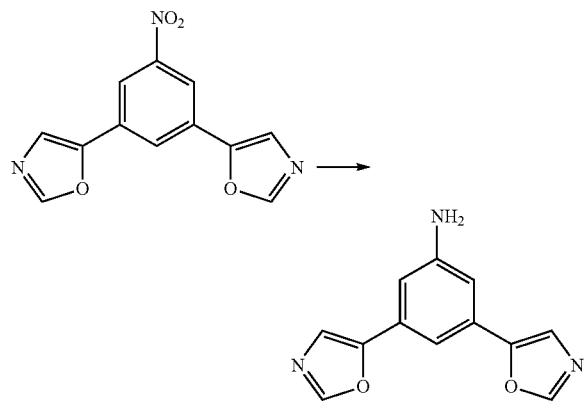

A mixture of 5,5'-(5-nitro-1,3-phenylene)bis(oxazole) (1.70 g, 6.61 mmol) and palladium on carbon (200 mg) in ethyl acetate (50 mL) was stirred under hydrogen for 4 h. The solid was filtered, and the filtrate concentrated in vacuo. The remaining residue was purified by silica gel chromatography (4:1 petroleum ether:ethyl acetate) to give 3,5-bis(oxazol-5-yl)aniline (1.30 g, 5.72 mmol, 87% yield). MS (ESI) calcd for $C_{12}H_9N_3O_2$: 227.1.

Example 78. Preparation of tert-butyl (2-(4-(3-aminophenyl)-1H-1,2,3-triazol-1-yl)ethyl)carbamate

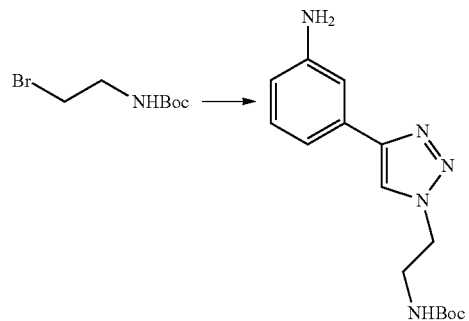 [SMILES: CC(C)(C)OC(=O)NCCBr ; CC(C)(C)OC(=O)NCCn1cc(-c2cccc(N)c2)nn1]

A 20 mL microwave vial was charged with tert-butyl (2-bromoethyl)carbamate (551 mg, 2.50 mmol), sodium azide (460 mg, 7.05 mmol), and DMF (5 mL). The vial was sealed, and heated in the microwave at 110° C. for 12 h. The reaction mixture was poured into water (8 mL), and extracted with ethyl acetate (2×10 mL). The combined organic layers were dried with magnesium sulfate, and all solvents removed in vacuo to give crude tert-butyl (2-azidoethyl)carbamate.

The crude tert-butyl (2-azidoethyl)carbamate was dissolved in THF (5 mL) and triethylamine (1 mL). 3-ethynylaniline (350 mg, 2.99 mmol) was added, followed by copper (I) iodide (15.0 mg, 0.0788 mmol). The reaction was stirred at 60° C. for 2 h, then all solvents removed in vacuo, and the remaining residue purified by flash chromatography (50% to 100% ethyl acetate in pentane) to give tert-butyl (2-(4-(3-aminophenyl)-1H-1,2,3-triazol-1-yl)ethyl)carbamate 415 mg, 1.37 mmol, 55% yield over 2 steps.) MS (ESI) calcd for $C_{15}H_{21}N_5O_2$: 303.2.

Example 79. Preparation of tert-butyl ((1-(3-aminophenyl)-1H-1,2,3-triazol-4-yl)methyl)carbamate

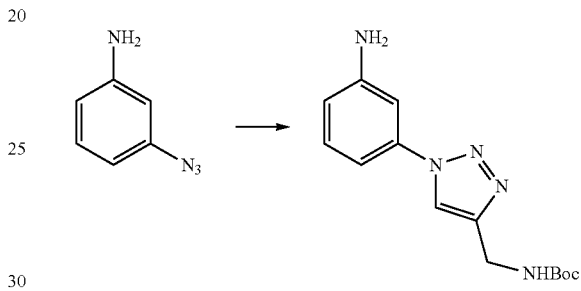

To a solution of 3-azidoaniline (Chem. Commun. 2004, 888) (1.34 g, 9.99 mmol) in THF (9.0 mL) and triethylamine (1.0 mL) was added tert-butyl prop-2-yn-1-ylcarbamate (1.55 g, 9.99 mmol) and copper (I) iodide (40 mg, 0.210 mmol). The reaction was stirred at 60° C. for 1 h, then all solvents removed in vacuo. The remaining residue was purified by flash chromatography (0% to 80% ethyl acetate in pentane) to give tert-butyl ((1-(3-aminophenyl)-1H-1,2,3-triazol-4-yl)methyl)carbamate (Compound #; 1.71 g, 5.91 mmol, 59% yield). MS (ESI) calcd for $C_{14}H_{19}N_5O_2$: 289.1. found: 290.1 [M+H].

Example 80: Preparation of tert-butyl ((1-(3-aminophenyl)-1H-1,2,3-triazol-5-yl)methyl)carbamate

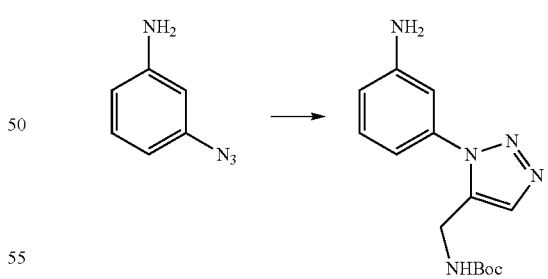

To a vial with 3-azidoaniline (1.33 g, 9.92 mmol), tert-butyl prop-2-yn-1-ylcarbamate (1.55 g, 9.99 mmol), and pentamethylcyclopentadienylbis(triphenylphosphine)ruthenium(II) chloride (15.9 mg, 0.020 mmol) was added toluene (10 mL). The reaction was stirred at 100° C. for 72 h, then the reaction cooled to room temperature. Dichloromethane (5 mL) was added to dissolve any solids, and the remaining solution purified by silica gel chromatography (50% to 80% ethyl acetate in pentane) to give tert-butyl ((1-(3-aminophenyl)-1H-1,2,3-triazol-5-yl)methyl)carbamate (970 mg, 3.35 mmol, 34% yield). MS (ESI) calcd for $C_{14}H_{19}N_5O_2$: 289.2.

Example 81: Preparation of N⁴,N⁴-dimethylpyrimidine-2,4-diamine

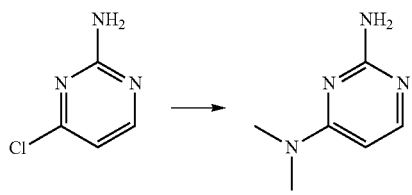

4-chloro-2-aminopyrimidine (495 mg, 3.82 mmol) was dissolved in aqueous dimethylamine (33%) in a sealed tube, and the reaction stirred at 100° C. overnight. After cooling, the reaction was diluted with water, and extracted with dichloromethane. The organic layer was washed with water and brine, and dried with sodium sulfate, and the solvents removed in vacuo to give N⁴,N⁴-dimethylpyrimidine-2,4-diamine (400 mg, 2.89 mmol, 76% yield). MS (ESI) calcd for $C_6H_{10}N_4$: 138.1.

Example 82: Preparation of tert-butyl 4-(2-aminopyrimidin-4-yl)piperazine-1-carboxylate

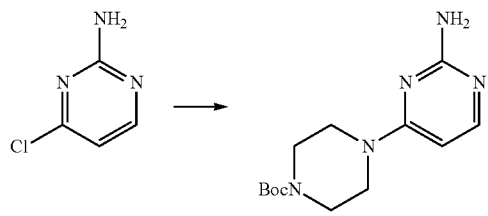 [SMILES: Nc1nccc(Cl)n1 ; CC(C)(C)OC(=O)N1CCN(c2ccnc(N)n2)CC1]

THF (20 mL) was added to a mixture of 4-chloro-2-aminopyrimidine (500 mg, 3.87 mmol) and N-Boc piperazine (7.21 g, 38.7 mmol). The reaction was stirred at 70° C. overnight. After cooling, the solvent was removed in vacuo and the remaining residue purified by silica gel chromatography (1:1 petroleum ether:ethyl acetate) to give tert-butyl 4-(2-aminopyrimidin-4-yl)piperazine-1-carboxylate (650 mg, 2.33 mmol, 60% yield). MS (ESI) calcd for $C_{13}H_{21}N_5O_2$: 279.2.

The following compound was made in an analogous manner: 4-(4-methylpiperazin-1-yl)pyrimidin-2-amine

Example 83. Preparation of tert-butyl (3-(4-amino-2-(oxazol-5-yl)phenyl)prop-2-yn-1-yl)carbamate

Step 1. Synthesis of 2-bromo-5-nitrobenzaldehyde

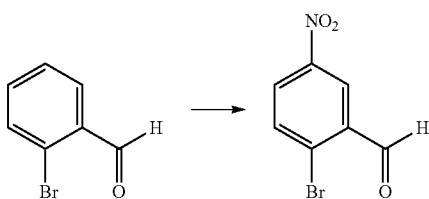 [SMILES: O=Cc1ccccc1Br ; O=Cc1cc([N+](=O)[O-])ccc1Br]

To a solution of 2-bromobenzaldehyde (10.0 g, 53.7 mmol) in $H_2SO_4$ (100 mL) was added KNO₃ (5.43 g, 53.7 mmol) in portions over 1 h at 0° C. The mixture was stirred for 40 min and additional KNO₃ (0.72 g) was added. The reaction mixture was stirred at 0° C. for 3 h then poured into ice water. The resulting precipitate was collected by filtration, rinsed with water and recrystallized from EtOAc/Pentane to give 2-bromo-5-nitrobenzaldehyde (11.7 g, 94% yield) as a white solid. MS (ESI) calcd for $C_7H_4BrNO_3$: 228.9.

Step 2. Synthesis of 5-(2-bromo-5-nitrophenyl)oxazole

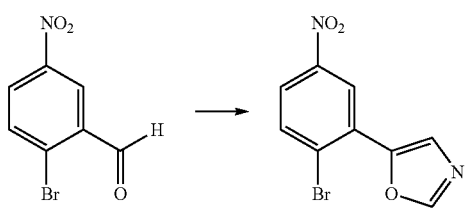 [SMILES: O=Cc1cc([N+](=O)[O-])ccc1Br ; O=[N+]([O-])c1ccc(Br)c(-c2cnco2)c1]

A mixture of 2-bromo-5-nitrobenzaldehyde (1.0 g, 4.33 mmol), $K_2CO_3$ (1.79 g, 12.9 mmol) and TosMIC (2.12 g, 10.8 mmmol) in MeOH was heated at 60° C. for 1.5 h. The mixture was concentrated. Water was added and the solid collected by filtration, rinsed with water, MeOH then petroleum ether to give 5-(2-bromo-5-nitrophenyl)oxazole (750 mg, yield 65%). as grey solid. MS (ESI) calcd for $C_9H_5BrN_2O_3$: 228.9.

Step 3. Synthesis of tert-butyl (3-(4-nitro-2-(oxazol-5-yl)phenyl)prop-2-yn-1-yl)carbamate

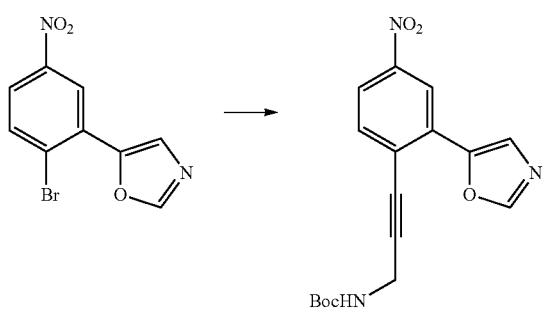 [SMILES: O=[N+]([O-])c1ccc(Br)c(-c2cnco2)c1 ; CC(C)(C)OC(=O)NCC#Cc1ccc([N+](=O)[O-])cc1-c1cnco1]

To a solution of 5-(2-bromo-5-nitrophenyl)oxazole (300 mg, 1.11 mmol) in DME (20 mL) was added tert-butyl prop-2-yn-1-ylcarbamate (431 mg, 2.77 mmol) under N₂. CuI (21 mg, 0.11 mmol) and Pd(dppf)Cl₂ (78 mg, 0.11 mmol) were added followed by TEA (0.5 mL). The reaction mixture was heated at 80° C. for 4 h, cooled to room temperature, poured into water, and extracted with EtOAc (3×50 mL). The combined organic layers were washed with brine, dried and concentrated. The residue was purified by silica gel column chromatography (EtOAc:Pentane=1:5) to give tert-butyl (3-(4-nitro-2-(oxazol-5-yl)phenyl)prop-2-yn-1-yl)carbamate (350 mg, yield 92%) as a yellow oil. MS (ESI) calcd for $C_{17}H_{17}N_3O_5$: 343.1.

Step 4. Synthesis of tert-butyl (3-(4-amino-2-(oxazol-5-yl)phenyl)prop-2-yn-1-yl)carbamate

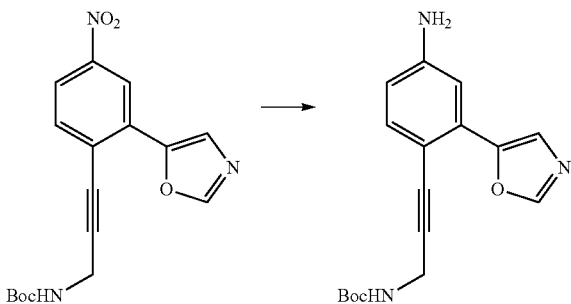 [SMILES: CC(C)(C)OC(=O)NCC#Cc1ccc([N+](=O)[O-])cc1-c1cnco1 ; CC(C)(C)OC(=O)NCC#Cc1ccc(N)cc1-c1cnco1]

A suspension of tert-butyl (3-(4-nitro-2-(oxazol-5-yl)phenyl)prop-2-yn-1-yl)carbamate (3.8 g, 11.1 mmol) and Fe (4.96 g, 8.86 mmol) in sat.aq NH$_4$Cl/MeOH (V/V=1:3) was heated at 60° C. for 4.5 h. The mixture was cooled to room temperature, passed through a pad of celite and the filtrate was concentrated. The residue was dissolved in EtOAc, washed with water, dried (Na$_2$SO$_4$) and concentrated. The crude residue was purified by silica gel column chromatography to give tert-butyl (3-(4-amino-2-(oxazol-5-yl)phenyl)prop-2-yn-1-yl)carbamate (1.51 g, yield 44%) as a yellow oil. MS (ESI) calcd for C$_{17}$H$_{19}$N$_3$O$_3$: 228.9.

tert-butyl (3-(3-amino-5-(oxazol-5-yl)phenyl)prop-2-yn-1-yl)carbamate was prepared from 3-bromo-5-nitrobenzaldehyde in a similar manner to that described for tert-butyl (3-(4-amino-2-(oxazol-5-yl)phenyl)prop-2-yn-1-yl)carbamate.

Example 84. Preparation of tert-butyl (3-(4-amino-2-(oxazol-5-yl)phenyl)propyl)carbamate

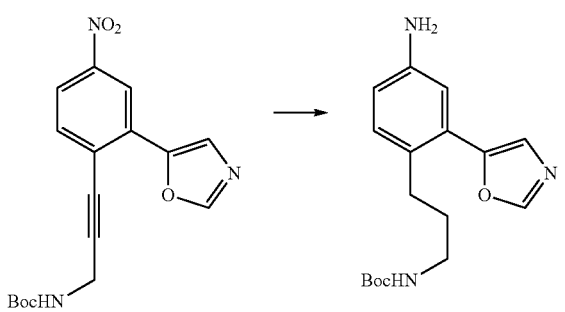 [SMILES: CC(C)(C)OC(=O)NCC#Cc1ccc([N+](=O)[O-])cc1-c1cnco1 ; CC(C)(C)OC(=O)NCCCc1ccc(N)cc1-c1cnco1]

A mixture of tert-butyl (3-(4-nitro-2-(oxazol-5-yl)phenyl)prop-2-yn-1-yl)carbamate (3.0 g, 8.75 mmol) and 10 wt % Pd/C (1.0 g) in MeOH (100 mL) was stirred under H$_2$ atmosphere (50 psi) for 16 h. The mixture catalyst was removed by filtration, and the filtrate concentrated. The residue was purified by silica gel column chromatography to give tert-butyl (3-(4-amino-2-(oxazol-5-yl)phenyl)propyl)carbamate (940 mg, yield 35%) as a yellow oil. MS (ESI) calcd for C$_{17}$H$_{23}$N$_3$O$_3$: 228.9.

tert-butyl (3-(3-amino-5-(oxazol-5-yl)phenyl)propyl)carbamate was prepared from tert-butyl (3-(3-nitro-5-(oxazol-5-yl)phenyl)prop-2-yn-1-yl)carbamate in a similar manner to that described for tert-butyl (3-(4-amino-2-(oxazol-5-yl)phenyl)propyl)carbamate.

Example 85. Preparation of 2-(3,3-difluoropyrrolidin-1-yl)-4-(4,4,5,5-tetramethyl-1,3,2-dioxaborolan-2-yl)pyridine

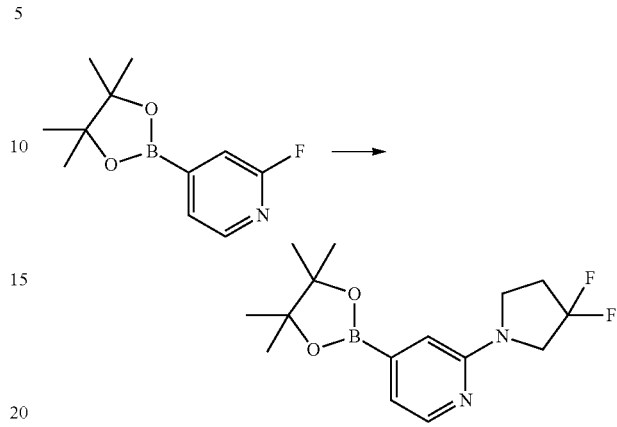

A mixture of 2-fluoro-4-(4,4,5,5-tetramethyl-1,3,2-dioxaborolan-2-yl)pyridine (1 g, 4.48 mmol), 3,3-difluoropyrrolidine hydrochloride (1.9 g, 13.4 mmol), and K$_2$CO$_3$ (3 g, 22.4 mmol) in NMP (13 mL) was stirred at 110° C. overnight. A second portion of 3,3-difluoropyrrolidine hydrochloride (0.5 g) was added and stirred overnight. The mixture was filtered, washed with H$_2$O, added 2N HCl to adjust pH to 1. The mixture was washed with EtOAc to remove residual 2-fluoro-4-(4,4,5,5-tetramethyl-1,3,2-dioxaborolan-2-yl)pyridine. The aqueous layer was adjusted to pH 13 with K$_2$CO$_3$ solution, then extracted with EtOAc to afford 2-(3,3-difluoropyrrolidin-1-yl)-4-(4,4,5,5-tetramethyl-1,3,2-dioxaborolan-2-yl)pyridine (220 mg, 17%). MS (ESI) calcd for C$_{15}$H$_{21}$BF$_2$N$_2$O$_2$: 310.2.

This general procedure could be used to prepare 4-(4,4,5,5-tetramethyl-1,3,2-dioxaborolan-2-yl)-2-(3-(trifluoromethyl)pyrrolidin-1-yl)pyridine by using 3-(trifluoromethyl)pyrrolidine hydrochloride.

Example 86. Preparation of (S)-2-(3-fluoropyrrolidin-1-yl)-4-(4,4,5,5-tetramethyl-1,3,2-dioxaborolan-2-yl)pyridine

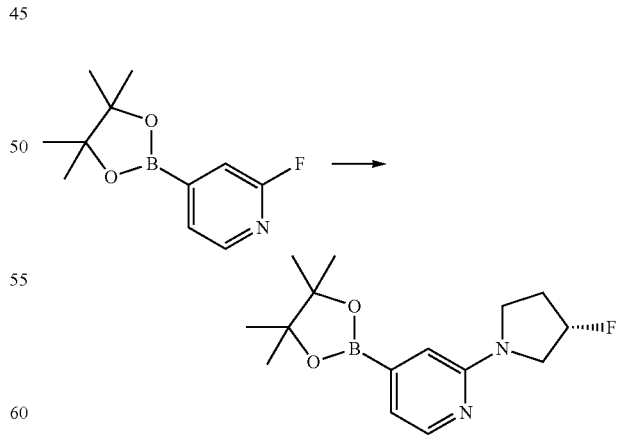

A mixture of 2-fluoro-4-(4,4,5,5-tetramethyl-1,3,2-dioxaborolan-2-yl)pyridine (200 mg), (S)-3-fluoropyrrolidine hydrochloride (350 mg), and Na$_2$CO$_3$ (480) in IPA (3.5 mL) was stirred at 91° C. for 17 hrs. The mixture was filtered and concentrated. 2N HCl was added to adjust pH to 1 and extracted with EtOAc. The aqueous layer was adjusted to pH 7 with Na₂CO₃ solution and the water was removed with toluene. The residue was taken up in EtOAc, filtered, and concentrated to afford (S)-2-(3-fluoropyrrolidin-1-yl)-4-(4,4,5,5-tetramethyl-1,3,2-dioxaborolan-2-yl)pyridine (95 mg, 36%). MS (ESI) calcd for C₁₅H₂₂BFN₂O₂: 292.2.

This general procedure could be used to prepare (R)-2-(3-fluoropyrrolidin-1-yl)-4-(4,4,5,5-tetramethyl-1,3,2-dioxaborolan-2-yl)pyridine by using (R)-3-fluoropyrrolidine hydrochloride.

Example 87. Preparation of 3,3-difluoro-1-(3-(4,4,5,5-tetramethyl-1,3,2-dioxaborolan-2-yl)phenyl)pyrrolidine Step 1. Synthesis of 1-(3-bromophenyl)-3,3-difluoropyrrolidine

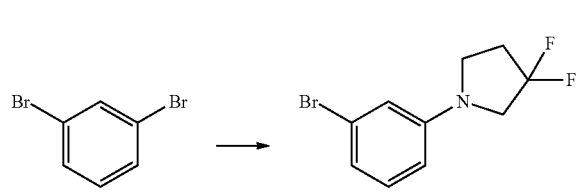 [SMILES: Brc1cccc(Br)c1 ; FC1(F)CCN(c2cccc(Br)c2)C1]

A mixture of 1,3-dibromobenzene (1 g, 4.24 mmol), 3,3-difluoropyrrolidine hydrochloride (669 mg, 4.66 mmol), Pd₂(dba)₃ (134 mg, 0.233 mmol), Cs₂CO₃ (3.32 g, 10.2 mmol), and BINAP (264 mg, 0.424 mmol) in toluene (20 mL) was heated to reflux under a N₂ atmosphere. After stirring overnight, the mixture was cooled to room temp. and concentrated. The concentrate was suspended in EtOAc (50 mL), washed with water (20 mL×3) and brine (20 mL), dried over Na₂SO₃ and concentrated. Purification by column chromatography (hexane/EtOAc=100/1) afforded 1-(3-bromophenyl)-3,3-difluoropyrrolidine (645 mg, >100%) as a colorless oil. MS (ESI) calcd for C₁₀H₁₀BrF₂N: 261.0.

Step 2. Synthesis of 3,3-difluoro-1-(3-(4,4,5,5-tetramethyl-1,3,2-dioxaborolan-2-yl)phenyl)pyrrolidine

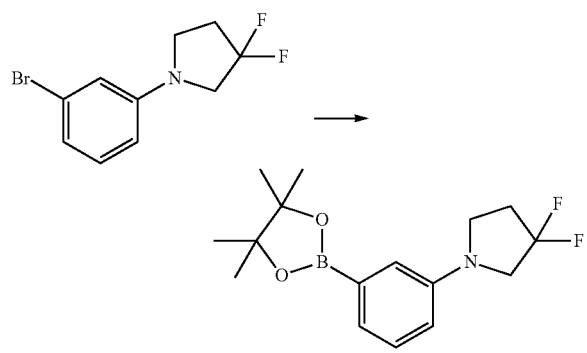

A suspension of 1-(3-bromophenyl)-3,3-difluoropyrrolidine (899 mg, 3.43 mmol), 4,4,4',4',5,5,5',5'-octamethyl-2,2'-bi(1,3,2-dioxaborolane) (957 mg, 3.77 mmol), Pd(dppf)Cl₂ (75 mg, 0.103 mmol), KOAc (1 g, 10.29 mmol) in dioxane (18 mL) was heated to 85° C. under a N₂ atmosphere. After stirring overnight, the suspension was cooled to room temp. and filtered. The filtrate was concentrated and purified by column chromatography (hexane, then hexane/EtOAc=100/1) to afford 3,3-difluoro-1-(3-(4,4,5,5-tetramethyl-1,3,2-dioxaborolan-2-yl)phenyl)pyrrolidine (Compound A#; 873 mg, 82%) as a white solid. MS (ESI) calcd for C₁₆H₂₂BF₂NO₂: 309.2.

This general two-step procedure could be used to prepare 1-(3-(4,4,5,5-tetramethyl-1,3,2-dioxaborolan-2-yl)phenyl)-3-(trifluoromethyl)pyrrolidine by using 3-(trifluoromethyl)pyrrolidine hydrochloride.

Example 88. Preparation of 2-(3-((2,2-dimethyl-1,3-dioxolan-4-yl)methyl)phenyl)-4,4,5,5-tetramethyl-1,3,2-dioxaborolane Step 1. Synthesis of 1-allyl-3-bromobenzene

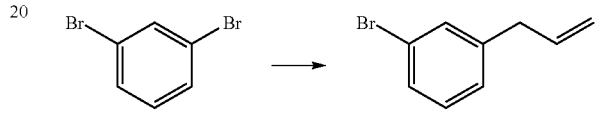

In a 3-neck flask, metal Mg (1.78 g, 73.76 mmol) was immersed in dry ether (20 mL) under N₂ atmosphere. One-third of the volume of 1,3-dibromobenzene (15 g, 63.58 mmol) in dry ether (20 mL) was added into the mixture. 1,2-Dibromoethane (0.1 mL) was added to initiate the reaction. After the reflux was steady, the remaining amount of the 1,3-dibromobenzene solution was added dropwise at a rate to maintain reflux. Upon completion of addition, the mixture was stirred at reflux for 1 hr. Then a solution of allylbromide (7.87 g, 65.12 mmol) in dry ether (20 mL) was added dropwise. Upon completion of addition, the suspension was stirred at reflux for 1 hr. The reaction was quenched with sat. NH₄Cl (100 mL) and the mixture was separated. The aqueous phase was extracted with ether (20 mL×2). The combined organic phases were washed with water (70 mL×2) and brine (30 mL), dried over Na₂SO₄, and concentrated to afford 1-allyl-3-bromobenzene (146 g) as a colorless oil. This material was used without further purification. MS (ESI) calcd for C₉H₉Br: 196.0.

Step 2. Synthesis of 3-(3-bromophenyl)propane-1,2-diol

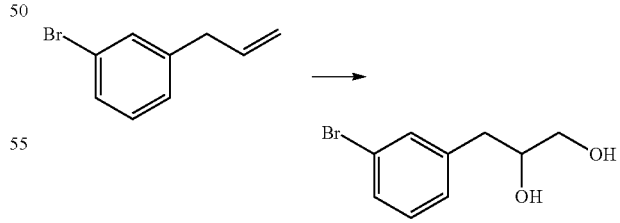

To a solution of 1-allyl-3-bromobenzene (A#; 1 g, 5.08 mmol) in CH₃CN/H₂O (20 mL, v/v=4/1) were added NMO (1.3 g, 11.16 mmol) and K₂OsO₄.2H₂O (187 mg, 0.508 mmol). The mixture was stirred at room temp. for 2 days. The CH₃CN was removed under reduced pressure and the concentrate was diluted with EtOAc. The mixture was filtered through Celite and the filtrate was concentrated to afford 3-(3-bromophenyl)propane-1,2-diol (Compound A#).

This material was used without further purification. MS (ESI) calcd for $C_9H_{11}BrO_2$: 230.0.

Step 3. Synthesis of 4-(3-bromobenzyl)-2,2-dimethyl-1,3-dioxolane

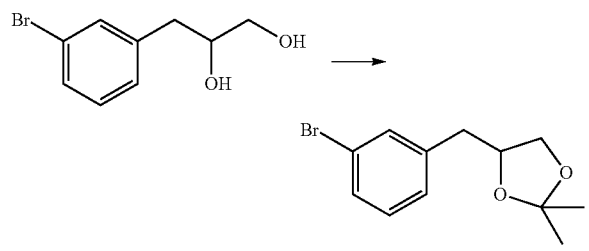

To a solution of 3-(3-bromophenyl)propane-1,2-diol (A#; 1.17 g, 5.06 mmol) in acetone (25 mL) were added 2,2-dimethoxypropane (1.8 mL, 15.18 mmol) and PTSA (96 mg, 0.506 mmol). The mixture was stirred at room temp. overnight. The reaction mixture was concentrated and purified by column chromatography (hexane/EtOAc=20/1) to afford 4-(3-bromobenzyl)-2,2-dimethyl-1,3-dioxolane (Compound A#; 200 mg, 15%) as a pale yellow oil. MS (ESI) calcd for $C_{12}H_{15}BrO_2$: 270.0.

Step 4. Synthesis of 2-(3-((2,2-dimethyl-1,3-dioxolan-4-yl)methyl)phenyl)-4,4,5,5-tetramethyl-1,3,2-dioxaborolane

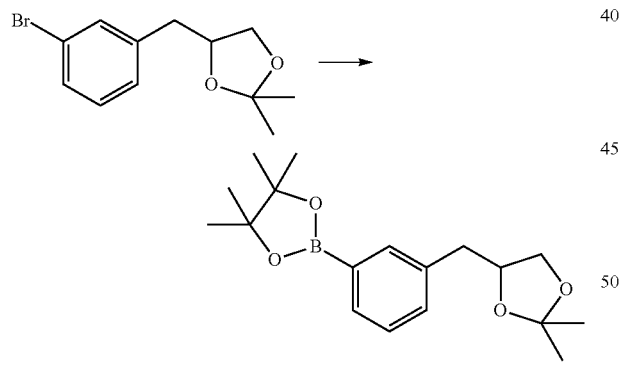

A mixture of 4-(3-bromo-benzyl)-2,2-dimethyl-[1,3]dioxolane (A#; 800 mg, 2.95 mmol) and bis(pinacolato)diboron (822 mg, 1.1 eq), Pd(dppf)Cl$_2$ (216 mg, 0.1 eq) and KOAc (868 mg, 3.0 eq) in dioxane (15 mL) was degassed and heated to 85° C. under N$_2$. After stirring overnight at 85° C., the black suspension was cooled to room temp. and filtered through Celite. The filtrate was concentrated and purified by column chromatography (hexane/EtOAc=40/1) to afford 2-(3-((2,2-dimethyl-1,3-dioxolan-4-yl)methyl)phenyl)-4,4,5,5-tetramethyl-1,3,2-dioxaborolane (Compound A#; 800 mg, 85%) as a colorless oil. MS (ESI) calcd for $C_{18}H_{27}BO_4$: 318.2.

Example 89. Preparation of (9S)—N-(4-(aminomethyl)phenyl)-2-(3-(trifluoromethyl)phenyl)-8,9-dihydro-6H-5,9-meth-anopyrido[2,3-b][1,4]diazocine-10(7H)-carboxamide hydrochloride and 2-(6-Hydroxy-3-oxo-3H-xanthen-9-yl)-5-((6-oxo-6-((4-((9S)-2-(3-(trifluoromethyl)phenyl)-7,8,9,10-tetrahydro-6H-5,9-methanopyrido[2,3-b][1,4]diazocine-10-carboxamido)benzyl) amino)hexyl) carbamoyl)benzoic acid

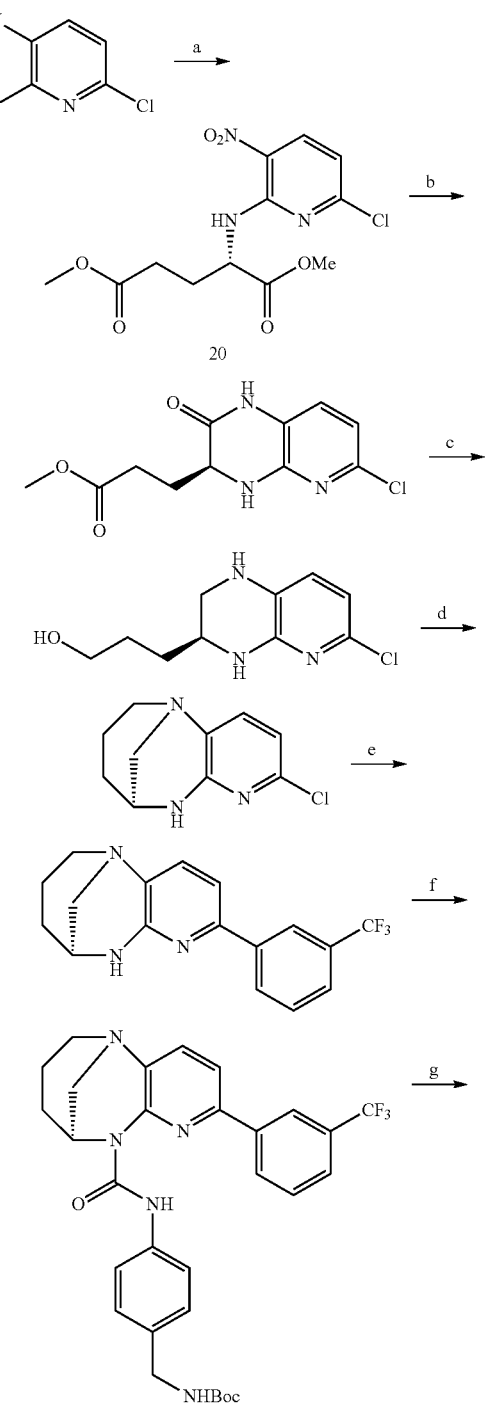

-continued

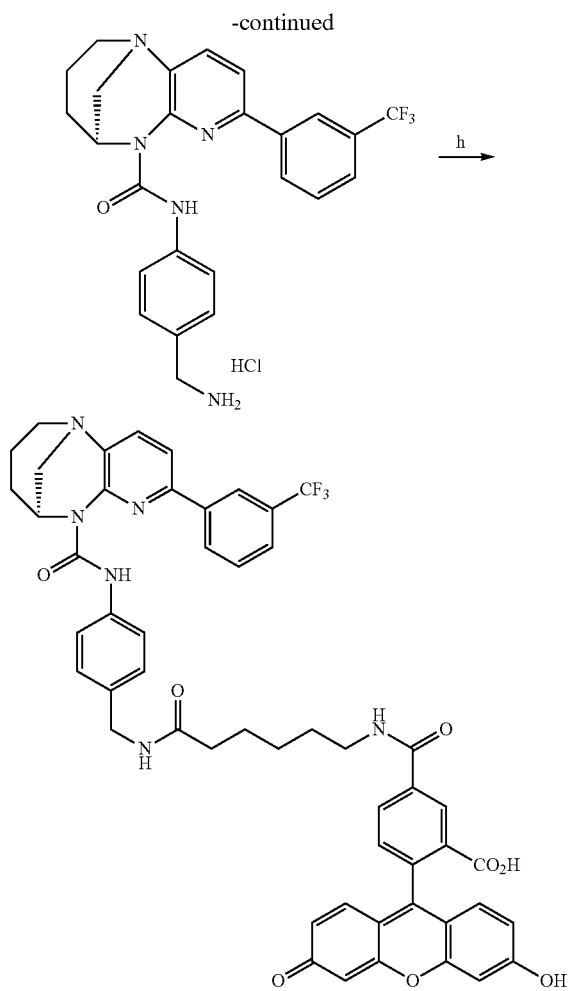

Reagents and conditions: a) NaHCO₃, THF, 40° C.; b) Fe, AcOH, IPA/Water, reflux; c) AlH₃, THF, -78° C. to rt; d) 48% HBr; e) 3-trifluorophenylboronic acid, Pd(OAc)₂, X-Phos, Cs₂CO₃, dioxane/water; f) triphosgene, DIEA, CH₂Cl₂; g) 4N HCl, dioxane; h) DIEA, 6[fluorescein-5(6)-carboxamido]hexanoic acid N-hydroxysuccinimide ester, CH₃CN.

Step 1. Synthesis of (S)-Dimethyl 2-((6-chloro-3-nitropyridin-2-yl)amino)glutarate To a mixture of 2,6-dichloro-3-nitropyridine (40.0 g, 207 mmol), L-glutamic acid dimethyl ester hydrochloride (87.7 g, 414 mmol) and NaHCO₃ (69.6 g, 829 mmol) was added tetrahydrofuran (600 mL). The mixture was stirred at 40° C. for 24 h, while monitoring for the disappearance of 2,6-dichloro-3-nitropyridine by HPLC. After the reaction was complete, the solids were filtered and washed with ethyl acetate (3×100 mL). The combined filtrate and washings were concentrated in vacuo, and the residue was purified via silica gel chromatography (eluting with 10:1 (v/v) hexanes/ethyl acetate) to obtain (S)-dimethyl 2-((6-chloro-3-nitropyridin-2-yl)amino)glutarate as a yellow solid. (60 g, 87%). LRMS (m/z) 332.1 [M+H]⁺; HRMS (m/z): [M+H]⁺ calcd for $C_{12}H_{15}N_3O_6Cl$, 332.0649. found, 332.0651.

Step 2. Synthesis of (S)-Methyl 3-(6-chloro-2-oxo-1,2,3,4-tetrahydropyrido[2,3-b]pyrazin-3-yl)propanoate To a mixture of (S)-dimethyl 2-((6-chloro-3-nitropyridin-2-yl)amino)pentanedioate (20 g, 60.2 mmol), and iron powder (16.8 g, 301 mmol) was added 2-propanol (375 mL) and water (125 mL). To the stirred mixture was added acetic acid (5.5 g, 90.3 mmol), and the reaction was stirred at reflux for 1 h while monitored for the disappearance of starting material by HPLC. After the reaction was complete, the solids were filtered and washed with 2-propanol (3×50 mL). The combined filtrate and washings were concentrated to dryness, then the residue was concentrated in vacuo to obtain (S)-methyl 3-(6-chloro-2-oxo-1,2,3,4-tetrahydropyrido[2,3-b]pyrazin-3-yl)propanoate as a dark yellow solid which was used in the next step without further purification (15 g, 81%). LRMS (m/z) 270.1 [M+H]⁺; HRMS (m/z): [M+H]⁺ calcd for $C_{11}H_{13}N_3O_3Cl$, 270.0645. found, 270.0645.

Step 3. Synthesis of (S)-3-(6-Chloro-1,2,3,4-tetrahydropyrido[2,3-b]pyrazin-3-yl)propan-1-ol To a solution of AlCl₃ (17.78 g, 133.3 mmol) in tetrahydrofuran (260 mL) under N₂ was added 2M LiAlH₄ in THF (200 mL, 400 mmol), dropwise, at a rate to control gas evolution. This gave a solution of alane (AlH₃) in THF. In a separate flask, a solution of (S)-methyl 3-(6-chloro-2-oxo-1,2,3,4-tetrahydropyrido[2,3-b]pyrazin-3-yl)propanoate (26.0 g, 96.4 mmol) in THF (460 mL) was prepared under N₂, then cooled with a dry ice/acetone bath. To this was added the alane solution, dropwise with stirring, over 2 h. When the addition was complete, the cooling bath was removed, and the reaction was allowed to warm to ambient temperature. After 1.5 h, LCMS analysis showed that the reaction was complete, and a solution of NaOH (17.6 g) in water (65 mL) was added slowly to control the evolution of H₂. The suspension was allowed to stir for 18 h, after which the solids were removed by filtration. The precipitate was washed with ethyl acetate, then the filtrate and washings were concentrated in vacuo. The product was purified via silica gel chromatography (0 to 10% gradient of MeOH in CH₂Cl₂) to obtain (S)-3-(6-chloro-1,2,3,4-tetrahydropyrido[2,3-b]pyrazin-3-yl)propan-1-ol as a yellow-orange solid (15.21 g, 69%). LRMS (m/z) 228.1 [M+H]⁺; HRMS (m/z): [M+H]⁺ calcd for $C_{10}H_{15}N_3OCl$, 228.0904. found, 228.0903.

Step 4. Synthesis of (5R,9S)-2-Chloro-7,8,9,10-tetrahydro-6H-5,9-methanopyrido[2,3-b][1,4]diazocine To (S)-3-(6-chloro-1,2,3,4-tetrahydropyrido[2,3-b]pyrazin-3-yl)propan-1-ol (12 g, 52.7 mmol) was added 48% (w/w) HBr$_{(aq.)}$ (160 mL), and the reaction was stirred at 90° C. for 18 h while monitoring the disappearance of the starting alcohol by HPLC. After the reaction was complete, it was cooled to ambient temperature, then 1.2 M aq. NaHCO₃ was added until pH 8 was achieved. The mixture was extracted with ethyl acetate (3×100 mL), then the organic phase was washed with brine (1×100 mL), dried (Na₂SO₄), filtered, and concentrated to dryness. The residue was purified by silica gel chromatography (eluting with 2:1 (v/v) hexanes/ethyl acetate) to obtain (5R,9S)-2-chloro-7,8,9,10-tetrahydro-6H-5,9-methanopyrido[2,3-b][1,4]diazocine as a light yellow solid (6.0 g, 55%). LRMS (m/z) 210.1 [M+H]⁺; HRMS (m/z): [M+H]⁺ calcd for $C_{10}H_{13}N_3Cl$, 210.0798. found, 210.0800.

Step 5. Synthesis of (9S)-2-(3-(Trifluoromethyl)phenyl)-7,8,9,10-tetrahydro-6H-5,9-methanopyrido[2,3-b][1,4]diazocine A solution of (9S)-2-chloro-7,8,9,10-tetrahydro-6H-5,9-methanopyrido[2,3-b][1,4]diazocine 3.0 g, 15.4 mmol), (3-

(trifluoromethyl)phenyl)boronic acid (4.4 g, 23.1 mmol), palladium acetate (344 mg, 1.54 mmol), 2-dicyclohexylphosphino-2',4',6'-triisopropylbiphenyl (X-Phos, 476 mg, 3.08 mmol), and cesium carbonate (15 g, 46.2 mmol) in a 10 to 1 (v/v) mixture of 1,4-dioxane and water (60 mL) was heated at 90° C. for 24 hours. The reaction was then cooled to ambient temperature, and diluted with ethyl acetate (150 mL). The mixture was washed with sat. aq. NaHCO$_3$ (200 mL×3), then the organic layers was dried (MgSO$_4$) and concentrated to dryness. The resulting residue was purified by silica gel chromatography (10-100% ethyl acetate gradient in pentane) to obtain (9S)-2-(3-(trifluoromethyl)phenyl)-7,8,9,10-tetrahydro-6H-5,9-methanopyrido[2,3-b][1,4]diazocine as a light yellow solid (3.7 g, 75%). LRMS (m/z) 320.2 [M+H]$^+$; HRMS (m/z): [M+H]$^+$ calcd for $C_{17}H_{17}N_3F_3$, 320.1375. found, 320.1375.

Step 6. Synthesis of tert-Butyl 4-((9S)-2-(3-(trifluoromethyl)phenyl)-7,8,9,10-tetrahydro-6H-5,9-methano-pyrido[2,3-b][1,4]diazocine-10-carboxamido)benzylcarbamate To a solution of (9S)-2-(3-(trifluoromethyl)phenyl)-7,8,9,10-tetrahydro-6H-5,9-methanopyrido[2,3-b][1,4]diazocine (999 mg, 3.23 mmol) in CH$_2$Cl$_2$ (30 mL) was added N,N-diisopropylethyl amine (1.7 mL, 9.78 mmol) and the reaction mixture was cooled to 0° C. with an ice bath. Triphosgene (482 mg, 1.63 mmol) was then added in four small portions. The ice bath was removed and the mixture was allowed to warm to room temperature. The reaction progress was monitored by removing a 500 uL aliquot and combining with methanol to assay for conversion to methyl carbamate via formation of the intermediate chloroformate. If any starting material remained, an additional portion of triphosgene (200 mg) was added and the reaction mixture stirred for five hours at room temperature. Next, tert-Butyl 4-aminobenzylcarbamate (800 mg, 3.60 mmol) was added in two equal portions (400 mg each) to the above mixture and the resulting mixture was stirred at room temperature for two hours. Saturated aqueous NaHCO$_3$ (30 mL) was added and the organic phase was then separated and concentrated to dryness under reduced pressure. The residue was purified by silica gel chromatography (15-100% ethyl acetate gradient in pentane) to obtain tert-butyl 4-((9S)-2-(3-(trifluoromethyl)phenyl)-7,8,9,10-tetrahydro-6H-5,9-methanopyrido[2,3-b][1,4]diazocine-10-carboxamido)benzyl-carbamate as a white solid. (761 mg, 42%). LRMS (m/z) 568.2 [M+H]$^+$; HRMS (m/z): [M+H]$^+$ calcd for $C_{30}H_{33}N_5O_3F_3$, 568.2536. found, 568.2538.

Step 7. Synthesis of (9S)—N-(4-(aminomethyl)phenyl)-2-(3-(trifluoromethyl)phenyl)-8,9-dihydro-6H-5,9-meth-anopyrido[2,3-b][1,4]diazocine-10(7H)-carboxamide hydrochloride tert-Butyl 4-((9S)-2-(3-(trifluoromethyl)phenyl)-7,8,9,10-tetrahydro-6H-5,9-methanopyrido[2,3-b][1,4]diazocine-10-carboxamido)benzylcarbamate (759 mg, 1.34 mmol) was dissolved in 4N HCl (10 mL) and 1,4-dioxane and stirred under nitrogen for 1 hour at ambient temperature. The solvents were removed under reduced pressure and the resulting solid was dried overnight under vacuum to obtain (9S)—N-(4-(aminomethyl)phenyl)-2-(3-(trifluoromethyl)phenyl)-8,9-dihydro-6H-5,9-methanopyrido[2,3-b][1,4]diazocine-10(7H)-carboxamide hydrochloride as a light tan solid (763 mg, 100%). LRMS (m/z) 468.1 [M+H]$^+$; HRMS (m/z): [M+H]$^+$ calcd for $C_{25}H_{25}N_5OF_3$, 468.2011. found, 468.2010.

Step 8. Synthesis of 2-(6-Hydroxy-3-oxo-3H-xanthen-9-yl)-5-((6-oxo-6-((4-((9S)-2-(3-(trifluoromethyl)phenyl)-7,8,9,10-tetrahydro-6H-5,9-methanopyrido[2,3-b][1,4]diazocine-10-carboxamido)benzyl)amino)hexyl)carbamoyl)benzoic acid (9S)—N-(4-(aminomethyl)phenyl)-2-(3-(trifluoromethyl)phenyl)-8,9-dihydro-6H-5,9-methanopyrido[2,3-b][1,4]diazocine-10(7H)-carboxamide hydrochloride (39 mg, 0.10 mmol) was dissolved in acetonitrile (2 mL) and methanol (0.2 mL). N,N-diisopropylethylamine (32 µL, 0.20 mmol) was then added followed by 6-[fluorescein-5(6)-carboxamido]hexanoic acid N-hydroxysuccinimide ester (50 mg, 0.085 mmol). The mixture was stirred at room temperature overnight, then the product was isolated by reversed phase HPLC (5-95% acetonitrile gradient in water modified with 0.1% TFA) to obtain 2-(6-hydroxy-3-oxo-3H-xanthen-9-yl)-5-((6-oxo-6-((4-((9S)-2-(3-(trifluoromethyl)phenyl)-7,8,9,10-tetra-hydro-6H-5,9-methanopyrido[2,3-b][1,4]diazocine-10-carboxamido)benzyl)amino)hexyl)carbamoyl)benzoic acid as a brown solid (26 mg, 35%). LRMS (m/z) 939.2 [M+H]$^+$; HRMS (m/z): [M+H]$^+$ calcd for $C_{52}H_{46}N_6O_8F_3$, 939.3329. found, 939.3328.

Example 90. Mini-hSIRT1 Design and Characterization

Proton-deuteron exchange mass spectrometry (HDX-MS) was performed on the full-length hSIRT1 protein to identify and characterize the key functional regions of hSIRT1. The rate of H-D exchange is highly dependent on the dynamic properties of the protein, with faster exchange occurring at solvent exposed and/or flexible regions and slower exchange occurring at the more buried and/or structurally rigid regions (Hamuro, Y. et al. (2003) J biomol Techniques: JBT 14, 171). Consistent with the previous study on hSIRT1(19-747) (Hubbard, B. P. et al. (2013) Science 339, 1216), full-length hSIRT1 contains three major structured regions: the catalytic core region, residues 229-516 (referred to as hSIRT1cc hereafter) (Jin, L. et al. (2009) J Biol Chem 284, 24394 and Frye, R. A. (2000) Biochem Biophys Res Commun 273, 793), the N-terminal region of 190-230 immediately preceding the catalytic core and a remote region in the C-terminus following the catalytic core around 640-670.

To probe the STAC binding site on hSIRT1, HDX-MS was performed in the absence or presence of STAC 1. Addition of 1 reduces the H-D exchange rate around residues 190-230 in the N-terminal domain of hSIRT1, suggesting that this region is involved in STAC binding. Additionally, the $^1$H, $^{15}$N HSQC spectrum of the $^{15}$N-labeled hSIRT1 (180-230) is well dispersed suggesting that it forms an autonomously folded domain. Addition of 1 to $^{15}$N-labeled hSIRT1(180-230) results in significant chemical shift perturbations and further supports direct interaction of 1 with this region, hereafter referred to as the STAC-binding domain (SBD). Addition of 1 to hSIRT1 in the presence of a p53-derived peptide substrate (Ac-p53(W5)) (Dai, H. et al. (2010) J Biol Chem 285, 32695) results in perturbation of the H-D exchange rates both around the SBD and at the presumed substrate binding site (residues 417-424) in the catalytic core, indicating that STAC binding in the N-terminal domain and substrate binding within the catalytic core of hSIRT1 are coupled. This is consistent with a previous observation that STACs enhance substrate binding to hSIRT1, thereby increasing hSIRT1 catalytic efficiency (Milne, J. C. et al. (2007) Nature 450, 712).

In contrast to the SBD, the C-terminal structural element (641-665) identified by HDX-MS is separated from the catalytic core by about 150 residues and is predicted to contain several β-strands, referred to here as C-terminal β-strands/sheet (CBS), similar to the previously reported murine Essential for SIRT1 Activity (ESA) peptide (19). hSIRT1cc only shows about one eighth of the activity of the full-length enzyme using deacetylation assay conditions previously reported (Dai, H. et al. (2010) J Biol Chem 285, 32695). The CBS peptide restores the catalytic activity of hSIRT1cc in trans, to 80% of that of full-length hSIRT1, with $EC_{50}$=59 nM, consistent with previous observations (Kang, H. et al. (2011) Mol Cell 44, 203 and Marmorstein, R. et al. (2012) J Biol Chem 287, 2468). We also designed a minimal CBS fragment covering only the β-stranded region (642-658), which behaves similarly to the parental CBS peptide. Kinetic characterization reveals that the CBS peptide restores activity by lowering the KM values for both peptide substrate and $NAD^+$ of hSIRT1cc by 4-5-fold (see Table 1).

TABLE 1

Steady-State Kinetics of hSIRT1 catalytic core in the absence or presence of CBS peptide.[a]

| Group | $k_{cat}$ (s$^{-1}$) | Ac-p53(W5)[b] | NAD[+c] |
|---|---|---|---|
| | | $K_M$ (μM) | |
| hSIRT1(229-516) | 0.29 ± 0.01 | 163 ± 8 | 988 ± 73 |
| hSIRT1(229-516) + CBS | 0.54 ± 0.01 | 37 ± 2.5 | 180 ± 14 |
| hSIRT1(229-516) + mini-CBS | 0.54 ± 0.01 | 49 ± 3 | 207 ± 19 |

[a]Data from PNC1/GDH assay.
[b]NAD$^+$ concentration fixed at 1 mM.
[c]Ac-p53(W) concentration fixed at 500 μM.

Taken together, the above data suggests a tri-partite architecture for a minimally functional hSIRT1 that includes; 1) the central core constituting the basic catalytic machinery, 2) the N-terminal SBD that mediates STAC binding and activation, and 3) the C-terminal CBS peptide which stabilizes the catalytic core resulting in more efficient deacetylase activity. Based on this, we designed hSIRT1 constructs encompassing all three of the minimal structural elements covalently bound, which we termed mini-hSIRT1s. The constructs span 183-505 or 183-516, which are connected to the CBS peptide via a flexible poly-glycine/serine linker (GS, (GGGS)$_2$, or (GGGS)$_3$) (Sauer, R. T. and Robinson, C. R. (1998) Proceedings of Nat Academy of Sciences of USA 95, 5929). The $K_M$ and $k_{cat}$ values are comparable between mini-hSIRT1 constructs and the full-length enzyme, as are the $IC_{50}$ values for the non-competitive hSIRT1 inhibitors EX-527 or nicotinamide (NAM) confirming functional fidelity of mini-hSIRT1s (see Table 2). In addition there is an excellent correlation between mini-hSIRT1 and the full length enzyme with respect to STAC-mediated activation across a broad set of chemotypes. Removal of the SBD completely abolishes STAC-mediated activation of mini-hSIRT1, confirming the critical importance of this domain for activation. In contrast, mini-hSIRT1 lacking the CBS retains a significant level of STAC activation demonstrating that the CBS enhances but, is not required for STAC-mediated activation. Finally, the E230K mutation also attenuates STAC-mediated activation in mini-hSIRT1 as in the full-length enzyme (Hubbard, B. P. et al. (2013) Science 339, 1216). Collectively, these observations demonstrate that at half the molecular size, mini-hSIRT1 is a fully functional and activatable surrogate for full-length hSIRT1.

TABLE 2

Steady-state kinetics of mini-hSIRT1 constructs.[a]

| hSIRT1 | $k_{cat}$ (s$^{-1}$) | Ac-p53(W5)[b] | NAD[+c] |
|---|---|---|---|
| | | $K_M$ (μM) | |
| hSIRT1 (1-747) | 0.37 ± 0.01 | 3.7 ± 0.8[d] | 70 ± 6 |
| hSIRT1 (183-516) | 0.38 ± 0.01 | 42 ± 4.9 | 769 ± 97 |
| hSIRT1 (183-516-(GGGS)$_2$-641-665) | 0.44 ± 0.02 | 16 ± 2.2 | 82 ± 6 |
| hSIRT1 (183-516-(GS)-641-665) | 0.54 ± 0.01 | 14 ± 1.1 | 78 ± 8 |
| hSIRT1 (183-505-(GGGS)$_2$-641-665) | 0.54 ± 0.02 | 13 ± 2 | 112 ± 10 |
| hSIRT1 (229-516-(GGGS)$_2$-641-665) | 0.49 ± 0.01 | 13 ± 3 | 222 ± 25 |
| hSIRT1 (229-505-(GGGS)$_2$-641-665) | 0.43 ± 0.02 | 11 ± 3 | 218 ± 34 |
| hSIRT1 (183-505-(GGGS)$_2$-641-665) (R446A) | 0.54 ± 0.01 | 42 ± 4.1 | 170 ± 19 |
| hSIRT1 (183-505-(GGGS)$_2$-641-665) (R446E) | 0.21 ± 0.01 | 30 ± 3 | 375 ± 24 |
| hSIRT1 (183-505-(GGGS)$_2$-641-665) (E230K, R446E) | 0.30 ± 0.01 | 33 ± 2 | 423 ± 41 |
| hSIRT1 (183-505-(GGGS)$_2$-641-665) (P231G, P232G) | 0.65 ± 0.01 | 23.4 ± 1 | 273 ± 26 |

[a]Data from PNC1/GDH assay.
[b]NAD$^+$ concentration fixed at 2 mM.
[c]Ac-p53(W) concentration fixed at 400 μM.
[d]Value from (1)

Example 91. Structure of the Mini-hSIRT1/STAC Complex

While the x-ray crystallographic structure of the hSIRT1 catalytic core has been reported (Zhao, X. et al. (2013) J Med Chem 56, 963), no structure of the full-length enzyme exists to our knowledge. Structure of the full length hSIRT1 has been challenging, in part, due to the conformational flexibility of the extended N- and C-terminal domains. The mini-hSIRT1 constructs afforded us the opportunity to crystallize an equivalently functional surrogate of the full-length enzyme. We successfully crystallized mini-hSIRT1 (183-505-(GGGS)2-CBS) with STAC 1 used in the HDX-MS experiments and determined the structure of the complex (mini-hSIRT1/1) at 3.1 Å by molecular replacement using a search model based on the homolog model of SIRT3 (Jin, L. et al. (2009) J Biol chem 284, 24394). Mini-hSIRT1 is composed of a catalytic core that assumes a Rossmann-fold large lobe and a zinc-binding small lobe common to all sirtuins, an N-terminal three-helical bundle SBD and a C-terminal β-hairpin CBS. Interestingly, a STAC-mediated dimer of mini-hSIRT1 related by crystallographic symmetry was observed in the crystal lattices. Size exclusion chromatography (SEC) confirms that mini-hSIRT1 forms dimer in solution in the presence of STAC 1. However, no formation of mini-hSIRT1 dimer is observed for a similar STAC 7 of the same chemotype. Given this observation and the fact that the STAC concentration used for crystallization is much higher than that used in the biochemical assay measuring activation, it would appear that dimerization observed in the crystal structure is not a requirement for hSIRT1 activation by STACs.

The CBS mediates β-augmentation with the six-stranded β-sheet of the Rossmann-fold lobe of the catalytic domain, in agreement with the HDX-MS results of hSIRT1cc perturbation upon CBS binding. The CBS-mediated β-augmentation appears to stabilize the active site of the hSIRT1 catalytic core which restores the $K_M$ values observed for both acetylated peptide and NAD$^+$ substrates. The N-terminal SBD forms an independently folded three-helical bundle with 1 binding to the helix-turn-helix (H2-T-H3) motif within the SBD, consistent with the HDX-MS, NMR and enzyme kinetic results. The major mini-hSIRT1/1 binding site is a relatively shallow hydrophobic surface with an off-center, deeper hydrophobic pocket, that the $CF_3$ group of 1 occupies. This is consistent with the observed structure activity relationship (SAR) developed across multiple STAC chemotypes indicating the requirement of overall flatness of the core scaffold maintained by an intramolecular hydrogen bond (Vu, et al. (2009) J Med Chem, 52, 1275). A remarkable similarity in terms of domain configuration is observed between the mini-hSIRT1 structure and that of yeast Sir2 with both having an N-terminal helical bundle and the C-terminal β-augmentation by a β-hairpin beyond the typical Rossmann-fold large lobe (Hsu, H. C. et al. (2013) Genes & Dev 27, 64). However, yeast Sir2 doesn't include the 150 amino acid insertion observed in hSIRT1 and appears as a natural "mini-SIRT1" in yeast. The N-terminal domain in Sir2 appears to be important for the allosteric activation by another yeast protein Sir4 (Hsu, H. C. et al. (2013) Genes & Dev 27, 64). Though the architecture of the Sir2 N-terminal domain differs from the hSIRT1 SBD, the two appear to have functionally conserved roles in allosteric activation of the catalytic core.

Example 92. Site-Directed Mutagenesis of the STAC Binding Pocket

We used site-directed mutagenesis of full-length hSIRT1 to confirm the key residues of the SBD that were identified by the mini-hSIRT1 structures. The following point mutants of full-length hSIRT1 were generated probing three classes of residues: a) residues which appear to directly interact with activators (T219A, I223A, N226A, and I227A), b) coupling modulator Glu$^{230}$ (Hubbard, B. P. et al. (2013) Science 339, 1216) (E230K, E230A, and E230Q), and c) SBD residues with no apparent role in activator binding (Q222A and V224A). None of the mutants significantly impaired the basal catalytic activity using the Ac-p53(W5) substrate or affected inhibition by EX-527, a TFA-p53 peptide (Ac-RHK-K$^{TFA}$-L-Nle-F-NH$_2$), or nicotinamide (NAM) (see Tables 4 and 5).

The general impact of the mutations on activation was assessed by comparing the fold-activation of wild-type versus mutant full-length SIRT1 using a structurally diverse set of 246 STACs tested at a fixed concentration of 25 μM. Additionally, we investigated the effect of the mutations on STAC binding versus activation by monitoring shifts in their $EC_{50}$ and maximum activation values respectively using a panel of five compounds (STACs 1, 6-9). T219A, I223A, and I227A all exhibit broad impairment of activation with increases in $EC_{50}$ compared to wild-type hSIRT1, implicating impaired activator binding consistent with the structures (see Table 6). Interestingly, I223A was the most compound-dependent mutant with STAC-mediated activation ranging from attenuated to enhanced. STACs showing enhanced activation are enriched for structures containing an ortho-$CF_3$ substituted phenyl ring. In the crystal structures, Ile$^{223}$ lies directly beneath the activator and lines the pocket into which the meta-$CF_3$ of 1 inserts. The cavity created by mutation of Ile$^{223}$ to Ala would be expected to better accommodate an ortho substituent versus a meta-substitution. This observation further validates the key molecular interactions governing STAC binding and points to strategies for altering STAC interaction with the SBD.

TABLE 4

Steady-state substrate substrate kinetics for wild-type and mutant full-length hSIRT1.

| hSIRT1 | $k_{cat}$ (s$^{-1}$)$^a$ | $K_M$ (μM) Ac-p53(W5)$^a$ | Ac-p53(W5)$^b$ | NAD$^{+a}$ |
|---|---|---|---|---|
| wild-type | 0.37 ± 0.01 | 3.7 ± 0.8$^c$ | 2.7 ± 0.4$^c$ | 70 ± 6 |
| T219A | 0.35 ± 0.01 | 2.7 ± 0.5 | 1.7 ± 0.2 | 45 ± 4 |
| Q222A | 0.34 ± 0.01 | 7.1 ± 2.3 | 4.8 ± 0.6 | 35 ± 6 |
| I223A | 0.33 ± 0.02 | 2.5 ± 0.3 | 4.2 ± 0.4 | 96 ± 14 |
| V224A | 0.31 ± 0.01 | 6.2 ± 0.7 | 4.2 ± 0.3 | 43 ± 4 |
| N226A | 0.34 ± 0.02 | 1.8 ± 0.7 | 2.5 ± 0.2 | 85 ± 9 |
| I227A | 0.36 ± 0.01 | 5.3 ± 0.7 | 3.4 ± 0.4 | 43 ± 6 |
| E230K | 0.36 ± 0.01 | 7.0 ± 0.7 | 5.4 ± 0.2 | 70 ± 5 |
| E230A | 0.41 ± 0.01 | 6.2 ± 0.6 | 6.2 ± 0.5 | 57 ± 2 |
| E230Q | 0.38 ± 0.01 | 3.2 ± 0.7 | 7.5 ± 0.9 | 99 ± 17 |
| I223R | 0.27 ± 0.01 | 3.5 ± 0.5 | 1.4 ± 0.2 | 91 ± 13 |

$^a$Data from PNC1/GDH assay.
$^b$Data from OAcADPr assay.
$^c$Values from (1)

TABLE 5

Inhibition of wild-type and mutant full-length hSIRT1.

| hSIRT1 | EX-527 | TFA-p53 7-mer$^b$ | NAM |
|---|---|---|---|
| wild-type | 0.140 ± 0.020 | 0.680 ± 0.070 | 92 ± 6 |
| T219A | 0.310 ± 0.040 | 0.490 ± 0.020 | 53 ± 4 |
| Q222A | 0.110 ± 0.010 | 0.630 ± 0.050 | 53 ± 5 |
| I223A | 0.180 ± 0.020 | 0.540 ± 0.150 | 108 ± 10 |
| V224A | 0.140 ± 0.010 | 0.860 ± 0.080 | 64 ± 3 |
| N226A | 0.190 ± 0.010 | 0.350 ± 0.040 | 100 ± 9 |
| I227A | 0.220 ± 0.020 | 0.940 ± 0.060 | 92 ± 4 |
| E230K | 0.150 ± 0.020 | 1.6 ± 0.3 | 54 ± 3 |
| E230A | 0.100 ± 0.030 | 1.3 ± 0.4 | 60 ± 3 |
| E230Q | 0.240 ± 0.020 | 0.860 ± 0.060 | 56 ± 3 |
| I223R | 0.210 ± 0.020 | 0.660 ± 0.060 | 87 ± 6 |

IC$_{50}$ (μM)$^a$ $^a$Data from OAcADPr assay using the Ac-p53(W5) substrate.
$^b$TFA-p53 peptide sequence: Ac-RHKK(TFA)L-Nle-F-NH$_2$.

TABLE 6

Substrate concentrations used in full-length hSIRT1 activation or inhibition assays.

| hSIRT1 | Activation assays | | Inhibition assays | |
|---|---|---|---|---|
| | Ac-p53(W5) (µM) | NAD⁺ (µM) | Ac-p53(W5) (µM) | NAD⁺ (µM) |
| wild-type | 0.20 | 8.0 | 2 | 80 |
| T219A | 0.20 | 4.5 | 2 | 45 |
| Q222A | 0.70 | 4.5 | 6.5 | 45 |
| I223A | 0.25 | 10 | 2.5 | 100 |
| V224A | 0.60 | 4.5 | 6.5 | 45 |
| N226A | 0.20 | 8.0 | 2 | 80 |
| I227A | 0.40 | 4.5 | 4 | 45 |
| E230K | 0.40 | 8.0 | 4 | 80 |
| E230A | 0.40 | 8.0 | 4 | 80 |
| E230Q | 0.30 | 8.0 | 3 | 80 |
| I223R | 0.14 | 10 | 1.4 | 100 |

Asn$^{226}$ appears to form a hydrogen bond between its carboxamide nitrogen and the carbonyl oxygen of 1 on the surface of the protein. However, activation of N226A was only minimally impaired compared to wild-type. The small contribution from this H-bond is likely due to its high solvent exposure.

Mutation of Glu$^{230}$ to either Lys or Ala has been recently reported to broadly impair activation by STACs although the mechanism by which this occurs is unclear (Hubbard, B. P. et al. (2013) Science 339, 1216). We tested activation of E230K, E230A, and E230Q full-length hSIRT1 proteins. In all three Glu$^{230}$ mutants, the maximum activation is impaired without shifting the EC$_{50}$ (see Tables 7 and 8) suggesting a role for Glu$^{230}$ in the formation or stabilization of the activated conformation of hSIRT1. Activation of E230Q is also broadly impaired, indicating that the negative charge of Glu$^{230}$ is important for stabilizing the activated conformation of hSIRT1 and that Glu$^{230}$ likely interacts with a positively charged residue in the activated conformation.

TABLE 7

Effect of hSIRT1 mutations on activator EC$_{50}$ values.

| | compound: | | | | | | | | | |
|---|---|---|---|---|---|---|---|---|---|---|
| | 1 | | 6 | | 7 | | 8 | | 9 | |
| hSIRT1 | EC$_{50}$ (µM) | fold shift$^a$ | EC$_{50}$ (µM) | fold shift$^a$ | EC$_{50}$ (µM) | fold shift$^a$ | EC$_{50}$ (µM) | fold shift$^a$ | EC$_{50}$ (µM) | fold shift$^a$ |
| WT | 0.30 | 1.00 | 0.77 | 1.00 | 2.20 | 1.00 | 0.48 | 1.00 | 0.77 | 1.00 |
| T219A | 1.00 | 3.30 | 2.38 | 3.10 | 8.83 | 4.01 | 3.96 | 8.26 | 4.12 | 5.36 |
| Q222A | 0.25 | 0.84 | 0.78 | 1.02 | 2.01 | 0.91 | 0.51 | 1.07 | 0.56 | 0.73 |
| I223A | 0.77 | 2.56 | 2.11 | 2.75 | 5.51 | 2.51 | 2.36 | 4.91 | 2.97 | 3.86 |
| V224A | 0.43 | 1.43 | 1.15 | 1.50 | 2.60 | 1.18 | 0.90 | 1.87 | 1.09 | 1.41 |
| N226A | 0.55 | 1.83 | 2.64 | 3.44 | 3.92 | 1.78 | 1.03 | 2.15 | 1.17 | 1.52 |
| I227A | 1.09 | 3.65 | 3.72 | 4.83 | 6.76 | 3.07 | 2.98 | 6.21 | 4.28 | 5.55 |
| E230A | 0.26 | 0.86 | 1.89 | 2.46 | 2.61 | 1.19 | 0.530 | 1.11 | 1.23 | 1.60 |
| E230K | 0.15 | 0.50 | 2.92 | 3.81 | 3.21 | 1.46 | 0.70 | 1.46 | 1.63 | 2.12 |
| E230Q | 0.37 | 1.23 | 2.15 | 2.80 | 3.36 | 1.53 | 0.58 | 1.21 | 1.34 | 1.74 |

$^a$Fold shift = (mutant EC$_{50}$/wild-type EC$_{50}$)

EC$_{50}$ values determined from activation dose-response curves using eq. 1. Activation was measured using the OAcADPr assay with Ac-p53(W5) substrate.

TABLE 8

Effect of hSIRT1 mutations on the maximum activation by STACs.

| | compound: | | | | | | | | | |
|---|---|---|---|---|---|---|---|---|---|---|
| | 1 | | 6 | | 7 | | 8 | | 9 | |
| hSIRT1 | RV$_{max}$ | fold shift$^a$ | RV$_{max}$ | fold shift$^a$ | RV$_{max}$ | fold shift$^a$ | RV$_{max}$ | fold shift$^a$ | RV$_{max}$ | fold shift$^a$ |
| WT | 10.5 | 1.00 | 14.7 | 1.00 | 7.16 | 1.00 | 6.28 | 1.00 | 14.9 | 1.00 |
| T219A | 5.76 | 1.99 | 14.3 | 1.03 | 3.25 | 2.73 | 4.22 | 1.64 | 10.4 | 1.47 |
| Q222A | 7.58 | 1.44 | 10.9 | 1.39 | 7.27 | 0.98 | 5.32 | 1.22 | 10.4 | 1.48 |
| I223A | 4.52 | 2.69 | 9.85 | 1.55 | 1.89 | 6.90 | 6.45 | 0.97 | 8.00 | 1.98 |
| V224A | 9.56 | 1.11 | 12.9 | 1.15 | 9.58 | 0.72 | 7.71 | 0.79 | 14.5 | 1.03 |
| N226A | 7.82 | 1.39 | 11.2 | 1.34 | 5.68 | 1.32 | 4.95 | 1.34 | 13.4 | 1.12 |
| I227A | 5.22 | 2.25 | 6.14 | 2.67 | 8.25 | 0.85 | 5.98 | 1.06 | 12.5 | 1.20 |
| E230A | 2.64 | 5.81 | 6.15 | 2.66 | 2.72 | 3.58 | 3.21 | 2.39 | 6.91 | 2.35 |
| E230K | 1.39 | 24.3 | 3.83 | 4.84 | 1.71 | 8.67 | 1.99 | 5.36 | 2.96 | 7.06 |
| E230Q | 2.28 | 7.40 | 4.67 | 3.73 | 2.57 | 3.93 | 2.72 | 3.07 | 5.14 | 3.35 |

$^a$ Fold shift = (wild-type RV$_{max}$−1)/(mutant RV$_{max}$−1)

Maximum activation values (RV$_{max}$) determined from activation dose-response curves using Eq. 1.
Activation was measured using the OAcADPr assay assay with Ac-p53(W5) substrate.

In contrast to the above mutants, Q222A and V224A displayed normal activation which is consistent with their positions away from the STAC in the mini-hSIRT1/1 structure. Importantly, all of these data obtained with full-length hSIRT1 are consistent with what the mini-SIRT1 crystal structures predict further validating the biochemical significance of these structures.

Despite the broad impact of the mutations described above, none of them completely abolished activation of hSIRT1 as seen with removal of the SBD. As $Ile^{223}$ lies directly beneath the bound STAC and activation of I223A is highly compound-dependent, we hypothesized that I223R hSIRT1 would constitute the most highly activation-impaired full-length enzyme to date. Substitution from Ile to Arg introduces bulk and charge into the hydrophobic STAC binding site which would be expected to disrupt compound binding based on the structure. I223R does not alter the basal catalytic activity with either the Ac-p53(W5) or FOXO-3a substrate peptides or inhibition by EX-527, TFA-p53 peptide, or NAM (see Tables 4, 5 and 9). However, activation is completely lost for all 246 activators for both substrates.

TABLE 9

Steady-state kinetics for full-length hSIRT1 with FOXO-3a 21-mer$^a$.

| hSIRT1 | $k_{cat}$ (s$^{-1}$) | $K_M$ peptide (µM) | $K_M$ NAD$^+$ (µM) |
|---|---|---|---|
| wild type | 0.39 ± 0.02 | 50 ± 6 | 280 ± 40 |
| I223R | 0.25 ± 0.01 | 90 ± 6 | 460 ± 50 |

$^a$Data from PNC1/GDH assay.

Example 93. Allosteric Coupling Between STAC and Substrate Binding

We investigated the mechanism of activation of hSIRT1 by STACs. To that end, we determined a 2.73 Å structure of a quaternary complex of mini-hSIRT1, 1, a 7 amino acid peptide substrate derived from p53 (Ac-p53), and the non-hydrolyzable NAD$^+$ analog carbaNAD and a 2.74 Å structure mini-hSIRT1/1 in complex with a novel active-site directed inhibitor 2 that occupies the peptide and NAD$^+$ binding sites. In the quaternary complex structure, the Ac-p53 peptide and carbaNAD bind to the active site cleft between the large and small lobes. Ac-p53 adopts an extended conformation, with main chain amide group forming hydrogen bonds with the residues Gly$^{415}$ and Glu$^{416}$ from the small lobe and the residues Lys$^{444}$ and Arg$^{446}$ from the large lobe. The hydrogen bonds between the amide of the peptide+1 position and that of Arg$^{446}$ render a potential interaction between the side chains for a hydrophobic+1 residue, which may be important in STAC-mediated hSIRT1 activation (Dai, H. et al. (2010) J Biol Chem 285, 32695). The acetyllysine side chain inserts into a hydrophobic cavity lined by Phe$^{414}$, Leu$^{418}$ and Val$^{445}$. The acetyl group is sandwiched between His$^{363}$ and Phe$^{297}$, with the ε-N of the acetyllysine hydrogen bonded with the carbonyl oxygen of Val$^{412}$, which maintains the orientation and the extended conformation of the acetyl-lysine side chain. CarbaNAD also makes multi-point contacts with hSIRT1, most of which are similar to those observed in the ternary complex of hSIRT1 catalytic core/NAD/EX-527 analog (Zhao, X. et al. (2013) J Med Chem 56, 963). Some differences were noted, such as the amide group of the nicotinamide ring forms hydrogen bonds with Ile$^{347}$ and Asp$^{348}$ in the C-pocket. In addition the 2' and 3' hydroxyl groups of the ribofuranose on the nicotinamide side form hydrogen bonds with the carbonyl oxygen atom of acetyl-lysine, which helps to orient the C-1' atom of NAD for subsequent nucleophilic attack by the peptide N-ε-acetyl group. Inhibitor 2 occupies both the acetyl-lysine binding site and the nicotinamide binding C-pocket of mini-hSIRT1, similar to the recently reported structure of the SIRT3/2 complex. Similar to SIRT3, binding of substrates or the active-site inhibitor leads to domain closure, bringing the small and large lobes together (Szczepankiewicz, B. G. et al. (2012) J Org chem 77, 7319 and Jin, L. et al. J Biol Chem (2009) 284, 24394). A more prominent conformational change upon active site occupancy is an upward movement of the N-terminal domain, which seems to hinge around Arg$^{234}$ and brings the SBD closer to the active site providing a potential mechanism for the allosteric coupling of STAC binding and substrate binding sites through concerted motions. The hinge residue, Arg$^{234}$, is located within the polybasic linker (residues 233-238) and anchors the N-terminal SBD to the catalytic core through a salt bridge formed between its guanidinium group and the carboxylate group of Asp$^{475}$ and hydrogen bonds to the carbonyl groups of His$^{473}$ and Val$^{459}$. Comparison of the SBDs in these three structures shows that the domain is relatively rigid, with a superimposable STAC-binding helix-turn-helix (H2-T-H3) motif with only the first helix tilting out slightly in the mini-hSIRT1/1/2 complex structure. We assessed if the short linker (230-233) between the SBD and the anchoring Arg$^{234}$ might be important for the allosteric coupling by modulating the rigidity of the linker through mutating Pro$^{231}$ and Pro$^{232}$ to Gly. Indeed, P231G/P232G exhibits markedly attenuated STAC activation of mini-hSIRT1, supporting the importance of this short linker to mediate the movement of the SBD and the consequential coupling of STAC binding and substrate binding.

HDX-MS data reveal that, in contrast to wild-type hSIRT1, STAC binding to the E230K mutant no longer confers protection around the peptide binding site in the E230K/1/Ac-p53(W5) complex. This indicates that the E230K mutation likely compromises the coupling between the STAC and substrate binding sites. To explore this further, a fluorescence polarization (FP) assay was developed to measure STAC binding to hSIRT1 and investigate the coupling effect in the presence of substrate. A fluorescein-linked STAC (3) which binds to full-length hSIRT1 with a IQ of 0.3 µM was used as an FP probe and was effectively competed off by its parent compound 4. Binding of 3 was severely impaired for I223R hSIRT1 confirming the role of this residue shown in the mini-hSIRT1/1 structures as being directly involved in STAC binding in the full-length enzyme. STACs were tested in the FP assay in the absence or presence of Ac-p53(W5) substrate exemplified by 5 which displayed enhanced binding affinity (K$_i$) in the presence of Ac-p53(W5) consistent with a K$_M$-lowering mechanism for activation. While the E230K mutant shows remarkably similar binding affinity for most STACs compared to the wild-type, enhancement of this binding by Ac-p53(W5) is absent or severely attenuated. The HDX-MS and activation data together suggest that Glu$^{230}$ is not directly involved in STAC binding but is instead, a critical residue mediating the coupling of STAC and substrate binding to promote activation. This was further verified by determining the structure of the E230K mini-hSIRT1 protein with compounds 1 and 2. The overall structures were similar to those of the wild-type mini-hSIRT1/1/2 ternary complexes, confirming that Glu$^{230}$ does not directly participate in STAC binding but instead likely plays a dynamic role during the allosteric coupling. Furthermore, a crystallographic dimer was observed with the E230K mini-hSIRT1/STAC structure, similar to that seen for the wild-type protein structures, further indicating that dimerization is unlikely to be required for the biochemical activation of hSIRT1 by STACs.

To assess the general requirement for a hydrophobic moiety on the acetyl-substrate for STAC-mediated SIRT1 activation (Dai, H. et al. (2010) J Biol Chem 285, 32695), we mutated the potential +1 Trp interacting residue $Arg^{446}$ to Ala based on the close proximity of $Arg^{446}$ to +1 position. R446A hSIRT1 has an increased $K_M$ value for Ac-p53(W5) (see Table 2) as expected. However, it also shows attenuated activation, similar to what is observed for E230K/A mutants. Given this observation, the cationic nature of $Arg^{446}$ and coupling between active site and STAC-binding site, we made the mini-hSIRT1 R446E/E230K double mutant to test if $Arg^{446}$ is a possible electrostatic partner for E230 with E230K and R446E mini-hSIRT1 as controls. Whereas either E230K or R446E results in significant attenuation of STAC activation of mini-hSIRT1, the R446E/E230K double mutant partially restores STAC-mediated activation of mini-hSIRT1 compared to E230K or R446E. These data support the existence of a salt bridge between $Glu^{230}$ and $Arg^{446}$ in the activated conformation and are consistent with the proposed movement of the SBD to interact with the catalytic core in the activated state.

All of mini-hSIRT1 constructs we discussed herein recapitulate three key features of full-length hSIRT1: 1) the steady state enzyme kinetics and inhibition, 2) the STAC activation profile across multiple chemotypes, 3) and STAC activation impairment by E230K. We then used the mini-hSIRT1 constructs to obtain the first reported structures of a fully functional form of hSIRT1 with a bound STAC. The biochemical and structural characterization reveals the hSIRT1 intra-molecular interactions between the CBS and catalytic core, which are essential for the basal deacetylation activity of hSIRT1. More importantly, the structures of the mini-hSIRT1/STAC complex reveal the detailed architecture of the STAC binding site providing important information for future structure-based drug design. The comparison of the hSIRT1 structures with different ligands bound suggests that the N-terminal SBD undergoes an upward movement along the conformational reaction coordinate, although the exact location of the SBD is likely influenced by crystal packing. A potential mechanism for STAC activation can thus be inferred, namely the concerted motions of an upward movement of the SBD and domain closure of the catalytic core to couple the STAC binding and the substrate binding. Biophysical characterization using FP and site-directed mutagenesis using full-length hSIRT1 are fully consistent with the structural observation of the mini-hSIRT1/STAC complex in support of this model of STAC binding and activation. To our knowledge, the structures of the mini-hSIRT1/STAC complexes reported here represent only the second example of a synthetic allosteric activator bound to an enzyme besides glucokinase (Grimsby, J. et al. (2005) Science 301, 370). In summary, the results presented here provide unambiguous visual and functional proof of direct allosteric activation of hSIRT1 by small molecules with peptide substrates and provide a basis for further elucidation of the mechanism of hSIRT1 activation by STACs, and potentially also by endogenous regulators of hSIRT1.

Example 94. Protein Cloning, Expression, and Purification

Mini-hSIRT1 constructs were cloned into a modified pET21b vector (Novagen). The protein was expressed in *E. coli* BL21-Gold (DE3) cells (Stratagene) as an N-terminal fusion to a hexahistidine affinity tag with integrated TEV protease site. A single colony was inoculated in LB media containing 100 μg/ml ampicillin at 37° C., 250 rpm until the A600 reached 0.3. The culture was then transferred to 16° C., 250 rpm until the A600 reached 0.6. Isopropyl 1-thio-β-D-galactopyranoside (IPTG) was added to a final concentration of 0.2 mM, and expression was continued at 16° C., 250 rpm overnight. Cells were collected by centrifugation, and the pellet was resuspended in lysis buffer (25 mM HEPES, pH 7.5, 200 mM NaCl, 5% glycerol, and 5 mM 2-mercaptoethanol) and sonicated to break the cells. Supernatant was separated from cell debris by centrifugation at 10,000×g for 40 min at 4° C. and loaded onto a Ni-NTA column (Qiagen) that equilibrated with the buffer containing 25 mM HEPES, pH 7.5, 200 mM NaCl, 5% glycerol, 5 mM 2-mercaptoethanol, and 20 mM imidazole. The column was washed with 5 column volumes of the buffer containing 25 mM HEPES, pH 7.5, 200 mM NaCl, 5% glycerol, 5 mM 2-mercaptoethanol, and 50 mM imidazole, and eluted with the buffer containing 25 mM HEPES, pH 7.5, 200 mM NaCl, 5% glycerol, 5 mM 2-mercaptoethanol, and 250 mM imidazole. The eluted protein was dialyzed in lysis buffer and digested with TEV protease (Invitrogen) to remove the N-terminal His tag at 4° C. overnight. The protein was loaded on a second Ni-NTA column equilibrated with lysis buffer. The untagged protein was eluted by the buffer containing 25 mM HEPES, pH 7.5, 200 mM NaCl, 5% glycerol, 5 mM 2-mercaptoethanol, and 5 mM imidazole. The purified protein was dialyzed against the dialyzing buffer containing 20 mM Tris-HCl, pH 8.0, 250 mM NaCl, 5% glycerol, and 10 mM DTT, and concentrated. The protein was further purified by a S200 column (GE Healthcare) to 95% purity as assessed by SDS-PAGE analysis stained by Coomassie Brilliant Blue R-250 and concentrated to 10-15 mg/ml in the dialyzing buffer.

Human hsirt1 180-230 were cloned into a modified pET21b vector (Novagen) between BamHI and XhoI, which places expression under the control of the T7-lacO promoter. The protein was expressed in *E. coli* BL21-Gold (DE3) cells (Stratagene) as an N-terminal fusion to a hexahistidine affinity tag with integrated TEV protease site. A single colony was inoculated in 100 ml LB media containing 100 ug/ml ampicillin at 37° C., 250 rpm for overnight. Then 20 ml LB media was inoculated to 1 L M9 media which contained $^{15}NH_4Cl$ and Incubate them at 37° C. on an orbital shaker (200 rpm) until OD600 was about 0.8. The culture was then transferred to 16° C., 250 rpm until the A600 reached 1.0. Isopropyl 1-thio-β-D-galactopyranoside was added to a final concentration of 0.3 mM, and expression was continued at 16° C., 200 rpm overnight. Cells were collected by centrifugation, and the pellet was resuspended in lysis buffer (50 mM Hepes, 200 mM NaCl, 5% glycerol, 5 mM β-ME, pH 7.5) and sonicated to open the cells. Supernatant was separated from cell debris by centrifugation at 10,000×g for 40 min at 4° C. and loaded onto a Ni-NTA column (Qiagen) that equilibrated with the buffer containing 50 mM Hepes, 200 mM NaCl, 5% glycerol, 5 mM β-ME, pH 7.5. The column was washed with 20 column volumes of the buffer containing 50 mM Hepes, 200 mM NaCl, 5% glycerol, 5 m MB-ME and 20 mM imidazole, pH 7.5 and then eluted with the buffer containing 50 mM Hepes, 200 mM NaCl, 5% glycerol, 5 mM β-ME and 250 mM imidazole, pH 7.5. The eluted protein was dialyzed in lysis buffer and digested with TEV protease (Invitrogen) to remove the N-terminal His tag at 4° C. overnight. The protein was loaded on a second Ni-NTA column equilibrated with lysis buffer. The untagged protein was eluted by the buffer containing 50 mM Hepes, 200 mM NaCl, 5% glycerol, 5 mM β-ME and 10 mM imidazole, pH 7.5. The purified protein was concentrated and further purified by a S200 column (GE Healthcare) to get 95% purity as assessed by SDS-PAGE analysis stained by Coomassie Brilliant Blue R-250 and concentrated to 10 mg/ml in the 50 mM HEPES, 50 mM NaCl, 0.5 mM TCEP, pH 6.5.

Example 95. Full-Length SIRT1 Production

Full-length human SIRT1 (hSIRT1) proteins were expressed with a C-terminal His$_6$ tag and purified as described in Hubbard. et al. (2013) Science 339, 1216, except for Q222A, and I223R SIRT1 which were purified using an ÄKTAxpress™ (GE Lifesciences). Each cell paste was resuspended in buffer A (50 mM Tris-HCl pH 7.5, 250 mM NaCl, 25 mM imidazole, and 0.1 mM TCEP) with 1,000 U Benzonase nuclease (Sigma Aldrich) supplemented with cOmplete, EDTA-free Protease Inhibitor Cocktail Tablets (Roche) on ice. Cells were disrupted by pulse sonication with 50% on and 50% off for 12 minutes total at 40 W. Insoluble debris was removed by centrifugation. Clarified supernatant was directly loaded onto a 1 mL HisTrap FF Crude column (GE Lifesciences). After washing with buffer A, SIRT1 was eluted with buffer B (50 mM Tris-HCl pH 7.5, 250 mM NaCl, 500 mM imidazole and 0.1 mM TCEP). Protein was further purified by size exclusion chromatography in buffer C (50 mM Tris-HCl pH 7.5, 300 mM NaCl, 0.1 mM TCEP) using a Hi-load Superdex 200 16/60 column (GE Lifesciences). Enzyme concentrations were determined by Bradford assay using BSA as a standard. Final protein purity was assessed by gel densitometry. Proteins were confirmed by LC/MS. All proteins were greater than 90% pure except V224A and T219A (80%) and E230A (85%).

Example 96. SIRT1 Deacetylation Reactions

SIRT1 deacetylation reactions were performed in reaction buffer (50 mM HEPES-NaOH, pH 7.5, 150 mM NaCl, 1 mM DTT, and 1% DMSO) at 25° C. monitoring either nicotinamide production using the continuous PNC1/GDH coupled assay (Smith, B. C. et al. (2009) Anal Biochem 394, 101) or O-acetyl ADP ribose (OAcADPr) production by mass spectrometry (Hubbard. et al. (2013) Science 339, 1216). Final concentrations of the PNC1/GDH coupling system components used were 20 units/mL bovine GDH (Sigma-Aldrich), 1 uM yeast PNC1, 3.4 mM α-ketoglutarate, and 220 μM NADH or NADPH. An extinction coefficient of 6.22 mM$^{-1}$ cm$^{-1}$ and a pathlength of 0.81 cm was used to convert the absorbance at 340 nm to product concentration for the 150 uL reactions used. Assays monitoring OAcADPr production were performed in reaction buffer with 0.05% BSA and time points were taken by quenching the deacetylation reaction with a stop solution which gave a final concentration of 1% formic acid and 5 mM nicotinamide. Quenched reactions were diluted 5-fold with 1:1 acetonitrile:methanol and spun at 5,000×g for 10 minutes to precipitate protein before being analyzed with an Agilent RapidFire 200 High-Throughput Mass Spectrometry System (Agilent, Wakefield, Mass.) coupled to an ABSciex API 4000 mass spectrometer fitted with an electrospray ionization source. The p53-based Ac-p53(W5) (Ac-RHKK$^{Ac}$W-NH$_2$) and FOXO-3a 21-mer (Ac-SADDSP-SQLSK$^{Ac}$WPGSPTSRSS-NH$_2$) peptides were obtained from Biopeptide, Inc. Deacetylation assays used the Ac-p53 (W5) substrate unless otherwise noted.

Substrate $K_M$ determinations were performed by varying one substrate concentration at a fixed, saturating concentration of the second substrate. SIRT1 activation and inhibition assays were run in reaction buffer with 0.05% BSA at 25° C. and analyzed using the OAcADPr assay. Enzyme and compound were pre-incubated for 20 minutes before addition of substrates. For the activation screen of full-length hSIRT1, a structurally diverse set of 246 compounds was tested in duplicate at a final concentration of 25 μM each. In order to be sensitive to $K_M$-modulating activators, substrate concentrations of approximately one-tenth their $K_M$ values were used (see Table 5). The dose-dependence of five compounds was tested and the fold-activation data were described by Eq. 1

$$\frac{v_x}{v_o} = b + \frac{RX_{max} - b}{1 + \frac{EC_{50}}{[X]_o}} \quad \text{(Eq.1)}$$

where $v_x/v_o$ is the ratio of the reaction rate in the presence ($v_x$) versus absence ($v_o$) of activator (X), $RV_{max}$ is the relative velocity at infinite activator concentration, $EC_{50}$ is the concentration of activator required to produce one-half $RV_{max}$ and b is the minimum value of $v_x/v_o$.

TABLE 5

Inhibition of wild-type and mutant full-length hSIRT1

| | IC$_{50}$ (μM)$^a$ | | |
| --- | --- | --- | --- |
| hSIRT1 | EX-527 | TFA-p53 7-mer$^b$ | NAM |
| wild-type | 0.140 ± 0.020 | 0.680 ± 0.070 | 92 ± 6 |
| T219A | 0.310 ± 0.040 | 0.490 ± 0.020 | 53 ± 4 |
| Q222A | 0.110 ± 0.010 | 0.630 ± 0.050 | 53 ± 5 |
| I223A | 0.180 ± 0.020 | 0.540 ± 0.150 | 108 ± 10 |
| V224A | 0.140 ± 0.010 | 0.860 ± 0.080 | 64 ± 3 |
| N226A | 0.190 ± 0.020 | 0.350 ± 0.040 | 100 ± 9 |
| I227A | 0.220 ± 0.020 | 0.940 ± 0.060 | 92 ± 4 |
| E230K | 0.150 ± 0.020 | 1.6 ± 0.3 | 54 ± 3 |
| E230A | 0.100 ± 0.030 | 1.3 ± 0.4 | 60 ± 3 |
| E230Q | 0.240 ± 0.020 | 0.860 ± 0.060 | 56 ± 3 |
| I223R | 0.210 ± 0.020 | 0.660 ± 0.060 | 87 ± 6 |

$^a$Data from OAcADPr assay using the Ac-p53(W5) substrate.
$^b$TFA-p53 peptide sequence: Ac-RHKK(TFA)L-Nle-F-NH$_2$.

Example 97. Protein Crystallization, Data Collection and Structure Determination The crystals of mini-hSIRT1/1 binary complex were obtained by hanging drop vapor diffusion method at 18° C. The drop was composed of 1 μl of protein/compound mixture and 1 μl crystallization buffer of 0.2 M Magnesium chloride, 0.1 M Tris pH 8.5, and 16% w/v PEG 4000. The crystals of mini-hSIRT1/1/2 were obtained by hanging drop vapor diffusion method at 18° C. The drop was composed of 1 μl of protein/compound mixture and 1 μl crystallization buffer of 0.55 M Sodium chloride, 0.1 M MES pH 6.5, and 20% w/v PEG 4000. The crystals of mini-hSIRT1/1/p53-7mer/carbaNAD complex were obtained by hanging drop vapor diffusion method at 18° C. The drop was composed of 1 ul of the protein/substrate mixture and 1 ul of the crystallization buffer of 5% v/v Tacsimate, pH 0.00.1 M HEPES pH 7.0 and 10% w/v PEG 5000 MME. The crystals of mini-hSIRT1(E230K)/1/2 were obtained by hanging drop vapor diffusion method at 18° C. The drop was composed of 1 µl of protein/compound mixture and 1 µl crystallization buffer of 0.2 M Lithium Sulfate, 0.1 M Bis-Tris pH 6.5, 29% w/v PEG 3350.

The crystals were cryo-protected in mother liquor containing 20% glycerol before being flash-frozen in liquid nitrogen. Diffraction data were collected at SSRF BL17U1, APS 21-ID-D or APS 21-ID-G beamlines and processed using the Xia2 program (Winter, G. (2010) J Appl Crystallogr 43, 186). The molecular replacement software Phaser (McCoy, A. J. et al. (2007) J Appl Crystallogr 40, 658) was used to solve the structure with a search model containing residues 242-494 based on the homolog model of SIRT3 (PDB code: 3GLU). Iterative structure refinement and model building were performed between Refmac5 (Murshudov, A. A. et al. (1997) Acta Crystallogr D Biol Crystallogr 53, 240) of the CCP4 package ((1994) Acta Crystallogr D Biol Crystallogr 50, 760) and Coot et al. (2004) Acta Crystallogr D Biol Crystallogr 60, 2126. Detailed information regarding the diffraction data, refinement, and structure statistics is listed in Table 3.

Example 98. Nuclear Magnetic Resonance (NMR) Spectroscopy

The $^1H,^{15}N$ HSQC NMR experiments were carried out at 25° C. on a Bruker AVANCE III 600 MHz NMR Spectrometer with cryoprobe using samples containing approximately 200 µM $^{15}N$-labeled SIRT1(180-230) in the presence or absence of 400 µM 1. All NMR data were processed with NMRPipe (Delaglio, F. et al. (1995) J Biomol NMR 6, 277) and analyzed with NMRView (Johnson, et al. (1994) J Biomol NMR 4, 603).

Example 99. Size Exclusion Chromatography (SEC) Assay

The assays were performed with a Superdex 75 10/300 GL column (GE healthcare) injecting 100 µL samples containing 10 µM mini-hSIRT1 in the absence or presence of 100 µM STAC, dissolved in 50 mM HEPES-NaOH, pH 7.5, 150 mM NaCl, and 0.5 mM TCEP. Binding reactions were incubated for 1 h at RT before injection into the column.

Example 100. Fluorescence Polarization (FP) Assay

FP experiments were carried out in 20 µL assay buffer (50 mM HEPES-NaOH, pH 7.5, 150 mM NaCl, and 1 mM DTT) at 25° C. The 384-well plates were read on PHERAstar FS with excitation and emission wavelengths at 502 nm and 533 nm, respectively. For probe binding, increasing concentrations of SIRT1 were added into 10 nM probe 3. The Binding isotherm was described by Eq. 2. For competitive binding mode, increasing concentrations of competitors were added into the mixture of 10 nM 3 and 0.3 µM SIRT1 wild-type or E230K mutant in the absence or presence or 15 µM Ac-p53(W5). The competition data were described by Eq. 3. The conversion of $IC_{50}$ to $K_i$ was described by Eq. 4, where $K_d$ is the binding affinity of 3 to SIRT1, $F_0$ is the fraction of probe bound B/(B+F) and $L_0$ is the concentration of probe 3.

TABLE 3

Data Processing and Refinement Statistics

| | Mini-SIRT1/1 | Mini-SIRT1/1/2 | Mini-SIRT1 (E230K)/1/2 | Mini-SIRT1/1/p53 7-mer/CarbaNAD |
|---|---|---|---|---|
| Data Collection | | | | |
| Resolution (Å)* | 45.67-3.10 (3.18-3.10) | 39.98-2.73 (2.81-2.73) | 40.17-3.22 (3.30-3.22) | 91.36-2.74 (2.81-2.74) |
| Space group | $I2_12_12_1$ | P6322 | P6322 | I4122 |
| Unit-cell parameters | | | | |
| a (Å) | 99.19 | 122.15 | 122.72 | 94.51 |
| b (Å) | 111.64 | 122.15 | 122.72 | 94.51 |
| c (Å) | 132.52 | 104.92 | 105.88 | 356.84 |
| α (°) | 90.00 | 90.00 | 90.00 | 90.00 |
| β (°) | 90.00 | 90.00 | 90.00 | 90.00 |
| γ (°) | 90.00 | 120.00 | 120.00 | 90.00 |
| Completeness (%)* | 99.5 (99.8) | 99.9 (100.0) | 99.9 (99.9) | 99.5 (99.4) |
| Redundancy* | 4.8 (4.9) | 17.6 (18.2) | 17.4 (18.4) | 9.6 (9.9) |
| Average I/σI* | 17.4 (2.0) | 38.8 (4.0) | 38.1 (4.4) | 20.7 (3.3) |
| Rmerge (%)* | 6.7 (78.1) | 5.3 (80.3) | 6.2 (80.6) | 8.2 (82.9) |
| Refinement | | | | |
| Resolution (Å)* | 45.71-3.10 (3.18-3.10) | 40.01-2.74 (2.81-2.73) | 40.17-3.22 (3.30-3.22) | 91.36-2.74 (2.81-2.74) |
| $R_{work}$ (%)* | 21.2 (33.9) | 22.4 (33.6) | 22.8 (28.8) | 18.3 (31.8) |
| $R_{free}$ (%)* | 25.0 (37.6) | 27.1 (43.8) | 25.1 (40.3) | 23.5 (36.7) |
| R.M.S.D in bond lengths (Å) | 0.005 | 0.007 | 0.006 | 0.010 |
| R.M.S.D in bond angles (°) | 1.089 | 1.14 | 1.079 | 1.538 |
| Mean B factors (Å2) | 100.1 | 78.6 | 104.5 | 67.3 |

*Values in parentheses are for the highest-resolution shell $$y = \frac{x(B-A)}{x + K_d} + Nx + A \quad \text{(Eq.2)}$$

$$y = \frac{1}{1 + \frac{x}{IC_{50}}} \quad \text{(Eq.3)}$$

$$K_i = \frac{IC_{50}}{\frac{1}{1-F_0} + \frac{L_0(2-F_0)}{2K_d}} - K_d \frac{F_0}{2-F_0} \quad \text{(Eq.4)}$$

Example 101. Hydrogen-Deuterium Exchange Mass Spectrometry (HDX-MS)

On-Exchange Experiment of SIRT1.

H/D-exchange reactions followed by pepsin digestion, desalting, HPLC separation, and MS analysis were carried out using a fully automated system, described in detail elsewhere (Hamuro, Y. et al. (2003) J Biomol Techniques: JBT 14, 171). Particular to this set of experiments, on-exchange reactions were initiated by mixing 20 µL of a SIRT1 stock solution (0.77 mg/mL SIRT1, ±3.88 mM Ac-p53(W5), ±192 µM ligand, in 1.9% DMSO) and 20 µL of 100 mM phosphate, pH read 7.0 in D2O. The 50% $D_2O$ mixture was incubated at 0° C. for 15, 50, 150, 500, 1,500, or 5,000 s. For SIRT1 (229-516), on-exchange reactions were initiated by mixing 4 µL of a SIRT1 stock solution (1.36 mg/mL SIRT1 (229-516), ±1.67 mM Trp-25mer) and 36 µL of 200 mM phosphate, pH read 7.0 in D2O. The 90% $D_2O$ mixture was incubated at 0° C. for 15, 50, 150, 500, 1,500, or 5,000 s. Addition of 20 µL of 1.6 M guanidine hydrochloride (GuHCl), 0.8% formic acid, pH 2.3, quenched the on-exchange reaction immediately prior to being analyzed.

Example 102. General Protein Process for Standard HDX Sample

The quenched solution was passed through a pepsin column (104 µL bed volume) filled with porcine pepsin (Sigma, St Louis, Mo.) immobilized on Poros 20 AL media (Life Technologies, Carlsbad, Calif.) per the manufacturer's instructions, with 0.05% aqueous TFA (200 µL/min) for 2 min. The digested fragments were temporarily collected onto a reverse phase trap column (4 µL bed volume) and desalted. The peptide fragments were then eluted from the trap column and separated by a C18 column (BioBacis-18; Thermo Scientific, San Jose, Calif.) with a linear gradient of 13% solvent B to 40% solvent B over 23 min (solvent A, 0.05% TFA in water; solvent B, 95% acetonitrile, 5% buffer A; flow rate 10 µL/min). Mass spectrometric analyses were carried out using a LTQ OrbiTrap XL mass spectrometer (Thermo Fisher Scientific, San Jose, Calif.) with capillary temperature at 200° C.

Example 103. Digestion/Separation Optimization and Non-Deuterated Experiment of SIRT1

Prior to H/D-exchange experiment, digestion and separation conditions were optimized to yield high sequence coverage of SIRT1 by peptic fragments with high resolution under non-deuterated conditions. In this step, a mixture of 20 µL, of 0.77 mg/mL (9.2 µM) SIRT1 and 20 µL of $H_2O$ was quenched by the addition of 20 µL of various acidic buffers. For SIRT1 (229-516), a mixture of 4 µL of a SIRT1 stock solution (1.36 mg/mL SIRT1 (229-516), ±1.67 mM Trp-25mer) and 36 µL of $H_2O$ was quenched by the addition of 20 µL of various acidic buffers. The quenched mixtures were subjected to aforementioned general protein process. The non-deuterated peptic fragments were identified by Sequest in Proteome Discoverer 1.1 (Thermo Fisher Scientific, San Jose, Calif.).

Example 104. Fully Deuterated Experiment of SIRT1

The fully deuterated sample was prepared by incubating a mixture of 45 µL of 0.77 mg/mL (9.2 µM) SIRT1 with 45 µL of 100 mM TCEP in $D_2O$, pH 2.5 at 60° C. for 3 h. For SIRT1 (229-516), the fully deuterated sample was prepared by incubating a mixture of 9 µL of 1.36 mg/mL (41.7 µM) SIRT1 (229-516) with 81 µL of 100 mM TCEP in $D_2O$, pH 2.5 at 60° C. for 3 h. After incubation, the sample was kept at 0° C. before being quenched identically to an on-exchanged solution and subjected to the general protein process.

Example 105. Determination of Deuteration Level of Each Peptide after On-Exchange Reaction The centroids of peptide isotopic envelopes were measured using the in-house-program developed in collaboration with Sierra Analytics (Modesto, Calif.). Corrections for back-exchange during the protein processing step were made employing the following standard equation Eq. 5 (Zhang, Z. et al. (1993) Protein Science 2, 522):

$$\text{Deuteration Level (\%)} = \frac{m(P) - m(N)}{m(F) - m(N)} \times 100 \quad \text{(Eq.5)}$$

where m(P), m(N), and m(F) are the centroid value of partially deuterated (on-exchanged) peptide, non-deuterated peptide, and fully deuterated peptide, respectively.

Example 106. Biological Activity

Mass spectrometry based assays were used to identify modulators of SIRT1 activity. The TAMRA based assay utilized a peptide having 20 amino acid residues as follows: Ac-EE-K(biotin)-GQSTSSHSK(Ac)NleSTEG-K(5TMR)-EE-$NH_2$ (SEQ ID NO: 1), wherein K(Ac) is an acetylated lysine residue and Nle is a norleucine. The peptide was labeled with the fluorophore 5TMR (excitation 540 nm/emission 580 nm) at the C-terminus. The sequence of the peptide substrate was based on p53 with several modifications. In addition, the methionine residue naturally present in the sequence was replaced with the norleucine because the methionine may be susceptible to oxidation during synthesis and purification. The Trp based assay utilized a peptide having an amino acid residues as follows: Ac-R-H-K-K(Ac)-W-NH2 (SEQ ID NO: 2).

The TAMRA based mass spectrometry assay was conducted as follows: 0.5 µM peptide substrate and 120 µM $\beta NAD^+$ was incubated with 10 nM SIRT1 for 25 minutes at 25° C. in a reaction buffer (50 mM Tris-acetate pH 8, 137 mM NaCl, 2.7 mM KCl, 1 mM $MgCl_2$, 5 mM DTT, 0.05% BSA). The SIRT1 protein was obtained by cloning the SirT1 gene into a T7-promoter containing vector, which was then transformed and expressed in BL21(DE3) bacterial cells. Test compound was added at varying concentrations to this reaction mixture and the resulting reactions were monitored.

After the 25 minute incubation with SIRT1, 10 μL of 10% formic acid was added to stop the reaction. The resulting reactions were sealed and frozen for later mass spec analysis. Determination of the amount of deacetylated substrate peptide formed (or, alternatively, the amount of 0-acetyl-ADP-ribose (OAADPR) generated) by the sirtuin-mediated NAD-dependent deacetylation reaction allowed for the precise measurement of relative SIRT1 activity in the presence of varying concentrations of the test compound versus control reactions lacking the test compound.

The Trp mass spectrometry assay was conducted as follows. 0.5 μM peptide substrate and 120 μM βNAD+ were incubated with 10 nM SIRT1 for 25 minutes at 25° C. in a reaction buffer (50 mM HEPES pH 7.5, 1500 mM NaCl, 1 mM DTT, 0.05% BSA). The SIRT1 protein was obtained by cloning the SirT1 gene into a T7-promoter containing vector, which was then expressed in BL21(DE3) bacterial cells and purified as described in further detail below. Test compound was added at varying concentrations to this reaction mixture and the resulting reactions were monitored. After the 25 minute incubation with SIRT1, 10 μL of 10% formic acid was added to stop the reaction. The resulting reactions were sealed and frozen for later mass spec analysis. The relative SIRT1 activity was then determined by measuring the amount of 0-acetyl-ADP-ribose (OAADPR) formed (or, alternatively, the amount of deacetylated Trp peptide generated) by the NAD-dependent sirtuin deacetylation reaction in the presence of varying concentrations of the test compound versus control reactions lacking the test compound. The degree to which the test agent activated deacetylation by SIRT1 was expressed as $EC_{1.5}$ (i.e., the concentration of compound required to increase SIRT1 activity by 50% over the control lacking test compound), and Percent Maximum Activation (i.e., the maximum activity relative to control (100%) obtained for the test compound).

A control for inhibition of sirtuin activity was conducted by adding 1 μL of 500 mM nicotinamide as a negative control at the start of the reaction (e.g., permits determination of maximum sirtuin inhibition). A control for activation of sirtuin activity was conducted using 10 nM of sirtuin protein, with 1 μL of DMSO in place of compound, to determine the amount of deacetylation of the substrate at a given time point within the linear range of the assay. This time point was the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl] phosphine (TCEP), 10 μM $ZnCl_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Iris-HCl, 2 mM TCEP) overnight. The protein was aliquoted and frozen at −80° C. until further use.

Sirtuin-modulating compounds of Formula (I) that activated SIRT1 were identified using the assay described above and are shown below in Table 1. The $EC_{1.5}$ values represent the concentration of test compounds that result in 150% activation of SIRT1. The $EC_{1.5}$ values for the activating compounds of Formula (I) are represented by A ($EC_{1.5}$<1 μM), B ($EC_{1.5}$ 1-25 μM), C ($EC_{1.5}$>25 μM). The percent maximum fold activation is represented by A (Fold activation ≥150%) or B (Fold Activation <150%). "NT" means not tested; "ND" means not determinable. The compound numbering in the table starts with compound number 10, and parenthetic numbering (#) corresponding to the STAC numbering system in FIG. 4 and Examples 90-106 (i.e., compound no. 68 is also STAC 1, so it is shown as 68(1), and further STACs: 546(3), 444(4), 314(5), 816(7), 76(8), and 81(9)).

TABLE 1

Compounds of Formula (I).

| Compound No. | [M + H]+$_{[calc]}$ | Structure | Tryp AVG $EC_{1.5}$ (μM) | Tryp % Fold Act |
|---|---|---|---|---|
| 10 | 427 | 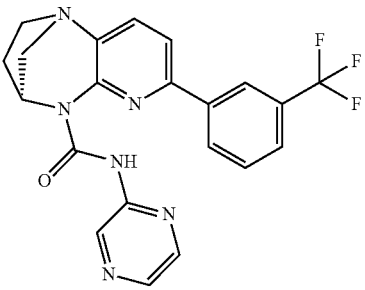 [SMILES: O=C(Nc1cnccn1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 11 | 427 | 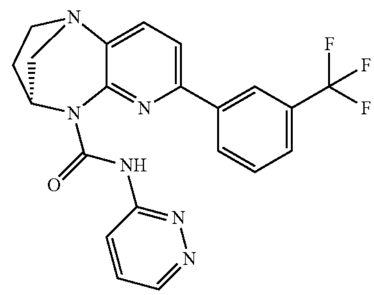 [SMILES: O=C(Nc1cccnn1)N1c2nc(-c3cccc(C(F)(F)F)c3)ccc2N2CC[C@H]1C2] | A | A |
| 12 | 427 | 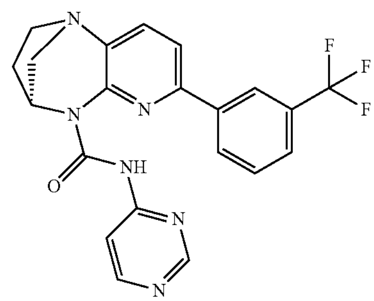 [SMILES: O=C(Nc1ccncn1)N1c2nc(-c3cccc(C(F)(F)F)c3)ccc2N2CC[C@H]1C2] | A | A |
| 13 | 454 | 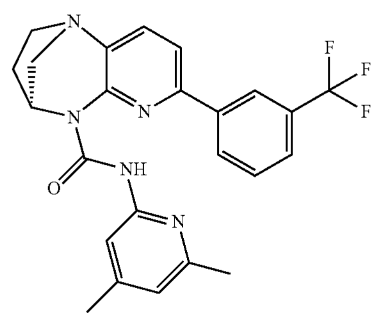 [SMILES: Cc1cc(C)nc(NC(=O)N2c3nc(-c4cccc(C(F)(F)F)c4)ccc3N3CC[C@H]2C3)c1] | B | A |
| 14 | 440 | 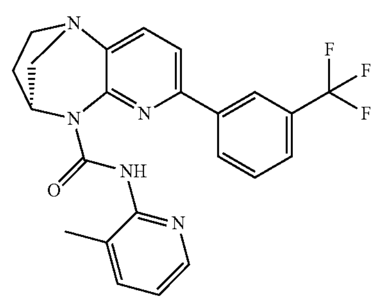 [SMILES: Cc1cccnc1NC(=O)N1c2nc(-c3cccc(C(F)(F)F)c3)ccc2N2CC[C@H]1C2] | C | B |
| 15 | 444 | 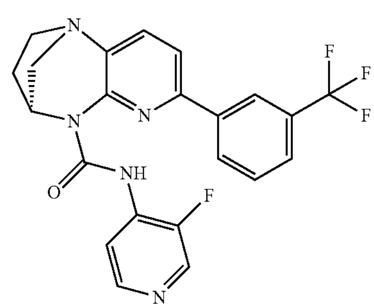 [SMILES: O=C(Nc1ccncc1F)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 16 | 513 | 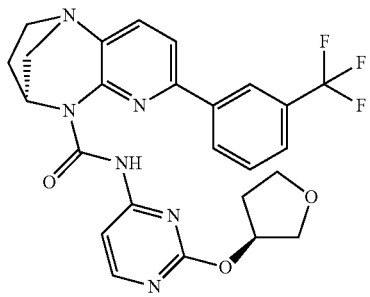 [SMILES: O=C(Nc1ccnc(O[C@H]2CCOC2)n1)N1c2nc(-c3cccc(C(F)(F)F)c3)ccc2N2CC[C@H]1C2] | A | A |
| 17 | 426 | 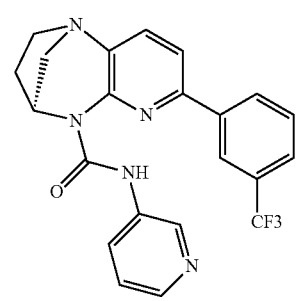 [SMILES: O=C(Nc1cccnc1)N1c2nc(-c3cccc(C(F)(F)F)c3)ccc2N2CC[C@H]1C2] | A | A |
| 18 | 517 | 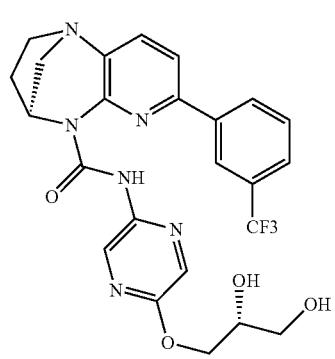 [SMILES: O=C(Nc1cnc(OC[C@H](O)CO)cn1)N1c2nc(-c3cccc(C(F)(F)F)c3)ccc2N2CC[C@H]1C2] | A | A |
| 19 | 392 | 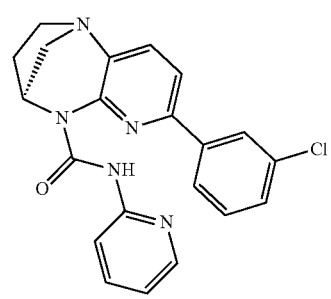 [SMILES: O=C(Nc1ccccn1)N1c2nc(-c3cccc(Cl)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 20 | 444 | 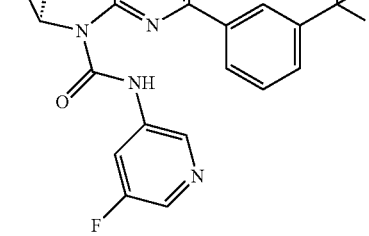 | A | A |
| 21 | 440 | 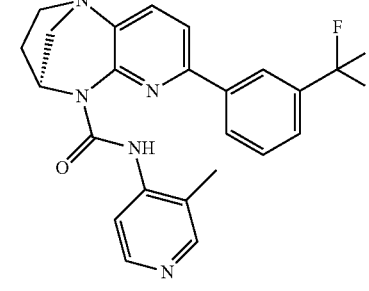 | B | A |
| 22 | 487 | 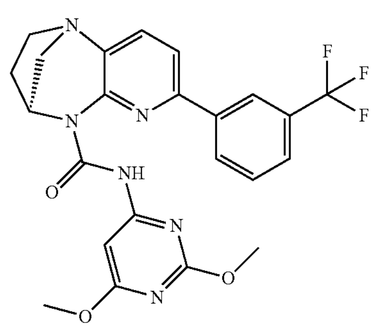 [SMILES: COc1cc(NC(=O)N2c3nc(-c4cccc(C(F)(F)F)c4)ccc3N3CC[C@H]2C3)nc(OC)n1] | B | A |
| 23 | 427 | 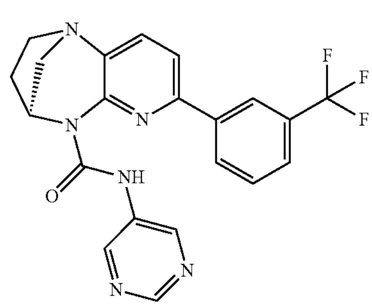 [SMILES: O=C(Nc1cncnc1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 24 | 410 | 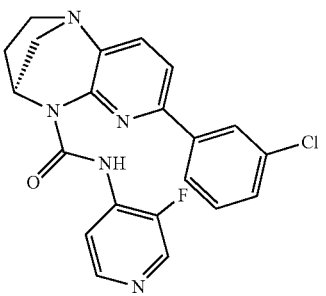 [SMILES: O=C(Nc1ccncc1F)N1c2nc(-c3cccc(Cl)c3)ccc2N2CC[C@H]1C2] | B | A |
| 25 | 429 | 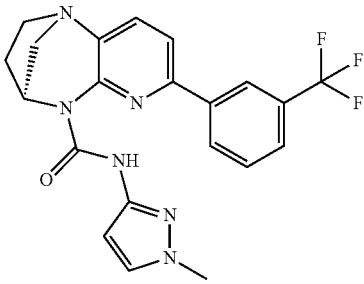 [SMILES: Cn1ccc(NC(=O)N2c3nc(-c4cccc(C(F)(F)F)c4)ccc3N3CC[C@H]2C3)n1] | A | A |
| 26 | 531 | 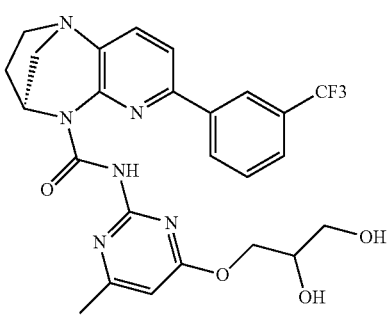 [SMILES: Cc1cc(OCC(O)CO)nc(NC(=O)N2c3nc(-c4cccc(C(F)(F)F)c4)ccc3N3CC[C@H]2C3)n1] | B | A |
| 27 | 441 | 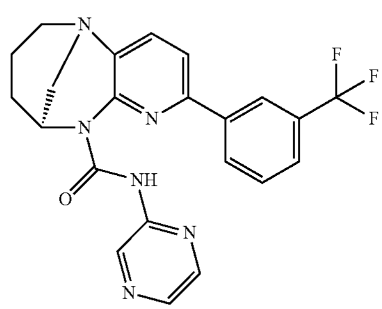 [SMILES: O=C(Nc1cnccn1)N1c2nc(-c3cccc(C(F)(F)F)c3)ccc2N2CCC[C@H]1C2] | A | A |
| 28 | 441 | 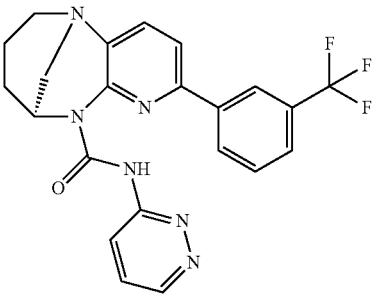 [SMILES: O=C(Nc1cccnn1)N1c2nc(-c3cccc(C(F)(F)F)c3)ccc2N2CCC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 29 | 441 | 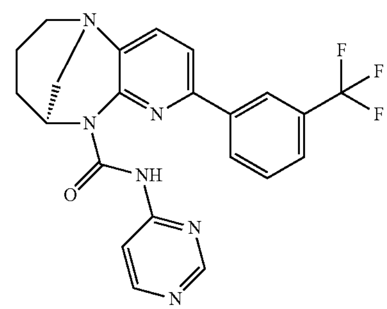 [SMILES: O=C(Nc1ccncn1)N1c2nc(-c3cccc(C(F)(F)F)c3)ccc2N2CCC[C@H]1C2] | A | A |
| 30 | 468 | 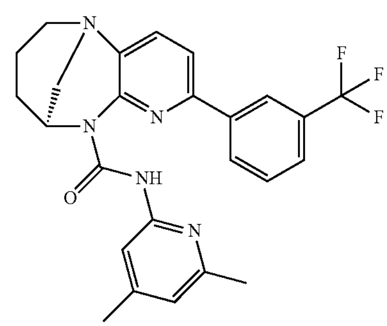 [SMILES: Cc1cc(C)nc(NC(=O)N2c3nc(-c4cccc(C(F)(F)F)c4)ccc3N3CCC[C@H]2C3)c1] | A | A |
| 31 | 501 | 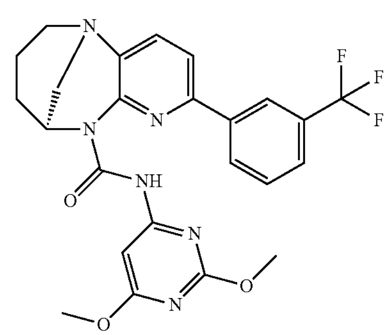 [SMILES: COc1cc(NC(=O)N2c3nc(-c4cccc(C(F)(F)F)c4)ccc3N3CCC[C@H]2C3)nc(OC)n1] | A | A |
| 32 | 471 | 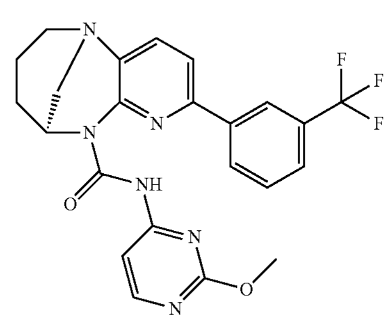 [SMILES: COc1nccc(NC(=O)N2c3nc(-c4cccc(C(F)(F)F)c4)ccc3N3CCC[C@H]2C3)n1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 33 | 474 | 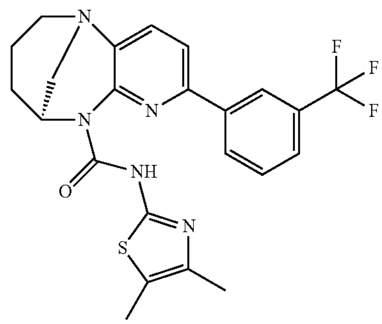 [SMILES: Cc1nc(NC(=O)N2c3nc(-c4cccc(C(F)(F)F)c4)ccc3N3CCC[C@H]2C3)sc1C] | A | A |
| 34 | 457 | 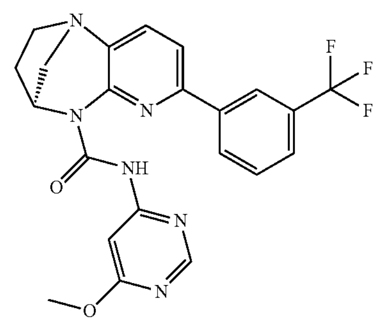 [SMILES: COc1cc(NC(=O)N2c3nc(-c4cccc(C(F)(F)F)c4)ccc3N3CC[C@H]2C3)ncn1] | A | A |
| 35 | 454 | 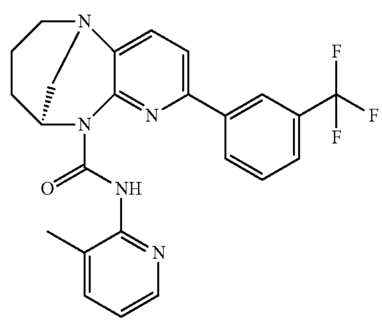 [SMILES: Cc1cccnc1NC(=O)N1c2nc(-c3cccc(C(F)(F)F)c3)ccc2N2CCC[C@H]1C2] | B | A |
| 36 | 443 | 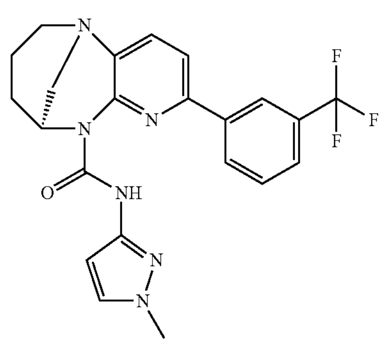 [SMILES: Cn1ccc(NC(=O)N2c3nc(-c4cccc(C(F)(F)F)c4)ccc3N3CCC[C@H]2C3)n1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 37 | 454 | 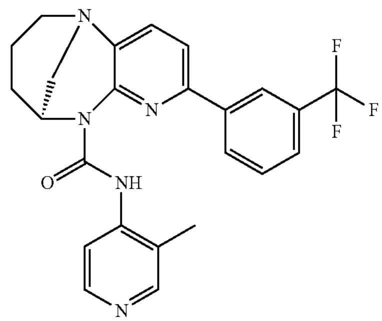 [SMILES: Cc1cnccc1NC(=O)N1c2nc(-c3cccc(C(F)(F)F)c3)ccc2N2CCC[C@H]1C2] | B | A |
| 38 | 441 | 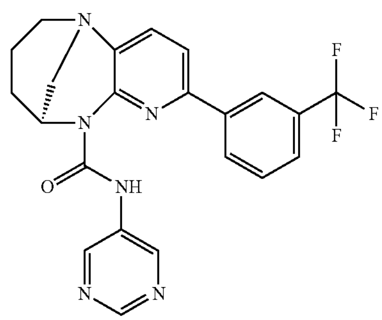 [SMILES: O=C(Nc1cncnc1)N1c2nc(-c3cccc(C(F)(F)F)c3)ccc2N2CCC[C@H]1C2] | A | A |
| 39 | 458 | 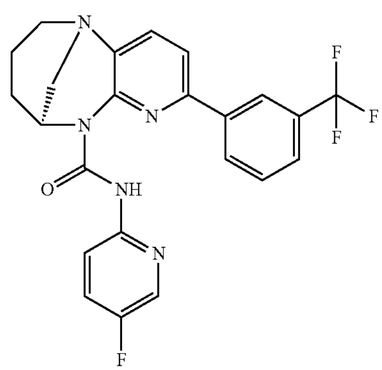 [SMILES: O=C(Nc1ccc(F)cn1)N1c2nc(-c3cccc(C(F)(F)F)c3)ccc2N2CCC[C@H]1C2] | A | A |
| 40 | 443 | 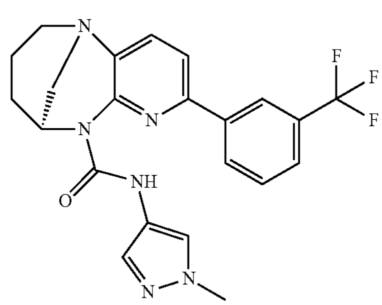 [SMILES: Cn1cc(NC(=O)N2c3nc(-c4cccc(C(F)(F)F)c4)ccc3N3CCC[C@H]2C3)cn1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 41 | 471 | 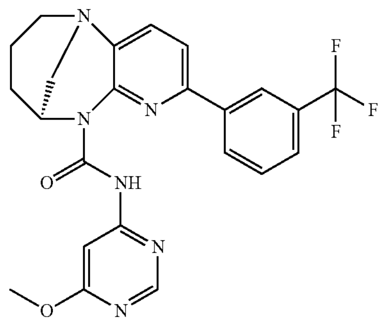 [SMILES: COc1cc(NC(=O)N2c3nc(-c4cccc(C(F)(F)F)c4)ccc3N3CCC[C@H]2C3)ncn1] | A | A |
| 42 | 458 | 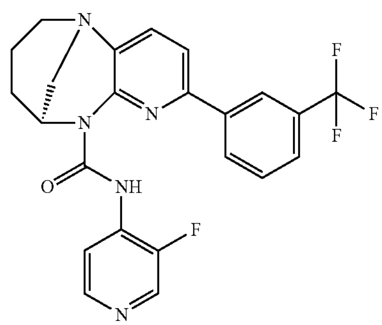 [SMILES: O=C(Nc1ccncc1F)N1c2nc(-c3cccc(C(F)(F)F)c3)ccc2N2CCC[C@H]1C2] | A | A |
| 43 | 410 | 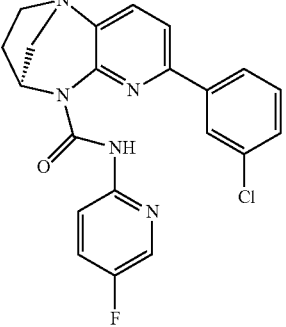 | B | A |
| 44 | 406 | 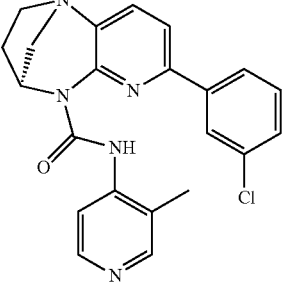 | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 45 | 458 | 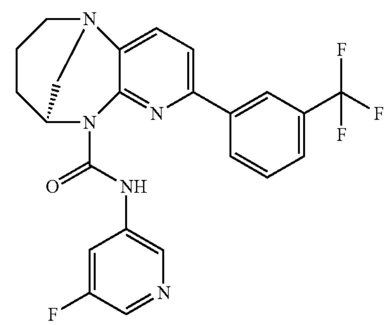 [SMILES: O=C(Nc1cncc(F)c1)N1c2nc(-c3cccc(C(F)(F)F)c3)ccc2N2CCC[C@H]1C2] | A | A |
| 46 | 444 | 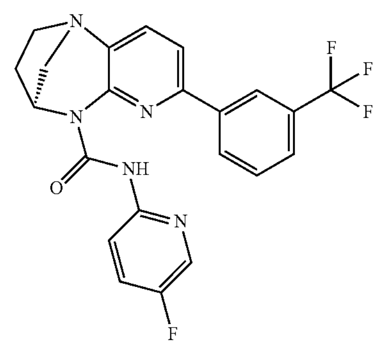 [SMILES: O=C(Nc1ccc(F)cn1)N1c2nc(-c3cccc(C(F)(F)F)c3)ccc2N2CC[C@H]1C2] | A | A |
| 47 | 457 | 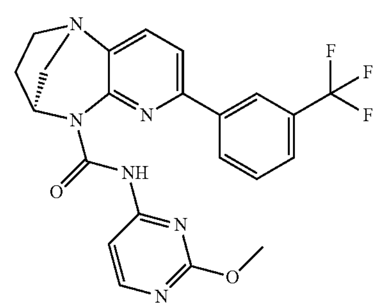 [SMILES: COc1nccc(NC(=O)N2c3nc(-c4cccc(C(F)(F)F)c4)ccc3N3CC[C@H]2C3)n1] | A | A |
| 48 | 460 | 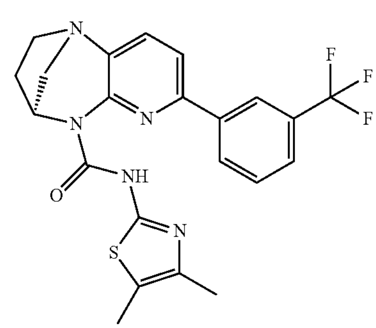 [SMILES: Cc1nc(NC(=O)N2c3nc(-c4cccc(C(F)(F)F)c4)ccc3N3CC[C@H]2C3)sc1C] | A | A |

225

226

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 49 | 429 | 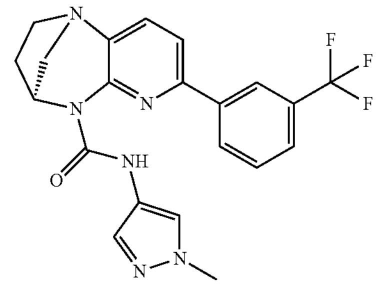 [SMILES: Cn1cc(NC(=O)N2c3nc(-c4cccc(C(F)(F)F)c4)ccc3N3CC[C@H]2C3)cn1] | A | A |
| 50 | 423 | 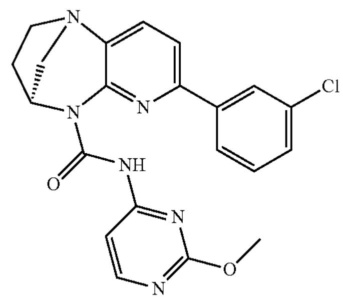 [SMILES: COc1nccc(NC(=O)N2c3nc(-c4cccc(Cl)c4)ccc3N3CC[C@H]2C3)n1] | B | A |
| 51 | 391 | 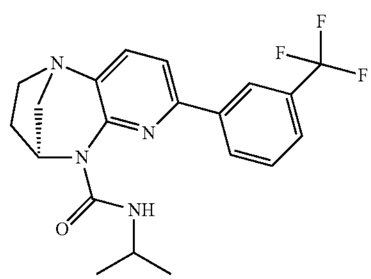 [SMILES: CC(C)NC(=O)N1c2nc(-c3cccc(C(F)(F)F)c3)ccc2N2CC[C@H]1C2] | B | A |
| 52 | 405 | 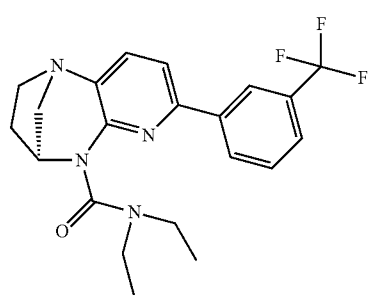 [SMILES: CCN(CC)C(=O)N1c2nc(-c3cccc(C(F)(F)F)c3)ccc2N2CC[C@H]1C2] | C | B |
| 53 | 516 | 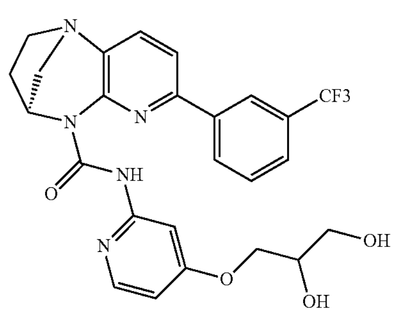 [SMILES: O=C(Nc1cc(OCC(O)CO)ccn1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 54 | 483 | 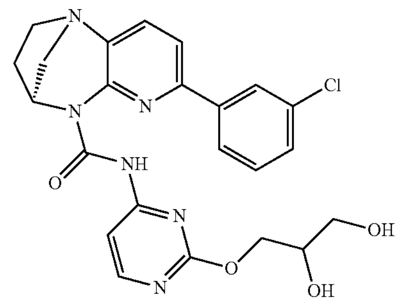 [SMILES: O=C(Nc1ccnc(OCC(O)CO)n1)N1c2nc(-c3cccc(Cl)c3)ccc2N2CC[C@H]1C2] | A | A |
| 55 | 497 | 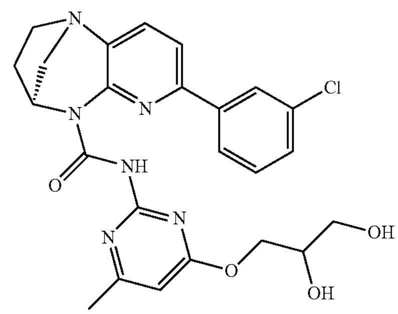 [SMILES: Cc1cc(OCC(O)CO)nc(NC(=O)N2c3nc(-c4cccc(Cl)c4)ccc3N3CC[C@H]2C3)n1] | B | A |
| 56 | 446 | 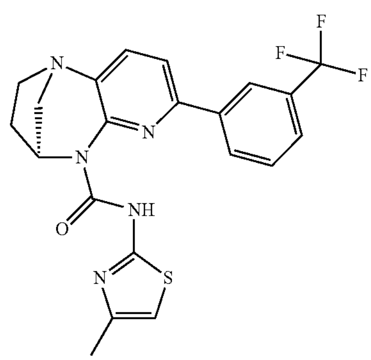 [SMILES: Cc1csc(NC(=O)N2c3nc(-c4cccc(C(F)(F)F)c4)ccc3N3CC[C@H]2C3)n1] | A | A |
| 57 | 376 | 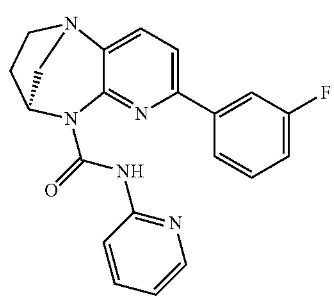 [SMILES: O=C(Nc1ccccn1)N1c2nc(-c3cccc(F)c3)ccc2N2CC[C@H]1C2] | A | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 58 | 377 | 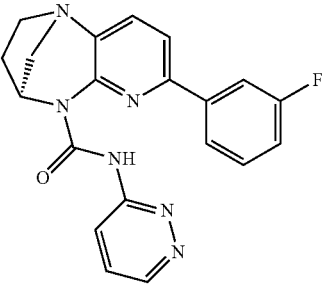 [SMILES: O=C(Nc1cccnn1)N1c2nc(-c3cccc(F)c3)ccc2N2CC[C@H]1C2] | B | A |
| 59 | 394 | 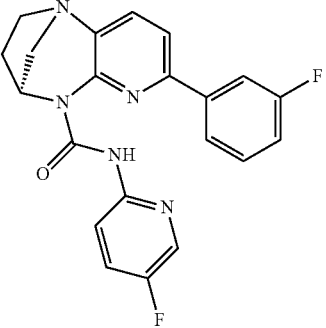 [SMILES: O=C(Nc1ccc(F)cn1)N1c2nc(-c3cccc(F)c3)ccc2N2CC[C@H]1C2] | A | A |
| 60 | 407 | 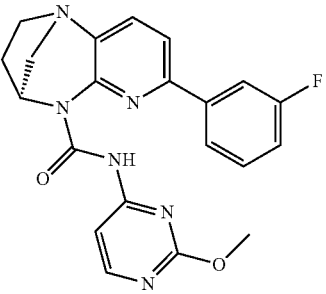 [SMILES: COc1nccc(NC(=O)N2c3nc(-c4cccc(F)c4)ccc3N3CC[C@H]2C3)n1] | B | A |
| 61 | 440 | 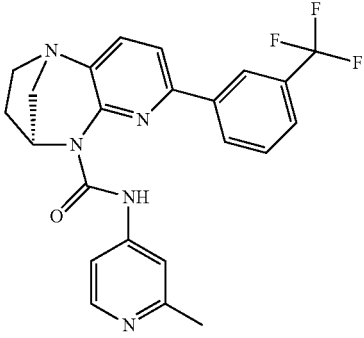 [SMILES: Cc1cc(NC(=O)N2c3nc(-c4cccc(C(F)(F)F)c4)ccc3N3CC[C@H]2C3)ccn1] | A | A |

TABLE 1-continued

Compounds of Formula (I).

| Compound No. | [M + H]+<sub>[calc]</sub> | Structure | Tryp AVG EC$_{1.5}$ (μM) | Tryp % Fold Act |
|---|---|---|---|---|
| 62 | 390 | 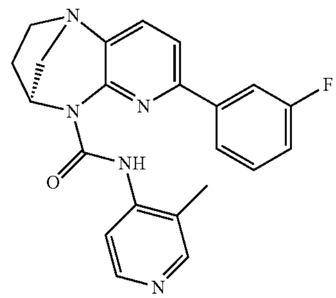 [SMILES: Cc1cnccc1NC(=O)N1c2nc(-c3cccc(F)c3)ccc2N2CC[C@H]1C2] | B | A |
| 63 | 483 | 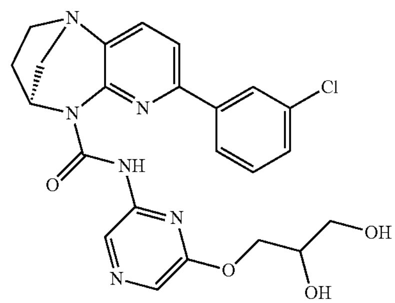 [SMILES: O=C(Nc1cncc(OCC(O)CO)n1)N1c2nc(-c3cccc(Cl)c3)ccc2N2CC[C@H]1C2] | A | A |
| 64 | 481 | 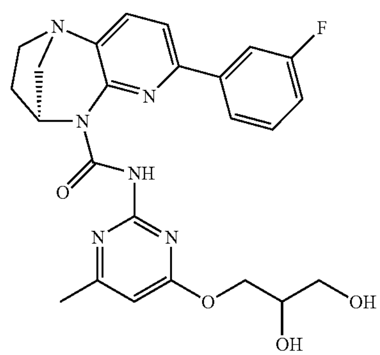 [SMILES: Cc1cc(OCC(O)CO)nc(NC(=O)N2c3nc(-c4cccc(F)c4)ccc3N3CC[C@H]2C3)n1] | B | A |
| 65 | 467 | 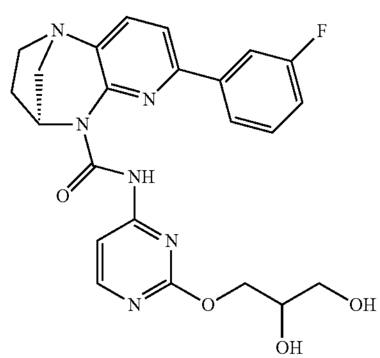 [SMILES: O=C(Nc1ccnc(OCC(O)CO)n1)N1c2nc(-c3cccc(F)c3)ccc2N2CC[C@H]1C2] | B | A |

TABLE 1-continued
Compounds of Formula (I).
| Compound No. | [M + H]+_[calc] | Structure | Tryp AVG EC_{1.5} (µM) | Tryp % Fold Act |
|---|---|---|---|---|
| 66 | 482 | 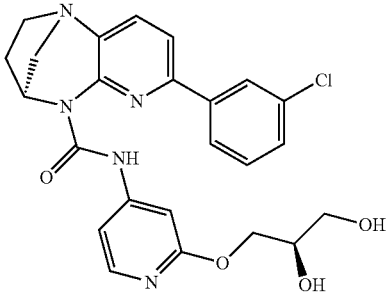 [SMILES: O=C(Nc1ccnc(OC[C@H](O)CO)c1)N1c2nc(-c3cccc(Cl)c3)ccc2N2CC[C@H]1C2] | A | A |
| 67 | 509 | 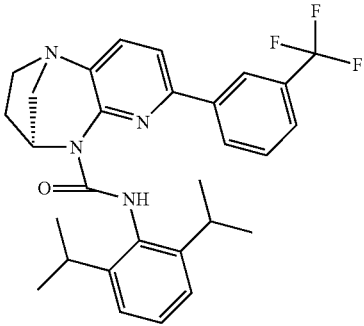 [SMILES: CC(C)c1cccc(C(C)C)c1NC(=O)N1c2nc(-c3cccc(C(F)(F)F)c3)ccc2N2CC[C@H]1C2] | C | B |
| 68 (1) | 492 | 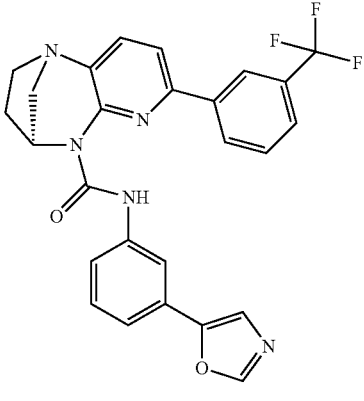 [SMILES: O=C(Nc1cccc(-c2cnco2)c1)N1c2nc(-c3cccc(C(F)(F)F)c3)ccc2N2CC[C@H]1C2] | A | A |
| 69 | 467 | 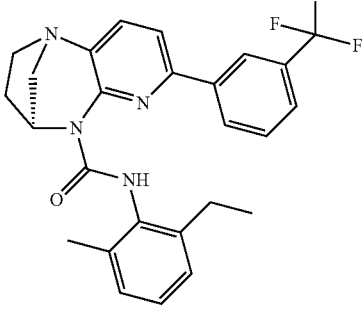 | C | B |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 70 | 481 | 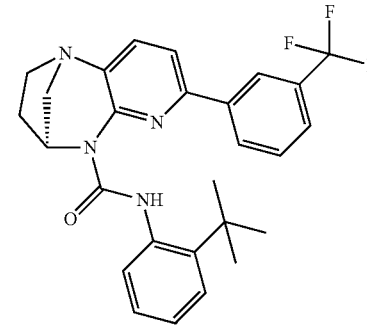 | C | B |
| 71 | 481 | 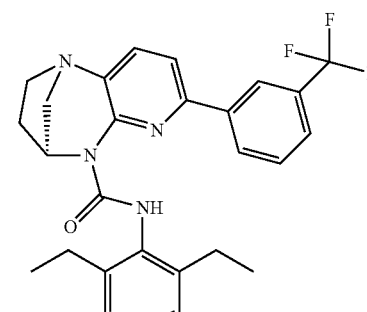 | C | B |
| 72 | 488 | 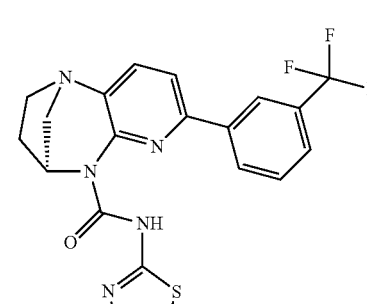 | B | A |
| 73 | 466 | 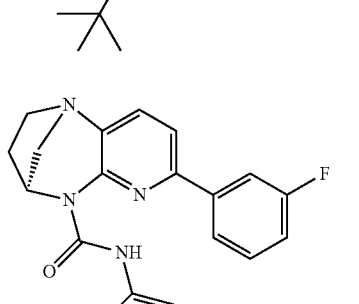 | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 74 | 394 | 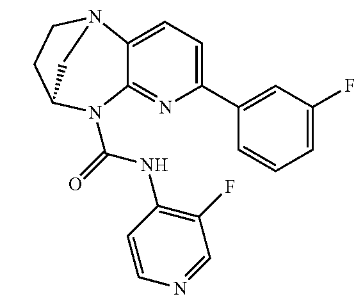 [SMILES: O=C(Nc1ccncc1F)N1c2nc(-c3cccc(F)c3)ccc2N2CC[C@H]1C2] | B | A |
| 75 | 488 | 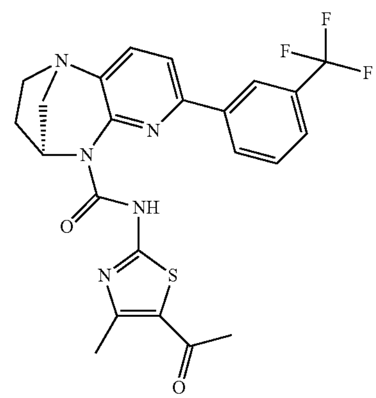 [SMILES: CC(=O)c1sc(NC(=O)N2c3nc(-c4cccc(C(F)(F)F)c4)ccc3N3CC[C@H]2C3)nc1C] | A | A |
| 76 (8) | 491 | 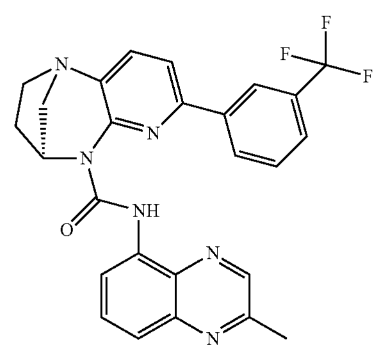 [SMILES: Cc1cnc2c(NC(=O)N3c4nc(-c5cccc(C(F)(F)F)c5)ccc4N4CC[C@H]3C4)cccc2n1] | A | A |
| 77 | 470 | 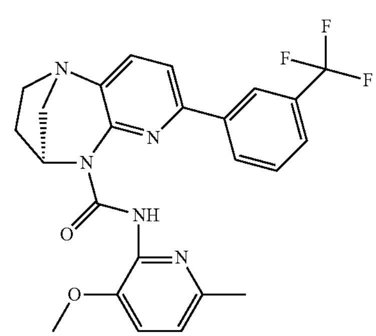 [SMILES: COc1ccc(C)nc1NC(=O)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 78 | 503 | 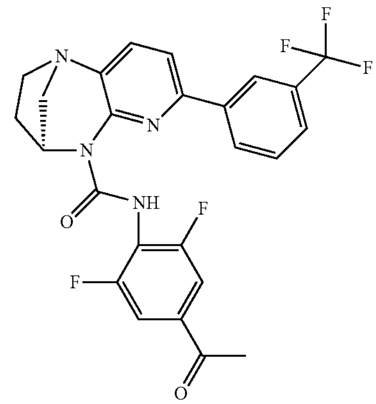 [SMILES: CC(=O)c1cc(F)c(NC(=O)N2c3nc(-c4cccc(C(F)(F)F)c4)ccc3N3CC[C@H]2C3)c(F)c1] | B | A |
| 79 | 517 | 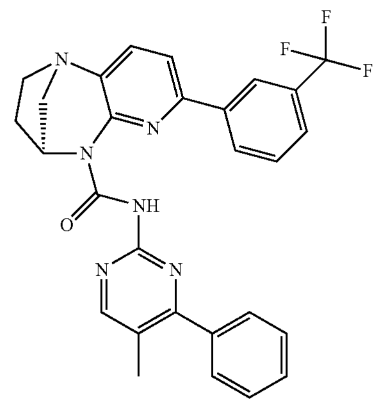 [SMILES: Cc1cnc(NC(=O)N2c3nc(-c4cccc(C(F)(F)F)c4)ccc3N3CC[C@H]2C3)nc1-c1ccccc1] | B | A |
| 80 | 486 | 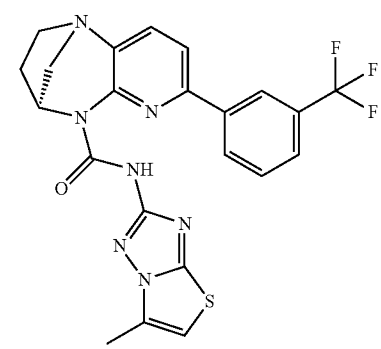 [SMILES: Cc1csc2nc(NC(=O)N3c4nc(-c5cccc(C(F)(F)F)c5)ccc4N4CC[C@H]3C4)nn12] | A | A |
| 81 (9) | 493 | 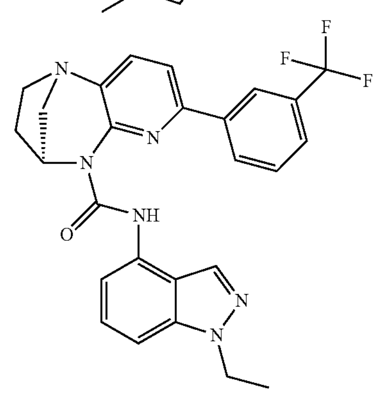 | A | A |

TABLE 1-continued

Compounds of Formula (I).

| Compound No. | [M + H]+[calc] | Structure | Tryp AVG EC$_{1.5}$ (µM) | Tryp % Fold Act |
|---|---|---|---|---|
| 82 | 443 | 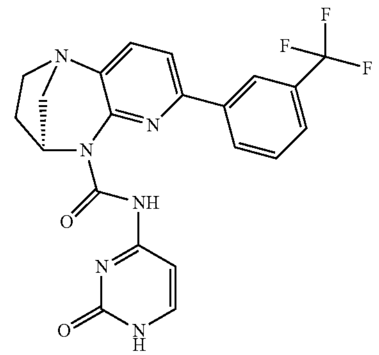 [SMILES: O=C(Nc1cc[nH]c(=O)n1)N1c2nc(-c3cccc(C(F)(F)F)c3)ccc2N2CC[C@H]1C2] | B | A |
| 83 | 477 | 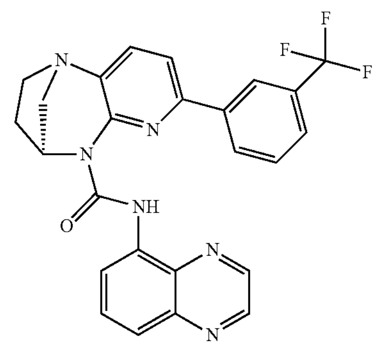 [SMILES: O=C(Nc1cccc2nccnc12)N1c2nc(-c3cccc(C(F)(F)F)c3)ccc2N2CC[C@H]1C2] | A | A |
| 84 | 490 | 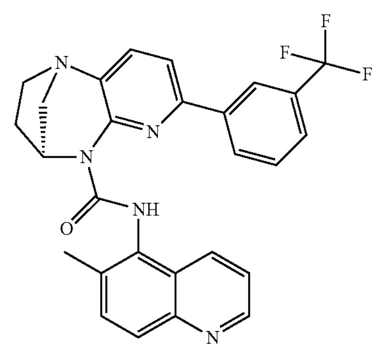 [SMILES: Cc1ccc2ncccc2c1NC(=O)N1c2nc(-c3cccc(C(F)(F)F)c3)ccc2N2CC[C@H]1C2] | C | B |
| 85 | 442 | 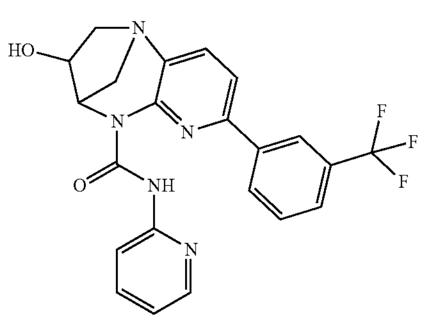 [SMILES: O=C(Nc1ccccn1)N1c2nc(-c3cccc(C(F)(F)F)c3)ccc2N2CC(O)C1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 86 | 491 | 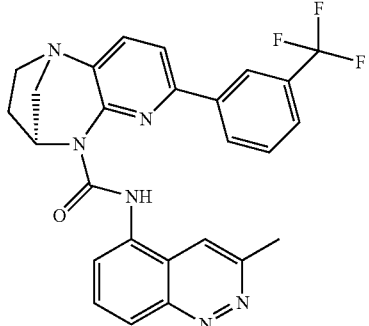 | A | A |
| 87 | 479 | 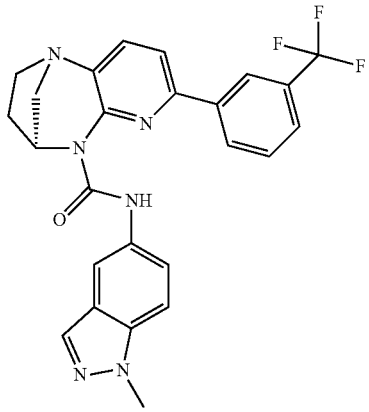 [SMILES: Cn1ncc2cc(NC(=O)N3c4nc(-c5cccc(C(F)(F)F)c5)ccc4N4CC[C@H]3C4)ccc21] | A | A |
| 90 | 482 | 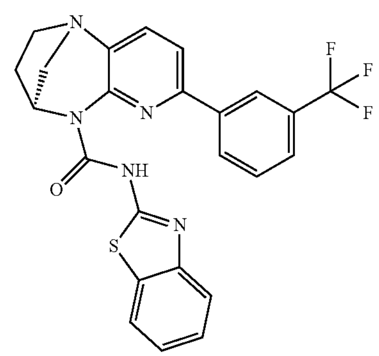 [SMILES: O=C(Nc1nc2ccccc2s1)N1c2nc(-c3cccc(C(F)(F)F)c3)ccc2N2CC[C@H]1C2] | A | A |
| 91 | 481 | 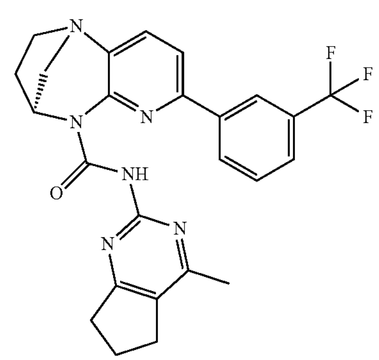 [SMILES: Cc1nc(NC(=O)N2c3nc(-c4cccc(C(F)(F)F)c4)ccc3N3CC[C@H]2C3)nc2c1CCC2] | B | A |

245
246
TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 92 | 443 | 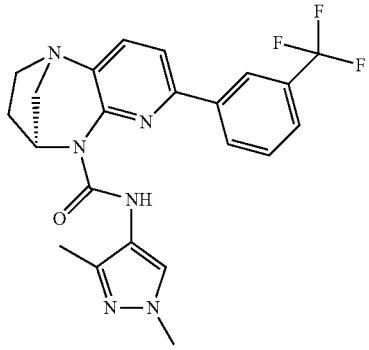 [SMILES: Cc1nn(C)cc1NC(=O)N1c2nc(-c3cccc(C(F)(F)F)c3)ccc2N2CC[C@H]1C2] | B | A |
| 93 | 481 | 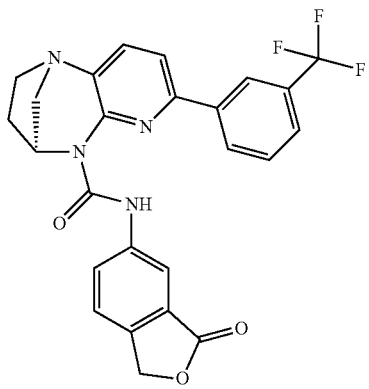 [SMILES: O=C1OCc2ccc(NC(=O)N3c4nc(-c5cccc(C(F)(F)F)c5)ccc4N4CC[C@H]3C4)cc21] | A | A |
| 94 | 509 | 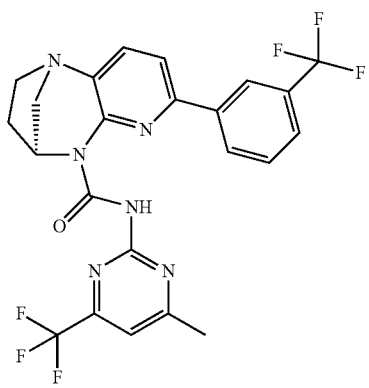 [SMILES: Cc1cc(C(F)(F)F)nc(NC(=O)N2c3nc(-c4cccc(C(F)(F)F)c4)ccc3N3CC[C@H]2C3)n1] | B | A |
| 95 | 497 | 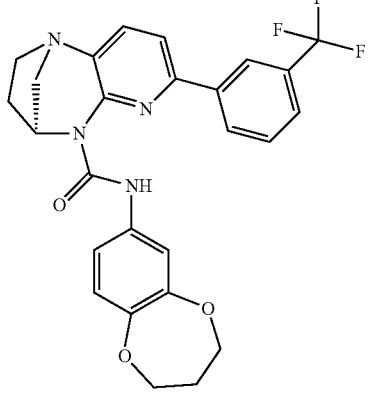 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 96 | 460 | 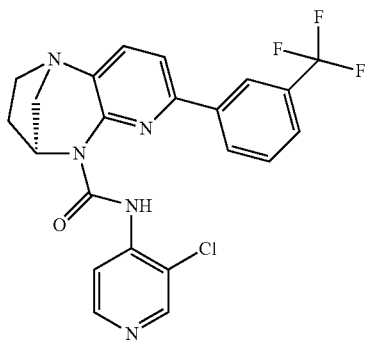 [SMILES: O=C(Nc1ccncc1Cl)N1c2nc(-c3cccc(C(F)(F)F)c3)ccc2N2CC[C@H]1C2] | B | A |
| 98 | 433 | 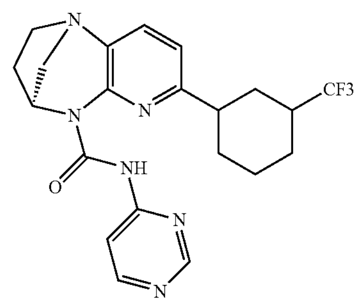 [SMILES: O=C(Nc1ccncn1)N1c2nc(C3CCCC(C(F)(F)F)C3)ccc2N2CC[C@H]1C2] | B | A |
| 99 | 432 | 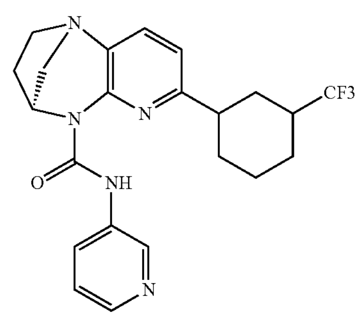 [SMILES: O=C(Nc1cccnc1)N1c2nc(C3CCCC(C(F)(F)F)C3)ccc2N2CC[C@H]1C2] | A | A |
| 100 | 446 | 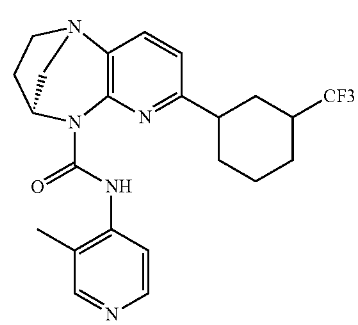 [SMILES: Cc1cnccc1NC(=O)N1c2nc(C3CCCC(C(F)(F)F)C3)ccc2N2CC[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 101 | 393 | 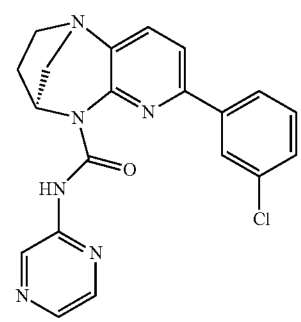 [SMILES: O=C(Nc1cnccn1)N1c2nc(-c3cccc(Cl)c3)ccc2N2CC[C@H]1C2] | A | A |
| 102 | 426 | 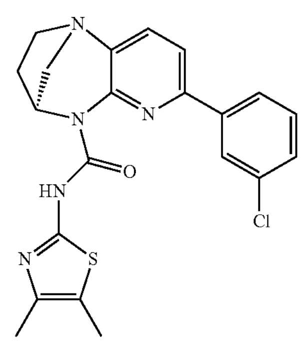 [SMILES: Cc1nc(NC(=O)N2c3nc(-c4cccc(Cl)c4)ccc3N3CC[C@H]2C3)sc1C] | A | A |
| 103 | 453 | 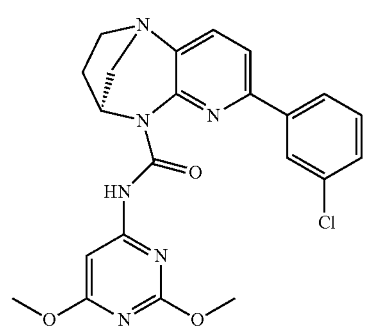 [SMILES: COc1cc(NC(=O)N2c3nc(-c4cccc(Cl)c4)ccc3N3CC[C@H]2C3)nc(OC)n1] | B | A |
| 104 | 423 | 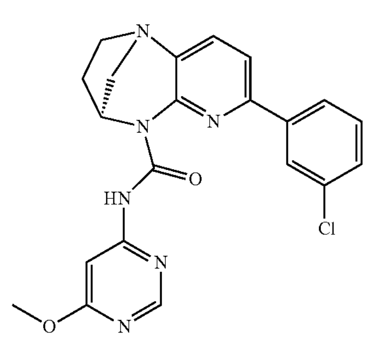 [SMILES: COc1cc(NC(=O)N2c3nc(-c4cccc(Cl)c4)ccc3N3CC[C@H]2C3)ncn1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 105 | 420 | 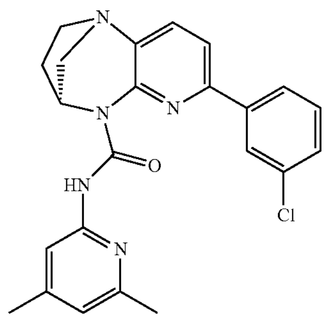 [SMILES: Cc1cc(C)nc(NC(=O)N2c3nc(-c4cccc(Cl)c4)ccc3N3CC[C@H]2C3)c1] | B | A |
| 106 | 406 | 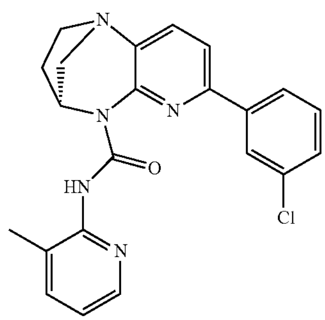 [SMILES: Cc1cccnc1NC(=O)N1c2nc(-c3cccc(Cl)c3)ccc2N2CC[C@H]1C2] | C | A |
| 107 | 392 | 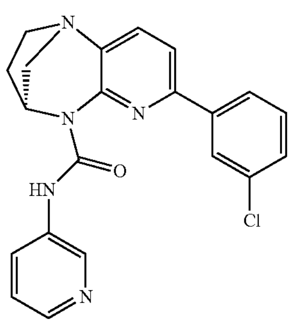 [SMILES: O=C(Nc1cccnc1)N1c2nc(-c3cccc(Cl)c3)ccc2N2CC[C@H]1C2] | A | A |
| 108 | 395 | 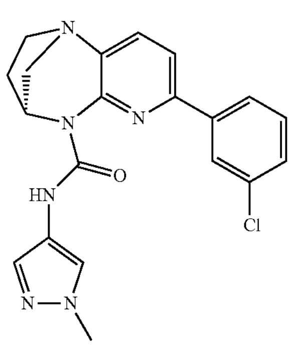 [SMILES: Cn1cc(NC(=O)N2c3nc(-c4cccc(Cl)c4)ccc3N3CC[C@H]2C3)cn1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 109 | 395 | 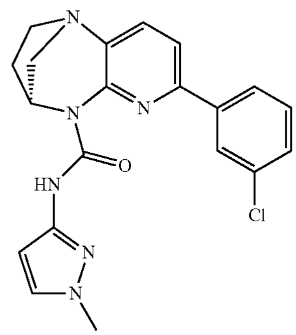 [SMILES: Cn1ccc(NC(=O)N2c3nc(-c4cccc(Cl)c4)ccc3N3CC[C@H]2C3)n1] | B | A |
| 110 | 393 | 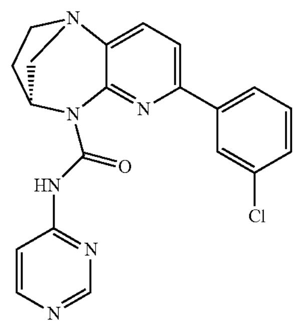 [SMILES: O=C(Nc1ccncn1)N1c2nc(-c3cccc(Cl)c3)ccc2N2CC[C@H]1C2] | A | A |
| 114 | 442 | 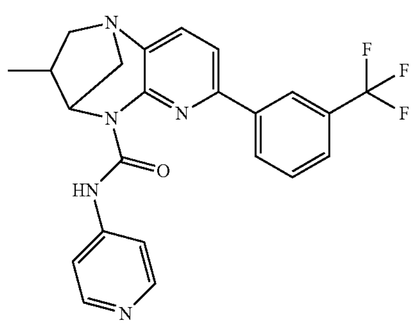 [SMILES: CC1CN2CC1N(C(=O)Nc1ccncc1)c1nc(-c3cccc(C(F)(F)F)c3)ccc12] | B | A |
| 118 | 445 | 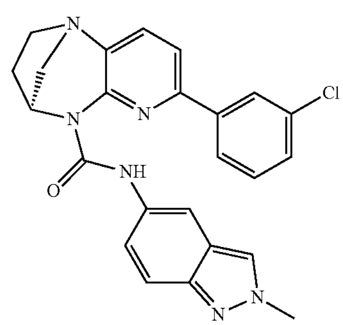 [SMILES: Cn1cc2cc(NC(=O)N3c4nc(-c5cccc(Cl)c5)ccc4N4CC[C@H]3C4)ccc2n1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 119 | 410 | 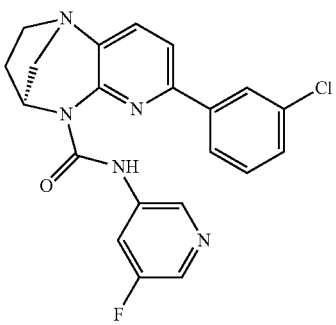 [SMILES: O=C(Nc1cncc(F)c1)N1c2nc(-c3cccc(Cl)c3)ccc2N2CC[C@H]1C2] | A | A |
| 120 | 393 | 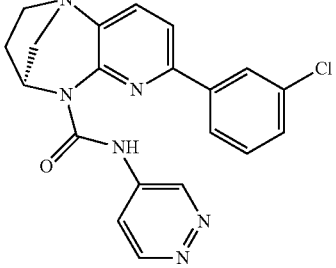 | A | A |
| 121 | 423 | 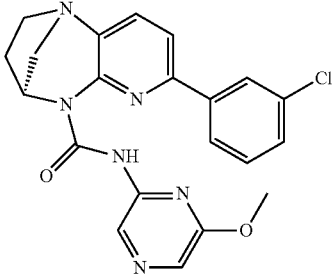 [SMILES: COc1cncc(NC(=O)N2c3nc(-c4cccc(Cl)c4)ccc3N3CC[C@H]2C3)n1] | A | A |
| 122 | 392 | 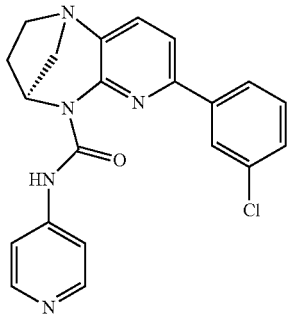 [SMILES: O=C(Nc1ccncc1)N1c2nc(-c3cccc(Cl)c3)ccc2N2CC[C@H]1C2] | A | A |

TABLE 1-continued
Compounds of Formula (I).
| Compound No. | [M + H]+[calc] | Structure | Tryp AVG EC1.5 (µM) | Tryp % Fold Act |
|---|---|---|---|---|
| 123 | 444 | 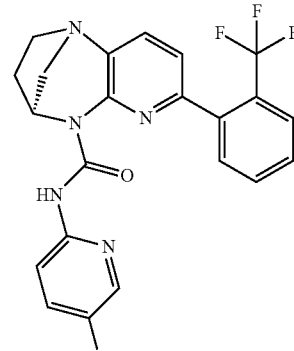 | C | B |
| 124 | 423 | 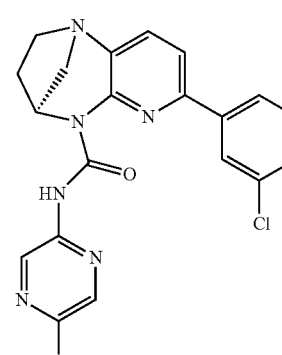 | B | A |
| 128 | 445 | 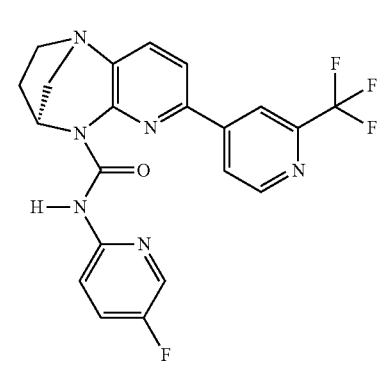 [SMILES: O=C(Nc1ccc(F)cn1)N1c2nc(-c3ccnc(C(F)(F)F)c3)ccc2N2CC[C@H]1C2] | A | A |
| 129 | 460 | 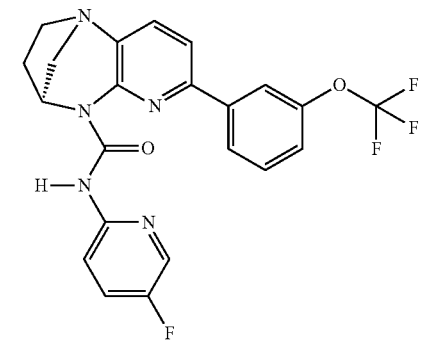 [SMILES: O=C(Nc1ccc(F)cn1)N1c2nc(-c3cccc(OC(F)(F)F)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 130 | 401 | 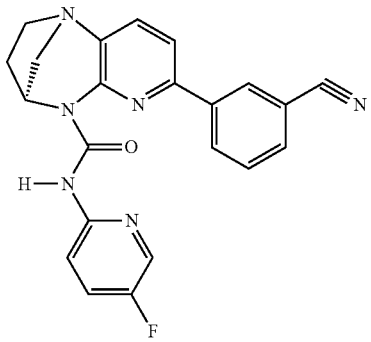 [SMILES: N#Cc1cccc(-c2ccc3c(n2)N(C(=O)Nc2ccc(F)cn2)[C@H]2CCN3C2)c1] | A | A |
| 131 | 445 | 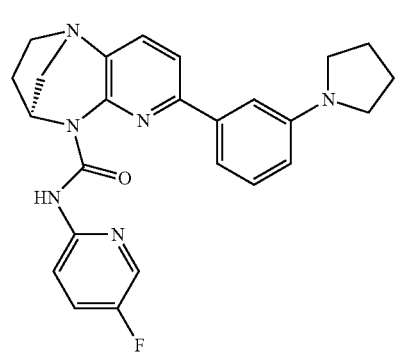 [SMILES: O=C(Nc1ccc(F)cn1)N1c2nc(-c3cccc(N4CCCC4)c3)ccc2N2CC[C@H]1C2] | B | A |
| 132 | 458 | 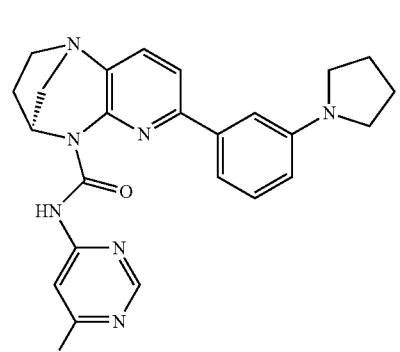 | B | A |
| 133 | 458 | 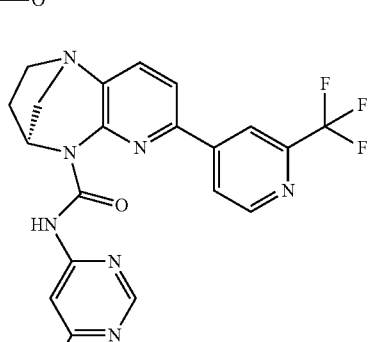 | A | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 134 | 457 | 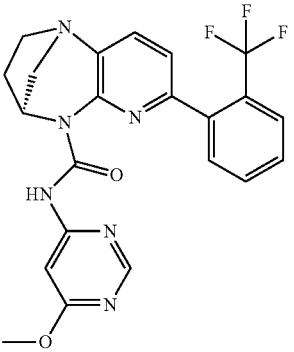 [SMILES: COc1cc(NC(=O)N2c3nc(-c4ccccc4C(F)(F)F)ccc3N3CC[C@H]2C3)ncn1] | C | B |
| 135 | 473 | 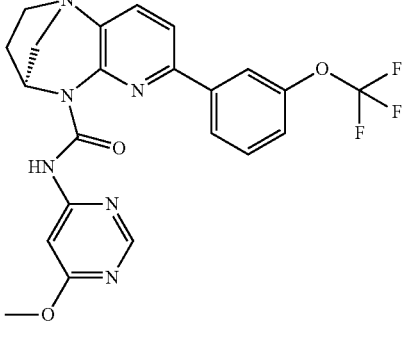 | A | A |
| 136 | 427 | 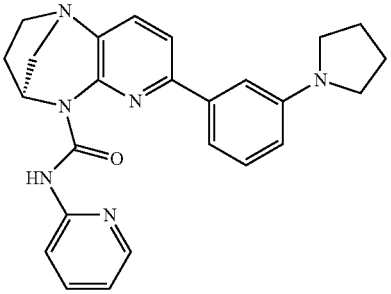 [SMILES: O=C(Nc1ccccn1)N1c2nc(-c3cccc(N4CCCC4)c3)ccc2N2CC[C@H]1C2] | A | A |
| 137 | 426 | 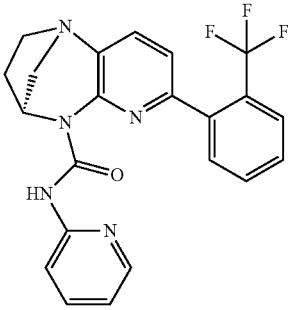 [SMILES: O=C(Nc1ccccn1)N1c2nc(-c3ccccc3C(F)(F)F)ccc2N2CC[C@H]1C2] | C | B |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 138 | 442 | 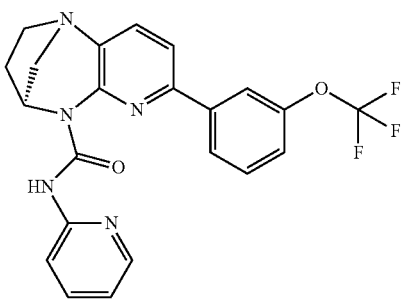 | A | A |
| 139 | 383 | 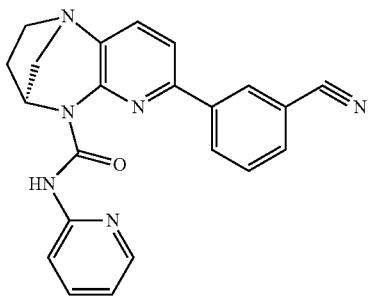 [SMILES: N#Cc1cccc(-c2ccc3c(n2)N(C(=O)Nc2ccccn2)[C@H]2CCN3C2)c1] | A | A |
| 140 | 414 | 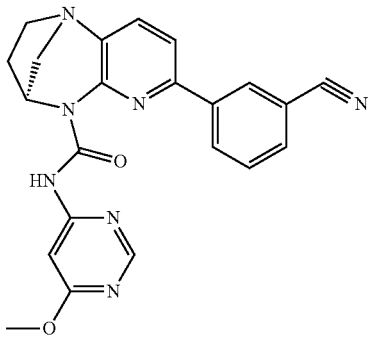 [SMILES: COc1cc(NC(=O)N2c3nc(-c4cccc(C#N)c4)ccc3N3CC[C@H]2C3)ncn1] | A | A |
| 141 | 424 | 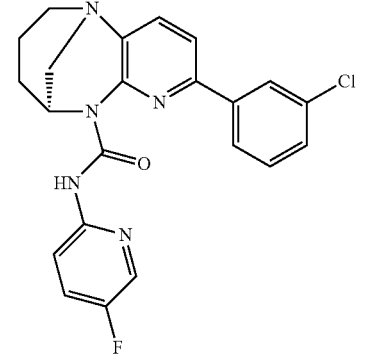 [SMILES: O=C(Nc1ccc(F)cn1)N1c2nc(-c3cccc(Cl)c3)ccc2N2CCC[C@H]1C2] | A | A |

TABLE 1-continued
Compounds of Formula (I).
| Compound No. | [M + H]+[calc] | Structure | Tryp AVG EC$_{1.5}$ (µM) | Tryp % Fold Act |
|---|---|---|---|---|
| 142 | 427 | 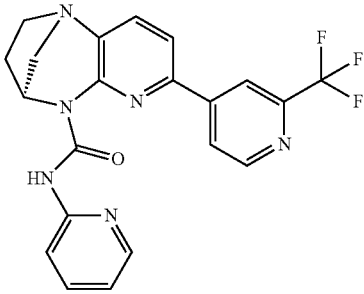 [SMILES: O=C(Nc1ccccn1)N1c2nc(-c3ccnc(C(F)(F)F)c3)ccc2N2CC[C@H]1C2] | A | A |
| 143 | 433 | 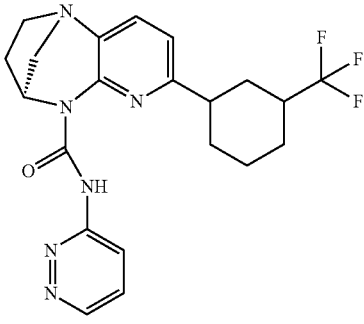 [SMILES: O=C(Nc1cccnn1)N1c2nc(C3CCCC(C(F)(F)F)C3)ccc2N2CC[C@H]1C2] | B | A |
| 144 | 450 | 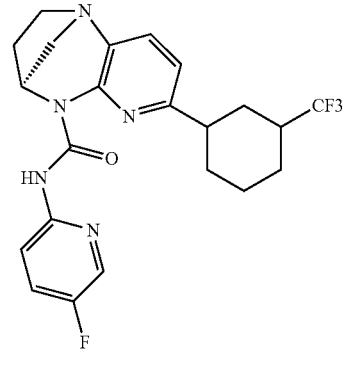 [SMILES: O=C(Nc1ccc(F)cn1)N1c2nc(C3CCCC(C(F)(F)F)C3)ccc2N2CC[C@H]1C2] | B | A |
| 145 | 450 | 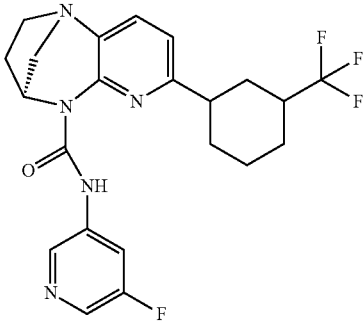 [SMILES: O=C(Nc1cncc(F)c1)N1c2nc(C3CCCC(C(F)(F)F)C3)ccc2N2CC[C@H]1C2] | A | A |

TABLE 1-continued

Compounds of Formula (I).

| Compound No. | [M + H]+[calc] | Structure | Tryp AVG EC$_{1.5}$ (µM) | Tryp % Fold Act |
|---|---|---|---|---|
| 146 | 466 | 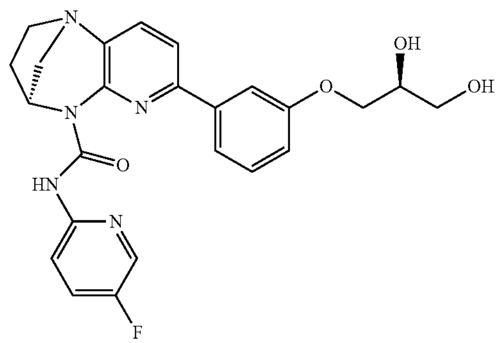 [SMILES: O=C(Nc1ccc(F)cn1)N1c2nc(-c3cccc(OC[C@@H](O)CO)c3)ccc2N2CC[C@H]1C2] | B | A |
| 147 | 401 | 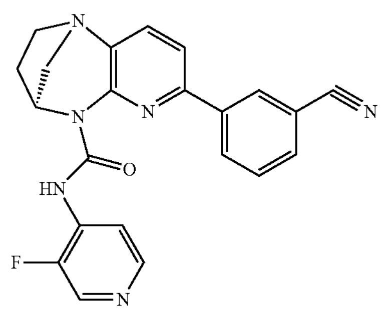 [SMILES: N#Cc1cccc(-c2ccc3c(n2)N(C(=O)Nc2ccncc2F)[C@H]2CCN3C2)c1] | B | A |
| 148 | 450 | 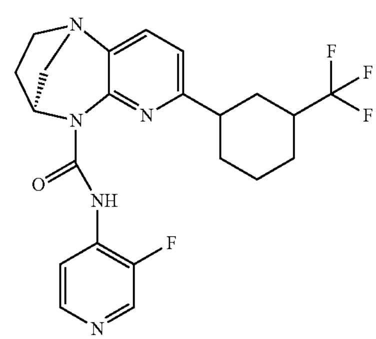 [SMILES: O=C(Nc1ccncc1F)N1c2nc(C3CCCC(C(F)(F)F)C3)ccc2N2CC[C@H]1C2] | B | A |
| 149 | 466 | 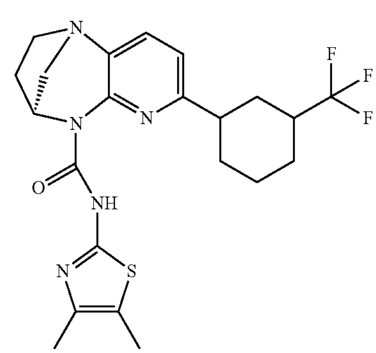 [SMILES: Cc1nc(NC(=O)N2c3nc(C4CCCC(C(F)(F)F)C4)ccc3N3CC[C@H]2C3)sc1C] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 150 | 445 | 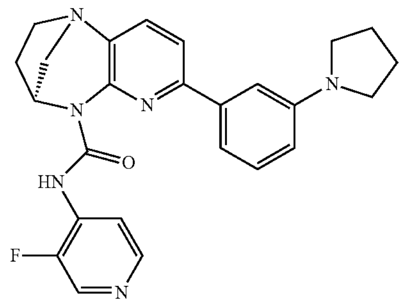 [SMILES: O=C(Nc1ccncc1F)N1c2nc(-c3cccc(N4CCCC4)c3)ccc2N2CC[C@H]1C2] | A | A |
| 151 | 445 | 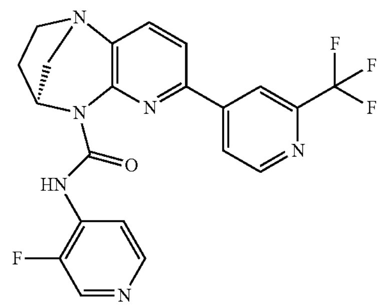 [SMILES: O=C(Nc1ccncc1F)N1c2nc(-c3ccnc(C(F)(F)F)c3)ccc2N2CC[C@H]1C2] | A | A |
| 152 | 444 | 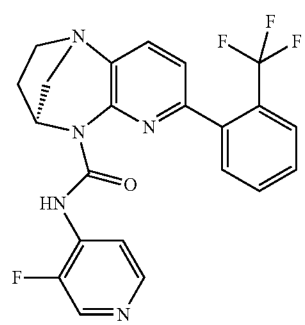 [SMILES: O=C(Nc1ccncc1F)N1c2nc(-c3ccccc3C(F)(F)F)ccc2N2CC[C@H]1C2] | C | A |
| 153 | 460 | 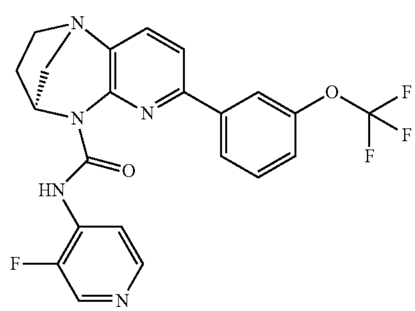 [SMILES: O=C(Nc1ccncc1F)N1c2nc(-c3cccc(OC(F)(F)F)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 154 | 450 | 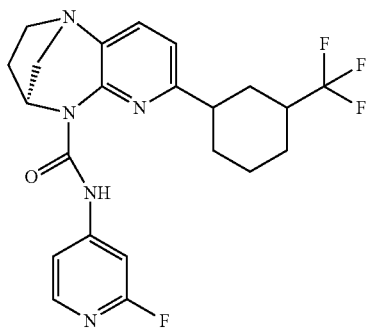 [SMILES: O=C(Nc1ccnc(F)c1)N1c2nc(C3CCCC(C(F)(F)F)C3)ccc2N2CC[C@H]1C2] | B | A |
| 155 | 448 | 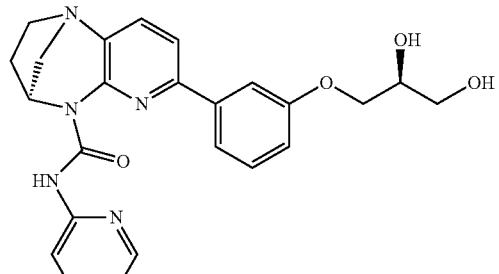 | B | A |
| 156 | 479 | 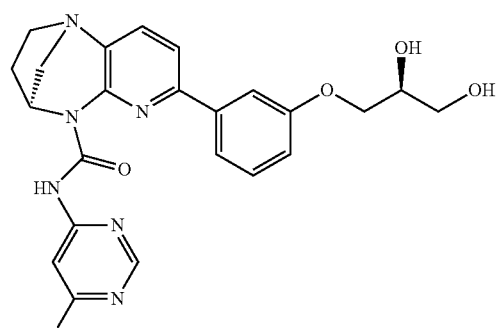 | A | A |
| 157 | 466 | 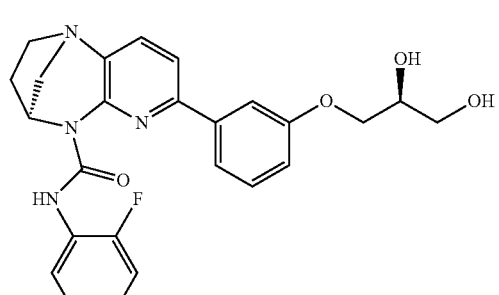 | B | A |

TABLE 1-continued
Compounds of Formula (I).
| Compound No. | [M + H]+_[calc] | Structure | Tryp AVG EC_{1.5} (μM) | Tryp % Fold Act |
|---|---|---|---|---|
| 158 | 440 | 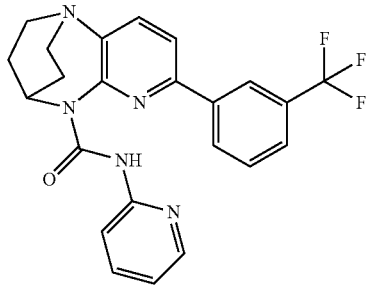 [SMILES: O=C(Nc1ccccn1)N1c2nc(-c3cccc(C(F)(F)F)c3)ccc2N2CCC1CC2] | B | A |
| 159 | 456 | 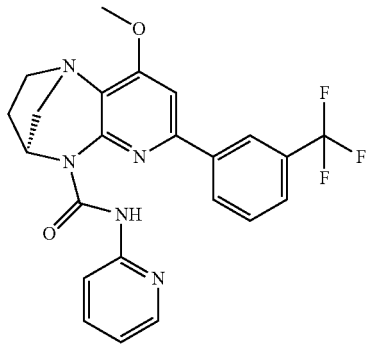 [SMILES: COc1cc(-c2cccc(C(F)(F)F)c2)nc2c1N1CC[C@@H](C1)N2C(=O)Nc1ccccn1] | A | A |
| 160 | 456 | 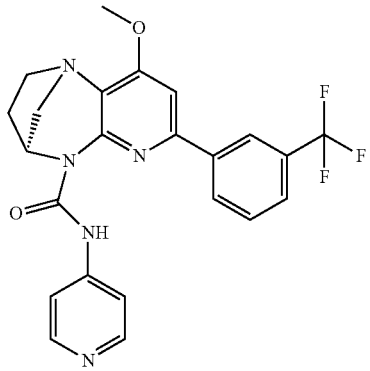 [SMILES: COc1cc(-c2cccc(C(F)(F)F)c2)nc2c1N1CC[C@@H](C1)N2C(=O)Nc1ccncc1] | A | A |
| 161 | 490 | 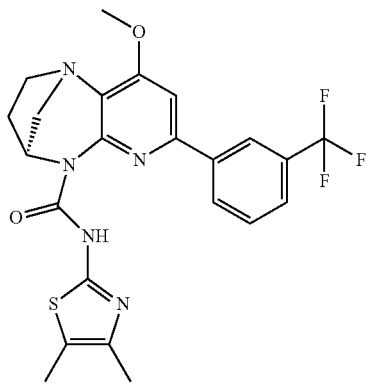 [SMILES: COc1cc(-c2cccc(C(F)(F)F)c2)nc2c1N1CC[C@@H](C1)N2C(=O)Nc1nc(C)c(C)s1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 162 | 508 | 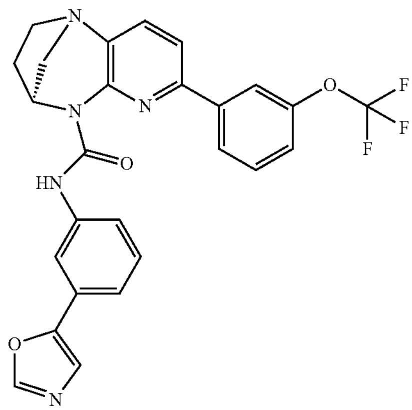 [SMILES: O=C(Nc1cccc(-c2cnco2)c1)N1c2nc(-c3cccc(OC(F)(F)F)c3)ccc2N2CC[C@H]1C2] | A | A |
| 163 | 442 | 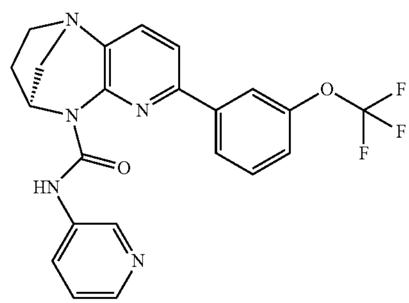 [SMILES: O=C(Nc1cccnc1)N1c2nc(-c3cccc(OC(F)(F)F)c3)ccc2N2CC[C@H]1C2] | A | A |
| 164 | 443 | 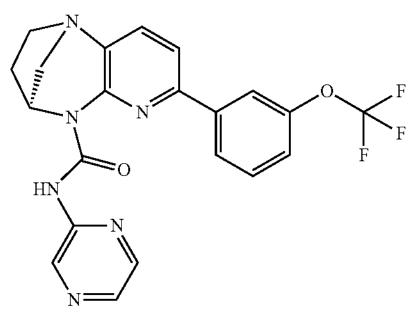 [SMILES: O=C(Nc1cnccn1)N1c2nc(-c3cccc(OC(F)(F)F)c3)ccc2N2CC[C@H]1C2] | A | A |
| 165 | 476 | 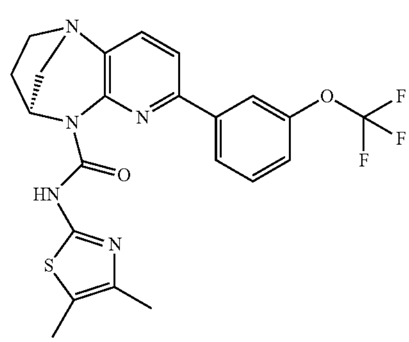 [SMILES: Cc1nc(NC(=O)N2c3nc(-c4cccc(OC(F)(F)F)c4)ccc3N3CC[C@H]2C3)sc1C] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 166 | 443 | 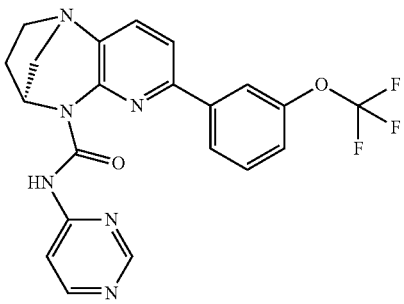 [SMILES: O=C(Nc1ccncn1)N1c2nc(-c3cccc(OC(F)(F)F)c3)ccc2N2CC[C@H]1C2] | A | A |
| 167 | 445 | 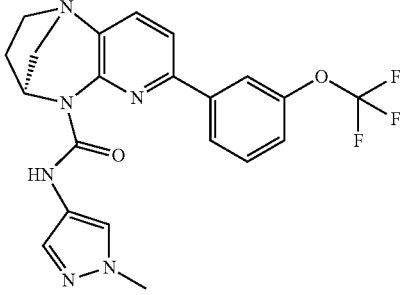 [SMILES: Cn1cc(NC(=O)N2c3nc(-c4cccc(OC(F)(F)F)c4)ccc3N3CC[C@H]2C3)cn1] | B | A |
| 168 | 471 | 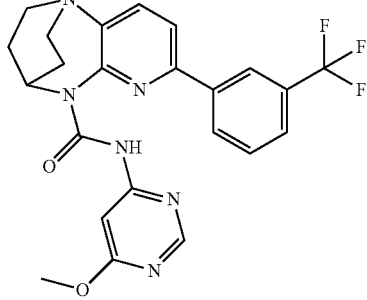 | A | A |
| 169 | 471 | 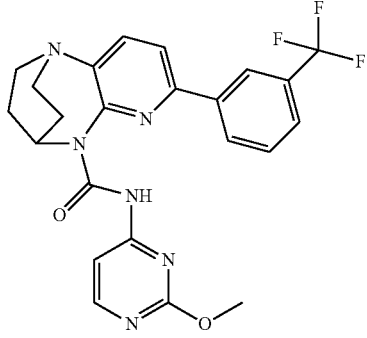 [SMILES: COc1nccc(NC(=O)N2c3nc(-c4cccc(C(F)(F)F)c4)ccc3N3CCC2CC3)n1] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 170 | 501 | 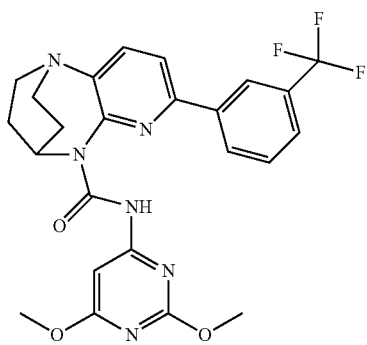 [SMILES: COc1cc(NC(=O)N2c3nc(-c4cccc(C(F)(F)F)c4)ccc3N3CCC2CC3)nc(OC)n1] | A | A |
| 171 | 441 | 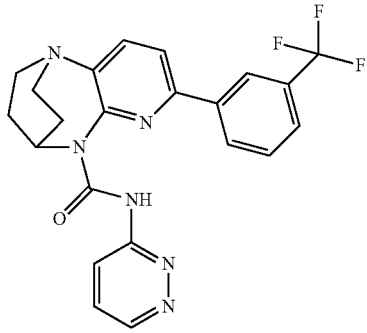 [SMILES: O=C(Nc1cccnn1)N1c2nc(-c3cccc(C(F)(F)F)c3)ccc2N2CCC1CC2] | B | A |
| 172 | 441 | 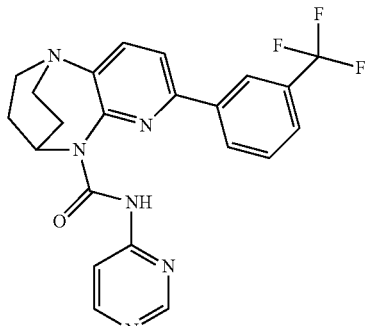 | B | A |
| 173 | 474 | 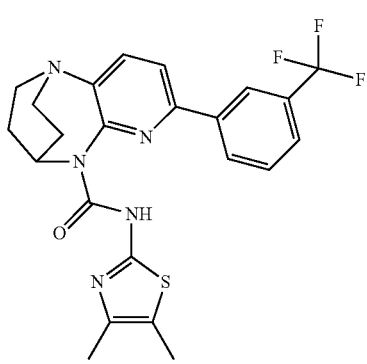 [SMILES: Cc1nc(NC(=O)N2c3nc(-c4cccc(C(F)(F)F)c4)ccc3N3CCC2CC3)sc1C] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 174 | 460 | 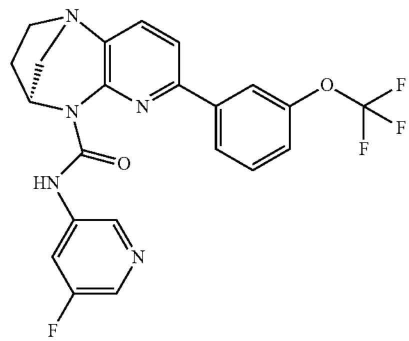 [SMILES: O=C(Nc1cncc(F)c1)N1c2nc(-c3cccc(OC(F)(F)F)c3)ccc2N2CC[C@H]1C2] | A | A |
| 175 | 495 | 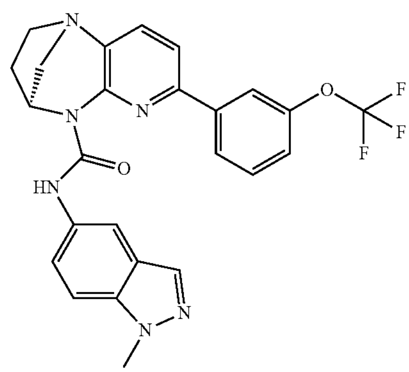 [SMILES: Cn1ncc2cc(NC(=O)N3c4nc(-c5cccc(OC(F)(F)F)c5)ccc4N4CC[C@H]3C4)ccc21] | A | A |
| 176 | 473 | 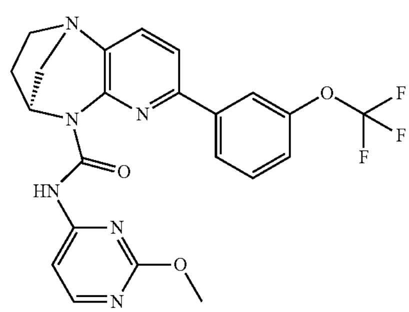 [SMILES: COc1nccc(NC(=O)N2c3nc(-c4cccc(OC(F)(F)F)c4)ccc3N3CC[C@H]2C3)n1] | A | A |
| 177 | 445 | 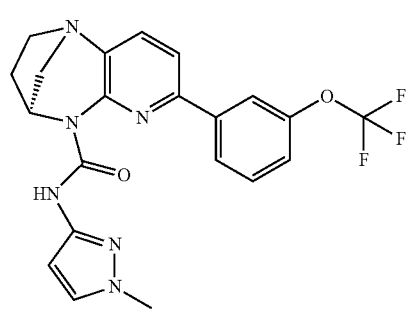 [SMILES: Cn1ccc(NC(=O)N2c3nc(-c4cccc(OC(F)(F)F)c4)ccc3N3CC[C@H]2C3)n1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 178 | 449 | 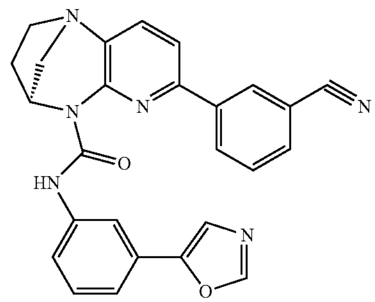 [SMILES: N#Cc1cccc(-c2ccc3c(n2)N(C(=O)Nc2cccc(-c4cnco4)c2)[C@H]2CCN3C2)c1] | A | A |
| 179 | 417 | 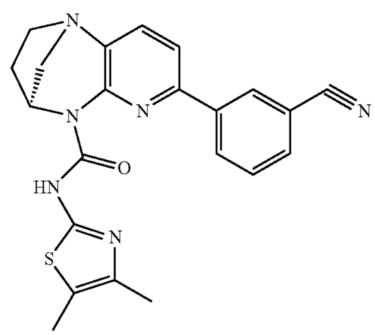 [SMILES: Cc1nc(NC(=O)N2c3nc(-c4cccc(C#N)c4)ccc3N3CC[C@H]2C3)sc1C] | A | A |
| 180 | 383 | 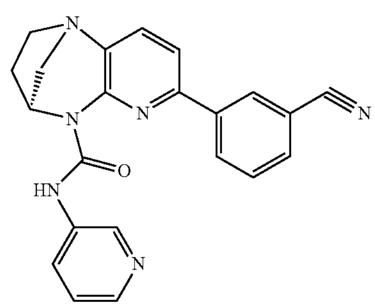 [SMILES: N#Cc1cccc(-c2ccc3c(n2)N(C(=O)Nc2cccnc2)[C@H]2CCN3C2)c1] | A | A |
| 181 | 384 | 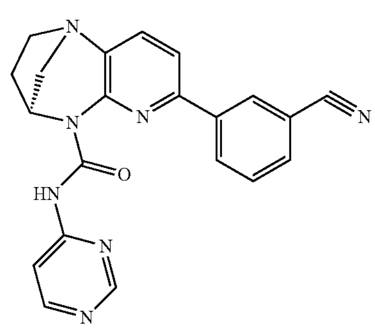 [SMILES: N#Cc1cccc(-c2ccc3c(n2)N(C(=O)Nc2ccncn2)[C@H]2CCN3C2)c1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 182 | 401 | 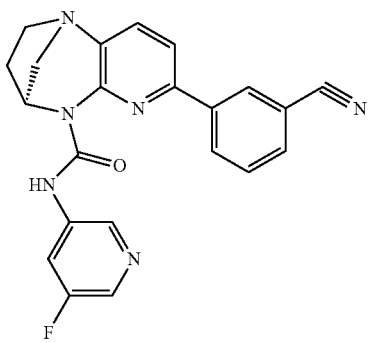 [SMILES: N#Cc1cccc(-c2ccc3c(n2)N(C(=O)Nc2cncc(F)c2)[C@H]2CCN3C2)c1] | A | A |
| 183 | 414 | 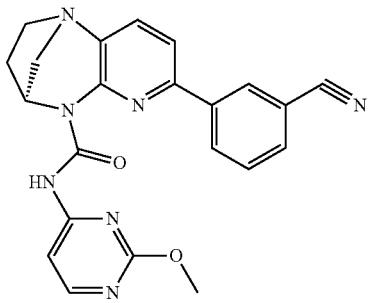 [SMILES: COc1nccc(NC(=O)N2c3nc(-c4cccc(C#N)c4)ccc3N3CC[C@H]2C3)n1] | B | A |
| 184 | 436 | 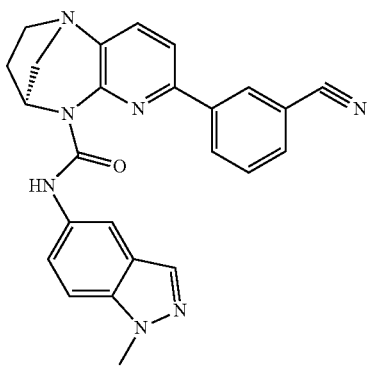 [SMILES: Cn1ncc2cc(NC(=O)N3c4nc(-c5cccc(C#N)c5)ccc4N4CC[C@H]3C4)ccc21] | A | A |
| 185 | 386 | 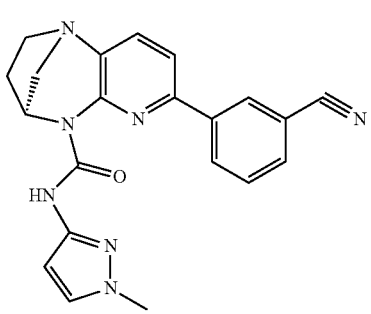 [SMILES: Cn1ccc(NC(=O)N2c3nc(-c4cccc(C#N)c4)ccc3N3CC[C@H]2C3)n1] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 186 | 386 | 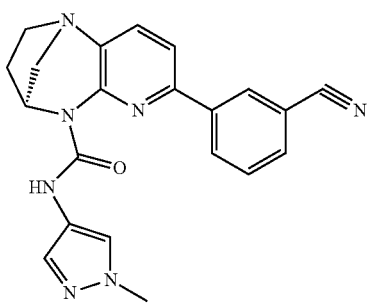 [SMILES: Cn1cc(NC(=O)N2c3nc(-c4cccc(C#N)c4)ccc3N3CC[C@H]2C3)cn1] | B | A |
| 187 | 461 | 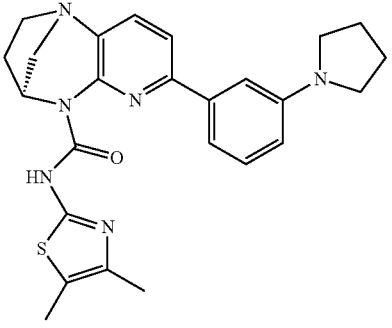 [SMILES: Cc1nc(NC(=O)N2c3nc(-c4cccc(N5CCCC5)c4)ccc3N3CC[C@H]2C3)sc1C] | B | A |
| 188 | 458 | 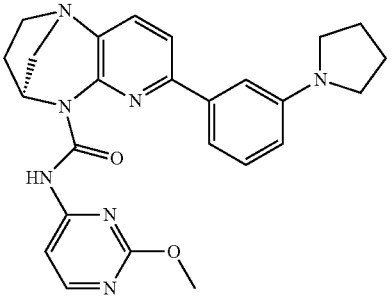 [SMILES: COc1nccc(NC(=O)N2c3nc(-c4cccc(N5CCCC5)c4)ccc3N3CC[C@H]2C3)n1] | B | A |
| 189 | 384 | 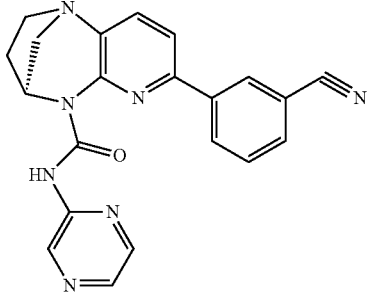 [SMILES: N#Cc1cccc(-c2ccc3c(n2)N(C(=O)Nc2cnccn2)[C@H]2CCN3C2)c1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 190 | 414 | 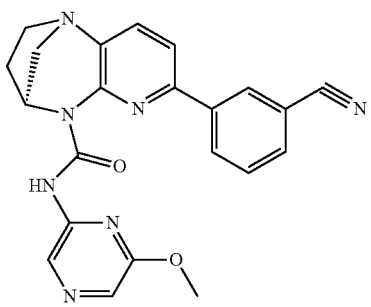 [SMILES: COc1cncc(NC(=O)N2c3nc(-c4cccc(C#N)c4)ccc3N3CC[C@H]2C3)n1] | B | A |
| 191 | 493 | 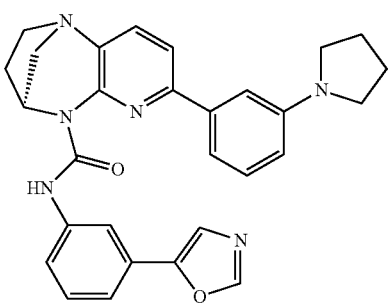 [SMILES: O=C(Nc1cccc(-c2cnco2)c1)N1c2nc(-c3cccc(N4CCCC4)c3)ccc2N2CC[C@H]1C2] | A | A |
| 192 | 427 | 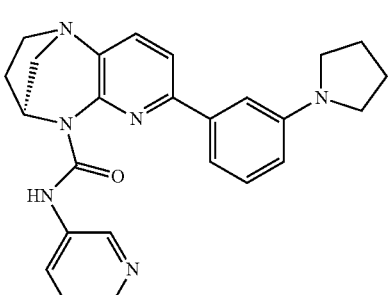 | B | A |
| 193 | 428 | 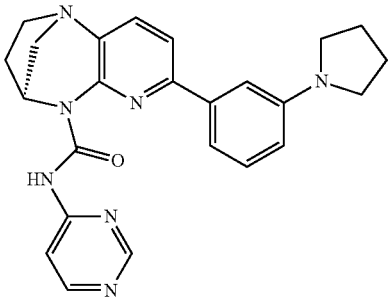 [SMILES: O=C(Nc1ccncn1)N1c2nc(-c3cccc(N4CCCC4)c3)ccc2N2CC[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 194 | 440 | 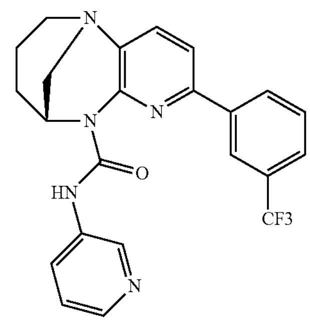 [SMILES: O=C(Nc1cccnc1)N1c2nc(-c3cccc(C(F)(F)F)c3)ccc2N2CCC[C@@H]1C2] | A | A |
| 195 | 440 | 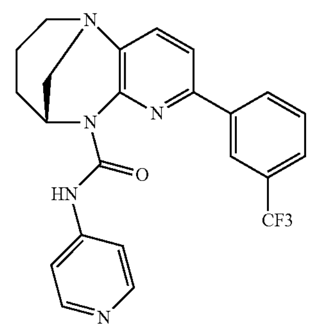 [SMILES: O=C(Nc1ccncc1)N1c2nc(-c3cccc(C(F)(F)F)c3)ccc2N2CCC[C@@H]1C2] | B | A |
| 196 | 441 | 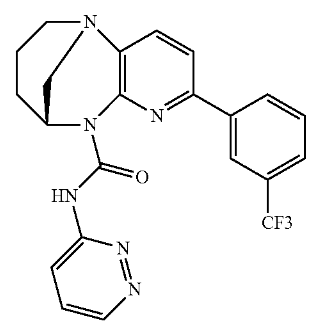 [SMILES: O=C(Nc1cccnn1)N1c2nc(-c3cccc(C(F)(F)F)c3)ccc2N2CCC[C@@H]1C2] | B | A |
| 197 | 473 | 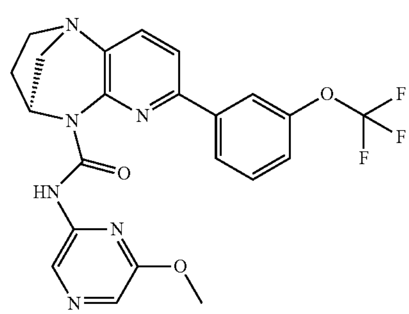 [SMILES: COc1cncc(NC(=O)N2c3nc(-c4cccc(OC(F)(F)F)c4)ccc3N3CC[C@H]2C3)n1] | A | A |

TABLE 1-continued

Compounds of Formula (I).

| Compound No. | [M + H]+[calc] | Structure | Tryp AVG EC₁.₅ (μM) | Tryp % Fold Act |
|---|---|---|---|---|
| 198 | 445 | 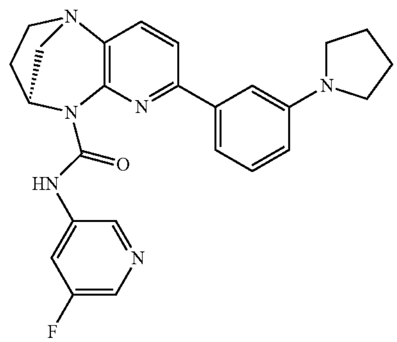 [SMILES: O=C(Nc1cncc(F)c1)N1c2nc(-c3cccc(N4CCCC4)c3)ccc2N2CC[C@H]1C2] | B | A |
| 199 | 430 | 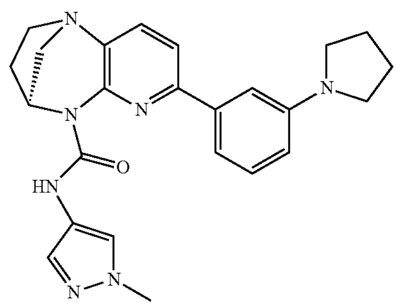 [SMILES: Cn1cc(NC(=O)N2c3nc(-c4cccc(N5CCCC5)c4)ccc3N3CC[C@H]2C3)cn1] | B | A |
| 200 | 440 | 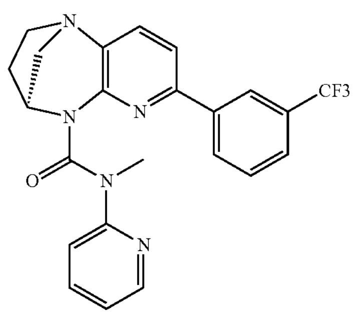 [SMILES: CN(C(=O)N1c2nc(-c3cccc(C(F)(F)F)c3)ccc2N2CC[C@H]1C2)c1ccccn1] | C | B |
| 201 | 460 | 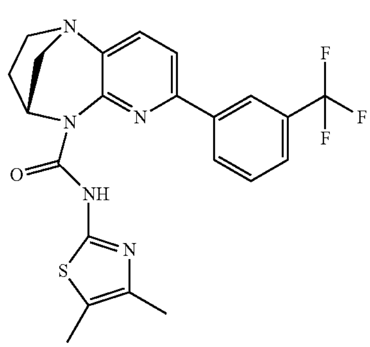 [SMILES: Cc1nc(NC(=O)N2c3nc(-c4cccc(C(F)(F)F)c4)ccc3N3CC[C@@H]2C3)sc1C] | B | A |

TABLE 1-continued

Compounds of Formula (I).

| Compound No. | [M + H]+<sub>[calc]</sub> | Structure | Tryp AVG EC<sub>1.5</sub> (µM) | Tryp % Fold Act |
|---|---|---|---|---|
| 202 | 427 | 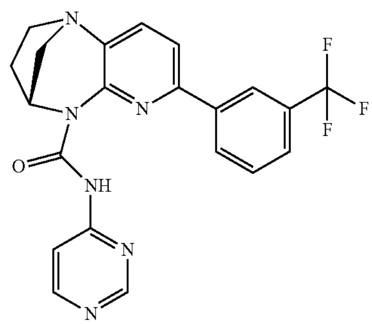 [SMILES: O=C(Nc1ccncn1)N1c2nc(-c3cccc(C(F)(F)F)c3)ccc2N2CC[C@@H]1C2] | B | A |
| 203 | 444 | 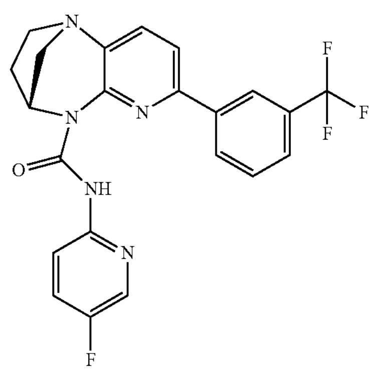 [SMILES: O=C(Nc1ccc(F)cn1)N1c2nc(-c3cccc(C(F)(F)F)c3)ccc2N2CC[C@@H]1C2] | B | A |
| 204 | 410 | 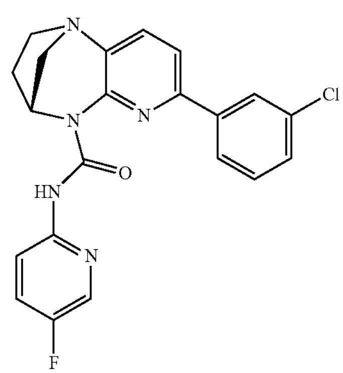 [SMILES: O=C(Nc1ccc(F)cn1)N1c2nc(-c3cccc(Cl)c3)ccc2N2CC[C@@H]1C2] | B | A |
| 205 | 406 | 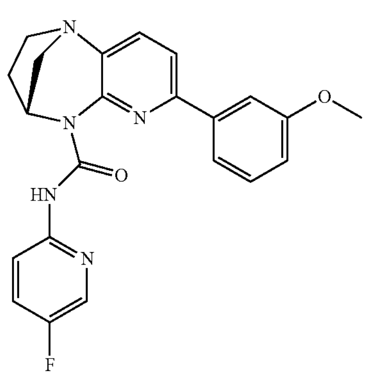 [SMILES: COc1cccc(-c2ccc3c(n2)N(C(=O)Nc2ccc(F)cn2)[C@@H]2CCN3C2)c1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 206 | 428 | 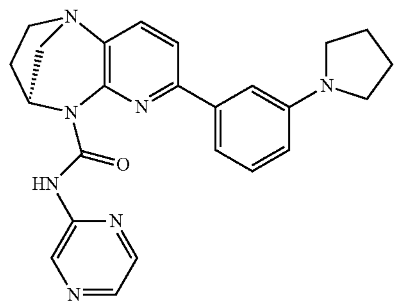 [SMILES: O=C(Nc1cnccn1)N1c2nc(-c3cccc(N4CCCC4)c3)ccc2N2CC[C@H]1C2] | B | A |
| 207 | 480 | 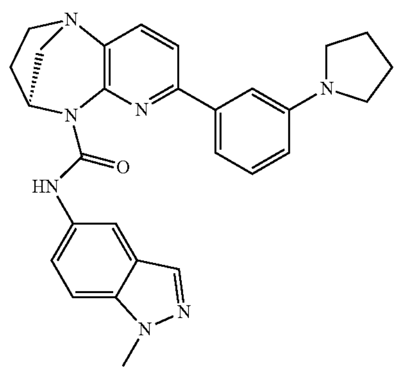 [SMILES: Cn1ncc2cc(NC(=O)N3c4nc(-c5cccc(N6CCCC6)c5)ccc4N4CC[C@H]3C4)ccc21] | A | A |
| 208 | 430 | 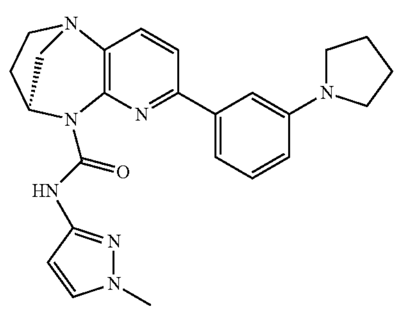 [SMILES: Cn1ccc(NC(=O)N2c3nc(-c4cccc(N5CCCC5)c4)ccc3N3CC[C@H]2C3)n1] | B | A |
| 209 | 428 | 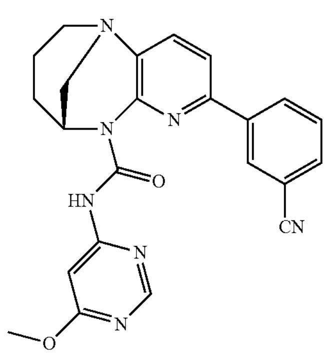 [SMILES: COc1cc(NC(=O)N2c3nc(-c4cccc(C#N)c4)ccc3N3CCC[C@@H]2C3)ncn1] | C | B |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 210 | 397 | 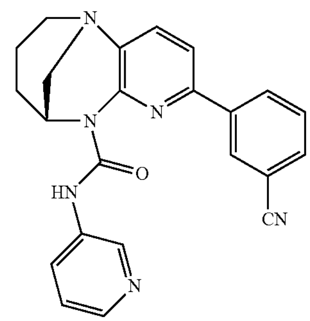 [SMILES: N#Cc1cccc(-c2ccc3c(n2)N(C(=O)Nc2cccnc2)[C@@H]2CCCN3C2)c1] | B | A |
| 211 | 434 | 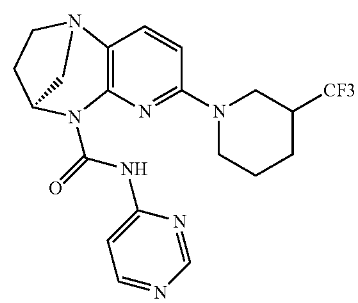 [SMILES: O=C(Nc1ccncn1)N1c2nc(N3CCCC(C(F)(F)F)C3)ccc2N2CC[C@H]1C2] | B | A |
| 212 | 499 | 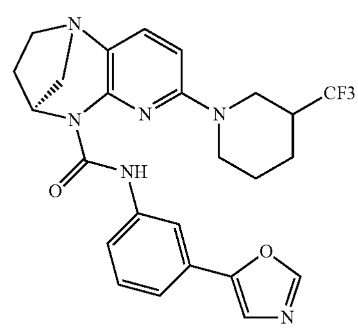 [SMILES: O=C(Nc1cccc(-c2cnco2)c1)N1c2nc(N3CCCC(C(F)(F)F)C3)ccc2N2CC[C@H]1C2] | A | A |
| 213 | 461 | 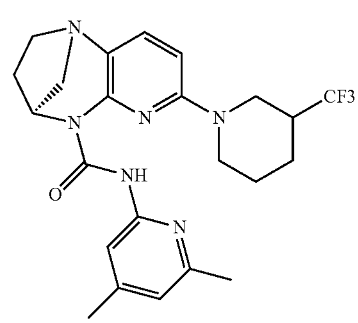 [SMILES: Cc1cc(C)nc(NC(=O)N2c3nc(N4CCCC(C(F)(F)F)C4)ccc3N3CC[C@H]2C3)c1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 214 | 453 | 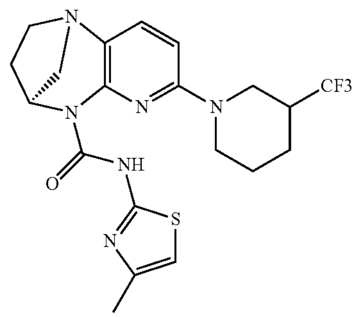 [SMILES: Cc1csc(NC(=O)N2c3nc(N4CCCC(C(F)(F)F)C4)ccc3N3CC[C@H]2C3)n1] | A | A |
| 215 | 467 | 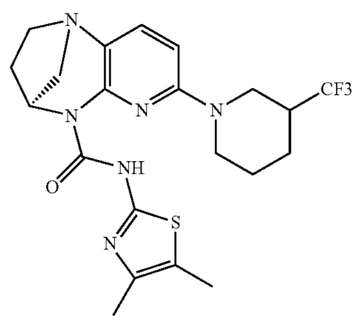 [SMILES: Cc1nc(NC(=O)N2c3nc(N4CCCC(C(F)(F)F)C4)ccc3N3CC[C@H]2C3)sc1C] | B | A |
| 216 | 476 | 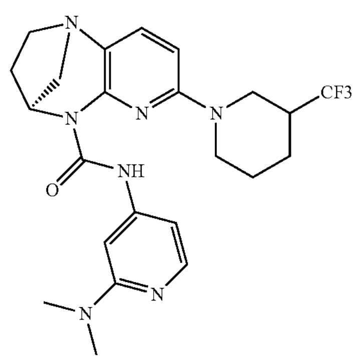 [SMILES: CN(C)c1cc(NC(=O)N2c3nc(N4CCCC(C(F)(F)F)C4)ccc3N3CC[C@H]2C3)ccn1] | A | A |
| 217 | 477 | 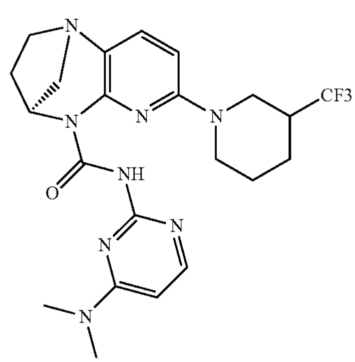 [SMILES: CN(C)c1ccnc(NC(=O)N2c3nc(N4CCCC(C(F)(F)F)C4)ccc3N3CC[C@H]2C3)n1] | B | A |

TABLE 1-continued
Compounds of Formula (I).
| Compound No. | [M + H]+_[calc] | Structure | Tryp AVG EC_{1.5} (μM) | Tryp % Fold Act |
|---|---|---|---|---|
| 218 | 410 | 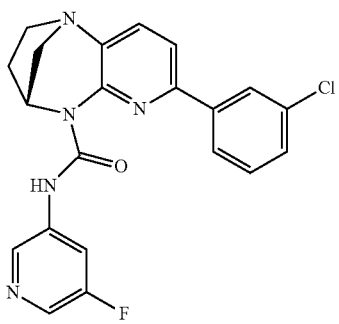 [SMILES: O=C(Nc1cncc(F)c1)N1c2nc(-c3cccc(Cl)c3)ccc2N2CC[C@@H]1C2] | A | A |
| 219 | 388 | 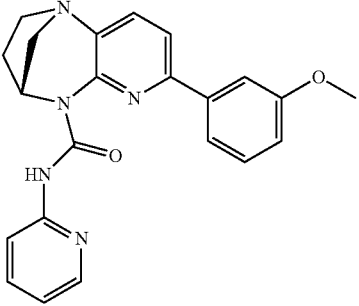 [SMILES: COc1cccc(-c2ccc3c(n2)N(C(=O)Nc2ccccn2)[C@@H]2CCN3C2)c1] | B | A |
| 220 | 373 | 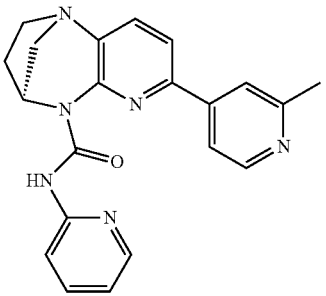 [SMILES: Cc1cc(-c2ccc3c(n2)N(C(=O)Nc2ccccn2)[C@H]2CCN3C2)ccn1] | A | A |
| 221 | 373 | 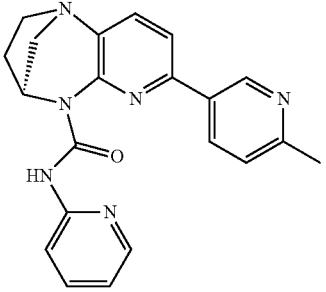 [SMILES: Cc1ccc(-c2ccc3c(n2)N(C(=O)Nc2ccccn2)[C@H]2CCN3C2)cn1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 222 | 374 | 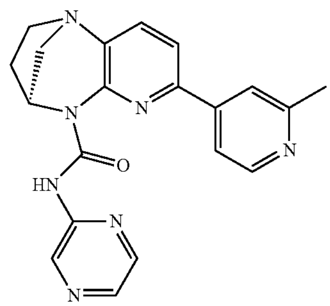 [SMILES: Cc1cc(-c2ccc3c(n2)N(C(=O)Nc2cnccn2)[C@H]2CCN3C2)ccn1] | A | A |
| 223 | 391 | 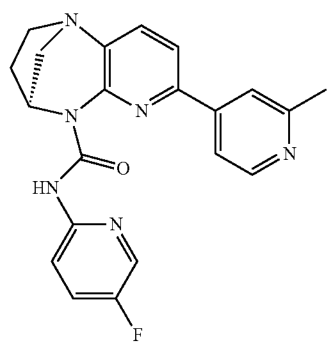 [SMILES: Cc1cc(-c2ccc3c(n2)N(C(=O)Nc2ccc(F)cn2)[C@H]2CCN3C2)ccn1] | A | A |
| 224 | 391 | 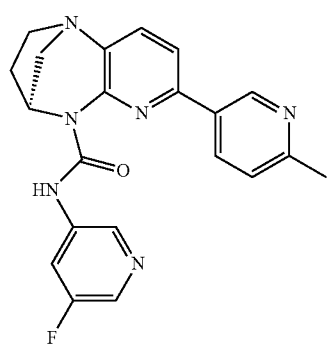 [SMILES: Cc1ccc(-c2ccc3c(n2)N(C(=O)Nc2cncc(F)c2)[C@H]2CCN3C2)cn1] | B | A |
| 225 | 397 | 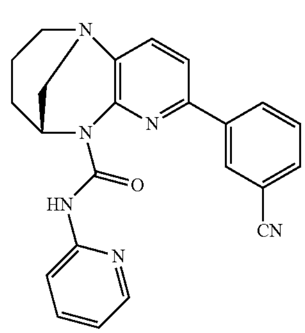 [SMILES: N#Cc1cccc(-c2ccc3c(n2)N(C(=O)Nc2ccccn2)[C@@H]2CCCN3C2)c1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 226 | 398 | 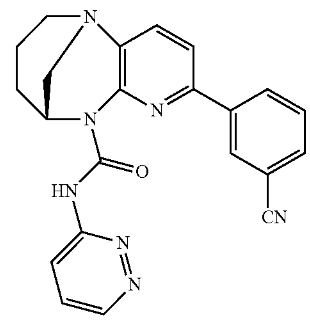 [SMILES: N#Cc1cccc(-c2ccc3c(n2)N(C(=O)Nc2cccnn2)[C@@H]2CCCN3C2)c1] | B | A |
| 227 | 415 | 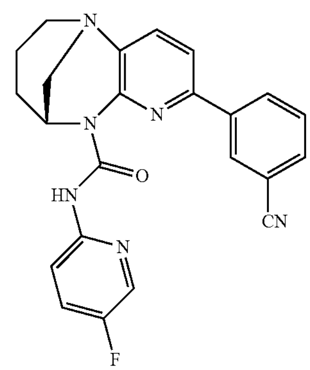 [SMILES: N#Cc1cccc(-c2ccc3c(n2)N(C(=O)Nc2ccc(F)cn2)[C@@H]2CCCN3C2)c1] | B | A |
| 228 | 415 | 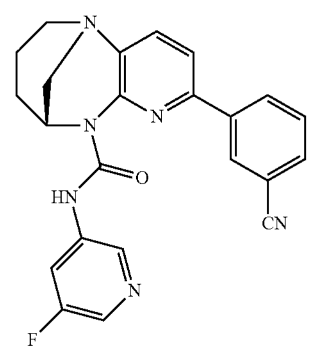 [SMILES: N#Cc1cccc(-c2ccc3c(n2)N(C(=O)Nc2cncc(F)c2)[C@@H]2CCCN3C2)c1] | B | A |
| 229 | 433 | 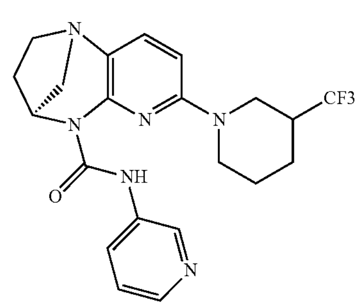 [SMILES: O=C(Nc1cccnc1)N1c2nc(N3CCCC(C(F)(F)F)C3)ccc2N2CC[C@H]1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 230 | 447 | 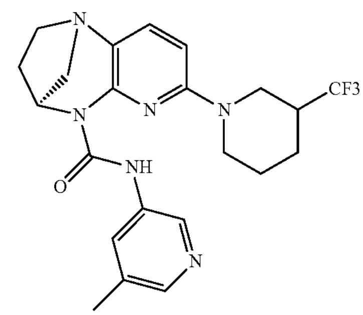 [SMILES: Cc1cncc(NC(=O)N2c3nc(N4CCCC(C(F)(F)F)C4)ccc3N3CC[C@H]2C3)c1] | A | A |
| 231 | 461 | 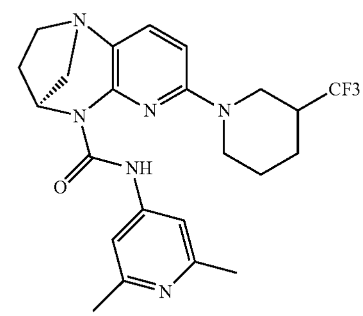 [SMILES: Cc1cc(NC(=O)N2c3nc(N4CCCC(C(F)(F)F)C4)ccc3N3CC[C@H]2C3)cc(C)n1] | B | A |
| 232 | 451 | 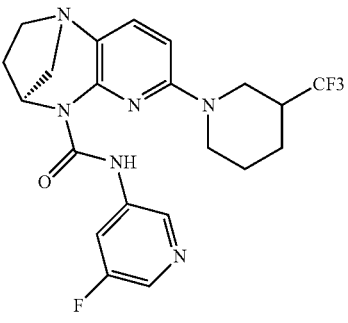 [SMILES: O=C(Nc1cncc(F)c1)N1c2nc(N3CCCC(C(F)(F)F)C3)ccc2N2CC[C@H]1C2] | B | A |
| 233 | 492 | 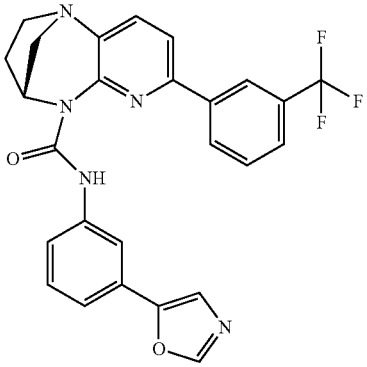 [SMILES: O=C(Nc1cccc(-c2cnco2)c1)N1c2nc(-c3cccc(C(F)(F)F)c3)ccc2N2CC[C@@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 234 | 393 | 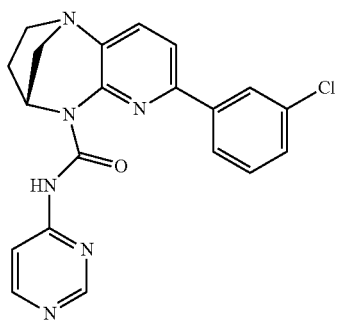 [SMILES: O=C(Nc1ccncn1)N1c2nc(-c3cccc(Cl)c3)ccc2N2CC[C@@H]1C2] | B | A |
| 235 | 458 | 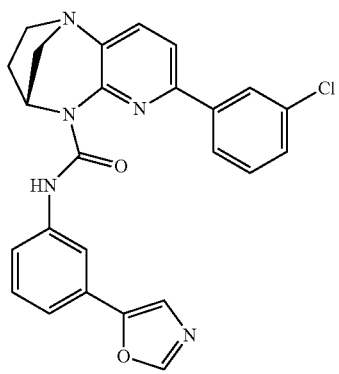 [SMILES: O=C(Nc1cccc(-c2cnco2)c1)N1c2nc(-c3cccc(Cl)c3)ccc2N2CC[C@@H]1C2] | A | A |
| 236 | 374 | 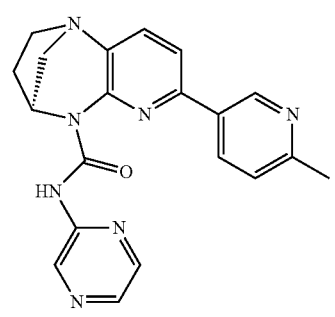 [SMILES: Cc1ccc(-c2ccc3c(n2)N(C(=O)Nc2cnccn2)[C@H]2CCN3C2)cn1] | B | A |
| 237 | 391 | 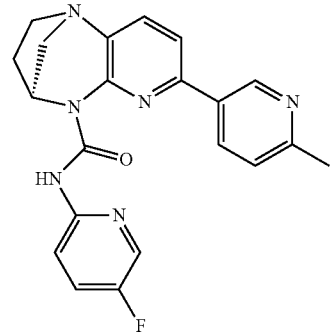 [SMILES: Cc1ccc(-c2ccc3c(n2)N(C(=O)Nc2ccc(F)cn2)[C@H]2CCN3C2)cn1] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 238 | 391 | 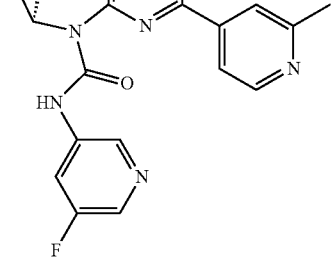 | B | A |
| 239 | 464 | 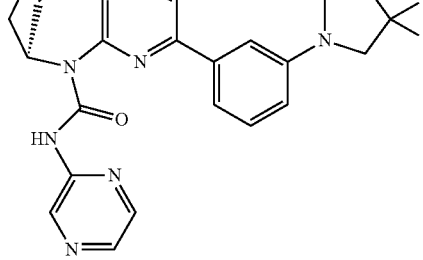 | A | A |
| 240 | 404 | 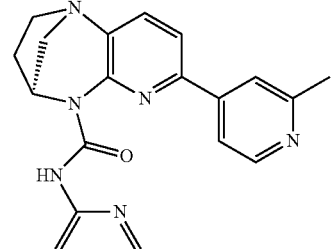 | B | A |
| 241 | 404 | 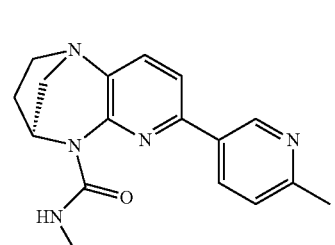 | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 242 | 394 | 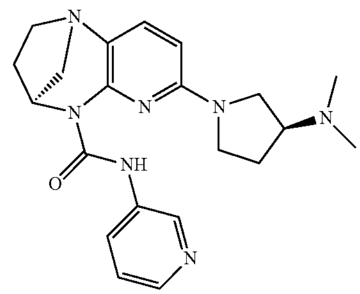 [SMILES: CN(C)[C@H]1CCN(c2ccc3c(n2)N(C(=O)Nc2cccnc2)[C@H]2CCN3C2)C1] | B | A |
| 243 | 408 | 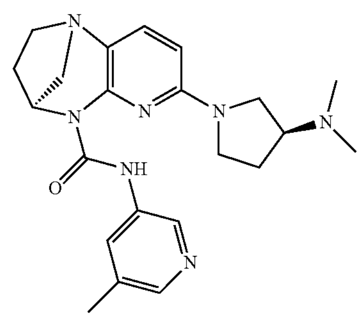 [SMILES: Cc1cncc(NC(=O)N2c3nc(N4CC[C@H](N(C)C)C4)ccc3N3CC[C@H]2C3)c1] | C | A |
| 244 | 412 | 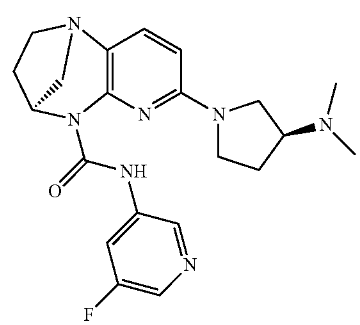 [SMILES: CN(C)[C@H]1CCN(c2ccc3c(n2)N(C(=O)Nc2cncc(F)c2)[C@H]2CCN3C2)C1] | B | A |
| 245 | 422 | 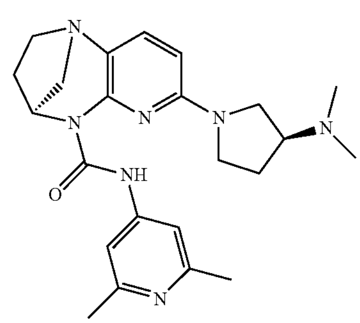 [SMILES: Cc1cc(NC(=O)N2c3nc(N4CC[C@H](N(C)C)C4)ccc3N3CC[C@H]2C3)cc(C)n1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 246 | 395 | 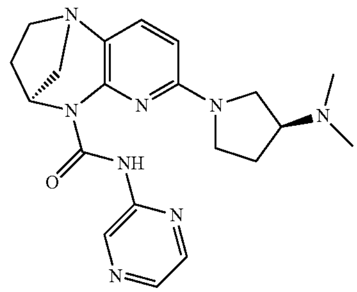 [SMILES: CN(C)[C@H]1CCN(c2ccc3c(n2)N(C(=O)Nc2cnccn2)[C@H]2CCN3C2)C1] | B | A |
| 247 | 400 | 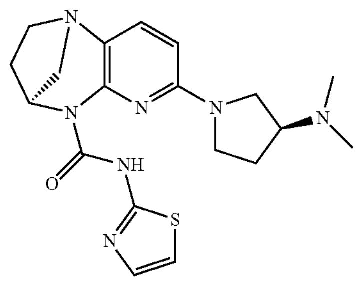 [SMILES: CN(C)[C@H]1CCN(c2ccc3c(n2)N(C(=O)Nc2nccs2)[C@H]2CCN3C2)C1] | B | A |
| 248 | 414 | 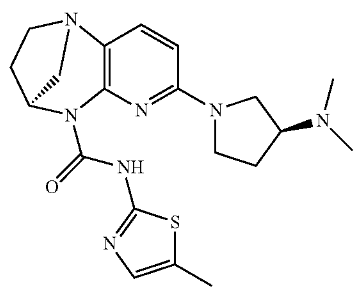 [SMILES: Cc1cnc(NC(=O)N2c3nc(N4CC[C@H](N(C)C)C4)ccc3N3CC[C@H]2C3)s1] | NT | NT |
| 249 | 394 | 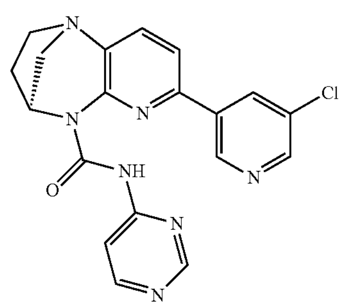 [SMILES: O=C(Nc1ccncn1)N1c2nc(-c3cncc(Cl)c3)ccc2N2CC[C@H]1C2] | B | A |
| 250 | 424 | 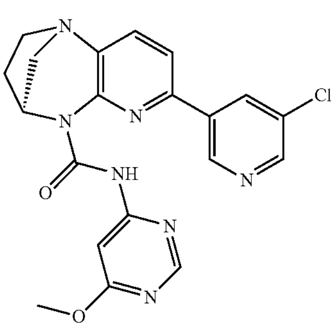 [SMILES: COc1cc(NC(=O)N2c3nc(-c4cncc(Cl)c4)ccc3N3CC[C@H]2C3)ncn1] | A | A |

TABLE 1-continued
Compounds of Formula (I).
| Compound No. | [M + H]+_{[calc]} | Structure | Tryp AVG EC_{1.5} (μM) | Tryp % Fold Act |
|---|---|---|---|---|
| 251 | 415 | 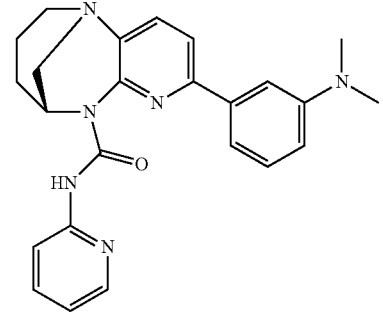 [SMILES: CN(C)c1cccc(-c2ccc3c(n2)N(C(=O)Nc2ccccn2)[C@@H]2CCCN3C2)c1] | C | A |
| 252 | 449 | 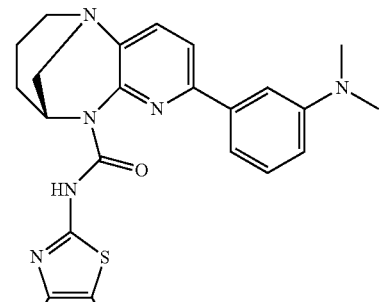 | C | A |
| 253 | 433 | 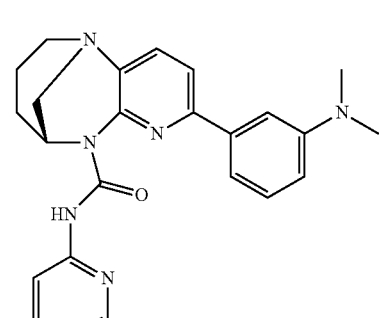 | C | B |
| 254 | 463 | 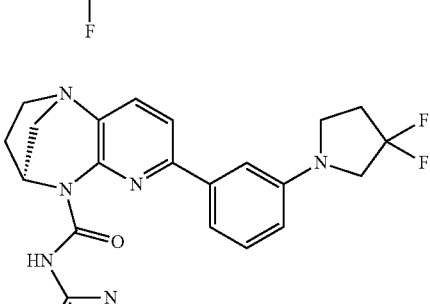 | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 255 | 476 | 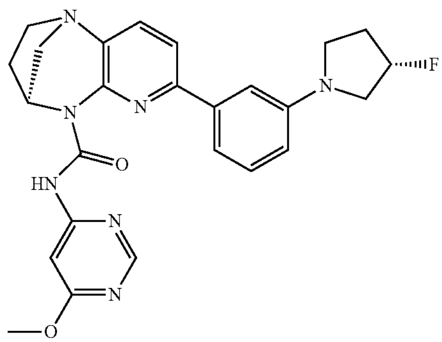 [SMILES: COc1cc(NC(=O)N2c3nc(-c4cccc(N5CC[C@H](F)C5)c4)ccc3N3CC[C@H]2C3)ncn1] | B | A |
| 256 | 494 | 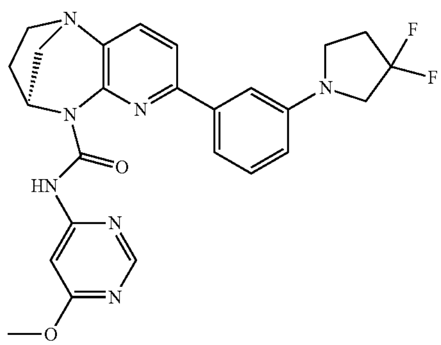 [SMILES: COc1cc(NC(=O)N2c3nc(-c4cccc(N5CCC(F)(F)C5)c4)ccc3N3CC[C@H]2C3)ncn1] | B | A |
| 257 | 481 | 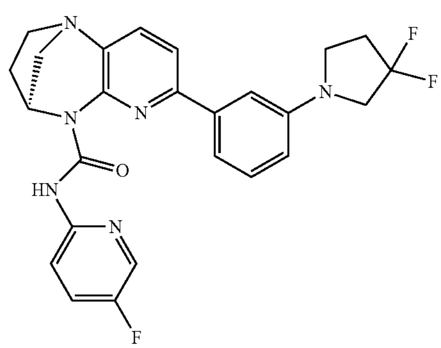 [SMILES: O=C(Nc1ccc(F)cn1)N1c2nc(-c3cccc(N4CCC(F)(F)C4)c3)ccc2N2CC[C@H]1C2] | B | A |
| 258 | 316 | 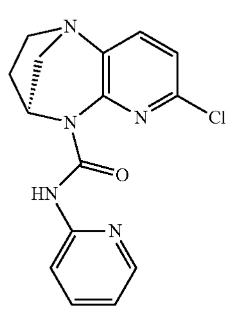 [SMILES: O=C(Nc1ccccn1)N1c2nc(Cl)ccc2N2CC[C@H]1C2] | C | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 259 | 334 | 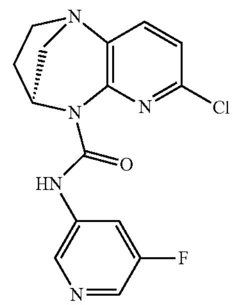 [SMILES: O=C(Nc1cncc(F)c1)N1c2nc(Cl)ccc2N2CC[C@H]1C2] | B | A |
| 260 | 393 | 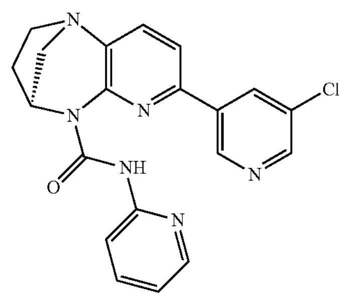 [SMILES: O=C(Nc1ccccn1)N1c2nc(-c3cncc(Cl)c3)ccc2N2CC[C@H]1C2] | A | A |
| 261 | 411 | 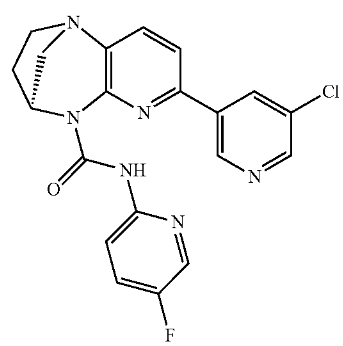 [SMILES: O=C(Nc1ccc(F)cn1)N1c2nc(-c3cncc(Cl)c3)ccc2N2CC[C@H]1C2] | A | A |
| 262 | 438 | 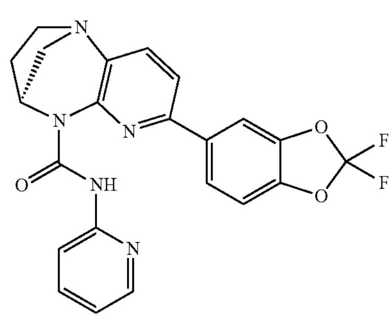 [SMILES: O=C(Nc1ccccn1)N1c2nc(-c3ccc4c(c3)OC(F)(F)O4)ccc2N2CC[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 263 | 420 | 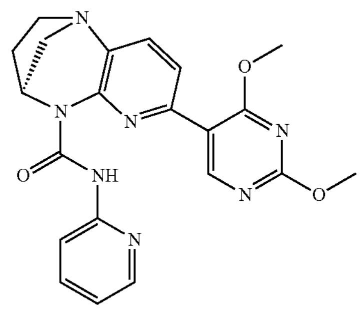 [SMILES: COc1ncc(-c2ccc3c(n2)N(C(=O)Nc2ccccn2)[C@H]2CCN3C2)c(OC)n1] | B | A |
| 264 | 481 | 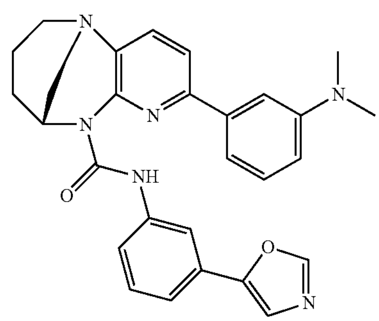 [SMILES: CN(C)c1cccc(-c2ccc3c(n2)N(C(=O)Nc2cccc(-c4cnco4)c2)[C@@H]2CCCN3C2)c1] | A | A |
| 265 | 446 | 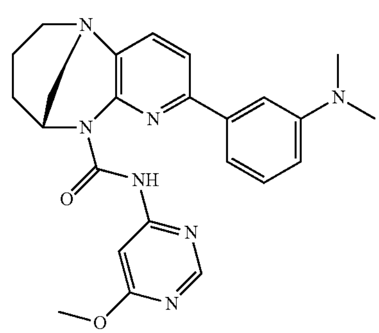 [SMILES: COc1cc(NC(=O)N2c3nc(-c4cccc(N(C)C)c4)ccc3N3CCC[C@@H]2C3)ncn1] | B | A |
| 266 | 416 | 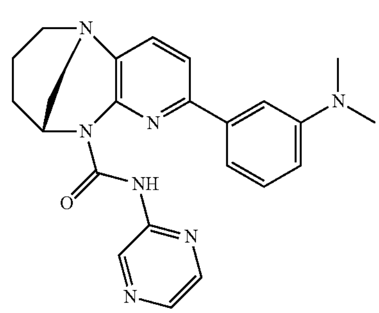 [SMILES: CN(C)c1cccc(-c2ccc3c(n2)N(C(=O)Nc2cnccn2)[C@@H]2CCCN3C2)c1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 267 | 446 | 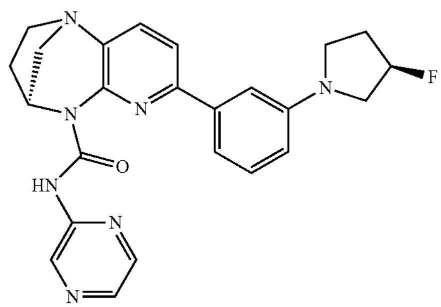 [SMILES: O=C(Nc1cnccn1)N1c2nc(-c3cccc(N4CC[C@@H](F)C4)c3)ccc2N2CC[C@H]1C2] | B | A |
| 268 | 446 | 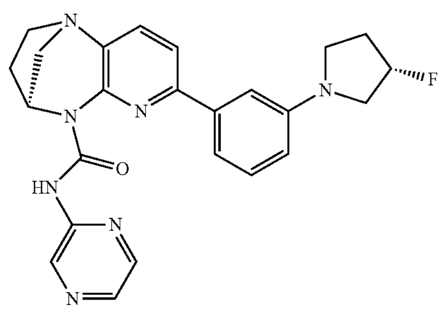 [SMILES: O=C(Nc1cnccn1)N1c2nc(-c3cccc(N4CC[C@H](F)C4)c3)ccc2N2CC[C@H]1C2] | A | A |
| 269 | 463 | 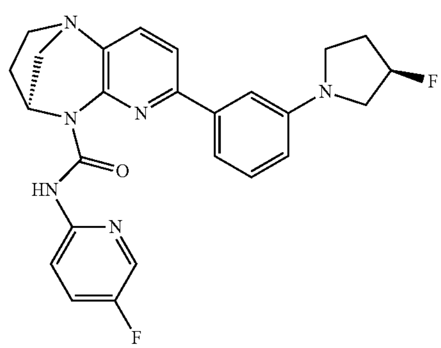 [SMILES: O=C(Nc1ccc(F)cn1)N1c2nc(-c3cccc(N4CC[C@@H](F)C4)c3)ccc2N2CC[C@H]1C2] | B | A |
| 270 | 463 | 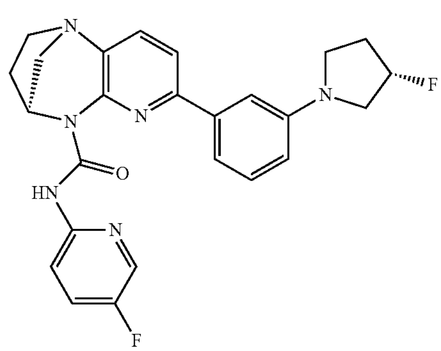 [SMILES: O=C(Nc1ccc(F)cn1)N1c2nc(-c3cccc(N4CC[C@H](F)C4)c3)ccc2N2CC[C@H]1C2] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 271 | 481 | 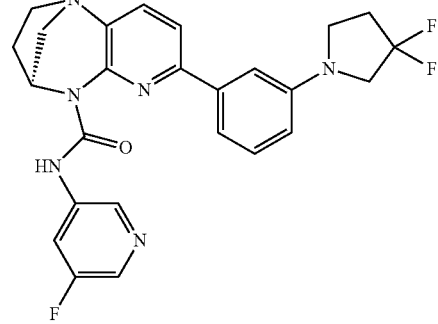 | A | A |
| 272 | 440 | 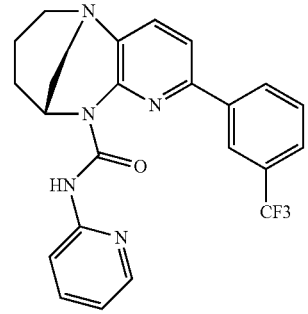 [SMILES: O=C(Nc1ccccn1)N1c2nc(-c3cccc(C(F)(F)F)c3)ccc2N2CCC[C@@H]1C2] | B | A |
| 273 | 458 | 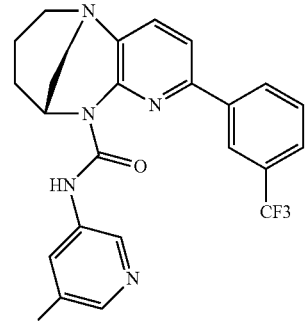 | A | A |
| 274 | 471 | 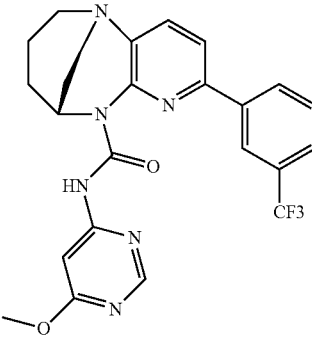 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 275 | 394 | 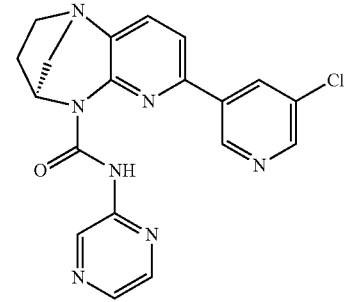 [SMILES: O=C(Nc1cnccn1)N1c2nc(-c3cncc(Cl)c3)ccc2N2CC[C@H]1C2] | A | A |
| 276 | 428 | 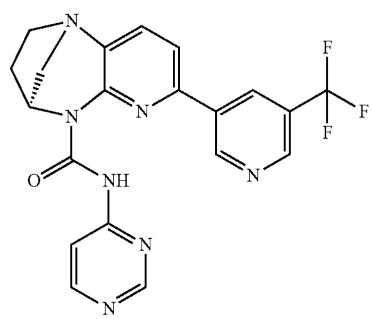 [SMILES: O=C(Nc1ccncn1)N1c2nc(-c3cncc(C(F)(F)F)c3)ccc2N2CC[C@H]1C2] | A | A |
| 277 | 445 | 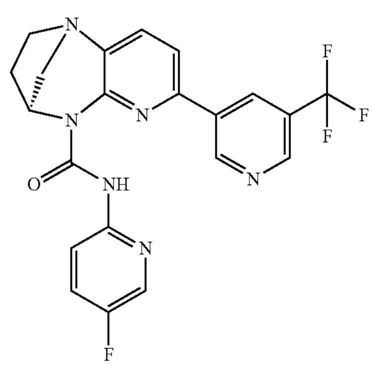 [SMILES: O=C(Nc1ccc(F)cn1)N1c2nc(-c3cncc(C(F)(F)F)c3)ccc2N2CC[C@H]1C2] | A | A |
| 278 | 428 | 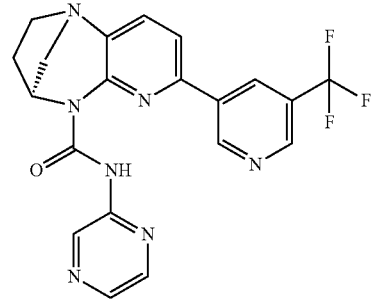 [SMILES: O=C(Nc1cnccn1)N1c2nc(-c3cncc(C(F)(F)F)c3)ccc2N2CC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 279 | 445 | 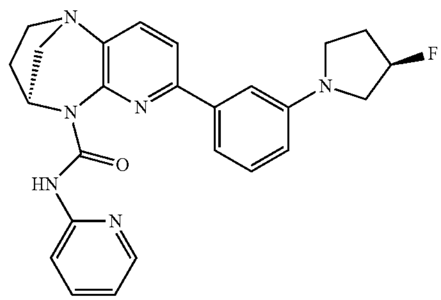 [SMILES: O=C(Nc1ccccn1)N1c2nc(-c3cccc(N4CC[C@@H](F)C4)c3)ccc2N2CC[C@H]1C2] | A | A |
| 280 | 445 | 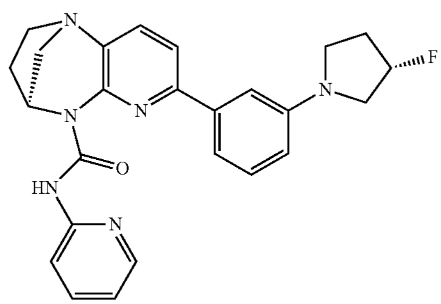 [SMILES: O=C(Nc1ccccn1)N1c2nc(-c3cccc(N4CC[C@H](F)C4)c3)ccc2N2CC[C@H]1C2] | A | A |
| 281 | 476 | 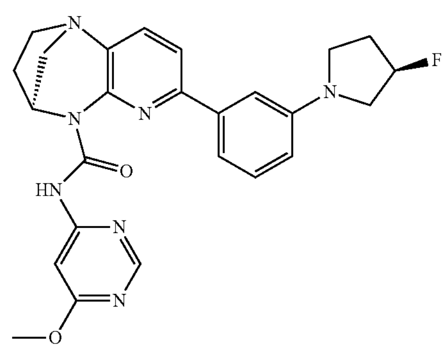 [SMILES: COc1cc(NC(=O)N2c3nc(-c4cccc(N5CC[C@@H](F)C5)c4)ccc3N3CC[C@H]2C3)ncn1] | A | A |
| 282 | 463 | 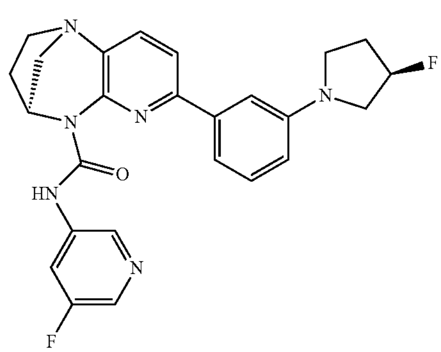 [SMILES: O=C(Nc1cncc(F)c1)N1c2nc(-c3cccc(N4CC[C@@H](F)C4)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 283 | 463 | 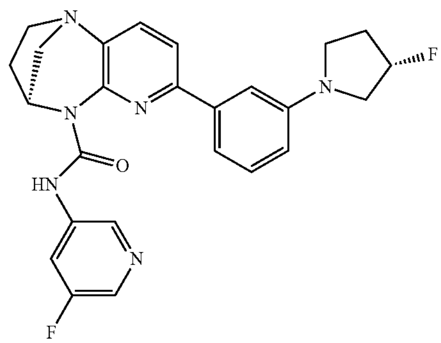 [SMILES: O=C(Nc1cncc(F)c1)N1c2nc(-c3cccc(N4CC[C@H](F)C4)c3)ccc2N2CC[C@H]1C2] | A | A |
| 284 | 378 | 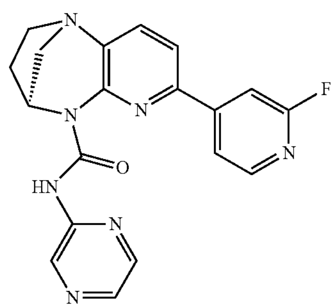 [SMILES: O=C(Nc1cnccn1)N1c2nc(-c3ccnc(F)c3)ccc2N2CC[C@H]1C2] | B | A |
| 285 | 513 | 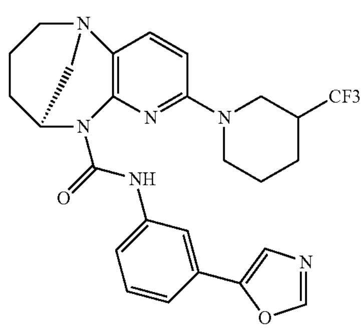 [SMILES: O=C(Nc1cccc(-c2cnco2)c1)N1c2nc(N3CCCC(C(F)(F)F)C3)ccc2N2CCC[C@H]1C2] | A | A |
| 286 | 447 | 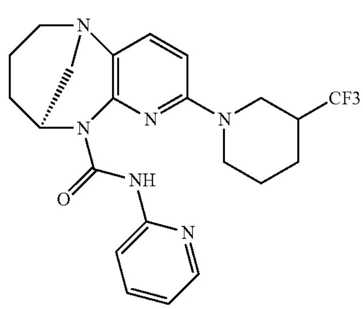 [SMILES: O=C(Nc1ccccn1)N1c2nc(N3CCCC(C(F)(F)F)C3)ccc2N2CCC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 287 | 475 | 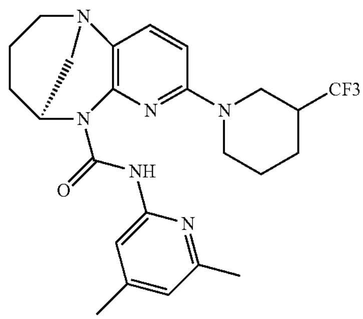 [SMILES: Cc1cc(C)nc(NC(=O)N2c3nc(N4CCCC(C(F)(F)F)C4)ccc3N3CCC[C@H]2C3)c1] | B | A |
| 288 | 447 | 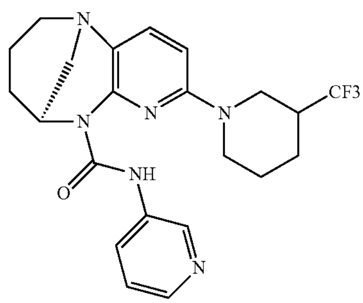 [SMILES: O=C(Nc1cccnc1)N1c2nc(N3CCCC(C(F)(F)F)C3)ccc2N2CCC[C@H]1C2] | A | A |
| 289 | 461 | 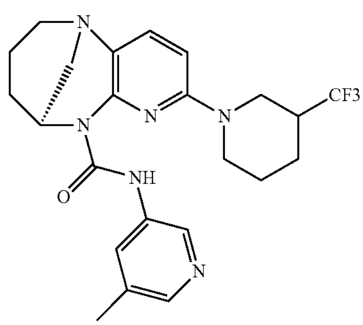 [SMILES: Cc1cncc(NC(=O)N2c3nc(N4CCCC(C(F)(F)F)C4)ccc3N3CCC[C@H]2C3)c1] | A | A |
| 290 | 465 | 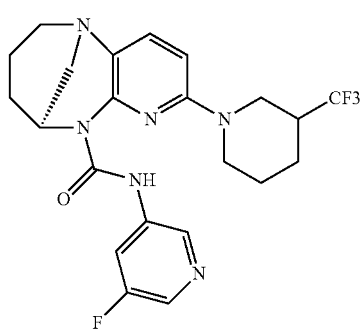 [SMILES: O=C(Nc1cncc(F)c1)N1c2nc(N3CCCC(C(F)(F)F)C3)ccc2N2CCC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 291 | 465 | 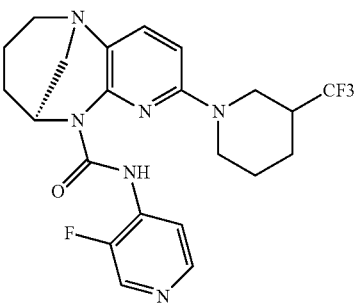 [SMILES: O=C(Nc1ccncc1F)N1c2nc(N3CCCC(C(F)(F)F)C3)ccc2N2CCC[C@H]1C2] | B | A |
| 292 | 448 | 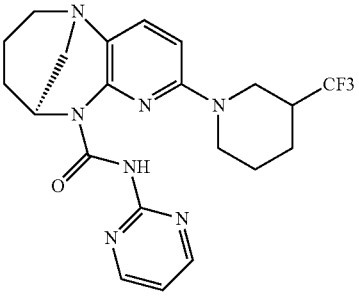 [SMILES: O=C(Nc1ncccn1)N1c2nc(N3CCCC(C(F)(F)F)C3)ccc2N2CCC[C@H]1C2] | A | A |
| 293 | 448 | 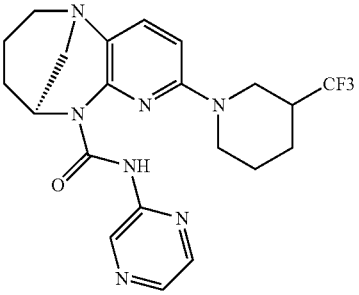 [SMILES: O=C(Nc1cnccn1)N1c2nc(N3CCCC(C(F)(F)F)C3)ccc2N2CCC[C@H]1C2] | A | A |
| 294 | 448 | 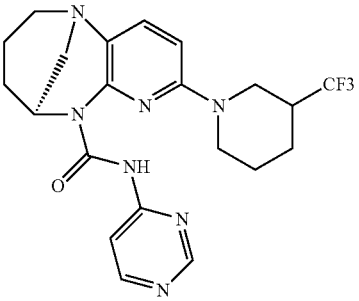 [SMILES: O=C(Nc1ccncn1)N1c2nc(N3CCCC(C(F)(F)F)C3)ccc2N2CCC[C@H]1C2] | B | A |
| 295 | 453 | 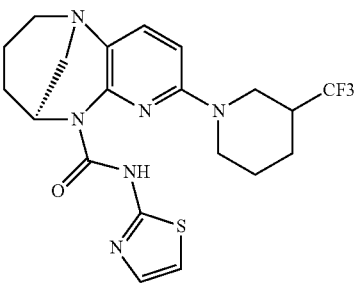 [SMILES: O=C(Nc1nccs1)N1c2nc(N3CCCC(C(F)(F)F)C3)ccc2N2CCC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 296 | 467 | 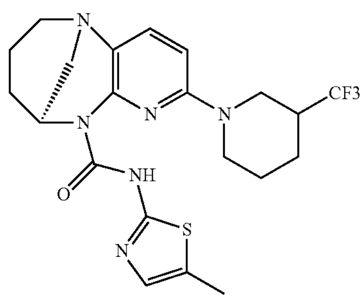 [SMILES: Cc1cnc(NC(=O)N2c3nc(N4CCCC(C(F)(F)F)C4)ccc3N3CCC[C@H]2C3)s1] | B | A |
| 297 | 467 | 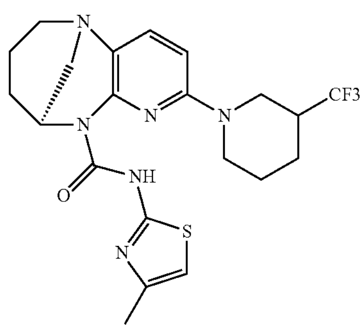 [SMILES: Cc1csc(NC(=O)N2c3nc(N4CCCC(C(F)(F)F)C4)ccc3N3CCC[C@H]2C3)n1] | B | A |
| 298 | 481 | 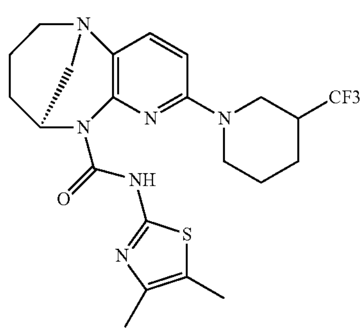 [SMILES: Cc1nc(NC(=O)N2c3nc(N4CCCC(C(F)(F)F)C4)ccc3N3CCC[C@H]2C3)sc1C] | B | A |
| 299 | 513 | 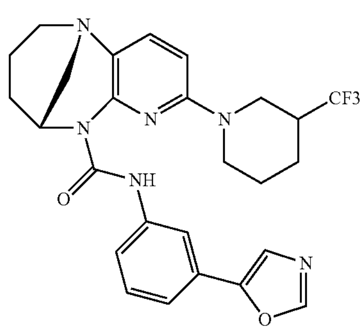 [SMILES: O=C(Nc1cccc(-c2cnco2)c1)N1c2nc(N3CCCC(C(F)(F)F)C3)ccc2N2CCC[C@@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 300 | 447 | 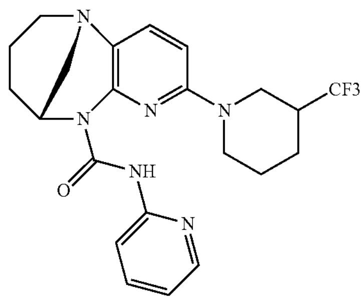 [SMILES: O=C(Nc1ccccn1)N1c2nc(N3CCCC(C(F)(F)F)C3)ccc2N2CCC[C@@H]1C2] | C | B |
| 301 | 475 | 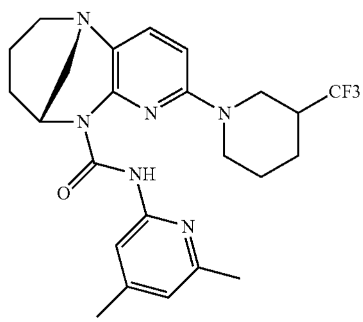 [SMILES: Cc1cc(C)nc(NC(=O)N2c3nc(N4CCCC(C(F)(F)F)C4)ccc3N3CCC[C@@H]2C3)c1] | C | B |
| 302 | 447 | 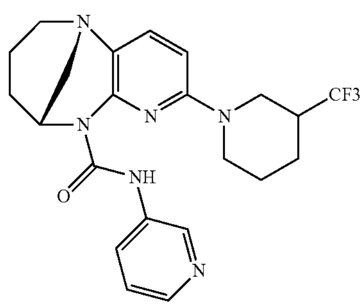 [SMILES: O=C(Nc1cccnc1)N1c2nc(N3CCCC(C(F)(F)F)C3)ccc2N2CCC[C@@H]1C2] | B | A |
| 303 | 461 | 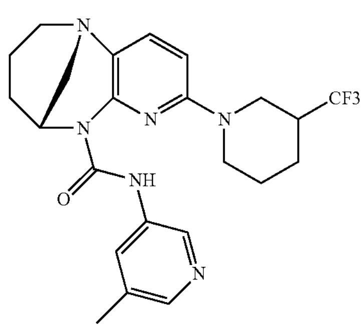 [SMILES: Cc1cncc(NC(=O)N2c3nc(N4CCCC(C(F)(F)F)C4)ccc3N3CCC[C@@H]2C3)c1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 304 | 465 | 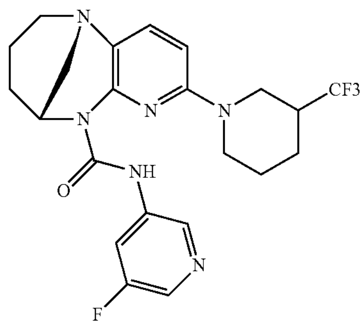 [SMILES: O=C(Nc1cncc(F)c1)N1c2nc(N3CCCC(C(F)(F)F)C3)ccc2N2CCC[C@@H]1C2] | B | A |
| 305 | 447 | 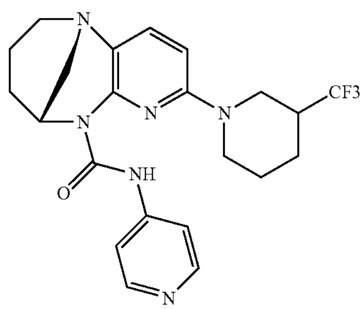 [SMILES: O=C(Nc1ccncc1)N1c2nc(N3CCCC(C(F)(F)F)C3)ccc2N2CCC[C@@H]1C2] | B | A |
| 306 | 448 | 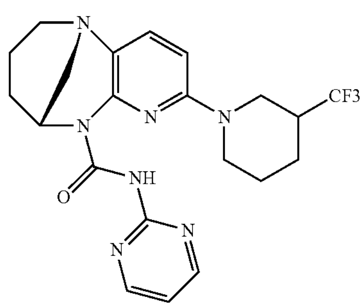 [SMILES: O=C(Nc1ncccn1)N1c2nc(N3CCCC(C(F)(F)F)C3)ccc2N2CCC[C@@H]1C2] | NT | NT |
| 307 | 448 | 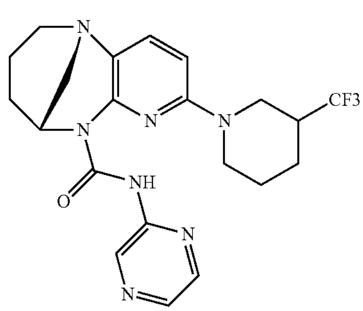 [SMILES: O=C(Nc1cnccn1)N1c2nc(N3CCCC(C(F)(F)F)C3)ccc2N2CCC[C@@H]1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 308 | 448 | 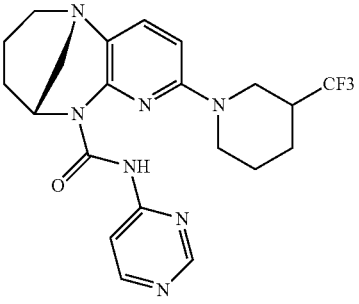 [SMILES: O=C(Nc1ccncn1)N1c2nc(N3CCCC(C(F)(F)F)C3)ccc2N2CCC[C@@H]1C2] | C | A |
| 309 | 477 | 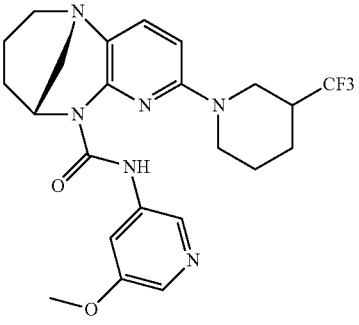 [SMILES: COc1cncc(NC(=O)N2c3nc(N4CCCC(C(F)(F)F)C4)ccc3N3CCC[C@@H]2C3)c1] | B | A |
| 310 | 453 | 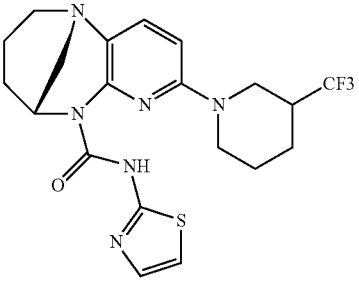 [SMILES: O=C(Nc1nccs1)N1c2nc(N3CCCC(C(F)(F)F)C3)ccc2N2CCC[C@@H]1C2] | B | A |
| 311 | 467 | 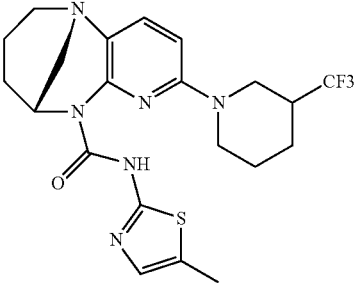 [SMILES: Cc1cnc(NC(=O)N2c3nc(N4CCCC(C(F)(F)F)C4)ccc3N3CCC[C@@H]2C3)s1] | C | B |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 312 | 467 | 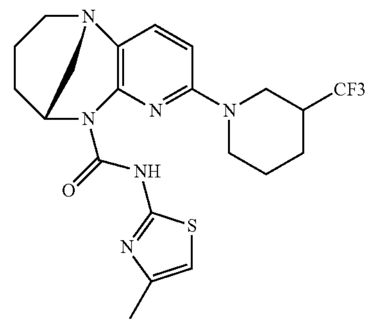 [SMILES: Cc1csc(NC(=O)N2c3nc(N4CCCC(C(F)(F)F)C4)ccc3N3CCC[C@@H]2C3)n1] | B | A |
| 313 | 481 | 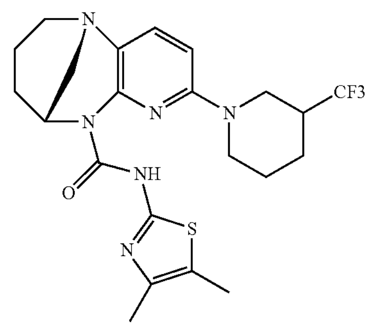 [SMILES: Cc1nc(NC(=O)N2c3nc(N4CCCC(C(F)(F)F)C4)ccc3N3CCC[C@@H]2C3)sc1C] | C | B |
| 314 (5) | 440 | 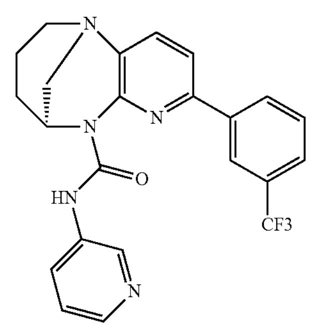 | A | A |
| 315 | 533 | 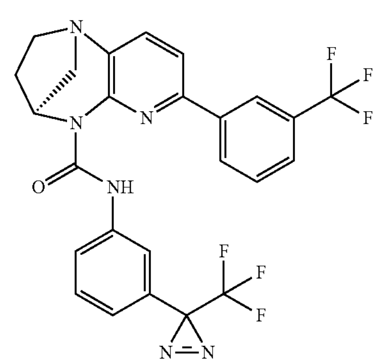 [SMILES: O=C(Nc1cccc(C2(C(F)(F)F)N=N2)c1)N1c2nc(-c3cccc(C(F)(F)F)c3)ccc2N2CC[C@H]1C2] | B | A |

TABLE 1-continued
Compounds of Formula (I).
| Compound No. | [M + H]+[calc] | Structure | Tryp AVG EC1.5 (µM) | Tryp % Fold Act |
|---|---|---|---|---|
| 316 | 427 | 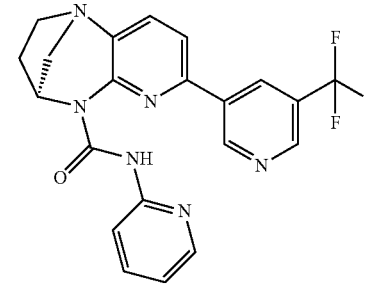 | A | A |
| 317 | 458 | 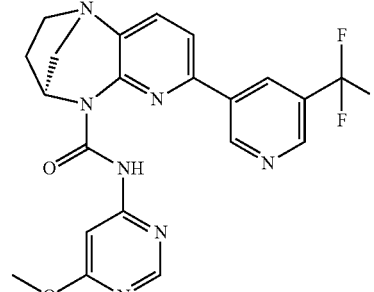 | B | A |
| 318 | 495 | 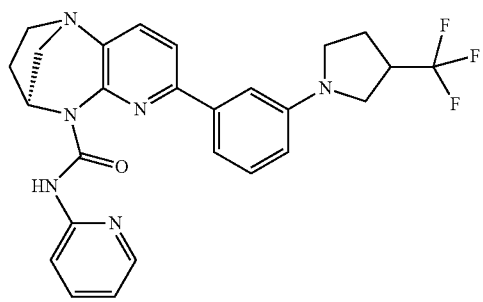 [SMILES: O=C(Nc1ccccn1)N1c2nc(-c3cccc(N4CCC(C(F)(F)F)C4)c3)ccc2N2CC[C@H]1C2] | B | A |
| 319 | 496 | 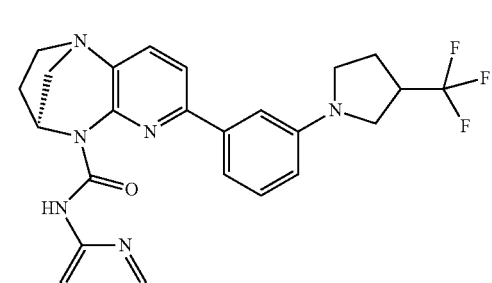 | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 320 | 526 | 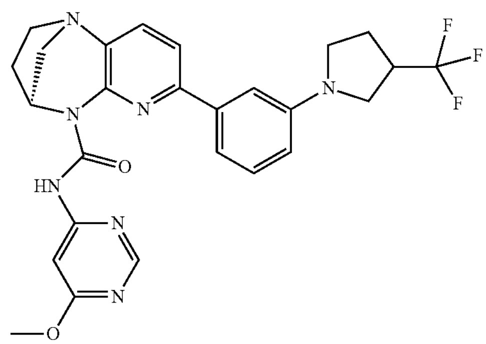 [SMILES: COc1cc(NC(=O)N2c3nc(-c4cccc(N5CCC(C(F)(F)F)C5)c4)ccc3N3CC[C@H]2C3)ncn1] | B | A |
| 321 | 513 | 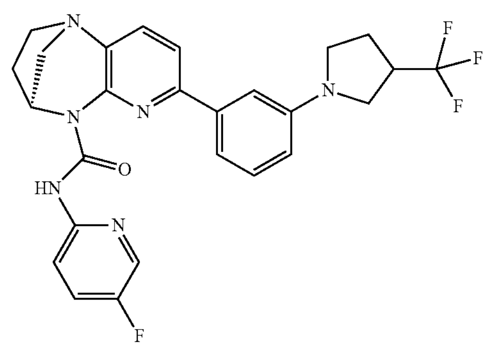 [SMILES: O=C(Nc1ccc(F)cn1)N1c2nc(-c3cccc(N4CCC(C(F)(F)F)C4)c3)ccc2N2CC[C@H]1C2] | B | A |
| 322 | 482 | 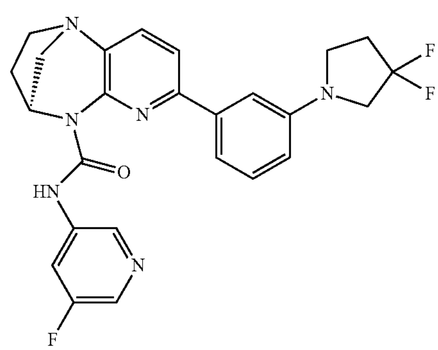 [SMILES: O=C(Nc1cncc(F)c1)N1c2nc(-c3cccc(N4CCC(F)(F)C4)c3)ccc2N2CC[C@H]1C2] | A | A |
| 323 | 513 | 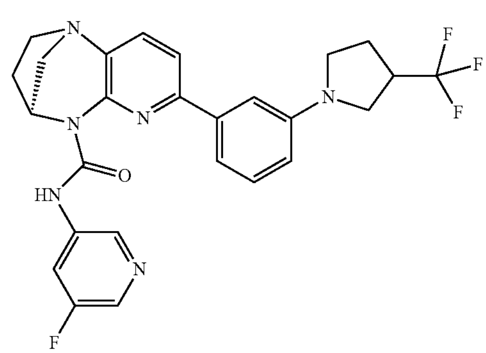 [SMILES: O=C(Nc1cncc(F)c1)N1c2nc(-c3cccc(N4CCC(C(F)(F)F)C4)c3)ccc2N2CC[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 324 | 426 | 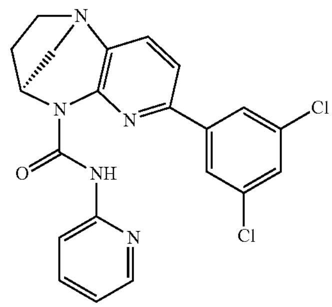 [SMILES: O=C(Nc1ccccn1)N1c2nc(-c3cc(Cl)cc(Cl)c3)ccc2N2CC[C@H]1C2] | A | A |
| 325 | 373 | 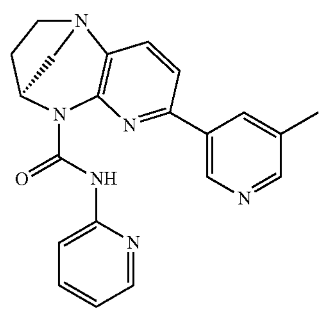 [SMILES: Cc1cncc(-c2ccc3c(n2)N(C(=O)Nc2ccccn2)[C@H]2CCN3C2)c1] | A | A |
| 326 | 436 | 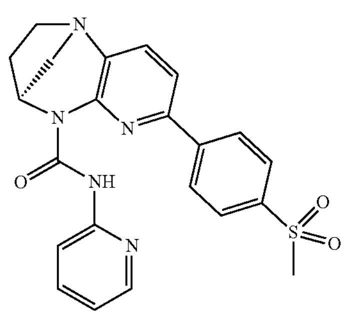 [SMILES: CS(=O)(=O)c1ccc(-c2ccc3c(n2)N(C(=O)Nc2ccccn2)[C@H]2CCN3C2)cc1] | B | A |
| 327 | 377 | 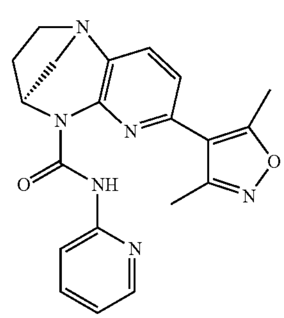 [SMILES: Cc1noc(C)c1-c1ccc2c(n1)N(C(=O)Nc1ccccn1)[C@H]1CCN2C1] | C | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 328 | 437 | 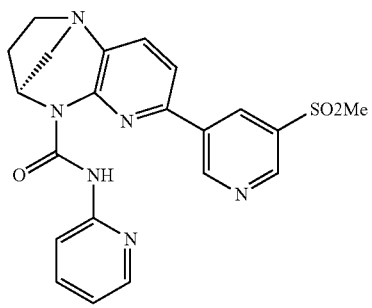 [SMILES: CS(=O)(=O)c1cncc(-c2ccc3c(n2)N(C(=O)Nc2ccccn2)[C@H]2CCN3C2)c1] | B | A |
| 329 | 410 | 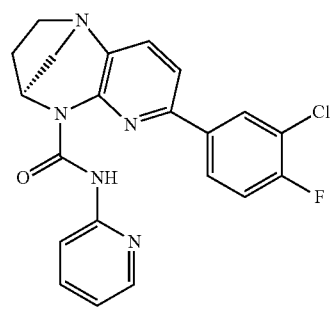 [SMILES: O=C(Nc1ccccn1)N1c2nc(-c3ccc(F)c(Cl)c3)ccc2N2CC[C@H]1C2] | A | A |
| 330 | 400 | 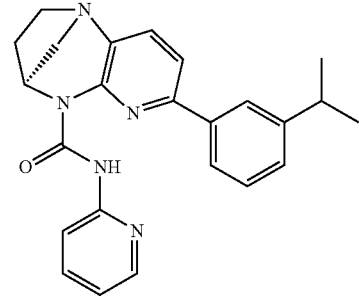 [SMILES: CC(C)c1cccc(-c2ccc3c(n2)N(C(=O)Nc2ccccn2)[C@H]2CCN3C2)c1] | A | A |
| 331 | 362 | 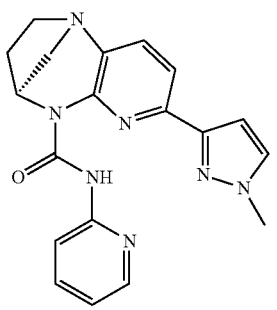 [SMILES: Cn1ccc(-c2ccc3c(n2)N(C(=O)Nc2ccccn2)[C@H]2CCN3C2)n1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 332 | 426 | 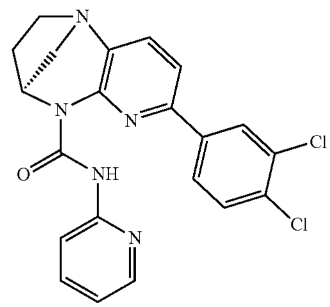 [SMILES: O=C(Nc1ccccn1)N1c2nc(-c3ccc(Cl)c(Cl)c3)ccc2N2CC[C@H]1C2] | A | A |
| 333 | 444 | 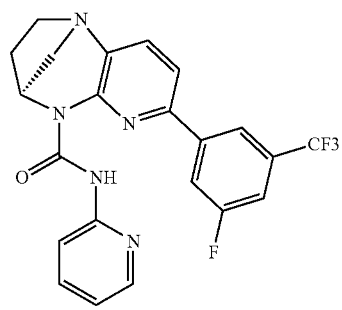 [SMILES: O=C(Nc1ccccn1)N1c2nc(-c3cc(F)cc(C(F)(F)F)c3)ccc2N2CC[C@H]1C2] | A | A |
| 334 | 444 | 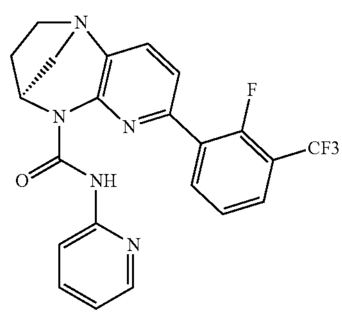 [SMILES: O=C(Nc1ccccn1)N1c2nc(-c3cccc(C(F)(F)F)c3F)ccc2N2CC[C@H]1C2] | B | A |
| 335 | 547 | 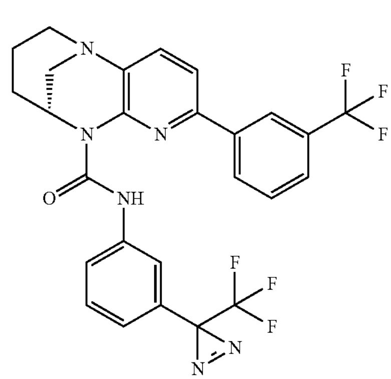 [SMILES: O=C(Nc1cccc(C2(C(F)(F)F)N=N2)c1)N1c2nc(-c3cccc(C(F)(F)F)c3)ccc2N2CCC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 336 | 427 | 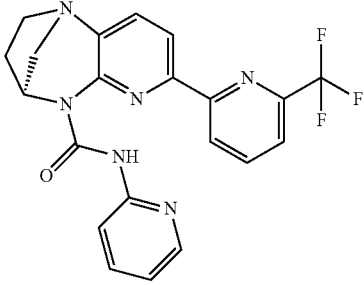 [SMILES: O=C(Nc1ccccn1)N1c2nc(-c3cccc(C(F)(F)F)n3)ccc2N2CC[C@H]1C2] | B | A |
| 337 | 428 | 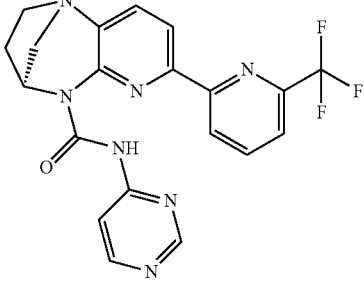 | B | A |
| 338 | 428 | 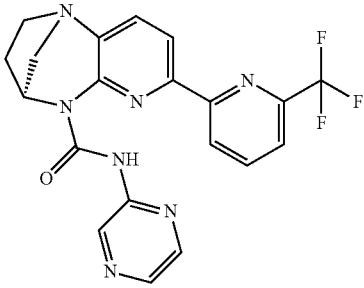 [SMILES: O=C(Nc1cnccn1)N1c2nc(-c3cccc(C(F)(F)F)n3)ccc2N2CC[C@H]1C2] | B | A |
| 339 | 458 | 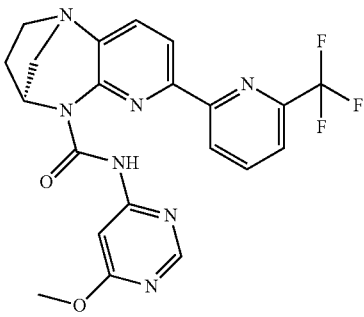 [SMILES: COc1cc(NC(=O)N2c3nc(-c4cccc(C(F)(F)F)n4)ccc3N3CC[C@H]2C3)ncn1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 340 | 445 | 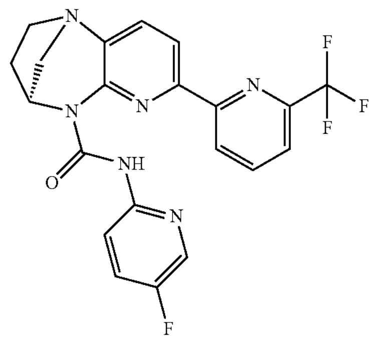 [SMILES: O=C(Nc1ccc(F)cn1)N1c2nc(-c3cccc(C(F)(F)F)n3)ccc2N2CC[C@H]1C2] | B | A |
| 341 | 401 | 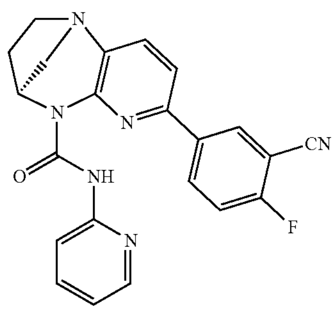 [SMILES: N#Cc1cc(-c2ccc3c(n2)N(C(=O)Nc2ccccn2)[C@H]2CCN3C2)ccc1F] | A | A |
| 342 | 389 | 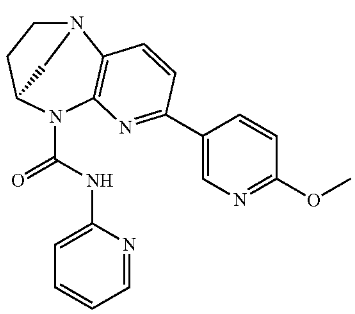 [SMILES: COc1ccc(-c2ccc3c(n2)N(C(=O)Nc2ccccn2)[C@H]2CCN3C2)cn1] | B | A |
| 343 | 415 | 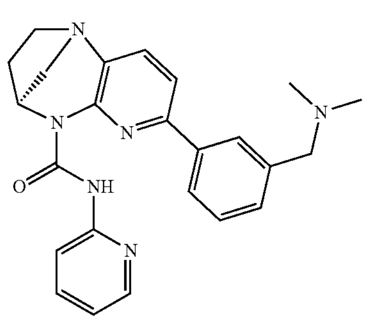 [SMILES: CN(C)Cc1cccc(-c2ccc3c(n2)N(C(=O)Nc2ccccn2)[C@H]2CCN3C2)c1] | B | A |

TABLE 1-continued
Compounds of Formula (I).
| Compound No. | [M + H]+_[calc] | Structure | Tryp AVG EC_{1.5} (μM) | Tryp % Fold Act |
|---|---|---|---|---|
| 344 | 394 | 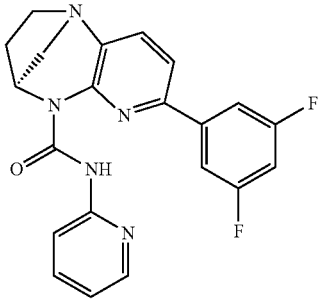 [SMILES: O=C(Nc1ccccn1)N1c2nc(-c3cc(F)cc(F)c3)ccc2N2CC[C@H]1C2] | A | A |
| 345 | 402 | 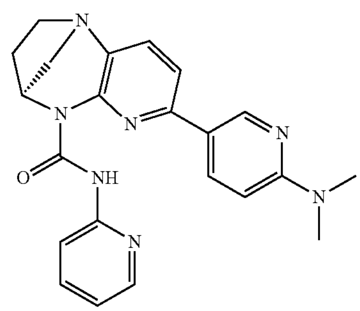 [SMILES: CN(C)c1ccc(-c2ccc3c(n2)N(C(=O)Nc2ccccn2)[C@H]2CCN3C2)cn1] | B | A |
| 346 | 389 | 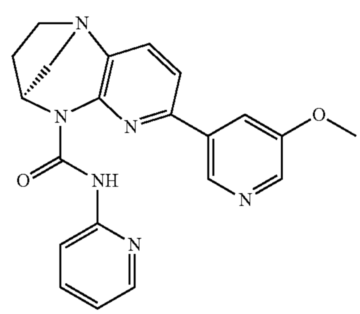 [SMILES: COc1cncc(-c2ccc3c(n2)N(C(=O)Nc2ccccn2)[C@H]2CCN3C2)c1] | B | A |
| 347 | 426 | 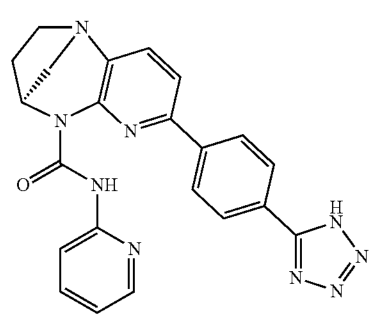 [SMILES: O=C(Nc1ccccn1)N1c2nc(-c3ccc(-c4nnn[nH]4)cc3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 348 | 397 | 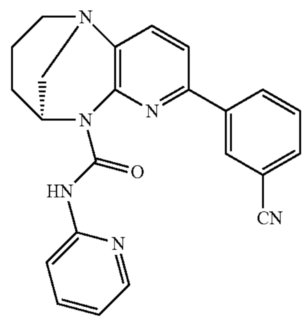 [SMILES: N#Cc1cccc(-c2ccc3c(n2)N(C(=O)Nc2ccccn2)[C@H]2CCCN3C2)c1] | A | A |
| 349 | 362 | 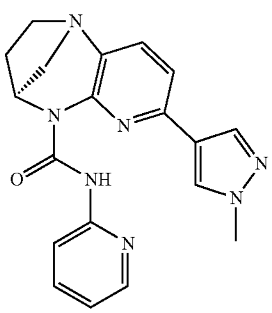 [SMILES: Cn1cc(-c2ccc3c(n2)N(C(=O)Nc2ccccn2)[C@H]2CCN3C2)cn1] | B | A |
| 350 | 397 | 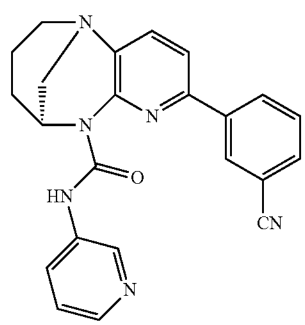 [SMILES: N#Cc1cccc(-c2ccc3c(n2)N(C(=O)Nc2cccnc2)[C@H]2CCCN3C2)c1] | A | A |
| 351 | 398 | 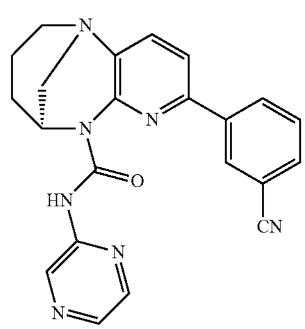 [SMILES: N#Cc1cccc(-c2ccc3c(n2)N(C(=O)Nc2cnccn2)[C@H]2CCCN3C2)c1] | A | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 352 | 398 | 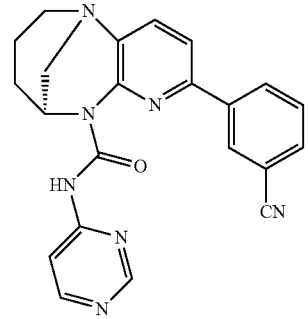 [SMILES: N#Cc1cccc(-c2ccc3c(n2)N(C(=O)Nc2ccncn2)[C@H]2CCCN3C2)c1] | A | A |
| 353 | 415 | 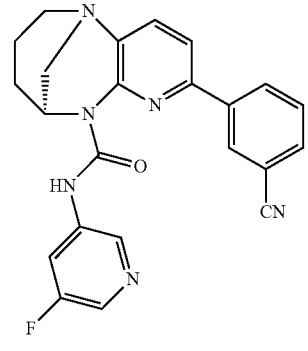 [SMILES: N#Cc1cccc(-c2ccc3c(n2)N(C(=O)Nc2cncc(F)c2)[C@H]2CCCN3C2)c1] | A | A |
| 354 | 432 | 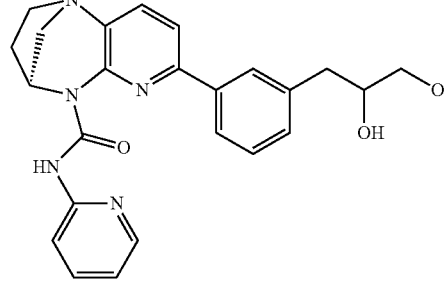 | A | A |
| 355 | 463 | 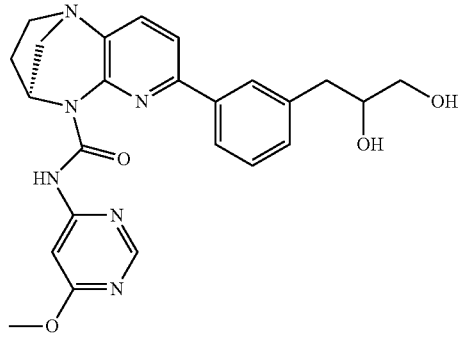 [SMILES: COc1cc(NC(=O)N2c3nc(-c4cccc(CC(O)CO)c4)ccc3N3CC[C@H]2C3)ncn1] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 356 | 450 | 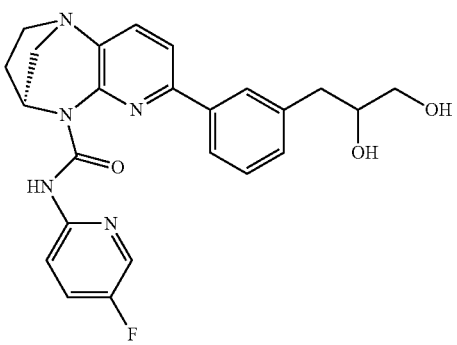 [SMILES: O=C(Nc1ccc(F)cn1)N1c2nc(-c3cccc(CC(O)CO)c3)ccc2N2CC[C@H]1C2] | A | A |
| 357 | 450 | 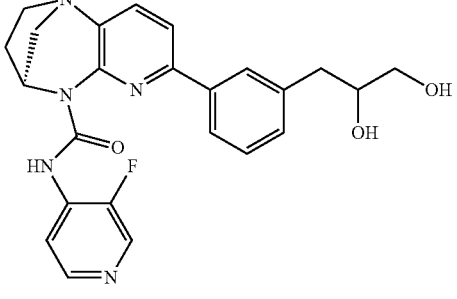 | B | A |
| 358 | 408 | 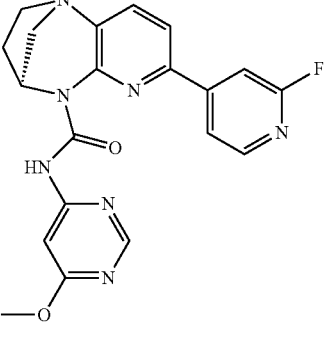 | C | B |
| 359 | 465 | 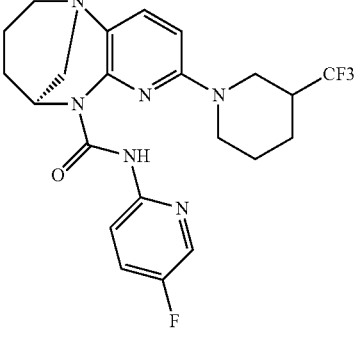 | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 360 | 447 | 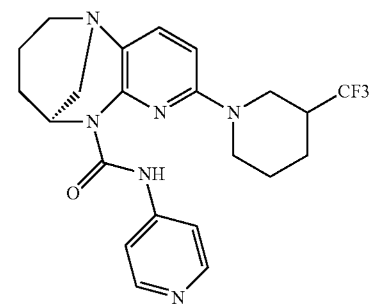 [SMILES: O=C(Nc1ccncc1)N1c2nc(N3CCCC(C(F)(F)F)C3)ccc2N2CCC[C@H]1C2] | A | A |
| 361 | 464 | 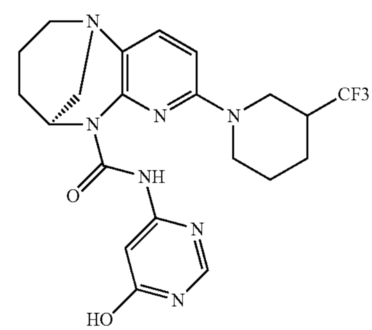 [SMILES: O=C(Nc1cc(O)ncn1)N1c2nc(N3CCCC(C(F)(F)F)C3)ccc2N2CCC[C@H]1C2] | A | A |
| 362 | 465 | 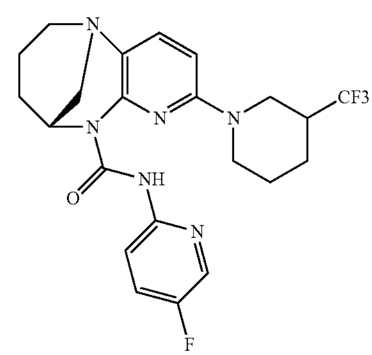 [SMILES: O=C(Nc1ccc(F)cn1)N1c2nc(N3CCCC(C(F)(F)F)C3)ccc2N2CCC[C@@H]1C2] | C | A |
| 363 | 495 | 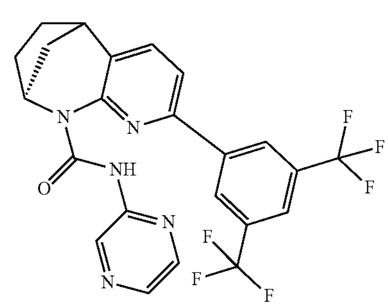 [SMILES: O=C(Nc1cnccn1)N1c2nc(-c3cc(C(F)(F)F)cc(C(F)(F)F)c3)ccc2C2CC[C@H]1C2] | B | A |

TABLE 1-continued

Compounds of Formula (I).

| Compound No. | [M + H]+[calc] | Structure | Tryp AVG EC1.5 (μM) | Tryp % Fold Act |
|---|---|---|---|---|
| 364 | 427 | 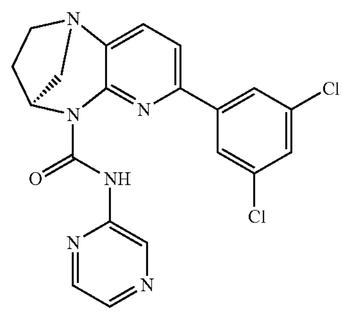 [SMILES: O=C(Nc1cnccn1)N1c2nc(-c3cc(Cl)cc(Cl)c3)ccc2N2CC[C@H]1C2] | B | A |
| 365 | 458 | 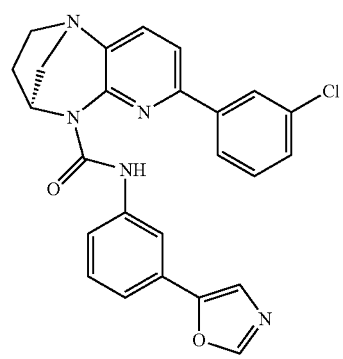 [SMILES: O=C(Nc1cccc(-c2cnco2)c1)N1c2nc(-c3cccc(Cl)c3)ccc2N2CC[C@H]1C2] | A | A |
| 366 | 458 | 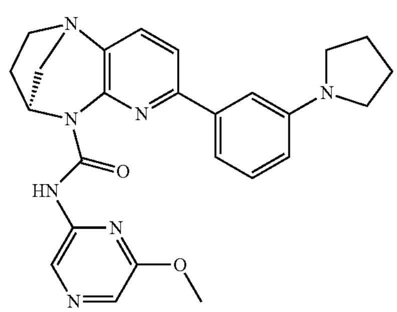 [SMILES: COc1cncc(NC(=O)N2c3nc(-c4cccc(N5CCCC5)c4)ccc3N3CC[C@H]2C3)n1] | A | A |
| 367 | 496 | 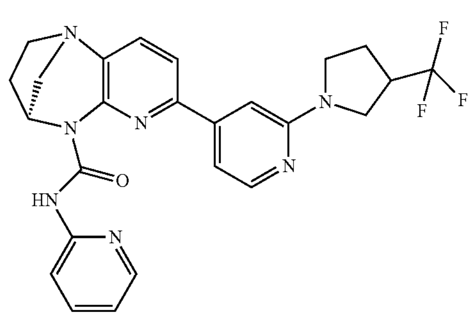 [SMILES: O=C(Nc1ccccn1)N1c2nc(-c3ccnc(N4CCC(C(F)(F)F)C4)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 368 | 527 | 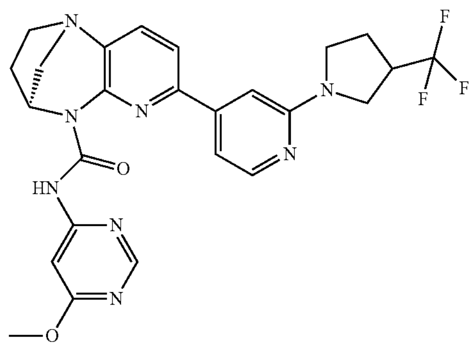 [SMILES: COc1cc(NC(=O)N2c3nc(-c4ccnc(N5CCC(C(F)(F)F)C5)c4)ccc3N3CC[C@H]2C3)ncn1] | B | A |
| 369 | 441 | 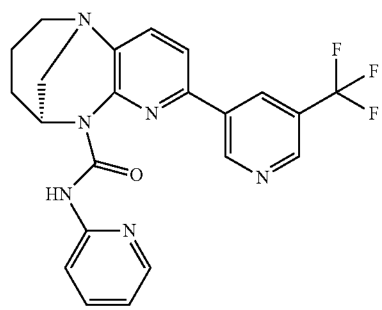 [SMILES: O=C(Nc1ccccn1)N1c2nc(-c3cncc(C(F)(F)F)c3)ccc2N2CCC[C@H]1C2] | A | A |
| 370 | 362 | 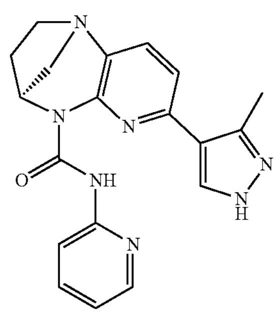 [SMILES: Cc1n[nH]cc1-c1ccc2c(n1)N(C(=O)Nc1ccccn1)[C@H]1CCN2C1] | B | A |
| 371 | 402 | 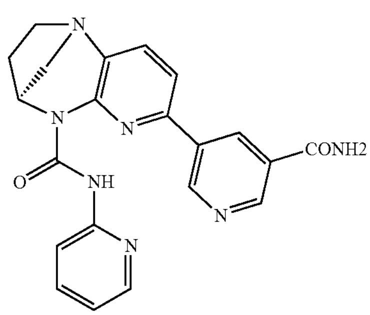 [SMILES: NC(=O)c1cncc(-c2ccc3c(n2)N(C(=O)Nc2ccccn2)[C@H]2CCN3C2)c1] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 372 | 400 | 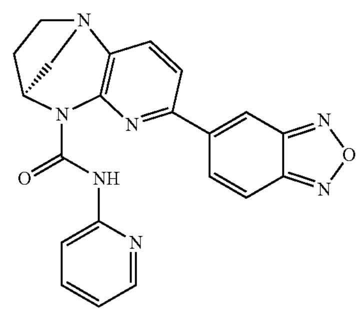 [SMILES: O=C(Nc1ccccn1)N1c2nc(-c3ccc4nonc4c3)ccc2N2CC[C@H]1C2] | B | A |
| 373 | 384 | 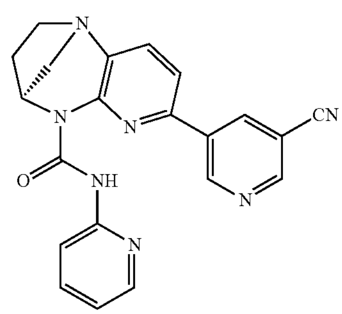 [SMILES: N#Cc1cncc(-c2ccc3c(n2)N(C(=O)Nc2ccccn2)[C@H]2CCN3C2)c1] | A | A |
| 374 | 377 | 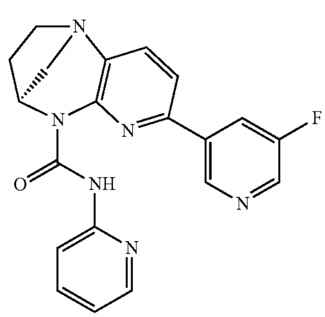 [SMILES: O=C(Nc1ccccn1)N1c2nc(-c3cncc(F)c3)ccc2N2CC[C@H]1C2] | B | A |
| 375 | 451 | 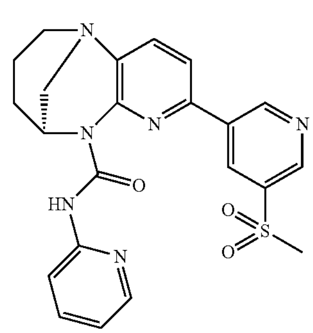 [SMILES: CS(=O)(=O)c1cncc(-c2ccc3c(n2)N(C(=O)Nc2ccccn2)[C@H]2CCCN3C2)c1] | A | A |

татЬLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 376 | 451 | 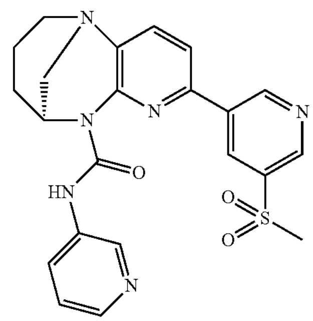 [SMILES: CS(=O)(=O)c1cncc(-c2ccc3c(n2)N(C(=O)Nc2cccnc2)[C@H]2CCCN3C2)c1] | A | A |
| 377 | 469 | 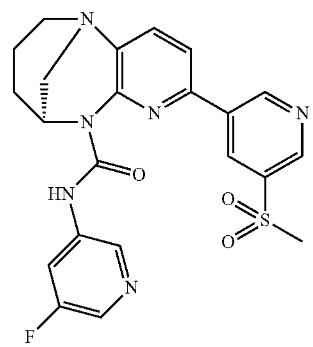 [SMILES: CS(=O)(=O)c1cncc(-c2ccc3c(n2)N(C(=O)Nc2cncc(F)c2)[C@H]2CCCN3C2)c1] | A | A |
| 378 | 452 | 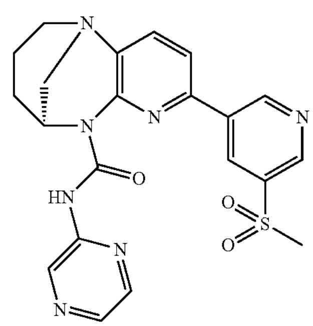 [SMILES: CS(=O)(=O)c1cncc(-c2ccc3c(n2)N(C(=O)Nc2cnccn2)[C@H]2CCCN3C2)c1] | A | A |
| 379 | 452 | 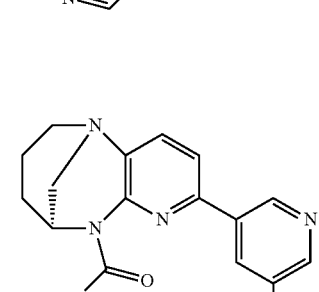 | A | A |

TABLE 1-continued

Compounds of Formula (I).

| Compound No. | [M + H]+_[calc] | Structure | Tryp AVG EC_{1.5} (μM) | Tryp % Fold Act |
|---|---|---|---|---|
| 380 | 452 | 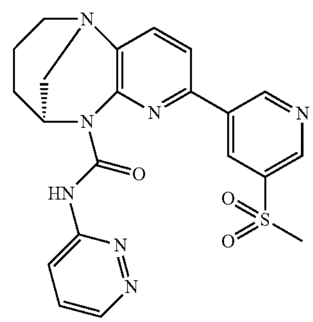 [SMILES: CS(=O)(=O)c1cncc(-c2ccc3c(n2)N(C(=O)Nc2cccnn2)[C@H]2CCCN3C2)c1] | A | A |
| 381 | 398 | 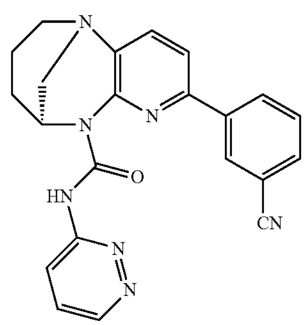 [SMILES: N#Cc1cccc(-c2ccc3c(n2)N(C(=O)Nc2cccnn2)[C@H]2CCCN3C2)c1] | B | A |
| 382 | 495 | 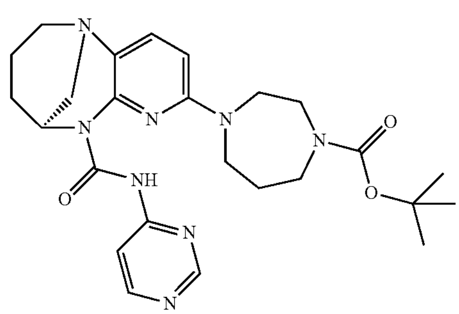 [SMILES: CC(C)(C)OC(=O)N1CCCN(c2ccc3c(n2)N(C(=O)Nc2ccncn2)[C@H]2CCCN3C2)CC1] | C | B |
| 383 | 449 | 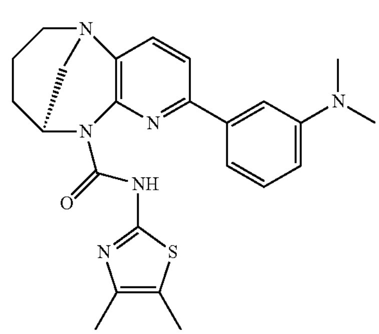 [SMILES: Cc1nc(NC(=O)N2c3nc(-c4cccc(N(C)C)c4)ccc3N3CCC[C@H]2C3)sc1C] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 384 | 433 | 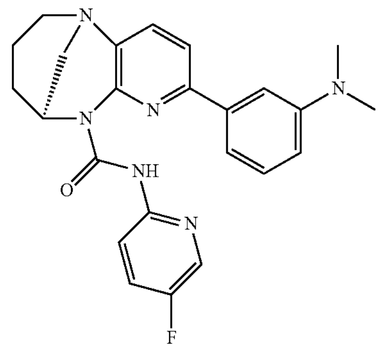 [SMILES: CN(C)c1cccc(-c2ccc3c(n2)N(C(=O)Nc2ccc(F)cn2)[C@H]2CCCN3C2)c1] | B | A |
| 385 | 446 | 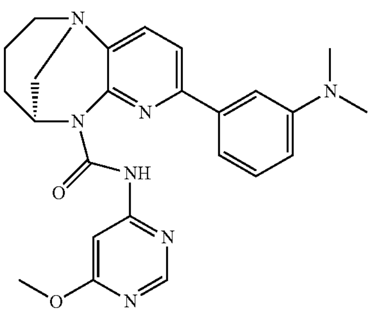 [SMILES: COc1cc(NC(=O)N2c3nc(-c4cccc(N(C)C)c4)ccc3N3CCC[C@H]2C3)ncn1] | A | A |
| 386 | 415 | 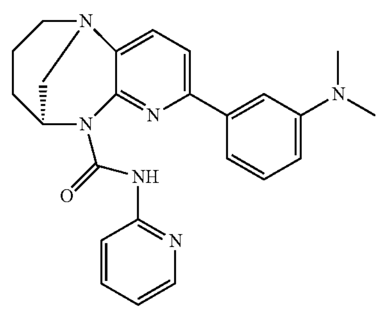 [SMILES: CN(C)c1cccc(-c2ccc3c(n2)N(C(=O)Nc2ccccn2)[C@H]2CCCN3C2)c1] | B | A |
| 387 | 406 | 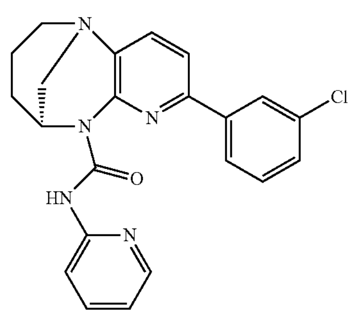 [SMILES: O=C(Nc1ccccn1)N1c2nc(-c3cccc(Cl)c3)ccc2N2CCC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 388 | 464 | 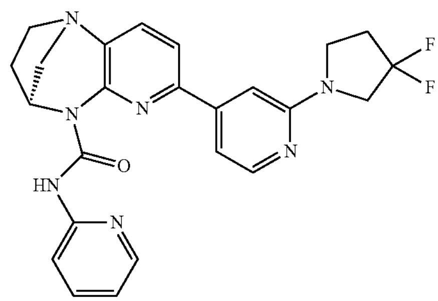 [SMILES: O=C(Nc1ccccn1)N1c2nc(-c3ccnc(N4CCC(F)(F)C4)c3)ccc2N2CC[C@H]1C2] | A | A |
| 389 | 497 | 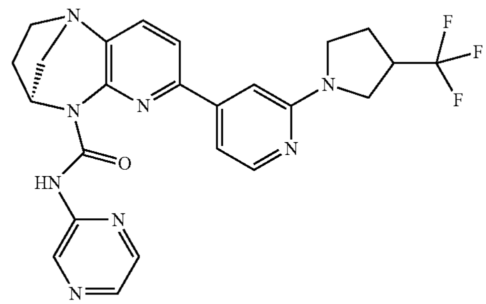 [SMILES: O=C(Nc1cnccn1)N1c2nc(-c3ccnc(N4CCC(C(F)(F)F)C4)c3)ccc2N2CC[C@H]1C2] | A | A |
| 390 | 495 | 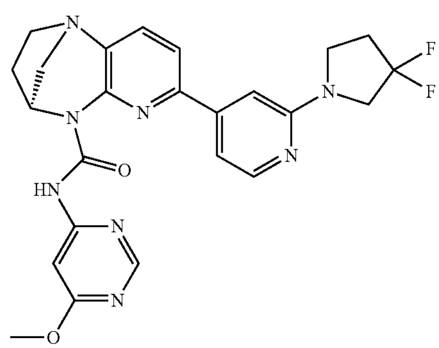 [SMILES: COc1cc(NC(=O)N2c3nc(-c4ccnc(N5CCC(F)(F)C5)c4)ccc3N3CC[C@H]2C3)ncn1] | B | A |
| 391 | 514 | 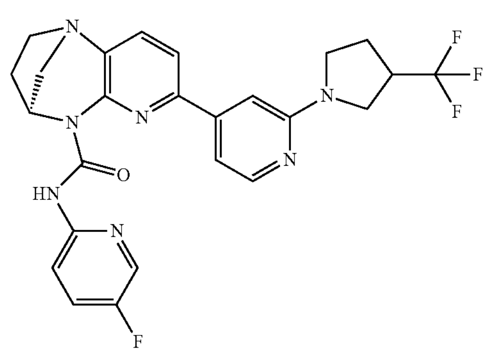 [SMILES: O=C(Nc1ccc(F)cn1)N1c2nc(-c3ccnc(N4CCC(C(F)(F)F)C4)c3)ccc2N2CC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 392 | 441 | 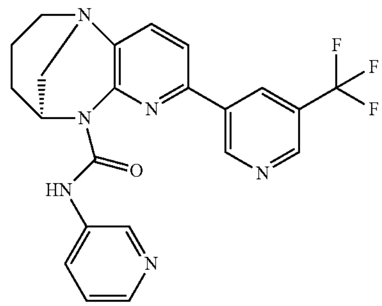 [SMILES: O=C(Nc1cccnc1)N1c2nc(-c3cncc(C(F)(F)F)c3)ccc2N2CCC[C@H]1C2] | A | A |
| 393 | 442 | 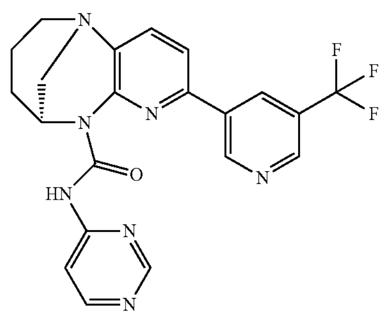 [SMILES: O=C(Nc1ccncn1)N1c2nc(-c3cncc(C(F)(F)F)c3)ccc2N2CCC[C@H]1C2] | A | A |
| 394 | 472 | 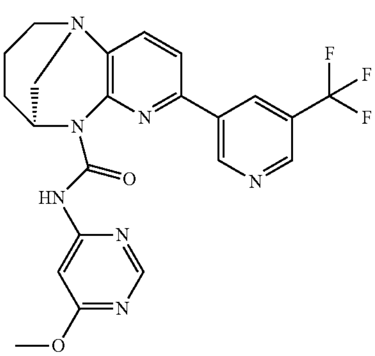 [SMILES: COc1cc(NC(=O)N2c3nc(-c4cncc(C(F)(F)F)c4)ccc3N3CCC[C@H]2C3)ncn1] | A | A |
| 395 | 362 | 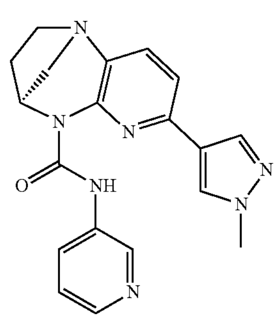 [SMILES: Cn1cc(-c2ccc3c(n2)N(C(=O)Nc2cccnc2)[C@H]2CCN3C2)cn1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 396 | 423 | 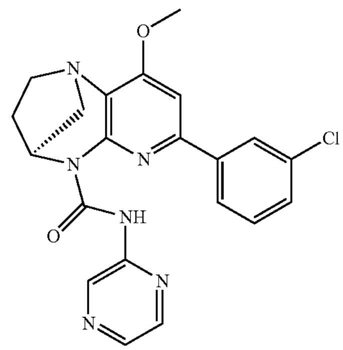 [SMILES: COc1cc(-c2cccc(Cl)c2)nc2c1N1CC[C@@H](C1)N2C(=O)Nc1cnccn1] | A | A |
| 397 | 395 | 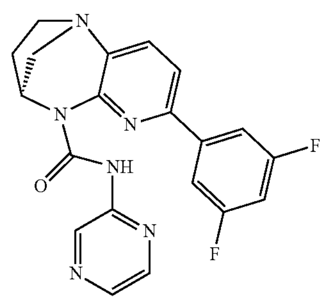 [SMILES: O=C(Nc1cnccn1)N1c2nc(-c3cc(F)cc(F)c3)ccc2N2CC[C@H]1C2] | C | A |
| 398 | 421 | 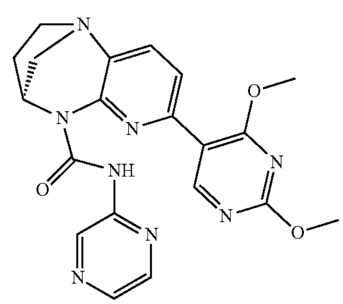 [SMILES: COc1ncc(-c2ccc3c(n2)N(C(=O)Nc2cnccn2)[C@H]2CCN3C2)c(OC)n1] | B | A |
| 399 | 390 | 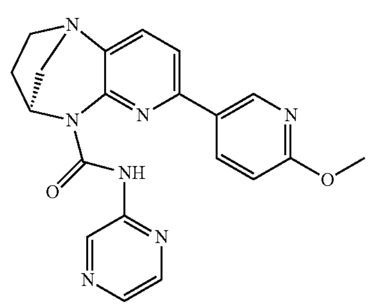 [SMILES: COc1ccc(-c2ccc3c(n2)N(C(=O)Nc2cnccn2)[C@H]2CCN3C2)cn1] | B | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 400 | 378 | 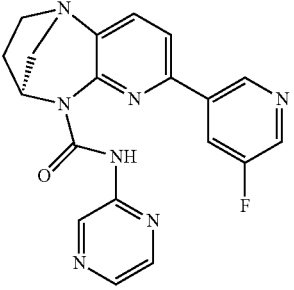 [SMILES: O=C(Nc1cnccn1)N1c2nc(-c3cncc(F)c3)ccc2N2CC[C@H]1C2] | B | A |
| 401 | 425 | 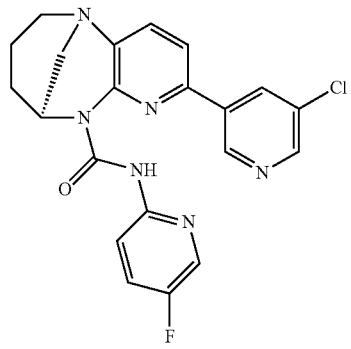 [SMILES: O=C(Nc1ccc(F)cn1)N1c2nc(-c3cncc(Cl)c3)ccc2N2CCC[C@H]1C2] | A | A |
| 402 | 441 | 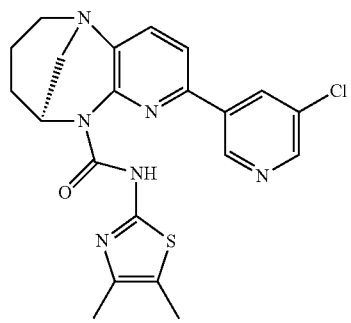 [SMILES: Cc1nc(NC(=O)N2c3nc(-c4cncc(Cl)c4)ccc3N3CCC[C@H]2C3)sc1C] | A | A |
| 403 | 416 | 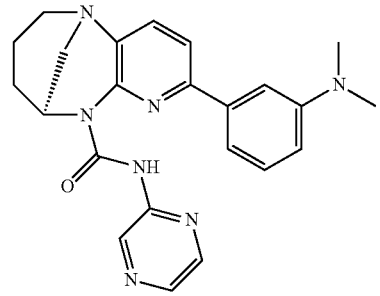 [SMILES: CN(C)c1cccc(-c2ccc3c(n2)N(C(=O)Nc2cnccn2)[C@H]2CCCN3C2)c1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 404 | 422 | 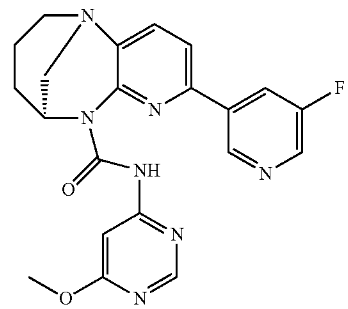 [SMILES: COc1cc(NC(=O)N2c3nc(-c4cncc(F)c4)ccc3N3CCC[C@H]2C3)ncn1] | A | A |
| 405 | 438 | 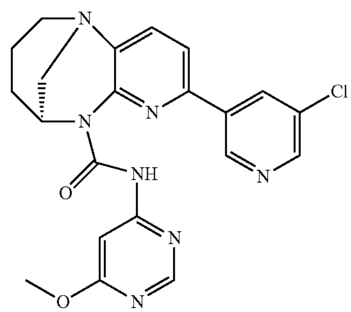 [SMILES: COc1cc(NC(=O)N2c3nc(-c4cncc(Cl)c4)ccc3N3CCC[C@H]2C3)ncn1] | A | A |
| 406 | 407 | 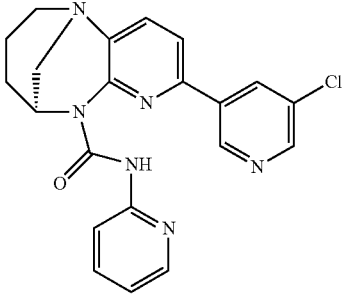 [SMILES: O=C(Nc1ccccn1)N1c2nc(-c3cncc(Cl)c3)ccc2N2CCC[C@H]1C2] | A | A |
| 407 | 406 | 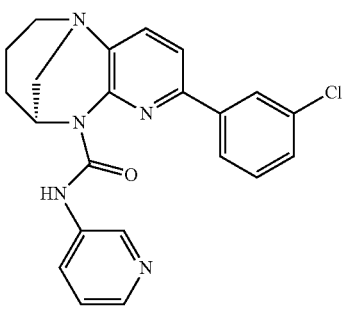 [SMILES: O=C(Nc1cccnc1)N1c2nc(-c3cccc(Cl)c3)ccc2N2CCC[C@H]1C2] | A | A |

TABLE 1-continued

Compounds of Formula (I).

| Compound No. | [M + H]+$_{calc}$ | Structure | Tryp AVG EC$_{1.5}$ (μM) | Tryp % Fold Act |
|---|---|---|---|---|
| 408 | 437 | 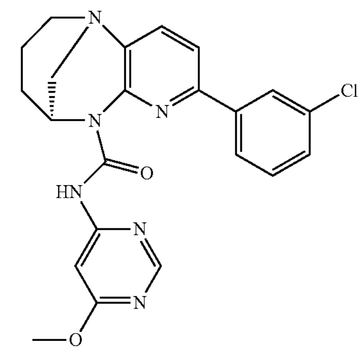 [SMILES: COc1cc(NC(=O)N2c3nc(-c4cccc(Cl)c4)ccc3N3CCC[C@H]2C3)ncn1] | A | A |
| 409 | 406 | 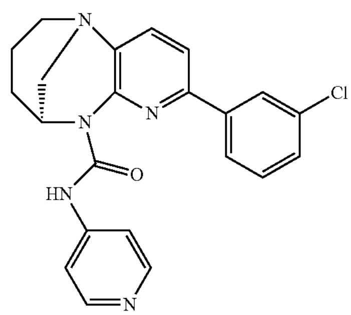 [SMILES: O=C(Nc1ccncc1)N1c2nc(-c3cccc(Cl)c3)ccc2N2CCC[C@H]1C2] | A | A |
| 410 | 514 | 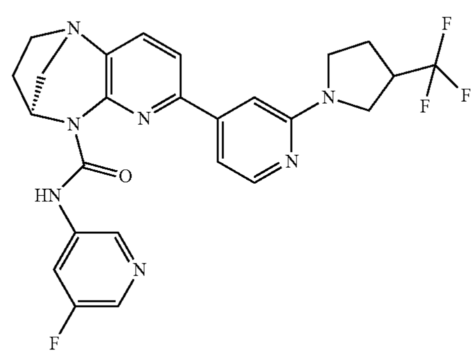 [SMILES: O=C(Nc1cncc(F)c1)N1c2nc(-c3ccnc(N4CCC(C(F)(F)F)C4)c3)ccc2N2CC[C@H]1C2] | A | A |
| 411 | 459 | 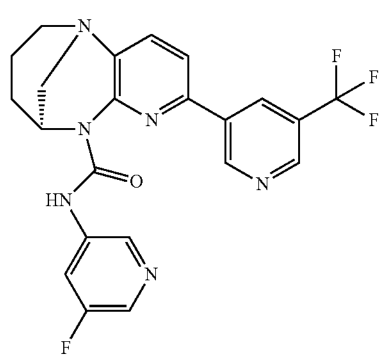 [SMILES: O=C(Nc1cncc(F)c1)N1c2nc(-c3cncc(C(F)(F)F)c3)ccc2N2CCC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 412 | 442 | 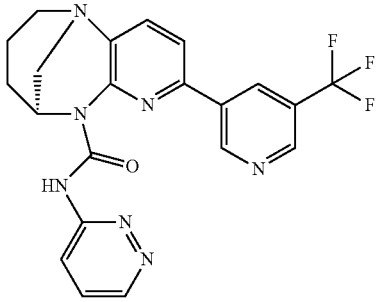 [SMILES: O=C(Nc1cccnn1)N1c2nc(-c3cncc(C(F)(F)F)c3)ccc2N2CCC[C@H]1C2] | A | A |
| 413 | 378 | 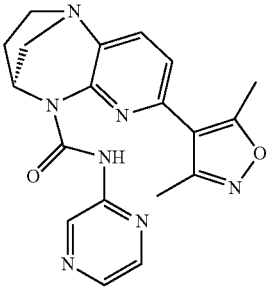 [SMILES: Cc1noc(C)c1-c1ccc2c(n1)N(C(=O)Nc1cnccn1)[C@H]1CCN2C1] | C | B |
| 414 | 363 | 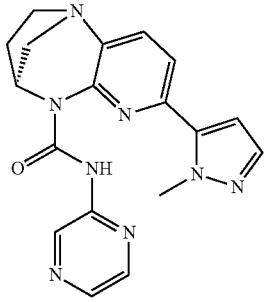 [SMILES: Cn1nccc1-c1ccc2c(n1)N(C(=O)Nc1cnccn1)[C@H]1CCN2C1] | B | A |
| 415 | 437 | 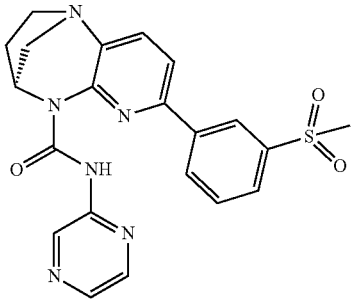 [SMILES: CS(=O)(=O)c1cccc(-c2ccc3c(n2)N(C(=O)Nc2cnccn2)[C@H]2CCN3C2)c1] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 416 | 413 | 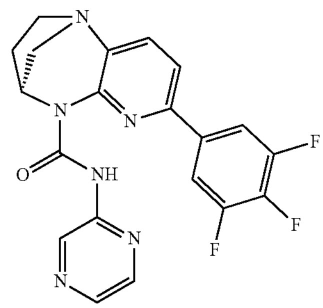 [SMILES: O=C(Nc1cnccn1)N1c2nc(-c3cc(F)c(F)c(F)c3)ccc2N2CC[C@H]1C2] | C | B |
| 417 | 408 | 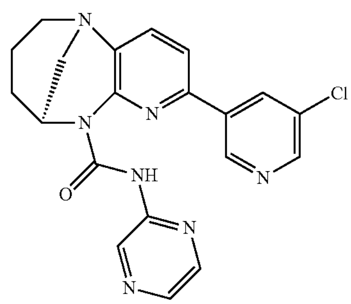 [SMILES: O=C(Nc1cnccn1)N1c2nc(-c3cncc(Cl)c3)ccc2N2CCC[C@H]1C2] | A | A |
| 418 | 452 | 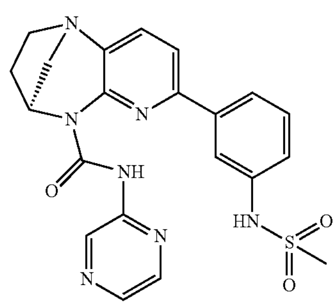 [SMILES: CS(=O)(=O)Nc1cccc(-c2ccc3c(n2)N(C(=O)Nc2cnccn2)[C@H]2CCN3C2)c1] | B | A |
| 419 | 402 | 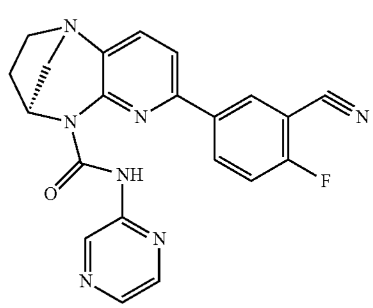 [SMILES: N#Cc1cc(-c2ccc3c(n2)N(C(=O)Nc2cnccn2)[C@H]2CCN3C2)ccc1F] | A | A |

TABLE 1-continued

Compounds of Formula (I).

| Compound No. | [M + H]+<sub>[calc]</sub> | Structure | Tryp AVG EC<sub>1.5</sub> (μM) | Tryp % Fold Act |
|---|---|---|---|---|
| 420 | 395 | 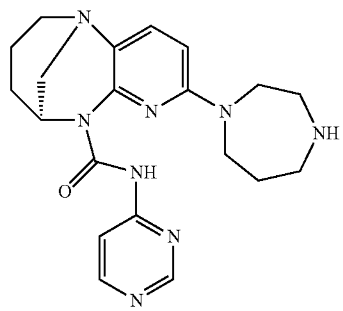 [SMILES: O=C(Nc1ccncn1)N1c2nc(N3CCCNCC3)ccc2N2CCC[C@H]1C2] | C | B |
| 421 | 424 | 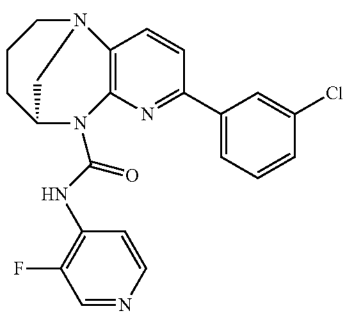 [SMILES: O=C(Nc1ccncc1F)N1c2nc(-c3cccc(Cl)c3)ccc2N2CCC[C@H]1C2] | A | A |
| 422 | 446 | 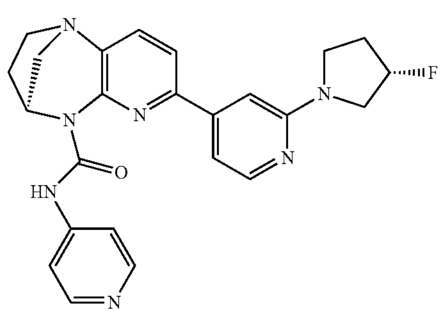 [SMILES: O=C(Nc1ccncc1)N1c2nc(-c3ccnc(N4CC[C@H](F)C4)c3)ccc2N2CC[C@H]1C2] | A | A |
| 423 | 465 | 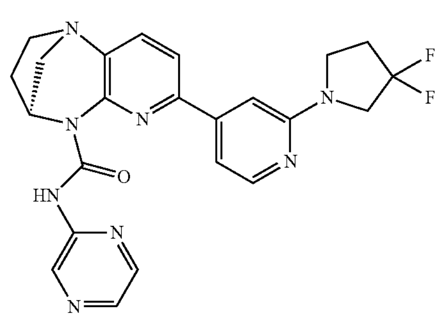 | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 424 | 477 | 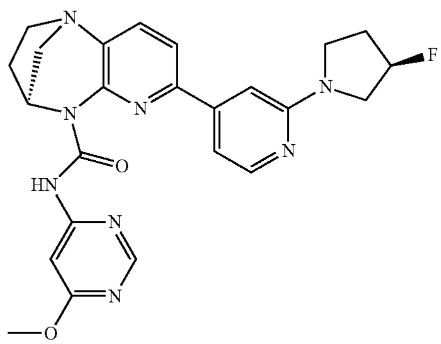 [SMILES: COc1cc(NC(=O)N2c3nc(-c4ccnc(N5CC[C@@H](F)C5)c4)ccc3N3CC[C@H]2C3)ncn1] | B | A |
| 425 | 482 | 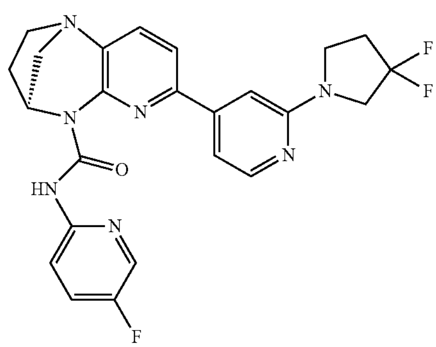 [SMILES: O=C(Nc1ccc(F)cn1)N1c2nc(-c3ccnc(N4CCC(F)(F)C4)c3)ccc2N2CC[C@H]1C2] | A | A |
| 426 | 398 | 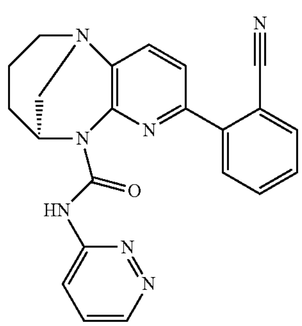 [SMILES: N#Cc1ccccc1-c1ccc2c(n1)N(C(=O)Nc1cccnn1)[C@H]1CCCN2C1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 427 | 475 | 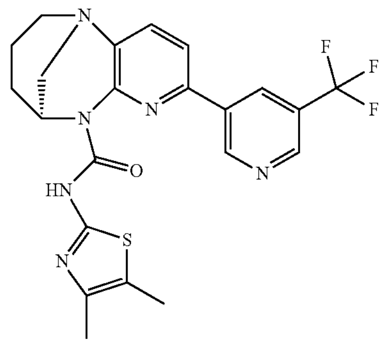 [SMILES: Cc1nc(NC(=O)N2c3nc(-c4cncc(C(F)(F)F)c4)ccc3N3CCC[C@H]2C3)sc1C] | A | A |
| 428 | 793 | 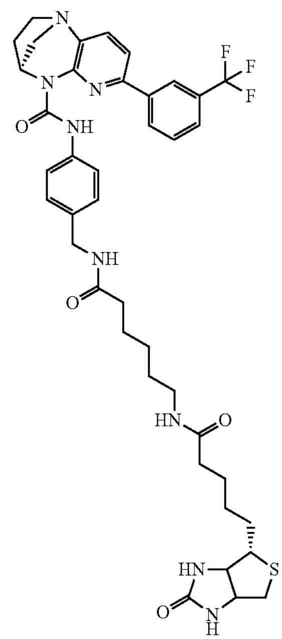 [SMILES: O=C(CCCC[C@@H]1SCC2NC(=O)NC21)NCCCCCC(=O)NCc1ccc(NC(=O)N2c3nc(-c4cccc(C(F)(F)F)c4)ccc3N3CC[C@H]2C3)cc1] | A | A |
| 429 | 454 | 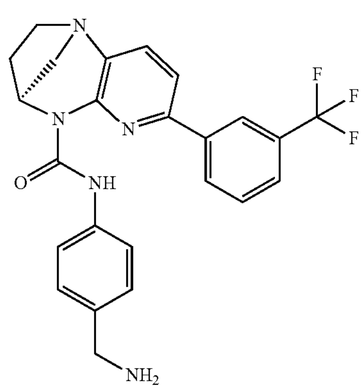 [SMILES: NCc1ccc(NC(=O)N2c3nc(-c4cccc(C(F)(F)F)c4)ccc3N3CC[C@H]2C3)cc1] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 430 | 807 | 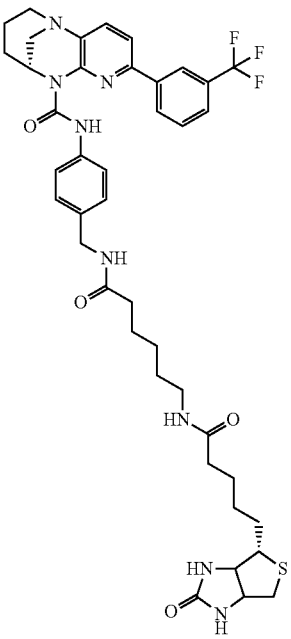 [SMILES: O=C(CCCC[C@@H]1SCC2NC(=O)NC21)NCCCCCC(=O)NCc1ccc(NC(=O)N2c3nc(-c4cccc(C(F)(F)F)c4)ccc3N3CCC[C@H]2C3)cc1] | A | A |
| 431 | 409 | 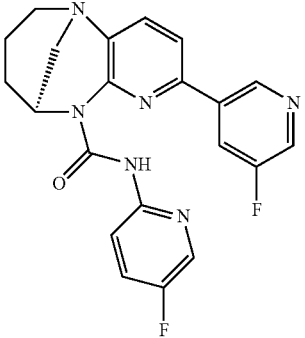 [SMILES: O=C(Nc1ccc(F)cn1)N1c2nc(-c3cncc(F)c3)ccc2N2CCC[C@H]1C2] | A | A |
| 432 | 392 | 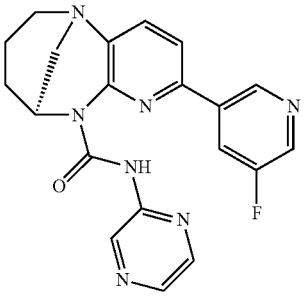 [SMILES: O=C(Nc1cnccn1)N1c2nc(-c3cncc(F)c3)ccc2N2CCC[C@H]1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 433 | 473 | 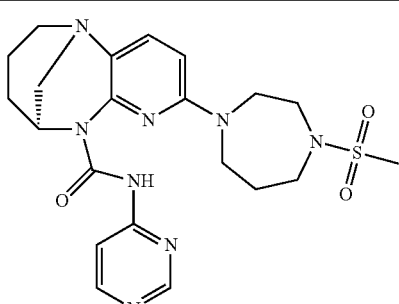 | B | A |
| 434 | 437 | 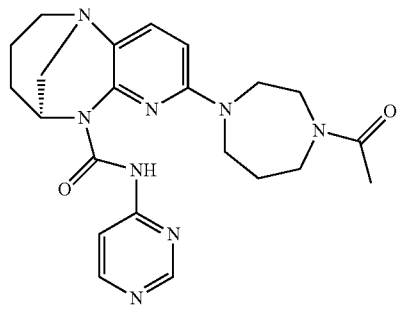 [SMILES: CC(=O)N1CCCN(c2ccc3c(n2)N(C(=O)Nc2ccncn2)[C@H]2CCCN3C2)CC1] | C | B |
| 435 | 461 | 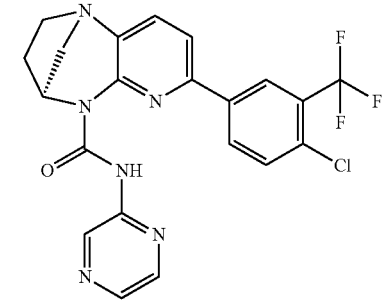 [SMILES: O=C(Nc1cnccn1)N1c2nc(-c3ccc(Cl)c(C(F)(F)F)c3)ccc2N2CC[C@H]1C2] | A | A |
| 436 | 447 | 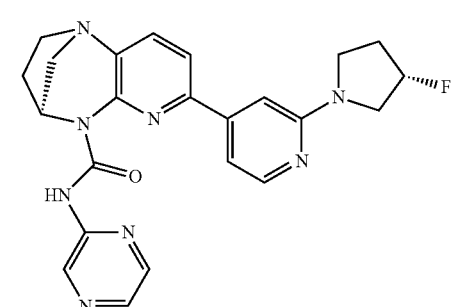 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 437 | 477 | 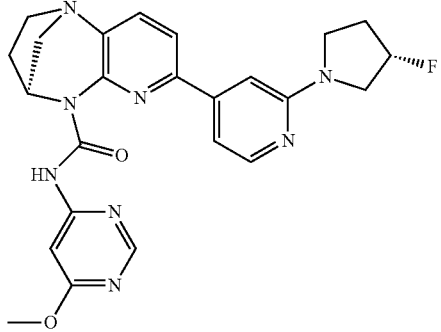 [SMILES: COc1cc(NC(=O)N2c3nc(-c4ccnc(N5CC[C@H](F)C5)c4)ccc3N3CC[C@H]2C3)ncn1] | B | A |
| 438 | 397 | 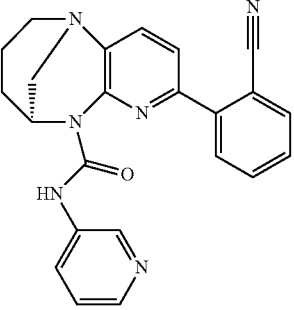 [SMILES: N#Cc1ccccc1-c1ccc2c(n1)N(C(=O)Nc1cccnc1)[C@H]1CCCN2C1] | B | A |
| 439 | 415 | 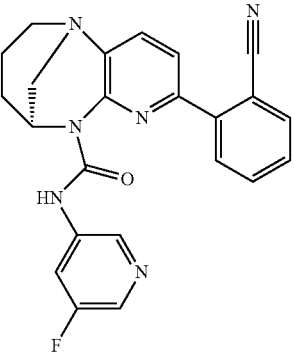 [SMILES: N#Cc1ccccc1-c1ccc2c(n1)N(C(=O)Nc1cncc(F)c1)[C@H]1CCCN2C1] | B | A |
| 440 | 428 | 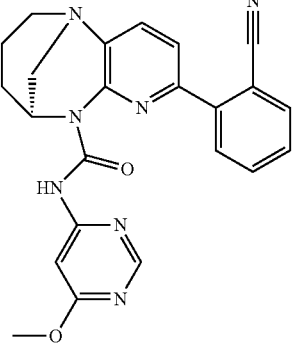 | C | B |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 441 | 373 | 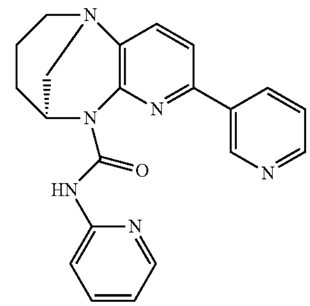 [SMILES: O=C(Nc1ccccn1)N1c2nc(-c3cccnc3)ccc2N2CCC[C@H]1C2] | B | A |
| 442 | 404 | 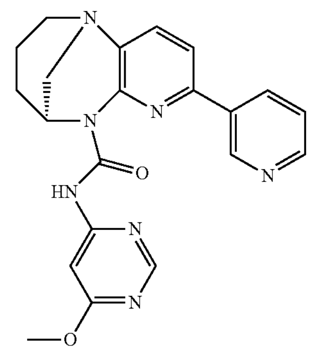 [SMILES: COc1cc(NC(=O)N2c3nc(-c4cccnc4)ccc3N3CCC[C@H]2C3)ncn1] | B | A |
| 443 | 409 | 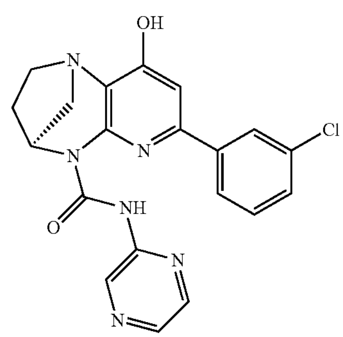 [SMILES: O=C(Nc1cnccn1)N1c2nc(-c3cccc(Cl)c3)cc(O)c2N2CC[C@H]1C2] | B | A |
| 444 (4) | 468 | 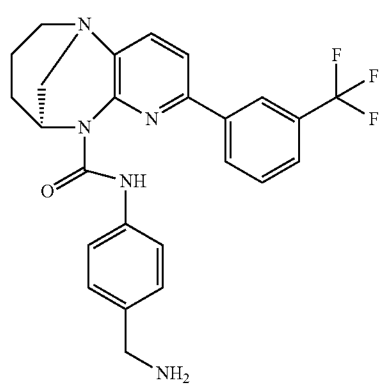 [SMILES: NCc1ccc(NC(=O)N2c3nc(-c4cccc(C(F)(F)F)c4)ccc3N3CCC[C@H]2C3)cc1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 445 | 568 | 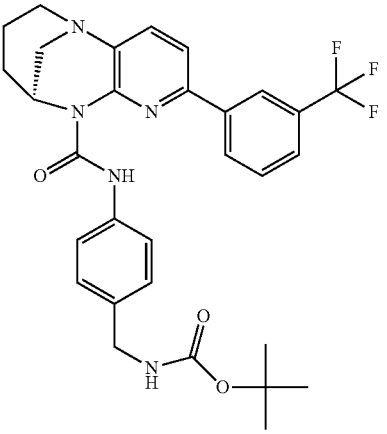 [SMILES: CC(C)(C)OC(=O)NCc1ccc(NC(=O)N2c3nc(-c4cccc(C(F)(F)F)c4)ccc3N3CCC[C@H]2C3)cc1] | A | A |
| 446 | 453 | 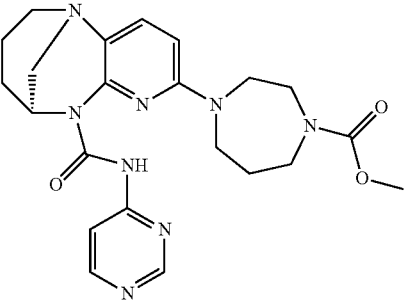 [SMILES: COC(=O)N1CCCN(c2ccc3c(n2)N(C(=O)Nc2ccncn2)[C@H]2CCCN3C2)CC1] | B | A |
| 447 | 437 | 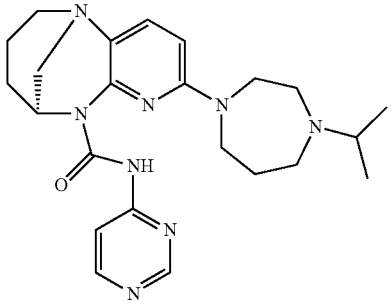 [SMILES: CC(C)N1CCCN(c2ccc3c(n2)N(C(=O)Nc2ccncn2)[C@H]2CCCN3C2)CC1] | C | B |
| 448 | 446 | 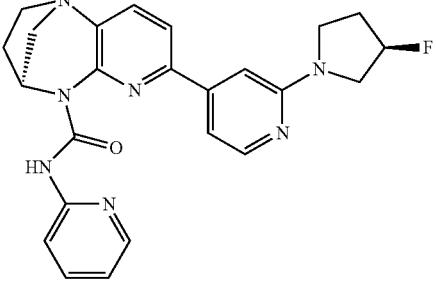 | B | A |

TABLE 1-continued

Compounds of Formula (I).

| Compound No. | [M + H]+[calc] | Structure | Tryp AVG EC₁.₅ (μM) | Tryp % Fold Act |
|---|---|---|---|---|
| 449 | 397 | 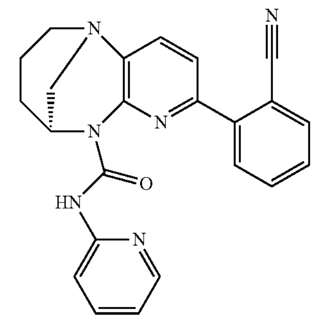 [SMILES: N#Cc1ccccc1-c1ccc2c(n1)N(C(=O)Nc1ccccn1)[C@H]1CCCN2C1] | B | A |
| 450 | 398 | 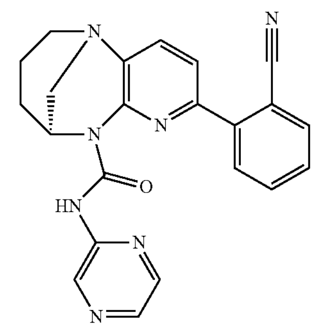 [SMILES: N#Cc1ccccc1-c1ccc2c(n1)N(C(=O)Nc1cnccn1)[C@H]1CCCN2C1] | B | A |
| 451 | 398 | 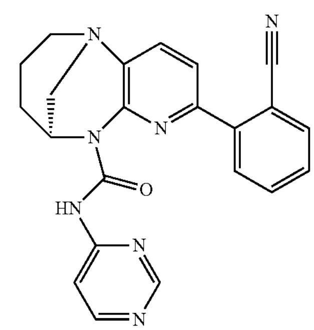 [SMILES: N#Cc1ccccc1-c1ccc2c(n1)N(C(=O)Nc1ccncn1)[C@H]1CCCN2C1] | B | A |
| 452 | 442 | 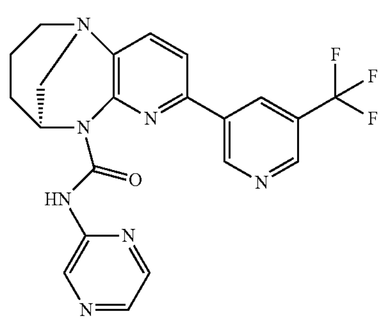 [SMILES: O=C(Nc1cnccn1)N1c2nc(-c3cncc(C(F)(F)F)c3)ccc2N2CCC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 453 | 391 | 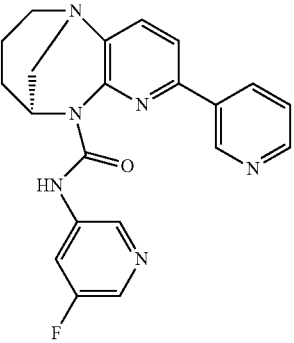 [SMILES: O=C(Nc1cncc(F)c1)N1c2nc(-c3cccnc3)ccc2N2CCC[C@H]1C2] | B | A |
| 454 | 374 | 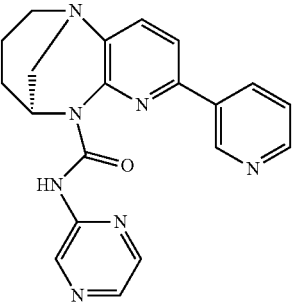 [SMILES: O=C(Nc1cnccn1)N1c2nc(-c3cccnc3)ccc2N2CCC[C@H]1C2] | B | A |
| 455 | 373 | 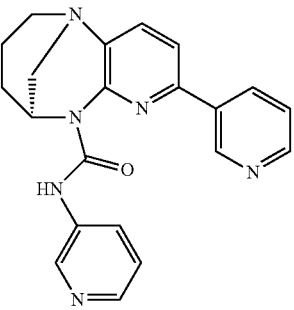 [SMILES: O=C(Nc1cccnc1)N1c2nc(-c3cccnc3)ccc2N2CCC[C@H]1C2] | B | A |
| 456 | 374 | 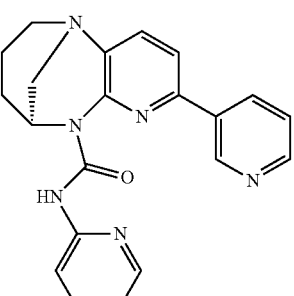 | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 457 | 374 | 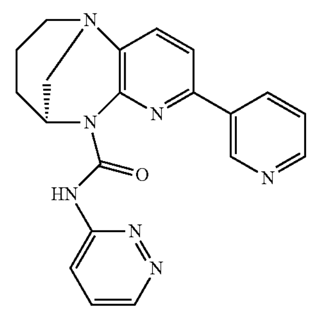 [SMILES: O=C(Nc1cccnn1)N1c2nc(-c3cccnc3)ccc2N2CCC[C@H]1C2] | B | A |
| 458 | 403 | 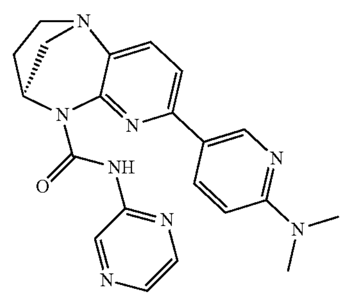 [SMILES: CN(C)c1ccc(-c2ccc3c(n2)N(C(=O)Nc2cnccn2)[C@H]2CCN3C2)cn1] | B | A |
| 459 | 385 | 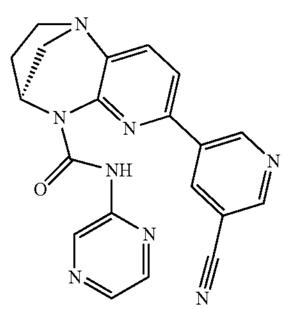 [SMILES: N#Cc1cncc(-c2ccc3c(n2)N(C(=O)Nc2cnccn2)[C@H]2CCN3C2)c1] | A | A |
| 460 | 508 | 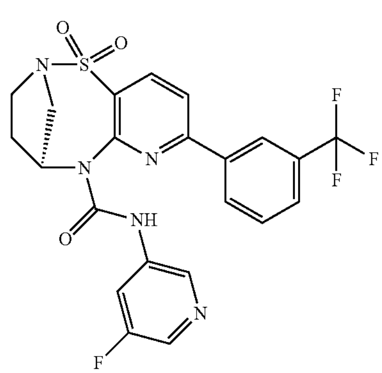 [SMILES: O=C(Nc1cncc(F)c1)N1c2nc(-c3cccc(C(F)(F)F)c3)ccc2S(=O)(=O)N2CC[C@H]1C2] | B | A |

TABLE 1-continued

Compounds of Formula (I).

| Compound No. | [M + H]+_[calc] | Structure | Tryp AVG EC_{1.5} (µM) | Tryp % Fold Act |
|---|---|---|---|---|
| 461 | 427 | 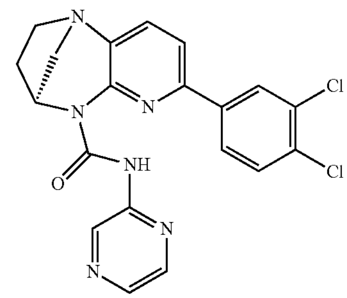 [SMILES: O=C(Nc1cnccn1)N1c2nc(-c3ccc(Cl)c(Cl)c3)ccc2N2CC[C@H]1C2] | A | A |
| 462 | 447 | 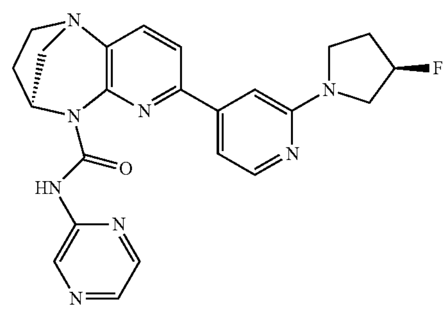 [SMILES: O=C(Nc1cnccn1)N1c2nc(-c3ccnc(N4CC[C@@H](F)C4)c3)ccc2N2CC[C@H]1C2] | B | A |
| 463 | 464 | 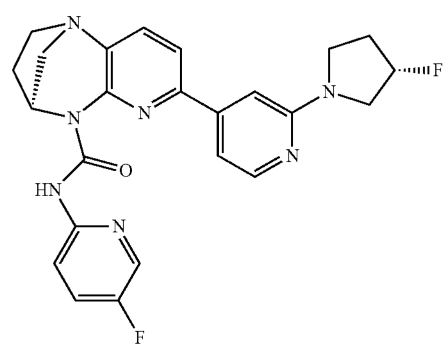 [SMILES: O=C(Nc1ccc(F)cn1)N1c2nc(-c3ccnc(N4CC[C@H](F)C4)c3)ccc2N2CC[C@H]1C2] | A | A |
| 464 | 464 | 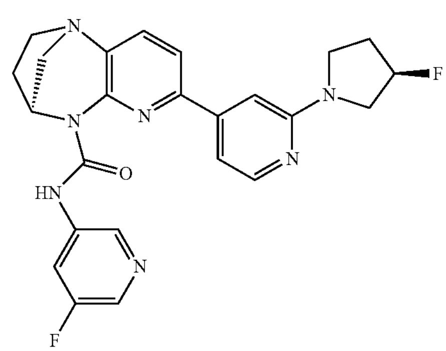 [SMILES: O=C(Nc1cncc(F)c1)N1c2nc(-c3ccnc(N4CC[C@@H](F)C4)c3)ccc2N2CC[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 465 | 387 | 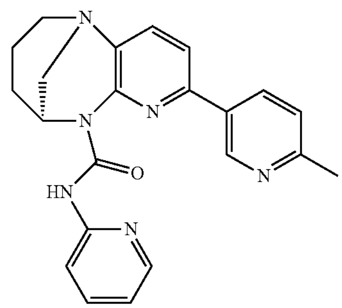 [SMILES: Cc1ccc(-c2ccc3c(n2)N(C(=O)Nc2ccccn2)[C@H]2CCCN3C2)cn1] | B | A |
| 466 | 407 | 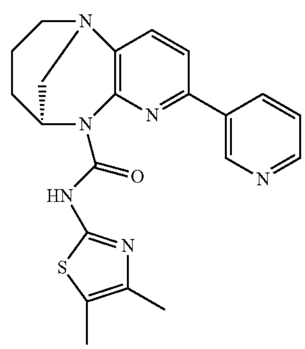 [SMILES: Cc1nc(NC(=O)N2c3nc(-c4cccnc4)ccc3N3CCC[C@H]2C3)sc1C] | B | A |
| 467 | 388 | 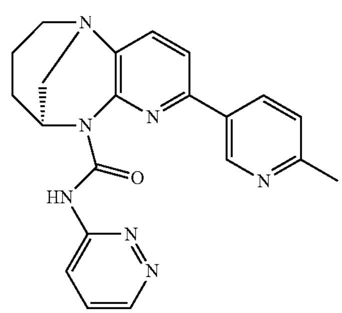 [SMILES: Cc1ccc(-c2ccc3c(n2)N(C(=O)Nc2cccnn2)[C@H]2CCCN3C2)cn1] | B | A |
| 468 | 374 | 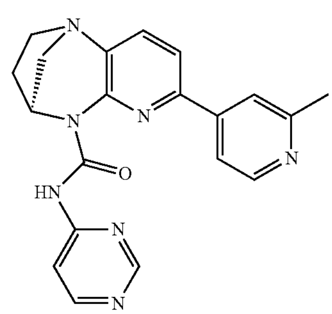 [SMILES: Cc1cc(-c2ccc3c(n2)N(C(=O)Nc2ccncn2)[C@H]2CCN3C2)ccn1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 469 | 451 | 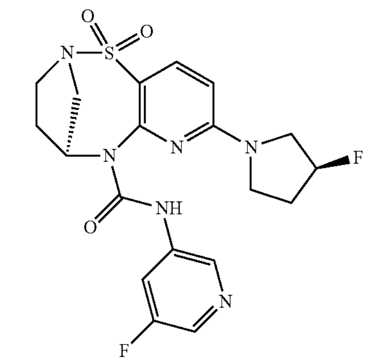 [SMILES: O=C(Nc1cncc(F)c1)N1c2nc(N3CC[C@H](F)C3)ccc2S(=O)(=O)N2CC[C@H]1C2] | C | B |
| 470 | 391 | 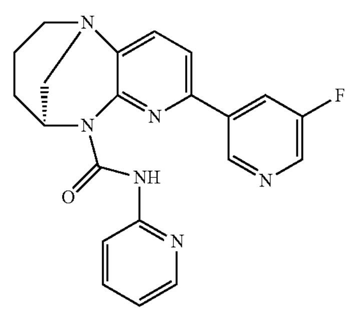 [SMILES: O=C(Nc1ccccn1)N1c2nc(-c3cncc(F)c3)ccc2N2CCC[C@H]1C2] | A | A |
| 471 | 425 | 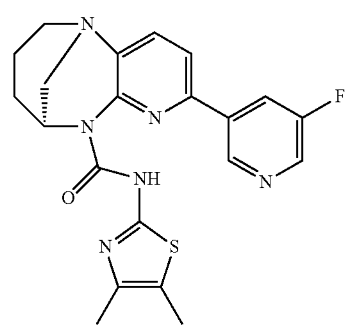 [SMILES: Cc1nc(NC(=O)N2c3nc(-c4cncc(F)c4)ccc3N3CCC[C@H]2C3)sc1C] | B | A |
| 472 | 441 | 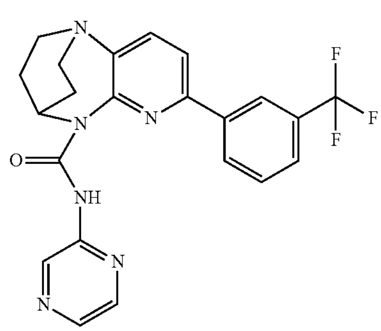 [SMILES: O=C(Nc1cnccn1)N1c2nc(-c3cccc(C(F)(F)F)c3)ccc2N2CCC1CC2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 473 | 506 | 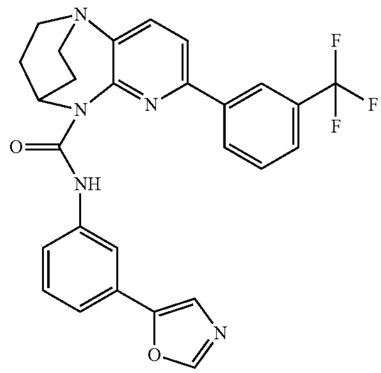 [SMILES: O=C(Nc1cccc(-c2cnco2)c1)N1c2nc(-c3cccc(C(F)(F)F)c3)ccc2N2CCC1CC2] | A | A |
| 474 | 464 | 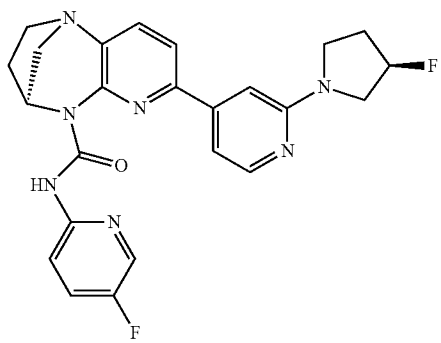 [SMILES: O=C(Nc1ccc(F)cn1)N1c2nc(-c3ccnc(N4CC[C@@H](F)C4)c3)ccc2N2CC[C@H]1C2] | A | A |
| 475 | 464 | 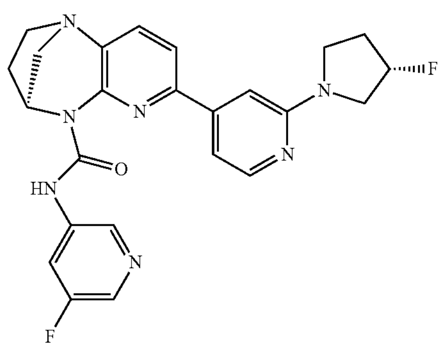 [SMILES: O=C(Nc1cncc(F)c1)N1c2nc(-c3ccnc(N4CC[C@H](F)C4)c3)ccc2N2CC[C@H]1C2] | A | A |
| 476 | 431 | 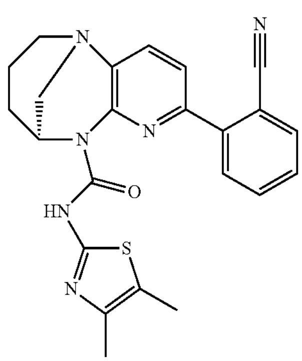 [SMILES: Cc1nc(NC(=O)N2c3nc(-c4ccccc4C#N)ccc3N3CCC[C@H]2C3)sc1C] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 477 | 405 | 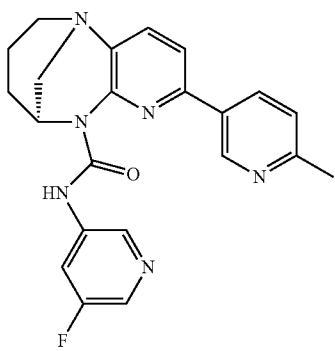 [SMILES: Cc1ccc(-c2ccc3c(n2)N(C(=O)Nc2cncc(F)c2)[C@H]2CCCN3C2)cn1] | B | A |
| 478 | 418 | 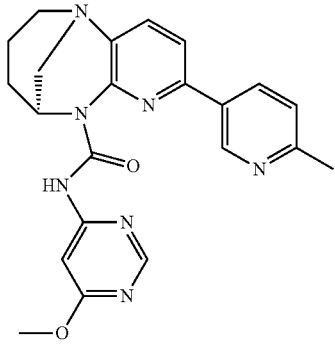 [SMILES: COc1cc(NC(=O)N2c3nc(-c4ccc(C)nc4)ccc3N3CCC[C@H]2C3)ncn1] | B | A |
| 479 | 388 | 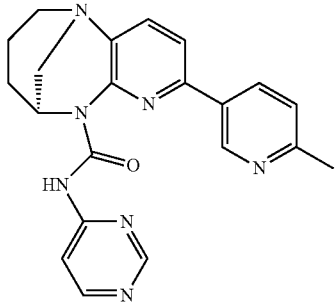 [SMILES: Cc1ccc(-c2ccc3c(n2)N(C(=O)Nc2ccncn2)[C@H]2CCCN3C2)cn1] | B | A |
| 480 | 439 | 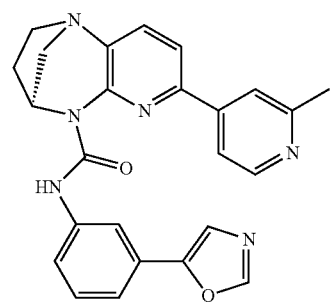 [SMILES: Cc1cc(-c2ccc3c(n2)N(C(=O)Nc2cccc(-c4cnco4)c2)[C@H]2CCN3C2)ccn1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 481 | 407 | 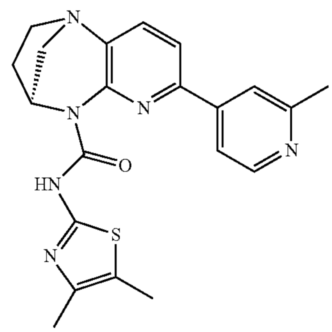 [SMILES: Cc1cc(-c2ccc3c(n2)N(C(=O)Nc2nc(C)c(C)s2)[C@H]2CCN3C2)ccn1] | A | A |
| 482 | 376 | 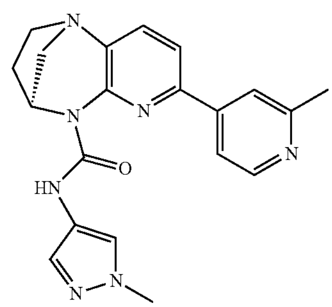 [SMILES: Cc1cc(-c2ccc3c(n2)N(C(=O)Nc2cnn(C)c2)[C@H]2CCN3C2)ccn1] | B | A |
| 483 | 426 | 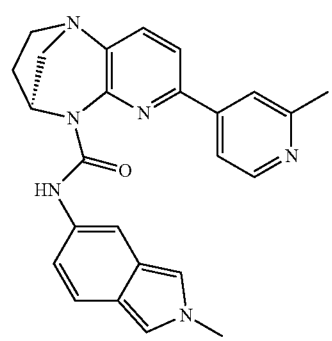 [SMILES: Cc1cc(-c2ccc3c(n2)N(C(=O)Nc2ccc4cn(C)cc4c2)[C@H]2CCN3C2)ccn1] | A | A |
| 484 | 409 | 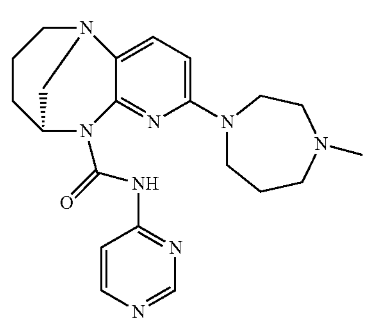 [SMILES: CN1CCCN(c2ccc3c(n2)N(C(=O)Nc2ccncn2)[C@H]2CCCN3C2)CC1] | C | B |

TABLE 1-continued

Compounds of Formula (I).

| Compound No. | [M + H]+[calc] | Structure | Tryp AVG EC$_{1.5}$ (µM) | Tryp % Fold Act |
|---|---|---|---|---|
| 485 | 440 | 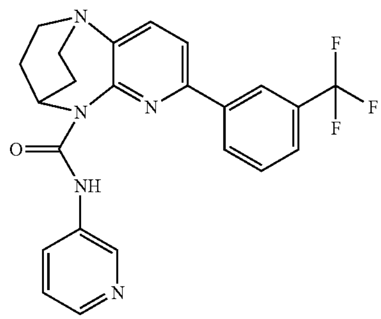 [SMILES: O=C(Nc1cccnc1)N1c2nc(-c3cccc(C(F)(F)F)c3)ccc2N2CCC1CC2] | A | A |
| 486 | 390 | 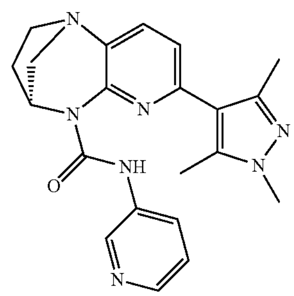 [SMILES: Cc1nn(C)c(C)c1-c1ccc2c(n1)N(C(=O)Nc1cccnc1)[C@H]1CCN2C1] | C | A |
| 487 | 390 | 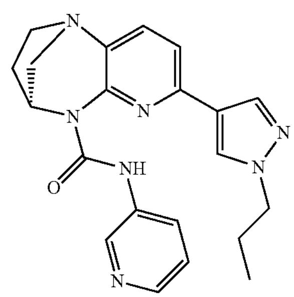 [SMILES: CCCn1cc(-c2ccc3c(n2)N(C(=O)Nc2cccnc2)[C@H]2CCN3C2)cn1] | B | A |
| 488 | 376 | 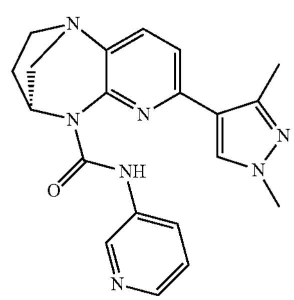 [SMILES: Cc1nn(C)cc1-c1ccc2c(n1)N(C(=O)Nc1cccnc1)[C@H]1CCN2C1] | B | A |
| 489 | 376 | 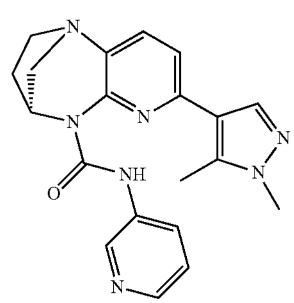 [SMILES: Cc1c(-c2ccc3c(n2)N(C(=O)Nc2cccnc2)[C@H]2CCN3C2)cnn1C] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 490 | 362 | 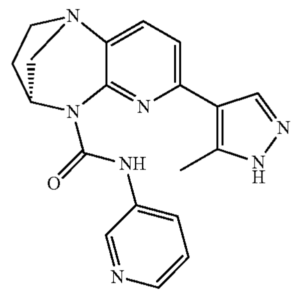 [SMILES: Cc1[nH]ncc1-c1ccc2c(n1)N(C(=O)Nc1cccnc1)[C@H]1CCN2C1] | B | A |
| 491 | 477 | 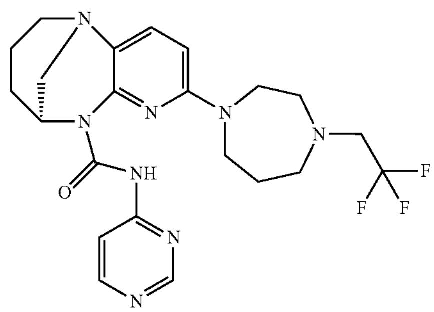 [SMILES: O=C(Nc1ccncn1)N1c2nc(N3CCCN(CC(F)(F)F)CC3)ccc2N2CCC[C@H]1C2] | A | A |
| 492 | 458 | 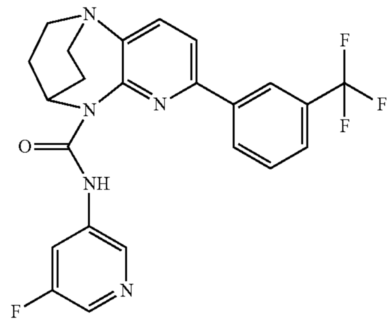 [SMILES: O=C(Nc1cncc(F)c1)N1c2nc(-c3cccc(C(F)(F)F)c3)ccc2N2CCC1CC2] | A | A |
| 493 | 348 | 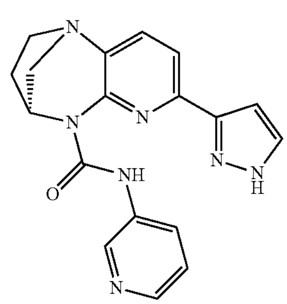 [SMILES: O=C(Nc1cccnc1)N1c2nc(-c3cc[nH]n3)ccc2N2CC[C@H]1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 494 | 390 | 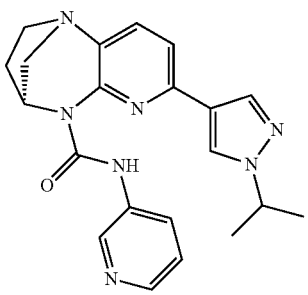 [SMILES: CC(C)n1cc(-c2ccc3c(n2)N(C(=O)Nc2cccnc2)[C@H]2CCN3C2)cn1] | B | A |
| 495 | 393 | 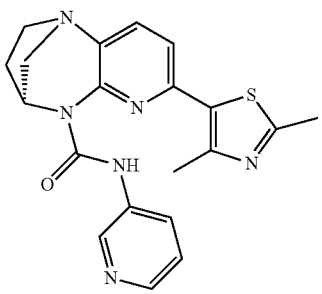 [SMILES: Cc1nc(C)c(-c2ccc3c(n2)N(C(=O)Nc2cccnc2)[C@H]2CCN3C2)s1] | B | A |
| 496 | 406 | 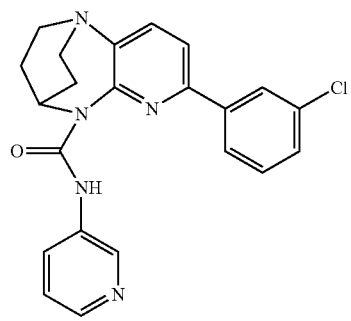 [SMILES: O=C(Nc1cccnc1)N1c2nc(-c3cccc(Cl)c3)ccc2N2CCC1CC2] | A | A |
| 497 | 472 | 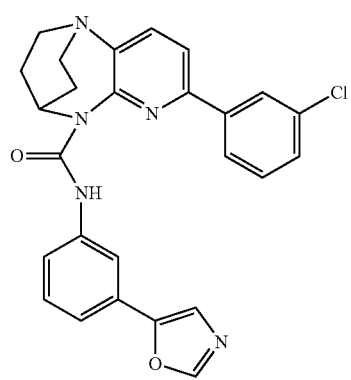 [SMILES: O=C(Nc1cccc(-c2cnco2)c1)N1c2nc(-c3cccc(Cl)c3)ccc2N2CCC1CC2] | A | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 498 | 373 | 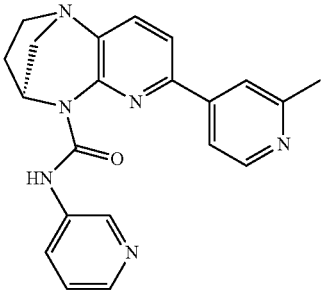 [SMILES: Cc1cc(-c2ccc3c(n2)N(C(=O)Nc2cccnc2)[C@H]2CCN3C2)ccn1] | A | A |
| 499 | 404 | 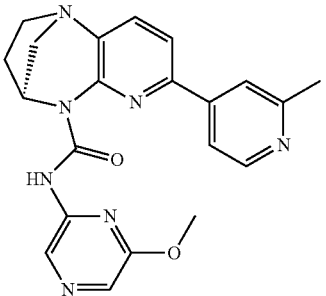 [SMILES: COc1cncc(NC(=O)N2c3nc(-c4ccnc(C)c4)ccc3N3CC[C@H]2C3)n1] | A | A |
| 500 | 404 | 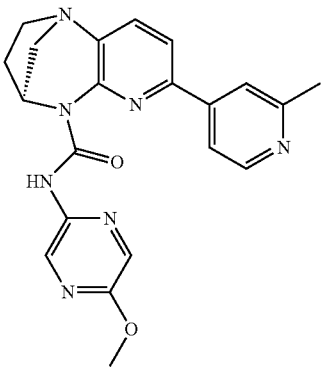 [SMILES: COc1cnc(NC(=O)N2c3nc(-c4ccnc(C)c4)ccc3N3CC[C@H]2C3)cn1] | A | A |
| 501 | 404 | 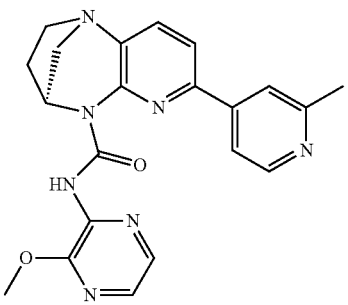 | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 502 | 426 | 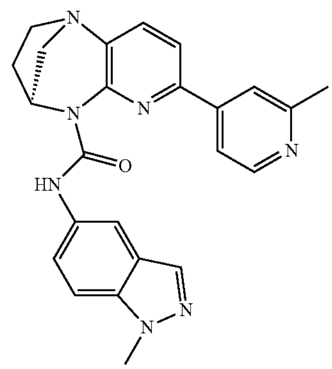 [SMILES: Cc1cc(-c2ccc3c(n2)N(C(=O)Nc2ccc4c(cnn4C)c2)[C@H]2CCN3C2)ccn1] | A | A |
| 503 | 388 | 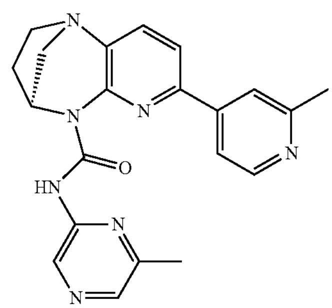 [SMILES: Cc1cc(-c2ccc3c(n2)N(C(=O)Nc2cncc(C)n2)[C@H]2CCN3C2)ccn1] | A | A |
| 504 | 387 | 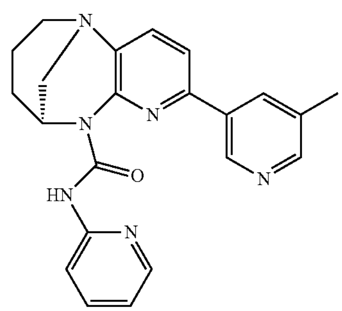 [SMILES: Cc1cncc(-c2ccc3c(n2)N(C(=O)Nc2ccccn2)[C@H]2CCCN3C2)c1] | A | A |
| 505 | 387 | 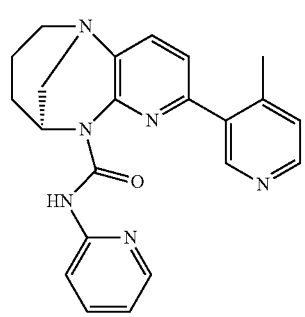 | C | B |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 506 | 421 | 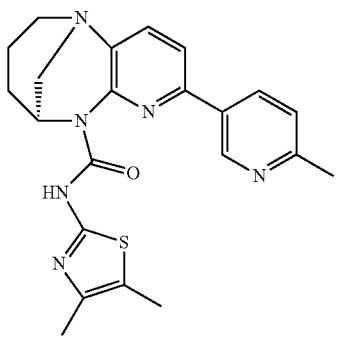 [SMILES: Cc1ccc(-c2ccc3c(n2)N(C(=O)Nc2nc(C)c(C)s2)[C@H]2CCCN3C2)cn1] | A | A |
| 507 | 421 | 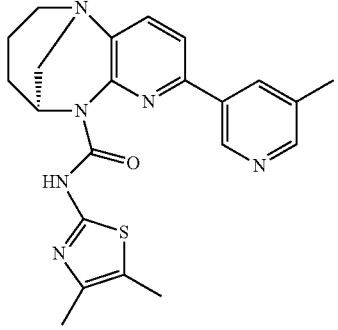 [SMILES: Cc1cncc(-c2ccc3c(n2)N(C(=O)Nc2nc(C)c(C)s2)[C@H]2CCCN3C2)c1] | A | A |
| 508 | 421 | 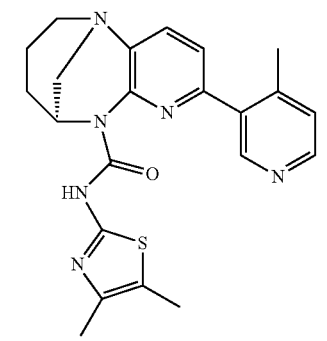 [SMILES: Cc1ccncc1-c1ccc2c(n1)N(C(=O)Nc1nc(C)c(C)s1)[C@H]1CCCN2C1] | C | A |
| 509 | 405 | 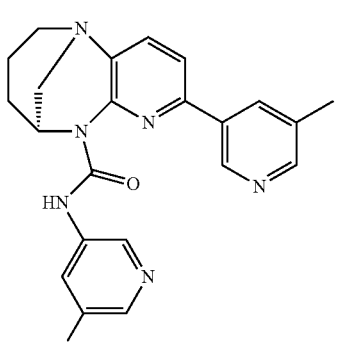 | A | A |

TABLE 1-continued

Compounds of Formula (I).

| Compound No. | $[M+H]+_{[calc]}$ | Structure | Tryp AVG $EC_{1.5}$ (μM) | Tryp % Fold Act |
|---|---|---|---|---|
| 510 | 405 | 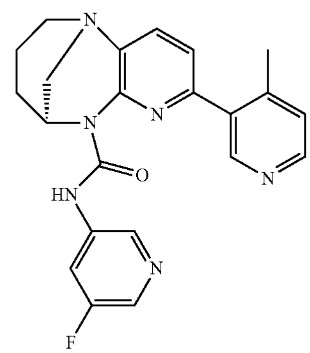 [SMILES: Cc1ccncc1-c1ccc2c(n1)N(C(=O)Nc1cncc(F)c1)[C@H]1CCCN2C1] | B | A |
| 511 | 418 | 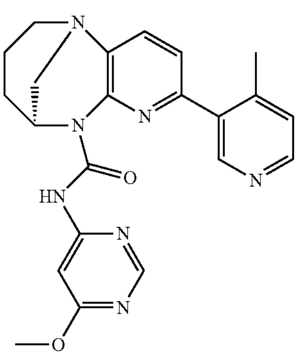 [SMILES: COc1cc(NC(=O)N2c3nc(-c4cnccc4C)ccc3N3CCC[C@H]2C3)ncn1] | C | B |
| 512 | 388 | 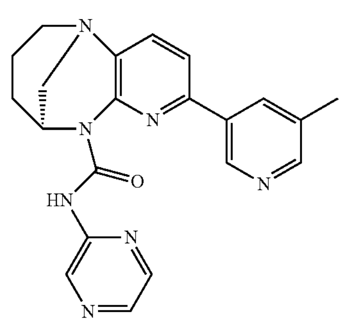 [SMILES: Cc1cncc(-c2ccc3c(n2)N(C(=O)Nc2cnccn2)[C@H]2CCCN3C2)c1] | B | A |
| 513 | 388 | 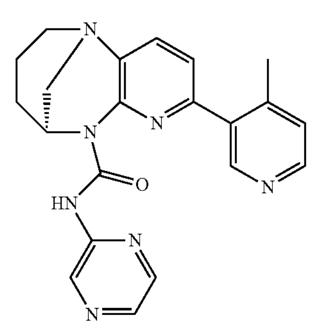 [SMILES: Cc1ccncc1-c1ccc2c(n1)N(C(=O)Nc1cnccn1)[C@H]1CCCN2C1] | C | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 514 | 387 | 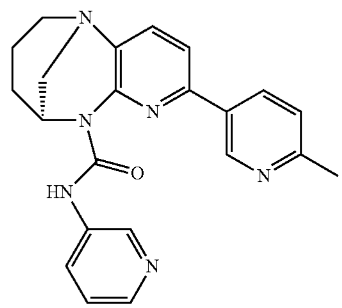 [SMILES: Cc1ccc(-c2ccc3c(n2)N(C(=O)Nc2cccnc2)[C@H]2CCCN3C2)cn1] | B | A |
| 515 | 387 | 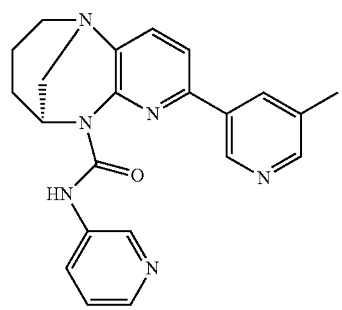 [SMILES: Cc1cncc(-c2ccc3c(n2)N(C(=O)Nc2cccnc2)[C@H]2CCCN3C2)c1] | A | A |
| 516 | 387 | 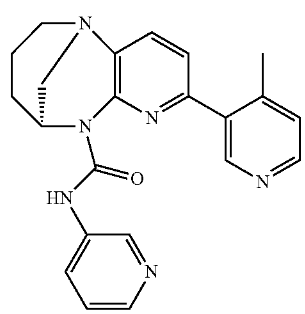 [SMILES: Cc1ccncc1-c1ccc2c(n1)N(C(=O)Nc1cccnc1)[C@H]1CCCN2C1] | B | A |
| 517 | 388 | 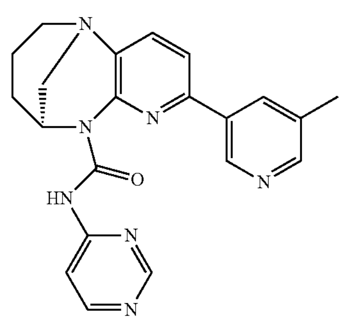 [SMILES: Cc1cncc(-c2ccc3c(n2)N(C(=O)Nc2ccncn2)[C@H]2CCCN3C2)c1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 518 | 388 | 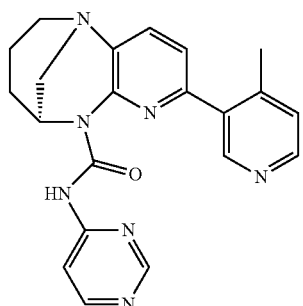 | C | B |
| 519 | 388 | 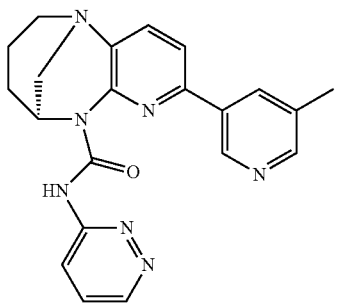 [SMILES: Cc1cncc(-c2ccc3c(n2)N(C(=O)Nc2cccnn2)[C@H]2CCCN3C2)c1] | A | A |
| 520 | 388 | 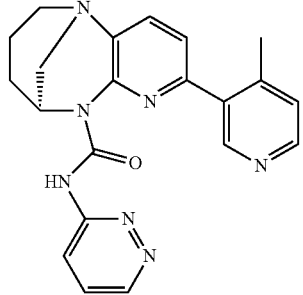 [SMILES: Cc1ccncc1-c1ccc2c(n1)N(C(=O)Nc1cccnn1)[C@H]1CCCN2C1] | C | A |
| 521 | 424 | 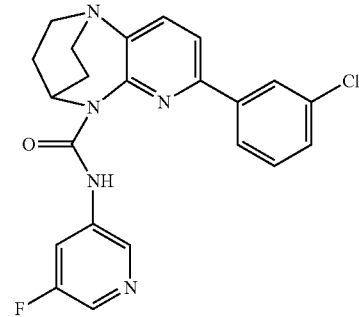 [SMILES: O=C(Nc1cncc(F)c1)N1c2nc(-c3cccc(Cl)c3)ccc2N2CCC1CC2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 522 | 437 | 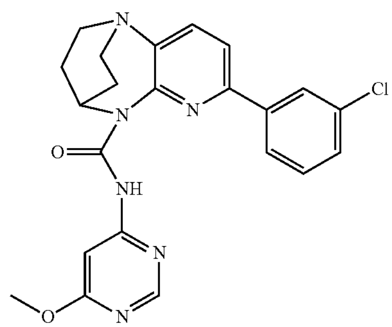 [SMILES: COc1cc(NC(=O)N2c3nc(-c4cccc(Cl)c4)ccc3N3CCC2CC3)ncn1] | B | A |
| 523 | 467 | 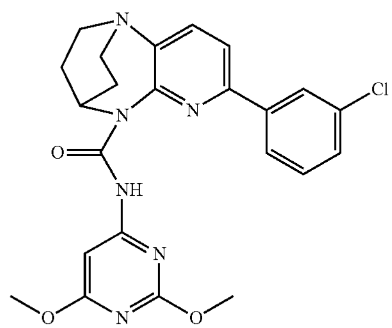 [SMILES: COc1cc(NC(=O)N2c3nc(-c4cccc(Cl)c4)ccc3N3CCC2CC3)nc(OC)n1] | A | A |
| 524 | 362 | 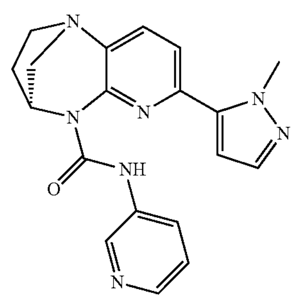 [SMILES: Cn1nccc1-c1ccc2c(n1)N(C(=O)Nc1cccnc1)[C@H]1CCN2C1] | B | A |
| 525 | 376 | 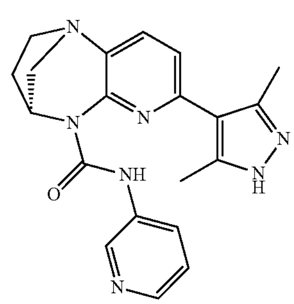 [SMILES: Cc1n[nH]c(C)c1-c1ccc2c(n1)N(C(=O)Nc1cccnc1)[C@H]1CCN2C1] | B | A |

TABLE 1-continued
Compounds of Formula (I).
| Compound No. | [M + H]+[calc] | Structure | Tryp AVG EC$_{1.5}$ (µM) | Tryp % Fold Act |
|---|---|---|---|---|
| 526 | 393 | 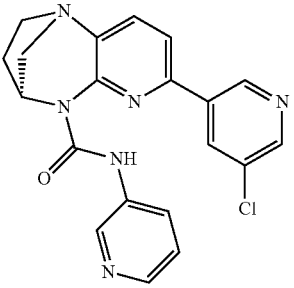 [SMILES: O=C(Nc1cccnc1)N1c2nc(-c3cncc(Cl)c3)ccc2N2CC[C@H]1C2] | A | A |
| 527 | 418 | 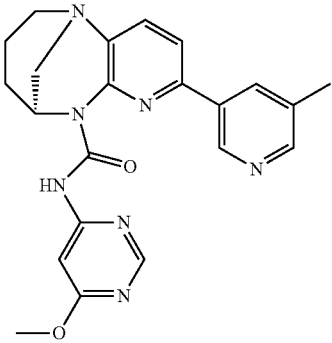 [SMILES: COc1cc(NC(=O)N2c3nc(-c4cncc(C)c4)ccc3N3CCC[C@H]2C3)ncn1] | A | A |
| 528 | 488 | 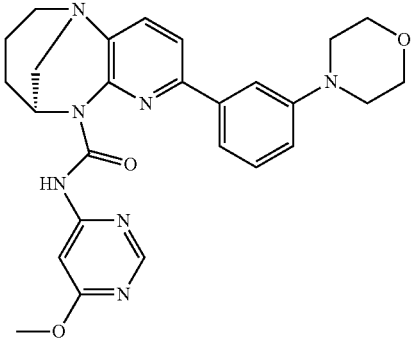 [SMILES: COc1cc(NC(=O)N2c3nc(-c4cccc(N5CCOCC5)c4)ccc3N3CCC[C@H]2C3)ncn1] | B | A |
| 529 | 458 | 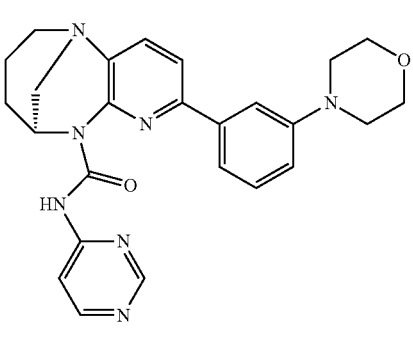 [SMILES: O=C(Nc1ccncn1)N1c2nc(-c3cccc(N4CCOCC4)c3)ccc2N2CCC[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 530 | 845 | 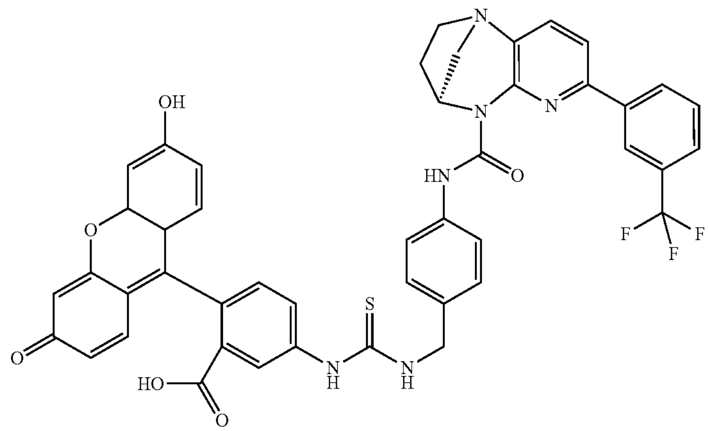 [SMILES: O=C1C=CC2=C(c3ccc(NC(=S)NCc4ccc(NC(=O)N5c6nc(-c7cccc(C(F)(F)F)c7)ccc6N6CC[C@H]5C6)cc4)cc3C(=O)O)C3C=CC(O)=CC3OC2=C1] | A | A |
| 531 | 376 | 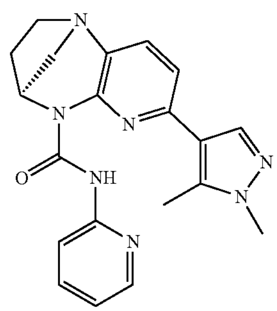 [SMILES: Cc1c(-c2ccc3c(n2)N(C(=O)Nc2ccccn2)[C@H]2CCN3C2)cnn1C] | B | A |
| 532 | 377 | 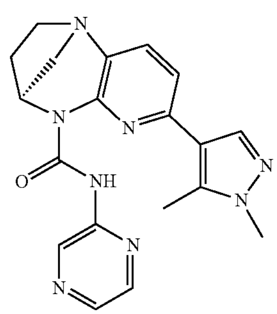 [SMILES: Cc1c(-c2ccc3c(n2)N(C(=O)Nc2cnccn2)[C@H]2CCN3C2)cnn1C] | B | A |
| 533 | 406 | 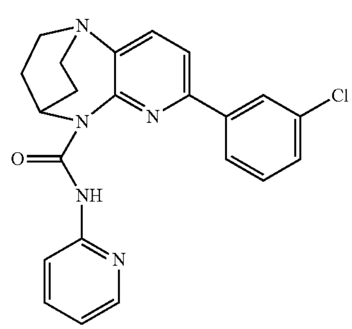 [SMILES: O=C(Nc1ccccn1)N1c2nc(-c3cccc(Cl)c3)ccc2N2CCC1CC2] | B | A |

TABLE 1-continued

Compounds of Formula (I).

| Compound No. | [M + H]+$_{[calc]}$ | Structure | Tryp AVG EC$_{1.5}$ (µM) | Tryp % Fold Act |
|---|---|---|---|---|
| 534 | 407 | 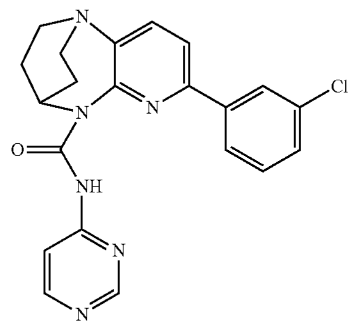 [SMILES: O=C(Nc1ccncn1)N1c2nc(-c3cccc(Cl)c3)ccc2N2CCC1CC2] | B | A |
| 535 | 416 | 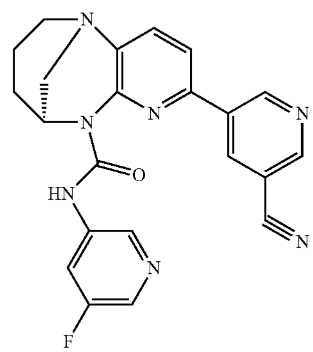 [SMILES: N#Cc1cncc(-c2ccc3c(n2)N(C(=O)Nc2cncc(F)c2)[C@H]2CCCN3C2)c1] | B | A |
| 536 | 457 | 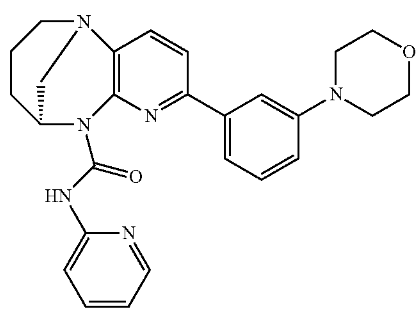 [SMILES: O=C(Nc1ccccn1)N1c2nc(-c3cccc(N4CCOCC4)c3)ccc2N2CCC[C@H]1C2] | B | A |
| 537 | 491 | 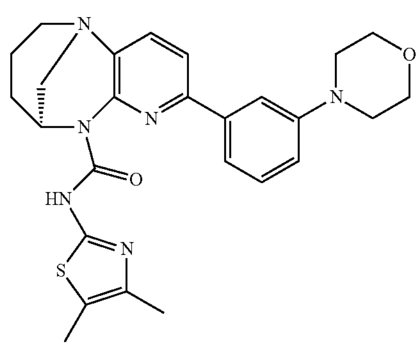 [SMILES: Cc1nc(NC(=O)N2c3nc(-c4cccc(N5CCOCC5)c4)ccc3N3CCC[C@H]2C3)sc1C] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 538 | 457 | 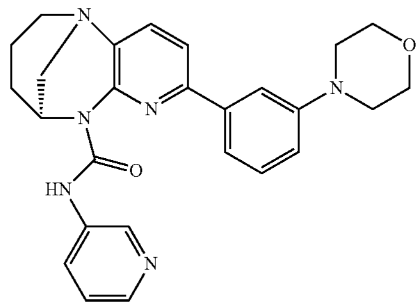 [SMILES: O=C(Nc1cccnc1)N1c2nc(-c3cccc(N4CCOCC4)c3)ccc2N2CCC[C@H]1C2] | A | A |
| 539 | 458 | 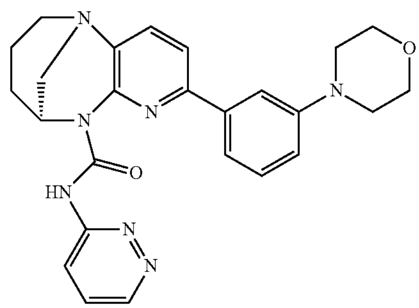 [SMILES: O=C(Nc1cccnn1)N1c2nc(-c3cccc(N4CCOCC4)c3)ccc2N2CCC[C@H]1C2] | B | A |
| 540 | 518 | 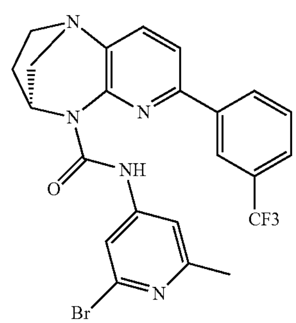 [SMILES: Cc1cc(NC(=O)N2c3nc(-c4cccc(C(F)(F)F)c4)ccc3N3CC[C@H]2C3)cc(Br)n1] | A | A |
| 541 | 504 | 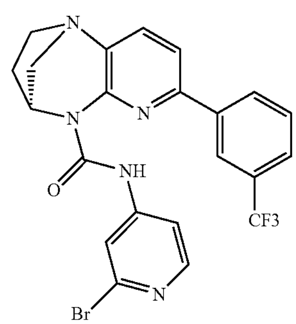 [SMILES: O=C(Nc1ccnc(Br)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 542 | 504 | 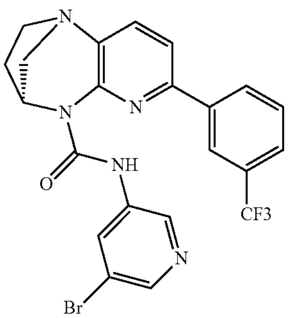 [SMILES: O=C(Nc1cncc(Br)c1)N1c2nc(-c3cccc(C(F)(F)F)c3)ccc2N2CC[C@H]1C2] | A | A |
| 543 | 407 | 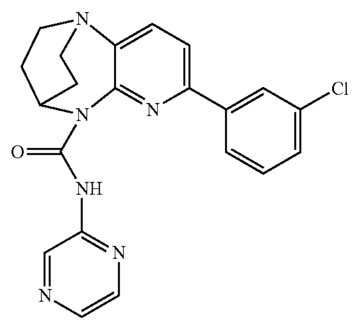 [SMILES: O=C(Nc1cnccn1)N1c2nc(-c3cccc(Cl)c3)ccc2N2CCC1CC2] | B | A |
| 544 | 407 | 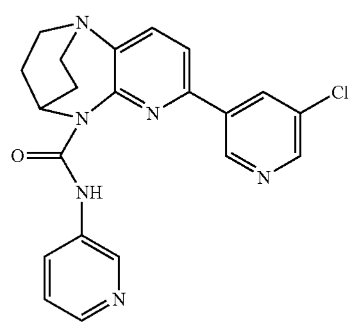 [SMILES: O=C(Nc1cccnc1)N1c2nc(-c3cncc(Cl)c3)ccc2N2CCC1CC2] | B | A |
| 545 | 425 | 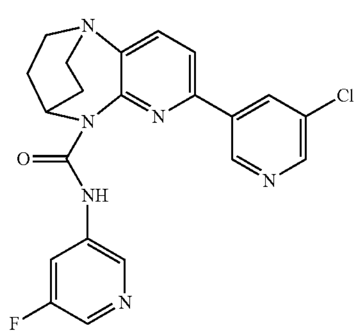 [SMILES: O=C(Nc1cncc(F)c1)N1c2nc(-c3cncc(Cl)c3)ccc2N2CCC1CC2] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 546 (3) | 939 | 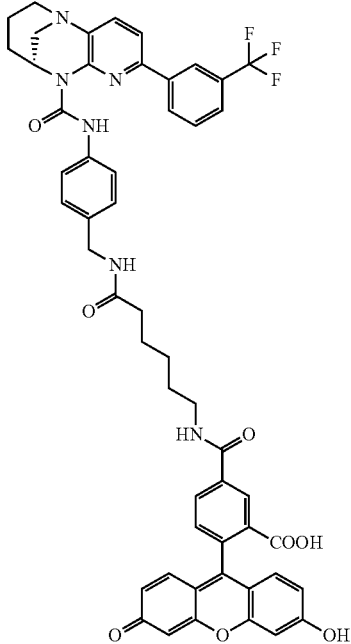 [SMILES: O=C(CCCCCNC(=O)c1ccc(-c2c3ccc(=O)cc-3oc3cc(O)ccc23)c(C(=O)O)c1)NCc1ccc(NC(=O)N2c3nc(-c4cccc(C(F)(F)F)c4)ccc3N3CCC[C@H]2C3)cc1] | B | B |
| 547 | 925 | 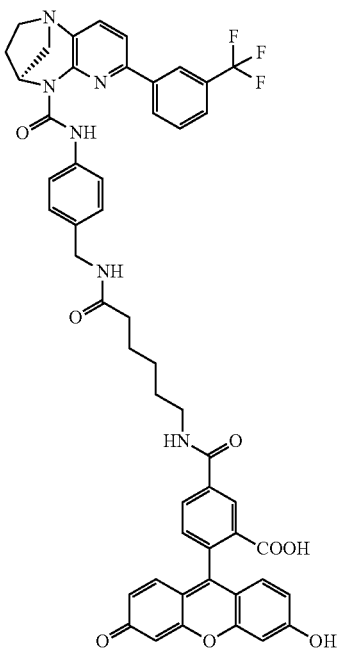 [SMILES: O=C(CCCCCNC(=O)c1ccc(-c2c3ccc(=O)cc-3oc3cc(O)ccc23)c(C(=O)O)c1)NCc1ccc(NC(=O)N2c3nc(-c4cccc(C(F)(F)F)c4)ccc3N3CC[C@H]2C3)cc1] | C | B |

TABLE 1-continued

Compounds of Formula (I).

| Compound No. | [M + H]+$_{[calc]}$ | Structure | Tryp AVG EC$_{1.5}$ (µM) | Tryp % Fold Act |
|---|---|---|---|---|
| 548 | 564 | 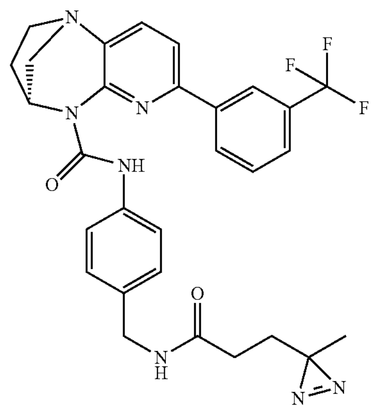 [SMILES: CC1(CCC(=O)NCc2ccc(NC(=O)N3c4nc(-c5cccc(C(F)(F)F)c5)ccc4N4CC[C@H]3C4)cc2)N=N1] | B | A |
| 549 | 424 | 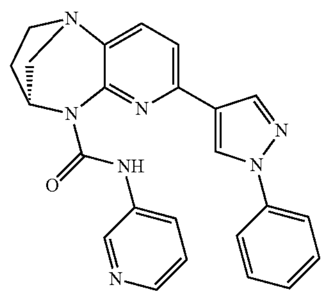 [SMILES: O=C(Nc1cccnc1)N1c2nc(-c3cnn(-c4ccccc4)c3)ccc2N2CC[C@H]1C2] | B | A |
| 550 | 408 | 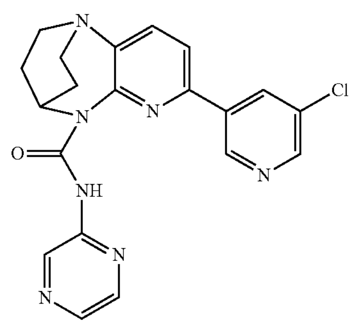 [SMILES: O=C(Nc1cnccn1)N1c2nc(-c3cncc(Cl)c3)ccc2N2CCC1CC2] | B | A |
| 551 | 407 | 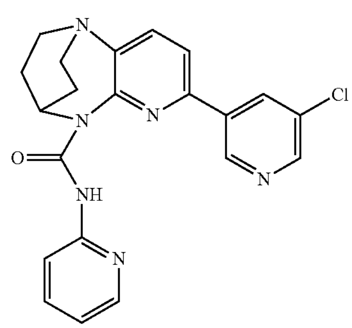 [SMILES: O=C(Nc1ccccn1)N1c2nc(-c3cncc(Cl)c3)ccc2N2CCC1CC2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 552 | 438 | 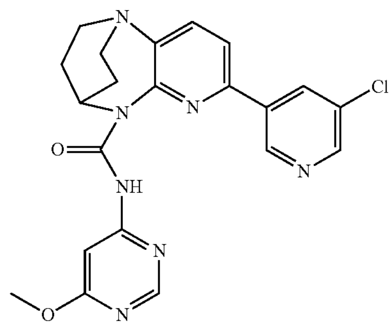 [SMILES: COc1cc(NC(=O)N2c3nc(-c4cncc(Cl)c4)ccc3N3CCC2CC3)ncn1] | C | B |
| 553 | 468 | 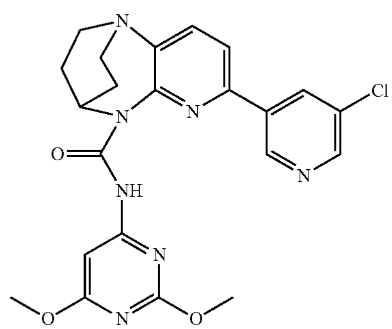 [SMILES: COc1cc(NC(=O)N2c3nc(-c4cncc(Cl)c4)ccc3N3CCC2CC3)nc(OC)n1] | B | A |
| 554 | 441 | 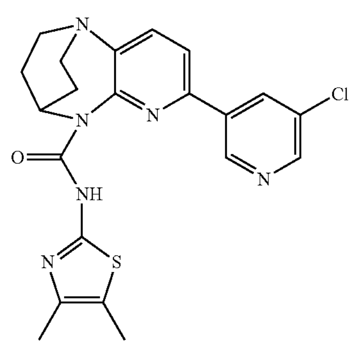 [SMILES: Cc1nc(NC(=O)N2c3nc(-c4cncc(Cl)c4)ccc3N3CCC2CC3)sc1C] | B | A |
| 555 | 392 | 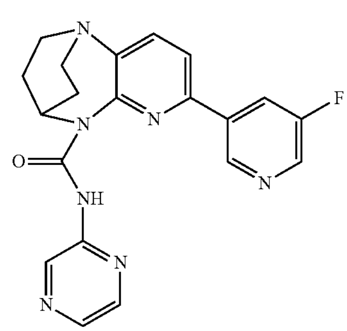 [SMILES: O=C(Nc1cnccn1)N1c2nc(-c3cncc(F)c3)ccc2N2CCC1CC2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 556 | 427 | 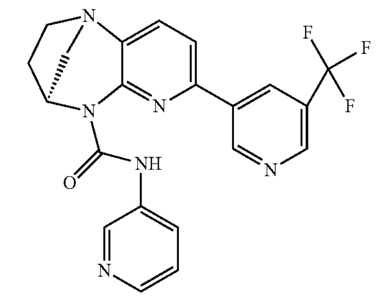 [SMILES: O=C(Nc1cccnc1)N1c2nc(-c3cncc(C(F)(F)F)c3)ccc2N2CC[C@H]1C2] | A | A |
| 557 | 398 | 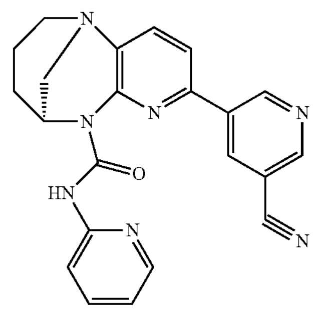 [SMILES: N#Cc1cncc(-c2ccc3c(n2)N(C(=O)Nc2ccccn2)[C@H]2CCCN3C2)c1] | A | A |
| 558 | 399 | 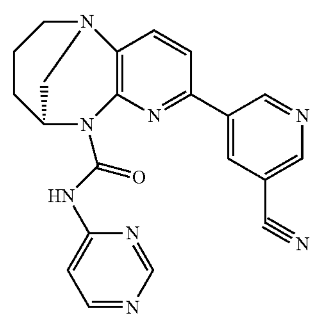 [SMILES: N#Cc1cncc(-c2ccc3c(n2)N(C(=O)Nc2ccncn2)[C@H]2CCCN3C2)c1] | B | A |
| 559 | 475 | 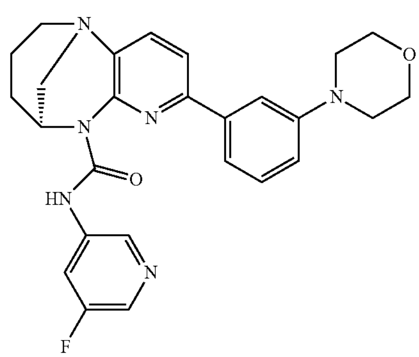 [SMILES: O=C(Nc1cncc(F)c1)N1c2nc(-c3cccc(N4CCOCC4)c3)ccc2N2CCC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 560 | 458 | 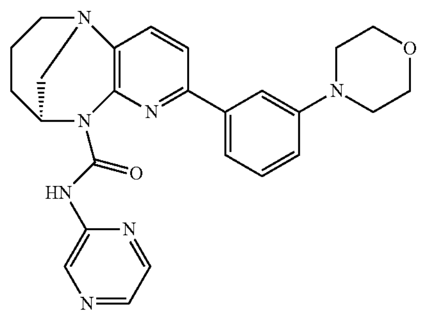 [SMILES: O=C(Nc1cnccn1)N1c2nc(-c3cccc(N4CCOCC4)c3)ccc2N2CCC[C@H]1C2] | B | A |
| 561 | 464 | 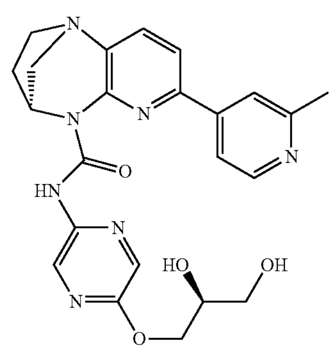 [SMILES: Cc1cc(-c2ccc3c(n2)N(C(=O)Nc2cnc(OC[C@@H](O)CO)cn2)[C@H]2CCN3C2)ccn1] | B | A |
| 562 | 570 | 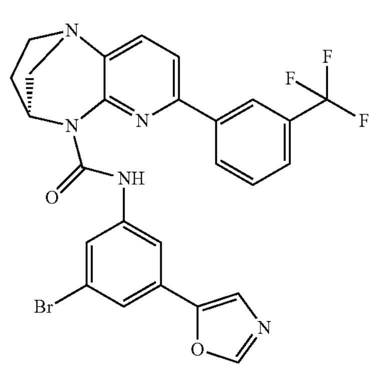 [SMILES: O=C(Nc1cc(Br)cc(-c2cnco2)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 563 | 857 | 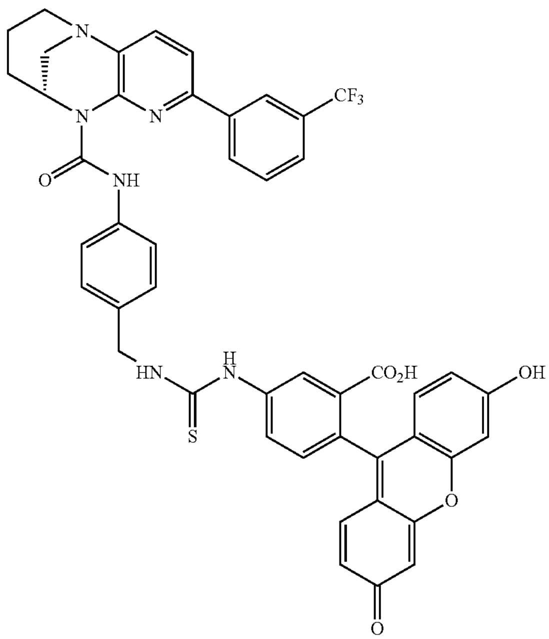 [SMILES: O=C(O)c1cc(NC(=S)NCc2ccc(NC(=O)N3c4nc(-c5cccc(C(F)(F)F)c5)ccc4N4CCC[C@H]3C4)cc2)ccc1-c1c2ccc(=O)cc-2oc2cc(O)ccc12] | A | A |
| 565 | 823 | 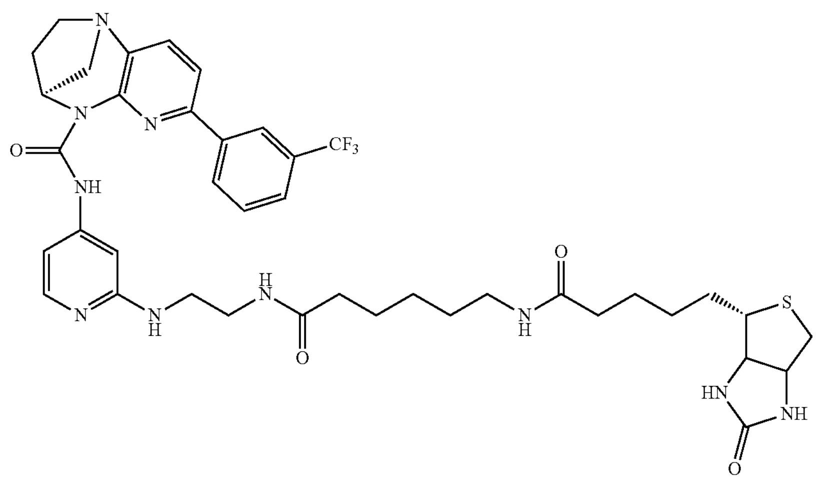 [SMILES: O=C(CCCC[C@@H]1SCC2NC(=O)NC21)NCCCCCC(=O)NCCNc1cc(NC(=O)N2c3nc(-c4cccc(C(F)(F)F)c4)ccc3N3CC[C@H]2C3)ccn1] | NT | NT |
| 569 | 440 | 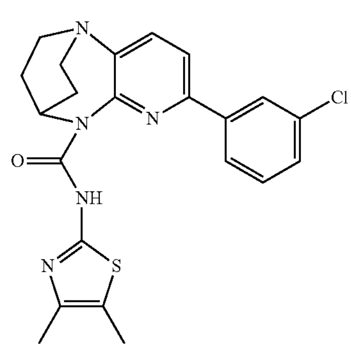 [SMILES: Cc1nc(NC(=O)N2c3nc(-c4cccc(Cl)c4)ccc3N3CCC2CC3)sc1C] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 570 | 391 | 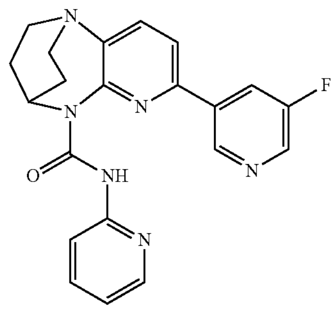 [SMILES: O=C(Nc1ccccn1)N1c2nc(-c3cncc(F)c3)ccc2N2CCC1CC2] | B | A |
| 571 | 409 | 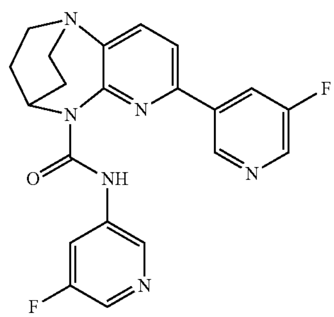 [SMILES: O=C(Nc1cncc(F)c1)N1c2nc(-c3cncc(F)c3)ccc2N2CCC1CC2] | B | A |
| 572 | 391 | 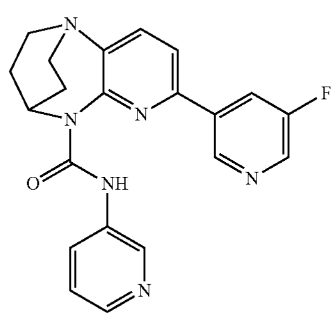 [SMILES: O=C(Nc1cccnc1)N1c2nc(-c3cncc(F)c3)ccc2N2CCC1CC2] | B | A |
| 573 | 392 | 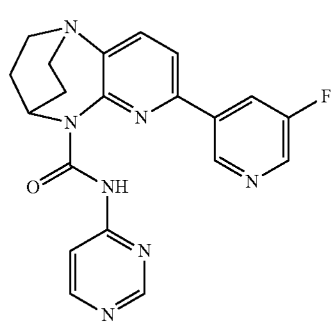 [SMILES: O=C(Nc1ccncn1)N1c2nc(-c3cncc(F)c3)ccc2N2CCC1CC2] | C | B |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 574 | 457 | 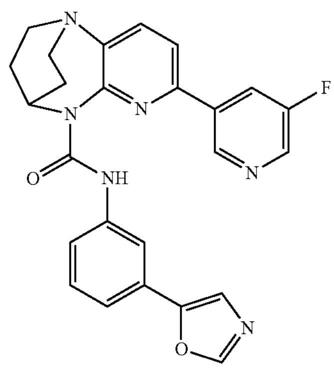 [SMILES: O=C(Nc1cccc(-c2cnco2)c1)N1c2nc(-c3cncc(F)c3)ccc2N2CCC1CC2] | A | A |
| 575 | 473 | 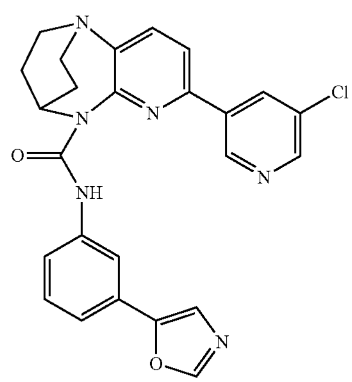 [SMILES: O=C(Nc1cccc(-c2cnco2)c1)N1c2nc(-c3cncc(Cl)c3)ccc2N2CCC1CC2] | A | A |
| 576 | 408 | 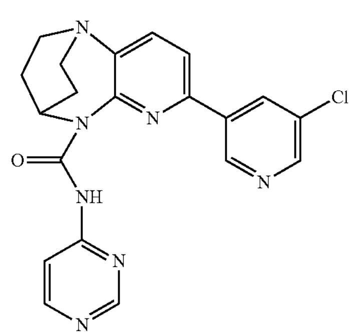 [SMILES: O=C(Nc1ccncn1)N1c2nc(-c3cncc(Cl)c3)ccc2N2CCC1CC2] | B | A |
| 577 | 425 | 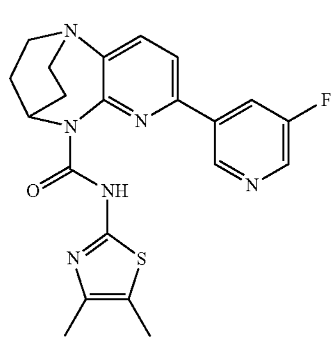 [SMILES: Cc1nc(NC(=O)N2c3nc(-c4cncc(F)c4)ccc3N3CCC2CC3)sc1C] | B | A |

TABLE 1-continued

Compounds of Formula (I).

| Compound No. | [M + H]+<sub>[calc]</sub> | Structure | Tryp AVG EC<sub>1.5</sub> (µM) | Tryp % Fold Act |
|---|---|---|---|---|
| 578 | 452 | 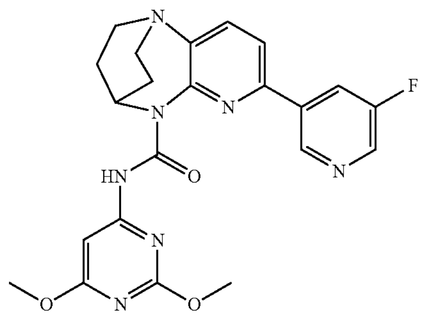 [SMILES: COc1cc(NC(=O)N2c3nc(-c4cncc(F)c4)ccc3N3CCC2CC3)nc(OC)n1] | B | A |
| 579 | 422 | 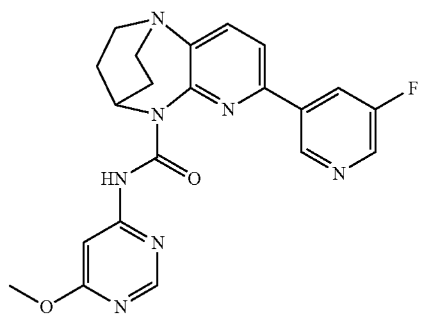 [SMILES: COc1cc(NC(=O)N2c3nc(-c4cncc(F)c4)ccc3N3CCC2CC3)ncn1] | B | A |
| 580 | 492 | 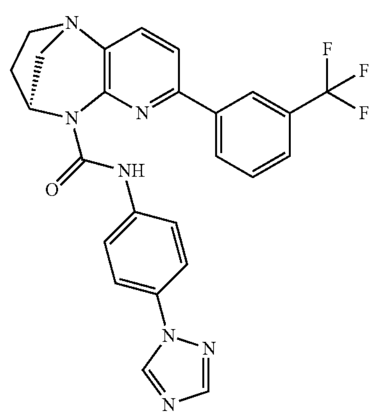 [SMILES: O=C(Nc1ccc(-n2cncn2)cc1)N1c2nc(-c3cccc(C(F)(F)F)c3)ccc2N2CC[C@H]1C2] | A | A |
| 581 | 492 | 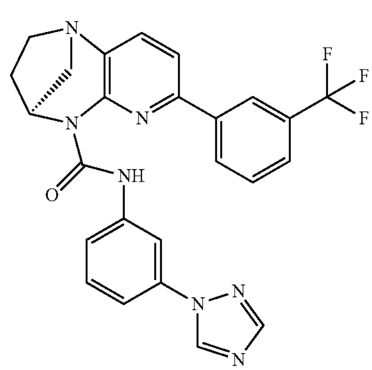 [SMILES: O=C(Nc1cccc(-n2cncn2)c1)N1c2nc(-c3cccc(C(F)(F)F)c3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 582 | 505 | 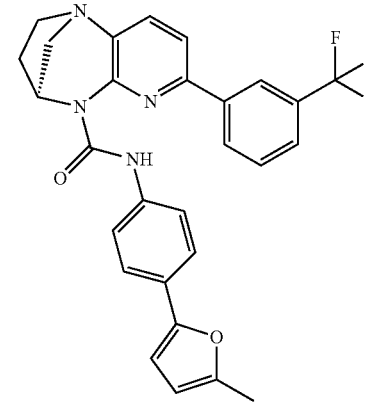 | B | A |
| 583 | 522 | 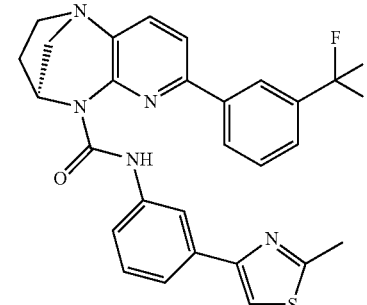 | A | A |
| 587 | 416 | 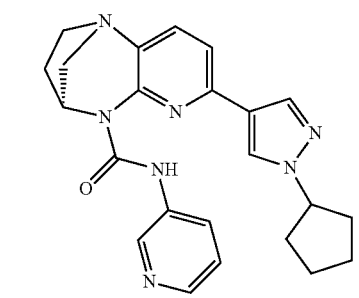 [SMILES: O=C(Nc1cccnc1)N1c2nc(-c3cnn(C4CCCC4)c3)ccc2N2CC[C@H]1C2] | B | A |
| 588 | 493 | 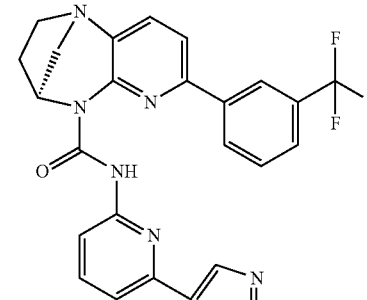 | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 589 | 493 | 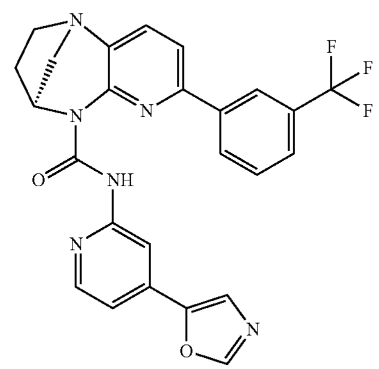 [SMILES: O=C(Nc1cc(-c2cnco2)ccn1)N1c2nc(-c3cccc(C(F)(F)F)c3)ccc2N2CC[C@H]1C2] | A | A |
| 590 | 507 | 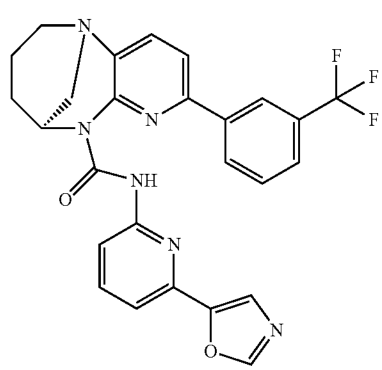 [SMILES: O=C(Nc1cccc(-c2cnco2)n1)N1c2nc(-c3cccc(C(F)(F)F)c3)ccc2N2CCC[C@H]1C2] | A | A |
| 591 | 507 | 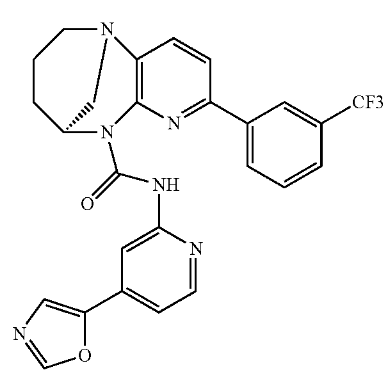 [SMILES: O=C(Nc1cc(-c2cnco2)ccn1)N1c2nc(-c3cccc(C(F)(F)F)c3)ccc2N2CCC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 592 | 594 | 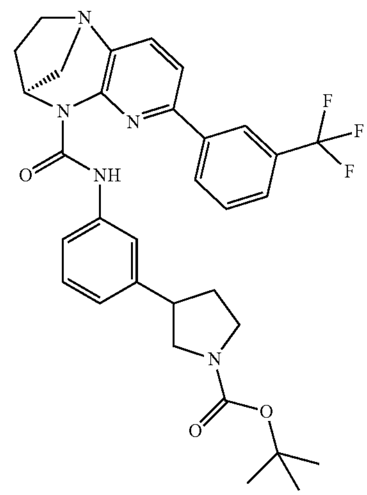 [SMILES: CC(C)(C)OC(=O)N1CCC(c2cccc(NC(=O)N3c4nc(-c5cccc(C(F)(F)F)c5)ccc4N4CC[C@H]3C4)c2)C1] | A | A |
| 593 | 494 | 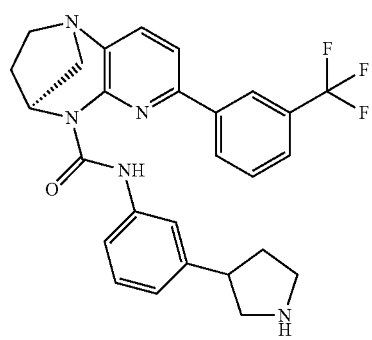 [SMILES: O=C(Nc1cccc(C2CCNC2)c1)N1c2nc(-c3cccc(C(F)(F)F)c3)ccc2N2CC[C@H]1C2] | A | A |
| 594 | 551 | 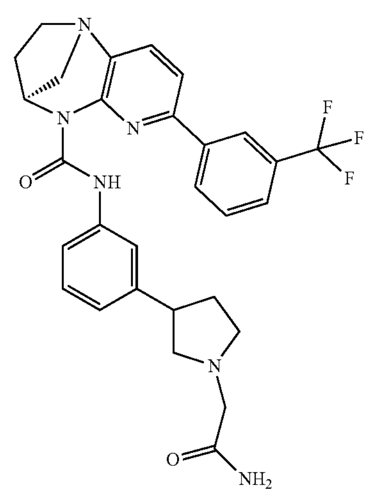 [SMILES: NC(=O)CN1CCC(c2cccc(NC(=O)N3c4nc(-c5cccc(C(F)(F)F)c5)ccc4N4CC[C@H]3C4)c2)C1] | A | A |

TABLE 1-continued

Compounds of Formula (I).

| Compound No. | [M + H]+<sub>[calc]</sub> | Structure | Tryp AVG EC<sub>1.5</sub> (μM) | Tryp % Fold Act |
|---|---|---|---|---|
| 595 | 507 | 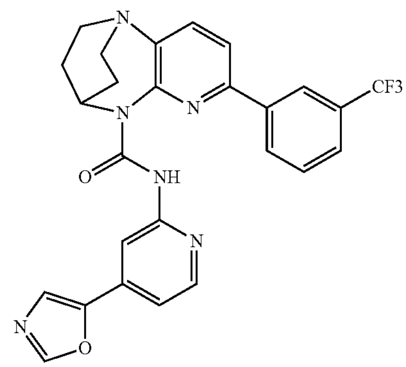 [SMILES: O=C(Nc1cc(-c2cnco2)ccn1)N1c2nc(-c3cccc(C(F)(F)F)c3)ccc2N2CCC1CC2] | A | A |
| 596 | 507 | 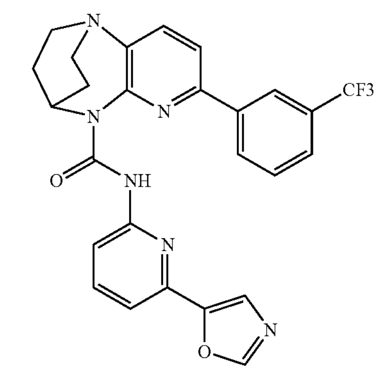 [SMILES: O=C(Nc1cccc(-c2cnco2)n1)N1c2nc(-c3cccc(C(F)(F)F)c3)ccc2N2CCC1CC2] | A | A |
| 597 | 439 | 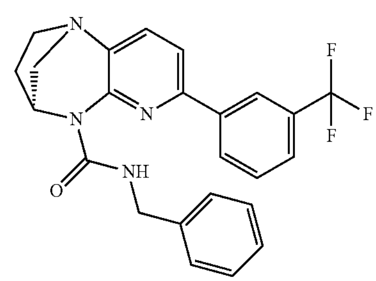 [SMILES: O=C(NCc1ccccc1)N1c2nc(-c3cccc(C(F)(F)F)c3)ccc2N2CC[C@H]1C2] | B | A |
| 598 | 453 | 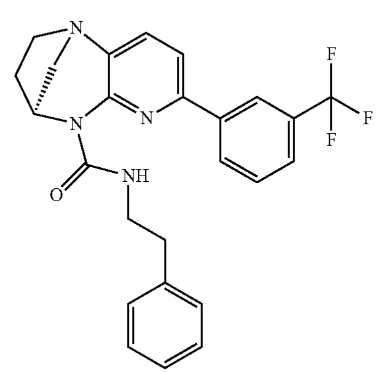 [SMILES: O=C(NCCc1ccccc1)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 599 | 467 | 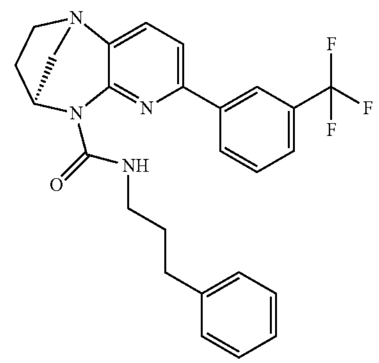 [SMILES: O=C(NCCCc1ccccc1)N1c2nc(-c3cccc(C(F)(F)F)c3)ccc2N2CC[C@H]1C2] | B | A |
| 600 | 481 | 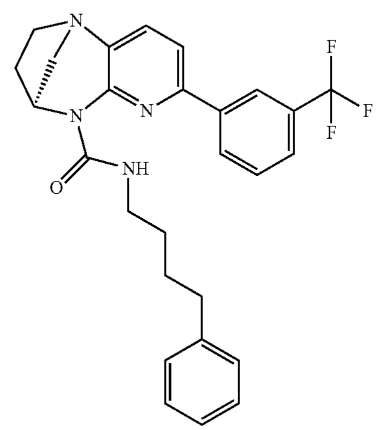 [SMILES: O=C(NCCCCc1ccccc1)N1c2nc(-c3cccc(C(F)(F)F)c3)ccc2N2CC[C@H]1C2] | B | A |
| 601 | 442 | 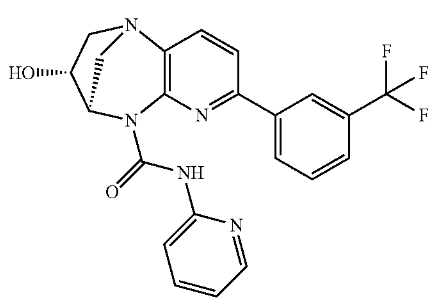 [SMILES: O=C(Nc1ccccn1)N1c2nc(-c3cccc(C(F)(F)F)c3)ccc2N2C[C@@H](O)[C@H]1C2] | A | A |
| 602 | 484 | 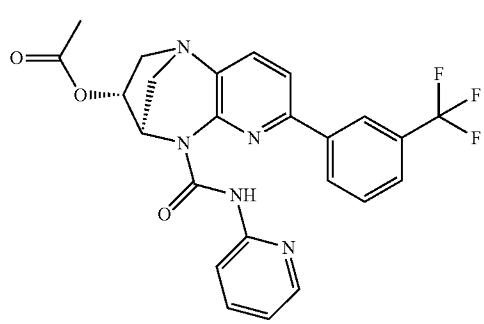 [SMILES: CC(=O)O[C@@H]1CN2C[C@H]1N(C(=O)Nc1ccccn1)c1nc(-c3cccc(C(F)(F)F)c3)ccc12] | B | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 603 | 546 | 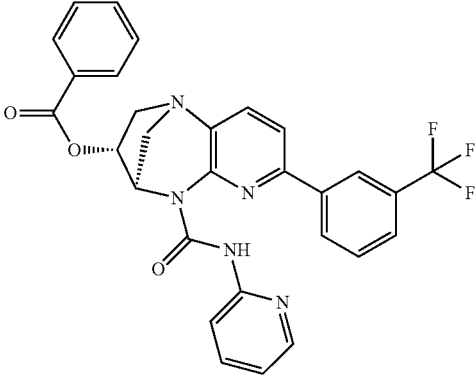 [SMILES: O=C(O[C@@H]1CN2C[C@H]1N(C(=O)Nc1ccccn1)c1nc(-c3cccc(C(F)(F)F)c3)ccc12)c1ccccc1] | C | B |
| 604 | 649 | 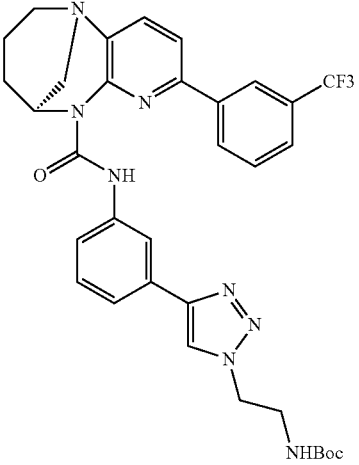 [SMILES: CC(C)(C)OC(=O)NCCn1cc(-c2cccc(NC(=O)N3c4nc(-c5cccc(C(F)(F)F)c5)ccc4N4CCC[C@H]3C4)c2)nn1] | A | A |
| 605 | 621 | 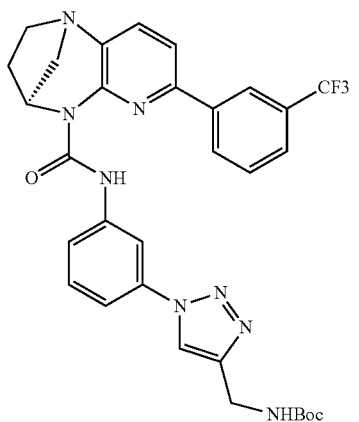 [SMILES: CC(C)(C)OC(=O)NCc1cn(-c2cccc(NC(=O)N3c4nc(-c5cccc(C(F)(F)F)c5)ccc4N4CC[C@H]3C4)c2)nn1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 606 | 521 | 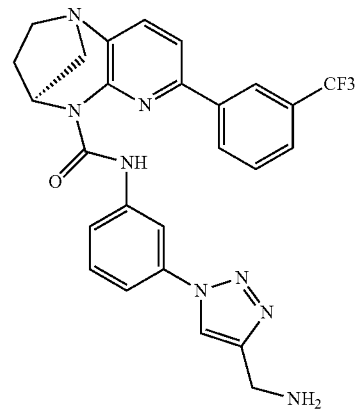 [SMILES: NCc1cn(-c2cccc(NC(=O)N3c4nc(-c5cccc(C(F)(F)F)c5)ccc4N4CC[C@H]3C4)c2)nn1] | A | A |
| 607 | 860 | 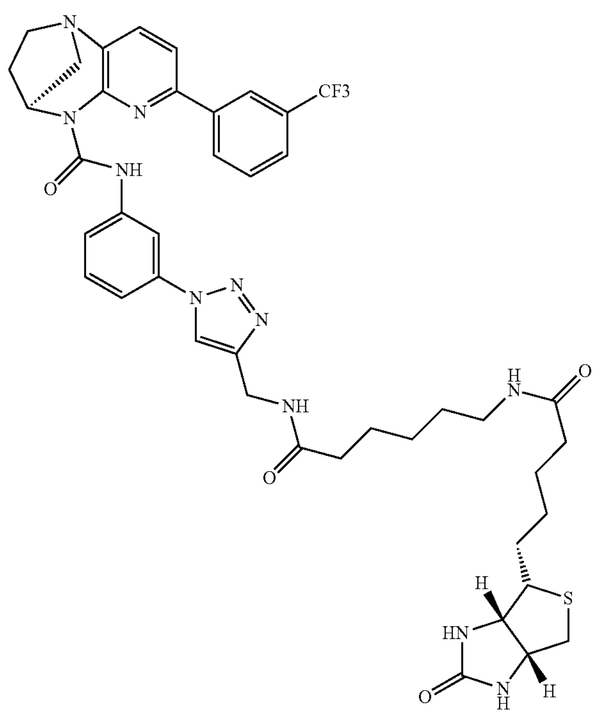 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 608 | 910 | 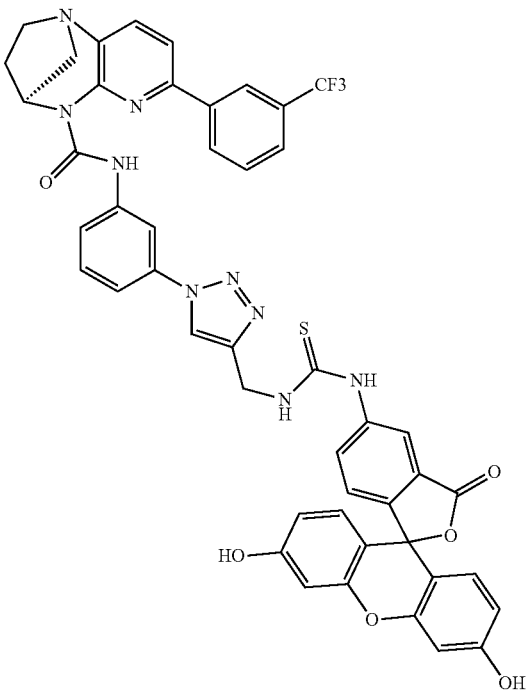 [SMILES: O=C1OC2(c3ccc(O)cc3Oc3cc(O)ccc32)c2ccc(NC(=S)NCc3cn(-c4cccc(NC(=O)N5c6nc(-c7cccc(C(F)(F)F)c7)ccc6N6CC[C@H]5C6)c4)nn3)cc21] | C | B |
| 609 | 580 | 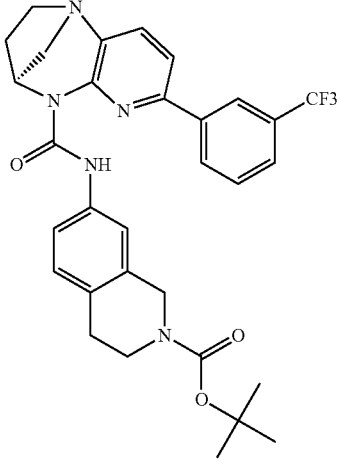 [SMILES: CC(C)(C)OC(=O)N1CCc2ccc(NC(=O)N3c4nc(-c5cccc(C(F)(F)F)c5)ccc4N4CC[C@H]3C4)cc2C1] | B | A |
| 610 | 580 | 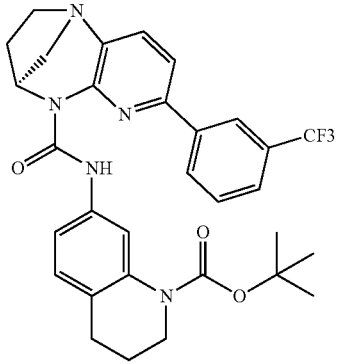 [SMILES: CC(C)(C)OC(=O)N1CCCc2ccc(NC(=O)N3c4nc(-c5cccc(C(F)(F)F)c5)ccc4N4CC[C@H]3C4)cc21] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 611 | 580 | 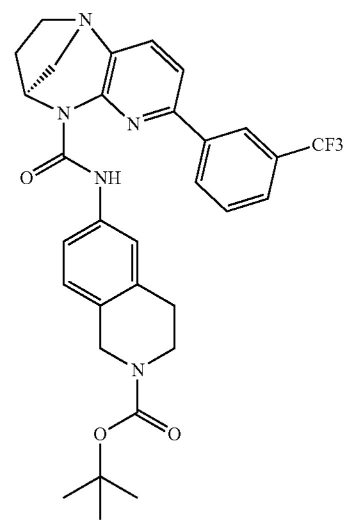 [SMILES: CC(C)(C)OC(=O)N1CCc2cc(NC(=O)N3c4nc(-c5cccc(C(F)(F)F)c5)ccc4N4CC[C@H]3C4)ccc2C1] | A | A |
| 612 | 476 | 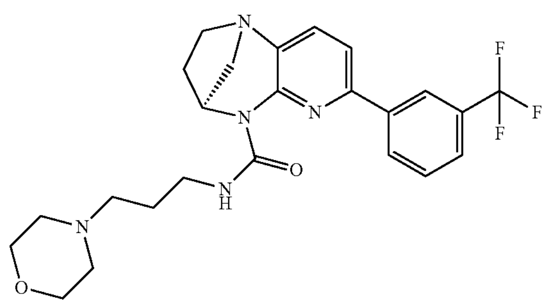 [SMILES: O=C(NCCCN1CCOCC1)N1c2nc(-c3cccc(C(F)(F)F)c3)ccc2N2CC[C@H]1C2] | B | A |
| 613 | 454 | 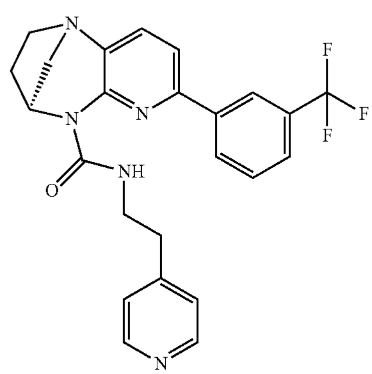 [SMILES: O=C(NCCc1ccncc1)N1c2nc(-c3cccc(C(F)(F)F)c3)ccc2N2CC[C@H]1C2] | B | A |

TABLE 1-continued
Compounds of Formula (I).
| Compound No. | [M + H]+[calc] | Structure | Tryp AVG EC$_{1.5}$ (µM) | Tryp % Fold Act |
|---|---|---|---|---|
| 614 | 454 | 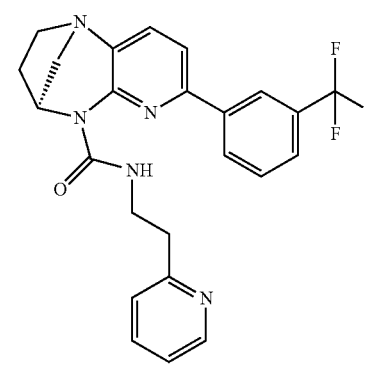 | B | A |
| 615 | 454 | 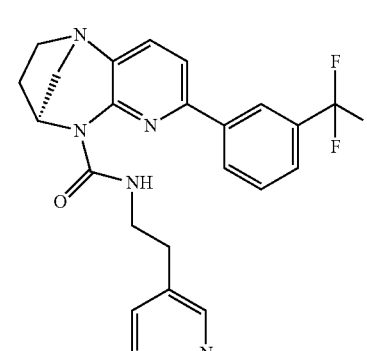 | B | A |
| 616 | 462 | 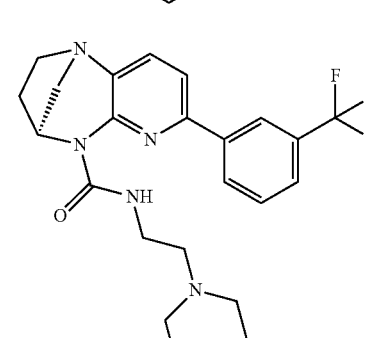 | B | A |
| 617 | 493 | 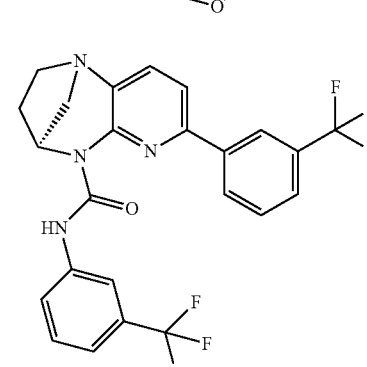 | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 618 | 570 | 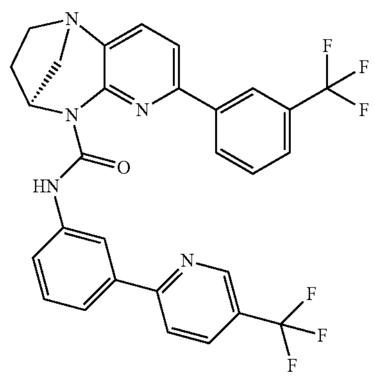 [SMILES: O=C(Nc1cccc(-c2ccc(C(F)(F)F)cn2)c1)N1c2nc(-c3cccc(C(F)(F)F)c3)ccc2N2CC[C@H]1C2] | B | A |
| 619 | 529 | 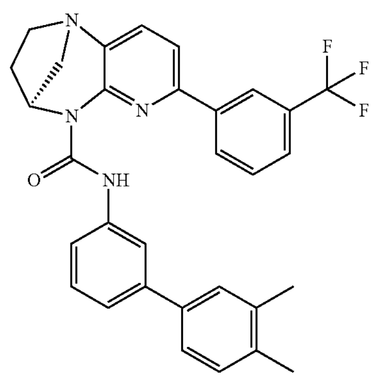 [SMILES: Cc1ccc(-c2cccc(NC(=O)N3c4nc(-c5cccc(C(F)(F)F)c5)ccc4N4CC[C@H]3C4)c2)cc1C] | C | B |
| 620 | 440 | 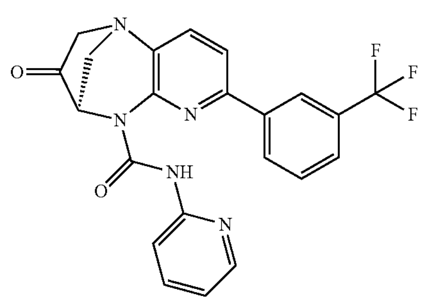 [SMILES: O=C1CN2C[C@H]1N(C(=O)Nc1ccccn1)c1nc(-c3cccc(C(F)(F)F)c3)ccc12] | B | A |
| 621 | 442 | 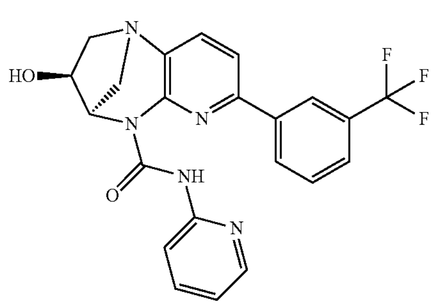 [SMILES: O=C(Nc1ccccn1)N1c2nc(-c3cccc(C(F)(F)F)c3)ccc2N2C[C@@H]1[C@@H](O)C2] | NT | NT |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 622 | 795 | 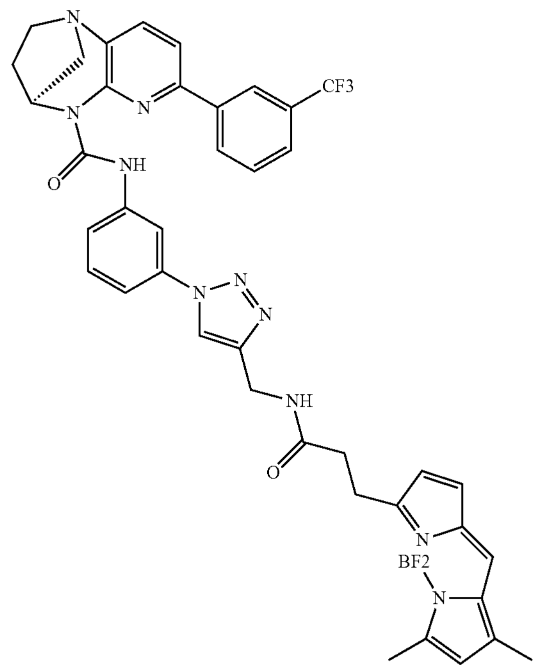 | C | B |
| 623 | 506 | 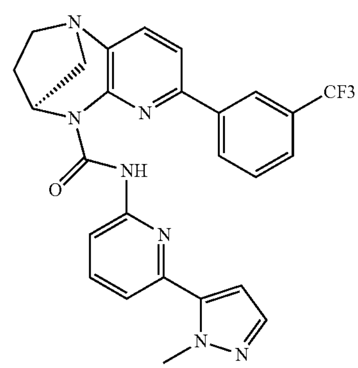 [SMILES: Cn1nccc1-c1cccc(NC(=O)N2c3nc(-c4cccc(C(F)(F)F)c4)ccc3N3CC[C@H]2C3)n1] | A | A |
| 624 | 465 | 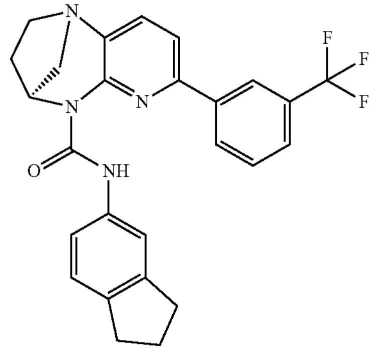 [SMILES: O=C(Nc1ccc2c(c1)CCC2)N1c2nc(-c3cccc(C(F)(F)F)c3)ccc2N2CC[C@H]1C2] | B | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 625 | 501 | 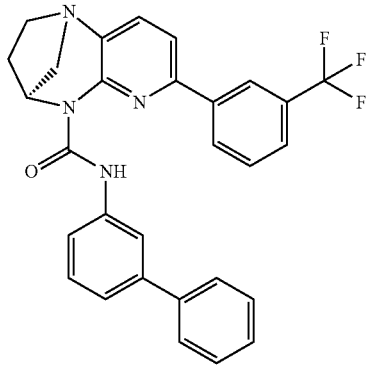 [SMILES: O=C(Nc1cccc(-c2ccccc2)c1)N1c2nc(-c3cccc(C(F)(F)F)c3)ccc2N2CC[C@H]1C2] | A | A |
| 626 | 483 | 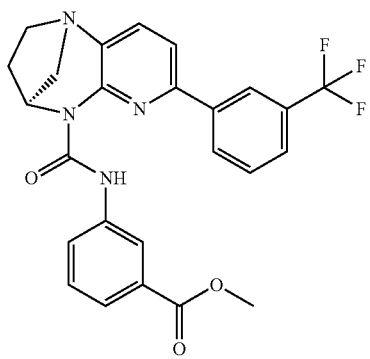 [SMILES: COC(=O)c1cccc(NC(=O)N2c3nc(-c4cccc(C(F)(F)F)c4)ccc3N3CC[C@H]2C3)c1] | A | A |
| 627 | 457 | 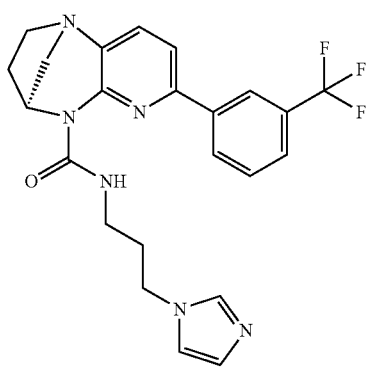 [SMILES: O=C(NCCCn1ccnc1)N1c2nc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 628 | 508 | 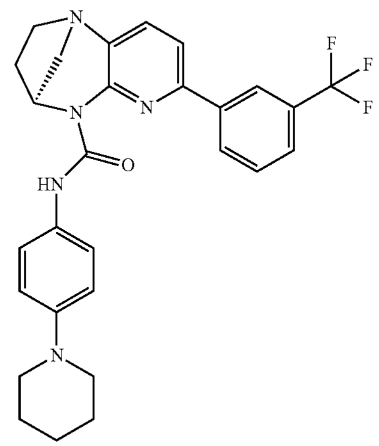 [SMILES: O=C(Nc1ccc(N2CCCCC2)cc1)N1c2nc(-c3cccc(C(F)(F)F)c3)ccc2N2CC[C@H]1C2] | B | A |
| 629 | 524 | 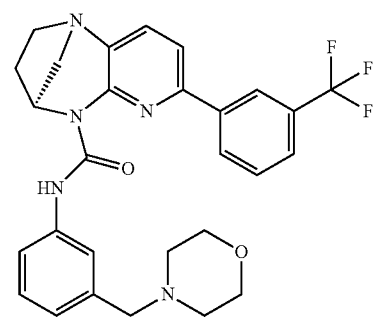 [SMILES: O=C(Nc1cccc(CN2CCOCC2)c1)N1c2nc(-c3cccc(C(F)(F)F)c3)ccc2N2CC[C@H]1C2] | A | A |
| 630 | 460 | 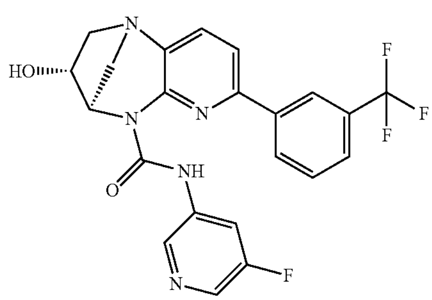 [SMILES: O=C(Nc1cncc(F)c1)N1c2nc(-c3cccc(C(F)(F)F)c3)ccc2N2C[C@@H](O)[C@H]1C2] | A | A |
| 631 | 443 | 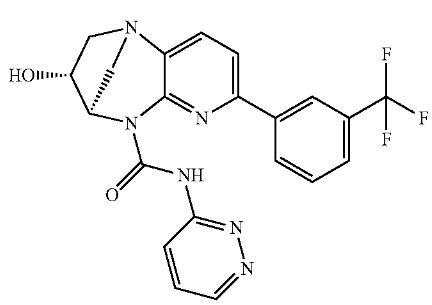 [SMILES: O=C(Nc1cccnn1)N1c2nc(-c3cccc(C(F)(F)F)c3)ccc2N2C[C@@H](O)[C@H]1C2] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 632 | 471 | 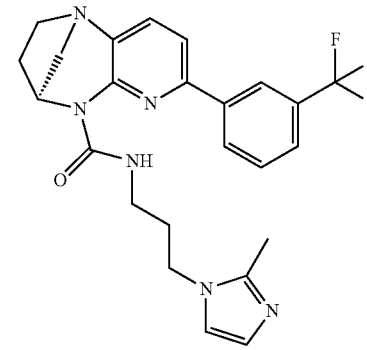 | C | A |
| 633 | 468 | 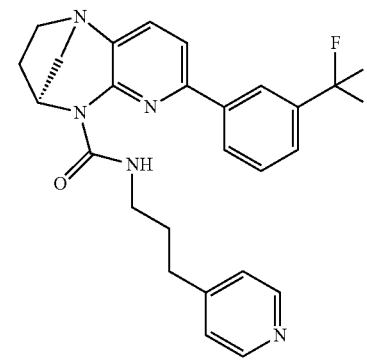 | B | A |
| 634 | 484 | 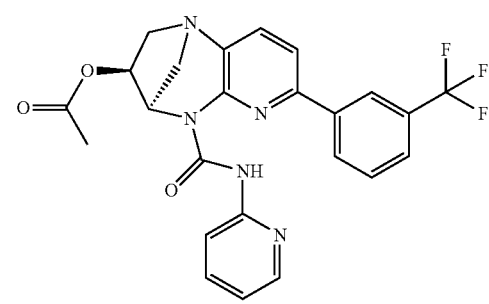 [SMILES: CC(=O)O[C@H]1CN2C[C@H]1N(C(=O)Nc1ccccn1)c1nc(-c3cccc(C(F)(F)F)c3)ccc12] | C | B |
| 635 | 536 | 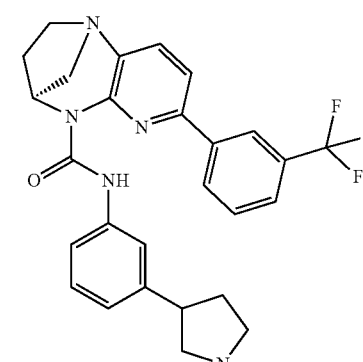 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 636 | 550 | 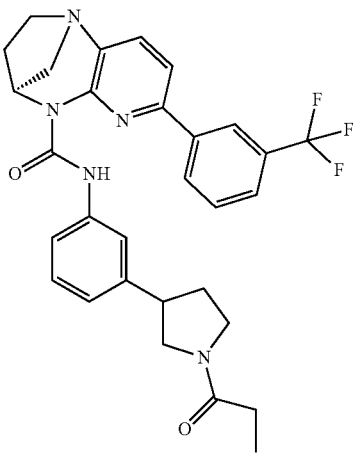 [SMILES: CCC(=O)N1CCC(c2cccc(NC(=O)N3c4nc(-c5cccc(C(F)(F)F)c5)ccc4N4CC[C@H]3C4)c2)C1] | A | A |
| 637 | 562 | 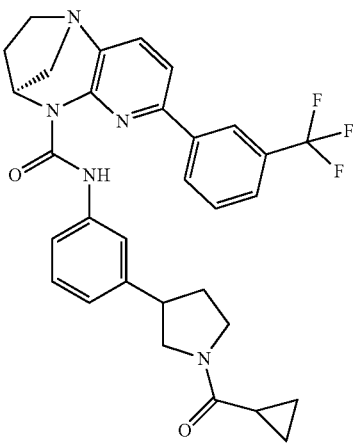 [SMILES: O=C(C1CC1)N1CCC(c2cccc(NC(=O)N3c4nc(-c5cccc(C(F)(F)F)c5)ccc4N4CC[C@H]3C4)c2)C1] | A | A |
| 638 | 621 | 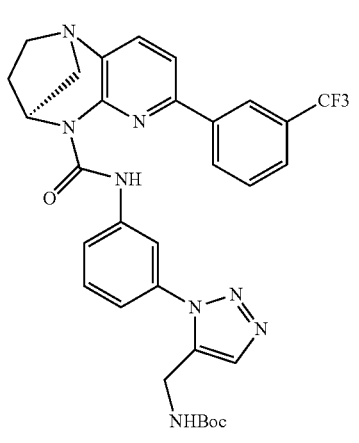 [SMILES: CC(C)(C)OC(=O)NCc1cnnn1-c1cccc(NC(=O)N2c3nc(-c4cccc(C(F)(F)F)c4)ccc3N3CC[C@H]2C3)c1] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 639 | 634 | 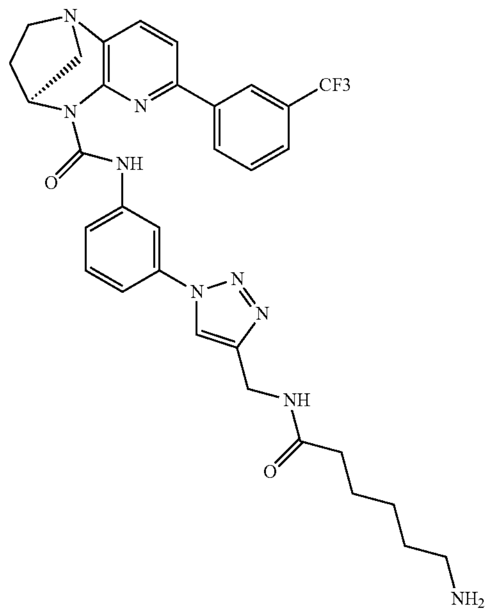 [SMILES: NCCCCCC(=O)NCc1cn(-c2cccc(NC(=O)N3c4nc(-c5cccc(C(F)(F)F)c5)ccc4N4CC[C@H]3C4)c2)nn1] | A | A |
| 640 | 521 | 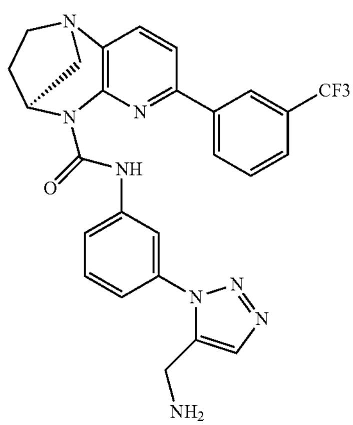 [SMILES: NCc1cnnn1-c1cccc(NC(=O)N2c3nc(-c4cccc(C(F)(F)F)c4)ccc3N3CC[C@H]2C3)c1] | A | A |
| 641 | 517 | 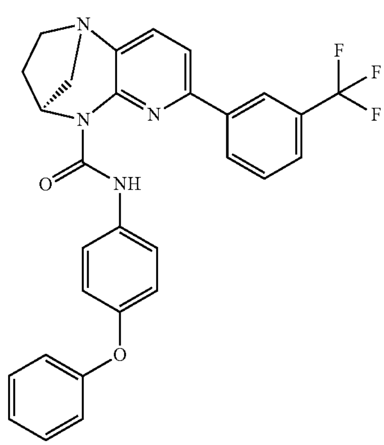 [SMILES: O=C(Nc1ccc(Oc2ccccc2)cc1)N1c2nc(-c3cccc(C(F)(F)F)c3)ccc2N2CC[C@H]1C2] | C | B |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 642 | 518 | 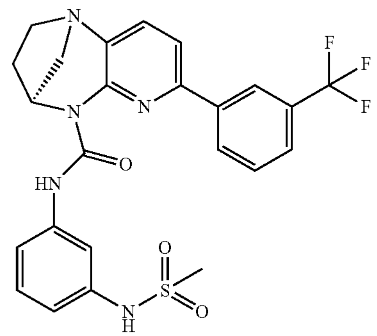 [SMILES: CS(=O)(=O)Nc1cccc(NC(=O)N2c3nc(-c4cccc(C(F)(F)F)c4)ccc3N3CC[C@H]2C3)c1] | A | A |
| 643 | 504 | 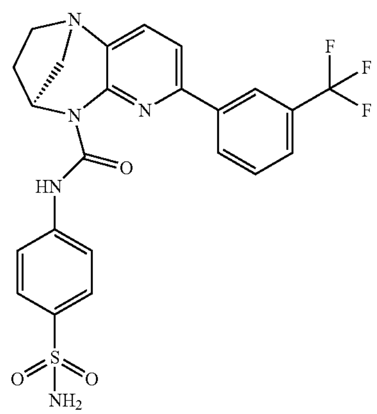 [SMILES: NS(=O)(=O)c1ccc(NC(=O)N2c3nc(-c4cccc(C(F)(F)F)c4)ccc3N3CC[C@H]2C3)cc1] | A | A |
| 644 | 473 | 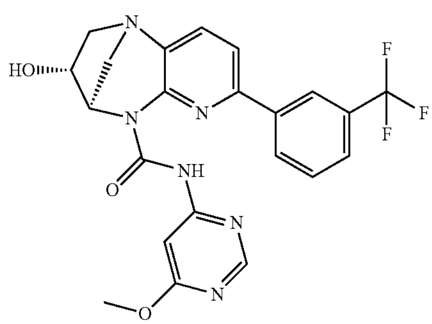 [SMILES: COc1cc(NC(=O)N2c3nc(-c4cccc(C(F)(F)F)c4)ccc3N3C[C@@H](O)[C@H]2C3)ncn1] | B | A |
| 645 | 443 | 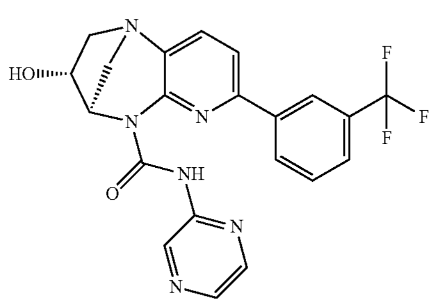 [SMILES: O=C(Nc1cnccn1)N1c2nc(-c3cccc(C(F)(F)F)c3)ccc2N2C[C@@H](O)[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 646 | 433 | 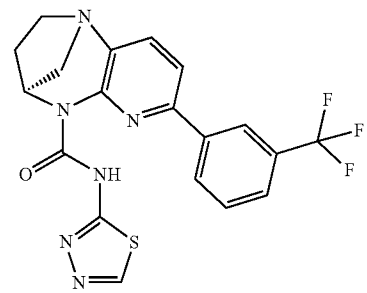 [SMILES: O=C(Nc1nncs1)N1c2nc(-c3cccc(C(F)(F)F)c3)ccc2N2CC[C@H]1C2] | A | A |
| 647 | 461 | 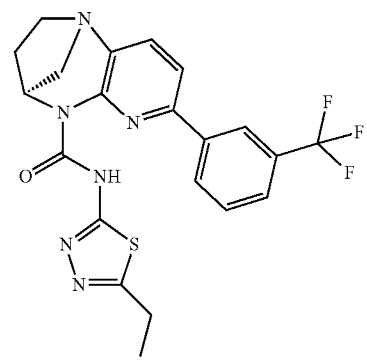 [SMILES: CCc1nnc(NC(=O)N2c3nc(-c4cccc(C(F)(F)F)c4)ccc3N3CC[C@H]2C3)s1] | A | A |
| 648 | 509 | 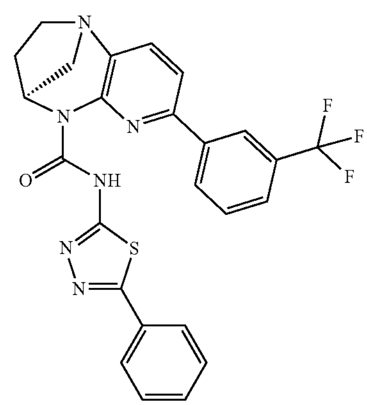 [SMILES: O=C(Nc1nnc(-c2ccccc2)s1)N1c2nc(-c3cccc(C(F)(F)F)c3)ccc2N2CC[C@H]1C2] | A | A |
| 649 | 489 | 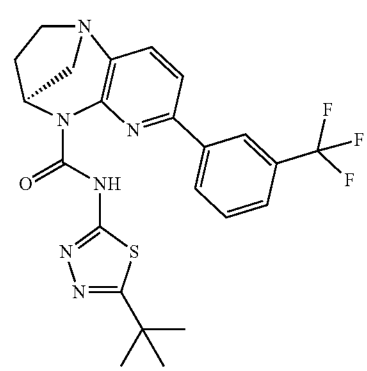 [SMILES: CC(C)(C)c1nnc(NC(=O)N2c3nc(-c4cccc(C(F)(F)F)c4)ccc3N3CC[C@H]2C3)s1] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 650 | 501 | 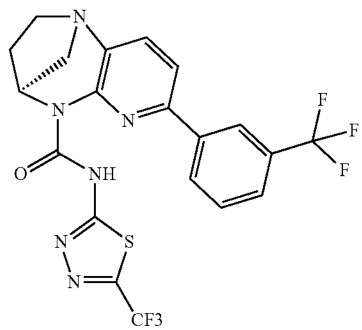 [SMILES: O=C(Nc1nnc(C(F)(F)F)s1)N1c2nc(-c3cccc(C(F)(F)F)c3)ccc2N2CC[C@H]1C2] | C | B |
| 651 | 510 | 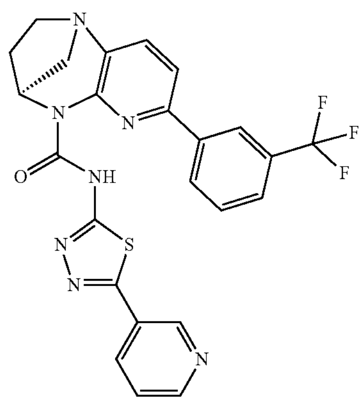 [SMILES: O=C(Nc1nnc(-c2cccnc2)s1)N1c2nc(-c3cccc(C(F)(F)F)c3)ccc2N2CC[C@H]1C2] | A | A |
| 652 | 504 | 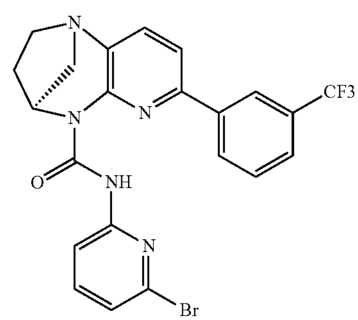 [SMILES: O=C(Nc1cccc(Br)n1)N1c2nc(-c3cccc(C(F)(F)F)c3)ccc2N2CC[C@H]1C2] | A | A |
| 653 | 508 | 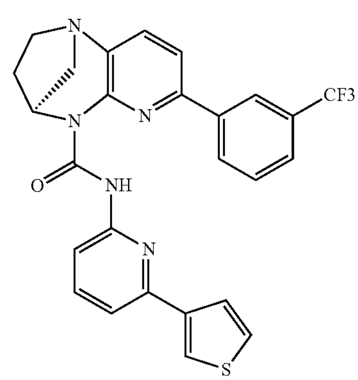 [SMILES: O=C(Nc1cccc(-c2ccsc2)n1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 654 | 492 | 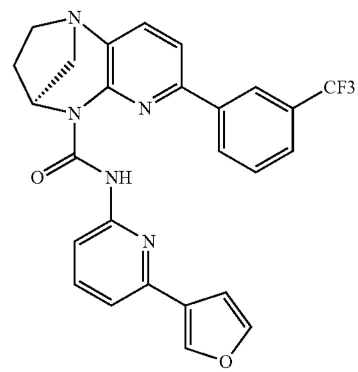 [SMILES: O=C(Nc1cccc(-c2ccoc2)n1)N1c2nc(-c3cccc(C(F)(F)F)c3)ccc2N2CC[C@H]1C2] | A | A |
| 655 | 503 | 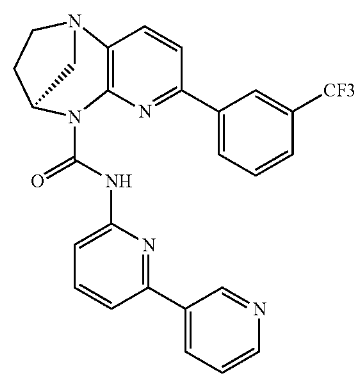 [SMILES: O=C(Nc1cccc(-c2cccnc2)n1)N1c2nc(-c3cccc(C(F)(F)F)c3)ccc2N2CC[C@H]1C2] | A | A |
| 656 | 534 | 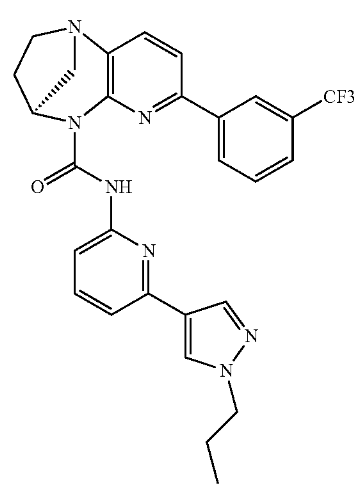 [SMILES: CCCn1cc(-c2cccc(NC(=O)N3c4nc(-c5cccc(C(F)(F)F)c5)ccc4N4CC[C@H]3C4)n2)cn1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 657 | 521 | 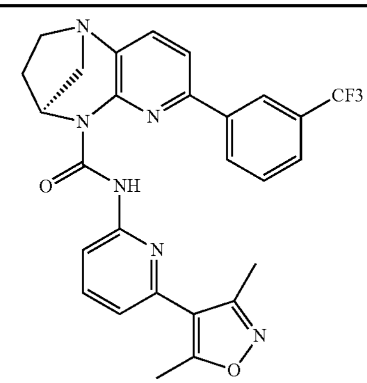 | A | A |
| 658 | 508 | 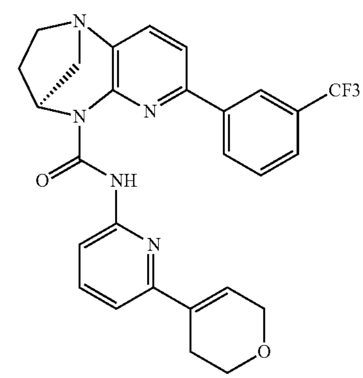 [SMILES: O=C(Nc1cccc(C2=CCOCC2)n1)N1c2nc(-c3cccc(C(F)(F)F)c3)ccc2N2CC[C@H]1C2] | A | A |
| 659 | 468 | 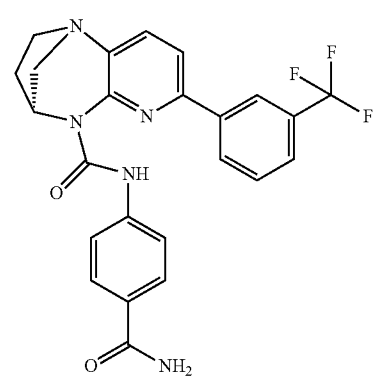 [SMILES: NC(=O)c1ccc(NC(=O)N2c3nc(-c4cccc(C(F)(F)F)c4)ccc3N3CC[C@H]2C3)cc1] | A | A |
| 660 | 502 | 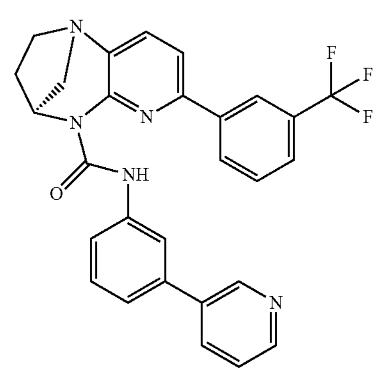 [SMILES: O=C(Nc1cccc(-c2cccnc2)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (µM) | Tryp % Fold Act |
|---|---|---|---|---|
| 661 | 443 | 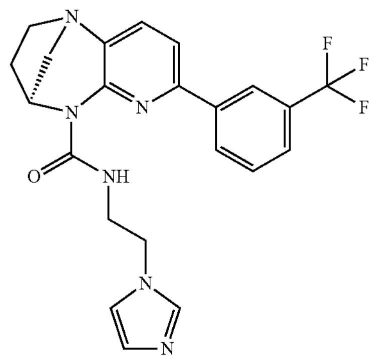 [SMILES: O=C(NCCn1ccnc1)N1c2nc(-c3cccc(C(F)(F)F)c3)ccc2N2CC[C@H]1C2] | C | A |
| 662 | 509 | 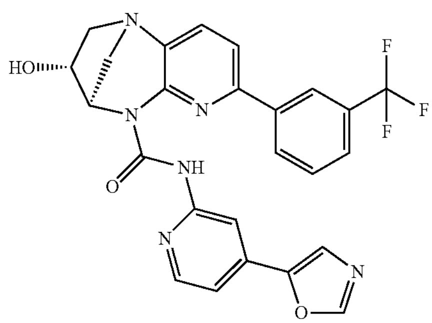 [SMILES: O=C(Nc1cc(-c2cnco2)ccn1)N1c2nc(-c3cccc(C(F)(F)F)c3)ccc2N2C[C@@H](O)[C@H]1C2] | B | A |
| 663 | 442 | 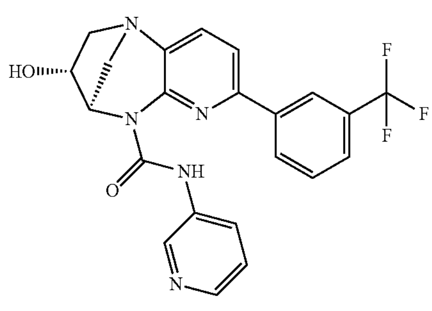 [SMILES: O=C(Nc1cccnc1)N1c2nc(-c3cccc(C(F)(F)F)c3)ccc2N2C[C@@H](O)[C@H]1C2] | A | A |
| 664 | 503 | 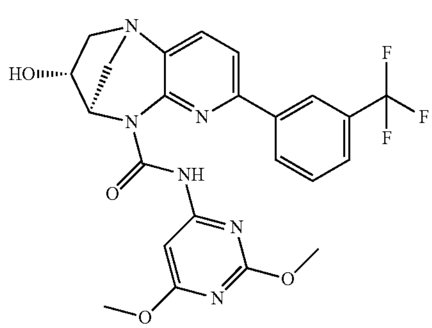 [SMILES: COc1cc(NC(=O)N2c3nc(-c4cccc(C(F)(F)F)c4)ccc3N3C[C@@H](O)[C@H]2C3)nc(OC)n1] | B | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 665 | 508 | 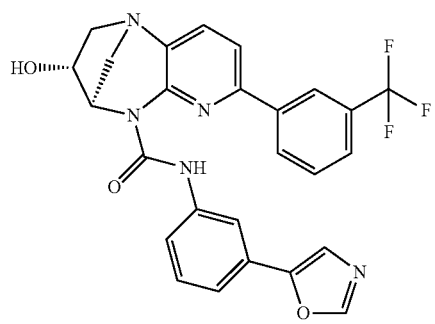 [SMILES: O=C(Nc1cccc(-c2cnco2)c1)N1c2nc(-c3cccc(C(F)(F)F)c3)ccc2N2C[C@@H](O)[C@H]1C2] | A | A |
| 666 | 465 | 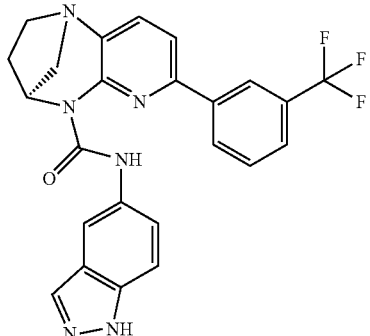 | A | A |
| 667 | 502 | 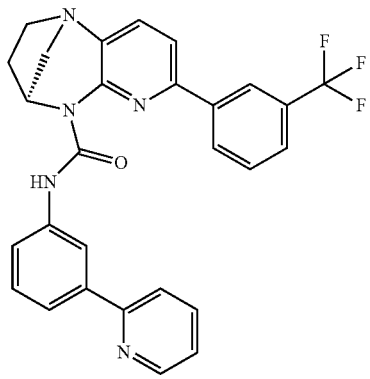 [SMILES: O=C(Nc1cccc(-c2ccccn2)c1)N1c2nc(-c3cccc(C(F)(F)F)c3)ccc2N2CC[C@H]1C2] | A | A |
| 668 | 467 | 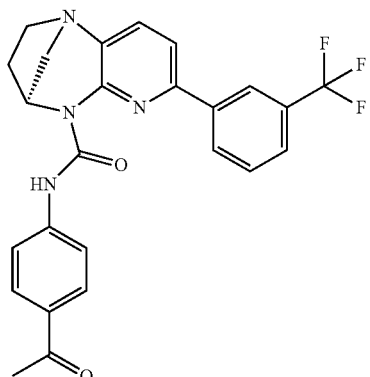 | A | A | ns
TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 669 | 443 | 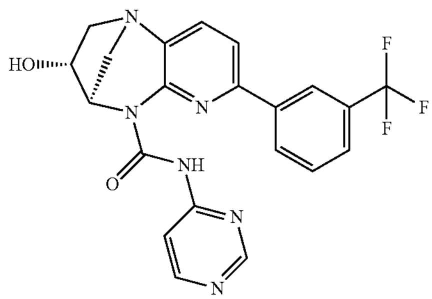 [SMILES: O=C(Nc1ccncn1)N1c2nc(-c3cccc(C(F)(F)F)c3)ccc2N2C[C@@H](O)[C@H]1C2] | B | A |
| 670 | 456 | 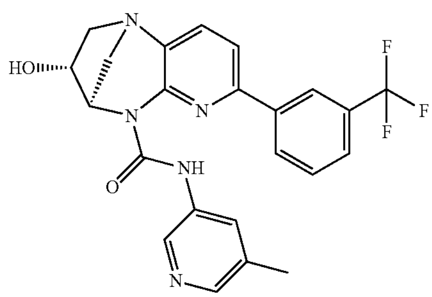 [SMILES: Cc1cncc(NC(=O)N2c3nc(-c4cccc(C(F)(F)F)c4)ccc3N3C[C@@H](O)[C@H]2C3)c1] | A | A |
| 671 | 467 | 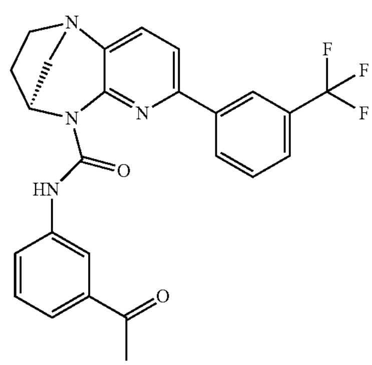 [SMILES: CC(=O)c1cccc(NC(=O)N2c3nc(-c4cccc(C(F)(F)F)c4)ccc3N3CC[C@H]2C3)c1] | A | A |
| 672 | 570 | 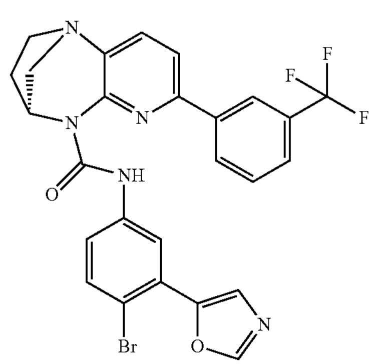 [SMILES: O=C(Nc1ccc(Br)c(-c2cnco2)c1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 673 | 468 | 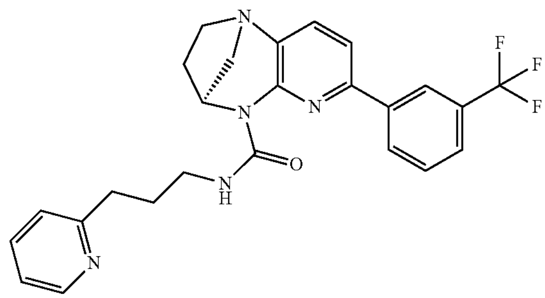 [SMILES: O=C(NCCCc1ccccn1)N1c2nc(-c3cccc(C(F)(F)F)c3)ccc2N2CC[C@H]1C2] | B | A |
| 674 | 468 | 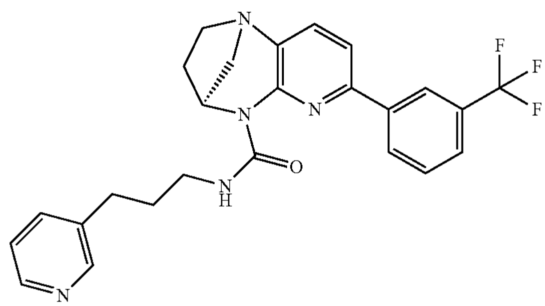 [SMILES: O=C(NCCCc1cccnc1)N1c2nc(-c3cccc(C(F)(F)F)c3)ccc2N2CC[C@H]1C2] | B | A |
| 675 | 408 | 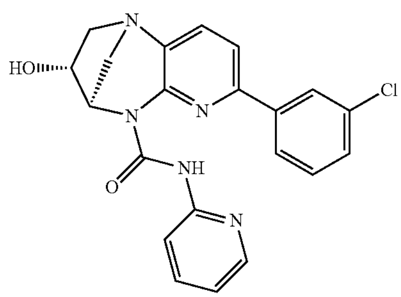 [SMILES: O=C(Nc1ccccn1)N1c2nc(-c3cccc(Cl)c3)ccc2N2C[C@@H](O)[C@H]1C2] | B | A |
| 676 | 422 | 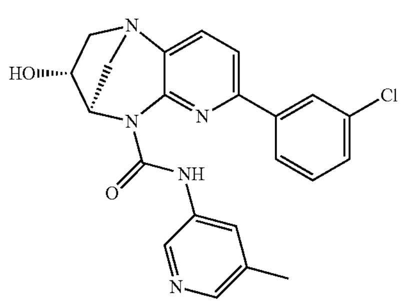 [SMILES: Cc1cncc(NC(=O)N2c3nc(-c4cccc(Cl)c4)ccc3N3C[C@@H](O)[C@H]2C3)c1] | A | A |
| 677 | 426 | 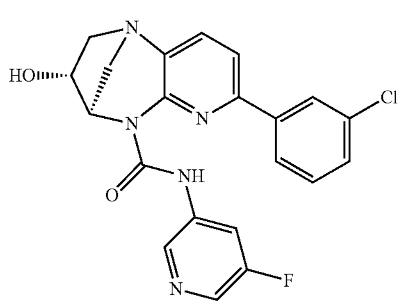 [SMILES: O=C(Nc1cncc(F)c1)N1c2nc(-c3cccc(Cl)c3)ccc2N2C[C@@H](O)[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 678 | 409 | 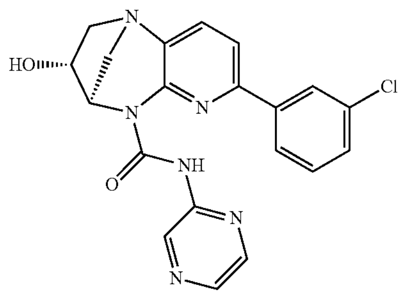 [SMILES: O=C(Nc1cnccn1)N1c2nc(-c3cccc(Cl)c3)ccc2N2C[C@@H](O)[C@H]1C2] | C | B |
| 679 | 439 | 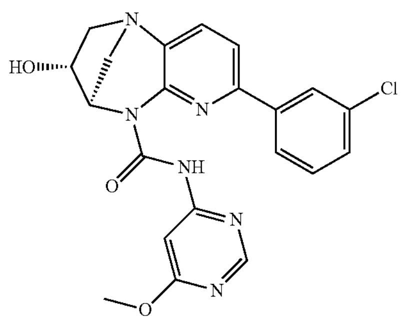 [SMILES: COc1cc(NC(=O)N2c3nc(-c4cccc(Cl)c4)ccc3N3C[C@@H](O)[C@H]2C3)ncn1] | B | A |
| 680 | 469 | 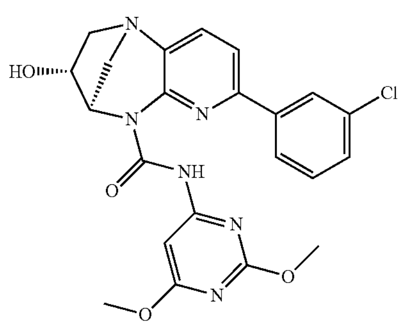 [SMILES: COc1cc(NC(=O)N2c3nc(-c4cccc(Cl)c4)ccc3N3C[C@@H](O)[C@H]2C3)nc(OC)n1] | B | A |
| 681 | 408 | 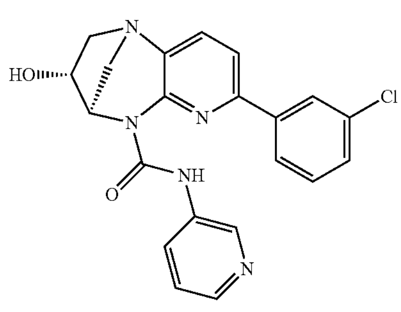 [SMILES: O=C(Nc1cccnc1)N1c2nc(-c3cccc(Cl)c3)ccc2N2C[C@@H](O)[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 682 | 409 | 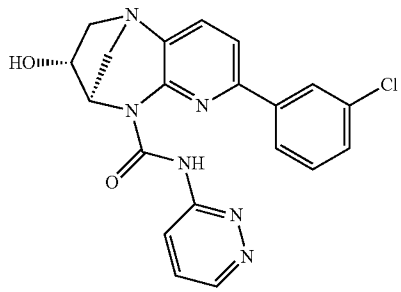 [SMILES: O=C(Nc1cccnn1)N1c2nc(-c3cccc(Cl)c3)ccc2N2C[C@@H](O)[C@H]1C2] | B | A |
| 683 | 474 | 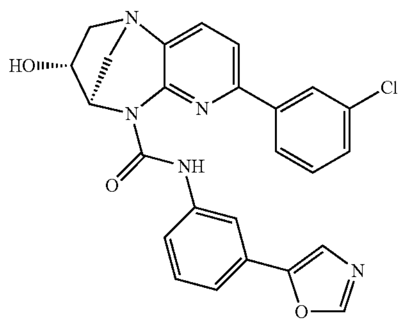 [SMILES: O=C(Nc1cccc(-c2cnco2)c1)N1c2nc(-c3cccc(Cl)c3)ccc2N2C[C@@H](O)[C@H]1C2] | A | A |
| 684 | 409 | 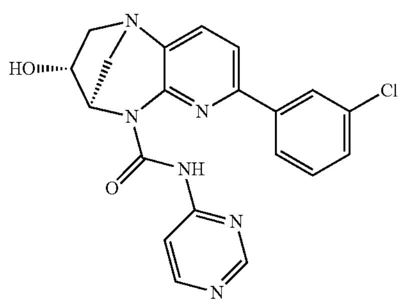 [SMILES: O=C(Nc1ccncn1)N1c2nc(-c3cccc(Cl)c3)ccc2N2C[C@@H](O)[C@H]1C2] | B | A |
| 685 | 475 | 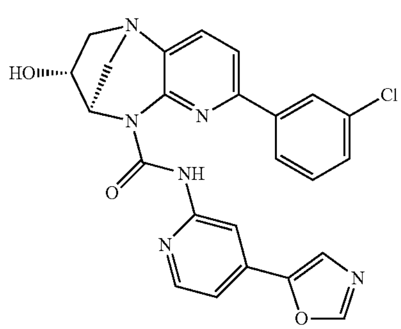 [SMILES: O=C(Nc1cc(-c2cnco2)ccn1)N1c2nc(-c3cccc(Cl)c3)ccc2N2C[C@@H](O)[C@H]1C2] | B | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 688 | 442 | 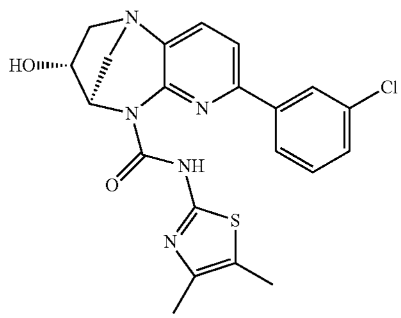 [SMILES: Cc1nc(NC(=O)N2c3nc(-c4cccc(Cl)c4)ccc3N3C[C@@H](O)[C@H]2C3)sc1C] | B | A |
| 689 | 471 | 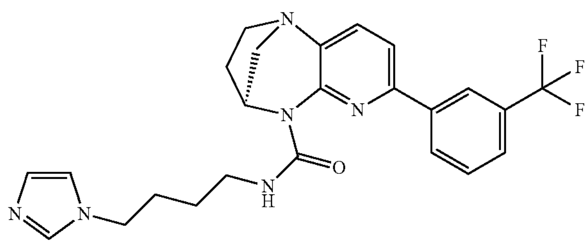 [SMILES: O=C(NCCCCn1ccnc1)N1c2nc(-c3cccc(C(F)(F)F)c3)ccc2N2CC[C@H]1C2] | B | A |
| 690 | 457 | 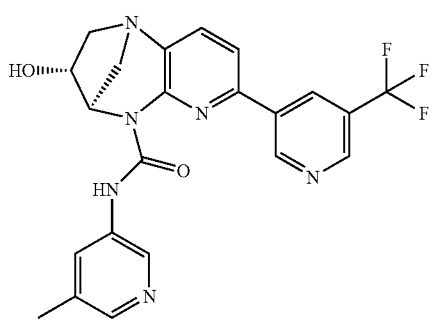 [SMILES: Cc1cncc(NC(=O)N2c3nc(-c4cncc(C(F)(F)F)c4)ccc3N3C[C@@H](O)[C@H]2C3)c1] | B | A |
| 691 | 461 | 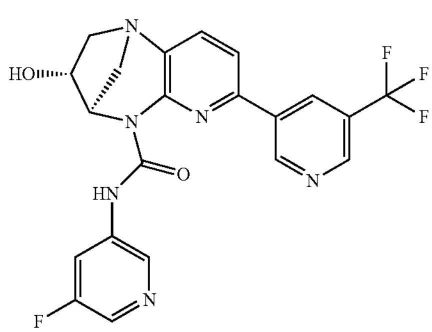 [SMILES: O=C(Nc1cncc(F)c1)N1c2nc(-c3cncc(C(F)(F)F)c3)ccc2N2C[C@@H](O)[C@H]1C2] | B | A |

TABLE 1-continued

Compounds of Formula (I).

| Compound No. | [M + H]+_[calc] | Structure | Tryp AVG EC_{1.5} (μM) | Tryp % Fold Act |
|---|---|---|---|---|
| 692 | 506 | 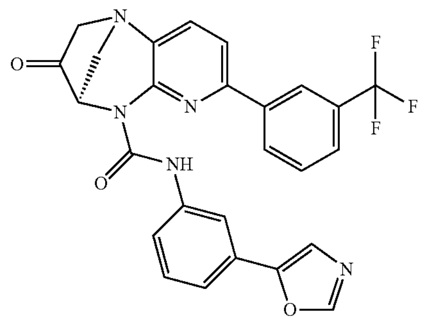 [SMILES: O=C1CN2C[C@H]1N(C(=O)Nc1cccc(-c3cnco3)c1)c1nc(-c3cccc(C(F)(F)F)c3)ccc12] | A | A |
| 693 | 475 | 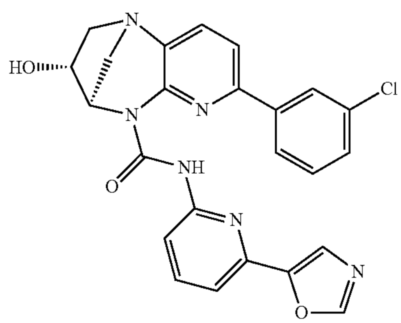 [SMILES: O=C(Nc1cccc(-c2cnco2)n1)N1c2nc(-c3cccc(Cl)c3)ccc2N2C[C@@H](O)[C@H]1C2] | A | A |
| 694 | 443 | 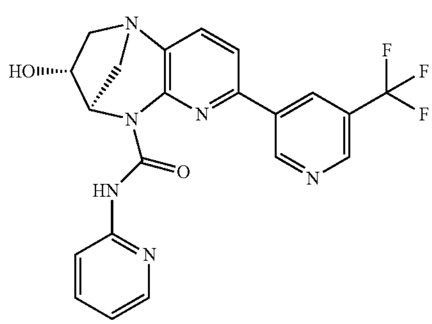 [SMILES: O=C(Nc1ccccn1)N1c2nc(-c3cncc(C(F)(F)F)c3)ccc2N2C[C@@H](O)[C@H]1C2] | A | A |
| 695 | 444 | 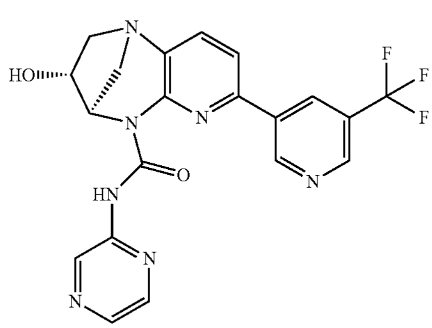 [SMILES: O=C(Nc1cnccn1)N1c2nc(-c3cncc(C(F)(F)F)c3)ccc2N2C[C@@H](O)[C@H]1C2] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 696 | 474 | 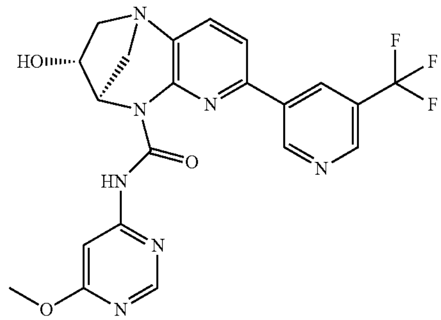 [SMILES: COc1cc(NC(=O)N2c3nc(-c4cncc(C(F)(F)F)c4)ccc3N3C[C@@H](O)[C@H]2C3)ncn1] | B | A |
| 697 | 477 | 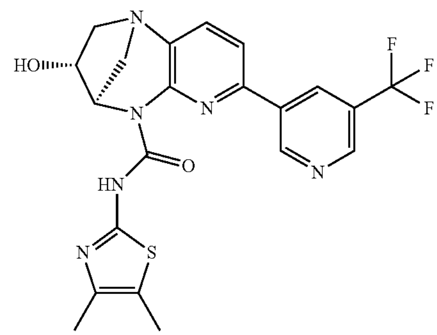 [SMILES: Cc1nc(NC(=O)N2c3nc(-c4cncc(C(F)(F)F)c4)ccc3N3C[C@@H](O)[C@H]2C3)sc1C] | B | A |
| 698 | 509 | 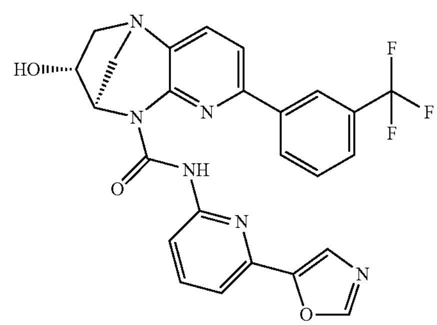 [SMILES: O=C(Nc1cccc(-c2cnco2)n1)N1c2nc(-c3cccc(C(F)(F)F)c3)ccc2N2C[C@@H](O)[C@H]1C2] | A | A |
| 699 | 476 | 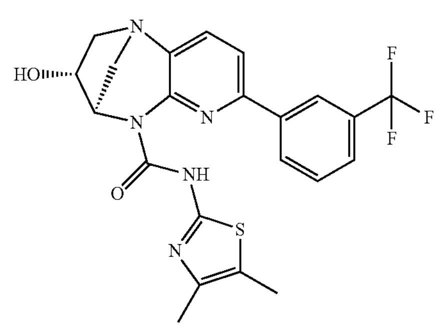 [SMILES: Cc1nc(NC(=O)N2c3nc(-c4cccc(C(F)(F)F)c4)ccc3N3C[C@@H](O)[C@H]2C3)sc1C] | B | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 700 | 444 | 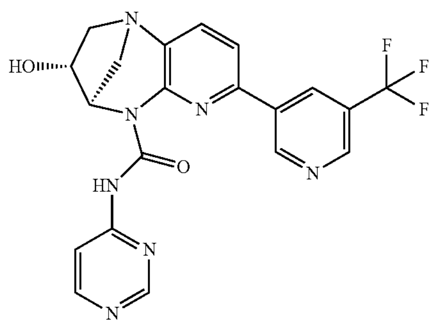 [SMILES: O=C(Nc1ccncn1)N1c2nc(-c3cncc(C(F)(F)F)c3)ccc2N2C[C@@H](O)[C@H]1C2] | B | A |
| 701 | 444 | 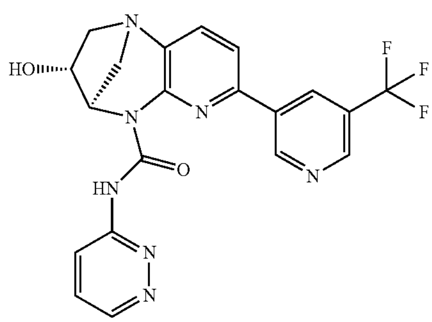 [SMILES: O=C(Nc1cccnn1)N1c2nc(-c3cncc(C(F)(F)F)c3)ccc2N2C[C@@H](O)[C@H]1C2] | B | A |
| 702 | 516 | 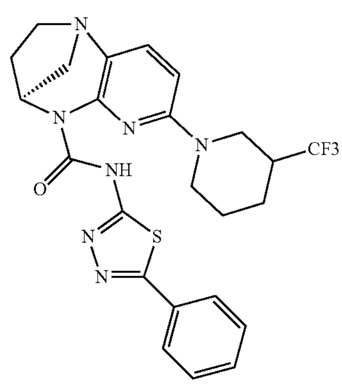 [SMILES: O=C(Nc1nnc(-c2ccccc2)s1)N1c2nc(N3CCCC(C(F)(F)F)C3)ccc2N2CC[C@H]1C2] | NT | NT |
| 703 | 510 | 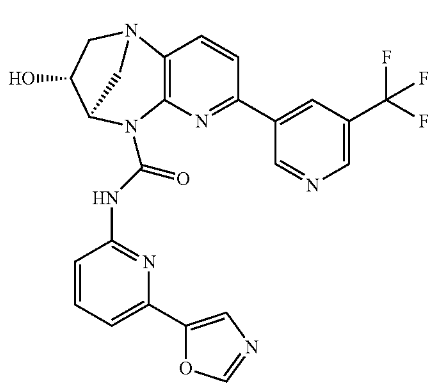 [SMILES: O=C(Nc1cccc(-c2cnco2)n1)N1c2nc(-c3cncc(C(F)(F)F)c3)ccc2N2C[C@@H](O)[C@H]1C2] | A | A |

TABLE 1-continued

Compounds of Formula (I).

| Compound No. | [M + H]+[calc] | Structure | Tryp AVG EC1.5 (µM) | Tryp % Fold Act |
|---|---|---|---|---|
| 704 | 504 | 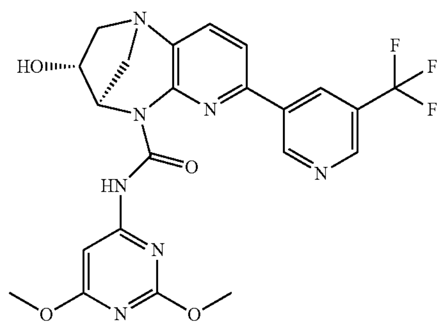 [SMILES: COc1cc(NC(=O)N2c3nc(-c4cncc(C(F)(F)F)c4)ccc3N3C[C@@H](O)[C@H]2C3)nc(OC)n1] | B | A |
| 705 | 443 | 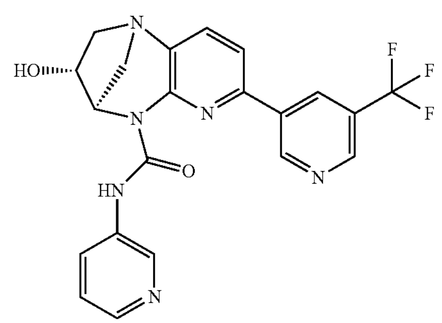 [SMILES: O=C(Nc1cccnc1)N1c2nc(-c3cncc(C(F)(F)F)c3)ccc2N2C[C@@H](O)[C@H]1C2] | B | A |
| 706 | 655 | 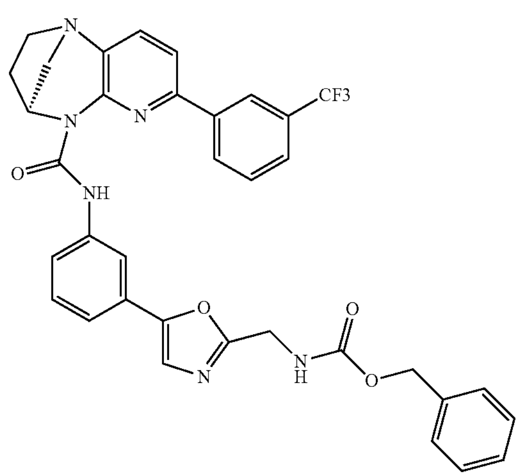 [SMILES: O=C(NCc1ncc(-c2cccc(NC(=O)N3c4nc(-c5cccc(C(F)(F)F)c5)ccc4N4CC[C@H]3C4)c2)o1)OCc1ccccc1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 708 | 992 | 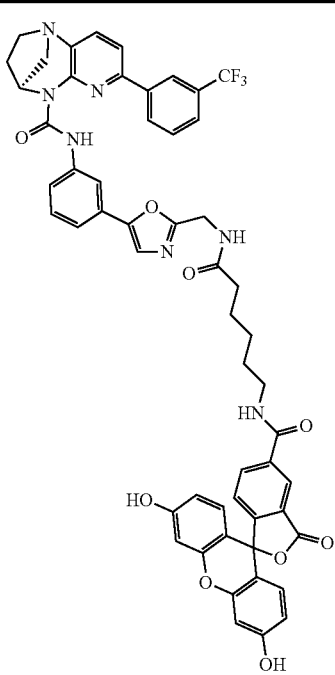 | A | A |
| 709 | 509 | 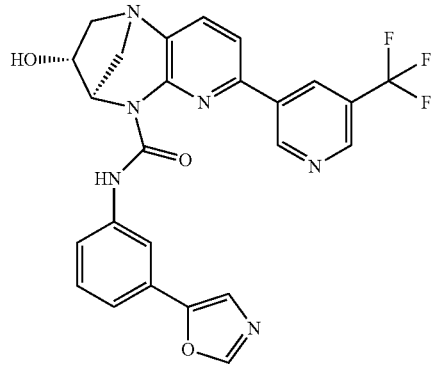 [SMILES: O=C(Nc1cccc(-c2cnco2)c1)N1c2nc(-c3cncc(C(F)(F)F)c3)ccc2N2C[C@@H](O)[C@H]1C2] | A | A |
| 710 | 502 | 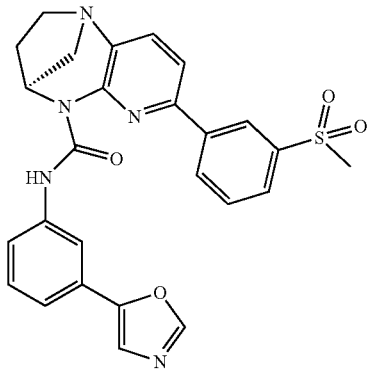 [SMILES: CS(=O)(=O)c1cccc(-c2ccc3c(n2)N(C(=O)Nc2cccc(-c4cnco4)c2)[C@H]2CCN3C2)c1] | A | A |

TABLE 1-continued
Compounds of Formula (I).
| Compound No. | [M + H]+[calc] | Structure | Tryp AVG EC$_{1.5}$ (µM) | Tryp % Fold Act |
|---|---|---|---|---|
| 714 | 481 | 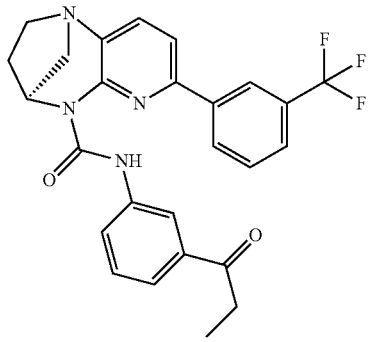 [SMILES: CCC(=O)c1cccc(NC(=O)N2c3nc(-c4cccc(C(F)(F)F)c4)ccc3N3CC[C@H]2C3)c1] | A | A |
| 715 | 503 | 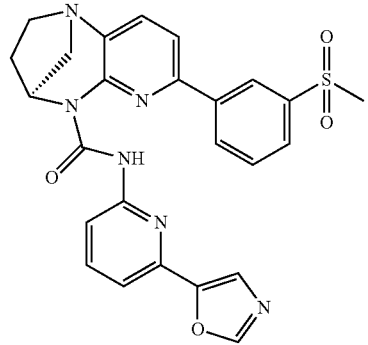 [SMILES: CS(=O)(=O)c1cccc(-c2ccc3c(n2)N(C(=O)Nc2cccc(-c4cnco4)n2)[C@H]2CCN3C2)c1] | B | A |
| 716 | 444 | 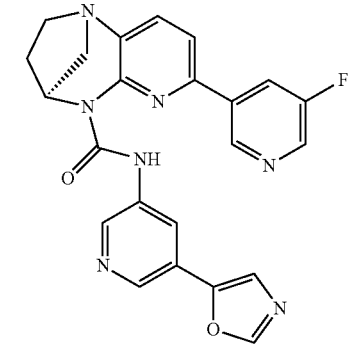 [SMILES: O=C(Nc1cncc(-c2cnco2)c1)N1c2nc(-c3cncc(F)c3)ccc2N2CC[C@H]1C2] | B | A |
| 717 | 499 | 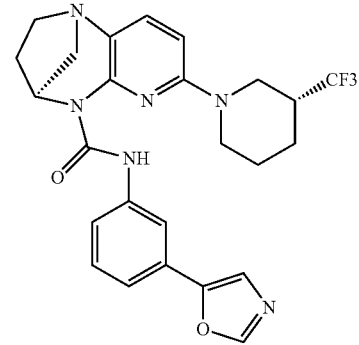 [SMILES: O=C(Nc1cccc(-c2cnco2)c1)N1c2nc(N3CCC[C@@H](C(F)(F)F)C3)ccc2N2CC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 718 | 499 | 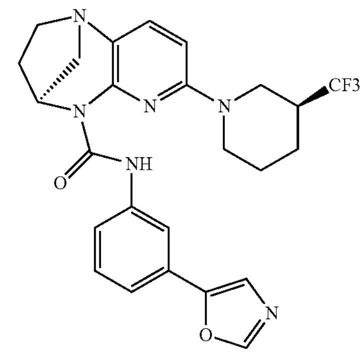 [SMILES: O=C(Nc1cccc(-c2cnco2)c1)N1c2nc(N3CCC[C@H](C(F)(F)F)C3)ccc2N2CC[C@H]1C2] | A | A |
| 719 | 493 | 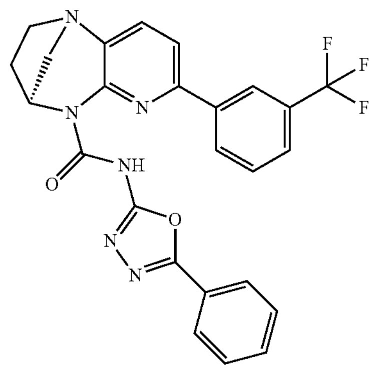 [SMILES: O=C(Nc1nnc(-c2ccccc2)o1)N1c2nc(-c3cccc(C(F)(F)F)c3)ccc2N2CC[C@H]1C2] | A | A |
| 720 | 494 | 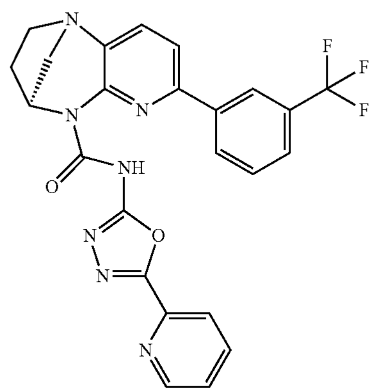 [SMILES: O=C(Nc1nnc(-c2ccccn2)o1)N1c2nc(-c3cccc(C(F)(F)F)c3)ccc2N2CC[C@H]1C2] | A | A |
| 721 | 494 | 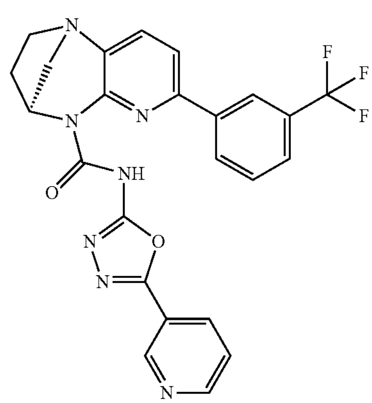 [SMILES: O=C(Nc1nnc(-c2cccnc2)o1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 722 | 443 | 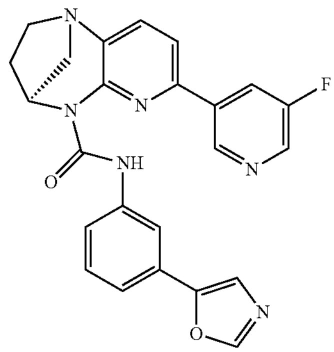 [SMILES: O=C(Nc1cccc(-c2cnco2)c1)N1c2nc(-c3cncc(F)c3)ccc2N2CC[C@H]1C2] | A | A |
| 723 | 503 | 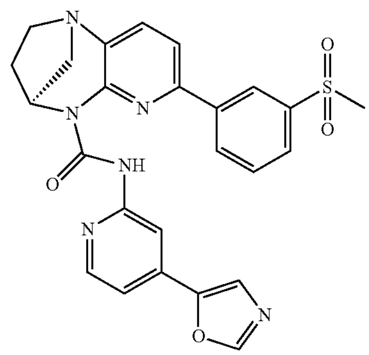 [SMILES: CS(=O)(=O)c1cccc(-c2ccc3c(n2)N(C(=O)Nc2cc(-c4cnco4)ccn2)[C@H]2CCN3C2)c1] | A | A |
| 724 | 503 | 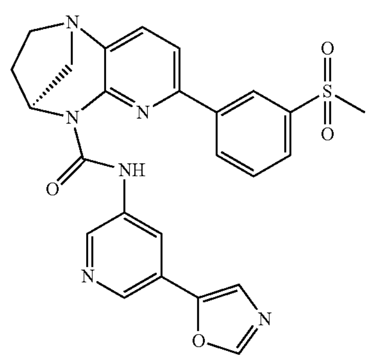 [SMILES: CS(=O)(=O)c1cccc(-c2ccc3c(n2)N(C(=O)Nc2cncc(-c4cnco4)c2)[C@H]2CCN3C2)c1] | A | A |
| 725 | 521 | 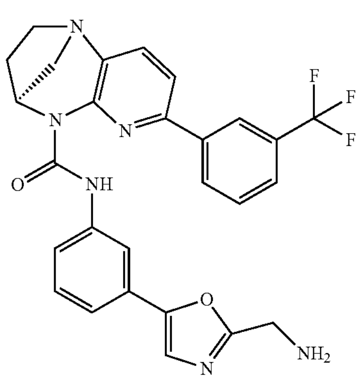 [SMILES: NCc1ncc(-c2cccc(NC(=O)N3c4nc(-c5cccc(C(F)(F)F)c5)ccc4N4CC[C@H]3C4)c2)o1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 726 | 510 | 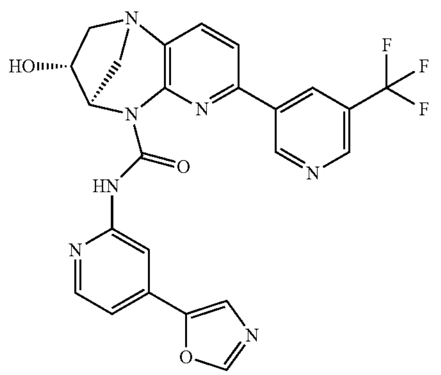 [SMILES: O=C(Nc1cc(-c2cnco2)ccn1)N1c2nc(-c3cncc(C(F)(F)F)c3)ccc2N2C[C@@H](O)[C@H]1C2] | B | B |
| 727 | 444 | 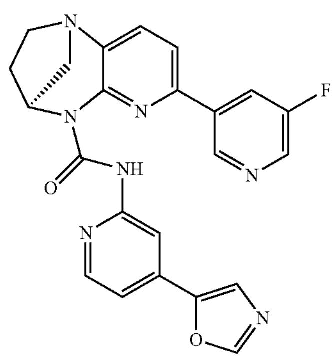 [SMILES: O=C(Nc1cc(-c2cnco2)ccn1)N1c2nc(-c3cncc(F)c3)ccc2N2CC[C@H]1C2] | A | A |
| 730 | 1013 | 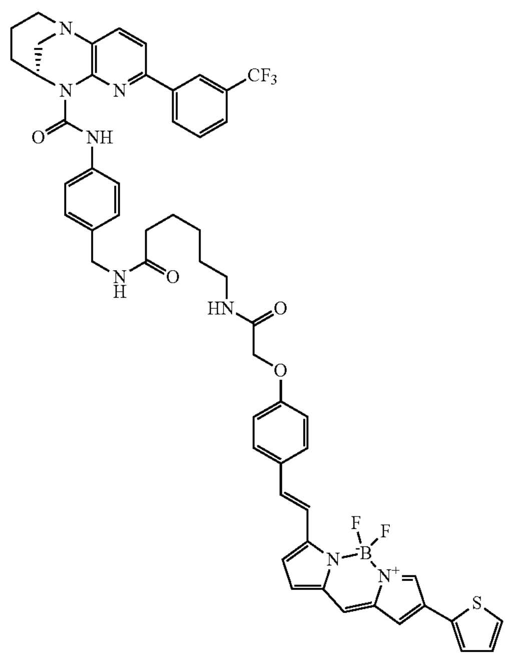 | A | A |

TABLE 1-continued
Compounds of Formula (I).
| Compound No. | [M + H]+[calc] | Structure | Tryp AVG EC1.5 (µM) | Tryp % Fold Act |
|---|---|---|---|---|
| 731 | 523 | 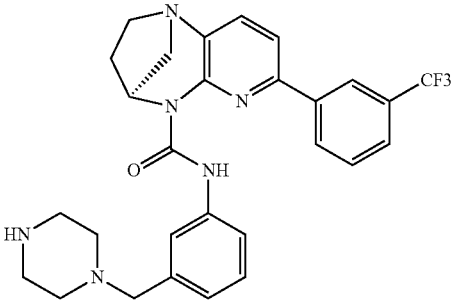 [SMILES: O=C(Nc1cccc(CN2CCNCC2)c1)N1c2nc(-c3cccc(C(F)(F)F)c3)ccc2N2CC[C@H]1C2] | A | A |
| 733 | 510 | 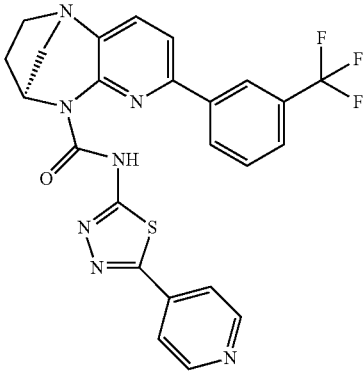 [SMILES: O=C(Nc1nnc(-c2ccncc2)s1)N1c2nc(-c3cccc(C(F)(F)F)c3)ccc2N2CC[C@H]1C2] | A | A |
| 734 | 508 | 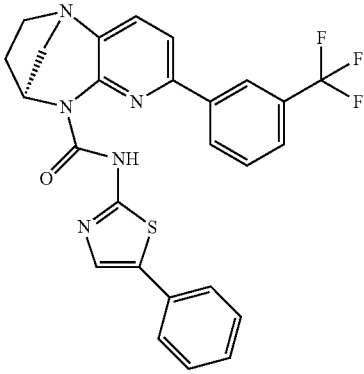 [SMILES: O=C(Nc1ncc(-c2ccccc2)s1)N1c2nc(-c3cccc(C(F)(F)F)c3)ccc2N2CC[C@H]1C2] | B | A |
| 736 | 495 | 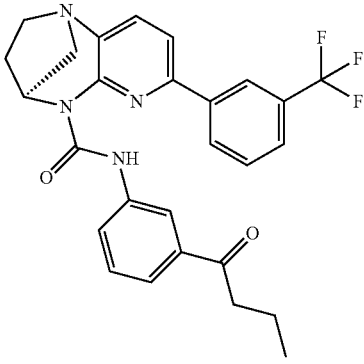 [SMILES: CCCC(=O)c1cccc(NC(=O)N2c3nc(-c4cccc(C(F)(F)F)c4)ccc3N3CC[C@H]2C3)c1] | A | A |

TABLE 1-continued

Compounds of Formula (I).

| Compound No. | [M + H]+[calc] | Structure | Tryp AVG EC1.5 (μM) | Tryp % Fold Act |
|---|---|---|---|---|
| 737 | 509 | 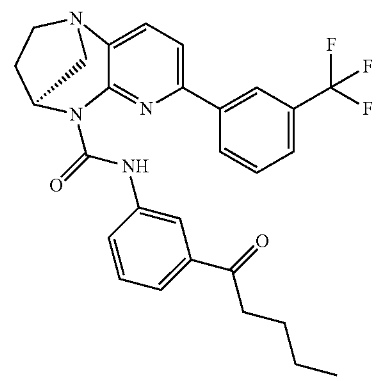 [SMILES: CCCCC(=O)c1cccc(NC(=O)N2c3nc(-c4cccc(C(F)(F)F)c4)ccc3N3CC[C@H]2C3)c1] | A | A |
| 739 | 444 | 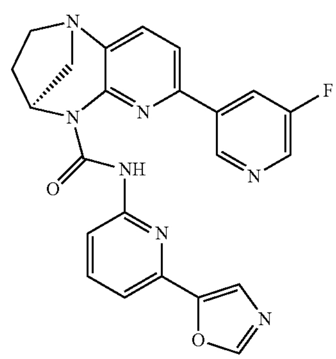 | A | A |
| 740 | 495 | 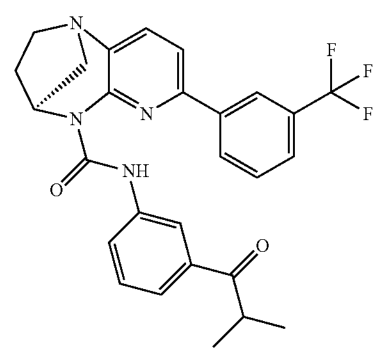 [SMILES: CC(C)C(=O)c1cccc(NC(=O)N2c3nc(-c4cccc(C(F)(F)F)c4)ccc3N3CC[C@H]2C3)c1] | A | A |
| 741 | 528 | 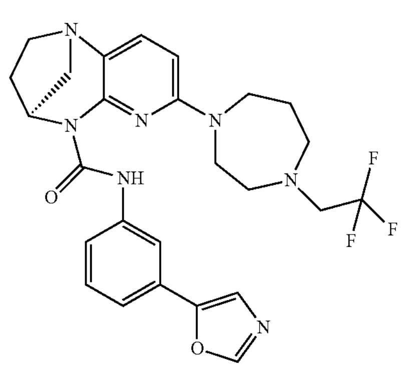 [SMILES: O=C(Nc1cccc(-c2cnco2)c1)N1c2nc(N3CCCN(CC(F)(F)F)CC3)ccc2N2CC[C@H]1C2] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 742 | 525 | 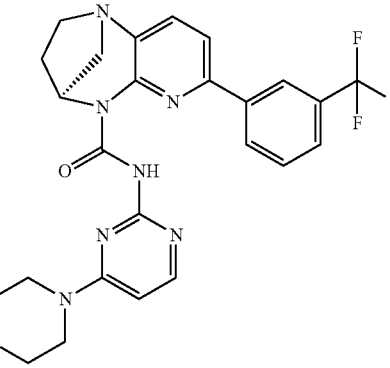 | A | A |
| 743 | 559 | 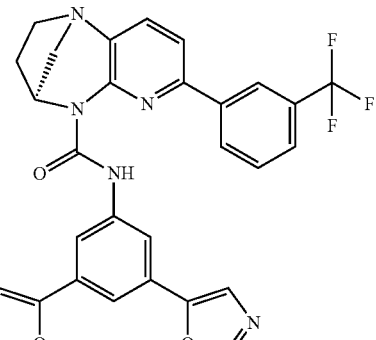 | A | A |
| 745 | 511 | 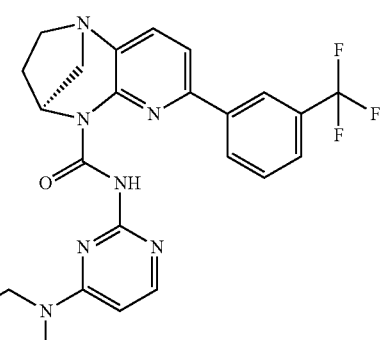 | B | A |
| 746 | 440 | 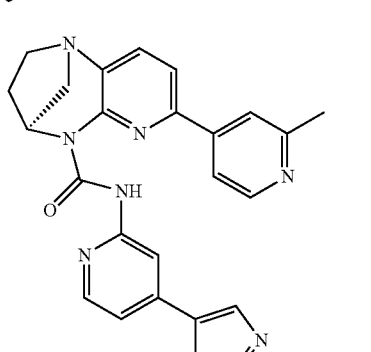 | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 747 | 470 | 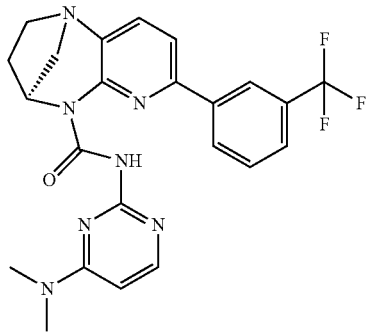 [SMILES: CN(C)c1ccnc(NC(=O)N2c3nc(-c4cccc(C(F)(F)F)c4)ccc3N3CC[C@H]2C3)n1] | A | A |
| 748 | 440 | 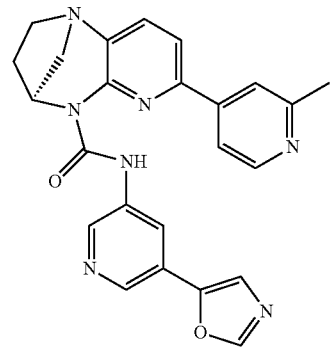 [SMILES: Cc1cc(-c2ccc3c(n2)N(C(=O)Nc2cncc(-c4cnco4)c2)[C@H]2CCN3C2)ccn1] | A | A |
| 749 | 645 | 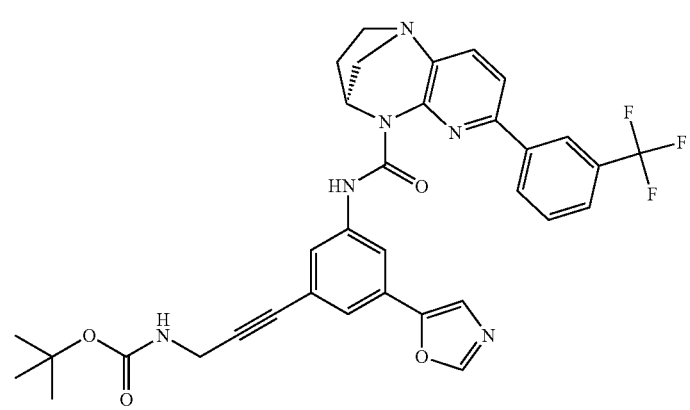 [SMILES: CC(C)(C)OC(=O)NCC#Cc1cc(NC(=O)N2c3nc(-c4cccc(C(F)(F)F)c4)ccc3N3CC[C@H]2C3)cc(-c2cnco2)c1] | A | A |

TABLE 1-continued
Compounds of Formula (I).
| Compound No. | [M + H]+[calc] | Structure | Tryp AVG EC1.5 (μM) | Tryp % Fold Act |
|---|---|---|---|---|
| 750 | 649 | 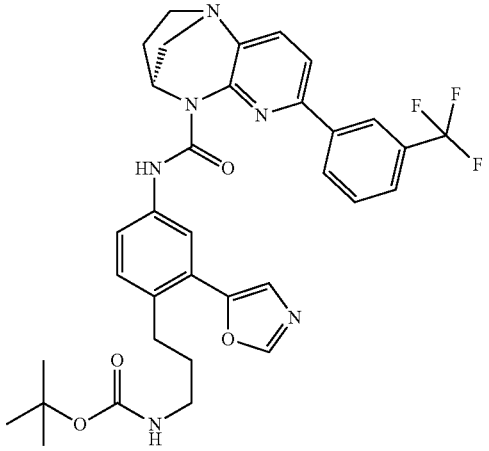 [SMILES: CC(C)(C)OC(=O)NCCCc1ccc(NC(=O)N2c3nc(-c4cccc(C(F)(F)F)c4)ccc3N3CC[C@H]2C3)cc1-c1cnco1] | A | A |
| 751 | 645 | 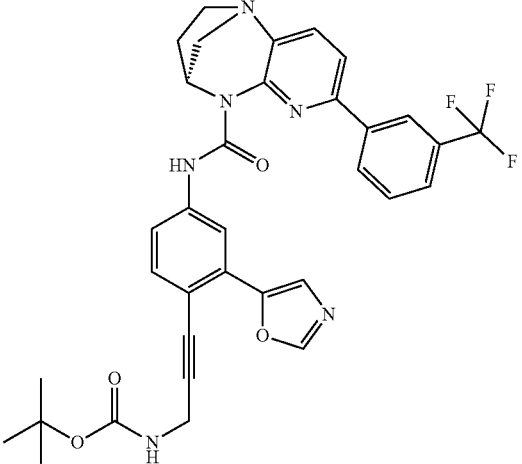 [SMILES: CC(C)(C)OC(=O)NCC#Cc1ccc(NC(=O)N2c3nc(-c4cccc(C(F)(F)F)c4)ccc3N3CC[C@H]2C3)cc1-c1cnco1] | A | A |
| 752 | 663 | 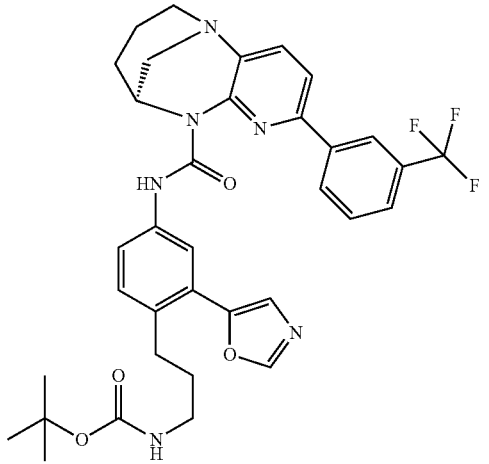 [SMILES: CC(C)(C)OC(=O)NCCCc1ccc(NC(=O)N2c3nc(-c4cccc(C(F)(F)F)c4)ccc3N3CCC[C@H]2C3)cc1-c1cnco1] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 753 | 659 | 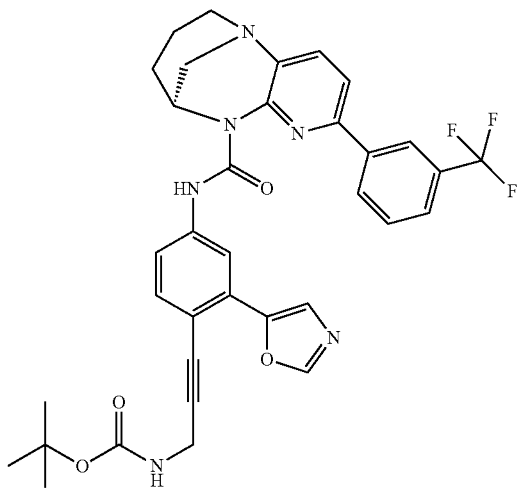 [SMILES: CC(C)(C)OC(=O)NCC#Cc1ccc(NC(=O)N2c3nc(-c4cccc(C(F)(F)F)c4)ccc3N3CCC[C@H]2C3)cc1-c1cnco1] | A | A |
| 754 | 663 | 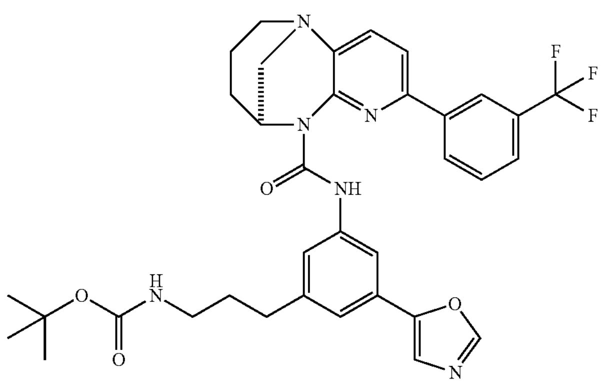 | A | A |
| 755 | 454 | 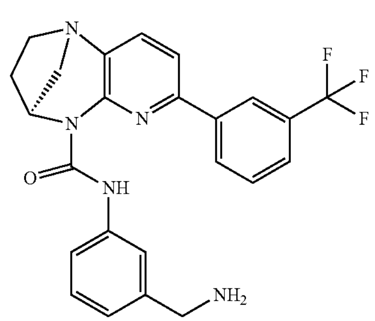 [SMILES: NCc1cccc(NC(=O)N2c3nc(-c4cccc(C(F)(F)F)c4)ccc3N3CC[C@H]2C3)c1] | B | A |

TABLE 1-continued

Compounds of Formula (I).

| Compound No. | [M + H]+$_{[calc]}$ | Structure | Tryp AVG EC$_{1.5}$ (µM) | Tryp % Fold Act |
|---|---|---|---|---|
| 756 | 581 | 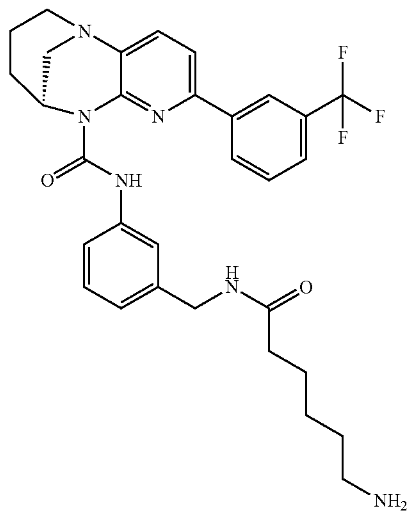 [SMILES: NCCCCCC(=O)NCc1cccc(NC(=O)N2c3nc(-c4cccc(C(F)(F)F)c4)ccc3N3CCC[C@H]2C3)c1] | A | A |
| 757 | 468 | 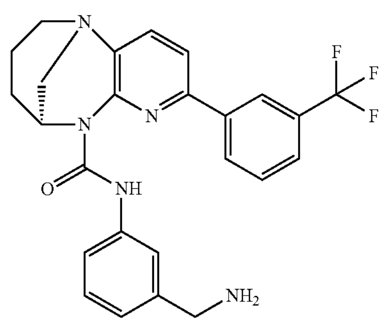 [SMILES: NCc1cccc(NC(=O)N2c3nc(-c4cccc(C(F)(F)F)c4)ccc3N3CCC[C@H]2C3)c1] | A | A |
| 758 | 567 | 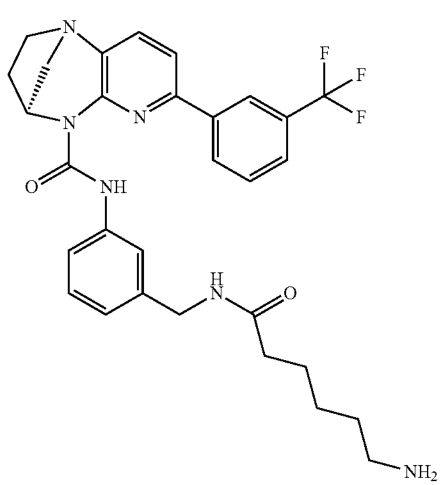 [SMILES: NCCCCCC(=O)NCc1cccc(NC(=O)N2c3nc(-c4cccc(C(F)(F)F)c4)ccc3N3CC[C@H]2C3)c1] | A | A |

TABLE 1-continued

Compounds of Formula (I).

| Compound No. | [M + H]+<sub>[calc]</sub> | Structure | Tryp AVG EC<sub>1.5</sub> (µM) | Tryp % Fold Act |
|---|---|---|---|---|
| 759 | 649 | 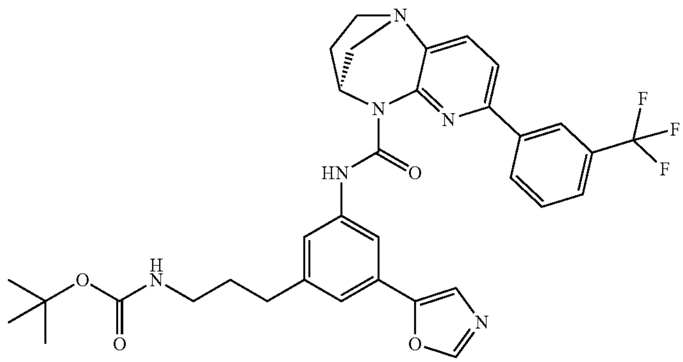 [SMILES: CC(C)(C)OC(=O)NCCCc1cc(NC(=O)N2c3nc(-c4cccc(C(F)(F)F)c4)ccc3N3CC[C@H]2C3)cc(-c2cnco2)c1] | B | A |
| 760 | 659 | 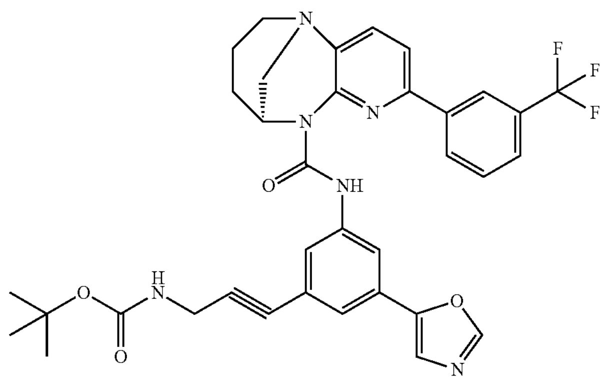 [SMILES: CC(C)(C)OC(=O)NCC#Cc1cc(NC(=O)N2c3nc(-c4cccc(C(F)(F)F)c4)ccc3N3CCC[C@H]2C3)cc(-c2cnco2)c1] | A | A |
| 763 | 508 | 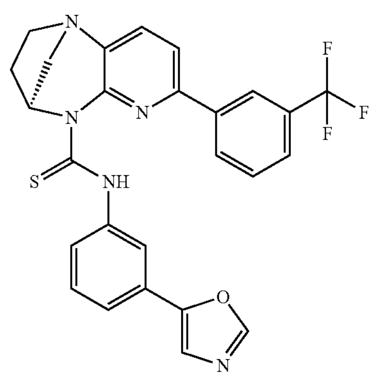 [SMILES: FC(F)(F)c1cccc(-c2ccc3c(n2)N(C(=S)Nc2cccc(-c4cnco4)c2)[C@H]2CCN3C2)c1] | A | A |
| 764 | 545 | 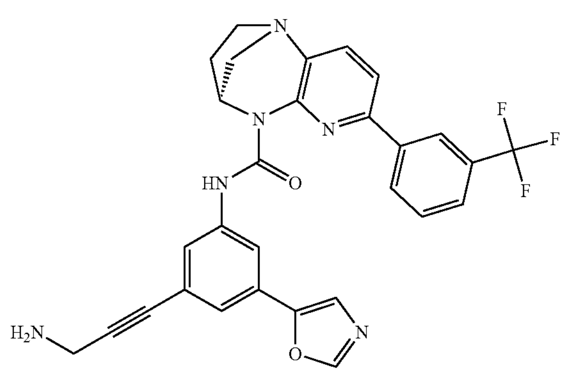 [SMILES: NCC#Cc1cc(NC(=O)N2c3nc(-c4cccc(C(F)(F)F)c4)ccc3N3CC[C@H]2C3)cc(-c2cnco2)c1] | NT | NT |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 765 | 549 | 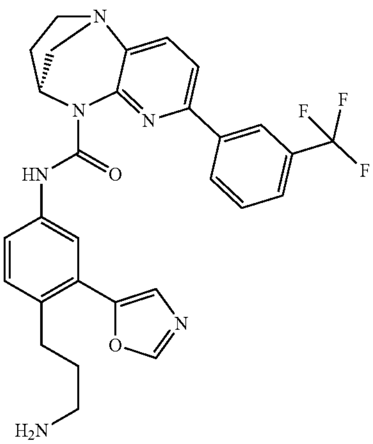 [SMILES: NCCCc1ccc(NC(=O)N2c3nc(-c4cccc(C(F)(F)F)c4)ccc3N3CC[C@H]2C3)cc1-c1cnco1] | A | A |
| 766 | 545 | 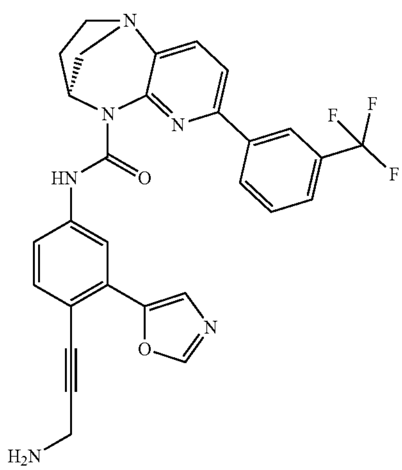 [SMILES: NCC#Cc1ccc(NC(=O)N2c3nc(-c4cccc(C(F)(F)F)c4)ccc3N3CC[C@H]2C3)cc1-c1cnco1] | A | A |
| 767 | 563 | 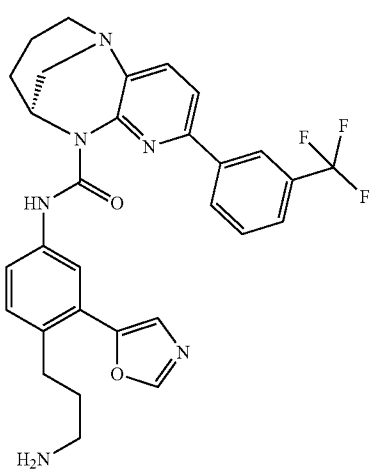 [SMILES: NCCCc1ccc(NC(=O)N2c3nc(-c4cccc(C(F)(F)F)c4)ccc3N3CCC[C@H]2C3)cc1-c1cnco1] | A | A |

TABLE 1-continued

Compounds of Formula (I).

| Compound No. | [M + H]+_[calc] | Structure | Tryp AVG EC_{1.5} (μM) | Tryp % Fold Act |
|---|---|---|---|---|
| 768 | 559 | 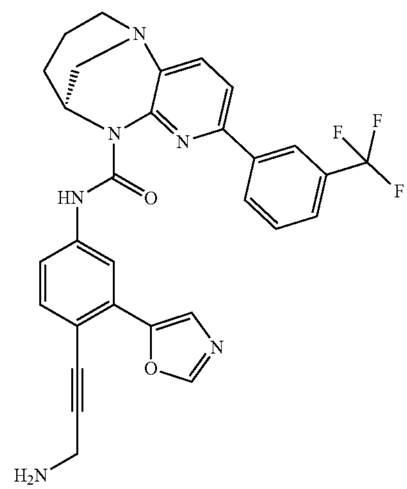 [SMILES: NCC#Cc1ccc(NC(=O)N2c3nc(-c4cccc(C(F)(F)F)c4)ccc3N3CCC[C@H]2C3)cc1-c1cnco1] | NT | NT |
| 769 | 563 | 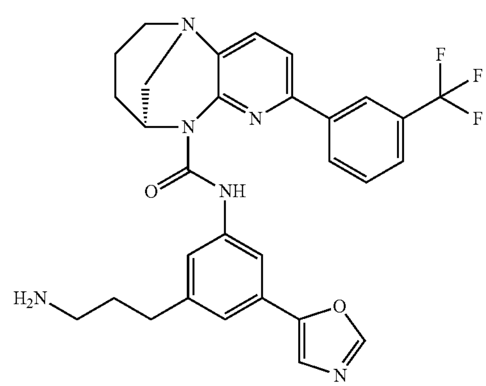 [SMILES: NCCCc1cc(NC(=O)N2c3nc(-c4cccc(C(F)(F)F)c4)ccc3N3CCC[C@H]2C3)cc(-c2cnco2)c1] | NT | NT |
| 770 | 549 | 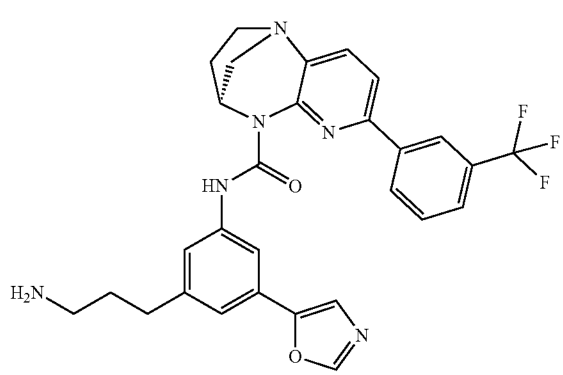 [SMILES: NCCCc1cc(NC(=O)N2c3nc(-c4cccc(C(F)(F)F)c4)ccc3N3CC[C@H]2C3)cc(-c2cnco2)c1] | A | A |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 771 | 559 | 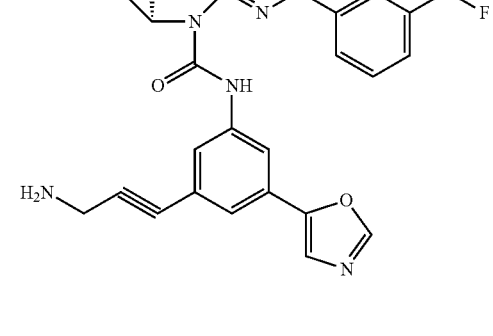 | NT | NT |
| 776 | 563 | 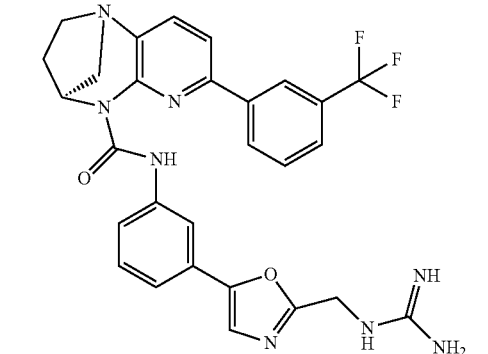 | A | A |
| 777 | 510 | 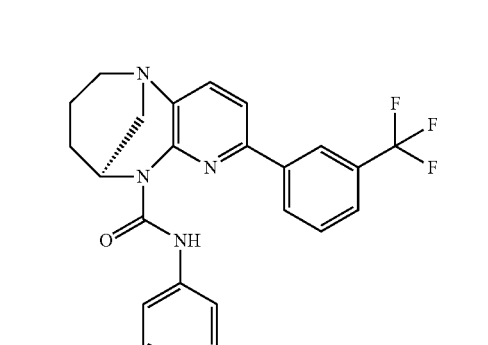 | A | A |

TABLE 1-continued

Compounds of Formula (I).

| Compound No. | [M + H]+[calc] | Structure | Tryp AVG EC1.5 (μM) | Tryp % Fold Act |
|---|---|---|---|---|
| 780 | 639 | 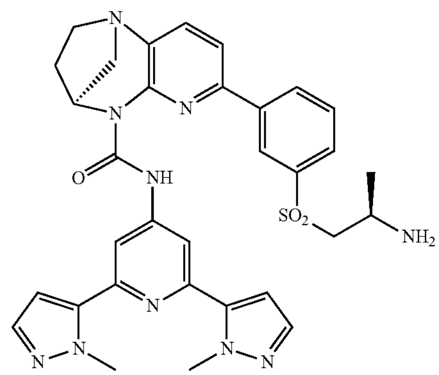 [SMILES: C[C@@H](N)CS(=O)(=O)c1cccc(-c2ccc3c(n2)N(C(=O)Nc2cc(-c4ccnn4C)nc(-c4ccnn4C)c2)[C@H]2CCN3C2)c1] | A | A |
| 785 | 425 | 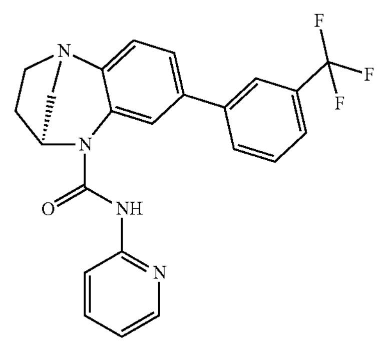 [SMILES: O=C(Nc1ccccn1)N1c2cc(-c3cccc(C(F)(F)F)c3)ccc2N2CC[C@H]1C2] | C | B |
| 786 | 491 | 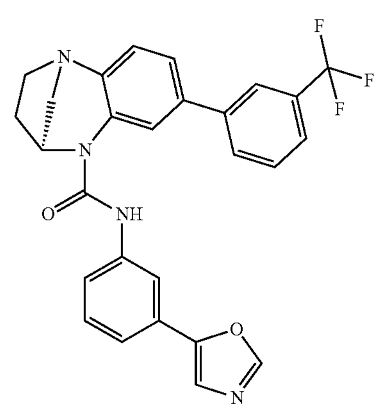 [SMILES: O=C(Nc1cccc(-c2cnco2)c1)N1c2cc(-c3cccc(C(F)(F)F)c3)ccc2N2CC[C@H]1C2] | B | A |

TABLE 1-continued

Compounds of Formula (I).

| Compound No. | [M + H]+[calc] | Structure | Tryp AVG EC1.5 (μM) | Tryp % Fold Act |
|---|---|---|---|---|
| 788 | 624 | 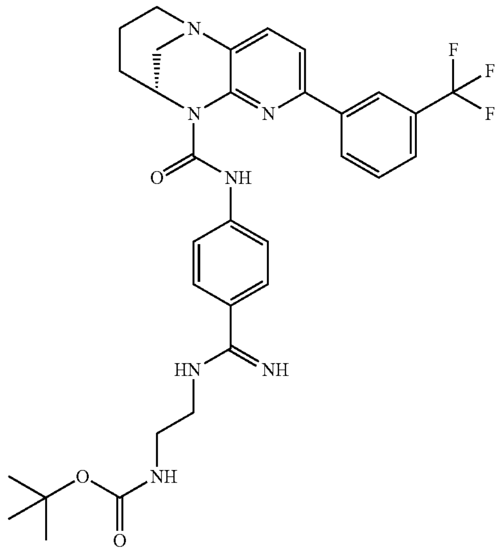 [SMILES: CC(C)(C)OC(=O)NCCNC(=N)c1ccc(NC(=O)N2c3nc(-c4cccc(C(F)(F)F)c4)ccc3N3CCC[C@H]2C3)cc1] | A | A |
| 790 | 510 | 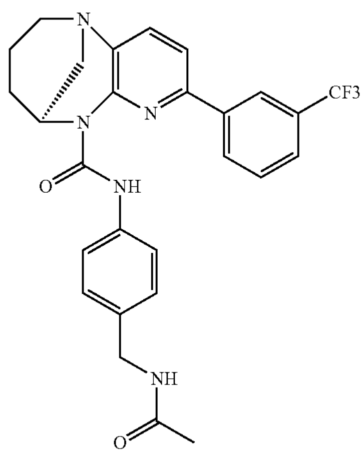 [SMILES: CC(=O)NCc1ccc(NC(=O)N2c3nc(-c4cccc(C(F)(F)F)c4)ccc3N3CCC[C@H]2C3)cc1] | A | A |
| 792 | 524 | 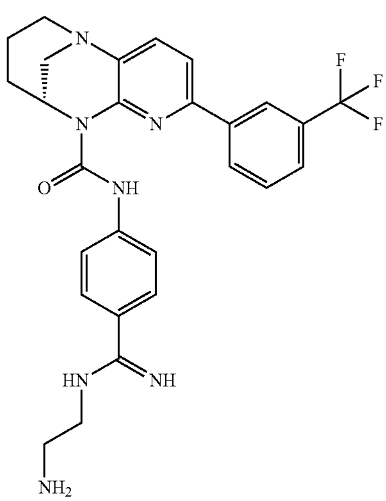 [SMILES: N=C(NCCN)c1ccc(NC(=O)N2c3nc(-c4cccc(C(F)(F)F)c4)ccc3N3CCC[C@H]2C3)cc1] | A | A |

TABLE 1-continued
Compounds of Formula (I).
| Compound No. | [M + H]+_[calc] | Structure | Tryp AVG EC_{1.5} (μM) | Tryp % Fold Act |
|---|---|---|---|---|
| 793 | 554 | 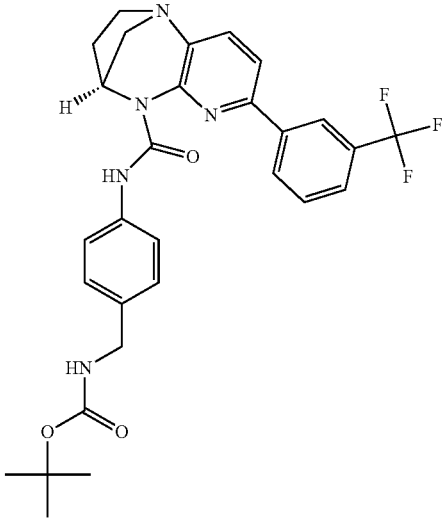 [SMILES: CC(C)(C)OC(=O)NCc1ccc(NC(=O)N2c3nc(-c4cccc(C(F)(F)F)c4)ccc3N3CC[C@H]2C3)cc1] | B | A |
| 794 | 487 | 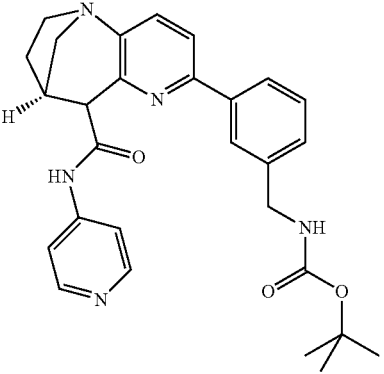 [SMILES: CC(C)(C)OC(=O)NCc1cccc(-c2ccc3c(n2)C(C(=O)Nc2ccncc2)[C@H]2CCN3C2)c1] | B | A |
| 795 | 501 | 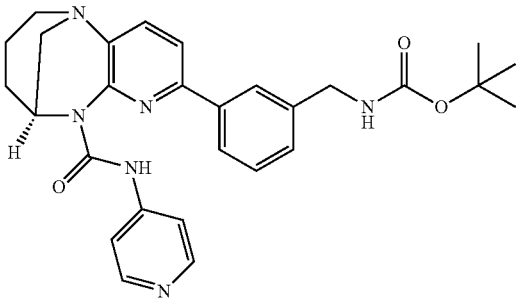 [SMILES: CC(C)(C)OC(=O)NCc1cccc(-c2ccc3c(n2)N(C(=O)Nc2ccncc2)[C@H]2CCCN3C2)c1] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 796 | 630 | 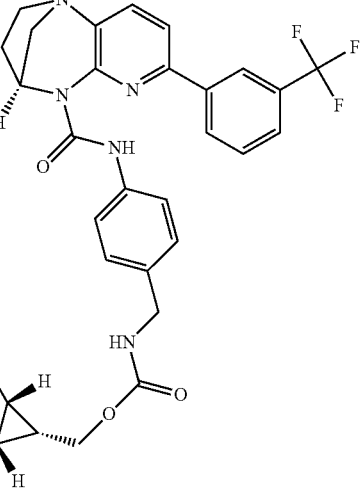 | B | A |
| 797 | 519 | 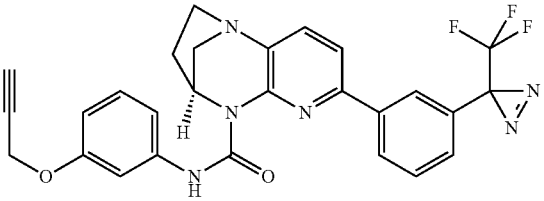 [SMILES: C#CCOc1cccc(NC(=O)N2c3nc(-c4cccc(C5(C(F)(F)F)N=N5)c4)ccc3N3CC[C@H]2C3)c1] | A | A |
| 798 | 548 | 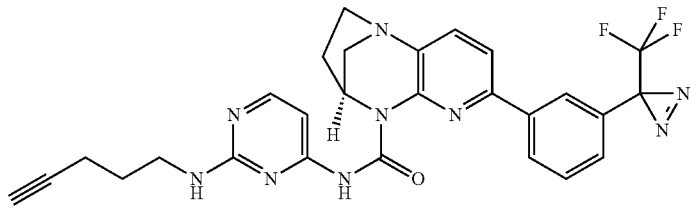 [SMILES: C#CCCCNc1nccc(NC(=O)N2c3nc(-c4cccc(C5(C(F)(F)F)N=N5)c4)ccc3N3CC[C@H]2C3)n1] | A | A |
| 799 | 537 | 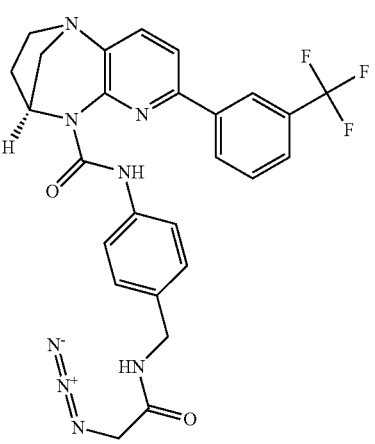 [SMILES: [N-]=[N+]=NCC(=O)NCc1ccc(NC(=O)N2c3nc(-c4cccc(C(F)(F)F)c4)ccc3N3CC[C@H]2C3)cc1] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 800 | 587 | 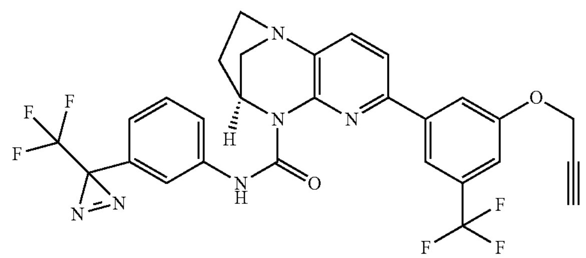 [SMILES: C#CCOc1cc(-c2ccc3c(n2)N(C(=O)Nc2cccc(C4(C(F)(F)F)N=N4)c2)[C@H]2CCN3C2)cc(C(F)(F)F)c1] | C | B |
| 801 | 548 | 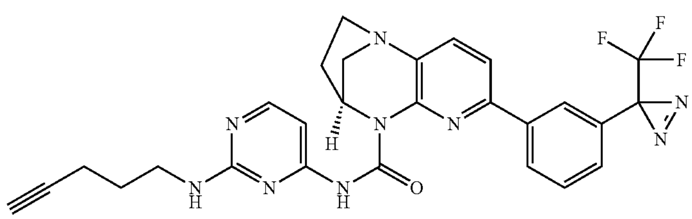 [SMILES: C#CCCCNc1nccc(NC(=O)N2c3nc(-c4cccc(C5(C(F)(F)F)N=N5)c4)ccc3N3CC[C@H]2C3)n1] | A | A |
| 802 | 519 | 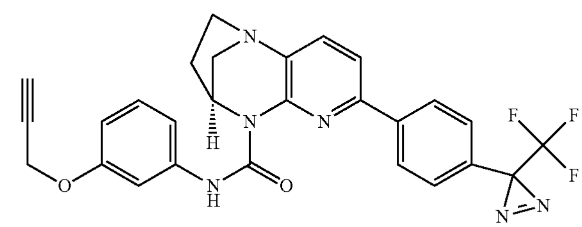 [SMILES: C#CCOc1cccc(NC(=O)N2c3nc(-c4ccc(C5(C(F)(F)F)N=N5)cc4)ccc3N3CC[C@H]2C3)c1] | B | A |
| 803 | 490 | 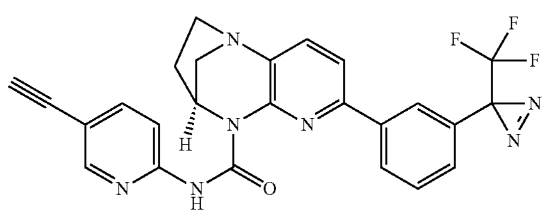 [SMILES: C#Cc1ccc(NC(=O)N2c3nc(-c4cccc(C5(C(F)(F)F)N=N5)c4)ccc3N3CC[C@H]2C3)nc1] | A | A |
| 804 | 520 | 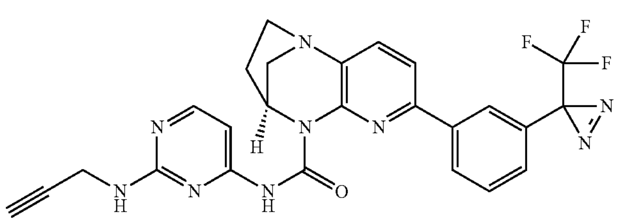 [SMILES: C#CCNc1nccc(NC(=O)N2c3nc(-c4cccc(C5(C(F)(F)F)N=N5)c4)ccc3N3CC[C@H]2C3)n1] | A | A |
| 805 | 520 | 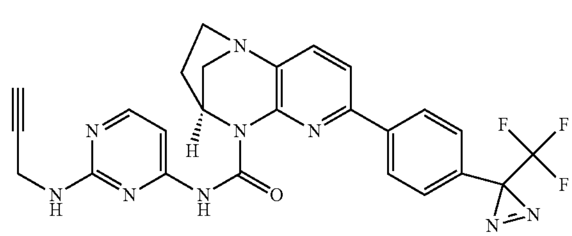 [SMILES: C#CCNc1nccc(NC(=O)N2c3nc(-c4ccc(C5(C(F)(F)F)N=N5)cc4)ccc3N3CC[C@H]2C3)n1] | B | A |

TABLE 1-continued

Compounds of Formula (I).

| Compound No. | [M + H]+$_{[calc]}$ | Structure | Tryp AVG EC$_{1.5}$ (µM) | Tryp % Fold Act |
|---|---|---|---|---|
| 806 | 472 | 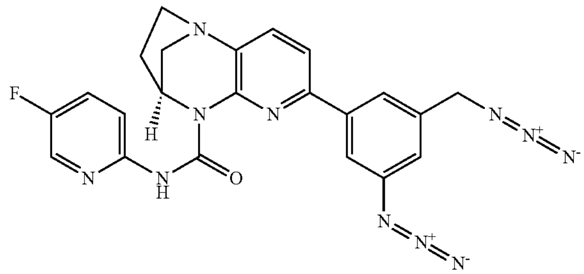 [SMILES: [N-]=[N+]=NCc1cc(N=[N+]=[N-])cc(-c2ccc3c(n2)N(C(=O)Nc2ccc(F)cn2)[C@H]2CCN3C2)c1] | A | A |
| 807 | 490 | 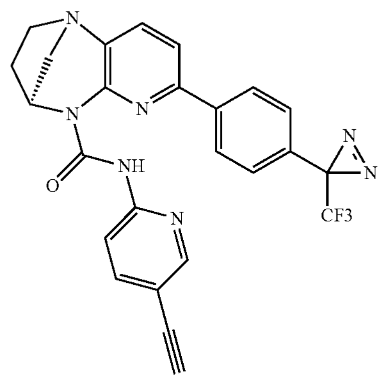 [SMILES: C#Cc1ccc(NC(=O)N2c3nc(-c4ccc(C5(C(F)(F)F)N=N5)cc4)ccc3N3CC[C@H]2C3)nc1] | C | B |
| 808 | 455 | 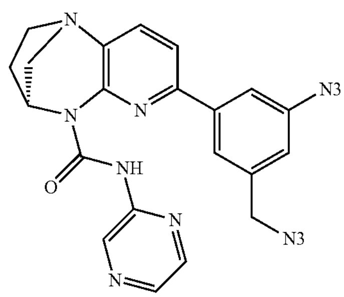 [SMILES: [N-]=[N+]=NCc1cc(N=[N+]=[N-])cc(-c2ccc3c(n2)N(C(=O)Nc2cnccn2)[C@H]2CCN3C2)c1] | A | A |
| 809 | 520 | 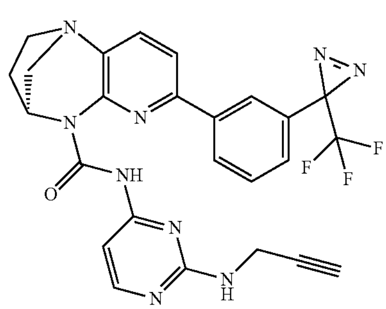 [SMILES: C#CCNc1nccc(NC(=O)N2c3nc(-c4cccc(C5(C(F)(F)F)N=N5)c4)ccc3N3CC[C@H]2C3)n1] | B | A |

TABLE 1-continued
Compounds of Formula (I).
| Compound No. | [M + H]+$_{[calc]}$ | Structure | Tryp AVG EC$_{1.5}$ (μM) | Tryp % Fold Act |
|---|---|---|---|---|
| 810 | 1308 | 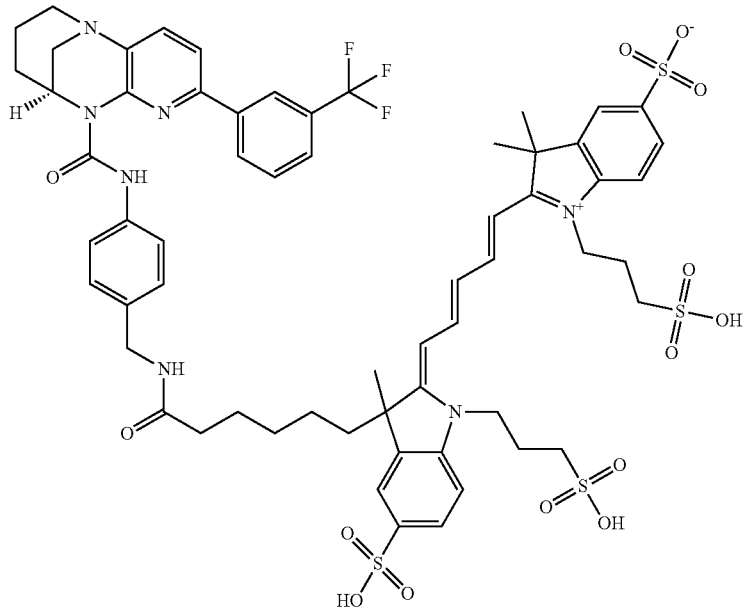 [SMILES: CC1(C)C(/C=C/C=C/C=C2\N(CCCS(=O)(=O)O)c3ccc(S(=O)(=O)O)cc3C2(C)CCCCCC(=O)NCc2ccc(NC(=O)N3c4nc(-c5cccc(C(F)(F)F)c5)ccc4N4CCC[C@H]3C4)cc2)=[N+](CCCS(=O)(=O)O)c2ccc(S(=O)(=O)[O-])cc21] | NT | NT |
| 811 | 1294 | 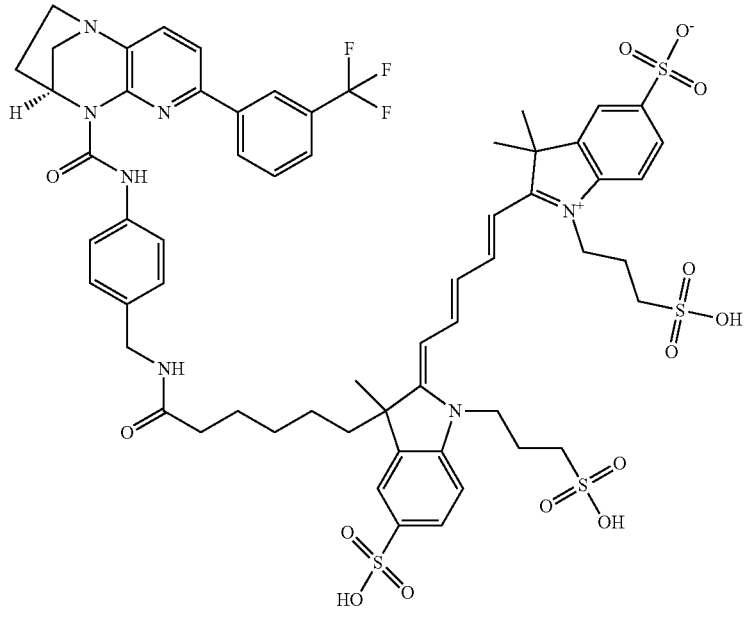 [SMILES: CC1(C)C(/C=C/C=C/C=C2\N(CCCS(=O)(=O)O)c3ccc(S(=O)(=O)O)cc3C2(C)CCCCCC(=O)NCc2ccc(NC(=O)N3c4nc(-c5cccc(C(F)(F)F)c5)ccc4N4CC[C@H]3C4)cc2)=[N+](CCCS(=O)(=O)O)c2ccc(S(=O)(=O)[O-])cc21] | NT | NT |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 812 | 1473 | 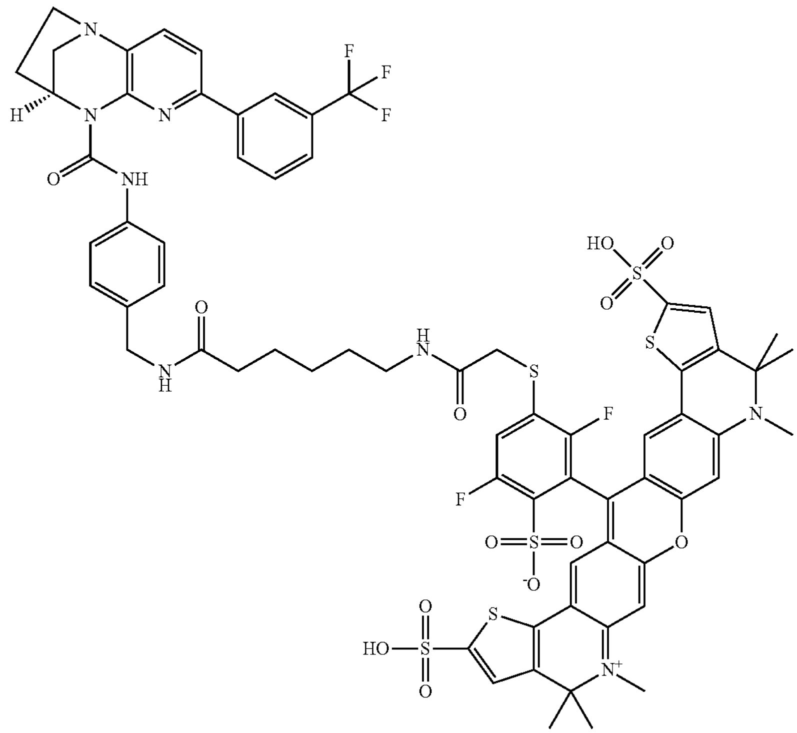 | NT | NT |
| 813 | 1487 | 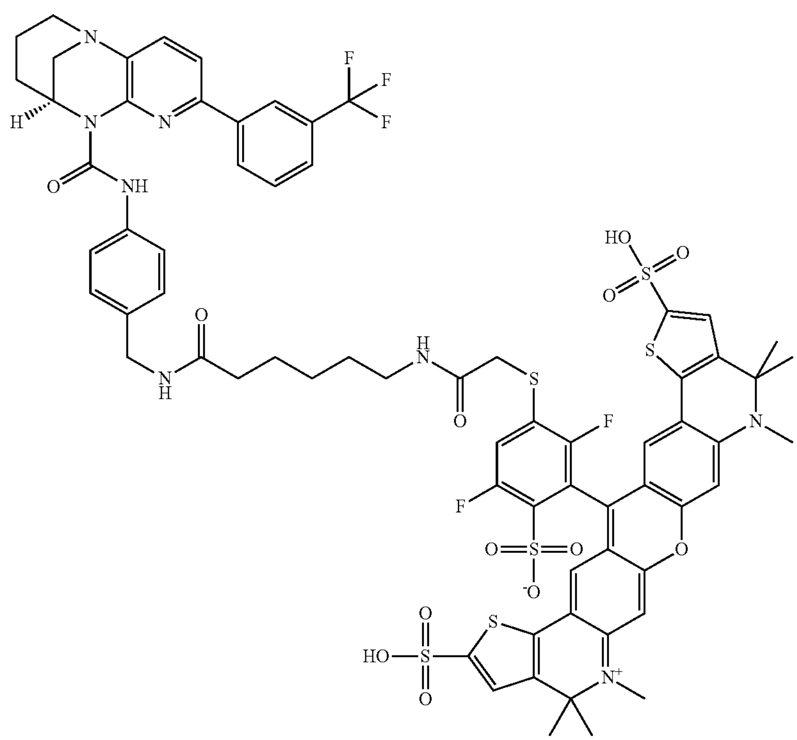 | NT | NT |

TABLE 1-continued
Compounds of Formula (I).
| Compound No. | [M + H]+[calc] | Structure | Tryp AVG EC$_{1.5}$ (μM) | Tryp % Fold Act |
|---|---|---|---|---|
| 814 | 1109 | 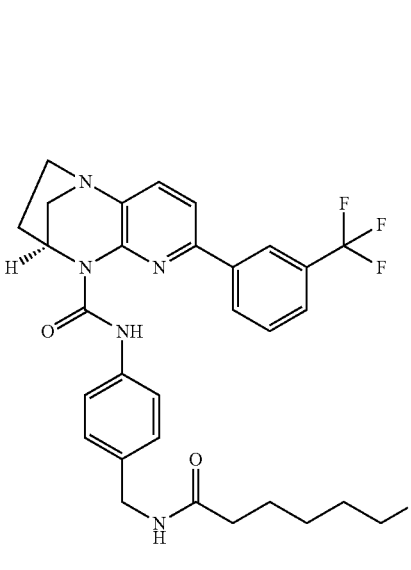 | NT | NT |
| 815 | 1123 | 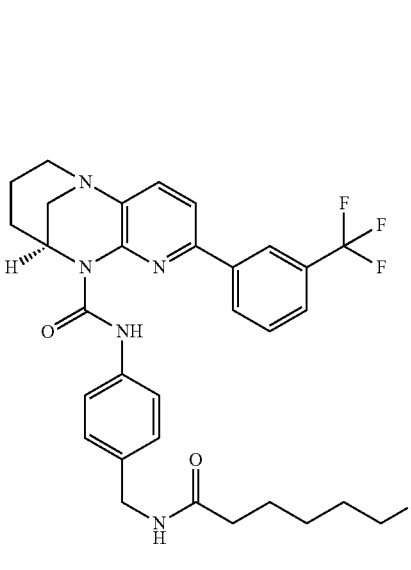 | NT | NT |
| 816 (7) | 426 | 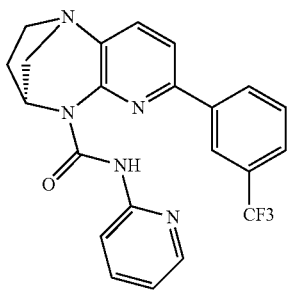 [SMILES: O=C(Nc1ccccn1)N1c2nc(-c3cccc(C(F)(F)F)c3)ccc2N2CC[C@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 817 | 426 | 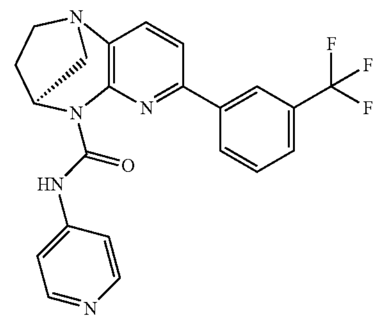 [SMILES: O=C(Nc1ccncc1)N1c2nc(-c3cccc(C(F)(F)F)c3)ccc2N2CC[C@H]1C2] | A | A |
| 818 | 517 | 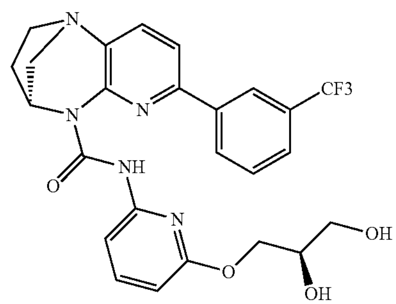 [SMILES: O=C(Nc1cccc(OC[C@H](O)CO)n1)N1c2nc(-c3cccc(C(F)(F)F)c3)ccc2N2CC[C@H]1C2] | A | A |
| 819 | 516 | 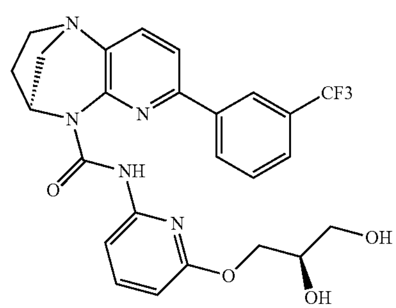 [SMILES: O=C(Nc1cccc(OC[C@H](O)CO)n1)N1c2nc(-c3cccc(C(F)(F)F)c3)ccc2N2CC[C@H]1C2] | A | A |
| 820 | 440 | 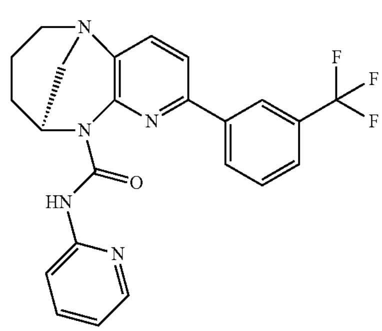 [SMILES: O=C(Nc1ccccn1)N1c2nc(-c3cccc(C(F)(F)F)c3)ccc2N2CCC[C@H]1C2] | A | A |

TABLE 1-continued

Compounds of Formula (I).

| Compound No. | [M + H]+[calc] | Structure | Tryp AVG EC$_{1.5}$ (μM) | Tryp % Fold Act |
|---|---|---|---|---|
| 821 | 440 | 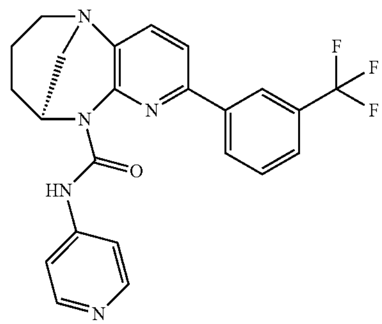 [SMILES: O=C(Nc1ccncc1)N1c2nc(-c3cccc(C(F)(F)F)c3)ccc2N2CCC[C@H]1C2] | A | A |
| 822 | 393 | 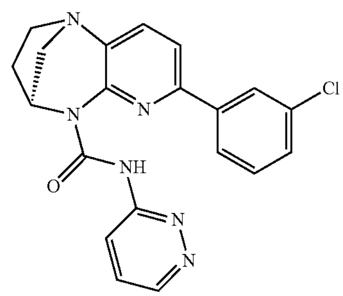 [SMILES: O=C(Nc1cccnn1)N1c2nc(-c3cccc(Cl)c3)ccc2N2CC[C@H]1C2] | A | A |
| 823 | 426 | 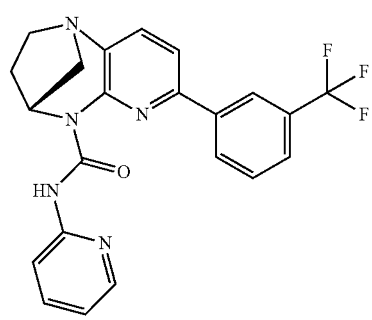 [SMILES: O=C(Nc1ccccn1)N1c2nc(-c3cccc(C(F)(F)F)c3)ccc2N2CC[C@@H]1C2] | A | A |
| 824 | 426 | 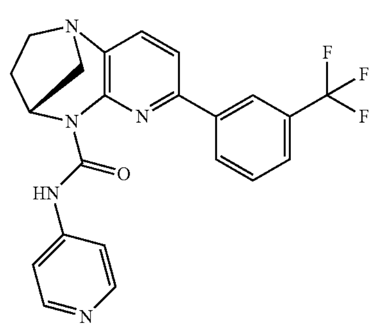 [SMILES: O=C(Nc1ccncc1)N1c2nc(-c3cccc(C(F)(F)F)c3)ccc2N2CC[C@@H]1C2] | A | A |

TABLE 1-continued

Compounds of Formula (I).

| Compound No. | [M + H]+$_{[calc]}$ | Structure | Tryp AVG EC$_{1.5}$ (μM) | Tryp % Fold Act |
|---|---|---|---|---|
| 825 | 426 | 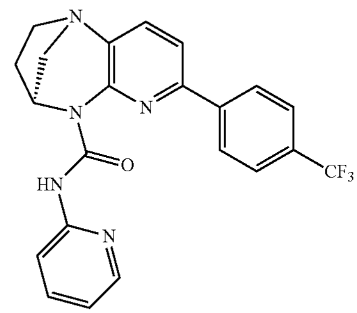 [SMILES: O=C(Nc1ccccn1)N1c2nc(-c3ccc(C(F)(F)F)cc3)ccc2N2CC[C@H]1C2] | NT | NT |
| 826 | 358 | 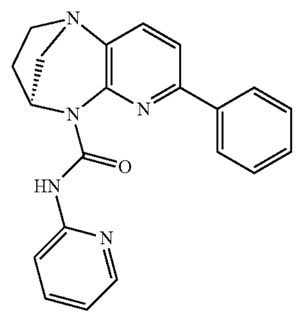 [SMILES: O=C(Nc1ccccn1)N1c2nc(-c3ccccc3)ccc2N2CC[C@H]1C2] | NT | NT |
| 827 | 425 | 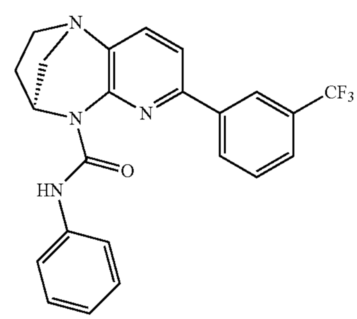 [SMILES: O=C(Nc1ccccc1)N1c2nc(-c3cccc(C(F)(F)F)c3)ccc2N2CC[C@H]1C2] | NT | NT |

In certain embodiments, the compound is any one of Compound Numbers 1, 3, 4, 5, 7, 8, 9, 10, 11, 12, 13, 14, 15, 16, 17, 18, 19, 20, 23, 25, 27, 28, 29, 30, 31, 32, 33, 34, 36, 38, 39, 40, 41, 42, 45, 46, 47, 48, 49, 53, 54, 56, 57, 59, 61, 63, 66, 68, 75, 76, 80, 81, 83, 86, 87, 90, 93, 95, 99, 101, 102, 107, 110, 118, 119, 120, 121, 122, 128, 129, 130, 133, 135, 136, 138, 139, 140, 141, 142, 145, 150, 151, 153, 156, 159, 160, 161, 162, 163, 164, 165, 166, 168, 170, 173, 174, 175, 176, 177, 178, 179, 180, 181, 182, 184, 189, 191, 194, 197, 207, 212, 214, 216, 218, 220, 222, 223, 230, 233, 235, 239, 250, 254, 260, 261, 264, 268, 271, 273, 274, 275, 276, 277, 278, 279, 280, 281, 282, 283, 285, 286, 288, 289, 290, 292, 293, 295, 299, 314, 316, 322, 324, 325, 329, 330, 332, 333, 335, 341, 344, 347, 348, 350, 351, 352, 353, 354, 356, 359, 360, 361, 365, 366, 367, 369, 373, 375, 376, 377, 378, 379, 380, 383, 385, 387, 388, 389, 391, 392, 393, 394, 396, 401, 402, 403, 404, 405, 406, 407, 408, 409, 410, 411, 412, 415, 417, 419, 421, 422, 423, 425, 427, 428, 430, 431, 435, 452, 459, 461, 463, 470, 472, 473, 474, 475, 480, 481, 483, 485, 491, 492, 496, 497, 498, 499, 500, 502, 503, 504, 505, 506, 507, 509, 515, 517, 519, 523, 526, 527, 530, 538, 540, 541, 542, 556, 557, 559, 562, 563, 574, 575, 580, 581, 583, 588, 589, 590, 591, 592, 593, 594, 595, 596, 601, 604, 605, 606, 607, 611, 617, 623, 625, 626, 629, 630, 635, 636, 637, 638, 639, 640, 642, 643, 645, 646, 647, 648, 651, 652, 653, 654, 655, 656, 657, 658, 659, 660, 663, 665, 666, 667, 668, 670, 671, 672, 676, 683, 692, 693, 694, 698, 703, 706, 708, 709, 710, 714, 717, 718, 719, 720, 721, 722, 723, 724, 725, 727, 730, 731, 733, 736, 737, 739, 740, 741, 742, 743, 746, 747, 748, 749, 750, 751, 752, 753, 754, 756, 757, 758, 760, 763, 765, 766, 767, 770, 776, 777, 780, 788, 790, 792, 797, 798, 799, 801, 803, 804, 806 and 808.

Example 107

(4S)—N-(pyridin-3-yl)-7-(4-(trifluoromethyl)piperidin-1-yl)-3,4-dihydro-1,4-methanopyrido[2,3-b][1,4]diazepine-5(2H)-carboxamide

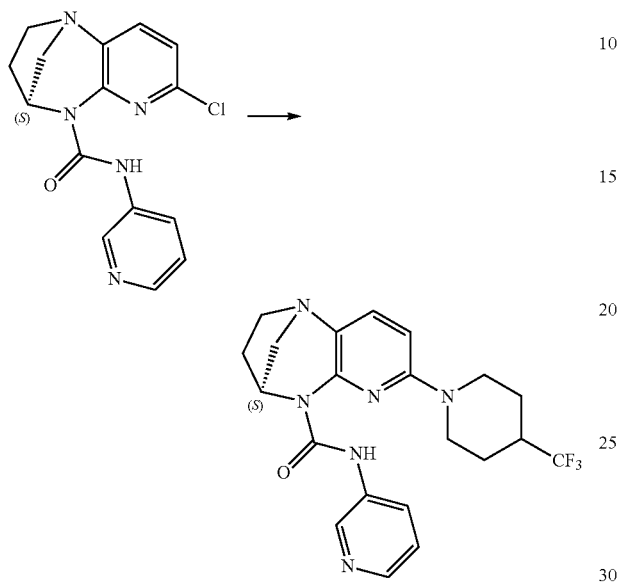

To a degassed solution of ((4S)-7-chloro-N-(pyridin-2-yl)-3,4-dihydro-1,4-methanopyrido[2,3-b][1,4]diazepine-5(2H)-carboxamide (700 mg, 2.217 mmol), 4-(trifluoromethyl)piperidine (679 mg, 4.43 mmol) in 1,4-Dioxane (20 mL) was added dicyclohexyl(2',4',6'-triisopropyl-[1,1'-biphenyl]-2-yl)phosphine (423 mg, 0.887 mmol), potassium carbonate (919 mg, 6.65 mmol) and palladium(II) acetate (100 mg, 0.443 mmol) subsequentially at 20° C. and the reaction mixture was stirred in a sealed tube at 90° C. for 16 hr. The reaction mixture was poured in to cold water (70 mL) and extracted with ethyl acetate (150 mL). The organics were separated and dried over anhydrous sodium sulphate, concentrated under reduced pressure to give the crude product. The crude product was added to a silica gel column and was eluted with 1% to 2% methanol in dichloro methane. Collected fractions to give 500 mg, It was again purified by GRACE reverse phase HPLC to give (4S)—N-(pyridin-3-yl)-7-(4-(trifluoromethyl)piperidin-1-yl)-3,4-dihydro-1,4-methanopyrido[2,3-b][1,4]diazepine-5(2H)-carboxamide (320 mg, 0.710 mmol, 32%). MS (ESI) calcd for $C_{21}H_{23}F_3N_6O$: 433.2.

EQUIVALENTS

The present invention provides among other things sirtuin-modulating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

We claim:

1. A compound which is:

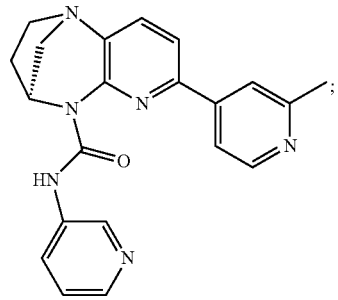 [SMILES: Cc1cc(-c2ccc3c(n2)N(C(=O)Nc2cccnc2)[C@H]2CCN3C2)ccn1]

or a pharmaceutically acceptable salt thereof.

2. A compound which is:

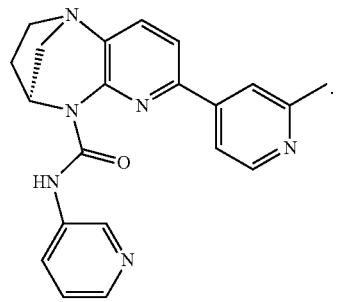 [SMILES: Cc1cc(-c2ccc3c(n2)N(C(=O)Nc2cccnc2)[C@H]2CCN3C2)ccn1]

3. A pharmaceutical composition comprising a compound of claim 1 or pharmaceutically acceptable salts thereof and a pharmaceutically acceptable excipient, carrier or diluent.

4. A pharmaceutical composition comprising a compound of claim 2 and a pharmaceutically acceptable excipient, carrier or diluent.

* * * * *